US012678444B2

(12) United States Patent
Nilsson-Lill et al.

(10) Patent No.: US 12,678,444 B2
(45) Date of Patent: Jul. 14, 2026

(54) SUBSTITUTED PYRAZINE-2-CARBOXAMIDES AS HPK1 INHIBITORS FOR THE TREATMENT OF CANCER

(71) Applicant: ASTRAZENECA AB, Södertälje (SE)

(72) Inventors: Sten Nilsson-Lill, Södertälje (SE); Kathryn Giblin, Cambridge (GB); Frederick Woolf Goldberg, Cambridge (GB); Jason Grant Kettle, Cambridge (GB); Amber Balazs, Gaithersburg, MD (US); Randolph Escobar, Gaithersburg, MD (US); Tyler Grebe, Gaithersburg, MD (US); Neil Patrick Grimster, Gaithersburg, MD (US); Anthony Metrano, Gaithersburg, MD (US); Adelphe Mfuh, Gaithersburg, MD (US); Lucas Morrill, Gaithersburg, MD (US); Li Sha, Gaithersburg, MD (US); James Sheppeck, Gaithersburg, MD (US); Jason Shields, Gaithersburg, MD (US); Kun Song, Gaithersburg, MD (US); Dedong Wu, Gaithersburg, MD (US); Ye Wu, Gaithersburg, MD (US); Robert Evans Ziegler, Gaithersburg, MD (US)

(73) Assignee: ASTRAZENECA AB, Södertälje (SE)

( * ) Notice: Subject to any disclaimer, the term of this patent is extended or adjusted under 35 U.S.C. 154(b) by 353 days.

(21) Appl. No.: 18/580,664

(22) PCT Filed: Jul. 19, 2022

(86) PCT No.: PCT/EP2022/070137
§ 371 (c)(1),
(2) Date: Jan. 19, 2024

(87) PCT Pub. No.: WO2023/001794
PCT Pub. Date: Jan. 26, 2023

(65) Prior Publication Data

US 2024/0374606 A1 Nov. 14, 2024

Related U.S. Application Data

(60) Provisional application No. 63/223,633, filed on Jul. 20, 2021.

(51) Int. Cl.

| | |
|---|---|
| ***A61K 31/5377*** | (2006.01) |
| ***A61K 31/497*** | (2006.01) |
| ***A61K 31/541*** | (2006.01) |
| ***C07D 401/14*** | (2006.01) |
| ***C07D 403/04*** | (2006.01) |
| ***C07D 403/14*** | (2006.01) |
| ***C07D 405/14*** | (2006.01) |
| ***C07D 471/04*** | (2006.01) |
| ***C07D 487/04*** | (2006.01) |

(52) U.S. Cl.
CPC ........ *A61K 31/5377* (2013.01); *A61K 31/497* (2013.01); *A61K 31/541* (2013.01); *C07D 401/14* (2013.01); *C07D 403/04* (2013.01); *C07D 403/14* (2013.01); *C07D 405/14* (2013.01); *C07D 471/04* (2013.01); *C07D 487/04* (2013.01)

(58) Field of Classification Search
CPC .................................................. A61K 31/5377
USPC ...................................................... 514/228.5
See application file for complete search history.

(56) References Cited

U.S. PATENT DOCUMENTS 7,582,761 B2 * 9/2009 Balan ........................ A61P 1/04
544/360
2018/0228786 A1 8/2018 Sokolsky et al.

FOREIGN PATENT DOCUMENTS

WO 2021032148 A1 2/2021

OTHER PUBLICATIONS

Degnan A. P., et al., "Discovery of Orally Active Isofuranones as Potent, Selective Inhibitors of Hematopoetic Progenitor Kinase 1", ACS Medicinal Chemistry Letters, vol. 12, No. 3, Feb. 19, 2021, pp. 443-450, XP055964950, US, ISSN: 1948-5875, DOI: 10.1021/acsmedchemlett.0c00660.
International Search Report and Written Opinion for International Application No. PCT/EP2022/070137, mailed Nov. 21, 2022, 15 Pages.
Vara B. A., et al., "Discovery of Diaminopyrimidine Carboxamide HPK1 Inhibitors as Preclinical Immunotherapy Tool Compounds", ACS Medicinal Chemistry Letters, vol. 12, No. 4, Mar. 19, 2021, pp. 653-661, XP055938211, US, ISSN: 1948-5875, DOI: 10.1021/acsmedchemlett.1c00096.
Yu E. C., et al., "Identification of Potent Reverse Indazole Inhibitors for HPK1", Acs Medicinal Chemistry Letters, vol. 12, No. 3, Mar. 1, 2021, pp. 459-466, XP055978410, US, ISSN: 1948-5875, DOI: 10.1021/acsmedchemlett.0c00672.

* cited by examiner

*Primary Examiner* — Niloofar Rahmani

(57) ABSTRACT

There are disclosed certain substituted pyrazine-2-carboxamides of Formula (I), and pharmaceutically acceptable salts thereof, together with compositions containing them and their use in therapy. The compounds are inhibitors of hematopoietic progenitor kinase 1 (HPK1) and are thereby particularly useful in the treatment or prophylaxis of cancer.

14 Claims, 26 Drawing Sheets

SUBSTITUTED PYRAZINE-2-CARBOXAMIDES AS HPK1 INHIBITORS FOR THE TREATMENT OF CANCER

TECHNICAL FIELD

The technical field relates to certain substituted pyrazine 2-carboxamides of Formula (I), and pharmaceutically acceptable salts thereof, together with compositions containing them and their use in therapy. The compounds of Formula (I) are inhibitors of hematopoietic progenitor kinase 1 (HPK1) and are thereby particularly useful in the treatment or amelioration of abnormal cell proliferative disorders such as cancer.

BACKGROUND

In recent years, discovery of immunological check points and their inhibition has unveiled a new avenue for targeting cancer by harnessing the body's own immune system to fight tumours. While check point therapy has shown great promise in several tumour types, only a fraction of cancer patients respond, novel therapies are needed to reach a broader range of patients.

T cells are critical in the cancer immunity cycle (Nature, 541 (2017), 321-330; Nature Reviews Immunology, 20, (2020), 651-668); they are the effector cells which recognize and kill tumour cells. In cancer patients, T cells are driven to exhaustion in the tumour microenvironment by chronic exposure to antigen and become non-functional. Additionally, suppressive signals in the tumour such as PGE2, TGFβ, adenosine, etc. hamper the function of these cells. Therapies that enhance T cell function and rescue the function of exhausted T cells therefore result in improved tumour control.

HIPK1 (hematopoietic progenitor kinase 1), also known as mitogen activated protein kinase 1 MAP4K1, a Ste20-related serine/threonine kinase that is expressed only in hematopoietic cells acts as a negative regulator of T cell signalling and tumouricidal cytokine production. Following TCR ligation, HPK1 phosphorylates its target SLP76 at Ser376 causing SLP76 to associate with 14-3-3 which results in disassociation of the LAT signalosome (J. Cell Biol., 195 (2011), 839-853; Nat. Immunol., 8 (2007), 84-91) and thus restricts T cell activation (J. Exp. Med., 204 (2007), 681-91). Loss of HPK1 or inactive kinase (kinase dead) causes enhanced activation of T cells resulting in increased cytokine secretion and proliferation (Nat Immunol., 8. (2007), 84-91; Cell Reports, 25 (2018), 80-94). HPK1 can also inhibit T cell signalling in response to immunosuppressive prostaglandin E2 (PGE2) through protein kinase A (PKA) (Blood, 101 (2003), 3687-89; J. Biol. Chem., 282 (2007), 34693-99; Cancer Immunol. Immunother., 59 (2010), 419-29). Recent literature has described the essential function of the kinase domain of HPK1 in driving tumour surveillance, inactivation of the kinase domain of HPK1 prevents tumour progression in murine tumour models. Importantly, studies comparing wildtype and kinase dead mice show that loss of kinase function of HPK1 can rescue T cells from exhaustion in chronic viral infection and PGE2 high tumour models (Nat Immunol., 8. (2007), 84-91; Cell Reports, 25 (2018), 80-94). Apart from its function in T cells, HPK1 is also reported to act as a negative regulator in other immune cells such as B cells, dendritic cells and NK cells which would also contribute to tumour immunity (Elife, 2020, 9). The kinase activity of HPK1 has been implicated as essential for the regulation of T cell function (Cell Reports, 25 (2018), 80-94), supporting the development of small molecule inhibitors of HPK1 for use in cancer immunotherapy to boost T cell function as well as other immune cell types. HPK1 protein contains an N-terminal kinase domain, which is the regulatory domain containing the ATP binding site amino acids 23-46 (EMBO J., 15, 1996, 7013-25). The intermediate domain has proline-rich motifs with binding sites for SH3-containing proteins such as Crkl, Grb2 and HIP-55 which suggests a scaffolding function. The Citron homology domain is at the C-terminal which may act as a regulatory domain in molecular interactions including T cell adhesion. LCK and ZAP70 induce HPK1 Tyr-379 phosphorylation and kinase activation (Oncogene, 20 (2001), 1703-14; Immunity, 12 (2000), 399-408; J. Biol. Chem., 276 (2001), 45207-16. Essential adapters for T cell (SLP76) and B cell (BLNK) signalling have been reported to bind to activated HPK1 aiding in blockade of downstream signalling in both T and B cells (J. Biol. Chem., 276 (2001), 18908-14). Collectively there is strong rationale for targeting HPK1 with small molecule kinase inhibitors for cancer immunotherapy.

An HPK1 inhibitor can be used alone or in combination with other therapeutic agents for the treatment of cancer. An HPK1 inhibitor could be used in combination with check point blockade PD-(L)1 axis or with CTLA4 in efforts to expand response rates to check point blockade. Primary or secondary resistance to check point blockade may be potential indications for an HPK1 inhibitor. Additional combinations may include radiation, chemotherapy, surgery, tumour targeted agents or other immune targeted agents.

An HPK1 inhibitor could be used as a therapeutic in multiple cancer indications.

A number of small molecule inhibitors of HPK1 have been disclosed in patent applications, for example as summarized in Expert Opinion on Therapeutic Patents, DOI: 10.1080/13543776.2021.1924671.

- WO2016/205942 HPK1 inhibitors and methods of using same
- WO2018/167147 Azaindoles as inhibitors of HPK1
- WO2020/061377 Spirocyclic 2,3-dihydro-7-azaindoles and uses there of
- WO2018/183964 Isoquinolines as inhibitors of HPK1
- WO2020/023551 Naphthyridine compounds and uses thereof
- WO2020/023560 Isoquinoline compounds and uses thereof
- WO2020/069402 Cinnoline compounds and for the treatment of HPK1-dependent disorders such as cancer
- WO2020/072627 Isoquinoline compounds for the treatment of cancer
- WO2020/072695 8-Aminoisoquinoline compounds and uses thereof
- WO2018/081531 Methods for Human T-cell activation
- WO2018/102366 Anilinopyrimidines as Haematopoietic progenitor kinase 1 (HPK1) inhibitors
- WO2018/228923 Substituted pyrrolopyridine-derivatives as MAP4K1 modulators for the treatment of cancer diseases
- WO2018/228920 Preparation of substituted pyrrolopyridine derivatives as anticancer agents
- WO2018/228925 Preparation of substituted pyrrolopyridine derivatives as anticancer agents
- WO2019/016071 Substituted pyrrolopyridine derivatives
- WO2020/120257 Substituted pyrrolopyridine derivatives
- WO2020/092528 Substituted 6-azabenzimidazole compounds having HPK1 inhibitory activity WO2020/092621 Substituted 6-azabenzimidazole compounds as HPK1 inhibitors WO2020/237025 Substituted exo-methylene-oxindoles which are HPK1/MAP4K1 inhibitors WO2020/193511 HPK1 inhibitors WO2020/193512 Bicyclic HPK1 inhibitors WO2020/100027 2,3-Dihydro-1H-pyrrolo[3,4-C]pyridine-1-one derivatives as HPK1 inhibitors for the treatment of cancer WO2020/070331 Indoline compounds for use as MAP4K1 inhibitors WO2020/070332 Oxindole compounds for use as MAP4K1 inhibitors WO2019/238067 Pyrrolo[2,3-b]pyridines or pyrrolo[2,3-b]pyrazines as HPK1 inhibitor and the use thereof WO2020/103896 Pyrrolo[2,3-b]pyridines as HPK1 inhibitor and uses thereof WO2021/000925 Pyrrolo[2,3-b]pyrazines as HPK1 inhibitor and the use thereof WO2021013083 Tricyclic compounds as HPK1 inhibitor and use thereof WO2021032148 Aminopyrazine compounds as HPK1 inhibitor and the use thereof WO2021/000935 HPK1 inhibitors and uses thereof WO2019/206049 HPK1 inhibitors, preparation method and application thereof WO2020/227325 Heterobifunctional Compounds as Degraders of HPK1

WO 2019/090198 Isofuranone compounds useful as HPK1 inhibitors in the treatment of cancer and viral infections and their preparation WO 2018/049152 Preparation of pyrazolopyrimidine derivatives as HPK1 modulators and their use for the treatment of cancer WO 2018/049191 Pyrazolopyridone derivatives as HPK1 modulator and uses thereof for the treatment of cancer WO 2018/049200 Pyrazolopyridine derivatives as HPK1 modulator and uses thereof for the treatment of cancer WO 2018/049214 Pyrazolopyridine derivatives as HPK1 modulators and uses thereof for the treatment of cancer WO 2018/152220 Pyrazolopyridine compounds and uses thereof WO 2019/051199 6-Cyano-indazole compounds as Hematopoietic Progenitor Kinase 1 (HPK1) Modulators US 2019/0256500 Preparation of indazolyl pyrimidines compounds and uses thereof.

US 2019/0256520 Indazole compounds and uses thereof

US 201900315717 Preparation of benzimidazole and indole compounds for inhibiting HPK1 activity WO 2019/164846 N-(Phenyl)-2-(phenyl) pyrimidine-4-carboxamide derivatives and related compounds as HPK1 inhibitors for treating cancer US 20200048141 Preparation of benzothiazole as HPK1 inhibitors for the treatment and prevention of cancer WO2021/026180 Solid Forms of an HPK1 inhibitor WO2020100027 2,3-Dihydro-1H-pyrrolo[3,4-C]pyridine-1-one derivatives as HPK1 inhibitors for the treatment of cancer WO 2021050964 HPK1 antagonists and uses thereof

SUMMARY

There is provided compounds that are inhibitors of hematopoietic progenitor kinase 1 (HPK1), their use as medicaments, pharmaceutical compositions containing them and synthetic routes to their production.

In one embodiment, there is provided a compound of Formula (I).

(I)

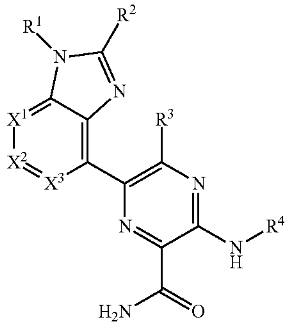

wherein $X^1$, $X^2$ and $X^3$ are independently selected from $CR^5$ or N, with the provisos that when $X^1$ is N, $X^3$ is $CR^5$ and when $X^3$ is N, $X^1$ is $CR^5$;

$R^1$ is cyclopropyl or $C_{1-3}$alkyl, wherein said $C_{1-3}$alkyl is substituted by 0, 1, 2 or 3 F;

$R^2$ is H, $NH_2$ or $C_{1-2}$alkyl, wherein said $C_{1-2}$alkyl is substituted by 0, 1, 2 or 3 F;

$R^3$ is selected from H, $R^6$, $OR^6$, $NHR^6$, Cl, CN, CCH, $NH_2$, $SCH_3$, cyclopropyl, cyclobutyl, NH((5- to 6-membered)heteroaryl containing 1 or 2 N), NH($C_{1-2}$alkyl)$N(CH_3)_2$, oxetan-3-yl, NH-cyclopropyl and O-cyclopropyl;

$R^4$ is selected from aryl or heteroaryl, wherein said aryl or heteroaryl is substituted by 0, 1, 2, 3 or 4 substituents independently selected from F, Cl and $R^6$, and 0, 1 or 2 substituents independently selected from $NH_2$, CN, $OR^6$, $R^7$, $R^8$, $R^9$, $OR^8$, $OCH_2R^8$, $C(O)R^8$, $C(O)CH_3$, $C(O)NHCH_3$, $CH_2C(O)NHCH_3$, $C(CH_3)_2R^8$, $CH(CH_3)R^8$ and $CH_2R^8$;

$R^5$ is independently selected from H, F, Cl and $C_{1-2}$alkyl, wherein said $C_{1-2}$alkyl is substituted by 0, 1, 2 or 3 substituents independently selected from F, CN, $NH_2$ and $OC_{1-2}$alkyl, wherein said $OC_{1-2}$alkyl is substituted by 0, 1, 2 or 3 substituents independently selected from F and Cl;

$R^6$ is $C_{1-4}$alkyl, wherein said $C_{1-4}$alkyl is substituted by 0, 1, 2 or 3 F, O($C_{1-2}$alkyl) and 0 or 1 substituents selected from OH, CN, $N(CH_3)_2$ and (4- to 5-membered)heterocycloalkyl containing one O;

$R^7$ is selected from NH-cyclopropyl, [dimethyl(oxo)-$\lambda^6$-sulfanylidene]amino, ($C_{1-4}$alkyl)sulfonimidoyl, $SO_2CH_3$, $OSO_2CH_3$, $C(CH_3)_2SO_2CH_3$, $SO_2NHCH_3$, $SO_2N(CH_3)_2$, morpholine-4-sulfonyl, 4-methylpiperazine-sulfonyl, morpholinyl, $CCCH_3$, cyclopropyl, wherein said cyclopropyl is substituted by 0 or 1 substituents selected from F, CN, OH or $SO_2CH_3$, cyclobutyl, wherein said cyclobutyl is substituted by 0 or 1 OH, and imidazolyl, wherein said imidazolyl is substituted by 0 or 1 $R^{11}$;

$R^8$ is selected from $SO_2CH_3$ or heterocycloalkyl, wherein said heterocycloalkyl is substituted by 0, 1, 2, 3 or 4 substituents independently selected from F, Cl, $R^6$ and $OR^6$, and 0, 1 or 2 substituents independently selected from cyclopropyl, OH, $C(O)CH_2OH$, 4-methylpiperazinyl, $C(O)CH_3$ and $C(O)N(CH_3)_2$;

$R^9$ is selected from $OR^{10}$, $N(R^{10})_2$, $NR^{11}(CH_2)_2N(CH_3)_2$, —$(CH_2)_2$ (5- to 6-membered)heterocycloalkyl, wherein said (5- to 6-membered)heterocycloalkyl is substituted by 0 or 1 substituents selected from $R^{11}$, —$O(CH_2)_2$ (5- to 6-membered)heterocycloalkyl, wherein said (5- to 6-membered)heterocycloalkyl is substituted by 0 or 1 substituents selected from $R^{11}$ and azetinyl substituted by 0 or 1 substituents selected from $N(CH_3)_2$ and $C(O)CH_3$;

$R^{10}$ is independently selected from H and $C_{1-2}$alkyl, wherein said $C_{1-2}$alkyl is substituted by 0, 1, 2 or 3 substituents independently selected from F, CN, $NH_2$ and $OC_{1-2}$alkyl, wherein said $C_{1-2}$alkyl is substituted by 0, 1, 2 or 3 substituents independently selected from F and Cl; and $R^{11}$ is $C_{1-3}$alkyl, wherein said $C_{1-3}$alkyl is substituted by 0, 1, 2 or 3 F and 0 or 1 cyclopropyl;

or a pharmaceutically acceptable salt thereof.

The compounds of Formula (I) are inhibitors of HPK1. Thus, the compounds of Formula (I) can be used as a medicament, in particular for disorders, disease or conditions responsive to inhibition of HPK1, and more specifically cancer.

In another embodiment there is provided a compound of Formula (I), or a pharmaceutically acceptable salt of a compound of Formula (I), wherein the stereochemistry is undefined, e.g. a racemate or a mixture of diastereomers.

In another embodiment there is provided a pharmaceutical formulation comprising a therapeutically effective amount of a compound of Formula (I), or a pharmaceutically acceptable salt of a compound of Formula (I), and a pharmaceutically acceptable diluent, excipient and/or inert carrier.

In a further embodiment there is provided a pharmaceutical formulation comprising a compound of Formula (I), or a pharmaceutically acceptable salt of a compound of Formula (I), for use in the treatment of a condition where inhibition of HPK1 would be beneficial.

In a further embodiment there is provided a compound of Formula (I), or a pharmaceutically acceptable salt of a compound of Formula (I), for use in therapy, especially in the treatment of cancer in a mammal, particularly a human.

In a further embodiment there is provided the use of a compound of Formula (I), or a pharmaceutically acceptable salt of a compound of Formula (I), for the manufacture of a medicament for the treatment of cancer.

In still a further embodiment, administration of a compound of Formula (I), or a pharmaceutically acceptable salt of a compound of Formula (I) results in a reduction in levels of activity of HPK1 in a mammal, particularly a human.

According to another aspect there is provided a process for the preparation of compounds of Formula (I), or pharmaceutically acceptable salts of compounds of Formula (I), and the intermediates used in the preparation thereof.

The compounds of Formula (I) herein exemplified have an $IC_{50}$ of less than 100 nmol/L for HPK1 in enzymatic activity assays. The compounds of Formula (I) also display promising pharmacological profiles by separating desired and undesired effects in vivo.

DETAILED DESCRIPTION

Figure 1:
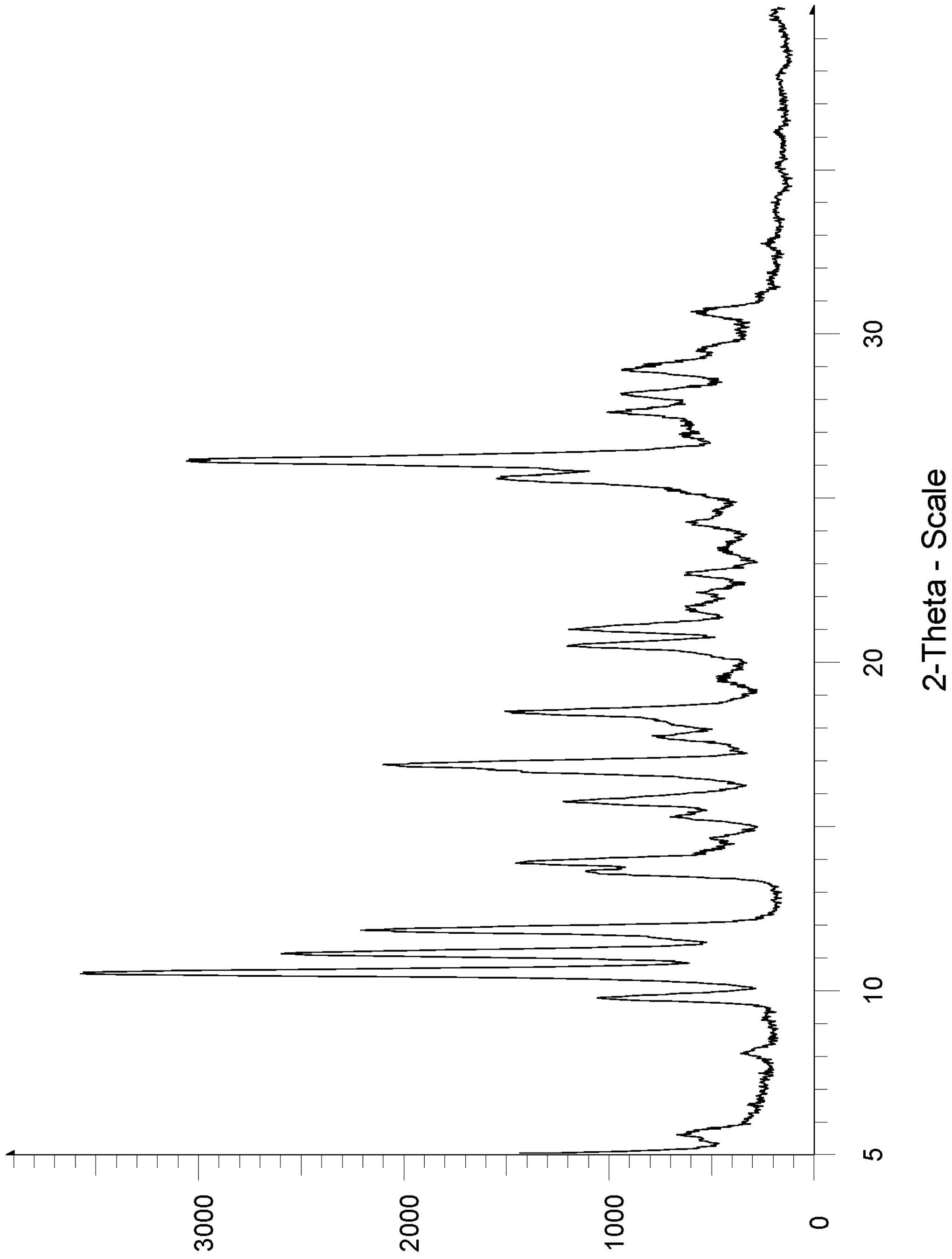
FIG. 1 shows the X-ray powder diffraction pattern for Example 8, form A: 5-(Methylamino)-6-(3-methylimidazo[4,5-c]pyridin-7-yl)-3-(4-morpholinoanilino)pyrazine-2-carboxamide.

This detailed description and its specific examples, while indicating embodiments, are intended for purposes of illustration only. Therefore, there is no limitation to the illustrative embodiments described in this specification. In addition, it is to be appreciated that various features that are, for clarity reasons, described in the context of separate embodiments, also may be combined to form a single embodiment. Conversely, various features that are, for brevity reasons, described in the context of a single embodiment, also may be combined to form sub-combinations thereof.

Listed below are definitions of various terms used in the specification and claims.

It is to be understood that where in this specification a group is qualified by "defined above" the said group encompasses the first occurring and broadest definition as well as each and all of the other definitions for that group.

It is to be understood that in this specification "$C_{1-4}$" means a carbon group having 1, 2, 3 or 4 carbon atoms.

It is to be understood that in this specification "$C_{1-3}$" means a carbon group having 1, 2 or 3 carbon atoms.

It is to be understood that in this specification "$C_{1-2}$" means a carbon group having 1 or 2 carbon atoms.

In this specification, unless stated otherwise, the term "alkyl" includes both straight and branched chain alkyl groups and may be, but is not limited to, methyl, ethyl, n-propyl, i-propyl, n-butyl, sec-butyl, iso-butyl or tert-butyl.

It is to be understood that in this specification "aryl" means an aromatic or partially aromatic group having 6 to 10 carbon atoms such as for example phenyl or naphtyl.

It is to be understood that in this specification "heteroaryl" means a mono- or bicyclic aromatic or partially aromatic ring with 5 to 10 atoms and containing one or more heteroatoms independently selected from nitrogen, oxygen or sulphur.

It is to be understood that in this specification "(5- to 6-membered)heteroaryl" means an aromatic ring with 5 to 6 atoms and containing one or more heteroatoms independently selected from nitrogen, oxygen or sulphur.

It is to be understood that in this specification "(6-membered)heteroaryl" means an aromatic ring with 6 atoms and containing one or more heteroatoms independently selected from nitrogen, oxygen or sulphur.

It is to be understood that in this specification "(6-membered)heteroaryl" means for example 2-pyridone.

It is to be understood that in this specification "(5-membered)heteroaryl" means an aromatic ring with 5 atoms and containing one or more heteroatoms independently selected from nitrogen, oxygen or sulphur.

It is to be understood that in this specification "heterocycloalkyl" means a partially or completely saturated monocyclic, bicyclic or bridged hydrocarbon ring system with 4 to 10 atoms and wherein at least one of the ring carbon atoms is replaced with a heteroatom independently selected from nitrogen, oxygen or sulphur.

It is to be understood that in this specification "(5- to 8-membered)heterocycloalkyl" means a partially or completely saturated monocyclic, bicyclic or bridged hydrocarbon ring system containing a total of 5 or 6 ring atoms, wherein at least one of the ring carbon atoms is replaced with a heteroatom independently selected from nitrogen, oxygen or sulphur.

It is to be understood that in this specification "(5- to 6-membered)heterocycloalkyl" means a partially or completely saturated monocyclic, bicyclic or bridged hydrocarbon ring system containing a total of 5 or 6 ring atoms, wherein at least one of the ring carbon atoms is replaced with a heteroatom independently selected from nitrogen, oxygen or sulphur.

It is to be understood that in this specification "(7-membered)heterocycloalkyl" means a partially or completely saturated monocyclic, bicyclic or bridged hydrocarbon ring system containing a total of 7 ring atoms, wherein at least one of the ring carbon atoms is replaced with a heteroatom independently selected from nitrogen, oxygen or sulphur.

It is to be understood that in this specification "(6-membered)heterocycloalkyl" means a partially or completely saturated monocyclic, bicyclic or bridged hydrocarbon ring system containing a total of 6 ring atoms, wherein at least one of the ring carbon atoms is replaced with a heteroatom independently selected from nitrogen, oxygen or sulphur.

It is to be understood that in this specification a "heterocycloalkyl" substituent may be attached via a nitrogen atom having the appropriate valences, or via any ring carbon atom.

In this specification, unless stated otherwise, the term "pharmaceutically acceptable" is used to characterize a moiety (e.g. a salt, dosage form, or excipient) as being appropriate for use in accordance with sound medical judgment. In general, a pharmaceutically acceptable moiety has one or more benefits that outweigh any deleterious effect that the moiety may have. Deleterious effects may include, for example, excessive toxicity, irritation, allergic response, and other problems and complications.

There is provided compounds of Formula (I) wherein $X^1$, $X^2$, $X^3$ and $R^1$-$R^{11}$ are as defined in Formula (I).

In one embodiment $X^1$, $X^2$ and $X^3$ are independently selected from $CR^5$ or N, with the provisos that when $X^1$ is N, $X^3$ is $CR^5$ and when $X^3$ is N, $X^1$ is $CR^5$.

In a further embodiment $X^1$, $X^2$ and $X^3$ are $CR^5$.

In still a further embodiment $X^2$ is N, $X^1$ and $X^3$ are $CR^5$.

In still a further embodiment $X^1$ and $X^2$ are N, $X^2$ is $CR^5$.

In still a further embodiment $X^2$ and $X^3$ are N, $X^1$ is $CR^5$.

$R^5$ is independently selected from H, F, Cl and $C_{1-2}$alkyl, wherein said $C_{1-2}$alkyl is substituted by 0, 1, 2 or 3 substituents independently selected from F, CN, $NH_2$ and $OC_{1-2}$alkyl, wherein said $OC_{1-2}$alkyl is substituted by 0, 1, 2 or 3 substituents independently selected from F and Cl.

In one embodiment $R^1$ is cyclopropyl or $C_{1-3}$alkyl, wherein said $C_{1-3}$alkyl is substituted by 0, 1, 2 or 3 F.

In a further embodiment $R^1$ is cyclopropyl or $C_{1-2}$alkyl, wherein said $C_{1-2}$alkyl is substituted by 0, 1, 2 or 3 F.

In still a further embodiment $R^1$ is cyclopropyl or $CH_3$.

In still a further embodiment $R^1$ is cyclopropyl.

In still a further embodiment $R^1$ is $CH_3$.

In still a further embodiment $R^1$ is $CH_2F$.

In still a further embodiment $R^1$ is $CHF_2$.

In still a further embodiment $R^1$ is $CF_3$.

In one embodiment $R^2$ is H, $NH_2$ or $C_{1-2}$alkyl, wherein said $C_{1-2}$alkyl is substituted by 0, 1, 2 or 3 F.

In a further embodiment $R^2$ is $NH_2$.

In still a further embodiment $R^2$ is $C_{1-2}$alkyl, wherein said $C_{1-2}$alkyl is substituted by 0, 1, 2 or 3 F.

In still a further embodiment $R^2$ is $CH_3$.

In still a further embodiment $R^2$ is $CH_2F$.

In still a further embodiment $R^2$ is $CHF_2$.

In still a further embodiment $R^2$ is $CF_3$.

In still a further embodiment $R^2$ is H.

In one embodiment $R^3$ is selected from H, $R^6$, $OR^6$, $NHR^6$, Cl, CN, CCH, $NH_2$, $SCH_3$, cyclopropyl, cyclobutyl, NH((5- to 6-membered)heteroaryl containing 1 or 2 N), NH($C_{1-2}$alkyl)$N(CH_3)_2$, oxetan-3-yl, NH-cyclopropyl and O-cyclopropyl.

In a further embodiment $R^3$ is selected from $R^6$, $OR^6$, $NHR^6$ and cyclopropyl.

In still a further embodiment $R^3$ is selected from $R^6$, $NHR^6$ and cyclopropyl.

$R^6$ is $C_{1-4}$alkyl, wherein said $C_{1-4}$alkyl is substituted by 0, 1, 2 or 3 F, O($C_{1-2}$alkyl) and 0 or 1 substituents selected from OH, CN, $N(CH_3)_2$ and (4- to 5-membered)heterocycloalkyl containing one O.

In still a further embodiment $R^3$ is selected from $C_{1-4}$alkyl, wherein said $C_{1-4}$alkyl is substituted by 0, 1, 2 or 3 F.

In still a further embodiment $R^3$ is selected from $C_{1-2}$alkyl, wherein said $C_{1-2}$alkyl is substituted by 0, 1, 2 or 3 F.

In still a further embodiment $R^3$ is $CH_3$.

In still a further embodiment $R^3$ is $CH_2F$.

In still a further embodiment $R^3$ is $CF_2$.

In still a further embodiment $R^3$ is $CF_3$.

In still a further embodiment $R^3$ is cyclopropyl.

In still a further embodiment $R^3$ is $NHC_{1-4}$alkyl, wherein said $C_{1-4}$alkyl is substituted by 0, 1, 2 or 3 F.

In still a further embodiment $R^3$ is $NHC_{1-2}$alkyl, wherein said $C_{1-2}$alkyl is substituted by 0, 1, 2 or 3 F.

In still a further embodiment $R^3$ is $NHCH_3$.

In still a further embodiment $R^3$ is $NHCH_2F$.

In still a further embodiment $R^3$ is $NHCHF_2$.

In still a further embodiment $R^3$ is $NHCF_3$.

In one embodiment $R^4$ is selected from aryl or heteroaryl, wherein said aryl or heteroaryl is substituted by 0, 1, 2, 3 or 4 substituents independently selected from F, Cl and $R^6$, and 0, 1 or 2 substituents independently selected from $NH_2$, CN, $OR^6$, $R^7$, $R^8$, $R^9$, $OR^8$, $OCH_2R^8$, $C(O)R^8$, $C(O)CH_3$, C(O)$NHCH_3$, $CH_2C(O)NHCH_3$, $C(CH_3)_2R^8$, $CH(CH_3)R^8$ and $CH_2R^8$.

$R^6$ is $C_{1-4}$alkyl, wherein said $C_{1-4}$alkyl is substituted by 0, 1, 2 or 3 F, O($C_{1-2}$alkyl) and 0 or 1 substituents selected from OH, CN, $N(CH_3)_2$ and (4- to 5-membered)heterocycloalkyl containing one O.

$R^7$ is selected from NH-cyclopropyl, [dimethyl(oxo)-$\lambda^6$-sulfanylidene]amino, ($C_{1-4}$alkyl)sulfonimidoyl, $SO_2CH_3$, $OSO_2CH_3$, $C(CH_3)_2SO_2CH_3$, $SO_2NHCH_3$, $SO_2N(CH_3)_2$, morpholine-4-sulfonyl, 4-methylpiperazine-sulfonyl, morpholinyl, $CCCH_3$, cyclopropyl, wherein said cyclopropyl is substituted by 0 or 1 substituents selected from F, CN, OH or $SO_2CH_3$, cyclobutyl, wherein said cyclobutyl is substituted by 0 or 1 OH, and imidazolyl, wherein said imidazolyl is substituted by 0 or 1 $R^{11}$.

$R^8$ is selected from $SO_2CH_3$ or heterocycloalkyl, wherein said heterocycloalkyl is substituted by 0, 1, 2, 3 or 4 substituents independently selected from F, Cl, $R^6$ and $OR^6$, and 0, 1 or 2 substituents independently selected from cyclopropyl, OH, $C(O)CH_2OH$, 4-methylpiperazinyl, C(O)$CH_3$ and $C(O)N(CH_3)_2$.

$R^9$ is selected from $OR^{10}$, $N(R^{10})_2$, $NR^{11}(CH_2)_2N(CH_3)_2$, —$(CH_2)_2$ (5- to 6-membered)heterocycloalkyl, wherein said (5- to 6-membered)heterocycloalkyl is substituted by 0 or 1 substituents selected from $R^{11}$, —$O(CH_2)_2$ (5- to 6-membered)heterocycloalkyl, wherein said (5- to 6-membered) heterocycloalkyl is substituted by 0 or 1 substituents selected from $R^{11}$ and azetinyl substituted by 0 or 1 substituents selected from $N(CH_3)_2$ and $C(O)CH_3$;

$R^{10}$ is independently selected from H and $C_{1-2}$alkyl, wherein said $C_{1-2}$alkyl is substituted by 0, 1, 2 or 3 substituents independently selected from F, CN, $NH_2$ and $OC_{1-2}$alkyl, wherein said $C_{1-2}$alkyl is substituted by 0, 1, 2 or 3 substituents independently selected from F and Cl; and $R^{11}$ is $C_{1-3}$alkyl, wherein said $C_{1-3}$alkyl is substituted by 0, 1, 2 or 3 F and 0 or 1 cyclopropyl.

In still a further embodiment $R^4$ is selected from aryl, wherein said aryl is substituted by 0, 1, 2, 3 or 4 substituents independently selected from F, Cl and $R^6$, and 0, 1 or 2 substituents independently selected from $NH_2$, CN, $OR^6$, $R^7$, $R^8$, $R^9$, $OR^8$, $OCH_2R^8$, $C(O)R^8$, $C(O)CH_3$, C(O)$NHCH_3$, $CH_2C(O)NHCH_3$, $C(CH_3)_2R^8$, $CH(CH_3)R^8$ and $CH_2R^8$.

In still a further embodiment $R^4$ is selected from phenyl, wherein said phenyl is substituted by 0, 1, 2, 3 or 4 substituents independently selected from F, Cl and $R^6$, and 0, 1 or 2 substituents independently selected from $NH_2$, CN, $OR^6$, $R^7$, $R^8$, $R^9$, $OR^8$, $OCH_2R^8$, $C(O)R^8$, $C(O)CH_3$, C(O)$NHCH_3$, $CH_2C(O)NHCH_3$, $C(CH_3)_2R^8$, $CH(CH_3)R^8$ and $CH_2R^8$.

In still a further embodiment $R^4$ is selected from phenyl, wherein said phenyl is substituted by 0, 1, 2 or 3 substituents independently selected from F, Cl and $R^6$, and 0, 1 or 2 substituents independently selected from $NH_2$, CN, $OR^6$, $R^7$, $R^8$, $R^9$, $OR^8$, $OCH_2R^8$, $C(O)R^8$, $C(O)CH_3$, C(O)$NHCH_3$, $CH_2C(O)NHCH_3$, $C(CH_3)_2R^8$, $CH(CH_3)R^8$ and $CH_2R^8$.

In still a further embodiment $R^4$ is selected from phenyl, wherein said phenyl is substituted by 0, 1 or 2 substituents independently selected from F, Cl and $R^6$, and 0, 1 or 2 substituents independently selected from $NH_2$, CN, $OR^6$, $R^7$, $R^8$, $R^9$, $OR^8$, $OCH_2R^8$, $C(O)R^8$, $C(O)CH_3$, C(O)$NHCH_3$, $CH_2C(O)NHCH_3$, $C(CH_3)_2R^8$, $CH(CH_3)R^8$ and $CH_2R^8$.

In still a further embodiment $R^4$ is selected from phenyl, wherein said phenyl is substituted by 0 or 1 substituent selected from F, Cl and $R^6$, and 0, 1 or 2 substituents independently selected from $NH_2$, CN, $OR^6$, $R^7$, $R^8$, $R^9$, $OR^8$, $OCH_2R^8$, $C(O)R^8$, $C(O)CH_3$, $C(O)NHCH_3$, $CH_2C(O)$$NHCH_3$, $C(CH_3)_2R^8$, $CH(CH_3)R^8$ and $CH_2R^8$.

In still a further embodiment $R^4$ is selected from phenyl, wherein said phenyl is substituted by 0 or 1 substituent selected from F, Cl and $R^6$, and a substituent selected from $NH_2$, CN, $OR^6$, $R^7$, $R^8$, $R^9$, $OR^8$, $OCH_2R^8$, $C(O)R^8$, $C(O)CH_3$, $C(O)NHCH_3$, $CH_2C(O)NHCH_3$, $C(CH_3)_2R^8$, $CH(CH_3)R^8$ and $CH_2R^8$.

In still a further embodiment $R^4$ is selected from phenyl, wherein said phenyl is substituted by a substituent selected from $NH_2$, CN, $OR^6$, $R^7$, $R^8$, $R^9$, $OR^8$, $OCH_2R^8$, $C(O)R^8$, $C(O)CH_3$, $C(O)NHCH_3$, $CH_2C(O)NHCH_3$, $C(CH_3)_2R^8$, $CH(CH_3)R^8$ and $CH_2R^8$.

In still a further embodiment $R^4$ is selected from phenyl, wherein said phenyl is substituted by 0 or 1 substituent selected from F, Cl and $R^6$, and a substituent selected from $OR^6$, $R^7$, $R^8$, $R^9$, $OR^8$, $OCH_2R^8$, $OR^8$, $OCH_2R^8$ and $CH_2R^8$.

In still a further embodiment $R^4$ is selected from phenyl, wherein said phenyl is substituted by 0 or 1 substituent selected from F, Cl and $R^6$, and a substituent selected from heterocycloalkyl, wherein said heterocycloalkyl is substituted by 0, 1, 2, 3 or 4 substituents independently selected from F, Cl, $R^6$ and $OR^6$, and 0, 1 or 2 substituents independently selected from cyclopropyl, $C(O)CH_3$ and $C(O)N(CH_3)_2$.

In still a further embodiment $R^4$ is selected from phenyl, wherein said phenyl is substituted by 0 or 1 substituent selected from F, Cl and $R^6$, and a substituent selected from (6-membered)heterocycloalkyl, wherein said (6-membered) heterocycloalkyl is substituted by 0, 1, 2, 3 or 4 substituents independently selected from F, Cl, $R^6$ and $OR^6$, and 0, 1 or 2 substituents independently selected from cyclopropyl, $C(O)CH_3$ and $C(O)N(CH_3)_2$.

In still a further embodiment $R^4$ is selected from phenyl, wherein said phenyl is substituted by 0 or 1 substituent selected from F, Cl and $R^6$, and a substituent selected from (6-membered)heterocycloalkyl, wherein said (6-membered) heterocycloalkyl is substituted by 0, 1 or 2 substituents independently selected from F, Cl, $R^6$ and $OR^6$, and 0, 1 or 2 substituents independently selected from cyclopropyl, $C(O)CH_3$ and $C(O)N(CH_3)_2$.

In still a further embodiment $R^4$ is selected from phenyl, wherein said phenyl is substituted by 0 or 1 substituent selected from F, Cl and $R^6$, and a substituent selected from (6-membered)heterocycloalkyl, wherein said (6-membered) heterocycloalkyl is substituted by 0, 1 or 2 substituents independently selected from F, Cl, $R^6$ and $OR^6$, and 0 or 1 substituent selected from cyclopropyl, $C(O)CH_3$ and $C(O)N(CH_3)_2$.

In still a further embodiment $R^4$ is selected from phenyl, wherein said phenyl is substituted by 0 or 1 substituent selected from F, Cl and $R^6$, and a substituent selected from morpholinyl, wherein said morpholinyl is substituted by 0, 1 or 2 substituents independently selected from F, Cl, $R^6$ and $OR^6$, and 0 or 1 substituent selected from cyclopropyl, $C(O)CH_3$ and $C(O)N(CH_3)_2$.

In still a further embodiment $R^4$ is selected from phenyl, wherein said phenyl is substituted by 0 or 1 substituent selected from F, Cl and $R^6$, and a substituent selected from morpholinyl, wherein said morpholinyl is substituted by 0, 1 or 2 substituents independently selected from F, Cl, $R^6$ and $OR^6$.

In still a further embodiment $R^4$ is selected from phenyl, wherein said phenyl is substituted by 0 or 1 substituent selected from F, Cl and $R^6$, and a substituent selected from $CH_2$heterocycloalkyl, wherein said heterocycloalkyl is substituted by 0, 1, 2, 3 or 4 substituents independently selected from F, Cl, $R^6$ and $OR^6$, and 0, 1 or 2 substituents independently selected from cyclopropyl, $C(O)CH_3$ and $C(O)N(CH_3)_2$.

In still a further embodiment $R^4$ is selected from phenyl, wherein said phenyl is substituted by 0 or 1 substituent selected from F, Cl and $R^6$, and a substituent selected from $CH_2$ (5- to 8-membered)heterocycloalkyl, wherein said (5- to 8-membered)heterocycloalkyl is substituted by 0, 1, 2, 3 or 4 substituents independently selected from F, Cl, $R^6$ and $OR^6$, and 0, 1 or 2 substituents independently selected from cyclopropyl, $C(O)CH_3$ and $C(O)N(CH_3)_2$.

In still a further embodiment $R^4$ is selected from phenyl, wherein said phenyl is substituted by 0 or 1 substituent selected from F, Cl and $R^6$, and a substituent selected from $CH_2$ (6-membered)heterocycloalkyl, wherein said (6-membered)heterocycloalkyl is substituted by 0, 1, 2, 3 or 4 substituents independently selected from F, Cl, $R^6$ and $OR^6$, and 0, 1 or 2 substituents independently selected from cyclopropyl, $C(O)CH_3$ and $C(O)N(CH_3)_2$.

In still a further embodiment $R^4$ is selected from phenyl, wherein said phenyl is substituted by 0 or 1 substituent selected from F, Cl and $R^6$, and a substituent selected from $CH_2$ (6-membered)heterocycloalkyl, wherein said (6-membered)heterocycloalkyl is substituted by 0, 1, 2, 3 or 4 substituents independently selected from F, Cl, $R^6$ and $OR^6$.

In still a further embodiment $R^4$ is selected from phenyl, wherein said phenyl is substituted by 0 or 1 substituent selected from F, Cl and $R^6$, and a substituent selected from $CH_2$ (6-membered)heterocycloalkyl, wherein said (6-membered)heterocycloalkyl is substituted by 0, 1 or 2 substituents independently selected from F, Cl, $R^6$ and $OR^6$.

In still a further embodiment $R^4$ is selected from phenyl, wherein said phenyl is substituted by 0 or 1 substituent selected from F, Cl and $R^6$, and a substituent selected from $CH_2$ (7-membered)heterocycloalkyl, wherein said (7-membered)heterocycloalkyl is substituted by 0, 1, 2, 3 or 4 substituents independently selected from F, Cl, $R^6$ and $OR^6$, and 0, 1 or 2 substituents independently selected from cyclopropyl, $C(O)CH_3$ and $C(O)N(CH_3)_2$.

In still a further embodiment $R^4$ is selected from phenyl, wherein said phenyl is substituted by 0 or 1 substituent selected from F, Cl and $R^6$, and a substituent selected from $CH_2$ (7-membered)heterocycloalkyl, wherein said (7-membered)heterocycloalkyl is substituted by 0, 1, 2, 3 or 4 substituents independently selected from F, Cl, $R^6$ and $OR^6$.

In still a further embodiment $R^4$ is selected from phenyl, wherein said phenyl is substituted by 0 or 1 substituent selected from F, Cl and $R^6$, and a substituent selected from $CH_2$ (7-membered)heterocycloalkyl, wherein said (7-membered)heterocycloalkyl is substituted by 0, 1 or 2 substituents independently selected from F, Cl, $R^6$ and $OR^6$.

In still a further embodiment $R^4$ is selected from heteroaryl, wherein said heteroaryl is substituted by 0, 1, 2, 3 or 4 substituents independently selected from F, Cl and $R^6$, and 0, 1 or 2 substituents independently selected from $NH_2$, CN, $OR^6$, $R^7$, $R^8$, $R^9$, $OR^8$, $OCH_2R^8$, $C(O)R^8$, $C(O)CH_3$, $C(O)NHCH_3$, $CH_2C(O)NHCH_3$, $C(CH_3)_2R^8$, $CH(CH_3)R^8$ and $CH_2R^8$.

In still a further embodiment $R^4$ is selected from (6-membered)heteroaryl, wherein said (6-membered)heteroaryl is substituted by 0, 1, 2, 3 or 4 substituents independently selected from F, Cl and $R^6$, and 0, 1 or 2 substituents independently selected from $NH_2$, CN, $OR^6$, $R^7$, $R^8$, $R^9$, $OR^8$, $OCH_2R^8$, $C(O)R^8$, $C(O)CH_3$, $C(O)NHCH_3$, $CH_2C(O)NHCH_3$, $C(CH_3)_2R^8$, $CH(CH_3)R^8$ and $CH_2R^8$.

In still a further embodiment $R^4$ is selected from (6-membered)heteroaryl, wherein said (6-membered)heteroaryl is substituted by 0, 1 or 2 substituents independently selected from F, Cl and $R^6$, and 0, 1 or 2 substituents independently selected from $NH_2$, CN, $OR^6$, $R^7$, $R^8$, $R^9$, $OR^8$, $OCH_2R^8$, $C(O)R^8$, $C(O)CH_3$, $C(O)NHCH_3$, $CH_2C(O)NHCH_3$, $C(CH_3)_2R^8$, $CH(CH_3)R^8$ and $CH_2R^8$.

In still a further embodiment $R^4$ is selected from (6-membered)heteroaryl, wherein said (6-membered)heteroaryl is substituted by 0, 1 or 2 substituents independently selected from F, Cl and $R^6$, and 0 or 1 substituent selected from $NH_2$, CN, $OR^6$, $R^7$, $R^8$, $R^9$, $OR^8$, $OCH_2R^8$, $C(O)R^8$, $C(O)CH_3$, $C(O)NHCH_3$, $CH_2C(O)NHCH_3$, $C(CH_3)_2R^8$, $CH(CH_3)R^8$ and $CH_2R^8$.

In still a further embodiment $R^4$ is selected from (6-membered)heteroaryl, wherein said (6-membered)heteroaryl is substituted by 0, 1 or 2 substituents independently selected from F, Cl and $R^6$, and 0 or 1 substituent selected from $OR^6$, $R^7$, $R^8$, $R^9$, $OR^8$, $OCH_2R^8$, $C(O)R^8$ and $CH_2R^8$.

In still a further embodiment $R^4$ is selected from (6-membered)heteroaryl, wherein said (6-membered)heteroaryl is substituted by 0, 1 or 2 substituents independently selected from F, Cl and $R^6$, and 0 or 1 substituent selected from $R^8$ and $CH_2R^8$.

In still a further embodiment $R^4$ is selected from (6-membered)heteroaryl, wherein said (6-membered)heteroaryl is substituted by 0, 1 or 2 substituents independently selected from F, Cl and $R^6$, and 0 or 1 substituent selected from (5- to 8-membered)heterocycloalkyl and $CH_2$ (5- to 8-membered)heterocycloalkyl.

In still a further embodiment $R^4$ is selected from (6-membered)heteroaryl, wherein said (6-membered)heteroaryl is substituted by 0, 1 or 2 substituents independently selected from F, Cl and $R^6$, and 0 or 1 substituent selected from (6-membered)heterocycloalkyl and $CH_2$ (6-membered)heterocycloalkyl.

In still a further embodiment $R^4$ is selected from (5-membered)heteroaryl, wherein said (5-membered)heteroaryl is substituted by 0, 1 or 2 substituents independently selected from F, Cl and $R^6$, and 0, 1 or 2 substituents independently selected from $NH_2$, CN, $OR^6$, $R^7$, $R^8$, $R^9$, $OR^8$, $OCH_2R^8$, $C(O)R^8$, $C(O)CH_3$, $C(O)NHCH_3$, $CH_2C(O)NHCH_3$, $C(CH_3)_2R^8$, $CH(CH_3)R^8$ and $CH_2R^8$.

In still a further embodiment $R^4$ is selected from (5-membered)heteroaryl, wherein said (5-membered)heteroaryl is substituted by 0, 1 or 2 substituents independently selected from F, Cl and $R^6$, and 0 or 1 substituent selected from $NH_2$, CN, $OR^6$, $R^7$, $R^8$, $R^9$, $OR^8$, $OCH_2R^8$, $C(O)R^8$, $C(O)CH_3$, $C(O)NHCH_3$, $CH_2C(O)NHCH_3$, $C(CH_3)_2R^8$, $CH(CH_3)R^8$ and $CH_2R^8$.

In still a further embodiment $R^4$ is selected from (5-membered)heteroaryl, wherein said (5-membered)heteroaryl is substituted by 0, 1 or 2 substituents independently selected from F, Cl and $R^6$, and 0 or 1 substituent selected from $OR^6$, $R^7$, $R^8$, $R^9$, $OR^8$, $OCH_2R^8$, $C(O)R^8$ and $CH_2R^8$.

In still a further embodiment $R^4$ is selected from (5-membered)heteroaryl, wherein said (5-membered)heteroaryl is substituted by 0, 1 or 2 substituents independently selected from F, Cl and $R^6$, and 0 or 1 substituent selected from $R^8$ and $CH_2R^8$.

In still a further embodiment $R^4$ is selected from (5-membered)heteroaryl, wherein said (5-membered)heteroaryl is substituted by 0, 1 or 2 substituents independently selected from F, Cl and $R^6$, and 0 or 1 substituent selected from (5- to 8-membered)heterocycloalkyl and $CH_2$ (5- to 8-membered)heterocycloalkyl.

In still a further embodiment $R^4$ is selected from (5-membered)heteroaryl, wherein said (5-membered)heteroaryl is substituted by 0, 1 or 2 substituents independently selected from F, Cl and $R^6$, and 0 or 1 substituent selected from (6-membered)heterocycloalkyl and $CH_2$ (6-membered)heterocycloalkyl.

In still a further embodiment $R^4$ is selected from (5-membered)heteroaryl, wherein said (5-membered)heteroaryl is substituted by 0, 1 or 2 substituents independently selected from F, Cl and $R^6$, and 0 or 1 substituent selected from $R^7$.

In still a further embodiment $R^4$ is pyrazolyl, wherein said pyrazolyl is substituted by 0, 1 or 2 substituents independently selected from F, Cl and $R^6$, and 0 or 1 substituent selected from $R^7$.

In still a further embodiment $R^4$ is 1H-pyrazol-4-yl, wherein said 1H-pyrazol-4-yl is substituted by 0, 1 or 2 substituents independently selected from F, Cl and $R^6$, and 0 or 1 substituent selected from $R^7$.

In still a further embodiment $R^4$ is 1H-pyrazol-4-yl, wherein said 1H-pyrazol-4-yl is substituted by 0, 1 or 2 substituents independently selected from F, Cl and $R^6$.

In still a further embodiment $R^4$ is 1H-pyrazol-4-yl, wherein said 1H-pyrazol-4-yl is substituted by 0, 1 or 2 substituents independently selected from $R^6$.

In one embodiment $R^5$ is independently selected from H, F, Cl and $C_{1-2}$alkyl, wherein said $C_{1-2}$alkyl is substituted by 0, 1, 2 or 3 substituents independently selected from F, CN, $NH_2$ and $OC_{1-2}$alkyl, wherein said $OC_{1-2}$alkyl is substituted by 0, 1, 2 or 3 substituents independently selected from F and Cl.

In a further embodiment $R^5$ is H.

In still a further embodiment $R^5$ is $C_{1-2}$alkyl, wherein said $C_{1-2}$alkyl is substituted by 0, 1, 2 or 3 substituents independently selected from F, CN, $NH_2$ and $OC_{1-2}$alkyl, wherein said $OC_{1-2}$alkyl is substituted by 0, 1, 2 or 3 substituents independently selected from F and Cl.

In still a further embodiment $R^5$ is $C_{1-2}$alkyl, wherein said $C_{1-2}$alkyl is substituted by 0, 1, 2 or 3 substituents independently selected from F.

In still a further embodiment $R^5$ is $CH_3$.

In still a further embodiment $R^5$ is $CH_2F$.

In still a further embodiment $R^5$ is $CHF_2$.

In still a further embodiment $R^5$ is $CF_3$.

In one embodiment $R^6$ is $C_{1-4}$alkyl, wherein said $C_{1-4}$alkyl is substituted by 0, 1, 2 or 3 F, $O(C_{1-2}alkyl)$ and 0 or 1 substituents selected from OH, CN, $N(CH_3)_2$ and (4- to 5-membered)heterocycloalkyl containing one O.

In a further embodiment $R^6$ is $C_{1-4}$alkyl, wherein said $C_{1-4}$alkyl is substituted by 0, 1, 2 or 3 F and 0 or 1 substituents selected from OH, CN, $N(CH_3)_2$ and (4- to 5-membered)heterocycloalkyl containing one O.

In still a further embodiment $R^6$ is $C_{1-4}$alkyl, wherein said $C_{1-4}$alkyl is substituted by 0, 1, 2 or 3 F and 0 or 1 substituents selected from OH, CN and $N(CH_3)_2$.

In still a further embodiment $R^6$ is $C_{1-4}$alkyl, wherein said $C_{1-4}$alkyl is substituted by 0, 1, 2 or 3 F.

In still a further embodiment $R^6$ is $C_{1-2}$alkyl, wherein said $C_{1-2}$alkyl is substituted by 0, 1, 2 or 3 F.

In one embodiment $R^7$ is selected from NH-cyclopropyl, [dimethyl(oxo)-$\lambda^6$-sulfanylidene]amino, ($C_{1-4}$alkyl)sulfonimidoyl, $SO_2CH_3$, $OSO_2CH_3$, $C(CH_3)_2SO_2CH_3$, $SO_2NHCH_3$, $SO_2N(CH_3)_2$, morpholine-4-sulfonyl, 4-methylpiperazine-sulfonyl, morpholinyl, $CCCH_3$, cyclopropyl, wherein said cyclopropyl is substituted by 0 or 1 substituents selected from F, CN, OH or $SO_2CH_3$, cyclobutyl, wherein said cyclobutyl is substituted by 0 or 1 OH, and imidazolyl, wherein said imidazolyl is substituted by 0 or 1 $R^{11}$.

In a further embodiment $R^7$ is selected from cyclopropyl, wherein said cyclopropyl is substituted by 0 or 1 substituents selected from F, CN, OH or $SO_2CH_3$, and cyclobutyl, wherein said cyclobutyl is substituted by 0 or 1 OH.

In still a further embodiment $R^7$ is selected from cyclopropyl, wherein said cyclopropyl is substituted by 0 or 1 substituents selected from F, CN, OH or $SO_2CH_3$.

In still a further embodiment $R^7$ is selected from cyclobutyl, wherein said cyclobutyl is substituted by 0 or 1 OH.

In one embodiment $R^8$ is selected from $SO_2CH_3$ or heterocycloalkyl, wherein said heterocycloalkyl is substituted by 0, 1, 2, 3 or 4 substituents independently selected from F, Cl, $R^6$ and $OR^6$, and 0, 1 or 2 substituents independently selected from cyclopropyl, OH, $C(O)CH_2OH$, 4-methylpiperazinyl, $C(O)CH_3$ and $C(O)N(CH_3)_2$.

In a further embodiment $R^8$ is selected from (5- to 8-membered)heterocycloalkyl, wherein said heterocycloalkyl is substituted by 0, 1, 2, 3 or 4 substituents independently selected from F, Cl, $R^6$ and $OR^6$, and 0, 1 or 2 substituents independently selected from cyclopropyl, OH, $C(O)CH_2OH$, 4-methylpiperazinyl, $C(O)CH_3$ and $C(O)N(CH_3)_2$.

In still a further embodiment $R^8$ is selected from (5- to 6-membered)heterocycloalkyl, wherein said heterocycloalkyl is substituted by 0, 1, 2, 3 or 4 substituents independently selected from F, Cl, $R^6$ and $OR^6$, and 0, 1 or 2 substituents independently selected from cyclopropyl, OH, $C(O)CH_2OH$, 4-methylpiperazinyl, $C(O)CH_3$ and $C(O)N(CH_3)_2$.

In still a further embodiment $R^8$ is selected from (6-membered)heterocycloalkyl, wherein said heterocycloalkyl is substituted by 0, 1, 2, 3 or 4 substituents independently selected from F, Cl, $R^6$ and $OR^6$, and 0, 1 or 2 substituents independently selected from c cyclopropyl, OH, $C(O)CH_2OH$, 4-methylpiperazinyl, $C(O)CH_3$ and $C(O)N(CH_3)_2$.

In still a further embodiment $R^8$ is selected from (5-membered)heterocycloalkyl, wherein said heterocycloalkyl is substituted by 0, 1, 2, 3 or 4 substituents independently selected from F, Cl, $R^6$ and $OR^6$, and 0, 1 or 2 substituents independently selected from cyclopropyl, OH, $C(O)CH_2OH$, 4-methylpiperazinyl, $C(O)CH_3$ and $C(O)N(CH_3)_2$.

In one embodiment $R^9$ is selected from $OR^{10}$, $N(R^{10})_2$, $NR^{11}(CH_2)_2N(CH_3)_2$, $-(CH_2)_2$ (5- to 6-membered)heterocycloalkyl, wherein said (5- to 6-membered)heterocycloalkyl is substituted by 0 or 1 substituents selected from $R^{11}$, $-O(CH_2)_2$ (5- to 6-membered)heterocycloalkyl, wherein said (5- to 6-membered)heterocycloalkyl is substituted by 0 or 1 substituents selected from $R^{11}$ and azetinyl substituted by 0 or 1 substituents selected from $N(CH_3)_2$ and $C(O)CH_3$.

In a further embodiment $R^9$ is selected from $-(CH_2)_2$ (5- to 6-membered)heterocycloalkyl, wherein said (5- to 6-membered)heterocycloalkyl is substituted by 0 or 1 substituents selected from $R^{11}$.

In still a further embodiment $R^9$ is selected from $-O(CH_2)_2$ (5- to 6-membered)heterocycloalkyl, wherein said (5- to 6-membered)heterocycloalkyl is substituted by 0 or 1 substituents selected from $R^{11}$ and azetinyl substituted by 0 or 1 substituents selected from $N(CH_3)_2$ and $C(O)CH_3$.

In one embodiment $R^{10}$ is independently selected from H and $C_{1-2}$alkyl, wherein said $C_{1-2}$alkyl is substituted by 0, 1, 2 or 3 substituents independently selected from F, CN, $NH_2$ and $OC_{1-2}$alkyl, wherein said $C_{1-2}$alkyl is substituted by 0, 1, 2 or 3 substituents independently selected from F and Cl.

In a further embodiment $R^{10}$ is H.

In still a further embodiment $R^{10}$ is independently selected from $C_{1-2}$alkyl, wherein said $C_{1-2}$alkyl is substituted by 0, 1, 2 or 3 substituents independently selected from F, CN, $NH_2$ and $OC_{1-2}$alkyl, wherein said $C_{1-2}$alkyl is substituted by 0, 1, 2 or 3 substituents independently selected from F and Cl.

In still a further embodiment $R^{10}$ is independently selected from $C_{1-2}$alkyl, wherein said $C_{1-2}$alkyl is substituted by 0, 1, 2 or 3 substituents independently selected from F, CN, and $NH_2$.

In still a further embodiment $R^{10}$ is independently selected from $C_{1-2}$alkyl, wherein said $C_{1-2}$alkyl is substituted by 0, 1, 2 or 3 substituents independently selected from F.

In one embodiment, there is provided a compound of Formula (IA), (IA)

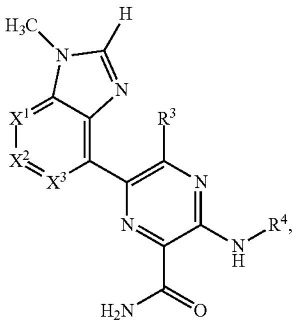

wherein $X^1$, $X^2$ and $X^3$ are independently selected from $CR^5$, $R^5$ is independently selected from H, F, Cl and $C_{1-2}$alkyl, wherein said $C_{1-2}$alkyl is substituted by 0, 1, 2 or 3 substituents independently selected from F, CN, $NH_2$ and $OC_{1-2}$alkyl, wherein said $OC_{1-2}$alkyl is substituted by 0, 1, 2 or 3 substituents independently selected from F and Cl;

$R^3$ is selected from H, $R^6$, $OR^6$, $NHR^6$, Cl, CN, CCH, $NH_2$, $SCH_3$, cyclopropyl, cyclobutyl, NH((5- to 6-membered)heteroaryl containing 1 or 2 N), $NH(C_{1-2}alkyl)N(CH_3)_2$, oxetan-3-yl, NH-cyclopropyl and O-cyclopropyl;

$R^6$ is $C_{1-4}$alkyl, wherein said $C_{1-4}$alkyl is substituted by 0, 1, 2 or 3 F, $O(C_{1-2}alkyl)$ and 0 or 1 substituents selected from OH, CN, $N(CH_3)_2$ and (4- to 5-membered)heterocycloalkyl containing one O;

$R^4$ is selected from aryl or heteroaryl, wherein said aryl or heteroaryl is substituted by 0, 1, 2, 3 or 4 substituents independently selected from F, Cl and $R^6$, and 0, 1 or 2 substituents independently selected from $NH_2$, CN, $OR^6$, $R^7$, $R^8$, $R^9$, $OR^8$, $OCH_2R^8$, $C(O)R^8$, $C(O)CH_3$, $C(O)NHCH_3$, $CH_2C(O)NHCH_3$, $C(CH_3)_2R^8$, $CH(CH_3)R^8$ and $CH_2R^8$;

$R^6$ is $C_{1-4}$alkyl, wherein said $C_{1-4}$alkyl is substituted by 0, 1, 2 or 3 F, $O(C_{1-2}alkyl)$ and 0 or 1 substituents selected from OH, CN, $N(CH_3)_2$ and (4- to 5-membered)heterocycloalkyl containing one O;

$R^7$ is selected from NH-cyclopropyl, [dimethyl(oxo)-$\lambda^6$-sulfanylidene]amino, ($C_{1-4}$alkyl)sulfonimidoyl, $SO_2CH_3$, $OSO_2CH_3$, $C(CH_3)_2SO_2CH_3$, $SO_2NHCH_3$, $SO_2N(CH_3)_2$, morpholine-4-sulfonyl, 4-methylpiperazine-sulfonyl, morpholinyl, $CCCH_3$, cyclopropyl, wherein said cyclopropyl is substituted by 0 or 1 substituents selected from F, CN, OH or $SO_2CH_3$, cyclobutyl, wherein said cyclobutyl is substituted by 0 or 1 OH, and imidazolyl, wherein said imidazolyl is substituted by 0 or 1 $R^{11}$;

$R^8$ is selected from $SO_2CH_3$ or heterocycloalkyl, wherein said heterocycloalkyl is substituted by 0, 1, 2, 3 or 4 substituents independently selected from F, Cl, $R^6$ and $OR^6$, and 0, 1 or 2 substituents independently selected from cyclopropyl, OH, $C(O)CH_2OH$, 4-methylpiperazinyl, $C(O)CH_3$ and $C(O)N(CH_3)_2$;

$R^9$ is selected from $OR^{10}$, $N(R^{10})_2$, $NR^{11}(CH_2)_2N(CH_3)_2$, $—(CH_2)_2$ (5- to 6-membered)heterocycloalkyl, wherein said (5- to 6-membered)heterocycloalkyl is substituted by 0 or 1 substituents selected from $R^{11}$, $—O(CH_2)_2$ (5- to 6-membered)heterocycloalkyl, wherein said (5- to 6-membered)heterocycloalkyl is substituted by 0 or 1 substituents selected from $R^{11}$ and azetinyl substituted by 0 or 1 substituents selected from $N(CH_3)_2$ and $C(O)CH_3$;

$R^{10}$ is independently selected from H and $C_{1-2}$alkyl, wherein said $C_{1-2}$alkyl is substituted by 0, 1, 2 or 3 substituents independently selected from F, CN, $NH_2$ and $OC_{1-2}$alkyl, wherein said $C_{1-2}$alkyl is substituted by 0, 1, 2 or 3 substituents independently selected from F and Cl; and $R^{11}$ is $C_{1-3}$alkyl, wherein said $C_{1-3}$alkyl is substituted by 0, 1, 2 or 3 F and 0 or 1 cyclopropyl;

or a pharmaceutically acceptable salt thereof.

In a further embodiment, there is provided a compound of Formula (IA), (IA)

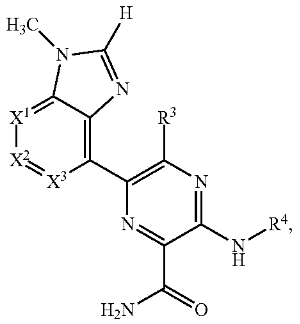

wherein $X^1$, $X^2$ and $X^3$ are $CR^5$;

$R^5$ is H;

$R^3$ is selected from H, $R^6$, $OR^6$, $NHR^6$, Cl, CN, CCH, $NH_2$, $SCH_3$, cyclopropyl, cyclobutyl, NH((5- to 6-membered)heteroaryl containing 1 or 2 N), $NH(C_{1-2}alkyl)N(CH_3)_2$, oxetan-3-yl, NH-cyclopropyl and O-cyclopropyl;

$R^6$ is $C_{1-4}$alkyl, wherein said $C_{1-4}$alkyl is substituted by 0, 1, 2 or 3 F, $O(C_{1-2}alkyl)$ and 0 or 1 substituents selected from OH, CN, $N(CH_3)_2$ and (4- to 5-membered)heterocycloalkyl containing one O;

$R^4$ is selected from aryl or heteroaryl, wherein said aryl or heteroaryl is substituted by 0, 1, 2, 3 or 4 substituents independently selected from F, Cl and $R^6$, and 0, 1 or 2 substituents independently selected from $NH_2$, CN, $OR^6$, $R^7$, $R^8$, $R^9$, $OR^8$, $OCH_2R^8$, $C(O)R^8$, $C(O)CH_3$, $C(O)NHCH_3$, $CH_2C(O)NHCH_3$, $C(CH_3)_2R^8$, $CH(CH_3)R^8$ and $CH_2R^8$;

$R^6$ is $C_{1-4}$alkyl, wherein said $C_{1-4}$alkyl is substituted by 0, 1, 2 or 3 F, $O(C_{1-2}alkyl)$ and 0 or 1 substituents selected from OH, CN, $N(CH_3)_2$ and (4- to 5-membered)heterocycloalkyl containing one O;

$R^7$ is selected from cyclopropyl, wherein said cyclopropyl is substituted by 0 or 1 substituents selected from F, CN, OH or $SO_2CH_3$, NH-cyclopropyl, [dimethyl(oxo)-$\lambda^6$-sulfanylidene]amino, $(C_{1-4}alkyl)$sulfonimidoyl, $SO_2CH_3$, $OSO_2CH_3$, $C(CH_3)_2SO_2CH_3$, $SO_2NHCH_3$, $SO_2N(CH_3)_2$, morpholine-4-sulfonyl, 4-methylpiperazine-sulfonyl, morpholinyl, $CCCH_3$ and cyclobutyl, wherein said cyclobutyl is substituted by 0 or 1 OH;

$R^8$ is selected from $SO_2CH_3$ or heterocycloalkyl, wherein said heterocycloalkyl is substituted by 0, 1, 2, 3 or 4 substituents independently selected from F, Cl, $R^6$ and $OR^6$, and 0, 1 or 2 substituents independently selected from cyclopropyl, OH, $C(O)CH_2OH$, 4-methylpiperazinyl, $C(O)CH_3$ and $C(O)N(CH_3)_2$;

$R^9$ is selected from $OR^{10}$, $N(R^{10})_2$, $NR^{11}(CH_2)_2N(CH_3)_2$, $—(CH_2)_2$ (5- to 6-membered)heterocycloalkyl, wherein said (5- to 6-membered)heterocycloalkyl is substituted by 0 or 1 substituents selected from $R^{11}$, $—O(CH_2)_2$ (5- to 6-membered)heterocycloalkyl, wherein said (5- to 6-membered)heterocycloalkyl is substituted by 0 or 1 substituents selected from $R^{11}$ and azetinyl substituted by 0 or 1 substituents selected from $N(CH_3)_2$ and $C(O)CH_3$;

$R^{10}$ is independently selected from H and $C_{1-2}$alkyl, wherein said $C_{1-2}$alkyl is substituted by 0, 1, 2 or 3 substituents independently selected from F, CN, $NH_2$ and $OC_{1-2}$alkyl, wherein said $C_{1-2}$alkyl is substituted by 0, 1, 2 or 3 substituents independently selected from F and Cl; and $R^{11}$ is $C_{1-3}$alkyl, wherein said $C_{1-3}$alkyl is substituted by 0, 1, 2 or 3 F and 0 or 1 cyclopropyl;

or a pharmaceutically acceptable salt thereof.

In still a further embodiment, there is provided a compound of Formula (IA), (IA)

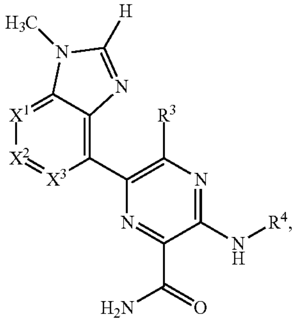

wherein $X^1$, $X^2$ and $X^3$ are $CR^5$;

$R^5$ is H;

$R^3$ is selected from $R^6$, $NHR^6$ and cyclopropyl;

$R^6$ is $C_{1-4}$alkyl, wherein said $C_{1-4}$alkyl is substituted by 0, 1, 2 or 3 F;

$R^4$ is selected from aryl or heteroaryl, wherein said aryl or heteroaryl is substituted by 0, 1, 2, 3 or 4 substituents independently selected from F, Cl and $R^6$, and 0, 1 or 2 substituents independently selected from $NH_2$, CN, $OR^6$, $R^7$, $R^8$, $R^9$, $OR^8$, $OCH_2R^8$, $C(O)R^8$, $C(O)CH_3$, $C(O)NHCH_3$, $CH_2C(O)NHCH_3$, $C(CH_3)_2R^8$, $CH(CH_3)R^8$ and $CH_2R^8$;

$R^6$ is $C_{1-4}$alkyl, wherein said $C_{1-4}$alkyl is substituted by 0, 1, 2 or 3 F, $O(C_{1-2}alkyl)$ and 0 or 1 substituents selected from OH, CN, $N(CH_3)_2$ and (4- to 5-membered)heterocycloalkyl containing one O;

$R^7$ is selected from cyclopropyl, wherein said cyclopropyl is substituted by 0 or 1 substituents selected from F, CN, OH or $SO_2CH_3$, NH-cyclopropyl, [dimethyl(oxo)-$\lambda^6$-sulfanylidene]amino, $(C_{1-4}alkyl)$sulfonimidoyl, $SO_2CH_3$, $OSO_2CH_3$, $C(CH_3)_2SO_2CH_3$, $SO_2NHCH_3$, $SO_2N(CH_3)_2$, morpholine-4-sulfonyl, 4-methylpiperazine-sulfonyl, morpholinyl, $CCCH_3$ and cyclobutyl, wherein said cyclobutyl is substituted by 0 or 1 OH;

$R^8$ is selected from $SO_2CH_3$ or heterocycloalkyl, wherein said heterocycloalkyl is substituted by 0, 1, 2, 3 or 4 substituents independently selected from F, Cl, $R^6$ and $OR^6$, and 0, 1 or 2 substituents independently selected from cyclopropyl, OH, $C(O)CH_2OH$, 4-methylpiperazinyl, $C(O)CH_3$ and $C(O)N(CH_3)_2$;

$R^9$ is selected from $OR^{10}$, $N(R^{10})_2$, $NR^{11}(CH_2)_2N(CH_3)_2$, $-(CH_2)_2$ (5- to 6-membered)heterocycloalkyl, wherein said (5- to 6-membered)heterocycloalkyl is substituted by 0 or 1 substituents selected from $R^{11}$, $-O(CH_2)_2$ (5- to 6-membered)heterocycloalkyl, wherein said (5- to 6-membered)heterocycloalkyl is substituted by 0 or 1 substituents selected from $R^{11}$ and azetinyl substituted by 0 or 1 substituents selected from $N(CH_3)_2$ and $C(O)CH_3$;

$R^{10}$ is independently selected from H and $C_{1-2}$alkyl, wherein said $C_{1-2}$alkyl is substituted by 0, 1, 2 or 3 substituents independently selected from F, CN, $NH_2$ and $OC_{1-2}$alkyl, wherein said $C_{1-2}$alkyl is substituted by 0, 1, 2 or 3 substituents independently selected from F and Cl; and $R^{11}$ is $C_{1-3}$alkyl, wherein said $C_{1-3}$alkyl is substituted by 0, 1, 2 or 3 F and 0 or 1 cyclopropyl;

or a pharmaceutically acceptable salt thereof.

In still a further embodiment, there is provided a compound of Formula (IA), (IA)

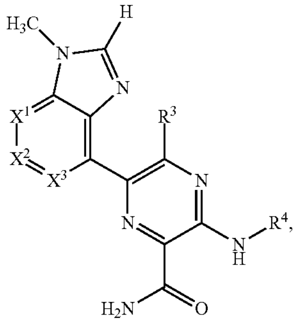

wherein $X^1$, $X^2$ and $X^3$ are $CR^5$;

$R^5$ is H;

$R^3$ is selected from $R^6$, $NHR^6$ and cyclopropyl;

$R^6$ is $C_{1-4}$alkyl, wherein said $C_{1-4}$alkyl is substituted by 0, 1, 2 or 3 F;

$R^4$ is selected from aryl, wherein said aryl is substituted by 0 or 1 substituent selected from F, Cl and $R^6$, and 0, 1 or 2 substituents independently selected from $NH_2$, CN, $OR^6$, $R^7$, $R^8$, $R^9$, $OR^8$, $OCH_2R^8$, $C(O)R^8$, $C(O)CH_3$, $C(O)NHCH_3$, $CH_2C(O)NHCH_3$, $C(CH_3)_2R^8$, $CH(CH_3)R^8$ and $CH_2R^8$;

$R^6$ is $C_{1-4}$alkyl, wherein said $C_{1-4}$alkyl is substituted by 0, 1, 2 or 3 F, $O(C_{1-2}alkyl)$ and 0 or 1 substituents selected from OH, CN, $N(CH_3)_2$ and (4- to 5-membered)heterocycloalkyl containing one O;

$R^7$ is selected from cyclopropyl, wherein said cyclopropyl is substituted by 0 or 1 substituents selected from F, CN, OH or $SO_2CH_3$, NH-cyclopropyl, [dimethyl(oxo)-$\lambda^6$-sulfanylidene]amino, ($C_{1-4}$alkyl)sulfonimidoyl, $SO_2CH_3$, $OSO_2CH_3$, $C(CH_3)_2SO_2CH_3$, $SO_2NHCH_3$, $SO_2N(CH_3)_2$, morpholine-4-sulfonyl, 4-methylpiperazine-sulfonyl, morpholinyl, $CCCH_3$ and cyclobutyl, wherein said cyclobutyl is substituted by 0 or 1 OH;

$R^8$ is selected from $SO_2CH_3$ or heterocycloalkyl, wherein said heterocycloalkyl is substituted by 0, 1, 2, 3 or 4 substituents independently selected from F, Cl, $R^6$ and $OR^6$, and 0, 1 or 2 substituents independently selected from cyclopropyl, OH, $C(O)CH_2OH$, 4-methylpiperazinyl, $C(O)CH_3$ and $C(O)N(CH_3)_2$;

$R^9$ is selected from $OR^{10}$, $N(R^{10})_2$, $NR^{11}(CH_2)_2N(CH_3)_2$, $-(CH_2)_2$ (5- to 6-membered)heterocycloalkyl, wherein said (5- to 6-membered)heterocycloalkyl is substituted by 0 or 1 substituents selected from $R^{11}$, $-O(CH_2)_2$ (5- to 6-membered)heterocycloalkyl, wherein said (5- to 6-membered)heterocycloalkyl is substituted by 0 or 1 substituents selected from $R^{11}$ and azetinyl substituted by 0 or 1 substituents selected from $N(CH_3)_2$ and $C(O)CH_3$;

$R^{10}$ is independently selected from H and $C_{1-2}$alkyl, wherein said $C_{1-2}$alkyl is substituted by 0, 1, 2 or 3 substituents independently selected from F, CN, $NH_2$ and $OC_{1-2}$alkyl, wherein said $C_{1-2}$alkyl is substituted by 0, 1, 2 or 3 substituents independently selected from F and Cl; and $R^{11}$ is $C_{1-3}$alkyl, wherein said $C_{1-3}$alkyl is substituted by 0, 1, 2 or 3 F and 0 or 1 cyclopropyl;

or a pharmaceutically acceptable salt thereof.

In still a further embodiment, there is provided a compound of Formula (IA), (IA)

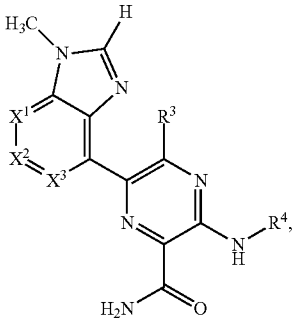

wherein $X^1$, $X^2$ and $X^3$ are $CR^5$;

$R^5$ is H;

$R^3$ is selected from $R^6$, $NHR^6$ and cyclopropyl;

$R^6$ is $C_{1-4}$alkyl, wherein said $C_{1-4}$alkyl is substituted by 0, 1, 2 or 3 F;

$R^4$ is selected from phenyl, wherein said phenyl is substituted by 0 or 1 substituent selected from F, Cl and $R^6$, and 0, 1 or 2 substituents independently selected from $NH_2$, CN, $OR^6$, $R^7$, $R^8$, $R^9$, $OR^8$, $OCH_2R^8$, $C(O)R^8$, $C(O)CH_3$, $C(O)NHCH_3$, $CH_2C(O)NHCH_3$, $C(CH_3)_2R^8$, $CH(CH_3)R^8$ and $CH_2R^8$;

$R^6$ is $C_{1-4}$alkyl, wherein said $C_{1-4}$alkyl is substituted by 0, 1, 2 or 3 F, $O(C_{1-2}alkyl)$ and 0 or 1 substituents selected from OH, CN, $N(CH_3)_2$ and (4- to 5-membered)heterocycloalkyl containing one O;

$R^7$ is selected from cyclopropyl, wherein said cyclopropyl is substituted by 0 or 1 substituents selected from F, CN, OH or $SO_2CH_3$, NH-cyclopropyl, [dimethyl(oxo)-$\lambda^6$-sulfanylidene]amino, ($C_{1-4}$alkyl)sulfonimidoyl, $SO_2CH_3$, $OSO_2CH_3$, $C(CH_3)_2SO_2CH_3$, $SO_2NHCH_3$, $SO_2N(CH_3)_2$, morpholine-4-sulfonyl, 4-methylpiperazine-sulfonyl, morpholinyl, $CCCH_3$ and cyclobutyl, wherein said cyclobutyl is substituted by 0 or 1 OH;

$R^8$ is selected from $SO_2CH_3$ or heterocycloalkyl, wherein said heterocycloalkyl is substituted by 0, 1, 2, 3 or 4 substituents independently selected from F, Cl, $R^6$ and $OR^6$, and 0, 1 or 2 substituents independently selected from cyclopropyl, OH, $C(O)CH_2OH$, 4-methylpiperazinyl, $C(O)CH_3$ and $C(O)N(CH_3)_2$;

$R^9$ is selected from $OR^{10}$, $N(R^{10})_2$, $NR^{11}(CH_2)_2N(CH_3)_2$, $—(CH_2)_2$ (5- to 6-membered)heterocycloalkyl, wherein said (5- to 6-membered)heterocycloalkyl is substituted by 0 or 1 substituents selected from $R^{11}$, $—O(CH_2)_2$ (5- to 6-membered)heterocycloalkyl, wherein said (5- to 6-membered)heterocycloalkyl is substituted by 0 or 1 substituents selected from $R^{11}$ and azetinyl substituted by 0 or 1 substituents selected from $N(CH_3)_2$ and $C(O)CH_3$;

$R^{10}$ is independently selected from H and $C_{1-2}$alkyl, wherein said $C_{1-2}$alkyl is substituted by 0, 1, 2 or 3 substituents independently selected from F, CN, $NH_2$ and $OC_{1-2}$alkyl, wherein said $C_{1-2}$alkyl is substituted by 0, 1, 2 or 3 substituents independently selected from F and Cl; and $R^{11}$ is $C_{1-3}$alkyl, wherein said $C_{1-3}$alkyl is substituted by 0, 1, 2 or 3 F and 0 or 1 cyclopropyl;

or a pharmaceutically acceptable salt thereof.

In still a further embodiment, there is provided a compound of Formula (IA), (IA)

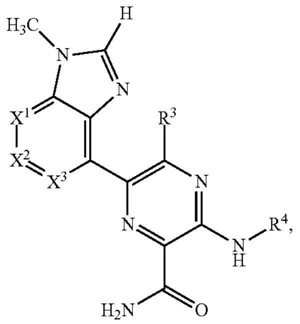

wherein $X^1$, $X^2$ and $X^3$ are $CR^5$;

$R^5$ is H;

$R^3$ is selected from $R^6$, $NHR^6$ and cyclopropyl;

$R^6$ is $C_{1-4}$alkyl, wherein said $C_{1-4}$alkyl is substituted by 0, 1, 2 or 3 F;

$R^4$ is selected from phenyl, wherein said phenyl is substituted by 0 or 1 substituent selected from F, Cl and $R^6$, and a substituent selected from morpholinyl, wherein said morpholinyl is substituted by 0, 1 or 2 substituents independently selected from F, Cl, $R^6$ and $OR^6$, and 0 or 1 substituent selected from cyclopropyl, $C(O)CH_3$ and $C(O)N(CH_3)_2$; and $R^6$ is $C_{1-4}$alkyl, wherein said $C_{1-4}$alkyl is substituted by 0, 1, 2 or 3 F, $O(C_{1-2}$alkyl) and 0 or 1 substituents selected from OH, CN, $N(CH_3)_2$ and (4- to 5-membered)heterocycloalkyl containing one O;

or a pharmaceutically acceptable salt thereof.

In still a further embodiment, there is provided a compound of Formula (IA), (IA)

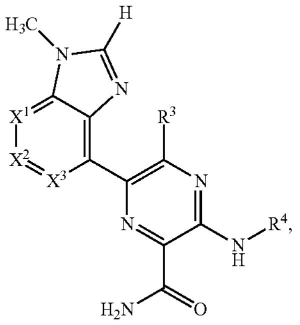

wherein $X^1$, $X^2$ and $X^3$ are $CR^5$;

$R^5$ is H;

$R^3$ is selected from $R^6$, $NHR^6$ and cyclopropyl;

$R^6$ is $C_{1-4}$alkyl, wherein said $C_{1-4}$alkyl is substituted by 0, 1, 2 or 3 F;

$R^4$ is selected from phenyl, wherein said phenyl is substituted by 0 or 1 substituent selected from F, Cl and $R^6$, and a substituent selected from morpholinyl, wherein said morpholinyl is substituted by 0, 1 or 2 substituents independently selected from F, Cl, $R^6$ and $OR^6$, and 0 or 1 substituent selected from cyclopropyl, $C(O)CH_3$ and $C(O)N(CH_3)_2$; and $R^6$ is $C_{1-4}$alkyl, wherein said $C_{1-4}$alkyl is substituted by 0, 1, 2 or 3 F;

or a pharmaceutically acceptable salt thereof.

In still a further embodiment, there is provided a compound of Formula (IA), (IA)

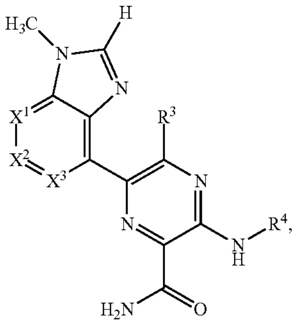

wherein $X^1$, $X^2$ and $X^3$ are $CR^5$;

$R^5$ is H;

$R^3$ is selected from $R^6$, $NHR^6$ and cyclopropyl;

$R^6$ is $C_{1-4}$alkyl, wherein said $C_{1-4}$alkyl is substituted by 0, 1, 2 or 3 F;

$R^4$ is selected from (5-membered)heteroaryl, wherein said (5-membered)heteroaryl is substituted by 0, 1 or 2 substituents independently selected from F, Cl and $R^6$, and 0, 1 or 2 substituents independently selected from $NH_2$, CN, $OR^6$, $R^7$, $R^8$, $R^9$, $OR^8$, $OCH_2R^8$, $C(O)R^8$, $C(O)CH_3$, $C(O)NHCH_3$, $CH_2C(O)NHCH_3$, $C(CH_3)_2R^8$, $CH(CH_3)R^8$ and $CH_2R^8$;

$R^6$ is $C_{1-4}$alkyl, wherein said $C_{1-4}$alkyl is substituted by 0, 1, 2 or 3 F, $O(C_{1-2}$alkyl) and 0 or 1 substituents selected from OH, CN, $N(CH_3)_2$ and (4- to 5-membered)heterocycloalkyl containing one O;

$R^7$ is selected from cyclopropyl, wherein said cyclopropyl is substituted by 0 or 1 substituents selected from F, CN, OH or $SO_2CH_3$, NH-cyclopropyl, [dimethyl(oxo)-$\lambda^6$-sulfanylidene]amino, ($C_{1-4}$alkyl)sulfonimidoyl, $SO_2CH_3$, $OSO_2CH_3$, $C(CH_3)_2SO_2CH_3$, $SO_2NHCH_3$, $SO_2N(CH_3)_2$, morpholine-4-sulfonyl, 4-methylpiperazine-sulfonyl, morpholinyl, $CCCH_3$ and cyclobutyl, wherein said cyclobutyl is substituted by 0 or 1 OH;

$R^8$ is selected from $SO_2CH_3$ or heterocycloalkyl, wherein said heterocycloalkyl is substituted by 0, 1, 2, 3 or 4 substituents independently selected from F, Cl, $R^6$ and $OR^6$, and 0, 1 or 2 substituents independently selected from cyclopropyl, OH, $C(O)CH_2OH$, 4-methylpiperazinyl, $C(O)CH_3$ and $C(O)N(CH_3)_2$;

$R^9$ is selected from $OR^{10}$, $N(R^{10})_2$, $NR^{11}(CH_2)_2N(CH_3)_2$, —$(CH_2)_2$ (5- to 6-membered)heterocycloalkyl, wherein said (5- to 6-membered)heterocycloalkyl is substituted by 0 or 1 substituents selected from $R^{11}$, —$O(CH_2)_2$ (5- to 6-membered)heterocycloalkyl, wherein said (5- to 6-membered)heterocycloalkyl is substituted by 0 or 1 substituents selected from $R^{11}$ and azetinyl substituted by 0 or 1 substituents selected from $N(CH_3)_2$ and $C(O)CH_3$;

$R^{10}$ is independently selected from H and $C_{1-2}$alkyl, wherein said $C_{1-2}$alkyl is substituted by 0, 1, 2 or 3 substituents independently selected from F, CN, $NH_2$ and $OC_{1-2}$alkyl, wherein said $C_{1-2}$alkyl is substituted by 0, 1, 2 or 3 substituents independently selected from F and Cl; and $R^{11}$ is $C_{1-3}$alkyl, wherein said $C_{1-3}$alkyl is substituted by 0, 1, 2 or 3 F and 0 or 1 cyclopropyl;

or a pharmaceutically acceptable salt thereof.

In still a further embodiment, there is provided a compound of Formula (IA), (IA)

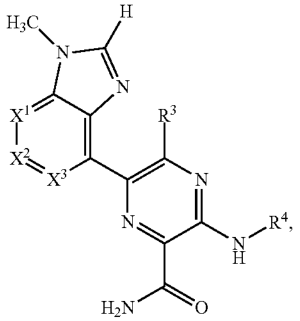

wherein $X^1$, $X^2$ and $X^3$ are $CR^5$;

$R^5$ is H;

$R^3$ is selected from $R^6$, $NHR^6$ and cyclopropyl;

$R^6$ is $C_{1-4}$alkyl, wherein said $C_{1-4}$alkyl is substituted by 0, 1, 2 or 3 F;

$R^4$ is selected from (5-membered)heteroaryl, wherein said (5-membered)heteroaryl is substituted by 0, 1 or 2 substituents independently selected from F, Cl and $R^6$, and 0 or 1 substituent selected from $NH_2$, CN, $OR^6$, $R^7$, $R^8$, $R^9$, $OR^8$, $OCH_2R^8$, $C(O)R^8$, $C(O)CH_3$, $C(O)NHCH_3$, $CH_2C(O)NHCH_3$, $C(CH_3)_2R^8$, $CH(CH_3)R^8$ and $CH_2R^8$;

$R^6$ is $C_{1-4}$alkyl, wherein said $C_{1-4}$alkyl is substituted by 0, 1, 2 or 3 F, $O(C_{1-2}$alkyl) and 0 or 1 substituents selected from OH, CN, $N(CH_3)_2$ and (4- to 5-membered)heterocycloalkyl containing one O;

$R^7$ is selected from cyclopropyl, wherein said cyclopropyl is substituted by 0 or 1 substituents selected from F, CN, OH or $SO_2CH_3$, NH-cyclopropyl, [dimethyl(oxo)-$\lambda^6$-sulfanylidene]amino, ($C_{1-4}$alkyl)sulfonimidoyl, $SO_2CH_3$, $OSO_2CH_3$, $C(CH_3)_2SO_2CH_3$, $SO_2NHCH_3$, $SO_2N(CH_3)_2$, morpholine-4-sulfonyl, 4-methylpiperazine-sulfonyl, morpholinyl, $CCCH_3$ and cyclobutyl, wherein said cyclobutyl is substituted by 0 or 1 OH;

$R^8$ is selected from $SO_2CH_3$ or heterocycloalkyl, wherein said heterocycloalkyl is substituted by 0, 1, 2, 3 or 4 substituents independently selected from F, Cl, $R^6$ and $OR^6$, and 0, 1 or 2 substituents independently selected from cyclopropyl, OH, $C(O)CH_2OH$, 4-methylpiperazinyl, $C(O)CH_3$ and $C(O)N(CH_3)_2$;

$R^9$ is selected from $OR^{10}$, $N(R^{10})_2$, $NR^{11}(CH_2)_2N(CH_3)_2$, —$(CH_2)_2$ (5- to 6-membered)heterocycloalkyl, wherein said (5- to 6-membered)heterocycloalkyl is substituted by 0 or 1 substituents selected from $R^{11}$, —$O(CH_2)_2$ (5- to 6-membered)heterocycloalkyl, wherein said (5- to 6-membered)heterocycloalkyl is substituted by 0 or 1 substituents selected from $R^{11}$ and azetinyl substituted by 0 or 1 substituents selected from $N(CH_3)_2$ and $C(O)CH_3$;

$R^{10}$ is independently selected from H and $C_{1-2}$alkyl, wherein said $C_{1-2}$alkyl is substituted by 0, 1, 2 or 3 substituents independently selected from F, CN, $NH_2$ and $OC_{1-2}$alkyl, wherein said $C_{1-2}$alkyl is substituted by 0, 1, 2 or 3 substituents independently selected from F and Cl; and $R^{11}$ is $C_{1-3}$alkyl, wherein said $C_{1-3}$alkyl is substituted by 0, 1, 2 or 3 F and 0 or 1 cyclopropyl;

or a pharmaceutically acceptable salt thereof.

In still a further embodiment, there is provided a compound of Formula (IA), (IA)

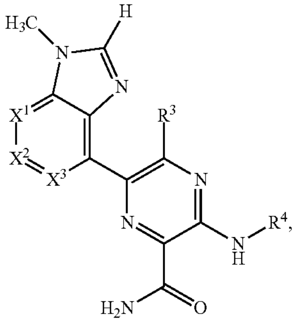

wherein $X^1$, $X^2$ and $X^3$ are $CR^5$;

$R^5$ is H;

$R^3$ is selected from $R^6$, $NHR^6$ and cyclopropyl;

$R^6$ is $C_{1-4}$alkyl, wherein said $C_{1-4}$alkyl is substituted by 0, 1, 2 or 3 F;

$R^4$ is selected from (5-membered)heteroaryl, wherein said (5-membered)heteroaryl is substituted by 0, 1 or 2 substituents independently selected from F, Cl and $R^6$, and 0 or 1 substituent selected from $OR^6$, $R^7$, $R^8$, $R^9$, $OR^8$, $OCH_2R^8$, $C(O)R^8$ and $CH_2R^8$;

$R^6$ is $C_{1-4}$alkyl, wherein said $C_{1-4}$alkyl is substituted by 0, 1, 2 or 3 F, $O(C_{1-2}$alkyl) and 0 or 1 substituents selected from OH, CN, $N(CH_3)_2$ and (4- to 5-membered)heterocycloalkyl containing one O;

$R^7$ is selected from cyclopropyl, wherein said cyclopropyl is substituted by 0 or 1 substituents selected from F, CN, OH or $SO_2CH_3$, NH-cyclopropyl, [dimethyl(oxo)-$\lambda^6$-sulfanylidene]amino, ($C_{1-4}$alkyl)sulfonimidoyl, $SO_2CH_3$, $OSO_2CH_3$, $C(CH_3)_2SO_2CH_3$, $SO_2NHCH_3$, $SO_2N(CH_3)_2$, morpholine-4-sulfonyl, 4-methylpiperazine-sulfonyl, morpholinyl, $CCCH_3$ and cyclobutyl, wherein said cyclobutyl is substituted by 0 or 1 OH;

$R^8$ is selected from $SO_2CH_3$ or heterocycloalkyl, wherein said heterocycloalkyl is substituted by 0, 1, 2, 3 or 4 substituents independently selected from F, Cl, $R^6$ and $OR^6$, and 0, 1 or 2 substituents independently selected from cyclopropyl, OH, $C(O)CH_2OH$, 4-methylpiperazinyl, $C(O)CH_3$ and $C(O)N(CH_3)_2$;

$R^9$ is selected from $OR^{10}$, $N(R^{10})_2$, $NR^{11}(CH_2)_2N(CH_3)_2$, $-(CH_2)_2$ (5- to 6-membered)heterocycloalkyl, wherein said (5- to 6-membered)heterocycloalkyl is substituted by 0 or 1 substituents selected from $R^{11}$, $-O(CH_2)_2$ (5- to 6-membered)heterocycloalkyl, wherein said (5- to 6-membered)heterocycloalkyl is substituted by 0 or 1 substituents selected from $R^{11}$ and azetinyl substituted by 0 or 1 substituents selected from $N(CH_3)_2$ and $C(O)CH_3$;

$R^{10}$ is independently selected from H and $C_{1-2}$alkyl, wherein said $C_{1-2}$alkyl is substituted by 0, 1, 2 or 3 substituents independently selected from F, CN, $NH_2$ and $OC_{1-2}$alkyl, wherein said $C_{1-2}$alkyl is substituted by 0, 1, 2 or 3 substituents independently selected from F and Cl; and $R^{11}$ is $C_{1-3}$alkyl, wherein said $C_{1-3}$alkyl is substituted by 0, 1, 2 or 3 F and 0 or 1 cyclopropyl;

or a pharmaceutically acceptable salt thereof.

In still a further embodiment, there is provided a compound of Formula (IA), (IA)

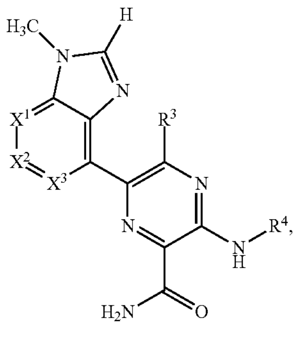

wherein $X^1$, $X^2$ and $X^3$ are $CR^5$;

$R^5$ is H;

$R^3$ is selected from $R^6$, $NHR^6$ and cyclopropyl;

$R^6$ is $C_{1-4}$alkyl, wherein said $C_{1-4}$alkyl is substituted by 0, 1, 2 or 3 F;

$R^4$ is selected from (5-membered)heteroaryl, wherein said (5-membered)heteroaryl is substituted by 0, 1 or 2 substituents independently selected from F, Cl and $R^6$, and 0 or 1 substituent selected from $R^8$ and $CH_2R^8$;

$R^6$ is $C_{1-4}$alkyl, wherein said $C_{1-4}$alkyl is substituted by 0, 1, 2 or 3 F, $O(C_{1-2}$alkyl) and 0 or 1 substituents selected from OH, CN, $N(CH_3)_2$ and (4- to 5-membered)heterocycloalkyl containing one O; and $R^8$ is selected from $SO_2CH_3$ or heterocycloalkyl, wherein said heterocycloalkyl is substituted by 0, 1, 2, 3 or 4 substituents independently selected from F, Cl, $R^6$ and $OR^6$, and 0, 1 or 2 substituents independently selected from cyclopropyl, OH, $C(O)CH_2OH$, 4-methylpiperazinyl, $C(O)CH_3$ and $C(O)N(CH_3)_2$;

or a pharmaceutically acceptable salt thereof.

In still a further embodiment, there is provided a compound of Formula (IA), (IA)

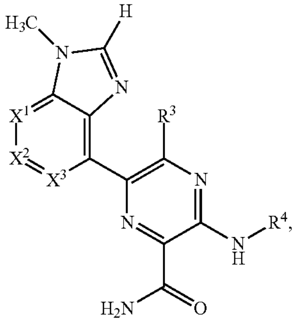

wherein $X^1$, $X^2$ and $X^3$ are $CR^5$;

$R^5$ is H;

$R^3$ is selected from $R^6$, $NHR^6$ and cyclopropyl;

$R^6$ is $C_{1-4}$alkyl, wherein said $C_{1-4}$alkyl is substituted by 0, 1, 2 or 3 F;

$R^4$ is selected from (5-membered)heteroaryl, wherein said (5-membered)heteroaryl is substituted by 0, 1 or 2 substituents independently selected from F, Cl and $R^6$, and 0 or 1 substituent selected from (5- to 8-membered) heterocycloalkyl and $CH_2$ (5- to 8-membered)heterocycloalkyl; and $R^6$ is $C_{1-4}$alkyl, wherein said $C_{1-4}$alkyl is substituted by 0, 1, 2 or 3 F, $O(C_{1-2}$alkyl) and 0 or 1 substituents selected from OH, CN, $N(CH_3)_2$ and (4- to 5-membered)heterocycloalkyl containing one O;

or a pharmaceutically acceptable salt thereof.

In still a further embodiment, there is provided a compound of Formula (IA), (IA)

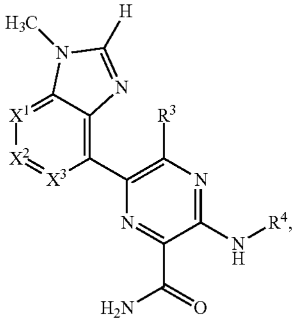

wherein $X^1$, $X^2$ and $X^3$ are $CR^5$;

$R^5$ is H;

$R^3$ is selected from $R^6$, $NHR^6$ and cyclopropyl;

$R^6$ is $C_{1-4}$alkyl, wherein said $C_{1-4}$alkyl is substituted by 0, 1, 2 or 3 F;

$R^4$ is selected from (5-membered)heteroaryl, wherein said (5-membered)heteroaryl is substituted by 0, 1 or 2 substituents independently selected from F, Cl and $R^6$, and 0 or 1 substituent selected from $R^7$;

$R^6$ is $C_{1-4}$alkyl, wherein said $C_{1-4}$alkyl is substituted by 0, 1, 2 or 3 F; and $R^7$ is selected from cyclopropyl, wherein said cyclopropyl is substituted by 0 or 1 substituents selected from F, CN, OH or $SO_2CH_3$;

or a pharmaceutically acceptable salt thereof.

In one embodiment, there is provided a compound of Formula (IB), (IB)

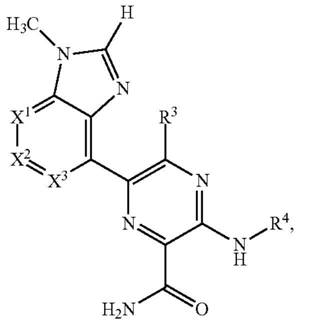

wherein $X^1$ and $X^3$ are independently selected from $CR^5$;

$R^5$ is independently selected from H, F, Cl and $C_{1-2}$alkyl, wherein said $C_{1-2}$alkyl is substituted by 0, 1, 2 or 3 substituents independently selected from F, CN, $NH_2$ and $OC_{1-2}$alkyl, wherein said $OC_{1-2}$alkyl is substituted by 0, 1, 2 or 3 substituents independently selected from F and Cl;

$R^3$ is selected from H, $R^6$, $OR^6$, $NHR^6$, Cl, CN, CCH, $NH_2$, $SCH_3$, cyclopropyl, cyclobutyl, NH((5- to 6-membered)heteroaryl containing 1 or 2 N), NH($C_{1-2}$alkyl)N$(CH_3)_2$, oxetan-3-yl, NH-cyclopropyl and O-cyclopropyl;

$R^6$ is $C_{1-4}$alkyl, wherein said $C_{1-4}$alkyl is substituted by 0, 1, 2 or 3 F, O($C_{1-2}$alkyl) and 0 or 1 substituents selected from OH, CN, N$(CH_3)_2$ and (4- to 5-membered)heterocycloalkyl containing one O;

$R^4$ is selected from aryl or heteroaryl, wherein said aryl or heteroaryl is substituted by 0, 1, 2, 3 or 4 substituents independently selected from F, Cl and $R^6$, and 0, 1 or 2 substituents independently selected from $NH_2$, CN, $OR^6$, $R^7$, $R^8$, $R^9$, $OR^8$, $OCH_2R^8$, C(O)$R^8$, C(O)$CH_3$, C(O)NH$CH_3$, $CH_2$C(O)NH$CH_3$, C$(CH_3)_2R^8$, CH$(CH_3)R^8$ and $CH_2R^8$;

$R^6$ is $C_{1-4}$alkyl, wherein said $C_{1-4}$alkyl is substituted by 0, 1, 2 or 3 F, O($C_{1-2}$alkyl) and 0 or 1 substituents selected from OH, CN, N$(CH_3)_2$ and (4- to 5-membered)heterocycloalkyl containing one O;

$R^7$ is selected from NH-cyclopropyl, [dimethyl(oxo)-$\lambda^6$-sulfanylidene]amino, ($C_{1-4}$alkyl)sulfonimidoyl, $SO_2CH_3$, $OSO_2CH_3$, C$(CH_3)_2SO_2CH_3$, $SO_2NHCH_3$, $SO_2N(CH_3)_2$, morpholine-4-sulfonyl, 4-methylpiperazine-sulfonyl, morpholinyl, $CCCH_3$, cyclopropyl, wherein said cyclopropyl is substituted by 0 or 1 substituents selected from F, CN, OH or $SO_2CH_3$, cyclobutyl, wherein said cyclobutyl is substituted by 0 or 1 OH, and imidazolyl, wherein said imidazolyl is substituted by 0 or 1 $R^{11}$;

$R^8$ is selected from $SO_2CH_3$ or heterocycloalkyl, wherein said heterocycloalkyl is substituted by 0, 1, 2, 3 or 4 substituents independently selected from F, Cl, $R^6$ and $OR^6$, and 0, 1 or 2 substituents independently selected from cyclopropyl, OH, C(O)$CH_2$OH, 4-methylpiperazinyl, C(O)$CH_3$ and C(O)N$(CH_3)_2$;

$R^9$ is selected from $OR^{10}$, N$(R^{10})_2$, $NR^{11}(CH_2)_2N(CH_3)_2$, —$(CH_2)_2$ (5- to 6-membered)heterocycloalkyl, wherein said (5- to 6-membered)heterocycloalkyl is substituted by 0 or 1 substituents selected from $R^{11}$, —O$(CH_2)_2$ (5- to 6-membered)heterocycloalkyl, wherein said (5- to 6-membered)heterocycloalkyl is substituted by 0 or 1 substituents selected from $R^{11}$ and azetinyl substituted by 0 or 1 substituents selected from N$(CH_3)_2$ and C(O)$CH_3$;

$R^{10}$ is independently selected from H and $C_{1-2}$alkyl, wherein said $C_{1-2}$alkyl is substituted by 0, 1, 2 or 3 substituents independently selected from F, CN, $NH_2$ and $OC_{1-2}$alkyl, wherein said $C_{1-2}$alkyl is substituted by 0, 1, 2 or 3 substituents independently selected from F and Cl; and $R^{11}$ is $C_{1-3}$alkyl, wherein said $C_{1-3}$alkyl is substituted by 0, 1, 2 or 3 F and 0 or 1 cyclopropyl;

or a pharmaceutically acceptable salt thereof.

In a further embodiment, there is provided a compound of Formula (IB), (IB)

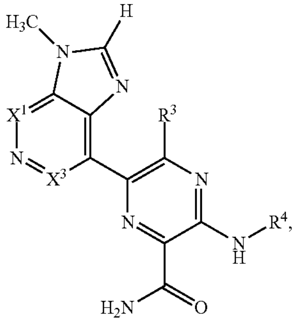

wherein $X^1$ and $X^3$ are independently selected from $CR^5$;

$R^5$ is H;

$R^3$ is selected from H, $R^6$, $OR^6$, $NHR^6$, Cl, CN, CCH, $NH_2$, $SCH_3$, cyclopropyl, cyclobutyl, NH((5- to 6-membered)heteroaryl containing 1 or 2 N), NH($C_{1-2}$ alkyl)N$(CH_3)_2$, oxetan-3-yl, NH-cyclopropyl and O-cyclopropyl;

$R^6$ is $C_{1-4}$alkyl, wherein said $C_{1-4}$alkyl is substituted by 0, 1, 2 or 3 F, O($C_{1-2}$alkyl) and 0 or 1 substituents selected from OH, CN, N$(CH_3)_2$ and (4- to 5-membered)heterocycloalkyl containing one O;

$R^4$ is selected from aryl or heteroaryl, wherein said aryl or heteroaryl is substituted by 0, 1, 2, 3 or 4 substituents independently selected from F, Cl and $R^6$, and 0, 1 or 2 substituents independently selected from $NH_2$, CN, $OR^6$, $R^7$, $R^8$, $R^9$, $OR^8$, $OCH_2R^8$, C(O)$R^8$, C(O)$CH_3$, C(O)NH$CH_3$, $CH_2$C(O)NH$CH_3$, C$(CH_3)_2R^8$, CH$(CH_3)R^8$ and $CH_2R^8$;

$R^6$ is $C_{1-4}$alkyl, wherein said $C_{1-4}$alkyl is substituted by 0, 1, 2 or 3 F, O($C_{1-2}$alkyl) and 0 or 1 substituents selected from OH, CN, N$(CH_3)_2$ and (4- to 5-membered)heterocycloalkyl containing one O;

$R^7$ is selected from cyclopropyl, wherein said cyclopropyl is substituted by 0 or 1 substituents selected from F, CN, OH or $SO_2CH_3$, NH-cyclopropyl, [dimethyl(oxo)-$\lambda^6$-sulfanylidene]amino, ($C_{1-4}$alkyl)sulfonimidoyl, $SO_2CH_3$, $OSO_2CH_3$, $C(CH_3)_2SO_2CH_3$, $SO_2NHCH_3$, $SO_2N(CH_3)_2$, morpholine-4-sulfonyl, 4-methylpiperazine-sulfonyl, morpholinyl, $CCCH_3$ and cyclobutyl, wherein said cyclobutyl is substituted by 0 or 1 OH;

$R^8$ is selected from $SO_2CH_3$ or heterocycloalkyl, wherein said heterocycloalkyl is substituted by 0, 1, 2, 3 or 4 substituents independently selected from F, Cl, $R^6$ and $OR^6$, and 0, 1 or 2 substituents independently selected from cyclopropyl, OH, $C(O)CH_2OH$, 4-methylpiperazinyl, $C(O)CH_3$ and $C(O)N(CH_3)_2$;

$R^9$ is selected from $OR^{10}$, $N(R^{10})_2$, $NR^{11}(CH_2)_2N(CH_3)_2$, —$(CH_2)_2$ (5- to 6-membered)heterocycloalkyl, wherein said (5- to 6-membered)heterocycloalkyl is substituted by 0 or 1 substituents selected from $R^{11}$, —$O(CH_2)_2$ (5- to 6-membered)heterocycloalkyl, wherein said (5- to 6-membered)heterocycloalkyl is substituted by 0 or 1 substituents selected from $R^{11}$ and azetinyl substituted by 0 or 1 substituents selected from $N(CH_3)_2$ and $C(O)CH_3$;

$R^{10}$ is independently selected from H and $C_{1-2}$alkyl, wherein said $C_{1-2}$alkyl is substituted by 0, 1, 2 or 3 substituents independently selected from F, CN, $NH_2$ and $OC_{1-2}$alkyl, wherein said $C_{1-2}$alkyl is substituted by 0, 1, 2 or 3 substituents independently selected from F and Cl; and $R^{11}$ is $C_{1-3}$alkyl, wherein said $C_{1-3}$alkyl is substituted by 0, 1, 2 or 3 F and 0 or 1 cyclopropyl;

or a pharmaceutically acceptable salt thereof.

In still a further embodiment, there is provided a compound of Formula (IB), (IB)

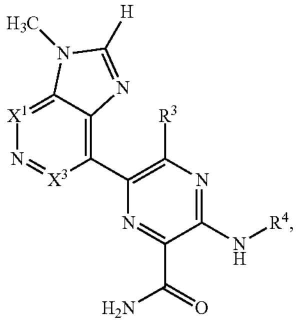

wherein $X^1$ and $X^3$ are independently selected from $CR^5$;

$R^5$ is H;

$R^3$ is selected from $R^6$, $NHR^6$ and cyclopropyl;

$R^6$ is $C_{1-4}$alkyl, wherein said $C_{1-4}$alkyl is substituted by 0, 1, 2 or 3 F;

$R^4$ is selected from aryl or heteroaryl, wherein said aryl or heteroaryl is substituted by 0, 1, 2, 3 or 4 substituents independently selected from F, Cl and $R^6$, and 0, 1 or 2 substituents independently selected from $NH_2$, CN, $OR^6$, $R^7$, $R^8$, $R^9$, $OR^8$, $OCH_2R^8$, $C(O)R^8$, $C(O)CH_3$, $C(O)NHCH_3$, $CH_2C(O)NHCH_3$, $C(CH_3)_2R^8$, $CH(CH_3)R^8$ and $CH_2R^8$;

$R^6$ is $C_{1-4}$alkyl, wherein said $C_{1-4}$alkyl is substituted by 0, 1, 2 or 3 F, $O(C_{1-2}$alkyl) and 0 or 1 substituents selected from OH, CN, $N(CH_3)_2$ and (4- to 5-membered)heterocycloalkyl containing one O;

$R^7$ is selected from cyclopropyl, wherein said cyclopropyl is substituted by 0 or 1 substituents selected from F, CN, OH or $SO_2CH_3$, NH-cyclopropyl, [dimethyl(oxo)-$\lambda^6$-sulfanylidene]amino, ($C_{1-4}$alkyl)sulfonimidoyl, $SO_2CH_3$, $OSO_2CH_3$, $C(CH_3)_2SO_2CH_3$, $SO_2NHCH_3$, $SO_2N(CH_3)_2$, morpholine-4-sulfonyl, 4-methylpiperazine-sulfonyl, morpholinyl, $CCCH_3$ and cyclobutyl, wherein said cyclobutyl is substituted by 0 or 1 OH;

$R^8$ is selected from $SO_2CH_3$ or heterocycloalkyl, wherein said heterocycloalkyl is substituted by 0, 1, 2, 3 or 4 substituents independently selected from F, Cl, $R^6$ and $OR^6$, and 0, 1 or 2 substituents independently selected from cyclopropyl, OH, $C(O)CH_2OH$, 4-methylpiperazinyl, $C(O)CH_3$ and $C(O)N(CH_3)_2$;

$R^9$ is selected from $OR^{10}$, $N(R^{10})_2$, $NR^{11}(CH_2)_2N(CH_3)_2$, —$(CH_2)_2$ (5- to 6-membered)heterocycloalkyl, wherein said (5- to 6-membered)heterocycloalkyl is substituted by 0 or 1 substituents selected from $R^{11}$, —$O(CH_2)_2$ (5- to 6-membered)heterocycloalkyl, wherein said (5- to 6-membered)heterocycloalkyl is substituted by 0 or 1 substituents selected from $R^{11}$ and azetinyl substituted by 0 or 1 substituents selected from $N(CH_3)_2$ and $C(O)CH_3$;

$R^{10}$ is independently selected from H and $C_{1-2}$alkyl, wherein said $C_{1-2}$alkyl is substituted by 0, 1, 2 or 3 substituents independently selected from F, CN, $NH_2$ and $OC_{1-2}$alkyl, wherein said $C_{1-2}$alkyl is substituted by 0, 1, 2 or 3 substituents independently selected from F and Cl; and $R^{11}$ is $C_{1-3}$alkyl, wherein said $C_{1-3}$alkyl is substituted by 0, 1, 2 or 3 F and 0 or 1 cyclopropyl;

or a pharmaceutically acceptable salt thereof.

In still a further embodiment, there is provided a compound of Formula (IB), (IB)

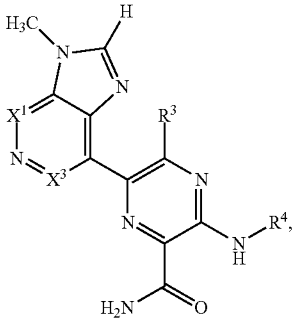

wherein $X^1$ and $X^3$ are independently selected from $CR^5$;

$R^5$ is H;

$R^3$ is selected from $R^6$, $NHR^6$ and cyclopropyl;

$R^6$ is $C_{1-4}$alkyl, wherein said $C_{1-4}$alkyl is substituted by 0, 1, 2 or 3 F;

$R^4$ is selected from aryl, wherein said aryl is substituted by 0 or 1 substituent selected from F, Cl and $R^6$, and 0, 1 or 2 substituents independently selected from $NH_2$, CN, $OR^6$, $R^7$, $R^8$, $R^9$, $OR^8$, $OCH_2R^8$, $C(O)R^8$, $C(O)CH_3$, $C(O)NHCH_3$, $CH_2C(O)NHCH_3$, $C(CH_3)_2R^8$, $CH(CH_3)R^8$ and $CH_2R^8$;

$R^6$ is $C_{1-4}$alkyl, wherein said $C_{1-4}$alkyl is substituted by 0, 1, 2 or 3 F, $O(C_{1-2}$alkyl) and 0 or 1 substituents selected from OH, CN, $N(CH_3)_2$ and (4- to 5-membered)heterocycloalkyl containing one O;

$R^7$ is selected from cyclopropyl, wherein said cyclopropyl is substituted by 0 or 1 substituents selected from F, CN, OH or $SO_2CH_3$, NH-cyclopropyl, [dimethyl(oxo)-$\lambda^6$-sulfanylidene]amino, ($C_{1-4}$alkyl)sulfonimidoyl, $SO_2CH_3$, $OSO_2CH_3$, $C(CH_3)_2SO_2CH_3$, $SO_2NHCH_3$, $SO_2N(CH_3)_2$, morpholine-4-sulfonyl, 4-methylpiperazine-sulfonyl, morpholinyl, $CCCH_3$ and cyclobutyl, wherein said cyclobutyl is substituted by 0 or 1 OH;

$R^8$ is selected from $SO_2CH_3$ or heterocycloalkyl, wherein said heterocycloalkyl is substituted by 0, 1, 2, 3 or 4 substituents independently selected from F, Cl, $R^6$ and $OR^6$, and 0, 1 or 2 substituents independently selected from cyclopropyl, OH, $C(O)CH_2OH$, 4-methylpiperazinyl, $C(O)CH_3$ and $C(O)N(CH_3)_2$;

$R^9$ is selected from $OR^{10}$, $N(R^{10})_2$, $NR^{11}(CH_2)_2N(CH_3)_2$, —$(CH_2)_2$ (5- to 6-membered)heterocycloalkyl, wherein said (5- to 6-membered)heterocycloalkyl is substituted by 0 or 1 substituents selected from $R^{11}$, —$O(CH_2)_2$ (5- to 6-membered)heterocycloalkyl, wherein said (5- to 6-membered)heterocycloalkyl is substituted by 0 or 1 substituents selected from $R^{11}$ and azetinyl substituted by 0 or 1 substituents selected from $N(CH_3)_2$ and $C(O)CH_3$;

$R^{10}$ is independently selected from H and $C_{1-2}$alkyl, wherein said $C_{1-2}$alkyl is substituted by 0, 1, 2 or 3 substituents independently selected from F, CN, $NH_2$ and $OC_{1-2}$alkyl, wherein said $C_{1-2}$alkyl is substituted by 0, 1, 2 or 3 substituents independently selected from F and Cl; and $R^{11}$ is $C_{1-3}$alkyl, wherein said $C_{1-3}$alkyl is substituted by 0, 1, 2 or 3 F and 0 or 1 cyclopropyl;

or a pharmaceutically acceptable salt thereof.

In still a further embodiment, there is provided a compound of Formula (IB),

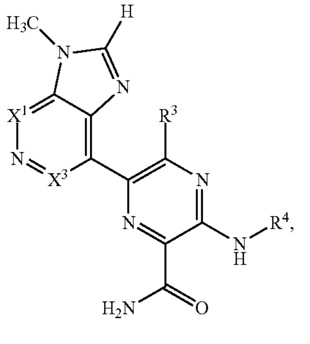

(IB)

wherein $X^1$ and $X^3$ are independently selected from $CR^5$;

$R^5$ is H;

$R^3$ is selected from $R^6$, $NHR^6$ and cyclopropyl;

$R^6$ is $C_{1-4}$alkyl, wherein said $C_{1-4}$alkyl is substituted by 0, 1, 2 or 3 F;

$R^4$ is selected from phenyl, wherein said phenyl is substituted by 0 or 1 substituent selected from F, Cl and $R^6$, and 0, 1 or 2 substituents independently selected from $NH_2$, CN, $OR^6$, $R^7$, $R^8$, $R^9$, $OR^8$, $OCH_2R^8$, $C(O)R^8$, $C(O)CH_3$, $C(O)NHCH_3$, $CH_2C(O)NHCH_3$, $C(CH_3)_2R^8$, $CH(CH_3)R^8$ and $CH_2R^8$;

$R^6$ is $C_{1-4}$alkyl, wherein said $C_{1-4}$alkyl is substituted by 0, 1, 2 or 3 F, $O(C_{1-2}$alkyl) and 0 or 1 substituents selected from OH, CN, $N(CH_3)_2$ and (4- to 5-membered)heterocycloalkyl containing one O;

$R^7$ is selected from cyclopropyl, wherein said cyclopropyl is substituted by 0 or 1 substituents selected from F, CN, OH or $SO_2CH_3$, NH-cyclopropyl, [dimethyl(oxo)-$\lambda^6$-sulfanylidene]amino, ($C_{1-4}$alkyl)sulfonimidoyl, $SO_2CH_3$, $OSO_2CH_3$, $C(CH_3)_2SO_2CH_3$, $SO_2NHCH_3$, $SO_2N(CH_3)_2$, morpholine-4-sulfonyl, 4-methylpiperazine-sulfonyl, morpholinyl, $CCCH_3$ and cyclobutyl, wherein said cyclobutyl is substituted by 0 or 1 OH;

$R^8$ is selected from $SO_2CH_3$ or heterocycloalkyl, wherein said heterocycloalkyl is substituted by 0, 1, 2, 3 or 4 substituents independently selected from F, Cl, $R^6$ and $OR^6$, and 0, 1 or 2 substituents independently selected from cyclopropyl, OH, $C(O)CH_2OH$, 4-methylpiperazinyl, $C(O)CH_3$ and $C(O)N(CH_3)_2$;

$R^9$ is selected from $OR^{10}$, $N(R^{10})_2$, $NR^{11}(CH_2)_2N(CH_3)_2$, —$(CH_2)_2$ (5- to 6-membered)heterocycloalkyl, wherein said (5- to 6-membered)heterocycloalkyl is substituted by 0 or 1 substituents selected from $R^{11}$, —$O(CH_2)_2$ (5- to 6-membered)heterocycloalkyl, wherein said (5- to 6-membered)heterocycloalkyl is substituted by 0 or 1 substituents selected from $R^{11}$ and azetinyl substituted by 0 or 1 substituents selected from $N(CH_3)_2$ and $C(O)CH_3$;

$R^{10}$ is independently selected from H and $C_{1-2}$alkyl, wherein said $C_{1-2}$alkyl is substituted by 0, 1, 2 or 3 substituents independently selected from F, CN, $NH_2$ and $OC_{1-2}$alkyl, wherein said $C_{1-2}$alkyl is substituted by 0, 1, 2 or 3 substituents independently selected from F and Cl; and $R^{11}$ is $C_{1-3}$alkyl, wherein said $C_{1-3}$alkyl is substituted by 0, 1, 2 or 3 F and 0 or 1 cyclopropyl;

or a pharmaceutically acceptable salt thereof.

In still a further embodiment, there is provided a compound of Formula (IB),

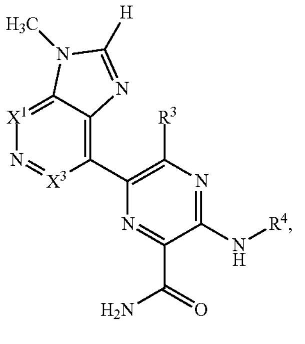

(IB)

wherein $X^1$ and $X^3$ are independently selected from $CR^5$;

$R^5$ is H;

$R^3$ is selected from $R^6$, $NHR^6$ and cyclopropyl;

$R^6$ is $C_{1-4}$alkyl, wherein said $C_{1-4}$alkyl is substituted by 0, 1, 2 or 3 F;

$R^4$ is selected from phenyl, wherein said phenyl is substituted by 0 or 1 substituent selected from F, Cl and $R^6$, and a substituent selected from morpholinyl, wherein said morpholinyl is substituted by 0, 1 or 2 substituents independently selected from F, Cl, $R^6$ and $OR^6$, and 0 or 1 substituent selected from cyclopropyl, $C(O)CH_3$ and $C(O)N(CH_3)_2$;

$R^6$ is $C_{1-4}$alkyl, wherein said $C_{1-4}$alkyl is substituted by 0, 1, 2 or 3 F, O($C_{1-2}$alkyl) and 0 or 1 substituents selected from OH, CN, $N(CH_3)_2$ and (4- to 5-membered)heterocycloalkyl containing one O;

or a pharmaceutically acceptable salt thereof.

In still a further embodiment, there is provided a compound of Formula (IB), (IB)

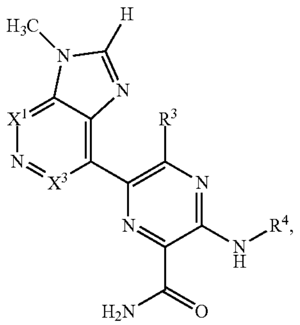

wherein $X^1$ and $X^3$ are independently selected from $CR^5$;

$R^5$ is H;

$R^3$ is selected from $R^6$, $NHR^6$ and cyclopropyl;

$R^6$ is $C_{1-4}$alkyl, wherein said $C_{1-4}$alkyl is substituted by 0, 1, 2 or 3 F;

$R^4$ is selected from phenyl, wherein said phenyl is substituted by 0 or 1 substituent selected from F, Cl and $R^6$, and a substituent selected from morpholinyl, wherein said morpholinyl is substituted by 0, 1 or 2 substituents independently selected from F, Cl, $R^6$ and $OR^6$, and 0 or 1 substituent selected from cyclopropyl, $C(O)CH_3$ and $C(O)N(CH_3)_2$;

$R^6$ is $C_{1-4}$alkyl, wherein said $C_{1-4}$alkyl is substituted by 0, 1, 2 or 3 F;

or a pharmaceutically acceptable salt thereof.

In still a further embodiment, there is provided a compound of Formula (IB), (IB)

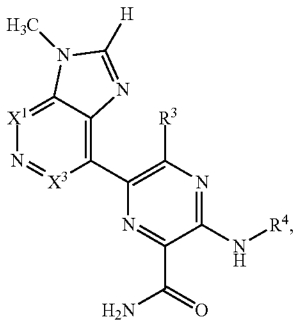

wherein $X^1$ and $X^3$ are independently selected from $CR^5$;

$R^5$ is H;

$R^3$ is selected from $R^6$, $NHR^6$ and cyclopropyl;

$R^6$ is $C_{1-4}$alkyl, wherein said $C_{1-4}$alkyl is substituted by 0, 1, 2 or 3 F;

$R^4$ is selected from (5-membered)heteroaryl, wherein said (5-membered)heteroaryl is substituted by 0, 1 or 2 substituents independently selected from F, Cl and $R^6$, and 0, 1 or 2 substituents independently selected from $NH_2$, CN, $OR^6$, $R^7$, $R^8$, $R^9$, $OR^8$, $OCH_2R^8$, $C(O)R^8$, $C(O)CH_3$, $C(O)NHCH_3$, $CH_2C(O)NHCH_3$, $C(CH_3)_2R^8$, $CH(CH_3)R^8$ and $CH_2R^8$;

$R^6$ is $C_{1-4}$alkyl, wherein said $C_{1-4}$alkyl is substituted by 0, 1, 2 or 3 F, O($C_{1-2}$alkyl) and 0 or 1 substituents selected from OH, CN, $N(CH_3)_2$ and (4- to 5-membered)heterocycloalkyl containing one O;

$R^7$ is selected from cyclopropyl, wherein said cyclopropyl is substituted by 0 or 1 substituents selected from F, CN, OH or $SO_2CH_3$, NH-cyclopropyl, [dimethyl(oxo)-$\lambda^6$-sulfanylidene]amino, ($C_{1-4}$alkyl)sulfonimidoyl, $SO_2CH_3$, $OSO_2CH_3$, $C(CH_3)_2SO_2CH_3$, $SO_2NHCH_3$, $SO_2N(CH_3)_2$, morpholine-4-sulfonyl, 4-methylpiperazine-sulfonyl, morpholinyl, $CCCH_3$ and cyclobutyl, wherein said cyclobutyl is substituted by 0 or 1 OH;

$R^8$ is selected from $SO_2CH_3$ or heterocycloalkyl, wherein said heterocycloalkyl is substituted by 0, 1, 2, 3 or 4 substituents independently selected from F, Cl, $R^6$ and $OR^6$, and 0, 1 or 2 substituents independently selected from cyclopropyl, OH, $C(O)CH_2OH$, 4-methylpiperazinyl, $C(O)CH_3$ and $C(O)N(CH_3)_2$;

$R^9$ is selected from $OR^{10}$, $N(R^{10})_2$, $NR^{11}(CH_2)_2N(CH_3)_2$, —$(CH_2)_2$ (5- to 6-membered)heterocycloalkyl, wherein said (5- to 6-membered)heterocycloalkyl is substituted by 0 or 1 substituents selected from $R^{11}$, —$O(CH_2)_2$ (5- to 6-membered)heterocycloalkyl, wherein said (5- to 6-membered)heterocycloalkyl is substituted by 0 or 1 substituents selected from $R^{11}$ and azetinyl substituted by 0 or 1 substituents selected from $N(CH_3)_2$ and $C(O)CH_3$;

$R^{10}$ is independently selected from H and $C_{1-2}$alkyl, wherein said $C_{1-2}$alkyl is substituted by 0, 1, 2 or 3 substituents independently selected from F, CN, $NH_2$ and $OC_{1-2}$alkyl, wherein said $C_{1-2}$alkyl is substituted by 0, 1, 2 or 3 substituents independently selected from F and Cl; and $R^{11}$ is $C_{1-3}$alkyl, wherein said $C_{1-3}$alkyl is substituted by 0, 1, 2 or 3 F and 0 or 1 cyclopropyl;

or a pharmaceutically acceptable salt thereof.

In still a further embodiment, there is provided a compound of Formula (IB), (IB)

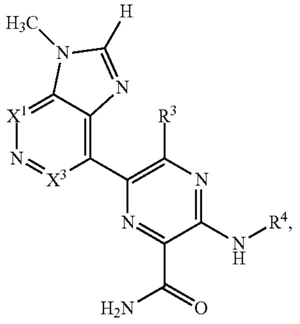

wherein $X^1$ and $X^3$ are independently selected from $CR^5$, $R^5$ is H;

$R^3$ is selected from $R^6$, $NHR^6$ and cyclopropyl;

$R^6$ is $C_{1-4}$alkyl, wherein said $C_{1-4}$alkyl is substituted by 0, 1, 2 or 3 F;

$R^4$ is selected from (5-membered)heteroaryl, wherein said (5-membered)heteroaryl is substituted by 0, 1 or 2 substituents independently selected from F, Cl and $R^6$, and 0 or 1 substituent selected from $NH_2$, CN, $OR^6$, $R^7$, $R^8$, $R^9$, $OR^8$, $OCH_2R^8$, $C(O)R^8$, $C(O)CH_3$, $C(O)NHCH_3$, $CH_2C(O)NHCH_3$, $C(CH_3)_2R^8$, $CH(CH_3)R^8$ and $CH_2R^8$;

$R^6$ is $C_{1-4}$alkyl, wherein said $C_{1-4}$alkyl is substituted by 0, 1, 2 or 3 F, $O(C_{1-2}alkyl)$ and 0 or 1 substituents selected from OH, CN, $N(CH_3)_2$ and (4- to 5-membered)heterocycloalkyl containing one O;

$R^7$ is selected from cyclopropyl, wherein said cyclopropyl is substituted by 0 or 1 substituents selected from F, CN, OH or $SO_2CH_3$, NH-cyclopropyl, [dimethyl(oxo)-$\lambda^6$-sulfanylidene]amino, ($C_{1-4}$alkyl)sulfonimidoyl, $SO_2CH_3$, $OSO_2CH_3$, $C(CH_3)_2SO_2CH_3$, $SO_2NHCH_3$, $SO_2N(CH_3)_2$, morpholine-4-sulfonyl, 4-methylpiperazine-sulfonyl, morpholinyl, $CCCH_3$ and cyclobutyl, wherein said cyclobutyl is substituted by 0 or 1 OH;

$R^8$ is selected from $SO_2CH_3$ or heterocycloalkyl, wherein said heterocycloalkyl is substituted by 0, 1, 2, 3 or 4 substituents independently selected from F, Cl, $R^6$ and $OR^6$, and 0, 1 or 2 substituents independently selected from cyclopropyl, OH, $C(O)CH_2OH$, 4-methylpiperazinyl, $C(O)CH_3$ and $C(O)N(CH_3)_2$;

$R^9$ is selected from $OR^{10}$, $N(R^{10})_2$, $NR^{11}(CH_2)_2N(CH_3)_2$, —$(CH_2)_2$ (5- to 6-membered)heterocycloalkyl, wherein said (5- to 6-membered)heterocycloalkyl is substituted by 0 or 1 substituents selected from $R^{11}$, —$O(CH_2)_2$ (5- to 6-membered)heterocycloalkyl, wherein said (5- to 6-membered)heterocycloalkyl is substituted by 0 or 1 substituents selected from $R^{11}$ and azetinyl substituted by 0 or 1 substituents selected from $N(CH_3)_2$ and $C(O)CH_3$;

$R^{10}$ is independently selected from H and $C_{1-2}$alkyl, wherein said $C_{1-2}$alkyl is substituted by 0, 1, 2 or 3 substituents independently selected from F, CN, $NH_2$ and $OC_{1-2}$alkyl, wherein said $C_{1-2}$alkyl is substituted by 0, 1, 2 or 3 substituents independently selected from F and Cl; and $R^{11}$ is $C_{1-3}$alkyl, wherein said $C_{1-3}$alkyl is substituted by 0, 1, 2 or 3 F and 0 or 1 cyclopropyl;

or a pharmaceutically acceptable salt thereof.

In still a further embodiment, there is provided a compound of Formula (IB), (IB)

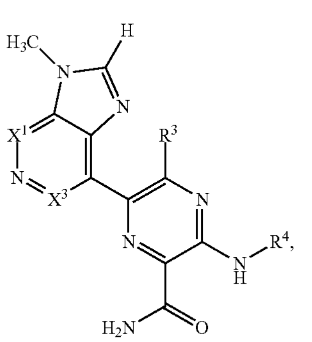

wherein $X^1$ and $X^3$ are independently selected from $CR^5$;

$R^5$ is H;

$R^3$ is selected from $R^6$, $NHR^6$ and cyclopropyl;

$R^6$ is $C_{1-4}$alkyl, wherein said $C_{1-4}$alkyl is substituted by 0, 1, 2 or 3 F;

$R^4$ is selected from (5-membered)heteroaryl, wherein said (5-membered)heteroaryl is substituted by 0, 1 or 2 substituents independently selected from F, Cl and $R^6$, and 0 or 1 substituent selected from $OR^6$, $R^7$, $R^8$, $R^9$, $OR^8$, $OCH_2R^8$, $C(O)R^8$ and $CH_2R^8$;

$R^6$ is $C_{1-4}$alkyl, wherein said $C_{1-4}$alkyl is substituted by 0, 1, 2 or 3 F, $O(C_{1-2}alkyl)$ and 0 or 1 substituents selected from OH, CN, $N(CH_3)_2$ and (4- to 5-membered)heterocycloalkyl containing one O;

$R^7$ is selected from cyclopropyl, wherein said cyclopropyl is substituted by 0 or 1 substituents selected from F, CN, OH or $SO_2CH_3$, NH-cyclopropyl, [dimethyl(oxo)-$\lambda^6$-sulfanylidene]amino, ($C_{1-4}$alkyl)sulfonimidoyl, $SO_2CH_3$, $OSO_2CH_3$, $C(CH_3)_2SO_2CH_3$, $SO_2NHCH_3$, $SO_2N(CH_3)_2$, morpholine-4-sulfonyl, 4-methylpiperazine-sulfonyl, morpholinyl, $CCCH_3$ and cyclobutyl, wherein said cyclobutyl is substituted by 0 or 1 OH;

$R^8$ is selected from $SO_2CH_3$ or heterocycloalkyl, wherein said heterocycloalkyl is substituted by 0, 1, 2, 3 or 4 substituents independently selected from F, Cl, $R^6$ and $OR^6$, and 0, 1 or 2 substituents independently selected from cyclopropyl, OH, $C(O)CH_2OH$, 4-methylpiperazinyl, $C(O)CH_3$ and $C(O)N(CH_3)_2$;

$R^9$ is selected from $OR^{10}$, $N(R^{10})_2$, $NR^{11}(CH_2)_2N(CH_3)_2$, —$(CH_2)_2$ (5- to 6-membered)heterocycloalkyl, wherein said (5- to 6-membered)heterocycloalkyl is substituted by 0 or 1 substituents selected from $R^{11}$, —$O(CH_2)_2$ (5- to 6-membered)heterocycloalkyl, wherein said (5- to 6-membered)heterocycloalkyl is substituted by 0 or 1 substituents selected from $R^{11}$ and azetinyl substituted by 0 or 1 substituents selected from $N(CH_3)_2$ and $C(O)CH_3$;

$R^{10}$ is independently selected from H and $C_{1-2}$alkyl, wherein said $C_{1-2}$alkyl is substituted by 0, 1, 2 or 3 substituents independently selected from F, CN, $NH_2$ and $OC_{1-2}$alkyl, wherein said $C_{1-2}$alkyl is substituted by 0, 1, 2 or 3 substituents independently selected from F and Cl; and $R^{11}$ is $C_{1-3}$alkyl, wherein said $C_{1-3}$alkyl is substituted by 0, 1, 2 or 3 F and 0 or 1 cyclopropyl;

or a pharmaceutically acceptable salt thereof.

In still a further embodiment, there is provided a compound of Formula (IB), (IB)

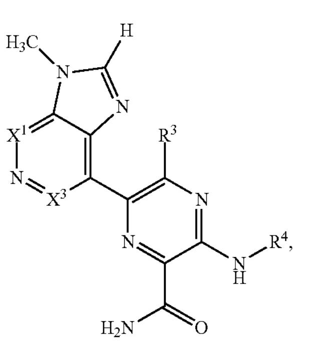

wherein $X^1$ and $X^3$ are independently selected from $CR^5$;

$R^5$ is H;

$R^3$ is selected from $R^6$, $NHR^6$ and cyclopropyl;

$R^6$ is $C_{1-4}$alkyl, wherein said $C_{1-4}$alkyl is substituted by 0, 1, 2 or 3 F;

$R^4$ is selected from (5-membered)heteroaryl, wherein said (5-membered)heteroaryl is substituted by 0, 1 or 2 substituents independently selected from F, Cl and $R^6$, and 0 or 1 substituent selected from $R^8$ and $CH_2R^8$;

$R^6$ is $C_{1-4}$alkyl, wherein said $C_{1-4}$alkyl is substituted by 0, 1, 2 or 3 F, $O(C_{1-2}$alkyl) and 0 or 1 substituents selected from OH, CN, $N(CH_3)_2$ and (4- to 5-membered)heterocycloalkyl containing one O; and $R^8$ is selected from $SO_2CH_3$ or heterocycloalkyl, wherein said heterocycloalkyl is substituted by 0, 1, 2, 3 or 4 substituents independently selected from F, Cl, $R^6$ and $OR^6$, and 0, 1 or 2 substituents independently selected from cyclopropyl, $C(O)CH_3$ and $C(O)N(CH_3)_2$; or a pharmaceutically acceptable salt thereof.

In still a further embodiment, there is provided a compound of Formula (IB), (IB)

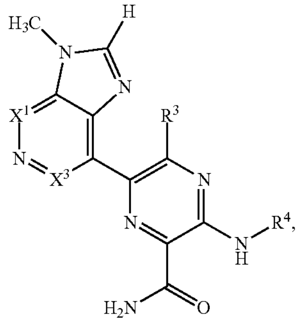

wherein $X^1$ and $X^3$ are independently selected from $CR^5$;

$R^5$ is H;

$R^3$ is selected from $R^6$, $NHR^6$ and cyclopropyl;

$R^6$ is $C_{1-4}$alkyl, wherein said $C_{1-4}$alkyl is substituted by 0, 1, 2 or 3 F;

$R^4$ is selected from (5-membered)heteroaryl, wherein said (5-membered)heteroaryl is substituted by 0, 1 or 2 substituents independently selected from F, Cl and $R^6$, and 0 or 1 substituent selected from (5- to 8-membered) heterocycloalkyl and $CH_2$ (5- to 8-membered)heterocycloalkyl; and $R^6$ is $C_{1-4}$alkyl, wherein said $C_{1-4}$alkyl is substituted by 0, 1, 2 or 3 F, $O(C_{1-2}$alkyl) and 0 or 1 substituents selected from OH, CN, $N(CH_3)_2$ and (4- to 5-membered)heterocycloalkyl containing one O;

or a pharmaceutically acceptable salt thereof.

In still a further embodiment, there is provided a compound of Formula (IB), (IB)

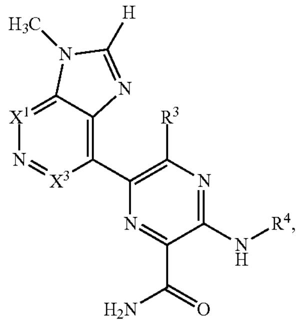

wherein $X^1$ and $X^3$ are independently selected from $CR^5$;

$R^5$ is H;

$R^3$ is selected from $R^6$, $NHR^6$ and cyclopropyl;

$R^6$ is $C_{1-4}$alkyl, wherein said $C_{1-4}$alkyl is substituted by 0, 1, 2 or 3 F;

$R^4$ is selected from (5-membered)heteroaryl, wherein said (5-membered)heteroaryl is substituted by 0, 1 or 2 substituents independently selected from F, Cl and $R^6$, and 0 or 1 substituent selected from $R^7$;

$R^6$ is $C_{1-4}$alkyl, wherein said $C_{1-4}$alkyl is substituted by 0, 1, 2 or 3 F; and $R^7$ is selected from cyclopropyl, wherein said cyclopropyl is substituted by 0 or 1 substituents selected from F, CN, OH or $SO_2CH_3$;

or a pharmaceutically acceptable salt thereof.

In one embodiment, there is provided a compound of Formula (IC), (IC)

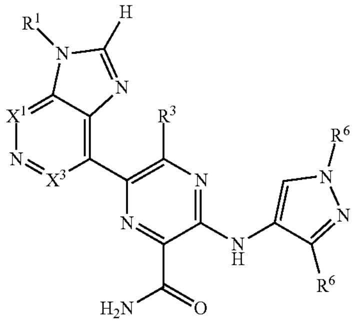

wherein $X^1$ and $X^3$ are independently selected from $CR^5$;

$R^5$ is independently selected from H, F, Cl and $C_{1-2}$alkyl, wherein said $C_{1-2}$alkyl is substituted by 0, 1, 2 or 3 substituents independently selected from F, CN, $NH_2$ and $OC_{1-2}$alkyl, wherein said $OC_{1-2}$alkyl is substituted by 0, 1, 2 or 3 substituents independently selected from F and Cl;

$R^1$ is cyclopropyl or $C_{1-3}$alkyl, wherein said $C_{1-3}$alkyl is substituted by 0, 1, 2 or 3 F;

$R^3$ is selected from H, $R^6$, $OR^6$, $NHR^6$, Cl, CN, CCH, $NH_2$, $SCH_3$, cyclopropyl, cyclobutyl, NH((5- to 6-membered)heteroaryl containing 1 or 2 N), $NH(C_{1-2}$ alkyl)$N(CH_3)_2$, oxetan-3-yl, NH-cyclopropyl and O-cyclopropyl;

$R^6$ is $C_{1-4}$alkyl, wherein said $C_{1-4}$alkyl is substituted by 0, 1, 2 or 3 F, $O(C_{1-2}$alkyl) and 0 or 1 substituents selected from OH, CN, $N(CH_3)_2$ and (4- to 5-membered)heterocycloalkyl containing one O;

or a pharmaceutically acceptable salt thereof.

In a further embodiment, there is provided a compound of Formula (IC), (IC)

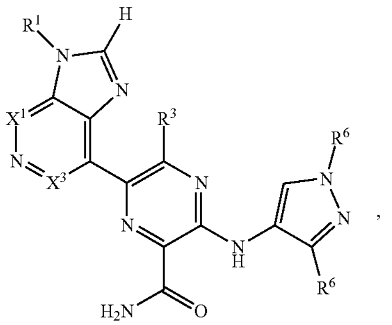

wherein $X^1$ and $X^3$ are independently selected from $CR^5$;

$R^5$ is independently selected from H, F, Cl and $C_{1-2}$alkyl, wherein said $C_{1-2}$alkyl is substituted by 0, 1, 2 or 3 substituents independently selected from F, CN, $NH_2$ and $OC_{1-2}$alkyl, wherein said $OC_{1-2}$alkyl is substituted by 0, 1, 2 or 3 substituents independently selected from F and Cl;

$R^1$ is $C_{1-3}$alkyl, wherein said $C_{1-3}$alkyl is substituted by 0, 1, 2 or 3 F;

$R^3$ is selected from H, $R^6$, $OR^6$, $NHR^6$, Cl, CN, CCH, $NH_2$, $SCH_3$, cyclopropyl, cyclobutyl, NH((5- to 6-membered)heteroaryl containing 1 or 2 N), NH($C_{1-2}$ alkyl)$N(CH_3)_2$, oxetan-3-yl, NH-cyclopropyl and O-cyclopropyl;

$R^6$ is $C_{1-4}$alkyl, wherein said $C_{1-4}$alkyl is substituted by 0, 1, 2 or 3 F, O($C_{1-2}$alkyl) and 0 or 1 substituents selected from OH, CN, $N(CH_3)_2$ and (4- to 5-membered)heterocycloalkyl containing one O;

or a pharmaceutically acceptable salt thereof.

In a further embodiment, there is provided a compound of Formula (IC), (IC)

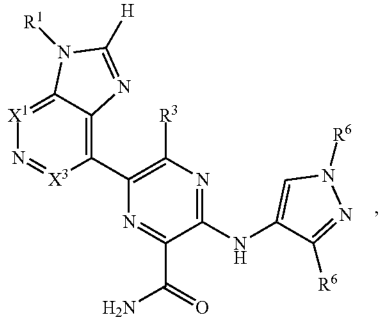

wherein $X^1$ and $X^3$ are independently selected from $CR^5$;

$R^5$ is H;

$R^1$ is $C_{1-3}$alkyl, wherein said $C_{1-3}$alkyl is substituted by 0, 1, 2 or 3 F;

$R^3$ is selected from $R^6$, $NHR^6$ and cyclopropyl;

$R^6$ is $C_{1-4}$alkyl, wherein said $C_{1-4}$alkyl is substituted by 0, 1, 2 or 3 F;

or a pharmaceutically acceptable salt thereof.

In still a further embodiment, there is provided a compound of Formula (IC), (IC)

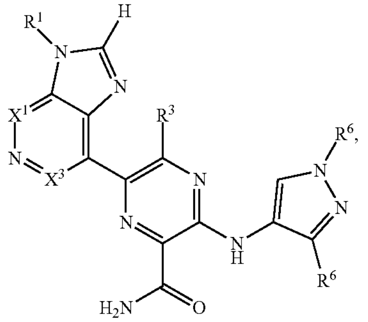

wherein $X^1$ and $X^3$ are independently selected from $CR^5$;

$R^5$ is H;

$R^1$ is $CH_3$;

$R^3$ is cyclopropyl;

$R^6$ is $C_{1-4}$alkyl, wherein said $C_{1-4}$alkyl is substituted by 0, 1, 2 or 3 F;

or a pharmaceutically acceptable salt thereof.

One or more above embodiments may be combined to provide further specific embodiments.

In one embodiment the compound of Formula (I) is selected from:

6-(1-Methylbenzimidazol-4-yl)-3-(4-morpholinoanilino)pyrazine-2-carboxamide,

5-Methyl-6-(1-methylbenzimidazol-4-yl)-3-(4-morpholinoanilino)pyrazine-2-carboxamide, 5-Methoxy-6-(1-methylbenzimidazol-4-yl)-3-(4-morpholinoanilino)pyrazine-2-carboxamide, 5-[2-(Dimethylamino)ethoxy]-6-(1-methylbenzimidazol-4-yl)-3-(4-morpholinoanilino)pyrazine-2-carboxamide, 5-Cyclopropyl-6-(1-methylbenzimidazol-4-yl)-3-(4-morpholinoanilino)pyrazine-2-carboxamide, 5-Methyl-6-(3-methylimidazo[4,5-c]pyridin-7-yl)-3-(4-morpholinoanilino)pyrazine-2-carboxamide, 5-(Methylamino)-6-(1-methylbenzimidazol-4-yl)-3-(4-morpholinoanilino)pyrazine-2-carboxamide, 5-(Methylamino)-6-(3-methylimidazo[4,5-c]pyridin-7-yl)-3-(4-morpholinoanilino)pyrazine-2-carboxamide, 6-(1-Methylbenzimidazol-4-yl)-5-methylsulfanyl-3-(4-morpholinoanilino)pyrazine-2-carboxamide, 5-(Ethylamino)-6-(1-methylbenzimidazol-4-yl)-3-(4-morpholinoanilino)pyrazine-2-carboxamide, 5-(Cyclopropylamino)-6-(1-methylbenzimidazol-4-yl)-3-(4-morpholinoanilino)pyrazine-2-carboxamide, 5-Amino-6-(1-methylbenzimidazol-4-yl)-3-(4-morpholinoanilino)pyrazine-2-carboxamide, 5-[[(2R)-2-Hydroxypropyl]amino]-6-(1-methylbenzimidazol-4-yl)-3-(4-morpholinoanilino)pyrazine-2-carboxamide, 5-[[(2S)-2-Hydroxypropyl]amino]-6-(1-methylbenzimidazol-4-yl)-3-(4-morpholinoanilino)pyrazine-2-carboxamide, 6-(1-Methylbenzimidazol-4-yl)-3-(4-morpholinoanilino)-5-(2,2,2-trifluoroethylamino)pyrazine-2-carboxamide, 5-(2,2-Difluoroethylamino)-6-(1-methylbenzimidazol-4-yl)-3-(4-morpholinoanilino)pyrazine-2-carboxamide, 5-[2-(Dimethylamino)ethylamino]-6-(1-methylbenzimidazol-4-yl)-3-(4-morpholinoanilino)pyrazine-2-carboxamide, 5-(2-Hydroxyethylamino)-6-(1-methylbenzimidazol-4-yl)-3-(4-morpholinoanilino)pyrazine-2-carboxamide, 6-(1-Methylbenzimidazol-4-yl)-3-(4-morpholinoanilino)-5-(prop-2-ynylamino)pyrazine-2-carboxamide, 6-(1-Methylbenzimidazol-4-yl)-3-(4-morpholinoanilino)-5-[[rel-(1R,2R)-2-methylcyclopropyl]amino]pyrazine-2-carboxamide, 6-(1-methylbenzimidazol-4-yl)-3-(4-morpholinoanilino)-5-[[rel-(1S,2S)-2-methylcyclopropyl]amino]pyrazine-2-carboxamide, 5-(Cyanomethylamino)-6-(1-methylbenzimidazol-4-yl)-3-(4-morpholinoanilino)pyrazine-2-carboxamide, 5-[[(2R)-2-Fluoropropyl]amino]-6-(1-methylbenzimidazol-4-yl)-3-(4-morpholinoanilino)pyrazine-2-carboxamide, 5-[[(2S)-2-Fluoropropyl]amino]-6-(1-methylbenzimidazol-4-yl)-3-(4-morpholinoanilino)pyrazine-2-carboxamide, 6-(1-Methylbenzimidazol-4-yl)-3-(4-morpholinoanilino)-5-(oxetan-3-ylmethylamino)pyrazine-2-carboxamide, 5-Ethynyl-6-(1-methylbenzimidazol-4-yl)-3-(4-morpholinoanilino)pyrazine-2-carboxamide, 5-(Difluoromethyl)-6-(1-methylbenzimidazol-4-yl)-3-(4-morpholinoanilino)pyrazine-2-carboxamide, 5-Chloro-6-(1-methylbenzimidazol-4-yl)-3-(4-morpholinoanilino)pyrazine-2-carboxamide, 6-(1-Methylbenzimidazol-4-yl)-5-[(1-methylpyrazol-4-yl)amino]-3-(4-morpholinoanilino)pyrazine-2-carboxamide, 6-(1-Methylbenzimidazol-4-yl)-3-(4-morpholinoanilino)-5-(2-pyridylamino)pyrazine-2-carboxamide, 6-(3-Methylimidazo[4,5-c]pyridin-7-yl)-3-(4-morpholinoanilino)-5-(oxetan-3-yl)pyrazine-2-carboxamide, 5-Ethoxy-6-(3-methylimidazo[4,5-c]pyridin-7-yl)-3-(4-morpholinoanilino)pyrazine-2-carboxamide, 6-(3-Methylimidazo[4,5-c]pyridin-7-yl)-3-(4-morpholinoanilino)-5-(trifluoromethyl)pyrazine-2-carboxamide, 6-(3-Methylimidazo[4,5-c]pyridin-7-yl)-5-methylsulfanyl-3-(4-morpholinoanilino)pyrazine-2-carboxamide, 5-[(1-Methylcyclopropyl)amino]-6-(3-methylimidazo[4,5-c]pyridin-7-yl)-3-(4-morpholinoanilino)pyrazine-2-carboxamide, 5-Cyano-6-(3-methylimidazo[4,5-c]pyridin-7-yl)-3-(4-morpholinoanilino)pyrazine-2-carboxamide, 5-(Cyclopropylamino)-6-(3-methylimidazo[4,5-c]pyridin-7-yl)-3-(4-morpholinoanilino)pyrazine-2-carboxamide, 5-Amino-6-(3-methylimidazo[4,5-c]pyridin-7-yl)-3-(4-morpholinoanilino)pyrazine-2-carboxamide, 6-(3-Methylimidazo[4,5-c]pyridin-7-yl)-3-(4-morpholinoanilino)pyrazine-2-carboxamide, 5-Methoxy-6-(3-methylimidazo[4,5-c]pyridin-7-yl)-3-(4-morpholinoanilino)pyrazine-2-carboxamide, 5-Cyclopropyl-6-(3-methylimidazo[4,5-c]pyridin-7-yl)-3-(4-morpholinoanilino)pyrazine-2-carboxamide, 5-(Difluoromethyl)-6-(3-methylimidazo[4,5-c]pyridin-7-yl)-3-(4-morpholinoanilino)pyrazine-2-carboxamide, 5-Methyl-6-(1-methylimidazo[4,5-d]pyridazin-4-yl)-3-(4-morpholinoanilino)pyrazine-2-carboxamide, 5-Methyl-6-(7-methylimidazo[4,5-c]pyridazin-4-yl)-3-(4-morpholinoanilino)pyrazine-2-carboxamide, 5-(Methylamino)-6-(7-methylimidazo[4,5-c]pyridazin-4-yl)-3-(4-morpholinoanilino)pyrazine-2-carboxamide, 6-(3-Ethylimidazo[4,5-c]pyridin-7-yl)-5-(methylamino)-3-(4-morpholinoanilino)pyrazine-2-carboxamide, 6-(3-Cyclopropylimidazo[4,5-c]pyridin-7-yl)-5-(methylamino)-3-(4-morpholinoanilino)pyrazine-2-carboxamide, 6-[3-(Difluoromethyl)imidazo[4,5-c]pyridin-7-yl]-5-(methylamino)-3-(4-morpholinoanilino)pyrazine-2-carboxamide, 6-(7-Chloro-1-methyl-benzimidazol-4-yl)-5-(methylamino)-3-(4-morpholinoanilino)pyrazine-2-carboxamide, 6-(7-Cyano-1-methyl-benzimidazol-4-yl)-5-(methylamino)-3-(4-morpholinoanilino)pyrazine-2-carboxamide, 6-(3,4-Dimethylimidazo[4,5-c]pyridin-7-yl)-5-(methylamino)-3-(4-morpholinoanilino)pyrazine-2-carboxamide, 3-(2-Fluoro-4-morpholino-anilino)-5-(methylamino)-6-(3-methylimidazo[4,5-c]pyridin-7-yl)pyrazine-2-carboxamide, 3-(2,3-Difluoro-4-morpholino-anilino)-5-(methylamino)-6-(3-methylimidazo[4,5-c]pyridin-7-yl)pyrazine-2-carboxamide, 3-(2-Fluoro-3-methyl-4-morpholino-anilino)-5-(methylamino)-6-(3-methylimidazo[4,5-c]pyridin-7-yl)pyrazine-2-carboxamide, 3-(3-Chloro-2-fluoro-4-morpholino-anilino)-5-(methylamino)-6-(3-methylimidazo[4,5-c]pyridin-7-yl)pyrazine-2-carboxamide, 5-(Methylamino)-6-(3-methylimidazo[4,5-c]pyridin-7-yl)-3-(2,3,5-trifluoro-4-morpholino-anilino)pyrazine-2-carboxamide, 3-(2-Fluoro-5-methyl-4-morpholino-anilino)-5-(methylamino)-6-(3-methylimidazo[4,5-c]pyridin-7-yl)pyrazine-2-carboxamide, 3-(3,5-Difluoro-4-morpholino-anilino)-5-(methylamino)-6-(3-methylimidazo[4,5-c]pyridin-7-yl)pyrazine-2-carboxamide, 3-(3-Chloro-4-morpholino-anilino)-5-(methylamino)-6-(1-methylbenzimidazol-4-yl)pyrazine-2-carboxamide, 3-(3-Chloro-4-morpholino-anilino)-5-(methylamino)-6-(3-methylimidazo[4,5-c]pyridin-7-yl)pyrazine-2-carboxamide, 5-(Methylamino)-6-(3-methylimidazo[4,5-c]pyridin-7-yl)-3-(3-methyl-4-morpholino-anilino)pyrazine-2-carboxamide, 3-(3,5-Dimethyl-4-morpholino-anilino)-5-(methylamino)-6-(3-methylimidazo[4,5-c]pyridin-7-yl)pyrazine-2-carboxamide, 3-(3-Cyano-4-morpholino-anilino)-5-(methylamino)-6-(3-methylimidazo[4,5-c]pyridin-7-yl)pyrazine-2-carboxamide, 3-(3-Methoxy-4-morpholino-anilino)-5-(methylamino)-6-(3-methylimidazo[4,5-c]pyridin-7-yl)pyrazine-2-carboxamide, 3-[3-(Difluoromethyl)-4-morpholino-anilino]-5-(methylamino)-6-(3-methylimidazo[4,5-c]pyridin-7-yl)pyrazine-2-carboxamide, 5-(Methylamino)-6-(3-methylimidazo[4,5-c]pyridin-7-yl)-3-(2-methyl-4-morpholino-anilino)pyrazine-2-carboxamide, 3-(2-Methoxy-4-morpholino-anilino)-5-(methylamino)-6-(3-methylimidazo[4,5-c]pyridin-7-yl)pyrazine-2-carboxamide, 3-(2-Chloro-4-morpholino-anilino)-5-(methylamino)-6-(3-methylimidazo[4,5-c]pyridin-7-yl)pyrazine-2-carboxamide, 5-(Methylamino)-6-(3-methylimidazo[4,5-c]pyridin-7-yl)-3-[(5-methyl-6-morpholino-3-pyridyl)amino]pyrazine-2-carboxamide, 5-(Methylamino)-6-(3-methylimidazo[4,5-c]pyridin-7-yl)-3-[[5-methyl-6-[(3S)-3-methylmorpholin-4-yl]-3-pyridyl]amino]pyrazine-2-carboxamide, 5-(Methylamino)-6-(3-methylimidazo[4,5-c]pyridin-7-yl)-3-[[5-methyl-6-[(2S)-2-methylmorpholin-4-yl]-3-pyridyl]amino]pyrazine-2-carboxamide, 5-Cyclopropyl-6-(3-methylimidazo[4,5-c]pyridin-7-yl)-3-[[6-[(3R)-3-methylmorpholin-4-yl]-3-pyridyl]amino]pyrazine-2-carboxamide, 3-[(5-Cyano-6-morpholino-3-pyridyl)amino]-5-(methylamino)-6-(3-methylimidazo[4,5-c]pyridin-7-yl)pyrazine-2-carboxamide, 3-((4-(1,4-Oxazepan-4-yl)phenyl)amino)-6-(3-methyl-3H-imidazo[4,5-c]pyridin-7-yl)-5-(methylamino)pyrazine-2-carboxamide, 5-(Methylamino)-6-(3-methylimidazo[4,5-c]pyridin-7-yl)-3-[[5-methyl-6-[(3R)-3-methylmorpholin-4-yl]-3-pyridyl]amino]pyrazine-2-carboxamide, 5-(Methylamino)-6-(3-methylimidazo[4,5-c]pyridin-7-yl)-3-[4-[(1R,4R)-2-oxa-5-azabicyclo[2.2.1]heptan-5-yl]anilino]pyrazine-2-carboxamide, 5-(Methylamino)-6-(3-methylimidazo[4,5-c]pyridin-7-yl)-3-[4-[(1S,4S)-2-oxa-5-azabicyclo[2.2.1]heptan-5-yl]anilino]pyrazine-2-carboxamide, 3-[2-Fluoro-4-[(1S,4S)-2-oxa-5-azabicyclo[2.2.1]heptan-5-yl]anilino]-5-(methylamino)-6-(3-methylimidazo[4,5-c]pyridin-7-yl)pyrazine-2-carboxamide, 3-[2,3-Difluoro-4-[(1S,4S)-2-oxa-5-azabicyclo[2.2.1]heptan-5-yl]anilino]-5-(methylamino)-6-(3-methylimidazo[4,5-c]pyridin-7-yl)pyrazine-2-carboxamide, 5-(Methylamino)-6-(3-methylimidazo[4,5-c]pyridin-7-yl)-3-[2,3,5-trifluoro-4-[(1S,4S)-2-oxa-5-azabicyclo[2.2.1]heptan-5-yl]anilino]pyrazine-2-carboxamide, 5-(Methylamino)-6-(3-methylimidazo[4,5-c]pyridin-7-yl)-3-[4-(6-oxa-3-azabicyclo[3.1.1]heptan-3-yl)anilino]pyrazine-2-carboxamide, 5-(Methylamino)-6-(3-methylimidazo[4,5-c]pyridin-7-yl)-3-[4-(8-oxa-3-azabicyclo[3.2.1]octan-3-yl)anilino]pyrazine-2-carboxamide, 5-(Methylamino)-6-(3-methylimidazo[4,5-c]pyridin-7-yl)-3-[4-(2-oxa-6-azaspiro[3.3]heptan-6-yl)anilino]pyrazine-2-carboxamide, 3-Anilino-5-(methylamino)-6-(3-methylimidazo[4,5-c]pyridin-7-yl)pyrazine-2-carboxamide, 3-[4-(Difluoromethoxy)anilino]-5-(methylamino)-6-(3-methylimidazo[4,5-c]pyridin-7-yl)pyrazine-2-carboxamide, 5-Cyclopropyl-3-[4-(1-hydroxy-1-methyl-ethyl)anilino]-6-(3-methylimidazo[4,5-c]pyridin-7-yl)pyrazine-2-carboxamide, 3-(4-Isopropoxyanilino)-5-(methylamino)-6-(3-methylimidazo[4,5-c]pyridin-7-yl)pyrazine-2-carboxamide,

[4-[[3-Carbamoyl-6-(methylamino)-5-(3-methylimidazo[4,5-c]pyridin-7-yl)pyrazin-2-yl]amino]phenyl]methanesulfonate, 3-[4-(2-Methoxyethoxy)anilino]-5-(methylamino)-6-(3-methylimidazo[4,5-c]pyridin-7-yl)pyrazine-2-carboxamide, 3-[4-[2-(Dimethylamino)ethoxy]anilino]-5-(methylamino)-6-(3-methylimidazo[4,5-c]pyridin-7-yl)pyrazine-2-carboxamide, 3-[4-(2-Hydroxyethoxy)anilino]-5-(methylamino)-6-(3-methylimidazo[4,5-c]pyridin-7-yl)pyrazine-2-carboxamide, 5-(Methylamino)-6-(3-methylimidazo[4,5-c]pyridin-7-yl)-3-[4-(2-morpholinoethoxy)anilino]pyrazine-2-carboxamide, 3-(4-Aminoanilino)-5-(methylamino)-6-(1-methylbenzimidazol-4-yl)pyrazine-2-carboxamide, 3-[4-[2-Methoxyethyl(methyl)amino]anilino]-5-(methylamino)-6-(3-methylimidazo[4,5-c]pyridin-7-yl)pyrazine-2-carboxamide, 3-[4-[Bis(2-methoxyethyl)amino]anilino]-5-(methylamino)-6-(3-methylimidazo[4,5-c]pyridin-7-yl)pyrazine-2-carboxamide, 5-(Methylamino)-6-(3-methylimidazo[4,5-c]pyridin-7-yl)-3-[(2-methyl-4-pyridyl)amino]pyrazine-2-carboxamide formate salt, 3-[(2-Methoxy-4-pyridyl)amino]-5-(methylamino)-6-(3-methylimidazo[4,5-c]pyridin-7-yl)pyrazine-2-carboxamide, 3-[(2-Methoxy-6-methyl-4-pyridyl)amino]-5-(methylamino)-6-(7-methylimidazo[4,5-c]pyridazin-4-yl)pyrazine-2-carboxamide hydrochloride, 3-[(2,6-Dimethyl-4-pyridyl)amino]-5-(methylamino)-6-(3-methylimidazo[4,5-c]pyridin-7-yl)pyrazine-2-carboxamide, 5-Cyclopropyl-3-[(2,6-dimethyl-4-pyridyl)amino]-6-(3-methylimidazo[4,5-c]pyridin-7-yl)pyrazine-2-carboxamide, 3-[(2-Methoxy-6-methyl-4-pyridyl)amino]-5-(methylamino)-6-(3-methylimidazo[4,5-c]pyridin-7-yl)pyrazine-2-carboxamide, 3-[[2-(2-Methoxyethoxy)-6-methyl-4-pyridyl]amino]-5-(methylamino)-6-(3-methylimidazo[4,5-c]pyridin-7-yl)pyrazine-2-carboxamide, 3-[(2-Cyano-6-methyl-4-pyridyl)amino]-5-(methylamino)-6-(3-methylimidazo[4,5-c]pyridin-7-yl)pyrazine-2-carboxamide, 3-[(1,5-Dimethyl-6-oxo-3-pyridyl)amino]-5-(methylamino)-6-(3-methylimidazo[4,5-c]pyridin-7-yl)pyrazine-2-carboxamide, 3-[[1-(Difluoromethyl)-6-oxo-3-pyridyl]amino]-5-(methylamino)-6-(3-methylimidazo[4,5-c]pyridin-7-yl)pyrazine-2-carboxamide, 5-(Methylamino)-3-[4-[(1R,4R)-5-methyl-2,5-diazabicyclo[2.2.1]heptan-2-yl]anilino]-6-(3-methylimidazo[4,5-c]pyridin-7-yl)pyrazine-2-carboxamide bis-formate salt, 5-(Methylamino)-3-[4-(8-methyl-3,8-diazabicyclo[3.2.1]octan-3-yl)anilino]-6-(3-methylimidazo[4,5-c]pyridin-7-yl)pyrazine-2-carboxamide, 3-[4-[(3 S,5R)-3,5-Dimethylpiperazin-1-yl]anilino]-6-(3-methylimidazo[4,5-c]pyridin-7-yl)-5-(trifluoromethyl)pyrazine-2-carboxamide, 3-[4-[(3 S,5R)-3,5-Dimethylpiperazin-1-yl]-3,5-difluoroanilino]-5-(methylamino)-6-(3-methylimidazo[4,5-c]pyridin-7-yl)pyrazine-2-carboxamide, 5-(Methylamino)-3-[4-(3-methyl-3,8-diazabicyclo[3.2.1]octan-8-yl)anilino]-6-(3-methylimidazo[4,5-c]pyridin-7-yl)pyrazine-2-carboxamide formate salt, 5-(Methylamino)-3-[4-[(1S,4S)-5-methyl-2,5-diazabicyclo[2.2.1]heptan-2-yl]anilino]-6-(3-methylimidazo[4,5-c]pyridin-7-yl)pyrazine-2-carboxamide, 3-[4-[(3 S,5R)-3,5-Dimethylpiperazin-1-yl]-3,5-dimethylanilino]-5-(methylamino)-6-(3-methylimidazo[4,5-c]pyridin-7-yl)pyrazine-2-carboxamide, 3-[4-[2-(Dimethylamino)ethyl-methyl-amino]anilino]-5-(methylamino)-6-(3-methylimidazo[4,5-c]pyridin-7-yl)pyrazine-2-carboxamide bis-formate salt, 3-[4-[3-(Dimethylamino)azetidin-1-yl]anilino]-5-(methylamino)-6-(3-methylimidazo[4,5-c]pyridin-7-yl)pyrazine-2-carboxamide bis-formate salt, 3-[3-Cyano-4-[(3 S,5R)-3,5-dimethylpiperazin-1-yl]anilino]-5-(methylamino)-6-(3-methylimidazo[4,5-c]pyridin-7-yl)pyrazine-2-carboxamide, 3-[2,3-Difluoro-4-[4-(4-methylpiperazin-1-yl)-1-piperidyl]anilino]-5-(methylamino)-6-(3-methylimidazo[4,5-c]pyridin-7-yl)pyrazine-2-carboxamide, 3-[[6-(4-Isopropylpiperazin-1-yl)-5-methyl-3-pyridyl]amino]-5-(methylamino)-6-(3-methylimidazo[4,5-c]pyridin-7-yl)pyrazine-2-carboxamide, 3-[[5-Methoxy-6-(4-methylpiperazin-1-yl)-3-pyridyl]amino]-5-(methylamino)-6-(3-methylimidazo[4,5-c]pyridin-7-yl)pyrazine-2-carboxamide, 5-(Methylamino)-6-(3-methylimidazo[4,5-c]pyridin-7-yl)-3-[[5-methyl-6-[(1R,4R)-5-methyl-2,5-diazabicyclo[2.2.1]heptan-2-yl]-3-pyridyl]amino]pyrazine-2-carboxamide, 3-[[5-Chloro-6-[(1R,4R)-5-methyl-2,5-diazabicyclo[2.2.1]heptan-2-yl]-3-pyridyl]amino]-5-(methylamino)-6-(3-methylimidazo[4,5-c]pyridin-7-yl)pyrazine-2-carboxamide, 5-(Methylamino)-3-[(6-methyl-5,7-dihydropyrrolo[3,4-b]pyridin-3-yl)amino]-6-(3-methylimidazo[4,5-c]pyridin-7-yl)pyrazine-2-carboxamide, 3-[(6-Ethyl-5,7-dihydropyrrolo[3,4-b]pyridin-3-yl)amino]-5-(methylamino)-6-(3-methylimidazo[4,5-c]pyridin-7-yl)pyrazine-2-carboxamide, 3-[(6-Isopropyl-5,7-dihydropyrrolo[3,4-b]pyridin-3-yl)amino]-5-(methylamino)-6-(3-methylimidazo[4,5-c]pyridin-7-yl)pyrazine-2-carboxamide formate salt, 3-[4-[(Dimethylamino)methyl]anilino]-5-(methylamino)-6-(3-methylimidazo[4,5-c]pyridin-7-yl)pyrazine-2-carboxamide, 5-(Methylamino)-6-(3-methylimidazo[4,5-c]pyridin-7-yl)-3-[4-(pyrrolidin-1-ylmethyl)anilino]pyrazine-2-carboxamide bis-formate salt, 5-(Methylamino)-6-(3-methylimidazo[4,5-c]pyridin-7-yl)-3-[4-(morpholinomethyl)anilino]pyrazine-2-carboxamide, 5-(Methylamino)-6-(3-methylimidazo[4,5-c]pyridin-7-yl)-3-[4-[(4-methylpiperazin-1-yl)methyl]anilino]pyrazine-2-carboxamide, 5-(Methylamino)-6-(3-methylimidazo[4,5-c]pyridin-7-yl)-3-[4-(2-oxa-6-azaspiro[3.3]heptan-6-ylmethyl)anilino]pyrazine-2-carboxamide, 5-(Methylamino)-6-(3-methylimidazo[4,5-c]pyridin-7-yl)-3-[4-[rel-(1R)-1-(4-methylpiperazin-1-yl)ethyl]anilino]pyrazine-2-carboxamide formate salt, 5-(Methylamino)-6-(3-methylimidazo[4,5-c]pyridin-7-yl)-3-[4-[rel-(1S)-1-(4-methylpiperazin-1-yl)ethyl]anilino]pyrazine-2-carboxamide formate salt, 5-(Methylamino)-6-(3-methylimidazo[4,5-c]pyridin-7-yl)-3-[4-[rel-(1R)-1-morpholinoethyl]anilino]pyrazine-2-carboxamide formate salt, 5-(Methylamino)-6-(3-methylimidazo[4,5-c]pyridin-7-yl)-3-[4-[rel-(1S)-1-morpholinoethyl]anilino]pyrazine-2-carboxamide formate salt, 5-(Methylamino)-6-(3-methylimidazo[4,5-c]pyridin-7-yl)-3-[4-[1-methyl-1-(4-methylpiperazin-1-yl)ethyl]anilino]pyrazine-2-carboxamide, 5-(Methylamino)-6-(3-methylimidazo[4,5-c]pyridin-7-yl)-3-[4-(1-methyl-1-morpholino-ethyl)anilino]pyrazine-2-carboxamide, (R)-3-((4-((3-Fluoropyrrolidin-1-yl)methyl)phenyl)amino)-6-(3-methyl-3H-imidazo[4,5-c]pyridin-7-yl)-5-(methylamino)pyrazine-2-carboxamide formate salt, 3-[4-[[(3 S)-3-Fluoropyrrolidin-1-yl]methyl]anilino]-5-(methylamino)-6-(3-methylimidazo[4,5-c]pyridin-7-yl)pyrazine-2-carboxamide formate salt, 3-[4-[(3,3-Difluoropyrrolidin-1-yl)methyl]anilino]-5-(methylamino)-6-(3-methylimidazo[4,5-c]pyridin-7-yl)pyrazine-2-carboxamide formate salt, 3-[4-[[(3 S)-3,4-Dimethylpiperazin-1-yl]methyl]anilino]-5-(methylamino)-6-(3-methylimidazo[4,5-c]pyridin-7-yl)pyrazine-2-carboxamide tris-formate salt, 3-[4-[[(3R)-3,4-dimethylpiperazin-1-yl]methyl]anilino]-5-(methylamino)-6-(3-methylimidazo[4,5-c]pyridin-7-yl)pyrazine-2-carboxamide formate salt, 5-(Methylamino)-6-(3-methylimidazo[4,5-c]pyridin-7-yl)-3-[[6-(morpholinomethyl)-3-pyridyl]amino]pyrazine-2-carboxamide formate salt, 3-[2-Fluoro-4-[(4-methylpiperazin-1-yl)methyl]anilino]-5-(methylamino)-6-(3-methylimidazo[4,5-c]pyridin-7-yl)pyrazine-2-carboxamide, 3-[3-Chloro-4-[(4-methylpiperazin-1-yl)methyl]anilino]-5-(methylamino)-6-(3-methylimidazo[4,5-c]pyridin-7-yl)pyrazine-2-carboxamide formate salt, 3-[2-Fluoro-4-(morpholinomethyl)anilino]-5-(methylamino)-6-(3-methylimidazo[4,5-c]pyridin-7-yl)pyrazine-2-carboxamide formate salt, 3-[2,3-Difluoro-4-(morpholinomethyl)anilino]-5-(methylamino)-6-(3-methylimidazo[4,5-c]pyridin-7-yl)pyrazine-2-carboxamide, 3-[2-Fluoro-4-[[(1S,4S)-2-oxa-5-azabicyclo[2.2.1]heptan-5-yl]methyl]anilino]-5-(methylamino)-6-(3-methylimidazo[4,5-c]pyridin-7-yl)pyrazine-2-carboxamide, 3-[2-Fluoro-4-[[(1S,4S)-2-oxa-5-azabicyclo[2.2.1]heptan-5-yl]methyl]anilino]-5-(methylamino)-6-(3-methylimidazo[4,5-c]pyridin-7-yl)pyrazine-2-carboxamide, 3-[2,3-Difluoro-4-[[(1R,4R)-2-oxa-5-azabicyclo[2.2.1]heptan-5-yl]methyl]anilino]-5-(methylamino)-6-(3-methylimidazo[4,5-c]pyridin-7-yl)pyrazine-2-carboxamide, 3-[2-Chloro-4-(2-oxa-6-azaspiro[3.3]heptan-6-ylmethyl)anilino]-5-(methylamino)-6-(3-methylimidazo[4,5-c]pyridin-7-yl)pyrazine-2-carboxamide formate salt, 5-(Methylamino)-6-(3-methylimidazo[4,5-c]pyridin-7-yl)-3-[4-(2-morpholinoethyl)anilino]pyrazine-2-carboxamide, 5-(Methylamino)-6-(3-methylimidazo[4,5-c]pyridin-7-yl)-3-[4-[2-(4-methylpiperazin-1-yl)ethyl]anilino]pyrazine-2-carboxamide, 5-Cyclopropyl-6-(3-methylimidazo[4,5-c]pyridin-7-yl)-3-[4-(pyrrolidin-1-ylmethyl)anilino]pyrazine-2-carboxamide, 5-Cyclopropyl-6-(3-methylimidazo[4,5-c]pyridin-7-yl)-3-[4-[(4-methylpiperazin-1-yl)methyl]anilino]pyrazine-2-carboxamide, 5-Methoxy-6-(3-methylimidazo[4,5-c]pyridin-7-yl)-3-[4-[(4-methylpiperazin-1-yl)methyl]anilino]pyrazine-2-carboxamide, 5-(Difluoromethyl)-6-(3-methylimidazo[4,5-c]pyridin-7-yl)-3-[4-[(4-methylpiperazin-1-yl)methyl]anilino]pyrazine-2-carboxamide, 5-(Difluoromethyl)-6-(3-methylimidazo[4,5-c]pyridin-7-yl)-3-[4-(morpholinomethyl)anilino]pyrazine-2-carboxamide, 3-[2-Fluoro-4-(morpholinomethyl)anilino]-5-methoxy-6-(3-methylimidazo[4,5-c]pyridin-7-yl)pyrazine-2-carboxamide, 3-[2,3-Difluoro-4-(morpholinomethyl)anilino]-5-methoxy-6-(3-methylimidazo[4,5-c]pyridin-7-yl)pyrazine-2-carboxamide, 5-Methyl-6-(1-methylbenzimidazol-4-yl)-3-[4-[rel-(3S)-4-methylmorpholin-3-yl]anilino]pyrazine-2-carboxamide, 5-Methyl-6-(1-methylbenzimidazol-4-yl)-3-[4-[rel-(3R)-4-methylmorpholin-3-yl]anilino]pyrazine-2-carboxamide, 5-Methyl-6-(1-methylbenzimidazol-4-yl)-3-[4-[rel-(2R)-4-methylmorpholin-2-yl]anilino]pyrazine-2-carboxamide, 5-Methyl-6-(1-methylbenzimidazol-4-yl)-3-[4-[rel-(2S)-4-methylmorpholin-2-yl]anilino]pyrazine-2-carboxamide, 5-(Methylamino)-6-(3-methylimidazo[4,5-c]pyridin-7-yl)-3-[4-(4-piperidyloxy)anilino]pyrazine-2-carboxamide, 3-[4-[(1-Acetyl-4-piperidyl)oxy]anilino]-5-(methylamino)-6-(3-methylimidazo[4,5-c]pyridin-7-yl)pyrazine-2-carboxamide, 5-(Methylamino)-6-(3-methylimidazo[4,5-c]pyridin-7-yl)-3-[4-[(1-methyl-4-piperidyl)oxy]anilino]pyrazine-2-carboxamide, 3-[4-[[1-(2-Hydroxyacetyl)-4-piperidyl]oxy]anilino]-5-(methylamino)-6-(3-methylimidazo[4,5-c]pyridin-7-yl)pyrazine-2-carboxamide, 5-Methoxy-6-(3-methylimidazo[4,5-c]pyridin-7-yl)-3-[4-[(1-methyl-4-piperidyl)oxy]anilino]pyrazine-2-carboxamide, 5-Cyclopropyl-6-(3-methylimidazo[4,5-c]pyridin-7-yl)-3-[4-[(1-methyl-4-piperidyl)oxy]anilino]pyrazine-2-carboxamide, 3-[3,5-Difluoro-4-[(1-methyl-4-piperidyl)oxy]anilino]-5-(methylamino)-6-(3-methylimidazo[4,5-c]pyridin-7-yl)pyrazine-2-carboxamide, 3-[4-[(1-Isopropyl-4-piperidyl)oxy]anilino]-5-(methylamino)-6-(3-methylimidazo[4,5-c]pyridin-7-yl)pyrazine-2-carboxamide formate salt, 3-[4-[[(2S,4R)-4-Hydroxy-1-methyl-pyrrolidin-2-yl]methoxy]anilino]-5-methyl-6-(1-methylbenzimidazol-4-yl)pyrazine-2-carboxamide, 3-[4-[[(2R,4S)-4-Hydroxy-1-methyl-pyrrolidin-2-yl]methoxy]anilino]-5-methyl-6-(1-methylbenzimidazol-4-yl)pyrazine-2-carboxamide, 3-[4-[[(2R,4S)-4-Methoxy-1-methyl-pyrrolidin-2-yl]methoxy]anilino]-5-methyl-6-(1-methylbenzimidazol-4-yl)pyrazine-2-carboxamide, 3-[4-[[(2S,4R)-4-Methoxy-1-methyl-pyrrolidin-2-yl]methoxy]anilino]-5-methyl-6-(1-methylbenzimidazol-4-yl)pyrazine-2-carboxamide, 5-(Methylamino)-6-(3-methylimidazo[4,5-c]pyridin-7-yl)-3-[3-(4-methylpiperazin-1-yl)anilino]pyrazine-2-carboxamide, 5-(Methylamino)-6-(3-methylimidazo[4,5-c]pyridin-7-yl)-3-[3-(1-methyl-4-piperidyl)anilino]pyrazine-2-carboxamide formate salt, 5-(Methylamino)-6-(3-methylimidazo[4,5-c]pyridin-7-yl)-3-[4-(4-methylimidazol-1-yl)anilino]pyrazine-2-carboxamide, 5-(Methylamino)-6-(3-methylimidazo[4,5-c]pyridin-7-yl)-3-([1,2,4]triazolo[4,3-a]pyridin-6-ylamino)pyrazine-2-carboxamide, 3-[4-(1-Hydroxy-1-methyl-ethyl)anilino]-5-(methylamino)-6-(3-methylimidazo[4,5-c]pyridin-7-yl)pyrazine-2-carboxamide, 5-Cyclopropyl-3-[[6-(1-hydroxy-1-methyl-ethyl)-3-pyridyl]amino]-6-(3-methylimidazo[4,5-c]pyridin-7-yl)pyrazine-2-carboxamide, 3-[(2-Imino-2-oxo-1,3-dihydro-2-benzothiophen-5-yl)amino]-5-methyl-6-(1-methylbenzimidazol-4-yl)pyrazine-2-carboxamide, rel-(R)-3-[4-(Ethylsulfonimidoyl)-3,5-dimethyl-anilino]-5-methyl-6-(1-methylbenzimidazol-4-yl)pyrazine-2-carboxamide, rel-(S)-3-[4-(Ethylsulfonimidoyl)-3,5-dimethyl-anilino]-5-methyl-6-(1-methylbenzimidazol-4-yl)pyrazine-2-carboxamide, 3-[(2,2-Dioxo-1,3-dihydro-2-benzothiophen-5-yl)amino]-5-(methylamino)-6-(3-methylimidazo[4,5-c]pyridin-7-yl)pyrazine-2-carboxamide, 5-(Methylamino)-3-[(1-methyl-2,2-dioxo-3H-2,1-benzothiazol-5-yl)amino]-6-(3-methylimidazo[4,5-c]pyridin-7-yl)pyrazine-2-carboxamide, 5-Cyclopropyl-3-[(1-methyl-2,2-dioxo-3H-2,1-benzothiazol-5-yl)amino]-6-(3-methylimidazo[4,5-c]pyridin-7-yl)pyrazine-2-carboxamide, 5-Methoxy-3-[(1-methyl-2,2-dioxo-3H-2,1-benzothiazol-5-yl)amino]-6-(3-methylimidazo[4,5-c]pyridin-7-yl)pyrazine-2-carboxamide, 3-[4-(1,1-Dioxo-1,4-thiazinan-4-yl)anilino]-5-(methylamino)-6-(3-methylimidazo[4,5-c]pyridin-7-yl)pyrazine-2-carboxamide, 3-[4-[[Dimethyl(oxo)-$\lambda^6$-sulfanylidene]amino]anilino]-5-(methylamino)-6-(3-methylimidazo[4,5-c]pyridin-7-yl)pyrazine-2-carboxamide, 3-[4-[[Dimethyl(oxo)-$\lambda^6$-sulfanylidene]amino]-2-fluoro-anilino]-5-(methylamino)-6-(3-methylimidazo[4,5-c]pyridin-7-yl)pyrazine-2-carboxamide, 3-[4-[[Dimethyl(oxo)-$\lambda^6$-sulfanylidene]amino]-2,3-difluoro-anilino]-5-(methylamino)-6-(3-methylimidazo[4,5-c]pyridin-7-yl)pyrazine-2-carboxamide formate salt, 3-[4-(1,1-Dioxo-1,2-thiazolidin-2-yl)anilino]-5-(methylamino)-6-(3-methylimidazo[4,5-c]pyridin-7-yl)pyrazine-2-carboxamide, 3-[4-(1,1-Dioxothiazinan-2-yl)anilino]-5-(methylamino)-6-(3-methylimidazo[4,5-c]pyridin-7-yl)pyrazine-2-carboxamide, 3-(2-Fluoro-4-methylsulfonyl-anilino)-5-(methylamino)-6-(3-methylimidazo[4,5-c]pyridin-7-yl)pyrazine-2-carboxamide, (R)-3-[4-(Ethylsulfonimidoyl)anilino]-5-(methylamino)-6-(3-methylimidazo[4,5-c]pyridin-7-yl)pyrazine-2-carboxamide, (S)-3-[4-(Ethylsulfonimidoyl)anilino]-5-(methylamino)-6-(3-methylimidazo[4,5-c]pyridin-7-yl)pyrazine-2-carboxamide, rel-(R)-3-[4-(Isopropylsulfonimidoyl)anilino]-5-(methylamino)-6-(3-methylimidazo[4,5-c]pyridin-7-yl)pyrazine-2-carboxamide, rel-(S)-3-[4-(Isopropylsulfonimidoyl)anilino]-5-(methylamino)-6-(3-methylimidazo[4,5-c]pyridin-7-yl)pyrazine-2-carboxamide, 3-[4-(tert-Butylsulfonimidoyl)anilino]-5-(methylamino)-6-(3-methylimidazo[4,5-c]pyridin-7-yl)pyrazine-2-carboxamide, 5-(Methylamino)-6-(3-methylimidazo[4,5-c]pyridin-7-yl)-3-[4-(1-methylsulfonylcyclopropyl)anilino]pyrazine-2-carboxamide, 5-Methoxy-6-(3-methylimidazo[4,5-c]pyridin-7-yl)-3-[4-(1-methylsulfonylcyclopropyl)anilino]pyrazine-2-carboxamide, 5-Methoxy-6-(3-methylimidazo[4,5-c]pyridin-7-yl)-3-[(1-methylpyrazol-4-yl)amino]pyrazine-2-carboxamide, 5-(Methylamino)-6-(3-methylimidazo[4,5-c]pyridin-7-yl)-3-[(1-tetrahydropyran-4-ylpyrazol-4-yl)amino]pyrazine-2-carboxamide, 3-[(1-Isopropylpyrazol-4-yl)amino]-5-(methylamino)-6-(3-methylimidazo[4,5-c]pyridin-7-yl)pyrazine-2-carboxamide, 3-[[1-(1,1-Dioxothian-4-yl)pyrazol-4-yl]amino]-5-(methylamino)-6-(3-methylimidazo[4,5-c]pyridin-7-yl)pyrazine-2-carboxamide, 5-(Methylamino)-6-(3-methylimidazo[4,5-c]pyridin-7-yl)-3-[[1-(1-methyl-4-piperidyl)pyrazol-4-yl]amino]pyrazine-2-carboxamide, 5-(Methylamino)-6-(1-methylbenzimidazol-4-yl)-3-[[3-methyl-1-(1-methyl-4-piperidyl)pyrazol-4-yl]amino]pyrazine-2-carboxamide formate salt, 3-[(1,3-Dimethylpyrazol-4-yl)amino]-5-(methylamino)-6-(3-methylimidazo[4,5-c]pyridin-7-yl)pyrazine-2-carboxamide, 5-(Methylamino)-6-(3-methylimidazo[4,5-c]pyridin-7-yl)-3-[[3-methyl-1-(2,2,2-trifluoroethyl)pyrazol-4-yl]amino]pyrazine-2-carboxamide, 3-[[1-(2,2-Difluoroethyl)-3-methyl-pyrazol-4-yl]amino]-5-(methylamino)-6-(3-methylimidazo[4,5-c]pyridin-7-yl)pyrazine-2-carboxamide, 3-[[1-(2,2-Difluoroethyl)-5-methyl-pyrazol-4-yl]amino]-5-(methylamino)-6-(3-methylimidazo[4,5-c]pyridin-7-yl)pyrazine-2-carboxamide, 3-[[1-(1-Cyano-1-methyl-ethyl)-3-methyl-pyrazol-4-yl]amino]-5-(methylamino)-6-(3-methylimidazo[4,5-c]pyridin-7-yl)pyrazine-2-carboxamide, 5-Cyclopropyl-3-[(1,3-dimethylpyrazol-4-yl)amino]-6-(3-methylimidazo[4,5-c]pyridin-7-yl)pyrazine-2-carboxamide, 5-Cyclopropyl-6-(3-methylimidazo[4,5-c]pyridin-7-yl)-3-[[3-methyl-1-(2,2,2-trifluoroethyl)pyrazol-4-yl]amino]pyrazine-2-carboxamide, 5-Cyclopropyl-6-(3-methylimidazo[4,5-c]pyridin-7-yl)-3-[[5-methyl-1-(2,2,2-trifluoroethyl)pyrazol-4-yl]amino]pyrazine-2-carboxamide, 5-Cyclopropyl-3-[[1-(2,2-difluoroethyl)-3-methyl-pyrazol-4-yl]amino]-6-(3-methylimidazo[4,5-c]pyridin-7-yl)pyrazine-2-carboxamide, 3-[[1-(1-Cyano-1-methyl-ethyl)-3-methyl-pyrazol-4-yl]amino]-5-cyclopropyl-6-(3-methylimidazo[4,5-c]pyridin-7-yl)pyrazine-2-carboxamide, 3-[[1-(1-Cyanocyclopropyl)-3-methyl-pyrazol-4-yl]amino]-5-cyclopropyl-6-(3-methylimidazo[4,5-c]pyridin-7-yl)pyrazine-2-carboxamide, 5-Cyclopropyl-3-[(1,5-dimethylpyrazol-4-yl)amino]-6-(3-methylimidazo[4,5-c]pyridin-7-yl)pyrazine-2-carboxamide, 5-Cyclopropyl-6-(3-methylimidazo[4,5-c]pyridin-7-yl)-3-[(3-methyl-1H-pyrazol-4-yl)amino]pyrazine-2-carboxamide, 5-Cyclopropyl-6-(3-methylimidazo[4,5-c]pyridin-7-yl)-3-[[3-methyl-1-[rel-(2R)-2,3-difluoropropyl]pyrazol-4-yl]amino]pyrazine-2-carboxamide, 5-Cyclopropyl-6-(3-methylimidazo[4,5-c]pyridin-7-yl)-3-[[3-methyl-1-[rel-(2S)-2,3-difluoropropyl]pyrazol-4-yl]amino]pyrazine-2-carboxamide, 5-Cyclopropyl-6-(3-methylimidazo[4,5-c]pyridin-7-yl)-3-[[5-methyl-1-[rel-(2R)-2,3-difluoropropyl]pyrazol-4-yl]amino]pyrazine-2-carboxamide, 5-Cyclopropyl-6-(3-methylimidazo[4,5-c]pyridin-7-yl)-3-[[5-methyl-1-[rel-(2S)-2,3-difluoropropyl]pyrazol-4-yl]amino]pyrazine-2-carboxamide, 5-Cyclopropyl-6-(3-methylimidazo[4,5-c]pyridin-7-yl)-3-[[3-methyl-1-(oxetan-3-yl)pyrazol-4-yl]amino]pyrazine-2-carboxamide, 5-Cyclopropyl-6-(3-methylimidazo[4,5-c]pyridin-7-yl)-3-[[5-methyl-1-(oxetan-3-yl)pyrazol-4-yl]amino]pyrazine-2-carboxamide, 5-Cyclopropyl-3-[[1-(2,2-difluoroethyl)-5-methyl-pyrazol-4-yl]amino]-6-(3-methylimidazo[4,5-c]pyridin-7-yl)pyrazine-2-carboxamide, 5-Cyclopropyl-3-[[1-(3,3-difluoropropyl)-3-methyl-pyrazol-4-yl]amino]-6-(3-methylimidazo[4,5-c]pyridin-7-yl)pyrazine-2-carboxamide, 5-Cyclopropyl-3-[[1-(3,3-difluoropropyl)-5-methyl-pyrazol-4-yl]amino]-6-(3-methylimidazo[4,5-c]pyridin-7-yl)pyrazine-2-carboxamide, 5-Cyclopropyl-6-(3-methylimidazo[4,5-c]pyridin-7-yl)-3-[(3-methyl-1-tetrahydropyran-4-yl-pyrazol-4-yl)amino]pyrazine-2-carboxamide, 5-Cyclopropyl-6-(3-methylimidazo[4,5-c]pyridin-7-yl)-3-[(5-methyl-1-tetrahydropyran-4-yl-pyrazol-4-yl)amino]pyrazine-2-carboxamide, 5-Cyclopropyl-6-(1-methylbenzimidazol-4-yl)-3-[[3-methyl-1-(1-methyl-4-piperidyl)pyrazol-4-yl]amino]pyrazine-2-carboxamide, 5-Cyclopropyl-6-(1-methylbenzimidazol-4-yl)-3-[[5-methyl-1-(1-methyl-4-piperidyl)pyrazol-4-yl]amino]pyrazine-2-carboxamide, and pharmaceutically acceptable salts thereof.

It shall be noted that any one of these specific compounds may be disclaimed from any of the herein mentioned embodiments.

In one embodiment there is provided a process for the preparation of compounds of Formula (I) or pharmaceutically acceptable salts of compounds of Formula (I), and the intermediates used in the preparation thereof.

Another embodiment is a product obtainable by any of the processes or examples disclosed herein.

Medical and Pharmaceutical Use

The compounds of Formula (I) and their pharmaceutically acceptable salts are useful because they possess pharmacological activity as inhibitors of hematopoietic progenitor kinase 1 (HPK1) and are thereby particularly useful in the treatment or amelioration of abnormal cell proliferative disorders such as cancer.

The compounds of Formula (I) are inhibitors of HPK1. Thus, the compounds of Formula (I) can be used as a medicament, in particular for disorders, disease or conditions responsive to inhibition of HPK1, and more specifically cancer.

In a further embodiment there is provided a pharmaceutical formulation comprising a compound of Formula (I), or a pharmaceutically acceptable salt of a compound of Formula (I), for use in the treatment of a condition where inhibition of HPK1 would be beneficial.

In a further embodiment there is provided a compound of Formula (I), or a pharmaceutically acceptable salt of a compound of Formula (I), for use in therapy, especially in the prevention or treatment of cancer in a mammal, particularly a human.

In a further embodiment there is provided the use of a compound of Formula (I), or a pharmaceutically acceptable salt of a compound of Formula (I), for the manufacture of a medicament for the treatment of cancer.

In still a further embodiment, administration of a compound of Formula (I), or a pharmaceutically acceptable salt of a compound of Formula (I) results in a reduction in levels of activity of HPK1 in a mammal, particularly a human.

For the above-mentioned therapeutic indications, the dosage administered will, of course, vary with the compound employed, the mode of administration and the treatment desired. However, in general, satisfactory results are obtained when the compounds are administered at a dosage of the solid form of between 1 mg and 2000 mg per day.

The compounds of Formula (I), and pharmaceutically acceptable derivatives thereof, may be used on their own, or in the form of appropriate pharmaceutical compositions in which the compound or derivative is in admixture with a pharmaceutically acceptable adjuvant, diluent or carrier. Thus, another aspect concerns a pharmaceutical composition comprising a novel compound of Formula (I), or a pharmaceutically acceptable salt thereof, in admixture with a pharmaceutically acceptable adjuvant, diluent or carrier. Administration may be by, but is not limited to, enteral (including oral, sublingual or rectal), intranasal, inhalation, intravenous, topical or other parenteral routes. Conventional procedures for the selection and preparation of suitable pharmaceutical formulations are described in, for example, *Pharmaceuticals—The Science of Dosage Form Designs*, M. E. Aulton, Churchill Livingstone, $2^{nd}$ Ed. 2002. The pharmaceutical composition preferably comprises less than 80% and more preferably less than 50% of a compound of Formula (I), or a pharmaceutically acceptable salt thereof.

Pharmacological Properties

The compounds of Formula (I) or pharmaceutically acceptable salts thereof are believed to be useful in the prevention or treatment of disorders, disease or conditions responsive to inhibition of HPK1, and more specifically cancer.

For the avoidance of doubt, as used herein, the term "treatment" includes therapeutic and/or prophylactic treatment.

When a compound or salt described herein is administered as therapy for treating a disorder, a "therapeutically effective amount" is an amount sufficient to reduce or completely alleviate symptoms or other detrimental effects of the disorder, cure the disorder, reverse, completely stop, or slow the progress of the disorder or reduce the risk of the disorder getting worse.

The compounds described herein are thus indicated both in the therapeutic and/or prophylactic treatment of these conditions.

The compounds described herein have the advantage that they may be more efficacious, be less toxic, be more selective, be more potent, produce fewer side effects, be more easily absorbed, and/or have a better pharmacokinetic profile (e.g. higher oral bioavailability and/or lower clearance), than compounds known in the prior art.

Combination Therapy

The compounds of Formula (I), or a pharmaceutically acceptable salt thereof, may also be administered in conjunction with other compounds used for the treatment of the above conditions.

In another embodiment, there is a combination therapy wherein a compound of Formula (I), or a pharmaceutically acceptable salt thereof, and a second active ingredient are administered concurrently, sequentially or in admixture, for the treatment of one or more of the conditions listed above. Such a combination may be used in combination with one or more further active ingredients.

A compound of Formula (I), or a pharmaceutically acceptable salt thereof, could be used in combination with check point blockade PD-$(L)_1$ axis or with CTLA4 in efforts to expand response rates to check point blockade. Primary or secondary resistance to check point blockade may be potential indications for a compound of Formula (I), or a pharmaceutically acceptable salt thereof. Additional combinations may include radiation, chemotherapy, surgery, tumour targeted agents or other immune targeted agents.

When used in a combination therapy, it is contemplated that the compounds of Formula (I) or pharmaceutically acceptable salts thereof and the other active ingredients may be administered in a single composition, completely separate compositions, or a combination thereof. It also is contemplated that the active ingredients may be administered concurrently, simultaneously, sequentially, or separately. The particular composition(s) and dosing frequency (ies) of the combination therapy will depend on a variety of factors, including, for example, the route of administration, the condition being treated, the species of the patient, any potential interactions between the active ingredients when combined into a single composition, any interactions between the active ingredients when they are administered to the animal patient, and various other factors known to physicians (in the context of human patients), veterinarians (in the context of non-human patients), and others skilled in the art.

Pharmaceutical Compositions

There is provided a method of treatment of a condition where inhibition of HPK1 is required, which method comprises administration of a therapeutically effective amount of a compound of Formula (I) to a person suffering from, or susceptible to, such a condition.

The compounds of Formula (I) will normally be administered via the oral, topical, parenteral, intravenous, intramuscular, subcutaneous or in other injectable ways, buccal, rectal, vaginal, transdermal and/or nasal route and/or via inhalation, in the form of pharmaceutical preparations comprising the active ingredient or a pharmaceutically acceptable salt thereof, in a pharmaceutically acceptable dosage form. Depending upon the disorder and patient to be treated and the route of administration, the compositions may be administered at varying doses. Conventional procedures for the selection and preparation of suitable pharmaceutical formulations are described in, for example, *Pharmaceuticals—The Science of Dosage Form Designs*, M. E. Aulton, Churchill Livingstone, $2^{nd}$ Ed. 2002.

Suitable daily doses of the compounds of Formula (I) in therapeutical treatment of humans are about 0.0001-100 mg/kg body weight, preferably 0.01-10 mg/kg body weight.

Oral formulations are preferred, particularly tablets or capsules which may be formulated by methods known to those skilled in the art to provide doses of the active compound in the range of 0.007 mg to 700 mg.

The optimum dosage and frequency of administration will depend on the particular condition being treated and its severity; the species of the patient; the age, sex, size and weight, diet, and general physical condition of the particular patient; brain/body weight ratio; other medication the patient may be taking; the route of administration; the formulation; and various other factors known to physicians and others skilled in the art.

According to a further aspect there is thus provided a pharmaceutical formulation comprising a compound of Formula (I), or pharmaceutically acceptable derivatives thereof, in admixture with a pharmaceutically acceptable adjuvant, diluent and/or carrier. The compounds of Formula (I) may be present in the pharmaceutical formulation in a concentration from 0.1 to 99.5%, such as from 0.5 to 95%, by weight of the total formulation.

The protection and deprotection of functional groups is described in *Protective Groups in Organic Synthesis,* $4^{th}$ Ed, T. W. Greene and P. G. M. Wuts, Wiley-Interscience (2006) and *Protecting Groups,* $3^{rd}$ Ed, P. J. Kocienski, Georg Thieme Verlag (2005).

A further embodiment encompasses pharmaceutically acceptable salts of the compounds of Formula (I).

A salt of a compound of Formula (I) may be advantageous due to one or more of its chemical or physical properties, such as stability in differing temperatures and humidities, or a desirable solubility in $H_2O$, oil, or other solvent. In some instances, a salt may be used to aid in the isolation or purification of the compound. In some embodiments (particularly where the salt is intended for administration to an animal, e.g. a human, or is a reagent for use in making a compound or salt intended for administration to an animal), the salt is pharmaceutically acceptable.

The term "pharmaceutically acceptable" is used to characterize a moiety (e.g. a salt, dosage form, or excipient) as being appropriate for use in accordance with sound medical judgment. In general, a pharmaceutically acceptable moiety has one or more benefits that outweigh any deleterious effect that the moiety may have. Deleterious effects may include, for example, excessive toxicity, irritation, allergic response, and other problems and complications.

Where the compound is sufficiently basic, pharmaceutically acceptable salts include, but are not limited to, inorganic or organic acid addition salts.

For reviews on suitable salts, see Berge et al., *J. Pharm. Sci.,* 1977, 66, 1-19 or *Handbook of Pharmaceutical Salts: Properties*, selection and use, P. H. Stahl, P. G. Vermuth, IUPAC, Wiley-VCH, 2002.

Where an acid co-former is a solid at r.t. and there is no or only partial proton transfer between the compound of Formula (I) and such an acid co-former, a co-crystal of the co-former and compound of Formula (I) may result rather than a salt. All such co-crystal forms of the compound of Formula (I) are encompassed herein.

It is also to be understood that certain compounds of Formula (I) may exist in solvated form, e.g. hydrates, including solvates of a pharmaceutically acceptable salt of a compound of Formula (I).

In a further embodiment, certain compounds of Formula (I) may exist as racemates and racemic mixtures, single enantiomers, individual diastereomers and diastereomeric mixtures. Certain compounds of Formula (I) may also contain linkages (e.g. carbon-carbon bonds, carbon-nitrogen bonds such as amide bonds) wherein bond rotation is restricted about that particular linkage, e.g. restriction resulting from the presence of a ring bond or double bond. Stereoisomers may be separated using conventional techniques, e.g. chromatography or fractional crystallization, or the stereoisomers may be made by stereoselective synthesis.

In a further embodiment, the compounds of Formula (I) encompass any isotopically-labelled (or "radio-labelled") derivatives of a compound of Formula (I). Such a derivative is a derivative of a compound of Formula (I) wherein one or more atoms are replaced by an atom having an atomic mass or mass number different from the atomic mass or mass number typically found in nature. Examples of isotopes that may be incorporated include $^{2}H$ (also written as "D" for deuterium).

In a further embodiment, the compounds of Formula (I) may be administered in the form of a prodrug which is broken down in the human or animal body to give a compound of the Formula (I).

Various forms of prodrugs are known in the art. For examples of prodrug derivatives, see: *Nature Reviews Drug Discovery* 2008, 7, 255 and references cited therein.

Intermediate compounds may also exist in enantiomeric forms and may be used as purified enantiomers, diastereomers, racemates or mixtures.

Pharmacological Activity

Assay Descriptions

HPK1, GLK, and LCK $IC_{50}$ assays: Activity of purified N-terminal GST-tagged, recombinant, human HPK1, GLK, and LCK enzymes expressed in insect cells (HPK1: amino acids 1-346, ThermoFisher Scientific, #PV6356, Carlsbad, CA; GLK: amino acids 1-380, ThermoFisher Scientific, #PV6351, Carlsbad, CA; LCK: full length, Abcam, #ab79626, Cambridge, MA) was determined in-vitro using ADP-Glo Max Assay (Promega, #V7002, Madison, WI), a luminescent ADP detection assay, by quantifying the amount of ADP produced in a kinase reaction.

The luminescent signal generated is proportional to the ADP concentration produced in a kinase assay in the presence and absence of the compound(s) and is correlated with the kinase activity. Two microlitres (μl) of enzyme mix consisting of 10 nM HPK1, 30 nM GLK, or 2 nM LCK in 1× reaction buffer (50 mM HEPES (pH7.2), 1 mM DL-Dithiothreitol (DTT), 0.005% (vol/vol) Brij35, 20 mM MgCl2) was spotted into Greiner 384-well low volume plate with 0.1 μl of compound, which was dosed at 100, 31.25, 12.5, 3.19, 1, 0.32, 0.1, 0.032, 0.01 and 0.003 μM of final test concentrations and preincubated for 30 minutes at room temperature. Enzymatic reactions were initiated with 2 μl of peptide substrate/ATP mix (for HPK1: 10 μM LRRKtide (RLGRDKYKTLRQIRQ-amide; Cambridge Research Biochemicals, Billingham, UK), 30 μM ATP; for GLK: 14 μM LRRKtide, 60 μM ATP; for LCK: 100 μM LCKtide (EQEDEDEPEGIYGVLE-amide; Intonation, Boston, MA), 50 μM ATP) in 1× reaction buffer and incubated at room temperature for 60 minutes. 4 μl ADP-Glo Reagent was added to terminate the reactions and deplete the remaining ATP and incubated at room temperature for 60 minutes. Finally, 8 μl ADP-Glo Max Detection Reagent was added to simultaneously convert ADP to ATP and incubated at room temperature for 60 minutes. The newly synthesized ATP is converted to light using a luciferase/luciferin reaction. Luminescence was read by PHERAstar FSX plate reader (BMG LABTECH, Cary, NC) and the data was captured by PHERAstar FSX MARS data analysis software. $IC_{50}$ values were processed using GeneData Screener (GeneData AG, Basel, Switzerland).

T Cell Assay

Materials

- RPMI 1640 (Sigma R5886)
- Heat inactivated FBS (Gibco 10270-10
- Glutamax 100× (Thermo Fisher 35050061)
- HEPES 1M (Thermo Fisher 15630080)
- Dulbecco's PBS (SigmaD8537)
- MultiCyt® QBeads® Human PlexScreen (2) Plex for 1×384 plate (Sartorius 90602)
- Ultra-LEAF™ Purified anti-human CD28 Antibody (Biolegend 302933)
- CD3 Monoclonal Antibody (OKT3), Functional Grade, eBioscience™ (Thermo Fisher 16-0037-85)
- β-mercaptoethanol (Sigma M3148)
- Propidium Iodide (Abcam ab14083)
- Pen/Strep (Sigma P0781)
- Non-essential amino acids (Sigma M7145)
- Sodium pyruvate (Sigma S8636)

T Cell Media Preparation

RPMI 1640+Heat inactivated FBS 10%+ Glutamax (100×) 1%+Pen/Strep 1%+Non-essential amino acids 1%+1M HEPES to make original media 100 mM final concentration Sodium pyruvate 1%+1.75 ul of 14.3 M original solution β-mercaptoethanol Method Cryo-preserved human CD3+ T cells are recovered in warm T cell media overnight. Recovered T cells are seeded at 70000 cells per well in a 384-well Black/Clear Round Bottom Ultra-Low Attachment Spheroid Microplate (Corning 3830). Compounds in a assay ready 384-well plate (Greiner 781280) are added to the seeded T cells using a Bravo liquid handler. T cells are then left in a humidified incubator at 37° C. for 1 hour. At the end of incubation, the cells are transferred to a 384-well flat bottom plate (Greiner 781090) coated with anti-CD3 antibody (5 ug/mL anti-CD3 in PBS, overnight incubation at 4° C.). Anti-CD28 antibody in T cell media is also added to the cells by Bravo liquid handler at 5 ug/mL or 1 μg/mL in a donor dependent manner. T cells are then incubated in a humidified incubator at 37° C. for 4 hours. Cell culture supernatant is collected using a Bravo liquid handler in a v-bottom 384 well plate (Greiner 781280) after the 4-hour incubation. IL2 is detected using a IL2 MultiCyt® QBeads® kit on an iQue Screener flow cytometer (Sartorius). Briefly, capture beads are diluted by 50× in the supplied capture bead diluent. 10 ul per well diluted capture beads is added to each well of a v-bottom 384 well plate (Greiner 781280) using a ThermoFisher multichannel pipette. Using a Bravo liquid handler, 10 ul cell culture supernatant is transferred to the v-bottom plate with diluted capture beads. The plate is then sealed in foil and incubate at room temperature on a plate shaker set to 900 rpm for 1 hour. At the end of incubation, 10 μL per well of the supplied detection reagent is added to the wells using a ThermoFisher multichannel pipette. The plate is then sealed in foil and incubate again at room temperature on a plate shaker set to 900 rpm for 2 hours before detection by iQue Screener. iQue Screener flow cytometer uses pre-configured analysis template supplied with the IL2 Multi-Cyt® QBeads® kit to detect IL2 in each sample wells.

The $IC_{50}/EC_{50}$ values for the Example compounds are set forth in Table 1 herein below.

TABLE 1

| Example No. | HPK1 $IC_{50}$ (μM) | GLK $IC_{50}$ (μM) | LCK $IC_{50}$ (μM) |
|---|---|---|---|
| 1 | 0.031 | 1.664 | 5.135 |
| 2 | <0.005 | 0.158 | 19.788 |
| 3 | <0.003 | 0.154 | 3.836 |
| 4 | <0.004 | 0.154 | 24.221 |
| 5 | <0.003 | 0.149 | 3.902 |
| 6 | <0.003 | 0.089 | 4.336 |
| 7 | <0.003 | 0.057 | 3.077 |
| 8 | <0.003 | 0.023 | 0.781 |
| 9 | 0.006 | 0.459 | 18.339 |
| 10 | <0.003 | 0.216 | 2.504 |
| 11 | <0.006 | 0.173 | 2.479 |
| 12 | <0.003 | 0.133 | >100.000 |
| 13 | 0.007 | 0.442 | 2.328 |
| 14 | <0.004 | 0.277 | 1.025 |
| 15 | <0.003 | 0.079 | 1.236 |
| 16 | <0.003 | 0.086 | 10.256 |
| 17 | <0.004 | 0.258 | 14.037 |
| 18 | <0.003 | 0.171 | 1.286 |
| 19 | <0.004 | 0.570 | >100.000 |
| 20 | 0.004 | 0.373 | 2.431 |
| 21 | 0.004 | 0.373 | 5.129 |
| 22 | <0.003 | 0.182 | 6.438 |
| 23 | <0.003 | 0.240 | 2.559 |
| 24 | 0.005 | 0.401 | 4.662 |
| 25 | <0.003 | 0.188 | 1.702 |
| 26 | 0.006 | 2.108 | 6.614 |
| 27 | <0.003 | 0.114 | 11.162 |
| 28 | <0.003 | 0.077 | 31.397 |
| 29 | 0.007 | 0.618 | 7.242 |
| 30 | <0.003 | 0.235 | 1.039 |
| 31 | <0.003 | 0.056 | 0.285 |
| 32 | <0.003 | 0.057 | 0.245 |
| 33 | <0.003 | 0.166 | 3.799 |
| 34 | 0.012 | 0.489 | 10.422 |
| 35 | 0.005 | 0.072 | 0.056 |
| 36 | 0.009 | 0.198 | 9.033 |
| 37 | <0.003 | 0.010 | 0.108 |
| 38 | <0.004 | 0.021 | 2.241 |
| 39 | <0.005 | 0.248 | >33.858 |
| 40 | <0.003 | 0.019 | 0.756 |
| 41 | <0.003 | 0.004 | 0.189 |
| 42 | <0.003 | 0.018 | 1.261 |
| 43 | 0.012 | 0.478 | 4.586 |
| 44 | <0.003 | 0.034 | 3.931 |

TABLE 1-continued

| Example No. | HPK1 $IC_{50}$ (μM) | GLK $IC_{50}$ (μM) | LCK $IC_{50}$ (μM) |
|---|---|---|---|
| 45 | <0.004 | 0.023 | 0.504 |
| 46 | <0.003 | 0.033 | 1.089 |
| 47 | <0.003 | 0.056 | 1.762 |
| 48 | <0.003 | 0.038 | 0.686 |
| 49 | <0.003 | 0.084 | 11.171 |
| 50 | <0.003 | 0.039 | 2.249 |
| 51 | 0.024 | 0.475 | >50.731 |
| 52 | <0.004 | 0.081 | >7.192 |
| 53 | <0.004 | 0.016 | 8.460 |
| 54 | <0.003 | 0.018 | >100.000 |
| 55 | <0.004 | 0.011 | 15.537 |
| 56 | <0.004 | 0.641 | >100.000 |
| 57 | <0.003 | 0.195 | >46.994 |
| 58 | 0.009 | 0.087 | 14.107 |
| 59 | <0.003 | 0.026 | 6.445 |
| 60 | <0.003 | <0.003 | 0.727 |
| 61 | <0.003 | 0.008 | 1.092 |
| 62 | <0.004 | 0.035 | 16.537 |
| 63 | <0.003 | 0.008 | 14.470 |
| 64 | <0.005 | 0.066 | 3.562 |
| 65 | <0.003 | 0.010 | 0.989 |
| 66 | <0.004 | 0.642 | 4.908 |
| 67 | 0.087 | 14.559 | 66.179 |
| 68 | 0.005 | 0.313 | 1.887 |
| 69 | <0.003 | 0.045 | 4.410 |
| 70 | <0.003 | 0.021 | 1.019 |
| 71 | <0.003 | 0.020 | 3.519 |
| 72 | 0.004 | 0.014 | 0.562 |
| 73 | 0.005 | 0.144 | >100.000 |
| 74 | 0.004 | 0.035 | 1.432 |
| 75 | <0.003 | 0.050 | 7.391 |
| 76 | <0.003 | 0.014 | 1.178 |
| 77 | <0.003 | 0.031 | 1.554 |
| 78 | 0.006 | 0.174 | 12.662 |
| 79 | <0.004 | 0.023 | 28.610 |
| 80 | <0.003 | 0.098 | >100.000 |
| 81 | <0.003 | 0.034 | 2.235 |
| 82 | <0.003 | 0.034 | 2.397 |
| 83 | <0.005 | 0.062 | 4.832 |
| 84 | <0.003 | 0.131 | 8.884 |
| 85 | <0.003 | 0.111 | 0.842 |
| 86 | <0.003 | 0.005 | 0.091 |
| 87 | <0.003 | 0.034 | 1.705 |
| 88 | <0.003 | 0.037 | 1.221 |
| 89 | <0.003 | 0.048 | 3.151 |
| 90 | <0.003 | 0.017 | 0.487 |
| 91 | <0.003 | 0.069 | 2.660 |
| 92 | <0.003 | 0.019 | 0.773 |
| 93 | <0.003 | 0.302 | 12.661 |
| 94 | <0.003 | 0.025 | 1.160 |
| 95 | <0.003 | 0.036 | 0.761 |
| 96 | <0.003 | 0.091 | >100.000 |
| 97 | <0.003 | 0.050 | 5.209 |
| 98 | <0.003 | 0.035 | >100.000 |
| 99 | <0.003 | 0.294 | >100.000 |
| 100 | <0.003 | <0.009 | 2.853 |
| 101 | <0.004 | 0.116 | >20.916 |
| 102 | 0.005 | 0.564 | >100.000 |
| 103 | <0.005 | 0.572 | 11.746 |
| 104 | <0.003 | 0.075 | 28.297 |
| 105 | 0.008 | 2.211 | 18.644 |
| 106 | <0.003 | 0.014 | 0.557 |
| 107 | <0.003 | <0.004 | 0.235 |
| 108 | <0.004 | 0.043 | 1.063 |
| 109 | <0.003 | <0.004 | 0.869 |
| 110 | <0.003 | 0.011 | 0.310 |
| 111 | <0.003 | 0.027 | 0.768 |
| 112 | <0.003 | 0.005 | 1.355 |
| 113 | <0.003 | 0.035 | 0.484 |
| 114 | <0.003 | 0.028 | 0.922 |
| 115 | <0.003 | <0.003 | 0.197 |
| 116 | <0.003 | <0.005 | 6.386 |
| 117 | <0.003 | 0.008 | 0.642 |
| 118 | <0.003 | 0.066 | 1.266 |
| 119 | <0.003 | 0.015 | 0.916 |
| 120 | <0.003 | 0.013 | 1.216 |
| 121 | <0.005 | 0.120 | 6.640 |

TABLE 1-continued

| Example No. | HPK1 $IC_{50}$ (μM) | GLK $IC_{50}$ (μM) | LCK $IC_{50}$ (μM) |
|---|---|---|---|
| 122 | <0.003 | 0.033 | 1.382 |
| 123 | <0.003 | 0.036 | 1.593 |
| 124 | <0.004 | 0.022 | 0.291 |
| 125 | <0.003 | 0.025 | 0.401 |
| 126 | <0.003 | 0.016 | 0.440 |
| 127 | <0.003 | 0.012 | 0.390 |
| 128 | <0.003 | 0.012 | 0.211 |
| 129 | <0.003 | 0.005 | 0.078 |
| 130 | <0.003 | 0.005 | 0.107 |
| 131 | <0.003 | 0.006 | 0.094 |
| 132 | <0.003 | 0.006 | 0.173 |
| 133 | <0.003 | 0.006 | 0.102 |
| 134 | <0.004 | <0.004 | 0.099 |
| 135 | <0.003 | 0.020 | 0.385 |
| 136 | <0.003 | 0.014 | 0.410 |
| 137 | <0.003 | 0.036 | 2.216 |
| 138 | <0.003 | 0.016 | 0.353 |
| 139 | <0.003 | 0.010 | 0.203 |
| 140 | <0.003 | 0.071 | 2.202 |
| 141 | <0.003 | 0.047 | 3.373 |
| 142 | <0.003 | 0.008 | 0.263 |
| 143 | <0.003 | 0.049 | 4.579 |
| 144 | <0.003 | 0.039 | >41.939 |
| 145 | <0.003 | 0.215 | 3.119 |
| 146 | <0.003 | 0.097 | 2.179 |
| 147 | <0.003 | 0.062 | >100.000 |
| 148 | <0.003 | 0.220 | 12.224 |
| 149 | <0.003 | 0.012 | 0.390 |
| 150 | <0.003 | 0.016 | 0.634 |
| 151 | <0.003 | <0.003 | 0.038 |
| 152 | <0.003 | 0.004 | 0.057 |
| 153 | <0.003 | 0.024 | 0.333 |
| 154 | <0.003 | 0.017 | 0.466 |
| 155 | <0.003 | 0.030 | 0.485 |
| 156 | <0.003 | 0.085 | 6.775 |
| 157 | <0.004 | 0.110 | >100.000 |
| 158 | <0.003 | 0.041 | 5.710 |
| 159 | 0.006 | 0.074 | 4.504 |
| 160 | 0.012 | 0.151 | 13.247 |
| 161 | 0.005 | 0.083 | 8.202 |
| 162 | <0.003 | 0.007 | 0.284 |
| 163 | <0.003 | 0.005 | 0.493 |
| 164 | <0.003 | <0.006 | 0.188 |
| 165 | <0.003 | 0.012 | 0.627 |
| 166 | <0.003 | 0.017 | 0.213 |
| 167 | <0.003 | <0.003 | 0.031 |
| 168 | <0.003 | 0.004 | 0.244 |
| 169 | <0.003 | 0.005 | 0.181 |
| 170 | 0.011 | 0.099 | 7.891 |
| 171 | <0.003 | 0.082 | 3.481 |
| 172 | 0.011 | 0.135 | 5.633 |
| 173 | 0.012 | 0.101 | 7.444 |
| 174 | <0.003 | 0.138 | 1.582 |
| 175 | <0.003 | 0.074 | 1.207 |
| 176 | <0.003 | 0.016 | 0.384 |
| 177 | <0.003 | 0.091 | >100.000 |
| 178 | <0.003 | 0.022 | 3.198 |
| 179 | <0.003 | 0.018 | 0.324 |
| 180 | <0.003 | 0.125 | 19.661 |
| 181 | <0.003 | 0.061 | >43.686 |
| 182 | <0.003 | 0.087 | >38.104 |
| 183 | <0.003 | 0.009 | 1.057 |
| 184 | <0.003 | <0.004 | 0.867 |
| 185 | <0.003 | <0.003 | 0.168 |
| 186 | <0.003 | 0.010 | 1.052 |
| 187 | <0.003 | 0.008 | 0.698 |
| 188 | <0.003 | 0.029 | 1.040 |
| 189 | <0.003 | 0.065 | 33.036 |
| 190 | <0.003 | 0.050 | 20.823 |
| 191 | <0.003 | 0.012 | 1.266 |
| 192 | <0.003 | 0.007 | 0.977 |
| 193 | <0.003 | 0.085 | >54.311 |
| 194 | <0.003 | 0.010 | 0.541 |
| 195 | <0.003 | 0.030 | 0.701 |
| 196 | <0.003 | 0.021 | 0.679 |
| 197 | <0.003 | 0.012 | 0.693 |
| 198 | <0.003 | 0.008 | 0.513 |

TABLE 1-continued

| Example No. | HPK1 $IC_{50}$ (μM) | GLK $IC_{50}$ (μM) | LCK $IC_{50}$ (μM) |
|---|---|---|---|
| 199 | <0.003 | <0.004 | 0.287 |
| 200 | <0.003 | 0.011 | 0.410 |
| 201 | <0.003 | 0.164 | 1.402 |
| 202 | <0.003 | 0.022 | 0.222 |
| 203 | <0.003 | 0.034 | 0.471 |
| 204 | 0.005 | 0.176 | 0.694 |
| 205 | <0.003 | 0.007 | 0.033 |
| 206 | <0.007 | 0.238 | 8.482 |
| 207 | <0.003 | 0.306 | >100.000 |
| 208 | <0.003 | 0.620 | >100.000 |
| 209 | 0.005 | 0.993 | >100.000 |
| 210 | 0.009 | 0.805 | 9.901 |
| 211 | <0.003 | 1.089 | >95.971 |
| 212 | <0.003 | 0.091 | 5.132 |
| 213 | <0.003 | 0.185 | >100.000 |
| 214 | 0.004 | 0.175 | 2.253 |
| 215 | <0.003 | 0.158 | 17.384 |
| 216 | <0.003 | 0.194 | 8.431 |
| 217 | <0.005 | 0.490 | >31.890 |
| 218 | <0.003 | 0.141 | 2.321 |
| 219 | <0.004 | 0.061 | 3.685 |
| 220 | <0.003 | 0.322 | 7.320 |
| 221 | <0.003 | 0.248 | 6.274 |
| 222 | <0.003 | 0.148 | 1.436 |
| 223 | <0.003 | 0.103 | 1.307 |
| 224 | <0.003 | 0.050 | 2.262 |
| 225 | <0.003 | 0.141 | 1.733 |
| 226 | <0.003 | 0.094 | 2.318 |
| 227 | <0.003 | 0.266 | 7.153 |
| 228 | <0.003 | 0.120 | 1.221 |
| 229 | 0.003 | 0.158 | 5.191 |
| 230 | <0.003 | 0.036 | 0.274 |
| 231 | <0.004 | 0.091 | 3.685 |
| 232 | 0.004 | 0.050 | 0.335 |

TABLE 2

| Example No. | IL-2 $EC_{50}$ (nM) | Max IL-2 conc (nM) | Flow pSLP76 $EC_{50}$ (nM) | WB pSLP76 $EC_{50}$ (nM) |
|---|---|---|---|---|
| 8 | 23 | 370 | 16 | 18 |
| 52 | 127 | 3330 | | |
| 146 | 23 | 370 | 65 | |
| 148 | 325 | 3330 | 1080 | |
| 206 | 91 | 1110 | 440 | 320 |
| 207 | 155 | 3330 | | |
| 211 | 276 | 3330 | | 340 |
| 212 | 90 | 1110 | 70 | 105 |
| 213 | 53 | 1110 | 50 | |
| 215 | 155 | 3330 | 180 | 150 |
| 216 | 107 | 3330 | 135 | 115 |
| 224 | 120 | 3330 | | |

EXAMPLES

The following examples are non-limiting examples.

The following abbreviations are employed herein:

BINAP (2,2'-bis(diphenylphosphino)-1,1'-binaphthyl), also known as [1-(2-diphenylphosphanyl-1-naphthyl)-2-naphthyl]-diphenyl-phosphane BrettPhos dicyclohexyl-[3,6-dimethoxy-2-(2,4,6-triisopropylphenyl)phenyl]phosphane BrettPhos Pd G3 [(dicyclohexyl-[3,6-dimethoxy-2-(2,4,6-triisopropylphenyl)phenyl]phosphane)-2-(2'-amino-1,1'-biphenyl)]palladium(II) methanesulfonate cataCXium A bis(1-adamantyl)-butyl-phosphane cataCXium A Pd G2 chloro[(bis(1-adamantyl)-butyl-phosphane)-2-(2-aminobiphenyl)]palladium(II)

cataCXium A Pd G3 [(bis(1-adamantyl)-butyl-phosphane)-2-(2'-amino-1,1'-biphenyl)]palladium(II) methanesulfonate dba dibenzylideneacetone, also known as (1E,4E)-1,5-diphenylpenta-1,4-dien-3-one DCE 1,2-dichloroethane DCM dichloromethane DIPEA N,N-diisopropylethylamine, also known as N-ethyl-N-isopropyl-propan-2-amine DMF N,N-dimethylformamide DPEPhos [2-(2-diphenylphosphanylphenoxy)phenyl]-diphenyl-phosphane DSC Differential Scanning Calorimetry HATU hexafluorophosphate azabenzotriazole tetramethyl uronium, also known as N,N,N',N'-tetramethyl-1-(3-oxidotriazolo[4,5-b]pyridin-3-ium-1-yl)methanediamine;hexafluorophosphate DIAD diisopropyl azodicarboxylate, also known as isopropyl (NE)-N-isopropoxycarbonyliminocarbamate DMA N,N-dimethylacetamide DMAP N,N-dimethylaminopyridine, also known as N,N-dimethylpyridin-4-amine DMSO dimethyl sulfoxide Dppf 1,1'-Bis(diphenylphosphino)ferrocene, also known as (Ferrocene-1,1'-diyl)bis(diphenylphosphane)

DTBAD di-tert-butyl azodicarboxylate, also known as tert-butyl (NE)-N-tert-butoxycarbonyliminocarbamate EPhos dicyclohexyl-[2-isopropoxy-6-(2,4,6-triisopropylphenyl)phenyl]phosphane EPhos Pd G4 [(dicyclohexyl-[2-isopropoxy-6-(2,4,6-triisopropylphenyl)phenyl]phosphane)-2-(2'-methylamino-1,1'-biphenyl)]palladium(II) methanesulfonate ES electrospray HPLC high-performance liquid chromatography IPA isopropanol, also known as propan-2-ol $Ir(dFCF_3ppy)_2(dtbbpy)$ [4,4'-Bis(1,1-dimethylethyl)-2,2'-bipyridine-N1,N1']bis[3,5-difluoro-2-[5-(trifluoromethyl)-2-pyridinyl-N]phenyl-C]Iridium(III) hexafluorophosphate LCMS liquid chromatography-mass spectrometry mCPBA meta-chloroperbenzoic acid, also known as 3-chlorobenzenecarboperoxoic acid MDAP mass-directed automated purification MHz megahertz MTBE methyl tert-butyl ether, also known as 2-methoxy-2-methyl-propane m/z mass divided by charge NMP 1-methylpyrrolidin-2-one NMR nuclear magnetic resonance $PCy_3$ Pd G3 [(tricyclohexylphosphane)-2-(2'-amino-1,1'-biphenyl)]palladium(II) methanesulfonate Pd-PEPPSI-IPent [(di(1-adamantyl)-butylphosphine)-2-(2'-amino-1,1'-biphenyl)]palladium(II) methanesulfonate $sCO_2$ supercritical carbon dioxide SFC supercritical fluid chromatography TBAF tetrabutylammonium fluoride t-BuXPhos di-tert-butyl-[2-(2,4,6-triisopropylphenyl)phenyl]phosphane t-BuXPhos Pd G3 [(di-tert-butyl-[2-(2,4,6-triisopropylphenyl)phenyl]phosphane)-2-(2'-amino-1,1'-biphenyl)]palladium(II) methanesulfonate TFA 2,2,2-trifluoroacetic acid TGA Thermogravimetric Analysis THE tetrahydrofuran XantPhos (5-diphenylphosphanyl-9,9-dimethyl-xanthen-4-yl)-diphenyl-phosphane XantPhos Pd G3 [((5-diphenylphosphanyl-9,9-dimethyl-xanthen-4-yl)-diphenyl-phosphane)-2-(2'-amino-1,1'-biphenyl)]palladium(II) methanesulfonate Xphos dicyclohexyl-[2-(2,4,6-triisopropylphenyl)phenyl]phosphane XPhos Pd G3 (dicyclohexyl-[2-(2,4,6-triisopropylphenyl)phenyl]phosphane)[2-(2'-amino-1,1'-biphenyl)]palladium(II) methanesulfonate The following general experimental procedures were used:

Unless otherwise noted, operations are carried out at room temperature, that is, in a range of 18 to 25 degrees Celsius.

Evaporation of organic solvent was carried out using a rotary evaporator under reduced pressure (4.5-30 mmHg) with a bath temperature of up to 60 degrees Celsius.

In general, the course of reactions was followed by TLC or liquid chromatography/mass spectrometry and reaction times are given for illustration only.

Yields are given for illustration only and not necessarily those which can be obtained by diligent process development. Preparations were repeated if more material was required. Microwave reactions were conducted in a Biotage Initiator or Emrys Optimizer, using Biotage microwave vials.

Silica gel chromatography was performed on Biotage Selekt, Biotage Isolera, or Teledyne ISCO Combiflash Companion automated purification instruments, using Biotage Sfar, Biotage SNAP, Agela Claricep, RediSep Rf Gold Silica, or Buchi FlashPure columns, in sizes ranging from 5 g to 300 g as appropriate.

Reverse phase chromatography was performed on Biotage Selekt, Biotage Isolera, Teledyne ISCO Combiflash Companion, or Agela Technologies automated purification instruments, using Biotage Sfar C18 Duo, RediSep Rf C18, or RediSep Rf Gold C18 columns, in sizes ranging from 5 g to 300 g as appropriate.

MDAP purification was carried out on an Agilent 1260 Infinity II (autosampler, DAD, quaternary pump, and isocratic pumps) and Agilent 1290 Infinity II (preparative pump and fraction collector) with an Agilent InfinityLab LC/MSD. Columns and gradients are specified in the examples.

Preparative HPLC purification was carried out on a Waters FractionLynx system fitted with an Acquity QDa Mass Detector, or an instrument comprising a Waters 2545, 2767, and 2489, fitted with QDa or SQ Detector 2 ESCi mass spectrometers. Columns and gradients are specified in the examples.

Preparative and analytical SFC purification was carried out on a Sepiatec Prep SFC 100, Sepiatec Prep SFC 250, Waters Prep 100, Waters SFC Method Station $X^5$, Waters Acquity $UPC^2$, Berger Multigram III, Waters Acquity $UPC^2$ with Xevo TQ-S Micro Triple Quadrupole Mass Spectrometer, Waters Prep 80, Waters Prep 150, or Waters Prep 350. Columns and gradients specified in the examples.

Ion exchange chromatography was performed using Waters PoraPak Rxn CX cartridges.

$^1H$ NMR measurements were performed on Bruker Avance Neo 300, Bruker Avance III 300, Bruker Avance III HD 300, Bruker Avance III 400, Bruker Avance III HD 400, Jeol JNM-ECZ400S/L1, Bruker AV3HD nano 400, Bruker NEO 500, or Bruker DRK 500 spectrometers operating at 1H frequencies of 300, 300, 300, 400, 400, 400, 400, 500, and 500 MHz, respectively. The experiments were typically recorded at 27 degrees Celsius. Shifts were referenced according to IUPAC 2001 guidelines, as described in DOI: 10.1006/snmr.2002.0063. In most cases, shifts were rereferenced during data processing according to the residual $^{1}H$ chemical shift of the deuterated solvent.

UPLC-MS was carried out using one of: 1) Waters Acquity UPLC and Waters SQD mass spectrometer (column temperature 30 degrees Celsius, UV detection=210-400 nm, mass spec=ESI with positive/negative switching) at a flow rate of 1 mL/min using a solvent gradient of 2 to 98% B over 1.5 minutes (total runtime with equilibration back to starting conditions 2 minutes), where A=0.1% formic acid in water and B=0.1% formic acid in acetonitrile (for acid work) or A=0.1% ammonium hydroxide in water and B=acetonitrile (for base work). For acid analysis the column used was Waters Acquity HSS T3, 1.8 micron, 2.1 mm×30 mm; for base analysis the column used was Waters Acquity BEH C18, 1.7 micron, 2.1 mm×30 mm; or 2) Shimadzu LCMS-2020 with electrospray ionization in positive ion detection mode with 20ADXR pump, SIL-20ACXR autosampler, CTO-20AC column oven, M20A PDA detector and LCMS 2020 MS detector, using one of three conditions: a) Halo C18 column (2.0 micron, 3 mm×30 mm) in combination with a gradient (5-100% B in 1.2 minutes) of water and formic acid (0.1%) (A) and acetonitrile and formic acid (0.1%) (B) at a flow rate of 1.5 mL/min; b) Halo C18 column (2.0 micron, 3 mm×30 mm) in combination with a gradient (5-100% B in 1.2 minutes) of water and trifluoroacetic acid (0.05%) (A) and acetonitrile and trifluoroacetic acid (0.05%) at a flow rate of 1.5 mL/min; or c) Poroshell HPH C18 column (2.7 micron, 3 mm×50 mm) in combination with a gradient (10-95% B in 2 minutes) of aqueous 46 mM ammonium carbonate/ammonia buffer at pH 10 (A) and acetonitrile (B) at a flow rate of 1.2 mL/min.

Photoredox chemistry was carried out using a 34 W Kessil H150 blue LED lamp (440 nm) as light source, in a HepatoChem EvoluChem™ PhotoRedOx reaction apparatus.

Optical rotation data were taken on a Jasco P-2000 polarimeter, using a 100 mm path length, 0.40 w/v % solutions of compound in DMSO, with the sodium D line (589 nm), at 25 degrees Celsius.

The X-ray diffraction analysis was performed according to standard methods, which can be found in e.g. Kitaigorodsky, A. I. (1973), Molecular Crystals and Molecules, Academic Press, New York; Bunn, C. W. (1948), Chemical Crystallography, Clarendon Press, London; or Klug, H. P. & Alexander, L. E. (1974), X-ray Diffraction Procedures, John Wiley & Sons, New York. Samples were mounted on single silicon crystal (SSC) wafer mounts and powder X-ray diffraction was recorded with a PANalytical X'Pert PRO (reflection geometry, wavelength of X-rays 1.5418 Å nickel-filtered Cu radiation, Voltage 45 kV, filament emission 40 mA). Automatic variable divergence and anti scatter slits were used and the samples were rotated during measurement. Samples were scanned from 2-50° 2Theta or 2-40° 2Theta using a 0.0130 step width and between 44 and 233 seconds count time using a PIXCEL detector (active length 3.35° 2Theta).

It is known in the art that an X-ray powder diffraction pattern may be obtained which has one or more measurement errors depending on measurement conditions (such as equipment, sample preparation or machine used). In particular, it is generally known that intensities in an X-ray powder diffraction pattern may fluctuate depending on measurement conditions and sample preparation. For example, persons skilled in the art of X-ray powder diffraction will realise that the relative intensities of peaks may vary according to the orientation of the sample under test and on the type and setting of the instrument used. The skilled person will also realise that the position of reflections can be affected by the precise height at which the sample sits in the diffractometer and the zero calibration of the diffractometer. The surface planarity of the sample may also have a small effect. Hence a person skilled in the art will appreciate that the diffraction pattern data presented herein is not to be construed as absolute and any crystalline form that provides a power diffraction pattern substantially identical to those disclosed herein fall within the scope of the present disclosure (for further information see Jenkins, R & Snyder, R. L. 'Introduction to X-Ray Powder Diffractometry' John Wiley & Sons, 1996). Generally, a measurement error of a diffraction angle in an X-ray powder diffractogram may be approximately plus or minus 0.1° 2-theta, and such a degree of a measurement error should be taken into account when considering the X-ray powder diffraction data. Furthermore, it should be understood that intensities might fluctuate depending on experimental conditions and sample preparation (e.g. preferred orientation). The following definitions have been used for the relative intensity (%): 81-100%, vs (very strong); 41-80%, str (strong); 21-40%, med (medium); 10-20%, w (weak); 1-9%, vw (very weak).

Chemical IUPAC names were generated by BioviaDraw using OpenEye Metachem 1.5.0 software.

General Intermediates

Intermediate 1

1-Methyl-4-(4,4,5,5-tetramethyl-1,3,2-dioxaborolan-2-yl)-1H-benzo[d]imidazole

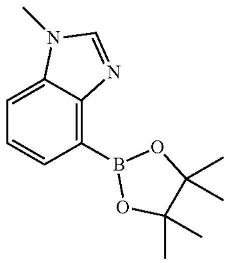 [SMILES: Cn1cnc2c(B3OC(C)(C)C(C)(C)O3)cccc21]

(a) 3 Bromo-N-methyl-2-nitro-aniline

1-Bromo-3-fluoro-2-nitro-benzene (25.0 g, 114 mmol) was added to a solution of 33% methanamine in ethanol (114 mL, 916 mmol) at 0° C. The resulting solution was stirred at 25° C. for 5 hours. The reaction was then concentrated. The resulting residue was dissolved in ethyl acetate and washed three times with water, dried over sodium sulfate, filtered, and concentrated to afford 3-bromo-N-methyl-2-nitro-aniline (27.3 g, quantitative) as a bright orange solid; 1H NMR (500 MHz, DICHLOROMETHANE-d2) 2.94 (3H, s), 5.51-5.90 (1H, m), 6.82 (1H, d), 6.99 (1H, dd), 7.23 (1H, t); m/z: (ES+), [M+H]+=231.1

(b) 3-Bromo-N1-methyl-benzene-1,2-diamine

Iron powder (61.3 g, 1.10 mol) was added to a solution of 3-bromo-N-methyl-2-nitro-aniline (25.4 g, 110 mmol) and ammonium chloride (58.8 g, 1.10 mol) in methanol (146 mL). The resulting suspension was stirred at 60° C. for 2 hours. The reaction mixture was then concentrated. The resulting residue was partitioned between ethyl acetate and a saturated aqueous potassium carbonate solution. The organic layer was dried over magnesium sulfate, filtered, and concentrated. The resulting residue was purified by silica gel chromatography using 0-100% ethyl acetate-hexane as eluent to afford 3-bromo-N1-methyl-benzene-1,2-diamine (22 g, 100%) as a purple oil; 1H NMR (500 MHz, DICHLOROMETHANE-d2) 2.89 (3H, s), 6.62-6.67 (1H, d), 6.69-6.75 (1H, t), 6.96 (1H, d); m/z: (ES+), [M+H]+=200.9

(c) 4-Bromo-1-methyl-benzimidazole

3-Bromo-N1-methyl-benzene-1,2-diamine (22.1 g, 110 mmol) was added to a solution of 4-toluenesulfonic acid (2.09 g, 11.0 mmol) in trimethyl orthoformate (36.5 mL, 330 mmol). The resulting suspension was stirred at 60° C. for 3 hours. The reaction was then concentrated. The resulting residue was dissolved in ethyl acetate and washed three times with 10% aqueous potassium carbonate, dried over sodium sulfate, filtered, and evaporated to afford 4-bromo-1-methyl-benzimidazole (21.6 g, 93%) as a purple solid; 1H NMR (500 MHz, DICHLOROMETHANE-d2) 3.87 (3H, s), 7.21-7.27 (1H, m), 7.40-7.46 (1H, m), 7.48-7.53 (1H, m), 7.95 (1H, s); m/z: (ES+), [M+H]+=210.9

(d) 1-Methyl-4-(4,4,5,5-tetramethyl-1,3,2-dioxaborolan-2-yl)benzimidazole

4-Bromo-1-methyl-1H-benzo[d]imidazole (5.00 g, 23.7 mmol), cataCXium A Pd G3 (1.73 g, 2.37 mmol), cataCXium A (0.849 g, 2.37 mmol), bis(pinacolato)diboron (15.0 g, 59.2 mmol), and potassium acetate (6.97 g, 71.1 mmol) were combined in a three-neck flask, which was then evacuated and backfilled three times with nitrogen. Cyclopentyl methyl ether (120 mL) was added and the reaction was stirred at 80° C. for 24 hours. The reaction was then diluted with ether (100 mL) and filtered through celite, rinsing with ether. The filtrate was concentrated to a brown solid, which was sonicated in hexanes (600 mL) for 40 minutes, then allowed to stand for 90 minutes, then filtered, rinsing sparingly with hexanes, to afford 1-methyl-4-(4,4,5,5-tetramethyl-1,3,2-dioxaborolan-2-yl)benzimidazole (4.77 g, 78%, 68% by weight) as a light gray solid; 1H NMR (500 MHz, DICHLOROMETHANE-d2) 1.39 (12H, s), 3.83 (3H, s), 7.31 (1H, t), 7.53 (1H, d), 7.70 (1H, d), 7.91 (1H, s). Poor behavior by LCMS.

Intermediate 2

(1-Methylbenzimidazol-4-yl)boronic acid

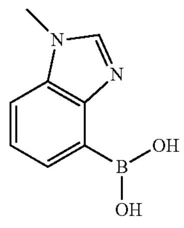

$PdCl_2$(dppf) (5.20 g, 7.11 mmol) was added to a suspension of potassium acetate (13.95 g, 142.1 mmol), 4-bromo-1-methyl-benzimidazole (10.00 g, 47.38 mmol), and bis(pinacolato)diboron (24.06 g, 94.76 mmol) in dioxane (400 mL). The resulting mixture was stirred at 100° C. for 3 days. The reaction was then concentrated. The resulting residue was purified by preparative HPLC, using a 5 micron, 50 mm×150 mm, XBridge Prep C18 OBD column, using decreasingly polar mixtures of MeCN-water as eluent, and 1% formic acid as modifier, to afford (1-methylbenzimidazol-4-yl)boronic acid (8.00 g, 96% yield) as a yellow solid. 1H NMR (300 MHz, DMSO) δ 3.85 (3H, s), 7.26 (1H, t), 7.56 (1H, d), 7.68 (1H, d), 8.22 (1H, s). The $B(OH)_2$ protons broadened to baseline. m/z: (ES+), [M+H]+=177.1

Intermediate 3

7-Bromo-3-methyl-imidazo[4,5-c]pyridine

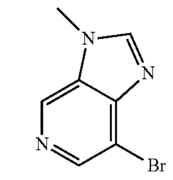

0.5 M Sodium methoxide in methanol (425 mL, 213 mmol) was added to a mixture of 5-bromopyridine-3,4-diamine (10.0 g, 53.2 mmol), paraformaldehyde (1.63 g, 54.3 mmol). The resulting mixture was stirred at 25° C. for 4 hours. Sodium borohydride (2.01 g, 53.2 mmol) was added to the reaction mixture. The resulting mixture was stirred at 60° C. for 1 hour. The reaction mixture was then concentrated. The resulting residue was treated with water and extracted with EtOAc. The extract was dried over sodium sulfate, filtered and concentrated. The resulting residue was suspended in triethyl orthoformate (200 mL) and stirred at 145° C. for 1 hour. The reaction was then cooled to 0° C. and acidified with 4 M HCl in dioxane (16.0 mL, 64.0 mmol). The resulting precipitate was filtered to afford a yellow solid, which was partitioned between saturated aqueous potassium carbonate and ethyl acetate and extracted twice with ethyl acetate. The combined organic layers were dried over magnesium sulfate, filtered, and concentrated to yield 7-bromo-3-methyl-imidazo[4,5-c]pyridine (9.00 g, 80%) as a yellow solid; 1H NMR (500 MHz, DMSO-d6) 3.96 (3H, s), 8.48 (1H, s), 8.51 (1H, s), 8.97 (1H, s); m/z: (ES+), [M+H]+=212.0

Intermediate 4

3-Methyl-7-(4,4,5,5-tetramethyl-1,3,2-dioxaborolan-2-yl)imidazo[4,5-c]pyridine

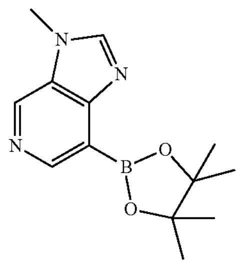 [SMILES: Cn1cnc2c(B3OC(C)(C)C(C)(C)O3)cncc21]

A mixture of 7-bromo-3-methyl-imidazo[4,5-c]pyridine (24.00 g, 113 mmol), bis(pinacolato)diboron (35.90 g, 141.5 mmol), palladium(II) acetate (2.54 g, 11.3 mmol), cataCXium A (8.12 g, 22.6 mmol), and potassium acetate (33.30 g, 339.5 mmol) was evacuated and backfilled three times with nitrogen. 2-Methyltetrahydrofuran (700 mL) was added, and the mixture was evacuated and backfilled with nitrogen two more times. The resulting mixture was stirred at 80° C. for 16 h. The reaction was then allowed to cool to room temperature, diluted with DCM (700 mL), filtered through Celite, and concentrated. The resulting residue was used in the subsequent step without further purification.

Intermediate 5

(3-Methylimidazo[4,5-c]pyridin-7-yl)boronic acid

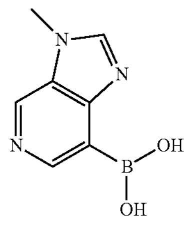

Dichlorobis(tricyclohexylphosphine)palladium(II) (418 mg, 0.570 mmol) was added to a suspension of 7-bromo-3-methyl-3H-imidazo[4,5-c]pyridine (600 mg, 2.83 mmol), bis(pinacolato)diboron (2.16 g, 8.49 mmol), and potassium acetate (833 mg, 8.49 mmol) in toluene (2 mL) under nitrogen. The resulting mixture was stirred at 100° C. for 16 hours. The reaction was then concentrated. The resulting residue was purified by silica gel chromatography, using 0 to 10% MeCN-water as eluent, and 0.1% formic acid as modifier, to afford (3-methyl-3H-imidazo[4,5-c]pyridin-7-yl)boronic acid (460 mg crude) as a white solid. m/z: (ES+), [M+H]+=178.1

Intermediate 6

2-(3-Methylimidazo[4,5-c]pyridin-7-yl)-1,3,6,2-dioxazaborocane

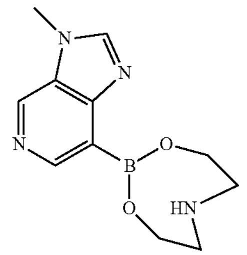 [SMILES: Cn1cnc2c(B3OCCNCCO3)cncc21]

A suspension of 7-bromo-3-methyl-imidazo[4,5-c]pyridine (29.7 g, 140 mmol), bis(pinacolato)diboron (42.7 g, 168 mmol), Palladium(II) acetate (3.14 g, 14.0 mmol), cataCXium A (10.04 g, 28.00 mmol), and potassium acetate (41.2 g, 420.00 mmol) in 2-methyl tetrahydrofuran (879 mL) sparged with argon for 20 min. The resulting mixture was stirred at 86° C. under argon for 16 h. The reaction was then allowed to cool to room temperature, then diluted with DCM (879 mL), filtered through a pad of celite, and washed twice with DCM (100 mL each). The resulting filtrate was concentrated. The resulting solid was redissolved in 2-methyl tetrahydrofuran (281 mL) and acetonitrile (167 mL). Diethanolamine (16.88 mL, 175.0 mmol) was added. The resulting mixture was stirred at room temperature for 16 h. Additional 2-methyl tetrahydrofuran (50 mL) and diethanolamine (6.75 mL, 70 mmol) were added. The resulting mixture was stirred at room temperature for 5 h. The reaction was then filtered and washed with MeCN to afford 2-(3-methyl-3H-imidazo[4,5-c]pyridin-7-yl)-1,3,6,2-dioxazaborocane (30.0 g, 87% yield) as a light yellow solid. 1H NMR (500 MHz, Deuterium oxide) 3.02 (4H, br t), 3.78 (4H, br t), 3.94 (3H, s), 8.32 (1H, s), 8.34 (1H, s), 8.77 (1H, s). The NH proton exchanged in $D_2O$.

Example 1

6-(1-Methylbenzimidazol-4-yl)-3-(4-morpholinoanilino)pyrazine-2-carboxamide

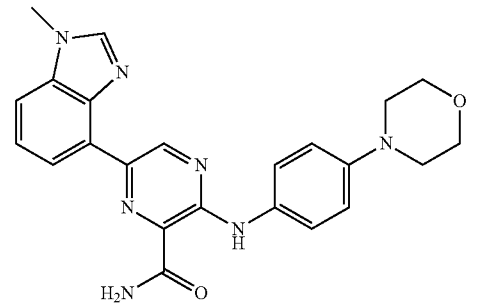 [SMILES: Cn1cnc2c(-c3cnc(Nc4ccc(N5CCOCC5)cc4)c(C(N)=O)n3)cccc21]

(a) Methyl 6-bromo-3-(4-morpholinoamino)pyrazine-2-carboxylate

Triethylamine (0.141 mL, 1.01 mmol) was added to a solution of methyl 3,6-dibromopyrazine-2-carboxylate (100 mg, 0.34 mmol) and 4-morpholinoaniline (60 mg, 0.34 mmol) in MeOH (10 mL) at 25° C. The resulting mixture was stirred at 70° C. for 16 hours. The solvent was then removed under reduced pressure. The residue was purified by silica gel chromatography, using 60-70% EtOAc-petroleum ether as eluent to afford methyl 6-bromo-3-(4-morpholinoanilino)pyrazine-2-carboxylate (80 mg, 60%) as a red solid; 1H NMR (300 MHz, DMSO-d6) δ 3.05 (4H, t), 3.72 (4H, t), 3.90 (3H, s), 6.92 (2H, d), 7.40 (2H, d), 8.49 (1H, s), 9.74 (1H, s); m/z: (ES+), [M+H]+=393.1.

(b) 6-Bromo-3-(4-morpholinoanilino)pyrazine-2-carboxamide

7 N Methanolic ammonia (30 mL, 210 mmol) was added to methyl 6-bromo-3-(4-morpholinoanilino)pyrazine-2-carboxylate (2.00 g, 5.09 mmol) at 25° C. The resulting mixture was stirred at 60° C. for 2 hours. The solvent was then removed under reduced pressure to afford 6-bromo-3-(4-morpholinoanilino)pyrazine-2-carboxamide (1.80 g, 94%) as a red solid; 1H NMR (400 MHz, DMSO-d6) δ 3.05-3.10 (4H, m), 3.70-3.79 (4H, m), 6.91-6.98 (2H, m), 7.44-7.49 (2H, m), 8.02 (1H, s), 8.27 (1H, s), 8.47 (1H, s), 10.99 (1H, s); m/z: (ES−), [M−H]−=377.1

(c) 6-(1-Methylbenzimidazol-4-yl)-3-(4-morpholinoanilino)pyrazine-2-carboxamide 1,1'-Bis(di-tert-butylphosphino)ferrocene palladium dichloride (35 mg, 0.050 mmol) was added to (1-methylbenzimidazol-4-yl)boronic acid (186 mg, 1.06 mmol), 6-bromo-3-((4-morpholinophenyl)amino)pyrazine-2-carboxamide (200 mg, 0.53 mmol) and potassium carbonate (219 mg, 1.59 mmol) in 1,4-dioxane (8 mL) and water (2 mL) at 25° C. under nitrogen. The resulting mixture was stirred at 100° C. for 4 hours. The solvent was removed under reduced pressure. The residue was purified by preparative HPLC, using a 5 micron, 50 mm×150 mm XBridge Prep C18 OBD column, decreasingly polar mixtures of MeCN—$H_2O$ as eluent, and 0.1% formic acid as modifier, to afford 6-(1-methylbenzimidazol-4-yl)-3-(4-morpholinoanilino)pyrazine-2-carboxamide (100 mg, 44%) as a brown solid; 1H NMR (400 MHz, DMSO-d6) δ 3.14 (4H, s), 3.79 (4H, s), 4.04 (3H, s), 7.06 (2H, s), 7.52-7.71 (3H, m), 7.85 (1H, d), 8.13 (1H, d), 8.24 (1H, d), 8.53 (1H, s), 9.12 (1H, s), 9.47 (1H, s), 11.25 (1H, s); m/z: (ES+) [M+H]+=430.3.

Example 2

5-Methyl-6-(1-methylbenzimidazol-4-yl)-3-(4-morpholinoanilino)pyrazine-2-carboxamide

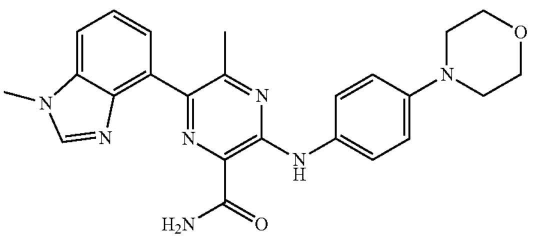 [SMILES: Cc1nc(Nc2ccc(N3CCOCC3)cc2)c(C(N)=O)nc1-c1cccc2c1ncn2C]

(a) 3-Amino-6-bromo-5 methyl-pyrazine-2-carboxylic acid

N-Bromosuccinimide (209.0 g, 1175 mmol) was added to 3-amino-5-methyl-pyrazine-2-carboxylic acid (180.0 g, 1175 mmol) in acetonitrile (1.4 L). The resulting mixture was stirred at 82° C. for 30 minutes. The reaction was then cooled to 0° C. The resulting precipitate was isolated by filtration, washed with acetonitrile, and dried under vacuum to afford 3-amino-6-bromo-5-methyl-pyrazine-2-carboxylic acid (248 g, 91% yield) as a beige solid. 1H NMR (400 MHz, DMSO) δ 2.37 (3H, s), 7.36 (2H, s), 13.08 (1H, br s).

(b) Methyl-3-amino-6-bromo-5-methyl-pyrazine-2-carboxylate

Sulfuric acid (6.00 mL, 113 mmol) was added to a suspension of 3-amino-6-bromo-5-methyl-pyrazine-2-carboxylic acid (9.06 g, 39.1 mmol) in MeOH (200 mL). The resulting mixture was stirred at 70° C. for 17 hours. The reaction was then concentrated. The resulting residue was taken up in water, basified with saturated aqueous sodium carbonate. The resulting precipitate was collected via filtration, washed with water, and dried under vacuum to afford methyl 3-amino-6-bromo-5-methyl-pyrazine-2-carboxylate (8.41 g, 88%) as a purple solid; 1H NMR (500 MHz, DMSO-d6) 2.45 (3H, s), 3.82 (3H, s), 7.45 (2H, br s). m/z: (ES+), [M+2+H]=248.0

(c) Methyl 3-amino-5-methyl-6-(1-methylbenzimidazol-4-yl)pyrazine-2-carboxylate

MeOH (14 mL) was added to a mixture of (1-methylbenzimidazol-4-yl)boronic acid (0.499 g, 2.84 mmol), methyl 3-amino-6-bromo-5-methyl-pyrazine-2-carboxylate (0.540 g, 2.19 mmol), CsF (1.000 g, 6.58 mmol) and $PdCl_2$(dppf) (0.161 g, 0.22 mmol). The resulting mixture was degassed and purged with nitrogen, then stirred at 100° C. for 1 hour in a Biotage microwave reactor. The reaction mixture was then concentrated. The residue was purified by silica gel chromatography, using 0-9% MeOH-DCM as eluent, to afford methyl 3-amino-5-methyl-6-(1-methylbenzimidazol-4-yl)pyrazine-2-carboxylate (0.646 g, 99%) as a brown solid; 1H NMR (500 MHz, DMSO-d6) 2.26 (3H, s), 3.80 (3H, s), 3.88 (3H, s), 7.21 (1H, dd), 7.32 (2H, s), 7.36 (1H, t), 7.64 (1H, dd), 8.20 (1H, s); m/z: (ES+) [M+H]+=298.1.

(d) Methyl 5-methyl-6-(1-methylbenzimidazol-4-yl)-3-(4-morpholinoanilino)pyrazine-2-carboxylate 1,4-dioxane (30 mL) was added to a mixture of methyl 3-amino-5-methyl-6-(1-methylbenzimidazol-4-yl)pyrazine-2-carboxylate (1.18 g, 3.98 mmol), 4-(4-bromophenyl)morpholine (0.963 g, 3.98 mmol), BrettPhos Pd G3 (0.721 g, 0.800 mmol) and cesium carbonate (3.89 g, 11.9 mmol). The resulting mixture was degassed and purged with nitrogen three times, then stirred at 100° C. for 7 hours. The reaction mixture was then treated with water and the resulting precipitate was filtered, washed with water, and dried under vacuum. The resulting solid was purified by silica gel chromatography four times, once using 0-5% MeOH-DCM as eluent and subsequent times using 0-3% MeOH-DCM as eluent, to afford methyl 5-methyl-6-(1-methylbenzimidazol-4-yl)-3-(4-morpholinoanilino)pyrazine-2-carboxylate (0.912 g, 50%) as an orange solid; 1H NMR (500 MHz, DMSO-d6) 2.32 (3H, s), 3.05-3.11 (4H, m), 3.71-3.77 (4H, m), 3.87 (3H, s), 3.89 (3H, s), 6.94-6.99 (2H, m), 7.27 (1H, dd), 7.39 (1H, t), 7.58-7.62 (2H, m), 7.66 (1H, dd), 8.21 (1H, s), 9.86 (1H, s); m/z: (ES+) [M+H]+=459.3.

(e) 5-Methyl-6-(1-methylbenzimidazol-4-yl)-3-(4-morpholinoanilino)pyrazine-2-carboxamide 7 N Methanolic ammonia (20 mL, 140 mmol) was added to methyl 5-methyl-6-(1-methylbenzimidazol-4-yl)-3-(4-morpholinoanilino)pyrazine-2-carboxylate (0.538 g, 1.17 mmol). The resulting mixture was stirred at 40° C. for 16 hours. Additional 7 N methanolic ammonia (10 mL, 70 mmol) was added, and the reaction mixture was stirred at 40° C. for 5 hours. The reaction was then filtered and washed with MeOH. The resulting solid was purified by silica gel chromatography, using 0-5% MeOH-DCM as eluent, to afford a yellow solid. This material was purified further by reverse phase chromatography, C18, using 10-60% MeCN—$H_2O$ as eluent and 0.2% ammonium hydroxide as modifier, to afford 5-methyl-6-(1-methylbenzimidazol-4-yl)-3-(4-morpholinoanilino)pyrazine-2-carboxamide (0.438 g, 84%) as a yellow solid; 1H NMR (500 MHz, DMSO-d6) 2.35 (3H, s), 3.03-3.10 (4H, m), 3.71-3.77 (4H, m), 3.88 (3H, s), 6.96 (2H, d), 7.36-7.41 (2H, m), 7.61 (2H, d), 7.63-7.67 (1H, m), 7.81 (1H, br d), 8.02 (1H, br d), 8.22 (1H, s), 11.01 (1H, s); m/z: (ES+) [M+H]+=444.2.

Example 3

5-Methoxy-6-(1-methylbenzimidazol-4-yl)-3-(4-morpholinoanilino)pyrazine-2-carboxamide

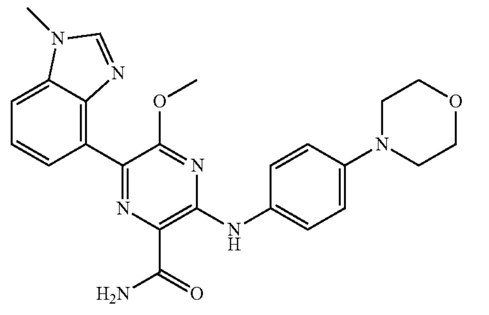 [SMILES: COc1nc(Nc2ccc(N3CCOCC3)cc2)c(C(N)=O)nc1-c1cccc2c1ncn2C]

(a) Methyl 3-amino-6-chloro-5-methoxy-pyrazine-2-carboxylate

Methyl 3-amino-5,6-dichloropyrazine-2-carboxylate (10 g, 45 mmol) and potassium carbonate (18.7 g, 135 mmol) were suspended in MeOH (175 mL). The resulting suspension was stirred at 25° C. for 16 hours. The solvent was removed under reduced pressure and the resulting residue was suspended in water (400 mL). The resulting suspension was stirred vigorously at 25° C. for 2 hours. The suspension was filtered and the filter cake was dried under vacuum to afford methyl 3-amino-6-chloro-5-methoxy-pyrazine-2-carboxylate (6.9 g, 70%) as a beige solid; 1H NMR (500 MHz, DMSO-d6) 3.79 (3H, s), 3.96 (3H, s), 7.60 (2H, br s); m/z: (ES+), [M+H]+=218.1

(b) Methyl 6-chloro-3-fluoro-5-methoxy-pyrazine-2-carboxylate

Sodium nitrite (2.3 g, 33 mmol) was added portion-wise to a stirred suspension of methyl 3-amino-6-chloro-5-methoxy-pyrazine-2-carboxylate (6.90 g, 31.7 mmol) in HF-pyridine (20 mL, 580 mmol) at −10° C. The resulting suspension was stirred at 25° C. for 1 hour. The reaction was then diluted with DCM (50 mL) and quenched with water (200 mL). The layers were separated and the aqueous layer was extracted twice with DCM (20 mL each). The combined organics were dried over magnesium sulfate, filtered, and concentrated to afford methyl 6-chloro-3-fluoro-5-methoxy-pyrazine-2-carboxylate (6.80 g, 97%) as a peach solid; 1H NMR (500 MHZ, DMSO-d6) 3.87 (3H, s), 4.06 (3H, s); m/z: (ES+), [M+H]+=221.1.

(c) Methyl 6-chloro-5-methoxy-3-(4-morpholinoanilino)pyrazine-2-carboxylate

DIPEA (6 mL, 34.35 mmol) was added to a solution of methyl 6-chloro-3-fluoro-5-methoxy-pyrazine-2-carboxylate (6.80 g, 30.8 mmol) and 4-morpholinoaniline (5.77 g, 32.4 mmol) in DMF (18 mL). The resulting solution was stirred at 100° C. for 15 minutes. The reaction was then removed from heat and allowed to cool to room temperature. The reaction was filtered, rinsing sparingly with EtOAc, to afford methyl 6-chloro-5-methoxy-3-(4-morpholinoanilino)pyrazine-2-carboxylate (9.28 g, 79%) as a yellow solid; 1H NMR (500 MHz, DMSO-d6) 2.93-3.13 (4H, m), 3.61-3.78 (4H, m), 3.86 (3H, s), 3.98 (3H, s), 6.95 (2H, d), 7.50 (2H, d), 10.01 (1H, s); m/z: (ES+), [M+H]+=379.5.

(d) Methyl 5-methoxy-6-(1-methylbenzimidazol-4-yl)-3-(4-morpholinoanilino)pyrazine-2-carboxylate The reaction was run in quintuplicate to fit in microwave vials. In each vial, methyl 6-chloro-5-methoxy-3-(4-morpholinoanilino)pyrazine-2-carboxylate (1.73 g, 4.57 mmol), 1-methyl-4-(4,4,5,5-tetramethyl-1,3,2-dioxaborolan-2-yl) benzimidazole (2.43 g, 63 wt %, 5.94 mmol), Pd(dppf)$Cl_2$ (0.400 g, 0.490 mmol), and cesium fluoride (2.08 g, 13.7 mmol) were combined and purged under nitrogen. MeOH (15 mL) was added to each and each reaction was stirred at 100° C. for 3 hours in a Biotage microwave reactor. The reaction vials were then combined, concentrated, loaded onto Celite, and purified via silica gel chromatography using 0-10% methanol-DCM as eluent and 0-1% ammonia as modifier, to afford an orange solid. Methanol (30 mL) was added to the solid and the resulting suspension was stirred at 40° C. for 1 hour, then allowed to stand at 25° C. for 30 minutes. The suspension was filtered, rinsing sparingly with methanol, to afford methyl 5-methoxy-6-(1-methylbenzimidazol-4-yl)-3-(4-morpholinoanilino)pyrazine-2-carboxylate (9.99 g, 92%) as a yellow solid; 1H NMR (500 MHz, DMSO-d6) 3.05-3.11 (4H, m), 3.69-3.75 (4H, m), 3.84 (3H, s), 3.84 (3H, s), 3.86 (3H, s), 6.98 (2H, d), 7.18-7.29 (1H, m), 7.33 (1H, t), 7.55-7.71 (3H, m), 8.13 (1H, s), 10.16 (1H, s); m/z: (ES+), [M+H]+=475.4

(e) 5-Methoxy-6-(1-methylbenzimidazol-4-yl)-3-(4-morpholinoanilino)pyrazine-2-carboxamide The reaction was run in quintuplicate to fit in microwave vials. In each vial, methyl 5-methoxy-6-(1-methylbenzimidazol-4-yl)-3-(4-morpholinoanilino)pyrazine-2-carboxylate (2.00 g, 4.22 mmol) was suspended in 7 N methanolic ammonia (20 mL, 140 mmol). Each reaction was stirred at 100° C. for 8 hours in a Biotage microwave reactor. The reaction vials were allowed to cool, then combined, filtered, and rinsed sparingly with MeOH to afford 8.0 g of a yellow solid. This material was combined with 3.64 g of another batch of the same material, which was then loaded onto celite and purified by silica gel chromatography, using 0-5% MeOH-DCM as eluent and 0-0.5% ammonia as modifier, to afford a yellow solid. Methanol (70 mL) was added and the resulting suspension was stirred at 40° C. for 1 hour, then allowed to stand at 25° C. for 1 hour. The suspension was filtered and dried under vacuum to afford 5-methoxy-6-(1-methylbenzimidazol-4-yl)-3-(4-morpholinoanilino)pyrazine-2-carboxamide (9.77 g, 84%) as a yellow solid; 1H NMR (600 MHz, DMSO-d6) 3.03-3.12 (4H, m), 3.68-3.76 (4H, m), 3.86 (3H, s), 3.89 (3H, s), 6.92-7.01 (2H, m), 7.33 (1H, t), 7.45 (1H, dd), 7.56-7.62 (3H, m), 7.64 (1H, d), 7.85 (1H, d), 8.16 (1H, s), 11.18 (1H, s); m/z: (ES+), [M+H]+=460.4

Example 4

5-[2-(Dimethylamino)ethoxy]-6-(1-methylbenzimidazol-4-yl)-3-(4-morpholinoanilino)pyrazine-2-carboxamide

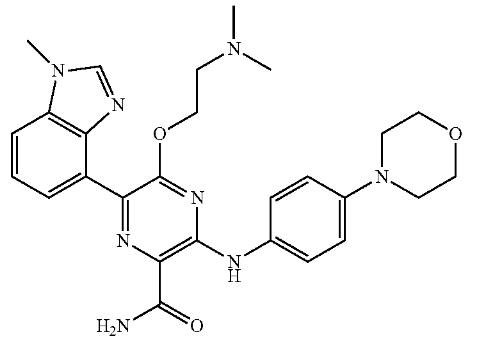 [SMILES: CN(C)CCOc1nc(Nc2ccc(N3CCOCC3)cc2)c(C(N)=O)nc1-c1cccc2c1ncn2C]

(a) Methyl 3-amino-6-chloro-5-[2-(dimethylamino)ethoxy]pyrazine-2-carboxylate

Sodium (0.311 g, 13.5 mmol) was added to methyl 3-amino-5,6-dichloro-pyrazine-2-carboxylate (3.00 g, 13.5 mmol), and 2-(dimethylamino) ethanol (5.00 mL, 13.5 mmol). The resulting mixture was stirred at 25° C. for 3 hours. The solvent was then removed under reduced pressure. The residue was purified by silica chromatography, using 0-20% MeOH-DCM as eluent, to afford methyl 3-amino-6-chloro-5-[2-(dimethylamino)ethoxy]pyrazine-2-carboxylate (1.50 g, 40%) as a yellow gum. 1H NMR (300 MHz, DMSO-d6) δ 2.21 (6H, s), 2.65 (2H, t), 3.79 (3H, s), 4.44 (2H, t), 7.59 (2H, s); m/z: (ES+), [M+H]+=275.0.

(b) Methyl 3-amino-5-[2-(dimethylamino)ethoxy]-6-(1-methylbenzimidazol-4-yl)pyrazine-2-carboxylate 1,4-dioxane (10 mL) was added to a mixture of (1-methylbenzimidazol-4-yl) boronic acid (480 mg, 2.73 mmol), methyl 3-amino-6-chloro-5-[2-(dimethylamino)ethoxy]pyrazine-2-carboxylate (500 mg, 1.82 mmol), CsF (829 mg, 5.46 mmol), and $PdCl_2$(dppf)-DCM adduct (223 mg, 0.27 mmol). The resulting mixture was stirred at 100° C. for 2 hours. The solvent was then removed under reduced pressure. The residue was purified by C18 reverse phase chromatography, using 0-50% MeCN—$H_2O$ as eluent, and 10 mM ammonium bicarbonate as modifier, to afford methyl 3-amino-5-[2-(dimethylamino)ethoxy]-6-(1-methylbenzimidazol-4-yl)pyrazine-2-carboxylate (180 mg, 27%) as a yellow gum; 1H NMR (300 MHz, DMSO-d6) δ 2.04 (6H, s), 2.40-2.5 (2H, m), 3.78 (3H, s), 3.87 (3H, s), 4.25-4.40 (2H, m), 7.21 (1H, d), 7.32 (1H, t), 7.50 (2H, s), 7.60 (1H, d), 8.14 (1H, s); m/z: (ES+), [M+H]+=371.3.

(c) 5-[2-(Dimethylamino)ethoxy]-6-(1-methylbenzimidazol-4-yl)-3-(4-morpholinoanilino)pyrazine-2-carboxylic acid 1,4-Dioxane (18 mL) was added to a mixture of methyl 3-amino-5-[2-(dimethylamino)ethoxy]-6-(1-methylbenzimidazol-4-yl)pyrazine-2-carboxylate (170 mg, 0.46 mmol), 4-(4-bromophenyl) morpholine (220 mg, 0.92 mmol), BrettPhos Pd G3 (62 mg, 0.070 mmol), and cesium carbonate (449 mg, 1.38 mmol). The resulting mixture was stirred at 25° C. for 8 hours. The solvent was removed under reduced pressure. The resulting residue was purified by C18 reverse phase chromatography, using 0-50% MeCN—H2O as eluent, to afford 5-[2-(dimethylamino)ethoxy]-6-(1-methylbenzimidazol-4-yl)-3-(4-morpholinoanilino)pyrazine-2-carboxylic acid (80 mg, 34%) as a yellow gum; 1H NMR (300 MHz, DMSO-d6) δ 2.39 (6H, s), 2.81-2.96 (2H, m), 3.04-3.12 (4H, m), 3.69-3.79 (4H, m), 3.89 (3H, s), 4.49-4.61 (2H, m), 6.96 (2H, d), 7.39 (2H, s), 7.51-7.72 (3H, m), 8.34 (1H, s); NH and COOH signals were broadened to the baseline; m/z: (ES+) [M+H]+=518.4.

(d) 5-[2-(Dimethylamino)ethoxy]-6-(1-methylbenzimidazol-4-yl)-3-(4-morpholinoanilino)pyrazine-2-carboxamide Triethylamine (0.061 mL, 0.43 mmol) was added to a suspension of 5-[2-(dimethylamino)ethoxy]-6-(1-methylbenzimidazol-4-yl)-3-(4-morpholinoanilino)pyrazine-2-carboxylic acid (75 mg, 0.14 mmol), ammonium chloride (47 mg, 0.87 mmol), and HATU (72 mg, 0.19 mmol) in DMF (5 mL). The resulting mixture was stirred at 25° C. for 2 hours. The solvent was then removed under reduced pressure. The resulting residue was purified by reverse phase chromatography on c18, using 0-100% MeCN—$H_2O$ as eluent and 10 mmol/L ammonium bicarbonate as modifier, to afford 5-[2-(dimethylamino)ethoxy]-6-(1-methylbenzimidazol-4-yl)-3-(4-morpholinoanilino)pyrazine-2-carboxamide (28.0 mg, 37%) as a yellow solid; 1H NMR (400 MHZ, DMSO-d6) δ 2.13 (6H, s), 3.08 (4H, t), 3.30 (2H, s), 3.71-3.78 (4H, m), 3.87 (3H, s), 4.44 (2H, s), 6.97 (2H, d), 7.34 (1H, t), 7.54 (2H, d), 7.57-7.62 (2H, m), 7.67 (1H, s), 7.88 (1H, s), 8.21 (1H, s), 11.14 (1H, s); m/z: (ES+), [M+H]+=517.6.

Example 5

5-Cyclopropyl-6-(1-methylbenzimidazol-4-yl)-3-(4-morpholinoanilino)pyrazine-2-carboxamide

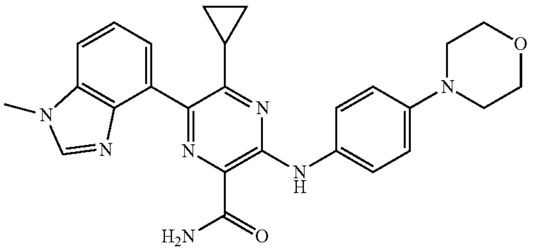 [SMILES: Cn1cnc2c(-c3nc(C(N)=O)c(Nc4ccc(N5CCOCC5)cc4)nc3C3CC3)cccc21]

(a) Methyl 3-amino-6-chloro-5-cyclopropyl-pyrazine-2-carboxylate

Potassium cyclopropyltrifluoroborate (0.800 g, 5.40 mmol) was added to a suspension of methyl 3-amino-5,6-dichloro-pyrazine-2-carboxylate (1.00 g, 4.50 mmol), palladium (II) acetate (0.15 g, 0.68 mmol), cataCXium A (0.484 g, 1.35 mmol) and cesium carbonate (2.93 g, 9.01 mmol) in water (1.5 mL) and toluene (15 mL). The resulting mixture was stirred at 100° C. for 10 hours. The solvent was then removed under reduced pressure. The resulting residue was purified by silica gel chromatography, using 0-30% EtOAc-pentane as eluent, to afford methyl 3-amino-6-chloro-5- cyclopropyl-pyrazine-2-carboxylate (0.65 g, 63%) as a yellow solid; 1H NMR (300 MHz, DMSO-d6) δ 1.02 (2H, d), 1.11 (2H, dt), 2.36 (1H, tt), 3.77 (3H, s), 7.35 (2H, s). m/z: (ES+), [M+H]+=227.90

(b) Methyl 3-amino-5-cyclopropyl-6-(1-methylbenzimidazol-4-yl)pyrazine-2-carboxylate (1-Methylbenzimidazol-4-yl) boronic acid (580 mg, 3.3 mmol) was added to a suspension of methyl 3-amino-6-chloro-5-cyclopropyl-pyrazine-2-carboxylate (625 mg, 2.75 mmol), $PdCl_2$(dppf) (402 mg, 0.550 mmol) and CsF (1.25 g, 8.24 mmol) in 1,4-dioxane (10 mL). The resulting mixture was stirred at 100° C. for 14 hours. The reaction mixture was then filtered through celite and the solvent was removed under reduced pressure. The resulting residue was purified by reverse phase chromatography on c18, using 0-30% MeCN—$H_2O$ as eluent and 0.1% formic acid as modifier, to afford methyl 3-amino-5-cyclopropyl-6-(1-methylbenzimidazol-4-yl)pyrazine-2-carboxylate (405 mg, 46%) as a yellow solid; 1H NMR (300 MHz, DMSO-d6) δ 0.81 (2H, dt), 0.98 (2H, q), 1.78 (1H, tt), 3.79 (3H, s), 3.91 (3H, s), 7.25 (2H, s), 7.38 (1H, t), 7.65 (1H, dd), 8.19 (2H, s). m/z: (ES+), [M+H]+=324.2.

(c) Methyl 5-cyclopropyl-6-(1-methylbenzimidazol-4-yl)-3-(4-morpholinoanilino)pyrazine-2-carboxylate 4-(4-Bromophenyl) morpholine (313 mg, 1.29 mmol) was added to a suspension of methyl 3-amino-5-cyclopropyl-6-(1-methylbenzimidazol-4-yl)pyrazine-2-carboxylate (380 mg, 1.18 mmol), cesium carbonate (766 mg, 2.35 mmol) and Brettphos Pd G3 (107 mg, 0.120 mmol) in 1,4-dioxane (4 mL). The resulting mixture was stirred at 100° C. for 12 hours. The solvent was then removed under reduced pressure. The resulting residue was purified by silica gel chromatography, using 0-10% MeOH-DCM as eluent, to afford methyl 5-cyclopropyl-6-(1-methylbenzimidazol-4-yl)-3-(4-morpholinoanilino)pyrazine-2-carboxylate (130 mg, 23%) as an orange solid; 1H NMR (300 MHz, DMSO-d6) δ 0.76-0.94 (4H, m), 1.83-1.95 (1H, m), 3.09-3.11 (4H, m), 3.71-3.80 (4H, m), 3.80 (3H, s), 3.87 (3H, s), 6.95-7.01 (2H, m), 7.25 (1H, d), 7.27-7.31 (1H, m), 7.40 (2H, q), 7.51-7.56 (2H, m), 9.90 (1H, s); m/z: (ES+), [M+H]+=485.2

(d) 5-Cyclopropyl-6-(1-methylbenzimidazol-4-yl)-3-(4-morpholinoanilino)pyrazine-2-carboxamide 7 N Methanolic ammonia (6.0 mL, 42 mmol) was added to methyl 5-cyclopropyl-6-(1-methylbenzimidazol-4-yl)-3-(4-morpholinoanilino)pyrazine-2-carboxylate (110 mg, 0.23 mmol). The resulting suspension was stirred at 70° C. for 3 hours. The solvent was then removed under reduced pressure. The resulting residue was purified by preparative HPLC Column, using a SunFire C18 OBD 5 μm, 19 mm×250 mm as the column, 19%-33% MeCN/$H_2O$ as eluent and 0.05% trifluoroacetic acid as modifier, to afford 5-cyclopropyl-6-(1-methylbenzimidazol-4-yl)-3-(4-morpholinoanilino)pyrazine-2-carboxamide (35 mg, 33%) as an orange solid; 1H NMR (400 MHZ, DMSO-d6) δ 1.00 (2H, dt), 1.13 (2H, dt), 1.98 (1H, dq), 3.04-3.19 (4H, m), 3.72-3.80 (4H, m), 4.09 (3H, s) 6.94-7.02 (2H, m), 7.51-7.57 (2H, m), 7.66-7.79 (2H, m), 7.88 (1H, s), 7.95-8.05 (2H, m), 9.41 (1H, br s), 11.15 (1H, s); m/z: (ES+), [M+H]+=470.2.

Example 6

5-Methyl-6-(3-methylimidazo[4,5-c]pyridin-7-yl)-3-(4-morpholinoanilino)pyrazine-2-carboxamide

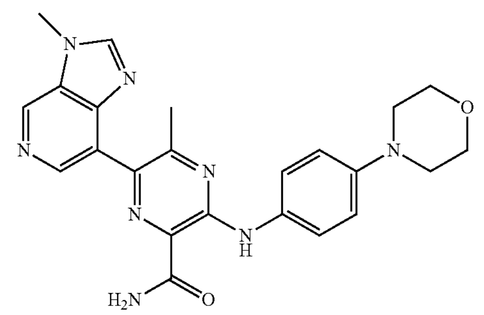

(a) Methyl 3-amino-5-methyl-6-(3-methylimidazo[4,5-c]pyridin-7-yl)pyrazine-2-carboxylate $PdCl_2$(dppf) (370 mg, 0.51 mmol) was added a suspension of CsF (773 mg, 5.09 mmol), methyl 3-amino-6-chloro-5-methyl-pyrazine-2-carboxylate (513 mg, 2.54 mmol) and (3-methylimidazo[4,5-c]pyridin-7-yl) boronic acid (450 mg, 2.54 mmol) in 1,4-dioxane (15 mL) under nitrogen. The resulting mixture was stirred at 100° C. for 16 hours. The solvent was then removed under reduced pressure. The resulting residue was purified by silica gel chromatography, using 0-10% MeOH-DCM as eluent, to afford methyl 3-amino-5-methyl-6-(3-methylimidazo[4,5-c]pyridin-7-yl) pyrazine-2-carboxylate (300 mg, 40% yield) as a yellow solid; 1H NMR (400 MHZ, DMSO-d6) δ 2.30 (3H, s), 3.82 (3H, s), 4.00 (3H, s), 7.41 (2H, s), 8.37 (1H, s), 8.43 (1H, s), 9.06 (1H, s); m/z: (ES+), [M+H]+=299.1

(b) Methyl 5-methyl-6-(3-methylimidazo[4,5-c]pyridin-7-yl)-3 (4-morpholinoanilino)pyrazine-2-carboxylate Methyl 3-amino-5-methyl-6-(3-methylimidazo[4,5-c]pyridin-7-yl)pyrazine-2-carboxylate (280 mg, 0.94 mmol) was added to a suspension of 4-(4-bromophenyl) morpholine (227 mg, 0.940 mmol), cesium carbonate (612 mg, 1.88 mmol) and Brettphos Pd G3 (170 mg, 0.19 mmol) in 1,4-dioxane (15 mL). The resulting mixture was stirred at 100° C. for 16 hours. The solvent was removed under reduced pressure. The resulting residue was purified by silica gel chromatography, using 0-40% MeOH-DCM as eluent, to afford methyl 5-methyl-6-(3-methylimidazo[4,5-c]pyridin-7-yl)-3-(4-morpholinoanilino)pyrazine-2-carboxylate (200 mg, 46%) as a yellow solid; 1H NMR (400 MHZ, DMSO-d6) δ 2.37 (3H, s), 3.10 (4H, t), 3.75 (4H, s), 3.90 (3H, s), 4.01 (3H, s), 6.98 (2H, d), 7.61 (2H, d), 8.40 (1H, s), 8.45 (1H, s), 9.06 (1H, s), 9.90 (1H, s); m/z: (ES+), $[M+2H]^{2+}$=230.7.

(c) 5-Methyl-6-(3-methylimidazo[4,5-c]pyridin-7-yl)-3-(4-morpholinoanilino)pyrazine-2-carboxamide 7 N Methanolic ammonia (8.0 mL, 56 mmol) was added to methyl 5-methyl-6-(3-methyl-3H-imidazo[4,5-c]pyridin- 7-yl)-3-((4-morpholinophenyl)amino) pyrazine-2-carboxylate (190 mg, 0.41 mmol). The resulting suspension was stirred at 80° C. for 1 hours. The solvent was then removed under reduced pressure. The resulting residue was purified by preparative HPLC, using a 5 micron, 30×150 mm, Sunfire prep C18 column, 10 to 28% MeCN-water as eluent, and 0.1% formic acid as modifier, to afford 5-methyl-6-(3-methylimidazo[4,5-c]pyridin-7-yl)-3-(4-morpholinoanilino) pyrazine-2-carboxamide (26 mg, 14%) as a yellow solid; 1H NMR (300 MHz, DMSO-d6) δ 2.38 (3H, s), 3.02-3.11 (4H, m), 3.69-3.78 (4H, m), 3.99 (3H, s), 6.96 (2H, d), 7.61 (2H, d), 7.83 (1H, s), 8.13 (1H, s), 8.44 (1H, s), 8.53 (1H, s), 9.02 (1H, s), 11.05 (1H, s). (ES+) [M+H]+=445.2.

Example 7

5-(Methylamino)-6-(1-methylbenzimidazol-4-yl)-3-(4-morpholinoanilino)pyrazine-2-carboxamide

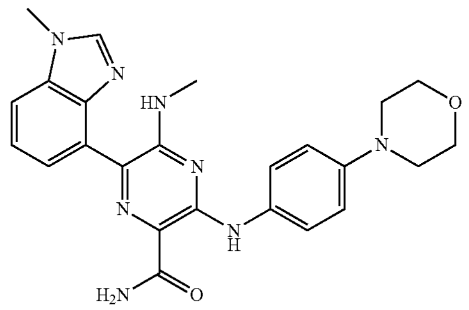 [SMILES: CNc1nc(Nc2ccc(N3CCOCC3)cc2)c(C(N)=O)nc1-c1cccc2c1ncn2C]

(a) Methyl 3-amino-6-chloro-5-(methylamino) pyrazine-2-carboxylate

2 M Methylamine in THF/MeOH (99 mL, 198.00 mmol) was added to methyl 3-amino-5,6-dichloropyrazine-2-carboxylate (11.0 g, 49.5 mmol). The resulting suspension was stirred at 25° C. for 30 minutes. It was then concentrated to half its original volume, diluted with water (200 mL), filtered, and rinsed with water. The filter cake was dried under vacuum to afford methyl 3-amino-6-chloro-5-(methylamino) pyrazine-2-carboxylate (9.88 g, 92%) as a pale yellow solid; 1H NMR (500 MHz, DMSO-d6) 2.85 (3H, d), 3.72 (3H, s), 7.25 (2H, br s), 7.53 (1H, br d). m/z: (ES+), [M+H]+=217.1

(b) Methyl 6-chloro-3-fluoro-5-(methylamino) pyrazine-2-carboxylate

Sodium nitrite (3.30 g, 47.89 mmol) was added portionwise to a suspension of methyl 3-amino-6-chloro-5-(methylamino) pyrazine-2-carboxylate (9.88 g, 45.6 mmol) in HF-pyridine (20 mL, 580 mmol) at −10° C. The reaction was stirred at 25° C. for 1 hour. The reaction was then quenched with DCM (50 mL) and water (100 mL). The layers were separated and the aqueous layer was extracted three times with DCM (50 mL each). The combined organic layers were washed with saturated aqueous ammonium chloride (50 mL). The combined aqueous layers were extracted a final time with DCM (50 mL). The combined organic layers were dried over magnesium sulfate, filtered, and concentrated to afford methyl 6-chloro-3-fluoro-5-(methylamino) pyrazine-2-carboxylate (9.50 g, 95%) as a peach-colored solid; 1H NMR (500 MHz, DMSO-d6) 2.88 (3H, d), 3.78 (3H, s), 8.34 (1H, br d); m/z: (ES+), [M+H]+=220.1

(c) Methyl 6-chloro-5-(methylamino)-3-(4-morpholinoanilino)pyrazine-2-carboxylate DIPEA (10.0 mL, 57.3 mmol) was added to a solution of methyl 6-chloro-3-fluoro-5-(methylamino) pyrazine-2-carboxylate (8.53 g, 38.8 mmol) and 4-morpholinoaniline (7.3 g, 41 mmol) in DMF (30 mL). The reaction was stirred at 100° C. for 90 minutes. The reaction was then cooled to room temperature and quenched with water (300 mL). The resulting suspension was filtered, and the filter cake was dried under vacuum to afford methyl 6-chloro-5-(methylamino)-3-(4-morpholinoanilino)pyrazine-2-carboxylate (9.48 g, 65%) as a yellow-brown solid; 1H NMR (500 MHz, DMSO-d6) 2.90 (3H, d), 3.01-3.09 (4H, m), 3.70-3.75 (4H, m), 3.79 (3H, s), 6.92 (2H, br d), 7.54 (2H, d), 7.82 (1H, br d), 10.08 (1H, s); m/z: (ES−), [M−H]−=376.4

(d) Methyl 5-(methylamino)-6-(1-methylbenzimidazol-4-yl)-3-(4-morpholinoanilino)pyrazine-2-carboxylate Methyl 6-chloro-5-(methylamino)-3-(4-morpholinoanilino)pyrazine-2-carboxylate (1.50 g, 3.97 mmol), 1-methyl-4-(4,4,5,5-tetramethyl-1,3,2-dioxaborolan-2-yl) benzimidazole (1.63 g, 69 wt %, 4.37 mmol), Pd(dppf)$Cl_2$ (0.29 g, 0.40 mmol), and cesium fluoride (1.81 g, 11.9 mmol) were combined in a microwave vial, which was then evacuated and backfilled three times with nitrogen. MeOH (15 mL) was added and the reaction was stirred at 100° C. for 8 hours in a Biotage microwave reactor. The reaction was then concentrated, loaded onto Celite, and purified by silica gel chromatography, using 0-10% MeOH-DCM as eluent and 0-1% ammonia as modifier, to afford a yellow-brown solid. This material was suspended in MeOH (40 mL), stirred at 40° C. for 30 minutes, and left to stand for 1 hour. The resulting suspension was then filtered and rinsed sparingly with MeOH to afford methyl 5-(methylamino)-6-(1-methylbenzimidazol-4-yl)-3-(4-morpholinoanilino)pyrazine-2-carboxylate (1.49 g, 79%) as a dark yellow solid; 1H NMR (500 MHZ, DMSO-d6) 2.90 (3H, d), 3.04-3.10 (4H, m), 3.68-3.78 (4H, m), 3.80 (3H, s), 3.90 (3H, s), 6.95 (2H, d), 7.36-7.44 (1H, m), 7.44-7.51 (1H, m), 7.58-7.74 (3H, m), 8.04 (1H, br d), 8.30 (1H, s), 10.23 (1H, s); m/z: (ES+), [M+H]+=474.4

(e) 5-(Methylamino)-6-(1-methylbenzimidazol-4-yl)-3-(4-morpholinoanilino)pyrazine-2-carboxylic acid bis-trifluoroacetate salt Lithium hydroxide monohydrate (2.64 g, 63.0 mmol) was added to a suspension of methyl 5-(methylamino)-6-(1-methylbenzimidazol-4-yl)-3-(4-morpholinoanilino)pyrazine-2-carboxylate (2.98 g, 6.30 mmol) in water (16 mL) and MeOH (16 mL). The resulting mixture was stirred at 100° C. for 90 minutes in a Biotage microwave reactor. The reaction was allowed to cool to room temperature, diluted with water (70 mL), and concentrated to a volume of 40 mL, then filtered and rinsed with water. The resulting yellow filter cake was purified by reverse phase chromatography, using 0-50% MeCN/$H_2O$ as eluent and 0.1% TFA as modifier, to afford 5-(methylamino)-6-(1-methylbenzimidazol-4-yl)-3-(4-morpholinoanilino)pyrazine-2-carboxylic acid (3.00 g, 70%) as an orange solid and presumed bis-trifluoroacetate salt; 1H NMR (500 MHZ, DMSO-d6) 2.87 (3H, br s), 3.04-3.11 (4H, m), 3.13-3.17 (3H, m), 3.62-3.86 (4H, m), 4.06 (3H, br s), 6.86-7.10 (2H, m), 7.12-7.46 (1H, m), 7.53-7.77 (4H, m), 7.94 (1H, br d), 8.98-9.57 (1H, m), 10.50 (1H, br s), 12.09 (1H, br s); m/z: (ES+), [M+H]+=460.3

(f) 5-(Methylamino)-6-(1-methylbenzimidazol-4-yl)-3-(4-morpholinoanilino)pyrazine-2-carboxamide DIPEA (7.00 mL, 40.1 mmol) was added to a suspension of 5-(methylamino)-6-(1-methylbenzimidazol-4-yl)-3-(4-morpholinoanilino)pyrazine-2-carboxylic acid, ditrifluoroacetate (5.52 g, 8.05 mmol), ammonium chloride (5.16 g, 96.6 mmol), and HATU (4.59 g, 12.1 mmol) in DMF (60 mL). The resulting mixture was stirred at 25° C. for 3 hours. The reaction was then diluted with saturated aqueous sodium bicarbonate (60 mL) and water (200 mL). The resulting yellow suspension was stirred at 25° C. for 30 min and was then filtered and rinsed with water. The bright yellow filtercake was dried under vacuum for 20 h to afford a yellow solid. This material was suspended in MeOH (70 mL), stirred at 40° C. for 2 hours, sonicated for 1 hour, and allowed to stand for 3 hours. The resulting suspension was filtered, rinsed sparingly with MeOH, and dried under vacuum to afford 5-(methylamino)-6-(1-methylbenzimidazol-4-yl)-3-(4-morpholinoanilino)pyrazine-2-carboxamide (3.54 g, 96%) as a yellow solid; 1H NMR (600 MHZ, DMSO-d6) 2.93 (3H, d), 3.02-3.08 (4H, m), 3.66-3.77 (4H, m), 3.90 (3H, s), 6.94 (2H, d), 7.30 (1H, br s), 7.40 (1H, t), 7.59-7.64 (3H, m), 7.64-7.68 (2H, m), 8.16 (1H, br q), 8.33 (1H, s), 11.23 (1H, s); m/z: (ES+), [M+H]+=459.4

Example 8

5-(Methylamino)-6-(3-methylimidazo[4,5-c]pyridin-7-yl)-3-(4-morpholinoanilino)pyrazine-2-carboxamide

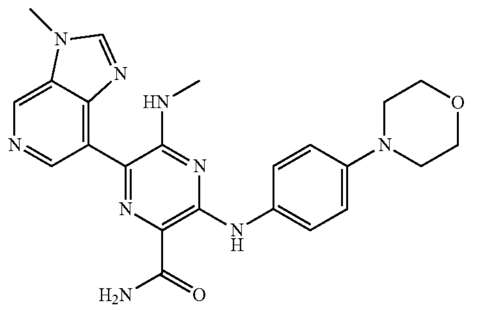 [SMILES: CNc1nc(Nc2ccc(N3CCOCC3)cc2)c(C(N)=O)nc1-c1cncc2c1ncn2C]

(a) Methyl 3-amino-6-chloro-5-(methylamino) pyrazine-2-carboxylate

33% Methanamine in EtOH (280 mL, 2.25 mol) was added to a mixture of methyl 3-amino-5,6-dichloro-pyrazine-2-carboxylate (100 g, 450 mmol) in MeOH (1 L). The resulting mixture was stirred at 65° C. for 16 h. The reaction was then cooled to 0° C., then filtered, washed with MeOH, and dried under vacuum, to afford methyl 3-amino-6-chloro-5-(methylamino) pyrazine-2-carboxylate (69.0 g, 71% yield) as a light beige solid. 1H NMR (500 MHZ, DMSO-d6) 2.87 (3H, d), 3.73 (3H, s), 7.27 (2H, br s), 7.55 (1H, br d). m/z: (ES+), [M+H]+=217.0

(b) Methyl 5-chloro-6-(methylamino)-2-oxo-1H-pyrazine-3-carboxylate

A solution of sodium nitrite (12.23 g, 177.3 mmol) in water (100 mL) was added dropwise over 2 h to a suspension of methyl 3-amino-6-chloro-5-(methylamino) pyrazine-2-carboxylate (32.00 g, 147.7 mmol) in 25% sulfuric acid (400 mL, 1.2 mol), hexane (100 mL) and water (400 mL). The resulting mixture was stirred vigorously at room temperature for 30 min. The reaction was then filtered, washed with water, and dried under vacuum to afford methyl 5-chloro-6-(methylamino)-2-oxo-1H-pyrazine-3-carboxylate (31.4 g, 98% yield) as a pale yellow solid. 1H NMR (500 MHz, DMSO-d6) 2.90 (3H, d), 3.82 (3H, s), 7.97 (1H, br d), 11.50 (1H, s). m/z: (ES+), [M+H]+=218.0

(c) Methyl 6-chloro-5-(methylamino)-3-(trifluoromethylsulfonyloxy) pyrazine-2-carboxylate Trifluoromethanesulfonic anhydride (21.4 mL, 126.4 mmol) was added dropwise to a suspension of methyl 5-chloro-6-(methylamino)-2-oxo-1H-pyrazine-3-carboxylate (25.0 g, 115 mmol) and DIPEA (40.0 mL, 230 mmol) in DCM (500 mL) at 0° C. The resulting mixture was stirred at 0° C. for 30 min. The reaction was then concentrated. The resulting solid was used in the next step without further purification.

(d) Methyl 6-chloro-5-(methylamino)-3-(4-morpholinoanilino)pyrazine-2-carboxylate A mixture of methyl 6-chloro-5-(methylamino)-3-(trifluoromethylsulfonyloxy) pyrazine-2-carboxylate (40.0 g, 114 mmol), 4-morpholinoaniline (24.47 g, 137.3 mmol) and DIPEA (59.9 mL, 343 mmol) was stirred at 100° C. for 3 h. The reaction was then allowed to cool to room temperature, diluted with EtOAc, and filtered. The resulting filtrate was washed with water, dried over sodium sulfate, filtered, and concentrated. The resulting solid was used in the next step without further purification.

(e) Methyl 5_(methylamino)-6-(3-methylimidazo[4,5-c]pyridin-7-yl)-3-(4-morpholinoanilino)pyrazine-2-carboxylate A mixture of methyl 6-chloro-5-(methylamino)-3-(4-morpholinoanilino)pyrazine-2-carboxylate (25.0 g, 66.2 mmol), 3-methyl-7-(4,4,5,5-tetramethyl-1,3,2-dioxaborolan-2-yl) imidazo[4,5-c]pyridine (20.5 g, 79.1 mmol), $PdCl_2$(dppf) dichloromethane adduct (5.40 g, 6.62 mmol), and cesium fluoride (20.10 g, 132.3 mmol) in 1,4-dioxane (500 mL) and water (50 mL) was evacuated and backfilled with nitrogen 3 times. The resulting mixture was stirred at 80° C. for 2 h. The reaction was then allowed to cool to room temperature, diluted with water (500 mL), and filtered. The filter cake was dried under vacuum. The resulting solid was used in the next step without further purification.

(f) 5-(Methylamino)-6-(3-methylimidazo[4,5-c]pyridin-7-yl)-3-(4-morpholinoanilino)pyrazine-2-carboxylic acid 2N Aqueous KOH (160 mL, 320 mmol) was added to a suspension of methyl 5-(methylamino)-6-(3-methylimidazo [4,5-c]pyridin-7-yl)-3-(4-morpholinoanilino)pyrazine-2-carboxylate (31.4 g, 66.2 mmol) in MeOH (100 mL) and THF (100 mL). The resulting mixture was stirred at 50° C.

for 1 h. The reaction was then allowed to cool to room temperature and acidified with 1N HCl (190 mL, 380 mmol). The resulting mixture was evaporated and the residue was used in the next step without further purification.

(g) 5-(Methylamino)-6-(3-methylimidazo[4,5-c]pyridin-7-yl)-3-(4-morpholinoanilino)pyrazine-2-carboxamide DIPEA (69.4 mL, 397 mmol) was added to a mixture of 5-(methylamino)-6-(3-methylimidazo[4,5-c]pyridin-7-yl)-3-(4-morpholinoanilino)pyrazine-2-carboxylic acid (30.5 g, 66.2 mmol), ammonium chloride (14.17 g, 264.9 mmol), and HATU (50.40 g, 132.5 mmol) in DMF (400 mL). The reaction mixture was stirred at room temperature for 1 h. The reaction was then concentrated. The resulting residue was purified by silica gel chromatography, using 0 to 10% methanol-dichloromethane as eluent, to afford 5-(methylamino)-6-(3-methylimidazo[4,5-c]pyridin-7-yl)-3-(4-morpholinoanilino)pyrazine-2-carboxamide (15.75 g, 52% yield) as a yellow solid. This material was combined with a batch of equal size and stirred at room temperature for 10 minutes in MeOH (1 L). The resulting slurry was filtered. The solid residue was found to be crystalline by XRPD (form A) and a typical diffractogram is displayed in FIG. 1. Characteristic peak positions are listed below in Tables 3 and 4.

TABLE 3

Five peaks characteristic for Example 8, form A

| °2-theta | Relative intensity |
|---|---|
| 10.5 | vs |
| 11.1 | s |
| 11.8 | s |
| 16.9 | s |
| 26.2 | vs |

TABLE 4

Peaks characteristic for Example 8, form A

| °2-theta | Relative intensity |
|---|---|
| 5.6 | w |
| 9.7 | m |
| 10.5 | vs |
| 11.1 | s |
| 11.8 | s |
| 13.6 | m |
| 13.9 | m |
| 15.3 | w |
| 15.7 | m |
| 16.9 | s |
| 17.7 | m |
| 18.5 | s |
| 20.5 | m |
| 21.0 | m |
| 24.3 | w |
| 25.6 | s |
| 26.2 | vs |
| 27.6 | m |
| 28.2 | m |
| 28.9 | m |

Figure 2:
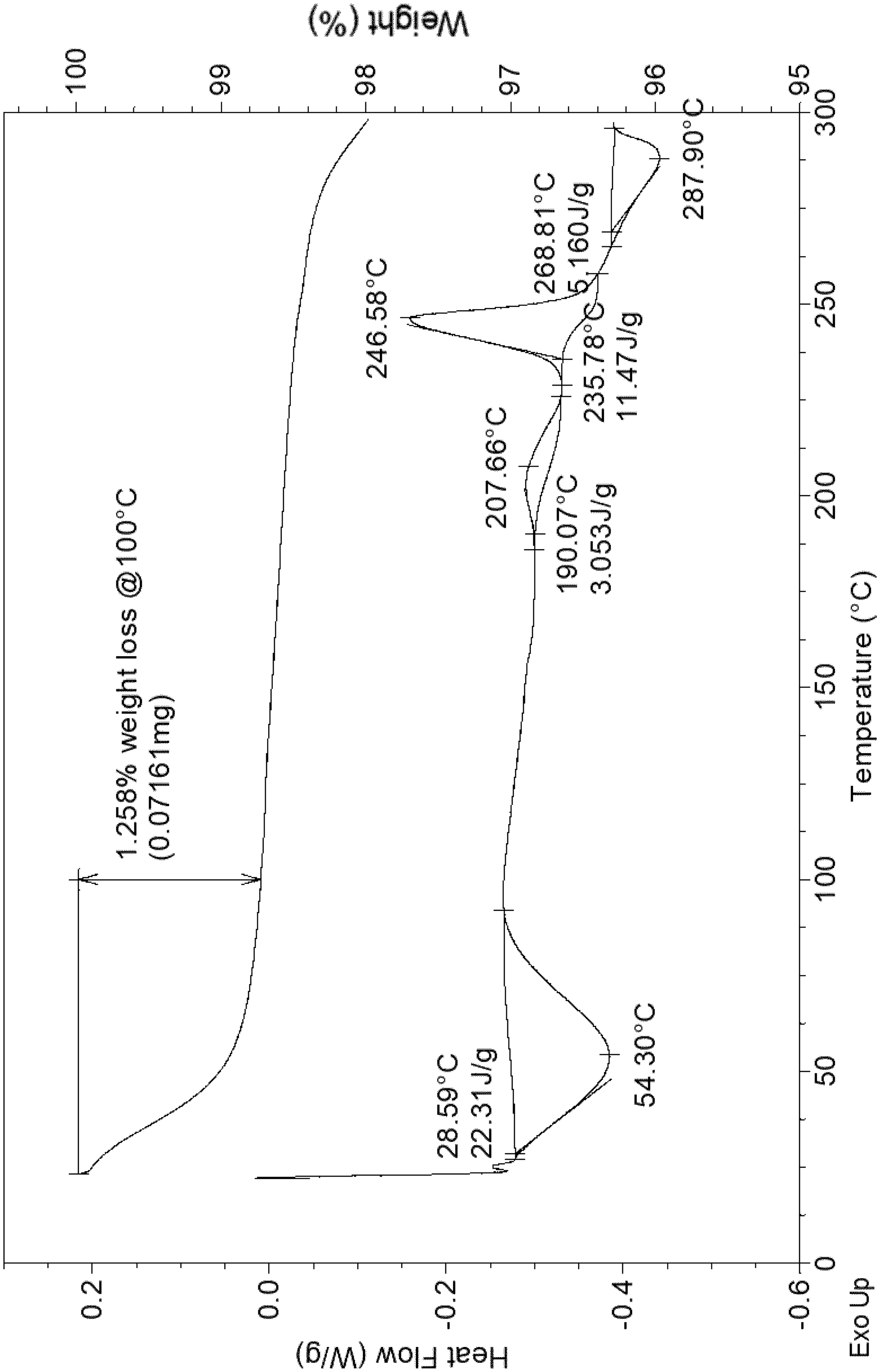
FIG. 2 shows a DSC/TGA thermogram of Example 8, form A: 5-(Methylamino)-6-(3-methylimidazo[4,5-c]pyridin-7-yl)-3-(4-morpholinoanilino)pyrazine-2-carboxamide.

Form A was further analyzed by thermal techniques. DSC analysis indicated that Form A starts to de-solvate with an onset at 29° C. and a peak at 54° C., followed by a several thermal events from 190° C. to 290° C. TGA indicated that Form A exhibits a mass loss of about 1.3% upon heating from about 25° C. to about 100° C. A representative DSC/TGA thermogram of Form A is shown in FIG. 2.

Figure 3:
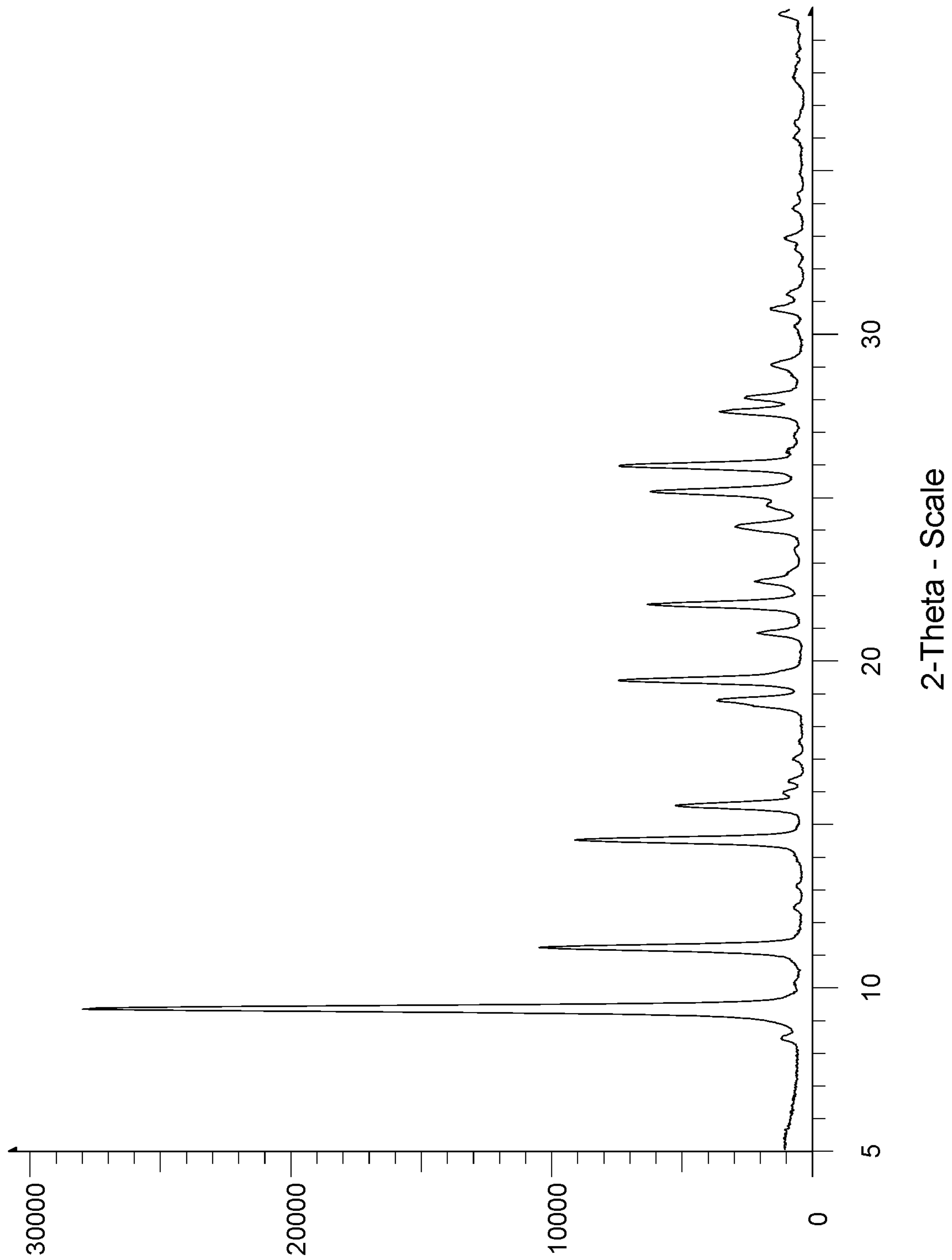
FIG. 3 shows the X-ray powder diffraction pattern for Example 8, form F: 5-(Methylamino)-6-(3-methylimidazo[4,5-c]pyridin-7-yl)-3-(4-morpholinoanilino)pyrazine-2-carboxamide.

The filter cake consisting of form A was suspended in 99.5% EtOH (750 mL) and treated with 20 mg seed crystals of Form F 5-(methylamino)-6-(3-methylimidazo[4,5-c]pyridin-7-yl)-3-(4-morpholinoanilino)pyrazine-2-carboxamide (obtainable by placing 3-5 mg of form A in a TGA or DSC pan, heating to 300° C. at a rate of 10° C./minute and then cooled down to the room temperature.) The resulting suspension was stirred at room temperature for 16 hours, then filtered. The filter cake was dried under vacuum to afford 5-(methylamino)-6-(3-methylimidazo[4,5-c]pyridin-7-yl)-3-(4-morpholinoanilino)pyrazine-2-carboxamide (31.5 g) as a yellow solid. The solid residue was found to be crystalline by XRPD (form F) and a typical diffractogram is displayed in FIG. 3. Characteristic peak positions are listed below in Tables 5 and 6.

TABLE 5

Five peaks characteristic for Example 8, form F

| °2-theta | Relative intensity |
|---|---|
| 9.3 | vs |
| 11.2 | m |
| 14.5 | m |
| 19.4 | m |
| 26.0 | m |

TABLE 6

Peaks characteristic for Example 8, form F

| °2-theta | Relative intensity |
|---|---|
| 8.4 | vw |
| 9.3 | vs |
| 11.2 | m |
| 14.5 | m |
| 15.6 | w |
| 18.8 | w |
| 19.4 | m |
| 20.9 | vw |
| 21.7 | m |
| 22.4 | vw |
| 24.1 | w |
| 24.8 | vw |
| 25.2 | m |
| 26.0 | m |
| 27.6 | w |
| 28.1 | vw |
| 29.1 | vw |
| 30.8 | vw |
| 31.3 | vw |
| 33.0 | vw |

Figure 4:
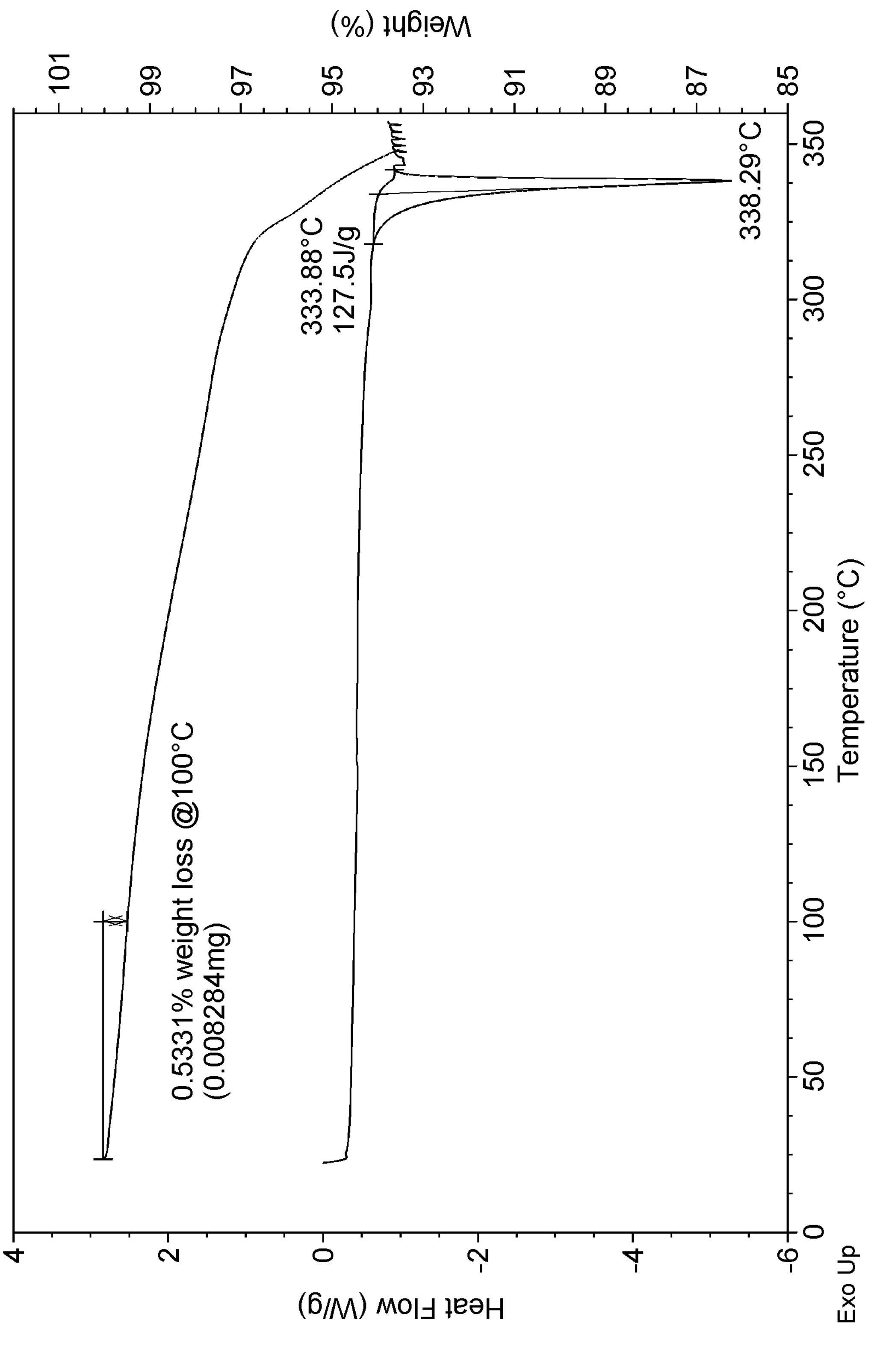
FIG. 4 shows a DSC/TGA thermogram of Example 8, form F: 5-(Methylamino)-6-(3-methylimidazo[4,5-c]pyridin-7-yl)-3-(4-morpholinoanilino)pyrazine-2-carboxamide.
Figure 5:
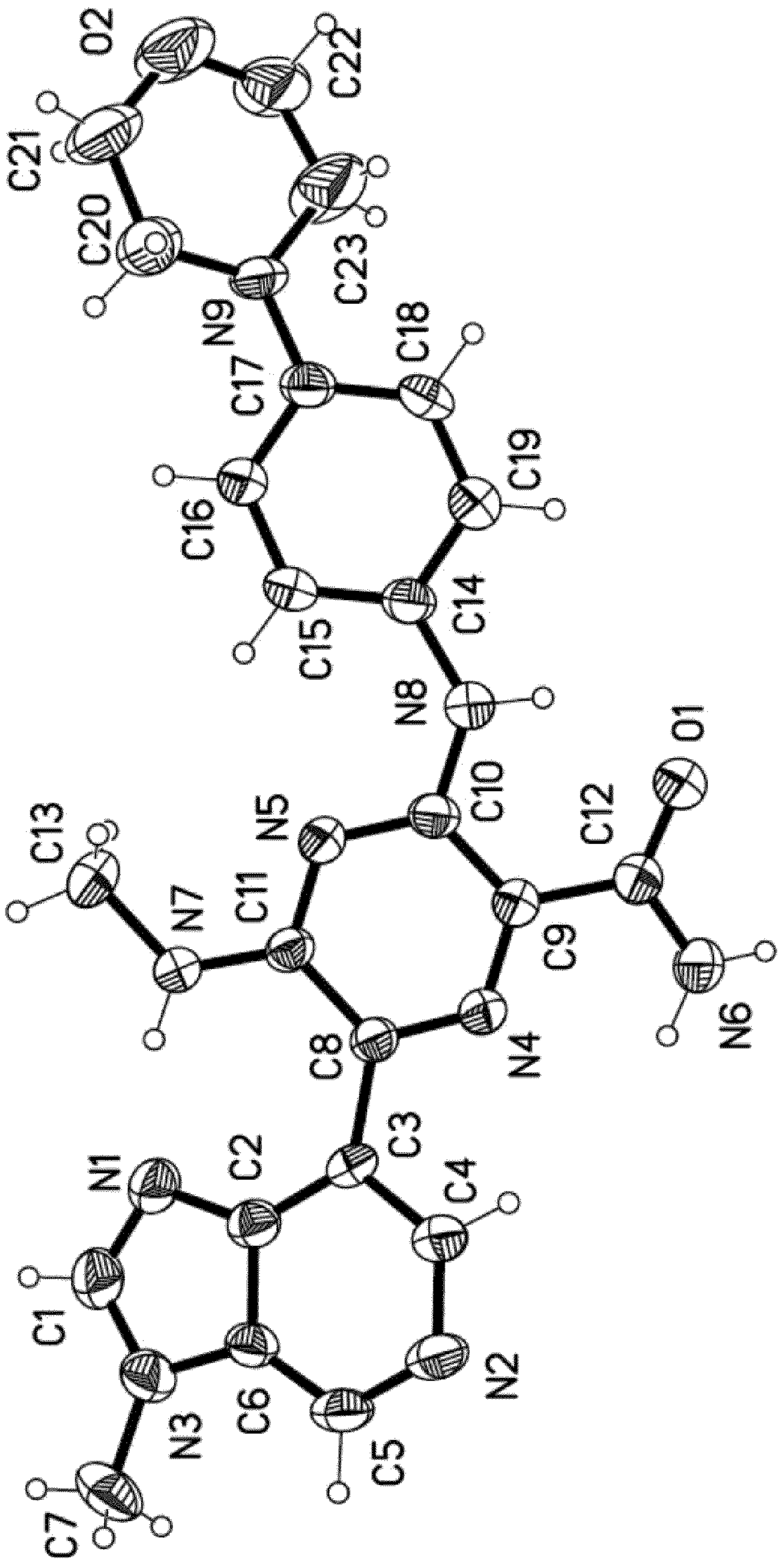
FIG. 5 shows the molecular structure of Example 8, form F: 5-(Methylamino)-6-(3-methylimidazo[4,5-c]pyridin-7-yl)-3-(4-morpholinoanilino)pyrazine-2-carboxamide.

Form F was further analyzed by thermal techniques. DSC analysis indicated that Form F has a melting/decomposition temperature with an onset at 334° C. and a peak at 338° C. TGA indicated that Form F exhibits a mass loss of about 0.5% upon heating from about 25° C. to about 100° C. A representative DSC/TGA thermogram of Form F is shown in FIG. 4. Single crystals of Form F were obtained from evaporation of the EtOH solution. Single crystal structure analysis confirmed that Form F is an anhydrous form. The molecular structure of Example 8-Form F is shown in FIG. 5. Crystallographic data: Space group monoclinic Pc, unit cell dimensions: a=7.9965 (4) Å, b=9.5420 (4) Å, c=14.3408 (6) Å, β=92.333 (1)°, V=1093.33 (8) Å$^3$.

Figure 6:
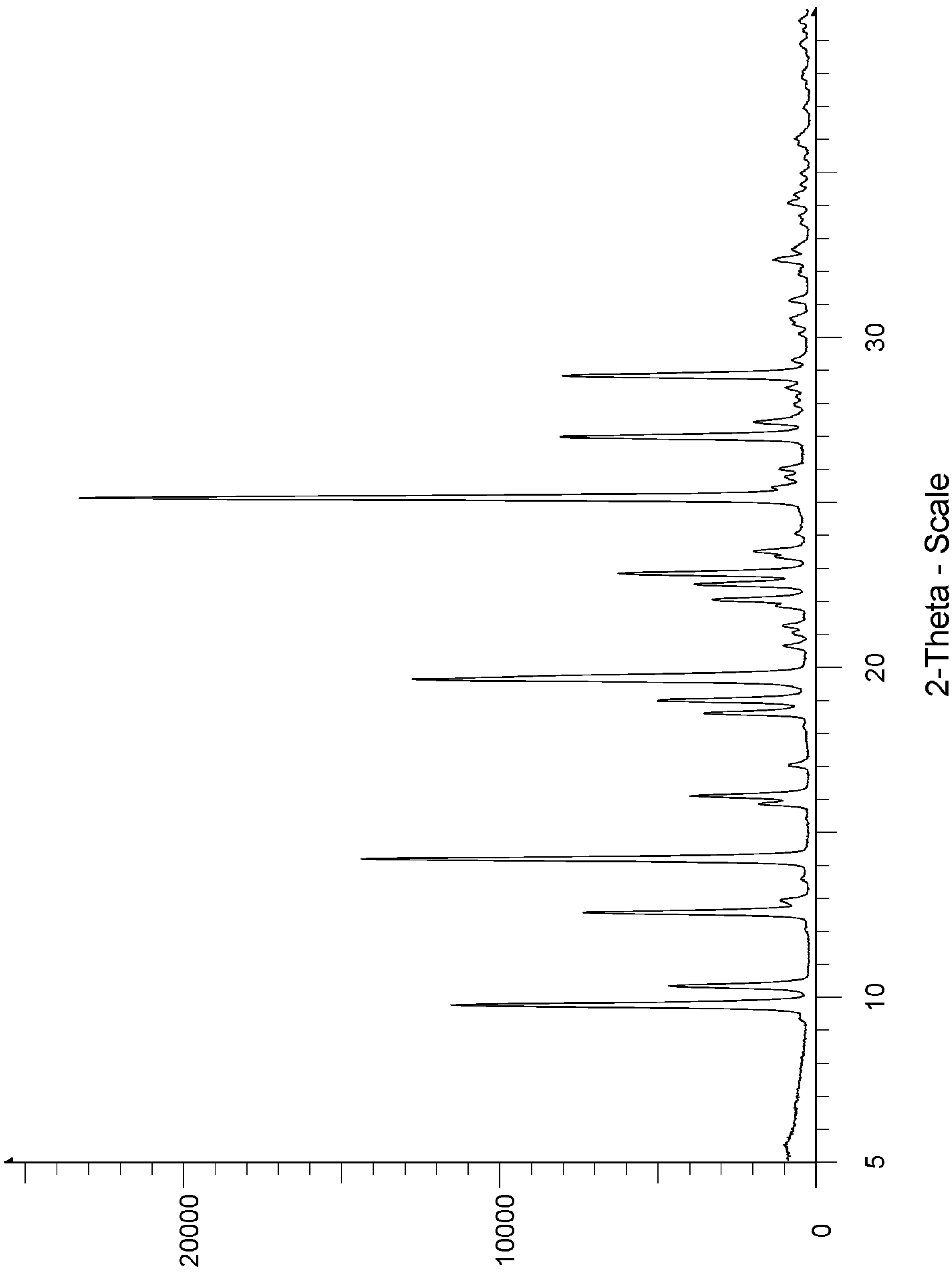
FIG. 6 shows the X-ray powder diffraction pattern for Example 8, form G: 5-(Methylamino)-6-(3-methylimidazo[4,5-c]pyridin-7-yl)-3-(4-morpholinoanilino)pyrazine-2-carboxamide.

By suspending 50 mg of the filter cake consisting of form A in 1.0 mL of ACN, and stirring the slurry at the room temperature for 5 days, following filtration 45 mg of yellow solid was obtained after filtration and air-drying. The solid residue was found to be crystalline by XRPD (form G) and a typical diffractogram is displayed in FIG. 6. Characteristic peak positions are listed below in Tables 7 and 8.

TABLE 7

| Five peaks characteristic for Example 8, form G | |
|---|---|
| °2-theta | Relative intensity |
| 9.7 | s |
| 14.2 | s |
| 19.7 | s |
| 25.2 | vs |
| 27.0 | m |

TABLE 8

| Peaks characteristic for Example 8, form G | |
|---|---|
| °2-theta | Relative intensity |
| 9.7 | s |
| 10.3 | w |
| 12.6 | m |
| 12.9 | vw |
| 14.2 | s |
| 15.8 | vw |
| 16.1 | w |
| 18.6 | w |
| 19.0 | m |
| 19.7 | s |
| 22.0 | w |
| 22.5 | w |
| 22.8 | m |
| 23.5 | vw |
| 25.2 | vs |
| 26.0 | vw |
| 27.0 | m |
| 27.5 | vw |
| 28.9 | m |
| 32.4 | vw |

Figure 7:
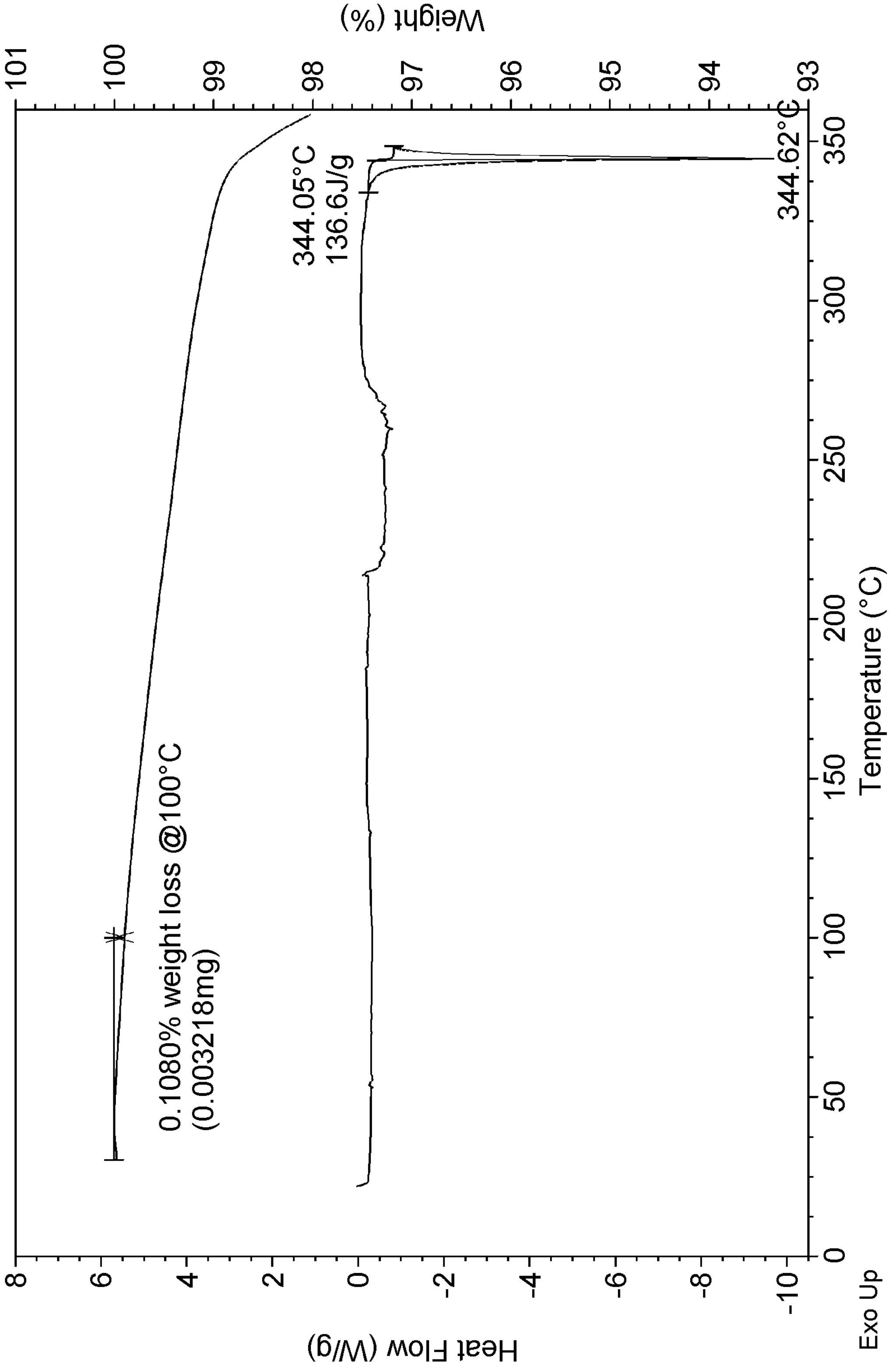
FIG. 7 shows a DSC/TGA thermogram of Example 8, form G: 5-(Methylamino)-6-(3-methylimidazo[4,5-c]pyridin-7-yl)-3-(4-morpholinoanilino)pyrazine-2-carboxamide.

Form G was further analyzed by thermal techniques. DSC analysis indicated that Form G has a melting/decomposition temperature with an onset at 344° C. and a peak at 345° C. TGA indicated that Form G exhibits a mass loss of about 0.1% upon heating from about 25° C. to about 100° C. A representative DSC/TGA thermogram of Form G is shown in FIG. 7.

Figure 8:
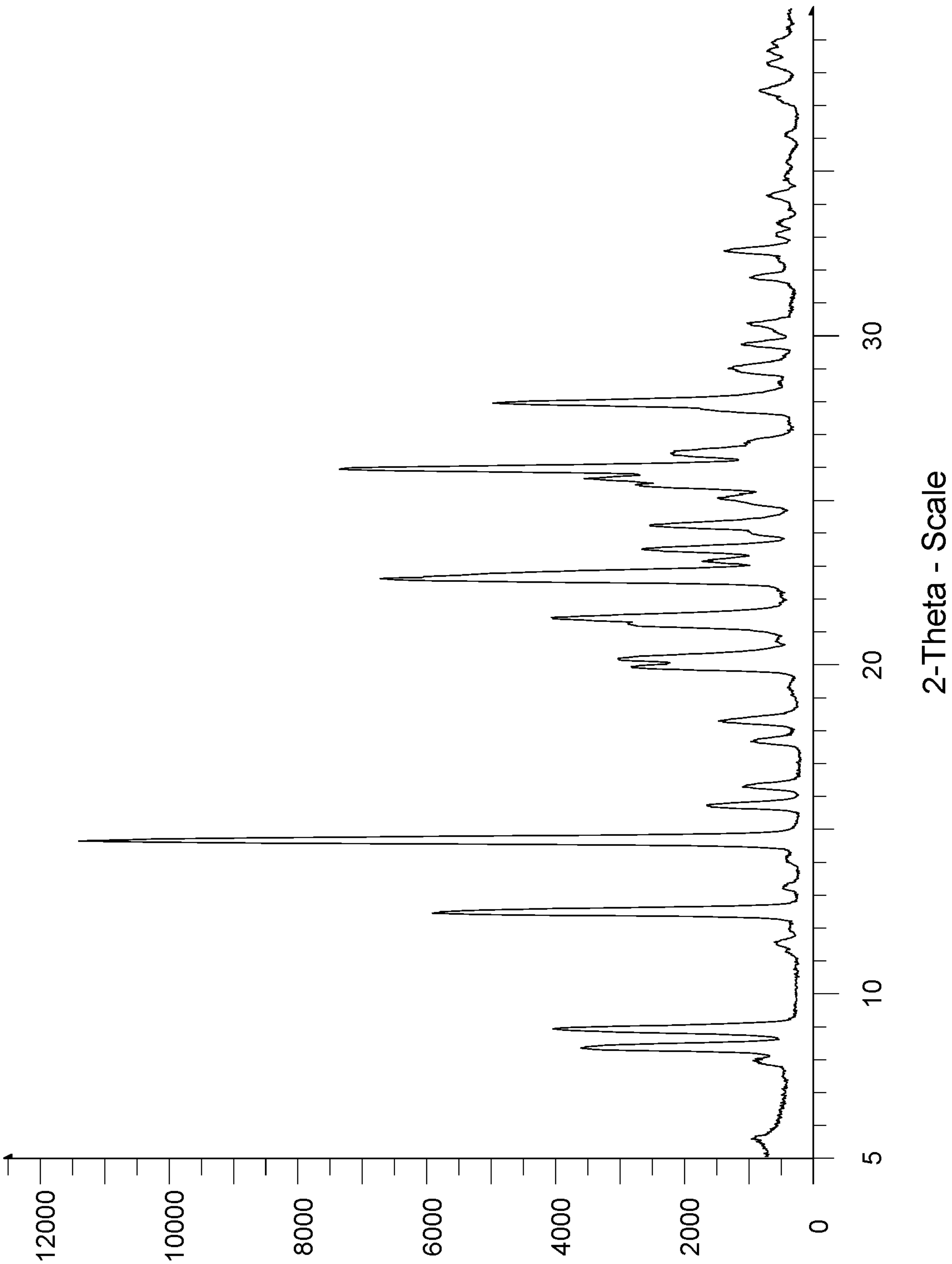
FIG. 8 shows the X-ray powder diffraction pattern for Example 8, form I: 5-(Methylamino)-6-(3-methylimidazo[4,5-c]pyridin-7-yl)-3-(4-morpholinoanilino)pyrazine-2-carboxamide.

By suspending 50 mg of the filter cake consisting of form A in 0.5 mL of $H_2O$, 0.5 mL of MeOH, and 0.5 mL of DCM, and stirring the slurry at the room temperature for 5 days, following filtration 48 mg of yellow solid was obtained after filtration and air-drying. The solid residue was found to be crystalline by XRPD (form I) and a typical diffractogram is displayed in FIG. 8. Characteristic peak positions are listed below in Tables 9 and 10.

TABLE 9

| Five peaks characteristic for Example 8, form I | |
|---|---|
| °2-theta | Relative intensity |
| 12.5 | s |
| 14.6 | vs |
| 22.6 | s |
| 26.0 | s |
| 28.0 | s |

TABLE 10

| Peaks characteristic for Example 8, form I | |
|---|---|
| °2-theta | Relative intensity |
| 8.3 | m |
| 8.9 | m |
| 12.5 | s |
| 14.6 | vs |
| 15.7 | w |
| 18.3 | w |
| 19.9 | m |
| 20.2 | m |
| 21.2 | m |
| 21.4 | m |
| 22.6 | s |
| 23.2 | w |
| 23.5 | m |
| 24.2 | m |
| 25.1 | w |
| 25.5 | m |
| 26.0 | s |
| 26.4 | w |
| 28.0 | s |
| 32.6 | w |

Figure 9:
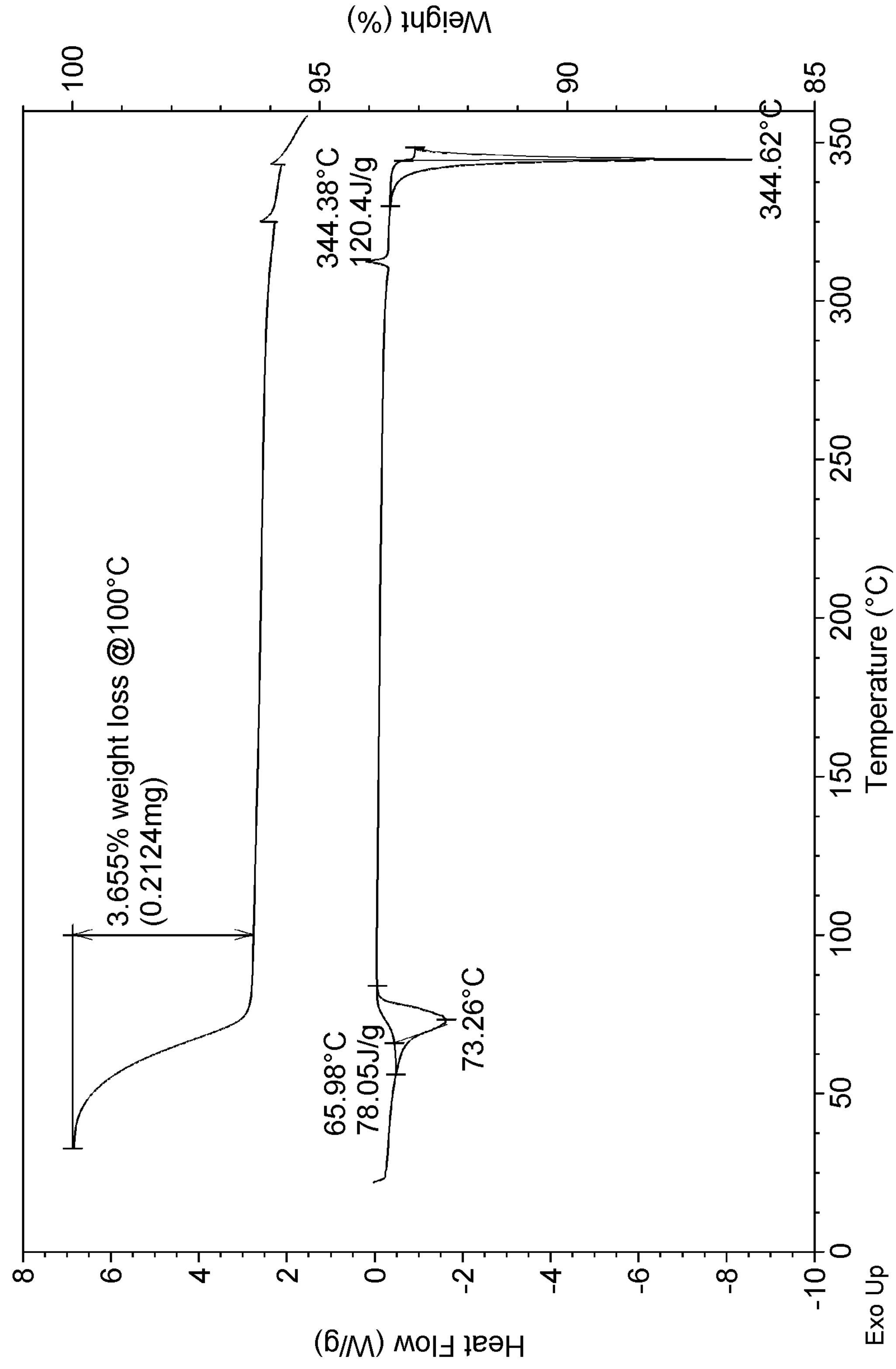
FIG. 9 shows a DSC/TGA thermogram of Example 8, form I: 5-(Methylamino)-6-(3-methylimidazo[4,5-c]pyridin-7-yl)-3-(4-morpholinoanilino)pyrazine-2-carboxamide.

Form I was further analyzed by thermal techniques. DSC analysis indicated that Form I starts to de-solvate with an onset at 66° C. and a peak at 73° C., followed by has a melting/decomposition temperature with an onset at 344° C. and a peak at 245° C. TGA indicated that Form I exhibits a mass loss of about 3.7% upon heating from about 25° C. to about 100° C. A representative DSC/TGA thermogram of Form I is shown in FIG. 9.

Figure 10:
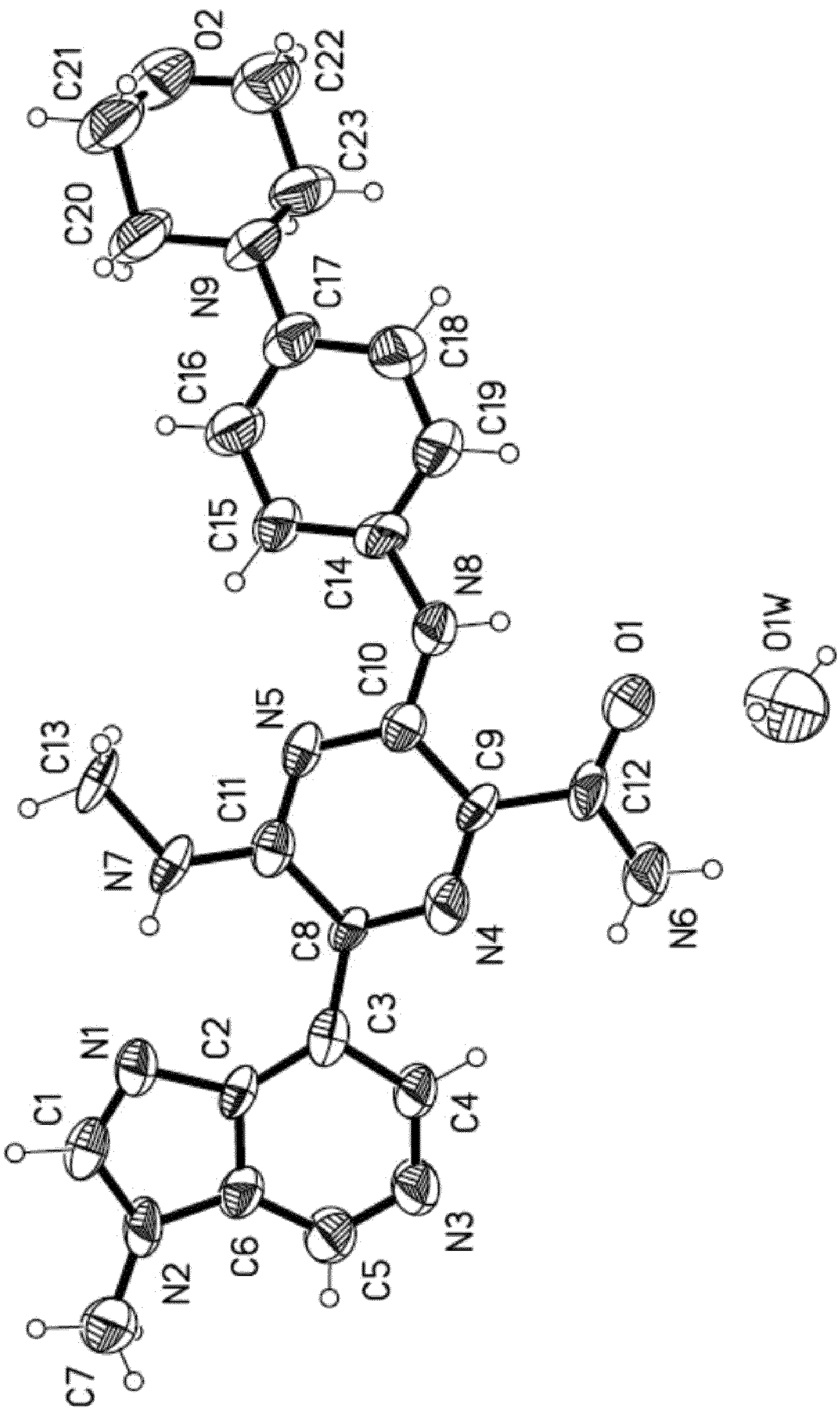
FIG. 10 shows the molecular structure of Example 8, form I: 5-(Methylamino)-6-(3-methylimidazo[4,5-c]pyridin-7-yl)-3-(4-morpholinoanilino)pyrazine-2-carboxamide.

Single crystals of Form I were obtained from evaporation of the MeOH/DCM/H2O (1:1:1) solution. Single crystal structure analysis confirmed that Form I is a monohydrate form. The molecular structure of Example 8-form I is shown in FIG. 10. Crystallographic data: Space group monoclinic P2 (1)/c, unit cell dimensions: a=21.504 (6) Å, b=4.5841 (12) Å, c=22.777 (6) Å, β=90.683 (5)°, V=2245.2 (10) $Å^3$.

1H NMR (500 MHz, DMSO-d6) 2.94 (3H, d), 3.02-3.13 (4H, m), 3.70-3.80 (4H, m), 4.02 (3H, s), 6.96 (2H, d), 7.31 (1H, br s), 7.67 (2H, d), 7.71 (1H, br s), 8.00 (1H, br q), 8.52 (1H, s), 8.73 (1H, s), 9.01 (1H, s), 11.30 (1H, s). m/z: (ES+), [M+H]+=459.9

Example 9

6-(1-Methylbenzimidazol-4-yl)-5-methylsulfanyl-3-(4-morpholinoanilino)pyrazine-2-carboxamide

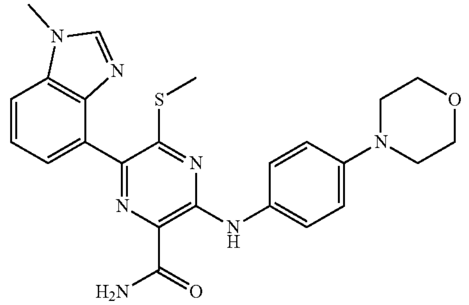 [SMILES: CSc1nc(Nc2ccc(N3CCOCC3)cc2)c(C(N)=O)nc1-c1cccc2c1ncn2C]

(a) Methyl 3-amino-6-chloro-5-methylsulfanyl-pyrazine-2-carboxylate

Aqueous sodium methanethiolate, 21 wt % (22 mL, 66 mmol) was added to a suspension of methyl 3-amino-5,6-dichloro-pyrazine-2-carboxylate (10 g, 45 mmol) in THF (100 mL). The resulting suspension was stirred at 25° C. for 3 hours. The reaction was then concentrated to one-sixth the original volume. The resulting orange suspension was diluted with water (100 mL) and stirred 10 minutes, then filtered, rinsed copiously with water, and dried under vacuum to afford methyl 3-amino-6-chloro-5-methylsulfanyl-pyrazine-2-carboxylate (9.65 g, 92%) as a yellow solid; 1H NMR (500 MHz, DMSO-d6) 2.52 (3H, s), 3.81 (3H, s), 7.59 (2H, br s); m/z: (ES+), [M+H]+=233.9.

(b) Methyl 3-amino-6-(1-methylbenzimidazol-4-yl)-5-methylsulfanyl-pyrazine-2-carboxylate A mixture of 1-methyl-4-(4,4,5,5-tetramethyl-1,3,2-dioxaborolan-2-yl)benzimidazole (497 mg, 1.93 mmol), methyl 3-amino-6-chloro-5-methylsulfanyl-pyrazine-2-carboxylate (250 mg, 1.07 mmol), cesium fluoride (488 mg, 3.21 mmol) and $PdCl_2$(dppf) (78 mg, 0.11 mmol) in MeOH (5 mL) was degassed and purged with nitrogen. The reaction mixture was stirred at 120° C. for 18 hours in a sealed vial. The reaction mixture was then filtered through Celite and concentrated. The resulting residue was purified by silica gel chromatography, using 0-100% EtOAc-Hexanes as eluent, followed by 0-20% MeOH-DCM as eluent, to afford methyl 3-amino-6-(1-methylbenzimidazol-4-yl)-5-methylsulfanyl-pyrazine-2-carboxylate (150 mg, 43%) as a dark brown solid. m/z: (ES+), [M+H]+=330.1.

(c) 6-(1-Methylbenzimidazol-4-yl)-5-methylsulfanyl-3-(4-morpholinoanilino)pyrazine-2-carboxylic acid Methyl 3-amino-6-(1-methylbenzimidazol-4-yl)-5-methylsulfanyl-pyrazine-2-carboxylate (80 mg, 0.24 mmol) was added to 1,4-dioxane (1.5 mL). The resulting solution was sparged with nitrogen 5 minutes. 4-(4-bromophenyl) morpholine (70.6 mg, 0.29 mmol), BrettPhos Pd G3 (22.02 mg, 0.02 mmol), and sodium tert-butoxide (117 mg, 1.21 mmol) were added to the reaction mixture, which was then stirred at 80° C. for 2 hours. 1M HCl was added and the aqueous layer was washed with 3:1 DCM/IPA, then concentrated. The resulting residue was used directly in the next step without purification assuming 100% yield. m/z: (ES+), [M+H]+=477.

(d) 6-(1-Methylbenzimidazol-4-yl)-5-methylsulfanyl-3-(4-morpholinoanilino)pyrazine-2-carboxamide DIPEA (0.253 mL, 1.45 mmol) was added to a suspension of 6-(1-methylbenzimidazol-4-yl)-5-methylsulfanyl-3-(4-morpholinoanilino)pyrazine-2-carboxylic acid (115 mg, 0.24 mmol), ammonium chloride (51.6 mg, 0.97 mmol), and HATU (184 mg, 0.48 mmol) in DMF (2 mL). The resulting mixture was stirred at 25° C. for 90 minutes, then purified directly by reverse phase chromatography on c18, using 0-80% MeCN—$H_2O$ as eluent and 0.1% ammonium hydroxide as modifier, to afford 6-(1-methylbenzimidazol-4-yl)-5-methylsulfanyl-3-(4-morpholinoanilino)pyrazine-2-carboxamide (9.0 mg, 7.8%) as a yellow solid; 1H NMR (500 MHz, DMSO-d6) δ 2.41 (3H, s), 3.07 (4H, br s), 3.73 (4H, br d), 3.87 (3H, s), 6.93-6.99 (2H, m), 7.29 (1H, br d), 7.33-7.39 (1H, m), 7.58 (2H, br d), 7.65 (1H, br d), 7.72 (1H, br s), 7.85 (1H, br s), 8.17 (1H, s), 11.16 (1H, s); m/z: (ES+), [M+H]+=476.2

Example 10

5-(Ethylamino)-6-(1-methylbenzimidazol-4-yl)-3-(4-morpholinoanilino)pyrazine-2-carboxamide

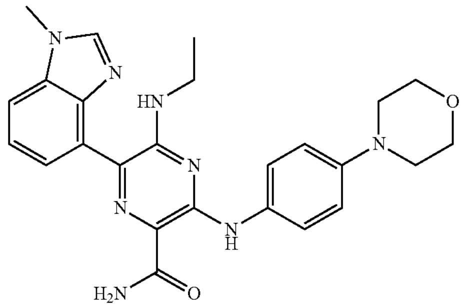 [SMILES: CCNc1nc(Nc2ccc(N3CCOCC3)cc2)c(C(N)=O)nc1-c1cccc2c1ncn2C]

(a) 6-(1-Methylbenzimidazol-4-yl)-5-methylsulfonyl-3-[4-(4-oxidomorpholin-4-ium-4-yl)anilino]pyrazine-2-carboxamide mCPBA (21 mg, 77 wt %, 0.090 mmol) was added to a suspension of 6-(1-methylbenzimidazol-4-yl)-5-methylsulfanyl-3-(4-morpholinoanilino)pyrazine-2-carboxamide (20 mg, 0.04 mmol) in DCM (1 mL) at 0° C. The resulting mixture was stirred at 0° C. for 30 minutes and then at 25° C. for 90 minutes. The reaction was then quenched with saturated aqueous sodium bicarbonate and extracted with 3:1 DCM/IPA. The combined organic layers were washed with brine, dried over sodium sulfate, filtered, and concentrated. The resulting residue was purified by silica gel chromatography, using 0-100% MeOH-DCM to afford a yellow material, which was purified further by reverse phase chromatography on c18, using 0-80% MeCN/H2O as eluent and 0.1% ammonium hydroxide as modifier, to afford 6-(1-methylbenzimidazol-4-yl)-5-methylsulfonyl-3-[4-(4-oxidomorpholin-4-ium-4-yl)anilino]pyrazine-2-carboxamide (15.00 mg, 68%) as a yellow solid; 1H NMR (500 MHZ, DMSO-d6) 2.88 (2H, br d), 3.36 (3H, s), 3.78 (2H, dd), 3.90 (3H, s), 4.03 (2H, td), 4.43 (2H, br t), 7.35-7.40 (1H, m), 7.45 (1H, d), 7.67 (1H, d), 7.87 (2H, d), 8.16-8.24 (3H, m), 8.27 (2H, br s), 11.55 (1H, s); m/z: (ES−), [M−H]−=522.1.

(b) 5-(Ethylamino)-6-(1-methylbenzimidazol-4-yl)-3-(4-morpholinoanilino)pyrazine-2-carboxamide 2 M Methanolic ethanamine (0.028 mL, 0.056 mmol) and DIPEA (0.024 mL, 0.14 mmol) were added to a solution of 6-(1-methylbenzimidazol-4-yl)-5-methylsulfonyl-3-[4-(4-oxidomorpholin-4-ium-4-yl)anilino]pyrazine-2-carboxamide (24 mg, 0.050 mmol) in THF (1 mL). The resulting mixture was stirred at 25° C. for 3 hours. Sodium hydrogen sulfite (14.1 mg, 0.140 mmol) was added and the reaction was stirred at 25° C. for 16 hours. The reaction was then concentrated. The resulting residue was purified by reverse phase chromatography on C18, using 0-80% MeCN/$H_2O$ as eluent and 0.1% ammonium hydroxide as modifier, to afford 55-(ethylamino)-6-(1-methylbenzimidazol-4-yl)-3-(4-morpholinoanilino)pyrazine-2-carboxamide (10.0 mg, 46%) as a yellow solid; 1H NMR (500 MHz, DMSO-d6) δ 1.20 (3H, t), 3.02-3.11 (4H, m), 3.45 (2H, quintet), 3.68-3.76 (4H, m), 3.90 (3H, s), 6.93 (2H, d), 7.33 (1H, br s), 7.36-7.49 (1H, m), 7.57-7.75 (5H, m), 8.35 (1H, s), 8.43 (1H, br t), 11.22 (1H, s); m/z: (ES+), [M+H]+=473.3.

Example 11

5-(Cyclopropylamino)-6-(1-methylbenzimidazol-4-yl)-3-(4-morpholinoanilino)pyrazine-2-carboxamide

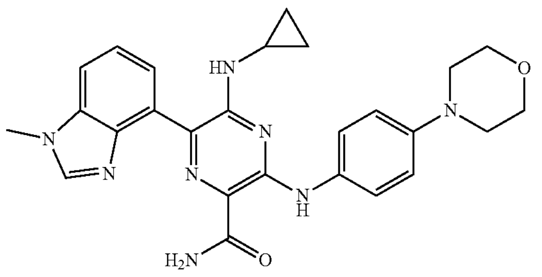 [SMILES: Cn1cnc2c(-c3nc(C(N)=O)c(Nc4ccc(N5CCOCC5)cc4)nc3NC3CC3)cccc21]

Cyclopropylamine (0.040 mL, 0.57 mmol) and DIPEA (0.10 mL, 0.57 mmol) were added to a solution of 6-(1-methylbenzimidazol-4-yl)-5-methylsulfonyl-3-[4-(4-oxidomorpholin-4-ium-4-yl)anilino]pyrazine-2-carboxamide (100 mg, 0.19 mmol) in DMF (1.5 mL). The resulting mixture was stirred at 25° C. for 1 hour. Sodium hydrogen sulfite (60 mg, 0.57 mmol) was added and the resulting mixture was stirred at 25° C. for 1 hour. The reaction was then concentrated. The resulting residue was purified by reverse phase chromatography on C18, using 10-80% MeCN/$H_2O$ as eluent, to afford 5-(cyclopropylamino)-6-(1-methylbenzimidazol-4-yl)-3-(4-morpholinoanilino)pyrazine-2-carboxamide (20 mg, 22%) as a yellow solid; 1H NMR (500 MHz, DMSO-d6) δ 0.43-0.52 (2H, m), 0.79-0.87 (2H, m), 2.88 (1H, ddd), 3.02-3.09 (4H, m), 3.69-3.76 (4H, m), 3.90 (3H, s), 6.94 (2H, d), 7.35-7.43 (2H, m), 7.63 (1H, d), 7.70 (1H, br s), 7.73 (1H, d), 7.80 (2H, d), 8.38 (1H, s), 9.08 (1H, d), 11.24 (1H, s); m/z: (ES+), [M+H]+=485.4.

Example 12

5-Amino-6-(1-methylbenzimidazol-4-yl)-3-(4-morpholinoanilino)pyrazine-2-carboxamide

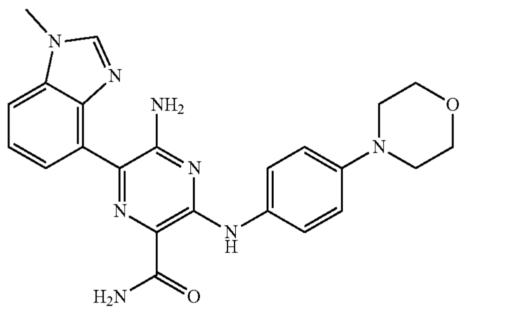 [SMILES: Cn1cnc2c(-c3nc(C(N)=O)c(Nc4ccc(N5CCOCC5)cc4)nc3N)cccc21]

(a) 6-(1-Methylbenzimidazol-4-yl)-5-methylsulfinyl-3-[4-(4-oxidomorpholin-4-ium-4-yl)anilino]pyrazine-2-carboxamide A solution of mCPBA (0.17 g, 0.75 mmol) in DCM (3 mL) was added dropwise to a mixture of 6-(1-methylbenzimidazol-4-yl)-5-methylsulfanyl-3-(4-morpholinoanilino) pyrazine-2-carboxamide (0.157 g, 0.330 mmol) in DCM (5.00 mL) at 0° C. The reaction was stirred at 0° C. for 5 minutes. The reaction was quenched with saturated aqueous sodium bicarbonate and extracted once with DCM and once with 5:1 DCM/IPA. The combined organic layers were dried over sodium sulfate, concentrated, and used in the next step without purification assuming 100% yield.

(b) 5-Amino-6-(1-methylbenzimidazol-4-yl)-3-(4-morpholinoanilino)pyrazine-2-carboxamide 7 N Methanolic ammonia (10 mL, 70 mmol) was added to 6-(1-methylbenzimidazol-4-yl)-5-methylsulfinyl-3-[4-(4-oxidomorpholin-4-ium-4-yl)anilino]pyrazine-2-carboxamide (0.255 g, 0.500 mmol). The resulting suspension was stirred at 70° C. for 2.5 hours. The reaction was then concentrated. The resulting residue was suspended in water, then filtered and rinsed with water. The filter cake was dried under vacuum to afford 5-amino-6-(1-methylbenzimidazol-4-yl)-3-(4-morpholinoanilino)pyrazine-2-carboxamide (0.198 g, 88%) as a yellow solid; (500 MHz, DMSO-d6) δ 3.03-3.12 (4H, m), 3.73-3.77 (4H, m), 4.05 (3H, s), 6.93 (2H, br d), 7.39 (1H, br s), 7.56-7.71 (4H, m), 7.77 (1H, br d), 7.88 (1H, br d), 9.14-9.41 (1H, m), 11.22 (1H, s). The amino $NH_2$ protons were buried underneath the residual water peak. m/z: (ES+), [M+H]+=445.4

Example 13

5-[[(2R)-2-Hydroxypropyl]amino]-6-(1-methylbenzimidazol-4-yl)-3-(4-morpholinoanilino)pyrazine-2-carboxamide

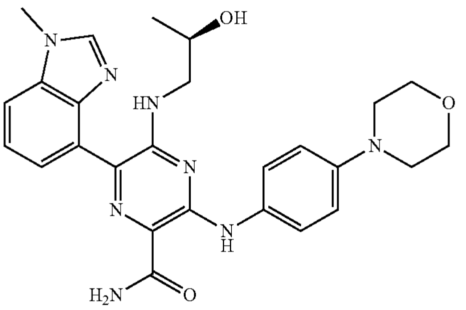 [SMILES: C[C@@H](O)CNc1nc(Nc2ccc(N3CCOCC3)cc2)c(C(N)=O)nc1-c1cccc2c1ncn2C]

(R)-1-Aminopropan-2-ol (77 mg, 1.02 mmol) was added to a suspension of 6-(1-methylbenzimidazol-4-yl)-5-methylsulfinyl-3-[4-(4-oxidomorpholin-4-ium-4-yl)anilino]pyrazine-2-carboxamide (26 mg, 0.051 mmol) in n-butanol (1 mL). The resulting mixture was stirred at 140° C. for 20 minutes in a Biotage microwave reactor. The reaction was then concentrated. The resulting residue was partitioned between DCM and water. The layers were separated, and the organic layer was dried over magnesium sulfate, filtered, and concentrated. The resulting residue was purified by silica gel chromatography, using 0-10% MeOH-DCM as eluent and 1% ammonium hydroxide as modifier, to afford 5-[[(2R)-2-hydroxypropyl]amino]-6-(1-methylbenzimidazol-4-yl)-3-(4-morpholinoanilino)pyrazine-2-carboxamide (11 mg, 43%) as a yellow solid; 1H NMR (500 MHz, dichloromethane-d2) δ 1.22 (3H, d), 3.02-3.09 (1H, m), 3.10-3.15 (4H, m), 3.80-3.87 (5H, m), 3.90 (3H, s), 4.17-4.28 (1H, m), 4.85 (1H, br s), 5.21 (1H, br s), 6.56 (1H, br t), 6.91 (2H, d), 7.43-7.56 (3H, m), 7.57-7.64 (2H, m), 7.67 (1H, dd), 7.98 (1H, s), 10.86 (1H, s); m/z: (ES+), [M+H]+=503.3

Example 14

5-[[(2S)-2-Hydroxypropyl]amino]-6-(1-methylbenzimidazol-4-yl)-3-(4-morpholinoanilino)pyrazine-2-carboxamide

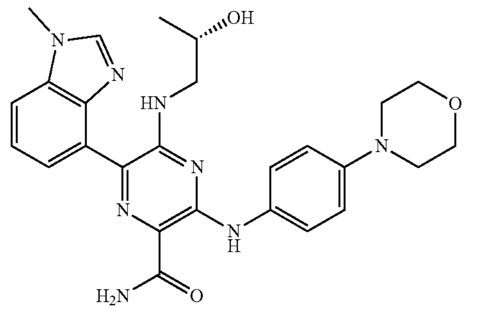 [SMILES: C[C@H](O)CNc1nc(Nc2ccc(N3CCOCC3)cc2)c(C(N)=O)nc1-c1cccc2c1ncn2C]

(2S)-1-Aminopropan-2-ol (77 mg, 1.02 mmol) was added to a suspension of 6-(1-methylbenzimidazol-4-yl)-5-methylsulfinyl-3-[4-(4-oxidomorpholin-4-ium-4-yl)anilino]pyrazine-2-carboxamide (26 mg, 0.051 mmol) in n-butanol (1 mL). The resulting mixture was stirred at 140° C. for 20 minutes in a Biotage microwave reactor. The reaction was then concentrated. The resulting residue was partitioned between DCM and water. The layers were separated, and the organic layer was dried over magnesium sulfate, filtered, and concentrated. The resulting residue was purified by silica gel chromatography, using 0-10% MeOH-DCM as eluent and 1% ammonium hydroxide as modifier, to afford 5-[[(2S)-2-hydroxypropyl]amino]-6-(1-methylbenzimidazol-4-yl)-3-(4-morpholinoanilino)pyrazine-2-carboxamide (12 mg, 47%) as a yellow solid; 1H NMR (500 MHZ, DICHLOROMETHANE-d2) δ 1.22 (3H, d), 3.02-3.09 (1H, m), 3.09-3.17 (4H, m), 3.80-3.87 (5H, m), 3.90 (3H, s), 4.18-4.27 (1H, m), 4.85 (1H, br s), 5.21 (1H, br s), 6.57 (1H, br t), 6.91 (2H, d), 7.45-7.54 (3H, m), 7.59-7.63 (2H, m), 7.67 (1H, dd), 7.98 (1H, s), 10.86 (1H, s); m/z: (ES+), [M+H]+=503.3

Example 15

6-(1-Methylbenzimidazol-4-yl)-3-(4-morpholinoanilino)-5-(2,2,2-trifluoroethylamino) pyrazine-2-carboxamide

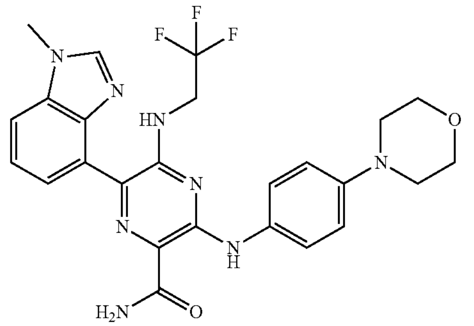 [SMILES: Cn1cnc2c(-c3nc(C(N)=O)c(Nc4ccc(N5CCOCC5)cc4)nc3NCC(F)(F)F)cccc21]

2,2,2-Trifluoroethanamine (101 mg, 1.02 mmol) was added to a suspension of 6-(1-methylbenzimidazol-4-yl)-5-methylsulfinyl-3-[4-(4-oxidomorpholin-4-ium-4-yl)anilino] pyrazine-2-carboxamide (26 mg, 0.051 mmol) in n-butanol (1 mL). The resulting mixture was stirred at 140° C. for 20 minutes in a Biotage microwave reactor. The reaction was then concentrated and the resulting residue was partitioned between DCM and H2O. The layers were separated and the organic layer was dried over magnesium sulfate, filtered, and concentrated. The resulting residue was purified by silica gel chromatography, using 0-10% MeOH-DCM as eluent and 0.1% ammonium hydroxide as modifier, to afford 6-(1-methylbenzimidazol-4-yl)-3-(4-morpholinoanilino)-5-(2,2,2-trifluoroethylamino) pyrazine-2-carboxamide (4.2 mg, 16%) as a yellow solid; 1H NMR (500 MHZ, DICHLOROMETHANE-d2) δ 3.08-3.15 (4H, m), 3.80-3.87 (4H, m), 3.91 (3H, s), 4.27 (2H, qd), 6.89-6.97 (2H, m), 7.45-7.60 (5H, m), 7.78 (1H, dd), 7.97 (1H, s), 9.44 (1H, br t), 10.83 (1H, s). One of the carboxamide $NH_2$ protons was exchanged to baseline. m/z: (ES+), [M+H]+=527.2

Example 16

5-(2,2-Difluoroethylamino)-6-(1-methylbenzimidazol-4-yl)-3-(4-morpholinoanilino)pyrazine-2-carboxamide

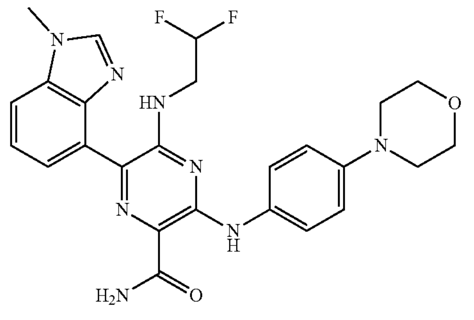 [SMILES: Cn1cnc2c(-c3nc(C(N)=O)c(Nc4ccc(N5CCOCC5)cc4)nc3NCC(F)F)cccc21]

2,2-Difluoroethanamine (83 mg, 1.0 mmol) was added to a suspension of 6-(1-methylbenzimidazol-4-yl)-5-methylsulfinyl-3-[4-(4-oxidomorpholin-4-ium-4-yl)anilino]pyrazine-2-carboxamide (26 mg, 0.051 mmol) in n-butanol (1 mL). The resulting mixture was stirred at 140° C. for 20 minutes in a Biotage microwave reactor. was heated at 140° c. for 20 m. The reaction was then concentrated and the resulting residue was partitioned between DCM and $H_2O$. The layers were separated and the organic layer was dried over magnesium sulfate, filtered, and concentrated. The resulting residue was purified by silica gel chromatography, using 0-10% MeOH-DCM as eluent and 0.1% ammonium hydroxide as modifier, to afford 5-(2,2-difluoroethylamino)-6-(1-methylbenzimidazol-4-yl)-3-(4-morpholinoanilino) pyrazine-2-carboxamide (9.6 mg, 37%) as a yellow solid; 1H NMR (500 MHz, DICHLOROMETHANE-d2) δ 3.09-3.15 (4H, m), 3.82-3.86 (4H, m), 3.86-3.94 (5H, m), 5.45-5.59 (1H, m), 6.03 (1H, tt), 6.89-6.96 (2H, m), 7.45-7.53 (2H, m), 7.54-7.64 (3H, m), 7.73 (1H, dd), 7.99 (1H, s), 8.84 (1H, br t), 10.81 (1H, s). m/z: (ES+), [M+H]+=509.2

Example 17

5-[2-(Dimethylamino)ethylamino]-6-(1-methylbenzimidazol-4-yl)-3-(4-morpholinoanilino)pyrazine-2-carboxamide

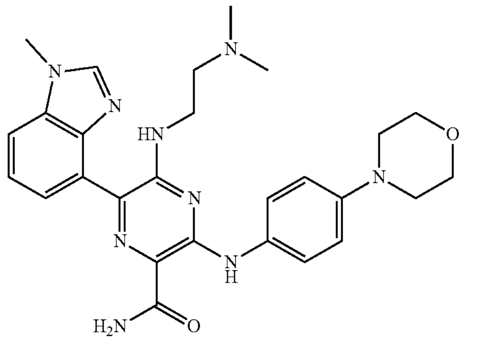 [SMILES: CN(C)CCNc1nc(Nc2ccc(N3CCOCC3)cc2)c(C(N)=O)nc1-c1cccc2c1ncn2C]

N',N'-Dimethylethane-1,2-diamine (90 mg, 1.0 mmol) was added to a suspension of 4-(4-((3-carbamoyl-5-(1-methyl-1H-benzo[d]imidazol-4-yl)-6-(methylsulfinyl) pyrazin-2-yl)amino)phenyl) morpholine 4-oxide (26 mg, 0.051 mmol) in n-butanol (1 mL). The resulting mixture was stirred at 140° C. for 20 minutes in a Biotage microwave reactor. The reaction was then concentrated and the resulting residue was partitioned between DCM and $H_2O$. The layers were separated and the organic layer was dried over magnesium sulfate, filtered, and concentrated. The resulting residue was purified by silica gel chromatography, using 0-10% MeOH-DCM as eluent and 0.1% ammonium hydroxide as modifier, to afford 5-[2-(dimethylamino)ethylamino]-6-(1-methylbenzimidazol-4-yl)-3-(4-morpholinoanilino) pyrazine-2-carboxamide (9.4 mg, 36%) as a yellow solid; 1H NMR (500 MHz, DICHLOROMETHANE-d2) δ 2.20 (6H, s), 2.53-2.56 (2H, m), 3.08-3.13 (4H, m), 3.58-3.65 (2H, m), 3.81-3.87 (4H, m), 3.90 (3H, s), 5.19 (1H, br s), 6.88-6.94 (2H, m), 7.43-7.55 (3H, m), 7.63 (1H, dd), 7.66-7.70 (2H, m), 7.89-7.95 (2H, m), 10.89 (1H, s). m/z: (ES+), [M+H]+=516.3

Example 18

5-(2-Hydroxyethylamino)-6-(1-methylbenzimidazol-4-yl)-3-(4-morpholinoanilino)pyrazine-2-carboxamide

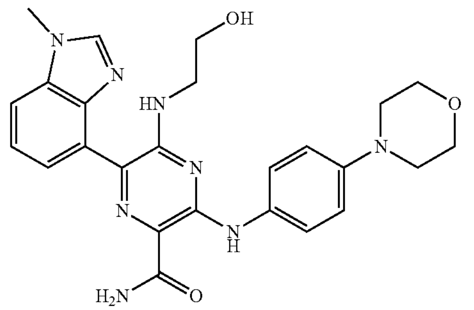 [SMILES: Cn1cnc2c(-c3nc(C(N)=O)c(Nc4ccc(N5CCOCC5)cc4)nc3NCCO)cccc21]

2-Aminoethanol (62.3 mg, 1.02 mmol) was added to a suspension of 6-(1-methylbenzimidazol-4-yl)-5-methylsulfinyl-3-[4-(4-oxidomorpholin-4-ium-4-yl)anilino]pyrazine-2-carboxamide (26 mg, 0.051 mmol) in n-butanol (1 mL). The resulting mixture was stirred at 140° C. for 20 minutes in a Biotage microwave reactor. The reaction was then concentrated. The resulting residue was partitioned between DCM and water. The layers were separated, and the organic layer was dried over magnesium sulfate, filtered, and concentrated. The resulting residue was purified by silica gel chromatography, using 0-10% MeOH-DCM as eluent and 1% ammonium hydroxide as modifier, to afford 5-(2-hydroxyethylamino)-6-(1-methylbenzimidazol-4-yl)-3-(4-morpholinoanilino)pyrazine-2-carboxamide (12 mg, 47%) as a yellow solid; 1H NMR (500 MHZ, DICHLOROMETHANE-d2) δ 3.08-3.14 (4H, m), 3.66 (2H, q), 3.80-3.87 (6H, m), 3.91 (3H, s), 4.54 (1H, br s), 5.20 (1H, br s), 6.48 (1H, br t), 6.92 (2H, d), 7.42-7.56 (3H, m), 7.61 (2H, d), 7.67 (1H, dd), 7.98 (1H, s), 10.88 (1H, s). m/z: (ES+), [M+H]+=489.3.

Example 19

6-(1-Methylbenzimidazol-4-yl)-3-(4-morpholinoanilino)-5-(prop-2-ynylamino) pyrazine-2-carboxamide

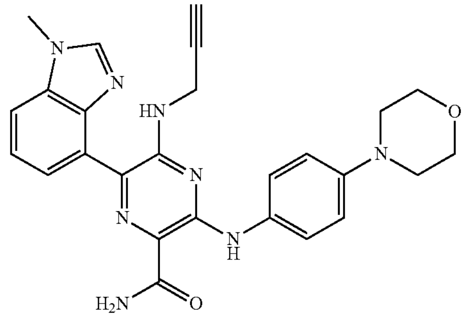 [SMILES: C#CCNc1nc(Nc2ccc(N3CCOCC3)cc2)c(C(N)=O)nc1-c1cccc2c1ncn2C]

Prop-2-yn-1-amine (0.071 mL, 1.1 mmol) was added to a suspension of 6-(1-methylbenzimidazol-4-yl)-5-methylsulfinyl-3-[4-(4-oxidomorpholin-4-ium-4-yl)anilino]pyrazine-2-carboxamide (28 mg, 0.060 mmol) in 1,4-dioxane (1 mL). The resulting mixture was stirred at 110° C. for 30 minutes. The reaction was then concentrated. The resulting residue was purified by silica gel chromatography, using 0-5% MeOH-DCM, to afford 6-(1-methylbenzimidazol-4-yl)-3-(4-morpholinoanilino)-5-(prop-2-ynylamino) pyrazine-2-carboxamide (4.6 mg, 17%) as a yellow solid; 1H NMR (500 MHZ, DMSO-d6) δ 3.03-3.09 (4H, m), 3.11 (1H, t), 3.70-3.76 (4H, m), 3.91 (3H, s), 4.16 (2H, dd), 6.93 (2H, d), 7.37-7.44 (2H, m), 7.63-7.74 (5H, m), 8.37 (1H, s), 8.94 (1H, t), 11.22 (1H, s). m/z: (ES+) [M+H]+=483.3

Examples 20 and 21

6-(1-Methylbenzimidazol-4-yl)-3-(4-morpholinoanilino)-5-[[rel-(1R,2R)-2-methylcyclopropyl]amino] pyrazine-2-carboxamide and 6-(1-methylbenzimidazol-4-yl)-3-(4-morpholinoanilino)-5-[[rel-(1S,2S)-2-methylcyclopropyl]amino]pyrazine-2-carboxamide

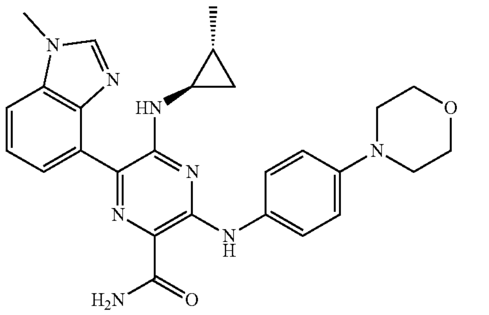

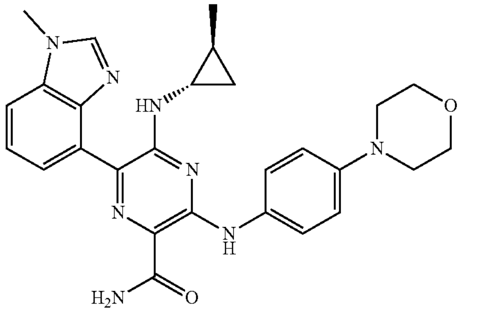

rac-(1R,2R)-2-Methylcyclopropanamine (30 μL, 0.38 mmol) and DIPEA (340 μL, 1.95 mmol) were sequentially added to a suspension of 6-(1-methylbenzimidazol-4-yl)-5-methylsulfinyl-3-[4-(4-oxidomorpholin-4-ium-4-yl)anilino] pyrazine-2-carboxamide in n-butanol (0.5 mL). The resulting mixture was stirred at 140° C. for 30 minutes in a Biotage microwave reactor. The reaction was then concentrated. The resulting residue was purified by reverse phase chromatography on C18, using 0-100% MeCN—$H_2O$ as eluent and 0.1% TFA as modifier, to afford an orange oil. This oil was purified further by chiral HPLC using a Chiralpak AD 4.6 mm×100 mm 5 micron column, using isocratic 40% methanol-s$CO_2$ as eluent and 0.2% ammonium hydroxide as modifier, to afford 6-(1-methylbenzimidazol-4-yl)-3-(4-morpholinoanilino)-5-[[rel-(1R,2R)-2-methylcyclopropyl]amino]pyrazine-2-carboxamide (7.0 mg, 19%) and 6-(1-methylbenzimidazol-4-yl)-3-(4-morpholinoanilino)-5-[[rel-(1S,2S)-2-methylcyclopropyl] amino]pyrazine-2-carboxamide (6.5 mg, 18%) as yellow solids; 1H NMR (500 MHZ, DMSO-d6) 0.51-0.63 (1H, m), 0.64-0.70 (1H, m), 0.76-0.90 (1H, m), 1.11 (3H, d), 2.63-2.68 (1H, m), 2.95-3.07 (4H, m), 3.63-3.79 (4H, m), 3.90 (3H, s), 6.91 (2H, d), 7.33-7.42 (2H, m), 7.62 (1H, d), 7.66-7.73 (2H, m), 7.77 (2H, d), 8.37 (1H, s), 8.91-8.96 (1H, m), 11.27 (1H, s); m/z: (ES+), [M+H]+=499.4

Example 22

5-(Cyanomethylamino)-6-(1-methylbenzimidazol-4-yl)-3-(4-morpholinoanilino)pyrazine-2-carboxamide

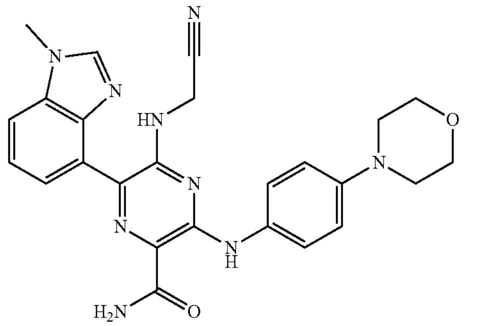 [SMILES: Cn1cnc2c(-c3nc(C(N)=O)c(Nc4ccc(N5CCOCC5)cc4)nc3NCC#N)cccc21]

2-Aminoacetonitrile (0.093 g, 1.7 mmol) was added to a suspension of 6-(1-methylbenzimidazol-4-yl)-5-methylsulfinyl-3-[4-(4-oxidomorpholin-4-ium-4-yl)anilino]pyrazine-2-carboxamide (0.042 g, 0.08 mmol) in dioxane (1.5 mL). The resulting mixture was stirred at 110° C. for 30 minutes. The reaction was then quenched with water and extracted with DCM. The organic layer was concentrated. The resulting residue was purified by reverse phase chromatography on c18, using 10-45% MeCN—$H_2O$ as eluent and 0.2% ammonium hydroxide as modifier, to afford 5-(cyanomethylamino)-6-(1-methylbenzimidazol-4-yl)-3-(4-morpholinoanilino)pyrazine-2-carboxamide (7.0 mg, 18%) as a yellow solid; 1H NMR (500 MHz, DMSO-d6) δ 3.04-3.13 (4H, m), 3.70-3.78 (4H, m), 3.91 (3H, s), 4.37 (2H, d), 6.94 (2H, d), 7.42 (1H, t), 7.48 (1H, br d), 7.62-7.71 (4H, m), 7.77 (1H, br s), 8.37 (1H, s), 8.84 (1H, t), 11.27 (1H, s). m/z: (ES+), [M+H]+=484.3

Example 23

5-[[(2R)-2-Fluoropropyl]amino]-6-(1-methylbenzimidazol-4-yl)-3-(4-morpholinoanilino)pyrazine-2-carboxamide

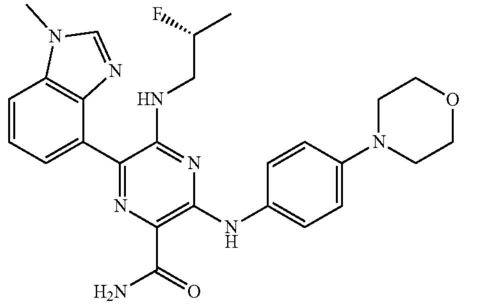 [SMILES: C[C@@H](F)CNc1nc(Nc2ccc(N3CCOCC3)cc2)c(C(N)=O)nc1-c1cccc2c1ncn2C]

Potassium carbonate (0.12 g, 0.88 mmol) was added to a suspension of (2R)-2-fluoropropan-1-amine hydrochloride (0.066 g, 0.58 mmol) and 6-(1-methylbenzimidazol-4-yl)-5-methylsulfinyl-3-[4-(4-oxidomorpholin-4-ium-4-yl)anilino]pyrazine-2-carboxamide (0.042 g, 0.08 mmol) in dioxane (1.5 mL). The resulting mixture was stirred at 110° C. for 30 minutes. The reaction was then quenched with water and extracted with DCM. The organic layer was concentrated. The resulting residue was purified by reverse phase chromatography on c18, using 10-55% MeCN—$H_2O$ as eluent and 0.2% $NH_4OH$ as modifier, to afford 5-[[(2R)-2-fluoropropyl]amino]-6-(1-methylbenzimidazol-4-yl)-3-(4-morpholinoanilino)pyrazine-2-carboxamide (7.0 mg, 17%) as a yellow solid; 1H NMR (500 MHz, DMSO-d6) δ 1.33 (3H, dd), 3.02-3.11 (4H, m), 3.52-3.71 (2H, m), 3.71-3.80 (4H, m), 3.91 (3H, s), 4.81-4.99 (1H, m), 6.93 (2H, d), 7.36 (1H, br d), 7.41 (1H, t), 7.55 (2H, d), 7.64 (1H, d), 7.67 (1H, br d), 7.69 (1H, d), 8.35 (1H, s), 8.75 (1H, t), 11.16 (1H, s). m/z: (ES+), [M+H]+=505.3

Example 24

5-[[(2S)-2-Fluoropropyl]amino]-6-(1-methylbenzimidazol-4-yl)-3-(4-morpholinoanilino)pyrazine-2-carboxamide

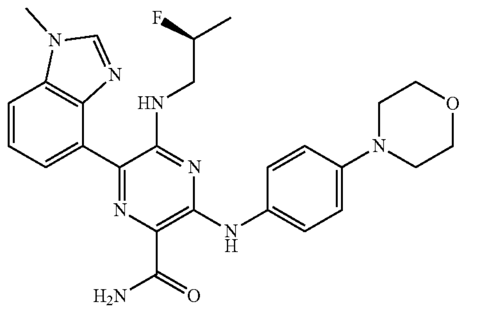 [SMILES: C[C@H](F)CNc1nc(Nc2ccc(N3CCOCC3)cc2)c(C(N)=O)nc1-c1cccc2c1ncn2C]

Potassium carbonate (0.120 g, 0.88 mmol) was added to a suspension of (2S)-2-fluoropropan-1-amine hydrochloride (0.047 g, 0.41 mmol) and 6-(1-methylbenzimidazol-4-yl)-5-methylsulfinyl-3-[4-(4-oxidomorpholin-4-ium-4-yl)anilino]pyrazine-2-carboxamide (0.042 g, 0.080 mmol) in dioxane (1.5 mL). The resulting mixture was stirred at 110° C. for 30 minutes. The reaction was then quenched with water and extracted with DCM. The organic layer was concentrated. The resulting residue was purified by reverse phase chromatography on C18, using 10-55% MeCN—$H_2O$ as eluent and 0.2% $NH_4OH$ as modifier, to afford 5-[[(2S)-2-fluoropropyl]amino]-6-(1-methylbenzimidazol-4-yl)-3-(4-morpholinoanilino)pyrazine-2-carboxamide (6.0 mg, 14%) as a yellow solid; 1H NMR (500 MHz, DMSO-d6) δ 1.33 (3H, dd), 3.01-3.11 (4H, m), 3.52-3.71 (2H, m), 3.71-3.76 (4H, m), 3.91 (3H, s), 4.80-5.01 (1H, m), 6.93 (2H, d), 7.36 (1H, br d), 7.41 (1H, t), 7.55 (2H, d), 7.64 (1H, d), 7.67 (1H, br d), 7.69 (1H, d), 8.35 (1H, s), 8.75 (1H, t), 11.16 (1H, s); m/z: (ES+), [M+H]=505.4

Example 25

6-(1-Methylbenzimidazol-4-yl)-3-(4-morpholinoanilino)-5-(oxetan-3-ylmethylamino) pyrazine-2-carboxamide

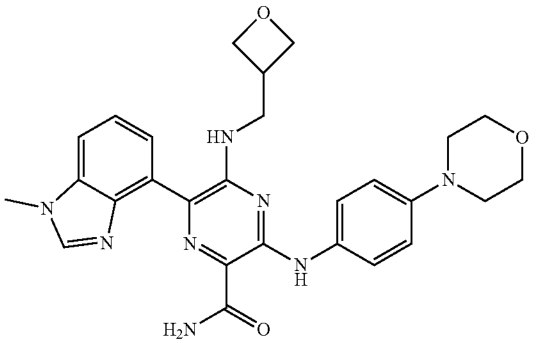 [SMILES: Cn1cnc2c(-c3nc(C(N)=O)c(Nc4ccc(N5CCOCC5)cc4)nc3NCC3COC3)cccc21]

Oxetan-3-ylmethanamine (36 mg, 0.41 mmol) was added to a solution of 6-(1-methylbenzimidazol-4-yl)-5-methylsulfinyl-3-[4-(4-oxidomorpholin-4-ium-4-yl)anilino]pyrazine-2-carboxamide (35 mg, 0.070 mmol) in DMF (690 μL). The resulting mixture was stirred at 25 C for 16 hours. The reaction was then quenched with sodium hydrogen sulfite (36 mg, 0.34 mmol) and stirred at 25 C for 1 hour. The resulting mixture was purified directly by C18 reverse phase chromatography, using 0-100% MeCN—$H_2O$ as eluent, to afford 6-(1-methylbenzimidazol-4-yl)-3-(4-morpholinoanilino)-5-(oxetan-3-ylmethylamino) pyrazine-2-carboxamide; 1H NMR (500 MHz, DMSO-d6) 3.05 (4H, t), 3.69 (2H, t), 3.74 (4H, t), 3.90 (3H, s), 4.38 (2H, t), 4.63-4.70 (2H, m), 6.93 (2H, d), 7.31-7.37 (1H, m), 7.41 (1H, t), 7.58 (2H, d), 7.61-7.67 (2H, m), 7.71 (1H, d), 8.34 (1H, s), 8.61 (1H, t), 11.18 (1H, s); the oxetanyl methine proton was buried beneath the residual water peak; m/z: (ES+), [M+H]+=515.3

Example 26

5-Ethynyl-6-(1-methylbenzimidazol-4-yl)-3-(4-morpholinoanilino)pyrazine-2-carboxamide

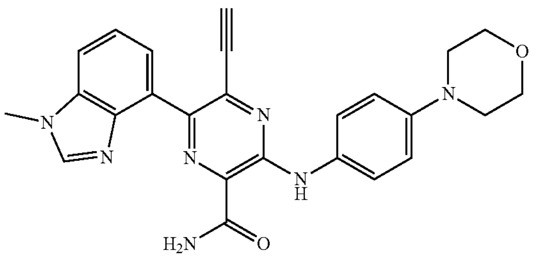 [SMILES: C#Cc1nc(Nc2ccc(N3CCOCC3)cc2)c(C(N)=O)nc1-c1cccc2c1ncn2C]

(a) Methyl 3-amino-6-(1-methylbenzimidazol-4-yl)-5-(2-triisopropylsilylethynyl)pyrazine-2-carboxylate Tricyclohexylphosphonium tetrafluoroborate (136 mg, 0.370 mmol) was added to a mixture of methyl 3-amino-6-chloro-5-(2-triisopropylsilylethynyl)pyrazine-2-carboxylate (680 mg, 1.85 mmol), (1-methylbenzimidazol-4-yl) boronic acid (650 mg, 3.70 mmol), potassium phosphate (785 mg, 3.70 mmol), and $PCy_3$ Pd G3 (240 mg, 0.370 mmol) in 1,4-dioxane/$H_2O$ (20 mL) under nitrogen. The resulting mixture was stirred at 100° C. for 16 hours. The reaction was then concentrated. The resulting residue was purified by silica gel chromatography, using 0-10% MeOH-DCM as eluent, to afford methyl 3-amino-6-(1-methylbenzimidazol-4-yl)-5-(2-triisopropylsilylethynyl)pyrazine-2-carboxylate (500 mg, 58% yield) as a yellow oil which solidified on standing. m/z: (ES+), [M+H]+=464.2

(b) Methyl 6-(1-methylbenzimidazol-4-yl)-3-(4-morpholinoanilino)-5-(2-triisopropylsilylethynyl) pyrazine-2-carboxylate BrettPhos Pd G3 (36 mg, 0.040 mmol) was added to a suspension of methyl 3-amino-6-(1-methylbenzimidazol-4-yl)-5-(2-triisopropylsilylethynyl)pyrazine-2-carboxylate (110 mg, 0.24 mmol), 4-(4-bromophenyl) morpholine (48 mg, 0.20 mmol), and cesium carbonate (193 mg, 0.590 mmol) in 1,4-dioxane (15 mL) under nitrogen. The resulting mixture was stirred at 100° C. for 5 hours. The reaction was then concentrated. The resulting residue was purified by silica gel chromatography, using 0-30% MeOH-DCM as eluent, to afford methyl 6-(1-methylbenzimidazol-4-yl)-3-(4-morpholinoanilino)-5-(2-triisopropylsilylethynyl)pyrazine-2-carboxylate as a red solid.

(c) 6-(1-Methylbenzimidazol-4-yl)-3-(4-morpholinoanilino)-5-(2-triisopropylsilylethynyl)pyrazine-2-carboxamide 7 N Methanolic ammonia (8.0 mL, 56 mmol) was added to methyl 6-(1-methylbenzimidazol-4-yl)-3-(4-morpholinoanilino)-5-(2-triisopropylsilylethynyl)pyrazine-2-carboxylate (260 mg, 0.42 mmol). The resulting mixture was stirred at 70° C. for 2 hours. The reaction was then concentrated. The resulting residue was purified by silica gel chromatography to afford 6-(1-methylbenzimidazol-4-yl)-3-(4-morpholinoanilino)-5-(2-triisopropylsilylethynyl)pyrazine-2-carboxamide (250 mg, 99%) as a brown solid. m/z: (ES+), [M+H]+=610.4

(d) 5-Ethynyl-6-(1-methylbenzimidazol-4-yl)-3-(4-morpholinoanilino)pyrazine-2-carboxamide 1 M TBAF in THF (2.0 mL, 2.00 mmol) was added to 6-(1-methylbenzimidazol-4-yl)-3-(4-morpholinoanilino)-5-(2-triisopropylsilylethynyl)pyrazine-2-carboxamide (100 mg, 0.16 mmol) in THF (5 mL). The resulting mixture was stirred at room temperature for 16 hours. The reaction was then concentrated. The resulting residue was purified by silica gel chromatography, using 0-8% MeOH-DCM as eluent. The resulting residue was purified further by preparative HPLC, using a 5 micron, 19 mm×150 mm SunFire Prep C18 OBD column, decreasingly polar mixtures of MeCN—$H_2O$ as eluent, and 0.1% formic acid as modifier, to afford 5-ethynyl-6-(1-methylbenzimidazol-4-yl)-3-(4-morpholinoanilino)pyrazine-2-carboxamide (28 mg, 38%) as a yellow solid; 1H NMR (400 MHz, DMSO-d6) δ 3.09 (4H, t), 3.72-3.79 (4H, m), 3.89 (3H, s), 4.23 (1H, s), 6.99 (2H, d), 7.37 (1H, t), 7.44-7.50 (1H, m), 7.53-7.62 (2H, m), 7.62-7.68 (1H, m), 8.00 (1H, s), 8.10 (1H, s), 8.20 (1H, s), 11.03 (1H, s); m/z: (ES+), [M+H]+=454.2

Example 27

5-(Difluoromethyl)-6-(1-methylbenzimidazol-4-yl)-3-(4-morpholinoanilino)pyrazine-2-carboxamide

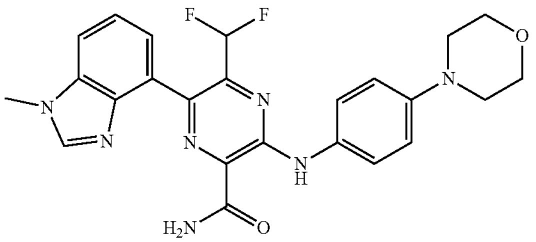 [SMILES: Cn1cnc2c(-c3nc(C(N)=O)c(Nc4ccc(N5CCOCC5)cc4)nc3C(F)F)cccc21]

(a) Methyl 3-amino-6-chloro-5-(difluoromethyl) pyrazine-2-carboxylate

Methyl 3-amino-5,6-dichloro-pyrazine-2-carboxylate (500 mg, 2.25 mmol) was added to a mixture of bis (dibenzylideneacetone) palladium (129 mg, 0.230 mmol), DPEPhos (243 mg, 0.450 mmol) and [1,3-bis(2,6-diisopropylphenyl) imidazolidin-2-ylidene]-(difluoromethyl) silver (1.24 g, 2.25 mmol) in toluene (30 mL) under nitrogen. The resulting solution was stirred at 80° C. for 18 hours. The reaction was then concentrated. The resulting residue was purified by C18 reverse phase chromatography, using 0-50% MeCN—$H_2O$ as eluent, to afford methyl 3-amino-6-chloro-5-(difluoromethyl)pyrazine-2-carboxylate (410 mg, 77%) as a brown solid; 1H NMR (400 MHZ, $CDCl_3$) δ 4.02 (3H, s), 6.79 (1H, t); the amino protons exchanged out in $CDCl_3$. m/z: (ES+), [M+H]+=238.0

(b) Methyl 3-amino-5-(difluoromethyl)-6-(1-methylbenzimidazol-4-yl)pyrazine-2-carboxylate Pd(dppf)$Cl_2$ (123 mg, 0.170 mmol) was added to a mixture of methyl 3-amino-5-chloro-6-(difluoromethyl)pyrazine-2-carboxylate (400 mg, 1.68 mmol), (1-methylbenzimidazol-4-yl) boronic acid (296 mg, 1.68 mmol), and cesium fluoride (511 mg, 3.37 mmol) in 1,4-dioxane (20 mL) under nitrogen. The resulting mixture was stirred at 100° C. for 16 hours. The reaction was then filtered through Celite. The filtrate was then concentrated. The resulting residue was purified by silica gel chromatography, using 0-10% MeOH-DCM as eluent. The resulting residue was purified by C18 reverse phase chromatography, using 0-50% MeCN—$H_2O$ as eluent, to afford methyl 3-amino-5-(difluoromethyl)-6-(1-methylbenzimidazol-4-yl)pyrazine-2-carboxylate (120 mg, 21%) as a yellow solid; 1H NMR (400 MHZ, DMSO-d6) δ 3.78 (3H, s), 3.91 (3H, s), 6.88 (1H, t), 7.34 (1H, dd), 7.42 (1H, t), 7.60-7.75 (3H, m), 8.27 (1H, s); m/z: (ES+), [M+H]+=334.1

(c) Methyl 5-(difluoromethyl)-6-(1-methylbenzimidazol-4-yl)-3-(4-morpholinoanilino)pyrazine-2-carboxylate BrettPhos Pd G3 (27 mg, 0.030 mmol) was added to a suspension of methyl 3-amino-5-(difluoromethyl)-6-(1-methylbenzimidazol-4-yl)pyrazine-2-carboxylate (100 mg, 0.30 mmol), 4-(4-bromophenyl) morpholine (73 mg, 0.30 mmol), and cesium carbonate (196 mg, 0.600 mmol) in 1,4-dioxane (2 mL) under nitrogen. The resulting mixture was stirred at 100° C. for 16 hours. The reaction was then concentrated. The resulting residue was purified by silica gel chromatography, using 0-6% MeOH-DCM as eluent, to afford methyl 5-(difluoromethyl)-6-(1-methylbenzimidazol-4-yl)-3-(4-morpholinoanilino)pyrazine-2-carboxylate (90 mg, 61%) as a yellow solid. m/z: (ES+), [M+H]+=495.1

(d) 5-(Difluoromethyl)-6-(1-methylbenzimidazol-4-yl)-3-(4-morpholinoanilino)pyrazine-2-carboxamide 7 N Methanolic ammonia (5.0 mL, 35 mmol) was added to methyl 5-(difluoromethyl)-6-(1-methylbenzimidazol-4-yl)-3-(4-morpholinoanilino)pyrazine-2-carboxylate (80 mg, 0.16 mmol). The resulting mixture was stirred at 60° C. for 16 hours. The reaction was then concentrated. The resulting residue was purified by preparative HPLC using a 5 micron, 30×100 mm SunFire Prep C18 OBD column, decreasingly polar mixtures of MeCN—$H_2O$ as eluent, and 0.1% formic acid as modifier to afford 5-(difluoromethyl)-6-(1-methylbenzimidazol-4-yl)-3-(4-morpholinoanilino)pyrazine-2-carboxamide (55 mg, 71%) as a yellow solid; 1H NMR (300 MHz, DMSO-d6) δ 3.10 (4H, t), 3.75 (4H, t), 3.92 (3H, s), 6.75-7.28 (3H, m), 7.45 (1H, t), 7.60 (1H, dd), 7.64-7.77 (3H, m), 8.12 (1H, s), 8.31 (2H, s), 11.21 (1H, s); m/z: (ES+), [M+H]+=480.3

Example 28

5-Chloro-6-(1-methylbenzimidazol-4-yl)-3-(4-morpholinoanilino)pyrazine-2-carboxamide

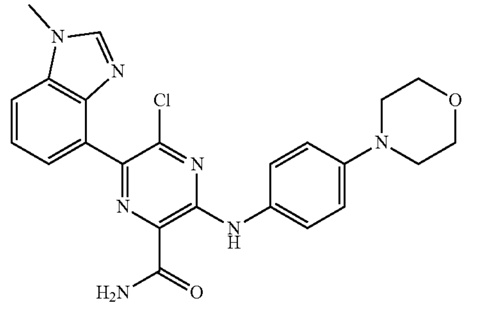 [SMILES: Cn1cnc2c(-c3nc(C(N)=O)c(Nc4ccc(N5CCOCC5)cc4)nc3Cl)cccc21]

(a) Methyl 3-amino-6-chloro-5-[(4-methoxyphenyl)methoxy]pyrazine-2-carboxylate (4-Methoxyphenyl) methanol (3.42 g, 24.8 mmol) was added to a suspension of methyl 3-amino-5,6-dichloropyrazine-2-carboxylate (5.00 g, 22.5 mmol) and potassium phosphate (14.3 g, 67.6 mmol) in MeCN (30 mL). The resulting mixture was stirred at 80° C. for 1 hour. The reaction was then concentrated. The resulting residue was purified by silica gel chromatography, using 0-10% MeOH-DCM as eluent, to afford methyl 3-amino-6-chloro-5-[(4-methoxyphenyl) methoxy]pyrazine-2-carboxylate (2.3 g, 32%) as a yellow solid; 1H NMR (400 MHZ, DMSO-d6) δ 3.73 (3H, s), 3.74-3.81 (3H, m), 4.41 (2H, s), 6.84-6.90 (2H, m), 6.95 (2H, dq), 7.18-7.25 (2H, m); m/z: (ES+), [M+H]+=324.1

(b) Methyl 3-amino-5-[(4-methoxyphenyl)methoxy]-6-(1-methylbenzimidazol-4-yl)pyrazine-2-carboxylate $PdCl_2$(dppf) (0.45 g, 0.62 mmol) was added to a suspension of methyl 3-amino-6-chloro-5-[(4-methoxyphenyl) methoxy]pyrazine-2-carboxylate (2.00 g, 6.18 mmol), (1-methylbenzimidazol-4-yl) boronic acid (1.09 g, 6.18 mmol), and cesium fluoride (1.88 g, 12.4 mmol) in 1,4-dioxane (20 mL). The resulting mixture was stirred at 100° C. for 4 hours. The reaction was then concentrated. The resulting residue was purified by silica gel chromatography, using 0-10% MeOH-DCM as eluent, to afford methyl 3-amino-5-[(4-methoxyphenyl) methoxy]-6-(1-methylbenzimidazol-4-yl)pyrazine-2-carboxylate (1.80 g, 70%) as a brown solid; 1H NMR (300 MHz, DMSO-d6) δ 3.71 (3H, s), 3.78 (3H, s), 3.87 (3H, s), 5.27 (2H, s), 6.83 (2H, d), 6.91-6.98 (2H, m), 7.28-7.58 (5H, m), 8.17 (1H, s). m/z: (ES+), [M+H]+=420.1

(c) Methyl 5-[(4-methoxyphenyl) methoxy]-6-(1-methylbenzimidazol-4-yl)-3-(4-morpholinoanilino)pyrazine-2-carboxylate Brettphos Pd G3 (0.389 g, 0.430 mmol) was added to a suspension of methyl 3-amino-5-[(4-methoxyphenyl)methoxy]-6-(1-methylbenzimidazol-4-yl)pyrazine-2-carboxylate (1.80 g, 4.29 mmol), 4-(4-bromophenyl) morpholine (1.04 g, 4.29 mmol), and cesium carbonate (4.19 g, 12.9 mmol) in 1,4-dioxane (20 mL). The resulting mixture was stirred at 100° C. for 16 hours. The reaction was then concentrated. The resulting residue was purified by silica gel chromatography, using 0-10% DCM-MeOH as eluent, to afford methyl 5-[(4-methoxyphenyl) methoxy]-6-(1-methylbenzimidazol-4-yl)-3-(4-morpholinoanilino)pyrazine-2-carboxylate (1.90 g, 76%) as a brown solid; 1H NMR (400 MHZ, DMSO-d6) δ 3.00-3.27 (4H, m), 3.70 (3H, s), 3.70-3.80 (4H, m), 3.86 (3H, s), 3.87 (3H, s), 5.27 (2H, s), 6.82 (2H, d), 6.97 (3H, d), 7.18-7.27 (3H, m), 7.50 (2H, d), 7.58 (1H, d), 8.20 (1H, s), 10.10 (1H, s). m/z: (ES+), [M+H]+ =581.3

(d) Methyl 5-hydroxy-6-(1-methylbenzimidazol-4-yl)-3-(4-morpholinoanilino)pyrazine-2-carboxylate Methyl 5-[(4-methoxyphenyl) methoxy]-6-(1-methylbenzimidazol-4-yl)-3-(4-morpholinoanilino)pyrazine-2-carboxylate (1.8 g, 3.10 mmol) was added to a mixture of TFA (5 mL) and DCM (20 mL). The resulting mixture was stirred at 25° C. for 1 hour. The reaction was then concentrated. The resulting residue was purified by silica gel chromatography, using 0-10% MeOH-DCM as eluent, to afford methyl 5-hydroxy-6-(1-methylbenzimidazol-4-yl)-3-(4-morpholinoanilino)pyrazine-2-carboxylate (1.10 g, 77%) as a brown solid; 1H NMR (300 MHz, DMSO-d6) δ 3.12-3.20 (4H, m), 3.74-3.81 (4H, m), 3.93 (3H, s), 4.13 (3H, s), 7.02-7.07 (2H, m), 7.54 (2H, d), 7.73 (1H, t), 7.97-8.03 (1H, m), 8.22 (1H, d), 8.44 (1H, s), 9.70 (1H, s), 10.09 (1H, s); m/z: (ES+), [M+H]+=461.2

(e) Methyl 5-chloro-6-(1-methylbenzimidazol-4-yl)-3-(4-morpholinoanilino)pyrazine-2-carboxylate Phosphoryl trichloride (5.00 mL, 53.7 mmol) was added to methyl 5-hydroxy-6-(1-methylbenzimidazol-4-yl)-3-(4-morpholinoanilino)pyrazine-2-carboxylate (0.30 g, 0.65 mmol). The resulting mixture was stirred at 100° C. for 16 hours. The reaction was then concentrated. The resulting residue was redissolved in EtOAc and washed sequentially with saturated aqueous sodium bicarbonate and brine. The organic layer was dried over sodium sulfate, filtered, and concentrated. The resulting residue was purified by silica gel chromatography, using 0-20% MeOH-DCM as eluent, to afford methyl 5-chloro-6-(1-methylbenzimidazol-4-yl)-3-(4-morpholinoanilino)pyrazine-2-carboxylate (0.200 g, 64%) as a brown solid; 1H NMR (400 MHZ, DMSO-d6) δ 3.14-3.18 (4H, m), 3.55-3.59 (4H, m), 3.92 (3H, s), 4.07 (3H, s), 7.04 (2H, d), 7.49-7.73 (5H, m), 8.01 (1H, s), 10.00 (1H, s); m/z: (ES+), [M+H]+=479.2

(f) 5-Chloro-6-(1-methylbenzimidazol-4-yl)-3-(4-morpholinoanilino)pyrazine-2-carboxamide 7 N Methanolic ammonia (10 mL, 70 mmol) was added to methyl 5-chloro-6-(1-methylbenzimidazol-4-yl)-3-(4-morpholinoanilino)pyrazine-2-carboxylate (200 mg, 0.42 mmol). The resulting suspension was stirred at 25° C. for 1 hour. The reaction was then concentrated. The resulting residue was purified by preparative HPLC, using a 30 mm×150 mm, 5 μm, CSH OBD column, using 20-35% MeCN—$H_2O$ as eluent and 0.1% formic acid as modifier, to afford 5-chloro-6-(1-methylbenzimidazol-4-yl)-3-(4-morpholinoanilino)pyrazine-2-carboxamide (17 mg, 8.8%) as a orange solid; 1H NMR (400 MHZ, DMSO-d6) δ 3.10 (4H, t), 3.75 (4H, t), 3.89 (3H, s), 7.00 (2H, d), 7.35-7.46 (2H, m), 7.54 (2H, d), 7.68 (1H, dd), 7.98 (1H, s), 8.08 (1H, s), 8.21 (1H, s), 11.14 (1H, s). m/z: (ES+), [M+H]+=464.2

Example 29

6-(1-Methylbenzimidazol-4-yl)-5-[(1-methylpyrazol-4-yl)amino]-3-(4-morpholinoanilino)pyrazine-2-carboxamide

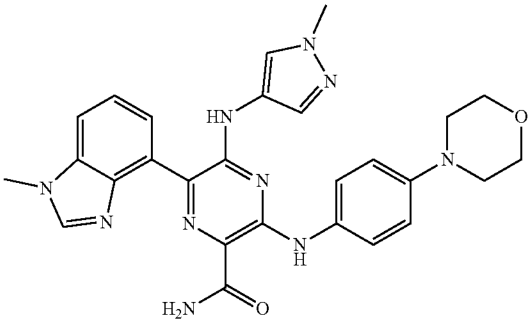 [SMILES: Cn1cc(Nc2nc(Nc3ccc(N4CCOCC4)cc3)c(C(N)=O)nc2-c2cccc3c2ncn3C)cn1]

mCPBA (63 mg, 0.27 mmol) in DCM (2.1 mL) was added dropwise to a solution of 6-(1-methylbenzimidazol-4-yl)-5-methylsulfanyl-3-(4-morpholinoanilino)pyrazine-2-carboxamide (50 mg, 0.11 mmol) in DCM (2.1 mL) at −5° C. The resulting mixture was stirred at room temperature for 5 minutes. The reaction was then concentrated. The resulting residue was redissolved in NMP (2 mL). 1-methylpyrazol-4-amine (31 mg, 0.32 mmol) was added. The resulting mixture was stirred at 150° C. for 3 hours. The reaction was then concentrated. The resulting residue was purified by preparative HPLC, using a 5 micron, 19 mm×100 mm Xbridge C18 column, 20-50% MeCN—$H_2O$ as eluent, and 0.2% ammonium hydroxide as eluent, to afford a bright yellow solid. This material was suspended in MeOH (2 mL) and sonicated for 30 minutes. The resulting suspension was filtered to afford 6-(1-methylbenzimidazol-4-yl)-5-[(1-methylpyrazol-4-yl)amino]-3-(4-morpholinoanilino)pyrazine-2-carboxamide (8.0 mg, 15%) as a bright yellow solid; 1H NMR (500 MHz, DMSO-d6) δ 3.09-3.12 (4H, m), 3.67 (3H, s), 3.71-3.77 (4H, m), 3.92 (3H, s), 7.00 (2H, br d), 7.32-7.40 (4H, m), 7.43 (1H, br t), 7.62-7.68 (2H, m), 7.70 (1H, br s), 7.80 (1H, br d), 8.39 (1H, s), 10.79 (1H, s), 10.90 (1H, s); m/z: (ES+), [M+H]+=525.4

Example 30

6-(1-Methylbenzimidazol-4-yl)-3-(4-morpholinoanilino)-5-(2-pyridylamino) pyrazine-2-carboxamide

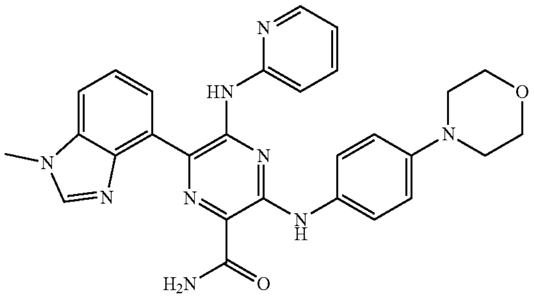 [SMILES: Cn1cnc2c(-c3nc(C(N)=O)c(Nc4ccc(N5CCOCC5)cc4)nc3Nc3ccccn3)cccc21]

(a) Methyl 3-amino-6-chloro-5-(2-pyridylamino) pyrazine-2-carboxylate 60 wt % Sodium hydride in mineral oil (397 mg, 9.92 mmol) was added to a solution of pyridin-2-amine (856 mg, 9.10 mmol) in THF (36 mL). The resulting mixture was stirred at room temperature for 1 hour. Methyl 3-amino-5,6-dichloro-pyrazine-2-carboxylate (1.74 g, 7.85 mmol) and DMF (9 mL) were sequentially added. The resulting suspension was stirred at room temperature for 12 hours. The reaction was then concentrated. The resulting residue was triturated in water, then filtered and dried under air to afford in vacuo and water was added to the mixture. Then the resulting solid was filtered and air-dried to afford methyl 3-amino-6-chloro-5-(2-pyridylamino) pyrazine-2-carboxylate (2.20 g, 95% yield) as a pale yellow solid. 1H NMR (500 MHZ, DMSO-d6) 3.98 (3H, s), 7.15 (1H, ddd), 7.75-7.92 (3H, m), 8.15 (1H, d), 8.33 (1H, dd), 9.63 (1H, s). m/z: (ES+), [M+2+H]+=281.9

(b) Methyl 6-chloro-3-fluoro-5-(2-pyridylamino) pyrazine-2-carboxylate

Sodium nitrite (154 mg, 2.24 mmol) was added portion-wise to a solution of methyl 3-amino-6-chloro-5-(2-pyridylamino) pyrazine-2-carboxylate (521 mg, 1.86 mmol) in HF*pyridine (8.40 mL, 245 mmol) at −10° C. The reaction was then stirred at 25 C for 1 hour. The reaction was then quenched with water and extracted with ethyl acetate. The organic layer was dried over magnesium sulfate, filtered, and concentrated to afford methyl 6-chloro-3-fluoro-5-(2-pyridylamino) pyrazine-2-carboxylate (0.420 g, 80% yield) as an orange solid. m/z: (ES−), [M−H]−=281.3

(c) Methyl 6-chloro-3-(4-morpholinoanilino)-5-(2-pyridylamino) pyrazine-2-carboxylate DIPEA (234 μL, 1.34 mmol) was added to a solution of methyl 6-chloro-3-fluoro-5-(2-pyridylamino) pyrazine-2-carboxylate (189 mg, 0.67 mmol) and 4-morpholinoaniline (119 mg, 0.670 mmol) in DMF (4 mL). The resulting mixture was heated at 100° C. for 12 hours. The reaction was then diluted with water. The resulting precipitate was collected by filtration and air-dried to afford methyl 6-chloro-3-(4-morpholinoanilino)-5-(2-pyridylamino) pyrazine-2-carboxylate (0.280 g, 95%) as a brown solid. m/z: (ES−), [M−H]−=439.3

(d) 6-Chloro-3-(4-morpholinoanilino)-5-(2-pyridylamino) pyrazine-2-carboxamide

7 N Methanolic ammonia (4.0 mL, 28 mmol) was added to methyl 6-chloro-3-(4-morpholinoanilino)-5-(2-pyridylamino) pyrazine-2-carboxylate (230 mg, 0.52 mmol). The resulting suspension was stirred at 100° C. for 12 hours. The reaction was then concentrated to afford 6-chloro-3-(4-morpholinoanilino)-5-(2-pyridylamino) pyrazine-2-carboxamide as a brown solid (165 mg, 74% yield).

(e) 6-(1-Methylbenzimidazol-4-yl)-3-(4-morpholinoanilino)-5-(2-pyridylamino) pyrazine-2-carboxamide $PdCl_2$(dppf) (28 mg, 0.040 mmol), 1-methyl-4-(4,4,5,5-tetramethyl-1,3,2-dioxaborolan-2-yl)benzimidazole (185 mg, 65 wt %, 0.46 mmol), cesium fluoride (177 mg, 1.16 mmol), and 6-chloro-3-(4-morpholinoanilino)-5-(2-pyridylamino) pyrazine-2-carboxamide (165 mg, 0.39 mmol) were combined in a microwave vial, which was evacuated and backfilled three times with nitrogen. Dioxane (1.55 mL) and water (0.39 mL) were added. The resulting mixture was stirred at 100° C. for 12 hours. The reaction was then concentrated. The resulting residue was purified by preparative HPLC, using 30-70% MeCN—$H_2O$ as eluent, and 0.2% ammonium hydroxide as modifier, to afford 6-(1-methylbenzimidazol-4-yl)-3-(4-morpholinoanilino)-5-(2-pyridylamino) pyrazine-2-carboxamide (50 mg, 25%) as pale yellow solid; 1H NMR (400 MHz, DMSO-d6) δ 3.04-3.13 (4H, m), 3.67-3.80 (4H, m), 3.95 (3H, s), 6.92 (2H, d), 6.97 (1H, dd), 7.42-7.51 (3H, m), 7.55-7.65 (2H, m), 7.69-7.78 (2H, m), 7.88 (1H, d), 7.91 (1H, br s), 8.17-8.24 (1H, m), 8.51 (1H, s), 10.92 (1H, s), 11.05 (1H, s); m/z: (ES+), [M+H]+=522.3

Example 31

6-(3-Methylimidazo[4,5-c]pyridin-7-yl)-3-(4-morpholinoanilino)-5-(oxetan-3-yl)pyrazine-2-carboxamide

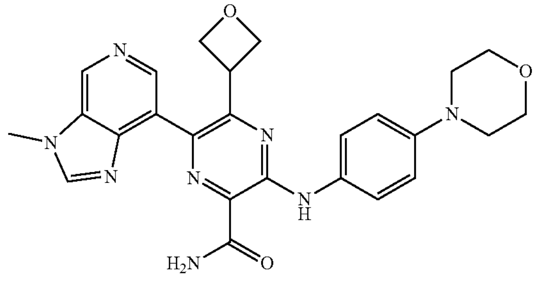 [SMILES: Cn1cnc2c(-c3nc(C(N)=O)c(Nc4ccc(N5CCOCC5)cc4)nc3C3COC3)cncc21]

(a) Methyl 3-amino-6-chloro-5-(oxetan-3-yl)pyrazine-2-carboxylate

Methyl 3-amino-5,6-dichloro-pyrazine-2-carboxylate (500 mg, 2.25 mmol), 4,4'-di-tert-butyl-2,2'-bipyridine (60 mg, 0.23 mmol), Ir ($dFCF_3ppy$)$_2$(dtbbpy) hexafluorophosphate (25 mg, 0.020 mmol), and $NiCl_2$ diglyme (50 mg, 0.23 mmol) were combined in a vial, which was sparged with nitrogen for five minutes. DME (13.6 mL) was then added. 3-iodooxetane (400 μL, 4.5 mmol), 1,1,1,3,3,3-hexamethyl-2-(trimethylsilyl)trisilane (1.04 mL, 3.38 mmol), and sodium carbonate (477 mg, 4.50 mmol) were sequentially added. The resulting mixture was sparged again with nitrogen for 5 minutes, then stirred in a photoreactor under blue light at ambient temperature, without a cooling fan, for 16 hours. The reaction was then concentrated. The resulting residue was purified by flash silica chromatography, using 0-30% EtOAc-hexanes as eluent, to afford methyl 3-amino-6-chloro-5-(oxetan-3-yl)pyrazine-2-carboxylate (0.120 g, 22%) as a yellow solid; 1H NMR (500 MHz, CHLOROFORM-d) δ 3.99 (3H, s), 4.61 (1H, tt), 4.92-4.99 (2H, m), 5.00-5.06 (2H, m). The NH2 signal exchanged out in chloroform-d; m/z: (ES+), [M+H]+=244.1

(b) Methyl 6-(3-methylimidazo[4,5-c]pyridin-7-yl)-3-(4-morpholinoanilino)-5-(oxetan-3-yl)pyrazine-2-carboxylate DMF (2.4 mL) was added to a mixture of bis(pinacolato) diboron (299 mg, 1.18 mmol), cataCXium A (17 mg, 0.050 mmol), cataCXium A Pd G3 (34 mg, 0.050 mmol), potassium acetate (139 mg, 1.41 mmol), and 7-bromo-3-methyl-imidazo[4,5-c]pyridine (100 mg, 0.47 mmol). The resulting suspension was sparged with nitrogen for 5 minutes, stirred at 80° C. for 16 hours, and then at 100° C. for 24 hours. The reaction was then allowed to cool to room temperature and set aside.

Sodium nitrite (37 mg, 0.54 mmol) was added to a solution of methyl 3-amino-6-chloro-5-(oxetan-3-yl)pyrazine-2-carboxylate (120 mg, 0.49 mmol) in HF*pyridine (5.30 mL, 155 mmol) at 0° C. The resulting mixture was allowed to warm to room temperature and stirred for 1 hour. The reaction was then poured into 75 mL of water and extracted three times with DCM (20 mL each). The combined organic layers were dried over sodium sulfate, filtered, and concentrated. The resulting residue was dissolved in DMF (2.4 mL). DIPEA (85 μL, 0.49 mmol) and 4-morpholinoaniline (87 mg, 0.49 mmol) were sequentially added. The resulting mixture was stirred at 100° C. for 1 hour. The reaction was then concentrated. Pd(dppf) C12 DCM (24 mg, 0.030 mmol) and cesium fluoride (90 mg, 0.59 mmol) were added to the resulting residue. The borylation mixture was added. The resulting suspension was sparged with nitrogen for 5 minutes, then stirred at 100° C. for 2 hours. The reaction was then concentrated onto celite. The resulting material was purified by silica gel chromatography, using 0-10% MeOH-DCM with 0-1% ammonia as eluent, to afford methyl 6-(3-methylimidazo[4,5-c]pyridin-7-yl)-3-(4-morpholinoanilino)-5-(oxetan-3-yl)pyrazine-2-carboxylate (0.089 g, 60%) as a brown solid; 1H NMR (500 MHz, DMSO-d6) δ 3.04-3.13 (4H, m), 3.68-3.77 (4H, m), 3.91 (3H, s), 4.00 (3H, s), 4.29-4.39 (1H, m), 4.51 (2H, dd), 4.67-4.75 (2H, m), 6.99 (2H, d), 7.71 (2H, d), 8.36 (1H, s), 8.42 (1H, s), 9.04 (1H, s), 9.99 (1H, s); m/z: (ES+), [M+H]+=502.3

(c) 6-(3-Methylimidazo[4,5-c]pyridin-7-yl)-3-(4-morpholinoanilino)-5-(oxetan-3-yl)pyrazine-2-carboxamide 7 N methanolic ammonia (2.0 mL, 14 mmol) was added to methyl 6-(3-methyl-3H-imidazo[4,5-c]pyridin-7-yl)-3-

((4-morpholinophenyl)amino)-5-(oxetan-3-yl)pyrazine-2-carboxylate (89 mg, 0.18 mmol). The resulting mixture was stirred at 100° C. for 2 hours in a Biotage microwave reactor. The reaction was then concentrated. The resulting residue was purified by preparative HPLC, using a 5 micron, 19 mm×250 mm, XSelect CSH Prep C18 OBD column, decreasingly polar mixtures of MeCN—$H_2O$ as eluent, and 0.2% ammonium hydroxide as modifier, to afford 6-(3-methylimidazo[4,5-c]pyridin-7-yl)-3-(4-morpholinoanilino)-5-(oxetan-3-yl)pyrazine-2-carboxamide (0.016 g, 18%) as a yellow solid; 1H NMR (500 MHz, DMSO-d6) 2.97-3.16 (4H, m), 3.65-3.82 (4H, m), 4.01 (3H, s), 4.29-4.46 (1H, m), 4.58 (2H, dd), 4.68-4.83 (2H, m), 6.99 (2H, d), 7.75 (2H, d), 7.84-7.97 (1H, m), 8.23 (1H, s), 8.44 (1H, s), 8.56 (1H, s), 9.04 (1H, s), 11.20 (1H, s); m/z: (ES+), [M+H]+=487.2

Example 32

5-Ethoxy-6-(3-methylimidazo[4,5-c]pyridin-7-yl)-3-(4-morpholinoanilino)pyrazine-2-carboxamide

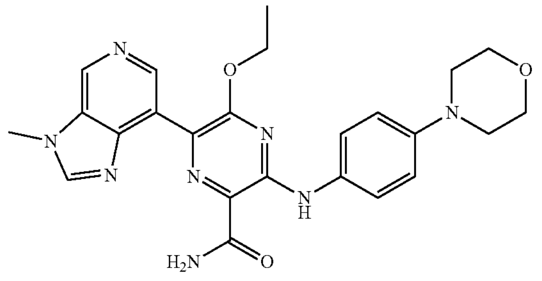 [SMILES: CCOc1nc(Nc2ccc(N3CCOCC3)cc2)c(C(N)=O)nc1-c1cncc2c1ncn2C]

(a) Ethyl 3-amino-6-chloro-5-ethoxy-pyrazine-2-carboxylate

21% Sodium ethoxide in ethanol (3.03 mL, 8.11 mmol) was added to a mixture of methyl 3-amino-5,6-dichloropyrazine-2-carboxylate (1.20 g, 5.40 mmol) in absolute ethanol (25 mL). The resulting mixture was stirred at 80° C. for 3 hours. The reaction was then concentrated. The resulting residue was treated with water and filtered. The solid was collected, washed with water, and dried to afford ethyl 3-amino-6-chloro-5-ethoxy-pyrazine-2-carboxylate (0.995 g, 75% yield) as a beige solid. 1H NMR (500 MHz, DMSO-d6) 1.28 (3H, t), 1.35 (3H, t), 4.26 (2H, q), 4.40 (2H, q), 7.56 (2H, br s). m/z: (ES+), [M+H]+=246.1

(b) 6-Chloro-5-ethoxy-3-(4-morpholinoanilino)pyrazine-2-carboxylic acid

1-BuXPhos Pd G3 (0.133 g, 0.170 mmol) was added to a suspension of ethyl 3-amino-6-chloro-5-ethoxy-pyrazine-2-carboxylate (0.410 g, 1.67 mmol), 4-(4-bromophenyl) morpholine (0.808 g, 3.34 mmol), 1-BuXPhos (0.071 g, 0.17 mmol), and sodium tert-butoxide (0.321 g, 3.34 mmol) in THF (16 mL) under nitrogen. The resulting mixture was stirred at 40° C. for 3 hours. The reaction was then diluted with water and extracted with EtOAc. The organic layer was washed with saturated aqueous sodium bicarbonate and water. The combined aqueous layers were acidified with 1 N HCl. The precipitate was collected by filtration, washed with water, and dried to afford 6-chloro-5-ethoxy-3-(4-morpholinoanilino)pyrazine-2-carboxylic acid (0.390 g, 62% yield). 1H NMR (500 MHz, DMSO-d6) 1.36 (3H, t), 3.04-3.08 (4H, m), 3.71-3.74 (4H, m), 4.41 (2H, q), 6.93 (2H, d), 7.47 (2H, d). The NH and COOH protons were broadened into the baseline. m/z: (ES+), [M+H]+=379.3

(c) 6-Chloro-5-ethoxy-3-(4-morpholinoanilino)pyrazine-2-carboxamide

Triethylamine (0.727 mL, 5.22 mmol) was added to a mixture of 6-chloro-5-ethoxy-3-(4-morpholinoanilino)pyrazine-2-carboxylic acid (0.494 g, 1.30 mmol), ammonium chloride (0.349 g, 6.52 mmol), and HATU (0.744 g, 1.96 mmol) in DMF (10 mL). The resulting mixture was stirred at room temperature for 3.5 hours. The reaction was then diluted with saturated aqueous sodium bicarbonate and water. The precipitate was collected by filtration, washed with water, and dried to afford 6-chloro-5-ethoxy-3-(4-morpholinoanilino)pyrazine-2-carboxamide (0.366 g, 74% yield) as a brown solid. 1H NMR (500 MHz, DMSO-d6) 1.37 (3H, t), 3.03-3.08 (4H, m), 3.70-3.74 (4H, m), 4.42 (2H, q), 6.94 (2H, d), 7.47 (2H, d), 7.65 (1H, br s), 7.87 (1H, s), 11.17 (1H, s). m/z: (ES+), [M+H]+=378.5

(d) 5-Ethoxy-6-(3-methylimidazo[4,5-c]pyridin-7-yl)-3-(4-morpholinoanilino)pyrazine-2-carboxamide A mixture of 2-(3-methyl-3H-imidazo[4,5-c]pyridin-7-yl)-1,3,6,2-dioxazaborocane (0.069 g, 0.28 mmol), 6-chloro-5-ethoxy-3-(4-morpholinoanilino)pyrazine-2-carboxamide (0.053 g, 0.14 mmol), and $PdCl_2$(dppf) (10.3 mg, 0.0100 mmol) in 2 M aqueous potassium phosphate (0.21 mL, 0.42 mmol) and 1,4-dioxane (1.5 mL) was purged with nitrogen. The reaction mixture was stirred in a microwave reactor at 100° C. for 2 hours. The reaction was then concentrated. The resulting residue was washed with water, dried and purified by flash silica chromatography, using 0-10% MeOH-DCM as eluent. The product was further purified by reverse phase C18 flash chromatography, using 0-20% MeCN—$H_2O$ as eluent, and 0.1% formic acid as modifier, to afford 5-ethoxy-6-(3-methylimidazo[4,5-c]pyridin-7-yl)-3-(4-morpholinoanilino)pyrazine-2-carboxamide (0.041 g, 62% yield) as a yellow solid. 1H NMR (500 MHz, DMSO-d6) 1.27 (3H, t), 3.00-3.15 (4H, m), 3.67-3.80 (4H, m), 3.97 (3H, s), 4.41 (2H, q), 6.97 (2H, d), 7.57 (2H, d), 7.66 (1H, br s), 7.94 (1H, br s), 8.39 (1H, s), 8.65 (1H, s), 8.96 (1H, s), 11.19 (1H, s). m/z: (ES+), [M+H]+=475.2

Example 33

6-(3-Methylimidazo[4,5-c]pyridin-7-yl)-3-(4-morpholinoanilino)-5-(trifluoromethyl)pyrazine-2-carboxamide

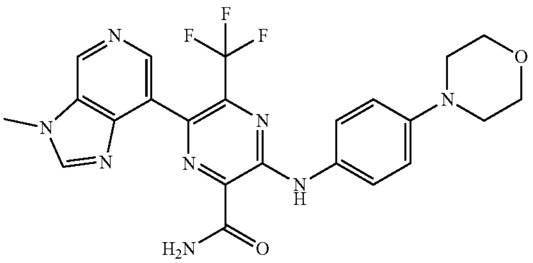 [SMILES: Cn1cnc2c(-c3nc(C(N)=O)c(Nc4ccc(N5CCOCC5)cc4)nc3C(F)(F)F)cncc21]

(a) Ethyl 3,3-diamino-2-nitroso-prop-2-enoate

Ethyl 3-ethoxy-3-imino-propanoate hydrochloride (5.00 g, 25.6 mmol) was added to 2 M ethanolic ammonia (40 mL, 80 mmol) at 0° C. The reaction mixture was stirred at 0° C. for 30 minutes at 25° C. for 3.5 hours. A solution of sodium nitrite (1.94 g, 28.1 mmol) in water (8 mL) was added. 6 N aqueous HCl (15 mL, 90 mmol) was added. The resulting mixture was stirred at 25° C. overnight. The reaction was then concentrated to one-third volume, diluted with water, and neutralized with saturated aqueous sodium bicarbonate. The resulting suspension was filtered, washed with water, and air-dried to afford ethyl 3,3-diamino-2-nitroso-prop-2-enoate (1.59 g, 39%); 1H NMR (500 MHz, DMSO-d6) δ 1.27 (3H, t), 4.26 (2H, q), 7.53 (2H, br s), 10.08 (2H, br s). Poor behavior by LCMS.

(b) Ethyl 2,3-diamino-3-imino-propanoate

A mixture of ethyl 3,3-diamino-2-nitroso-prop-2-enoate (0.935 g, 5.88 mmol), 10 wt % palladium on carbon (0.313 g, 0.290 mmol) and 6 M aqueous HCl (17.0 mL, 102 mmol) in ethanol (25 mL) was stirred under a hydrogen atmosphere at 25° C. for 16 hours. The reaction was then filtered through Celite. The filtrate was concentrated to afford ethyl 2,3-diamino-3-imino-propanoate (1.080 g, quantitative) as a white solid; 1H NMR (500 MHz, DMSO-d6) δ 1.24 (3H, t), 4.28 (2H, q), 5.24 (1H, s), 9.49 (2H, br s). The amino NH2 and guanidino NH were broadened to baseline. m/z: (ES+), [M+H]+=146.1

(c) Ethyl 3-amino-5-(trifluoromethyl)pyrazine-2-carboxylate and ethyl 3-amino-6-(trifluoromethyl) pyrazine-2-carboxylate 20 wt % Aqueous 3,3,3-trifluoro-2-oxo-propanal (9.96 g, 15.8 mmol) was added to a solution of ethyl 2,3-diamino-3-imino-propanoate (0.854 g, 5.88 mmol) in water (30 mL). Sodium acetate (3.38 g, 41.2 mmol) was added. The resulting mixture was stirred at 25° C. for 16 hours. The reaction was basified with saturated aqueous sodium bicarbonate. The resulting suspension was filtered, washed with water, and air-dried to afford a 1:1 mixture of ethyl 3-amino-5-(trifluoromethyl)pyrazine-2-carboxylate and ethyl 3-amino-6-(trifluoromethyl)pyrazine-2-carboxylate (498 mg, 36% yield); 1H NMR (500 MHz, DMSO-d6) δ 1.32 (3H, t), 4.35 (2H, q), 7.80 (2H, br s), 8.30 (1H, s), 8.67 (1H, s). m/z: (ES+), [M+H]+=236.1

(d) Ethyl 3-amino-6-bromo-5-(trifluoromethyl)pyrazine-2-carboxylate

N-Bromosuccinimide (0.338 g, 1.90 mmol) was added to a solution of 1:1 ethyl 3-amino-5-(trifluoromethyl)pyrazine-2-carboxylate and ethyl 3-amino-6-(trifluoromethyl)pyrazine-2-carboxylate (0.446 g, 1.90 mmol) in acetonitrile (15 mL). The reaction was stirred at 80° C. for 2 hours. The reaction was then concentrated. The resulting residue was purified twice by silica gel chromatography, using 0-20% EtOAc-hexanes as eluent each time, to afford ethyl 3-amino-6-bromo-5-(trifluoromethyl)pyrazine-2-carboxylate (0.270 g, 45% yield) as a pale yellow solid; 1H NMR (500 MHz, DMSO-d6) & 1.32 (3H, t), 4.36 (2H, q), 7.89 (2H, br s). m/z: (ES+), [M+H]+=314.1

(e) Ethyl 3-amino-6-(3-methylimidazo[4,5-c]pyridin-7-yl)-5-(trifluoromethyl)pyrazine-2-carboxylate DMF (2 mL) was added to a mixture of 7-bromo-3-methyl-imidazo[4,5-c]pyridine (115 mg, 0.54 mmol), bis (pinacolato)diboron (165 mg, 0.65 mmol), potassium acetate (159 mg, 1.62 mmol), cataCXium A Pd G3 (39 mg, 0.050 mmol), and cataCXium A (19 mg, 0.050 mmol). The resulting mixture was evacuated and backfilled three times with nitrogen, then stirred at 80° C. for 23 hours. Additional DMF (2 mL) was added. The reaction mixture was evacuated and backfilled three times with nitrogen. The reaction mixture was stirred at 100° C. for 24 hours. The reaction mixture was allowed to cool to room temperature and set aside.

Ethyl 3-amino-6-bromo-5-(trifluoromethyl)pyrazine-2-carboxylate (121 mg, 0.390 mmol), $PdCl_2$(dppf) (28 mg, 0.040 mmol), and cesium fluoride (117 mg, 0.770 mmol) were combined in a microwave vial, which was evacuated and backfilled three times with nitrogen. The borylation mixture was added via syringe. The resulting mixture was stirred at 100° C. for 2 hours. The reaction was then quenched with water. The resulting suspension filtered, washed with water, and air-dried. The filtrate was treated with saturated aqueous sodium bicarbonate, then extracted with 5:1 DCM/IPA. The organic layer was dried over magnesium sulfate, filtered, and concentrated. The resulting residue was combined with the dried filter cake, then purified by silica gel chromatography, using 0-10% MeOH-DCM as eluent, to afford ethyl 3-amino-6-(3-methylimidazo [4,5-c]pyridin-7-yl)-5-(trifluoromethyl)pyrazine-2-carboxylate (0.042 g, 30%) as a brown gum; 1H NMR (500 MHz, DMSO-d6) δ 1.26 (3H, t), 3.98 (3H, s), 4.33 (2H, q), 7.77-7.97 (2H, m), 8.30 (1H, s), 8.37 (1H, s), 9.05 (1H, s). m/z: (ES+), [M+H]+=367.2

(f) 6-(3-Methylimidazo[4,5-c]pyridin-7-yl)-3-(4-morpholinoanilino)-5-(trifluoromethyl)pyrazine-2-carboxylic acid A mixture of 4-(4-bromophenyl) morpholine (0.056 g, 0.23 mmol), ethyl 3-amino-6-(3-methylimidazo[4,5-c]pyridin-7-yl)-5-(trifluoromethyl)pyrazine-2-carboxylate (0.085 g, 0.23 mmol), BrettPhos Pd G3 (0.042 g, 0.05 mmol) and cesium carbonate (0.227 g, 0.70 mmol) in 1,4-dioxane (2.0 mL) was evacuated and backfilled three times with nitrogen. The resulting mixture was stirred at 100° C. for 4 hours. The reaction was then concentrated. The resulting residue was purified by C18 reverse phase chromatography, using 0-35% MeCN—$H_2O$ as eluent and 0.1% TFA as modifier, to afford 6-(3-methylimidazo[4,5-c]pyridin-7-yl)-3-(4-morpholinoanilino)-5-(trifluoromethyl)pyrazine-2-carboxylic acid (0.025 g, 22%) as a solid; 1H NMR (500 MHz, DMSO-d6) δ 3.10-3.14 (4H, m), 3.73-3.75 (4H, m), 4.09 (3H, s), 7.02 (2H, br d), 7.61 (2H, d), 8.71 (1H, s), 8.90 (1H, s), 9.55 (1H, s), 10.41 (1H, s); the COOH proton was broadened and indistinguishable from the baseline; m/z: (ES+), [M+H]+=500.3

(g) 6-(3-Methylimidazo[4,5-c]pyridin-7-yl)-3-(4-morpholinoanilino)-5-(trifluoromethyl)pyrazine-2-carboxamide DIPEA (0.026 mL, 0.15 mmol) was added to a mixture of 6-(3-methylimidazo[4,5-c]pyridin-7-yl)-3-(4-morpholinoanilino)-5-(trifluoromethyl)pyrazine-2-carboxylic acid (0.025 g, 0.050 mmol), ammonium chloride (0.013 g, 0.25 mmol), HATU (0.029 g, 0.080 mmol) in DMF (0.80 mL). The resulting mixture was stirred at 25 C for 2 hours. The reaction was then treated with saturated aqueous sodium bicarbonate and extracted with 5:1 DCM-IPA. The organic layer was concentrated. The resulting residue was purified by C18 reverse phase chromatography, using 10-50%

MeCN—$H_2O$ as eluent and 0.2% ammonium hydroxide as modifier, to afford 6-(3-methylimidazo[4,5-c]pyridin-7-yl)-3-(4-morpholinoanilino)-5-(trifluoromethyl)pyrazine-2-carboxamide (18 mg, 72%) as an orange solid; 1H NMR (500 MHz, DMSO-d6) δ 3.03-3.14 (4H, m), 3.66-3.78 (4H, m), 3.99 (3H, s), 7.00 (2H, d), 7.61 (2H, d), 8.13 (1H, br s), 8.26 (1H, br s), 8.40 (1H, s), 8.44 (1H, s), 9.05 (1H, s), 11.28 (1H, s); m/z: (ES+), [M+H]+=499.3

Example 34

6-(3-Methylimidazo[4,5-c]pyridin-7-yl)-5-methylsulfanyl-3-(4-morpholinoanilino)pyrazine-2-carboxamide

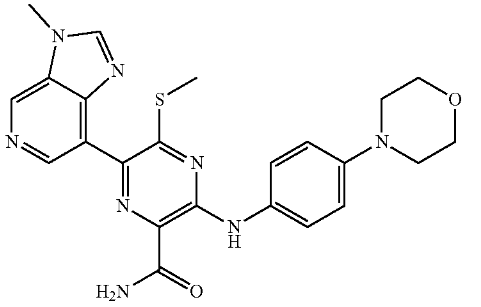 [SMILES: CSc1nc(Nc2ccc(N3CCOCC3)cc2)c(C(N)=O)nc1-c1cncc2c1ncn2C]

(a) Methyl 6-chloro-3-fluoro-5-methylsulfanyl-pyrazine-2-carboxylate

Sodium nitrite (3.00 g, 43.5 mmol) was added portionwise to a suspension of methyl 3-amino-6-chloro-5-(methylthio) pyrazine-2-carboxylate (9.65 g, 41.3 mmol) in HF-pyridine (20 mL, 580 mmol) at −10° C. The reaction was then stirred at 25° C. for 3 hours. The reaction was then diluted with DCM (30 mL) and quenched with water (50 mL). The layers were separated and the aqueous layer was extracted twice with DCM (10 mL each). The combined organics were dried over $MgSO_4$, filtered, and concentrated to afford methyl 6-chloro-3-fluoro-5-methylsulfanyl-pyrazine-2-carboxylate (9.46 g, 97%) as a pale yellow solid; 1H NMR (500 MHz, DMSO-d6) 2.59 (3H, s), 3.88 (3H, s); m/z: (ES+), [M+H]+=237.0

(b) Methyl 6-chloro-5-methylsulfanyl-3-(4-morpholinoanilino)pyrazine-2-carboxylate DIPEA (4.00 mL, 22.9 mmol) was added to a solution of methyl 6-chloro-3-fluoro-5-methylsulfanyl-pyrazine-2-carboxylate (5.00 g, 21.1 mmol) and 4-morpholinoaniline (3.95 g, 22.2 mmol) in DMF (17 mL). The resulting brown solution was stirred at 100° C. for 15 minutes. The reaction was allowed to cool to room temperature, then filtered, rinsed with EtOAc, and dried under vacuum to afford methyl 6-chloro-5-methylsulfanyl-3-(4-morpholinoanilino)pyrazine-2-carboxylate (6.23 g, 75%) as a light orange solid; 1H NMR (500 MHZ, DMSO-d6) 2.50 (3H, s), 3.02-3.16 (4H, m), 3.66-3.81 (4H, m), 3.89 (3H, s), 6.95 (2H, d), 7.49 (2H, d), 9.92 (1H, s); m/z: (ES+), [M+2+H]+=397.0.

(c) Methyl 6-(3-methylimidazo[4,5-c]pyridin-7-yl)-5-methylsulfanyl-3-(4-morpholinoanilino)pyrazine-2-carboxylate 7-Bromo-3-methyl-imidazo[4,5-c]pyridine (1.00 g, 4.72 mmol), bis(pinacolato)diboron (2.39 g, 9.42 mmol), cataCXium A Pd G3 (0.343 g, 0.470 mmol), cataCXium A (0.169 g, 0.470 mmol), and potassium acetate (0.895 g, 9.12 mmol) were combined in a multineck flask, which was evacuated and backfilled three times with nitrogen. DMF (15 mL) was added and the resulting mixture was stirred at 80° C. for 24 hours. The reaction was then allowed to cool to room temperature.

Methyl 6-chloro-5-methylsulfanyl-3-(4-morpholinoanilino)pyrazine-2-carboxylate (1.50 g, 3.80 mmol), Pd(dppf)$Cl_2$ (0.278 g, 0.380 mmol), and cesium fluoride (1.73 g, 11.4 mmol) were combined in a separate multineck flask, which was evacuated and backfilled three times with nitrogen. The borylation mixture was added via syringe. The resulting mixture and the reaction was stirred at 100° C. for 3 hours. The reaction was then allowed to cool to room temperature, diluted with water (150 mL), and extracted three times with 3:1 DCM/IPA (50 mL each). The combined organic layers were dried over magnesium sulfate, filtered, and concentrated over Celite. The resulting material was then purified by silica gel chromatography, using 0-10% MeOH-DCM as eluent and 0-1% ammonia as modifier, to afford methyl 6-(3-methylimidazo[4,5-c]pyridin-7-yl)-5-methylsulfanyl-3-(4-morpholinoanilino)pyrazine-2-carboxylate (0.742 g, 40%) as a dark orange foamy solid; 1H NMR (500 MHz, DMSO-d6) 2.39 (3H, s), 3.05-3.15 (4H, m), 3.67-3.82 (4H, m), 3.85 (3H, s), 3.99 (3H, s), 6.97 (2H, d), 7.57 (2H, d), 8.32 (1H, s), 8.38 (1H, s), 9.05 (1H, s), 10.05 (1H, s); m/z: (ES+), [M+H]+=492.1.

(d) 6-(3-Methylimidazo[4,5-c]pyridin-7-yl)-5-methylsulfanyl-3-(4-morpholinoanilino)pyrazine-2-carboxamide 7 N Methanolic ammonia (6.0 mL, 42 mmol) was added to methyl 6-(3-methylimidazo[4,5-c]pyridin-7-yl)-5-methylsulfanyl-3-(4-morpholinoanilino)pyrazine-2-carboxylate (742 mg, 1.51 mmol). The resulting dark orange solution was stirred at 100° C. for 4 hours in a Biotage microwave reactor. The reaction was allowed to cool to room temperature, then filtered and rinsed with MeOH. The resulting yellow ochre solid was purified by silica gel chromatography, using 0-10% MeOH-DCM as eluent and 0-1% ammonia as modifier, to afford 6-(3-methylimidazo[4,5-c]pyridin-7-yl)-5-methylsulfanyl-3-(4-morpholinoanilino)pyrazine-2-carboxamide (0.370 g, 51%) as a bright yellow solid; 1H NMR (500 MHz, DMSO-d6) 2.44 (3H, s), 3.01-3.12 (4H, m), 3.69-3.77 (4H, m), 3.98 (3H, s), 6.97 (2H, d), 7.58 (2H, d), 7.74 (1H, br d), 7.93 (1H, br s), 8.39 (1H, s), 8.42 (1H, s), 9.03 (1H, s), 11.20 (1H, s); m/z: (ES+), [M+H]+=477.1.

Example 35

5-[(1-Methylcyclopropyl)amino]-6-(3-methylimidazo[4,5-c]pyridin-7-yl)-3-(4-morpholinoanilino) pyrazine-2-carboxamide

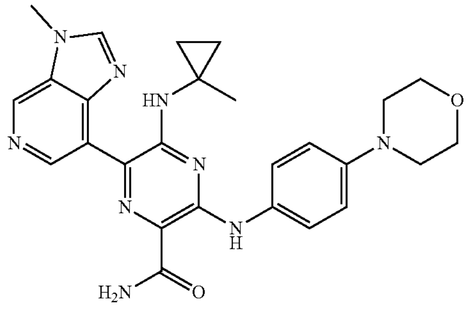 [SMILES: Cn1cnc2c(-c3nc(C(N)=O)c(Nc4ccc(N5CCOCC5)cc4)nc3NC3(C)CC3)cncc21]

mCPBA (194 mg, 0.790 mmol) was added as a solution in DCM (1 mL) to a suspension of 6-(3-methylimidazo[4,5-c]pyridin-7-yl)-5-methylsulfanyl-3-(4-morpholinoanilino)pyrazine-2-carboxamide (75 mg, 0.16 mmol) in DCM (3 mL) at 0° C. The resulting suspension was stirred at 25 C for 2 hours. The reaction was then concentrated. The resulting yellow solid was dissolved in DMF (2 mL). 1-methylcyclopropanamine hydrochloride (85 mg, 0.79 mmol) and DIPEA (500 μL, 2.86 mmol) were added and the resulting mixture was stirred at 100° C. for 1 hour. Tetrahydroxydiboron (42 mg, 0.47 mmol) was then added and the resulting mixture was stirred at 100° C. for 5 minutes. The reaction was allowed to cool to room temperature, then diluted with water (20 mL) and extracted three times with 3:1 DCM/IPA (25 mL each). The combined organics were washed with 5% aqueous LiCl (10 mL), dried over magnesium sulfate, filtered, and concentrated over Celite. This material was purified by silica gel chromatography, using 0-10% MeOH-DCM as eluent and 0-1% ammonia as modifier, to afford 5-[(1-methylcyclopropyl)amino]-6-(3-methylimidazo[4,5-c]pyridin-7-yl)-3-(4-morpholinoanilino)pyrazine-2-carboxamide (18 mg, 23%) as a fluffy yellow solid; 1H NMR (500 MHz, DMSO-d6) 0.70-0.82 (4H, m), 1.46 (3H, s), 3.01-3.10 (4H, m), 3.70-3.77 (4H, m), 4.00 (3H, s), 6.95 (2H, d), 7.35 (1H, br d), 7.76 (1H, br s), 7.83 (2H, d), 8.47-8.58 (2H, m), 8.76 (1H, s), 8.98 (1H, s), 11.31 (1H, s); m/z: (ES+), [M+H]+=500.2.

Example 36

5-Cyano-6-(3-methylimidazo[4,5-c]pyridin-7-yl)-3-(4-morpholinoanilino)pyrazine-2-carboxamide

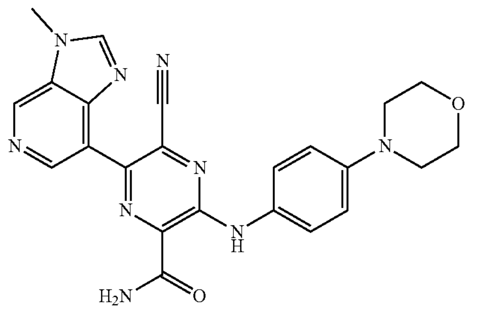 [SMILES: Cn1cnc2c(-c3nc(C(N)=O)c(Nc4ccc(N5CCOCC5)cc4)nc3C#N)cncc21]

mCPBA (194 mg, 0.790 mmol) was added as a solution in DCM (1 mL) to a suspension of 6-(3-methylimidazo[4,5-c]pyridin-7-yl)-5-methylsulfanyl-3-(4-morpholinoanilino)pyrazine-2-carboxamide (75 mg, 0.16 mmol) in DCM (3 mL) at 0° C. The resulting suspension was stirred for 2 hours at room temperature. The reaction was then concentrated to a yellow solid, which was dissolved in DMF (2 mL). Sodium cyanide (77 mg, 1.57 mmol) was added and the resulting mixture was stirred at 100° C. for 2 hours. The reaction was then allowed to cool to room temperature, treated with sodium bisulfite (82 mg, 0.79 mmol), and stirred for 10 minutes. Additional sodium bisulfite (82 mg, 0.79 mmol) was added and the resulting mixture was stirred for 1 hour. The reaction was then diluted with water (40 mL) and extracted three times with 3:1 DCM/IPA (25 mL each). The combined organics were dried over magnesium sulfate, filtered, and concentrated. The resulting residue was purified by silica gel chromatography, using 0-10% MeOH-DCM as eluent and 0-1% ammonia as modifier, to afford a red solid. This material was then purified further by preparatory HPLC using a 5 micron, 30 mm×150 mm Xselect CSH column, 25-50% MeCN—$H_2O$ as eluent, and 0.2% ammonium hydroxide as modifier, to afford 5-cyano-6-(3-methylimidazo[4,5-c]pyridin-7-yl)-3-(4-morpholinoanilino)pyrazine-2-carboxamide (12 mg, 17%) as an orange solid; 1H NMR (500 MHz, DMSO-d6) 3.05-3.14 (4H, m), 3.68-3.79 (4H, m), 4.02 (3H, s), 7.01 (2H, d), 7.54 (2H, d), 8.12-8.32 (1H, m), 8.51 (2H, s), 8.75 (1H, s), 9.10 (1H, s), 11.22 (1H, br s); m/z: (ES+), [M+H]+=456.2

Example 37

5-(Cyclopropylamino)-6-(3-methylimidazo[4,5-c]pyridin-7-yl)-3-(4-morpholinoanilino)pyrazine-2-carboxamide

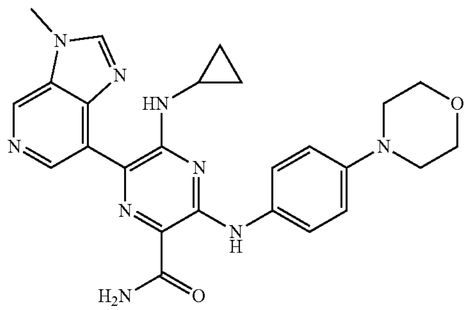 [SMILES: Cn1cnc2c(-c3nc(C(N)=O)c(Nc4ccc(N5CCOCC5)cc4)nc3NC3CC3)cncc21]

A solution of mCPBA (396 mg, 1.61 mmol) in DCM (2 mL) was added dropwise to a suspension of 6-(3-methylimidazo[4,5-c]pyridin-7-yl)-5-methylsulfanyl-3-(4-morpholinoanilino)pyrazine-2-carboxamide (153 mg, 0.320 mmol) in DCM (3 mL) at −10 C. The reaction was stirred at 25 C for 90 minutes. The reaction was then concentrated. The resulting orange solid was dissolved in DMF (2 mL). Cyclopropylamine (0.050 mL, 0.71 mmol) and DIPEA (0.500 mL, 2.86 mmol) were sequentially added and the reaction was stirred at 25 C for 30 minutes. The reaction was then stirred at 100 C for 1 hour in a Biotage microwave reactor. The reaction was then allowed to cool to room temperature. Sodium bisulfite (0.133 g, 1.28 mmol) was added and the reaction was stirred 10 minutes at room temperature. The reaction was then diluted with water (25 mL) and extracted three times with 3:1 DCM/IPA (20 mL each). The combined organic layers were dried over magnesium sulfate, filtered, and concentrated. The resulting residue was purified by silica gel chromatography, using 0-10% MeOH-DCM as eluent and 0-1% ammonia as modifier, to afford 39 mg of an orange solid. This material was purified further by preparative HPLC, using a 5 micron, 30 mm×100 mm, Waters XSelect CSH C18 OBD Prep column, 30-60% MeCN—$H_2O$ as eluent, and 0.1% ammonium hydroxide as modifier, to afford 5-(cyclopropylamino)-6-(3-methylimidazo[4,5-c]pyridin-7-yl)-3-(4-morpholinoanilino)pyrazine-2-carboxamide (23 mg, 15%) as a yellow solid; 1H NMR (500 MHz, DMSO-d6) 0.43-0.61 (2H, m), 0.76-0.93 (2H, m), 2.89 (1H, tt), 3.00-3.12 (4H, m), 3.65-3.79 (4H, m), 4.02 (3H, s), 6.96 (2H, d), 7.39 (1H, br s), 7.74-7.89 (3H, m), 8.57 (1H, s), 8.81 (1H, br d), 8.84 (1H, s), 9.00 (1H, s), 11.32 (1H, s); m/z: (ES+), [M+H]=486.2

Example 38

5-Amino-6-(3-methylimidazo[4,5-c]pyridin-7-yl)-3-(4-morpholinoanilino)pyrazine-2-carboxamide

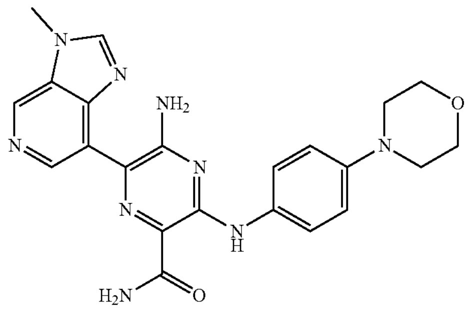 [SMILES: Cn1cnc2c(-c3nc(C(N)=O)c(Nc4ccc(N5CCOCC5)cc4)nc3N)cncc21]

(a) Methyl 3-amino-6-chloro-5-(cyclopropylamino) pyrazine-2-carboxylate

Cyclopropanamine (1.029 g, 18.02 mmol) was added to a suspension of methyl 3-amino-5,6-dichloro-pyrazine-2-carboxylate (1.00 g, 4.50 mmol) in THF (20 mL). The resulting mixture was stirred at 25 C for 4 hours. The reaction was then concentrated. The resulting residue was treated with water. The resulting suspension was filtered, and the solid was dried under vacuum to afford methyl 3-amino-6-chloro-5-(cyclopropylamino) pyrazine-2-carboxylate (1.10 g, quantitative) as an orange solid; 1H NMR (500 MHz, DMSO-d6) 0.54-0.80 (4H, m), 2.77-2.93 (1H, m), 3.72 (3H, s), 7.26 (2H, br s), 7.48 (1H, br d); m/z: (ES+), [M+H]+=243.1.

(b) Methyl 3-amino-5-(cyclopropylamino)-6-(3-methylimidazo[4,5-c]pyridin-7-yl)pyrazine-2-carboxylate CataCXium A (17 mg, 0.050 mmol), cataCXium A Pd G3 (34 mg, 0.050 mmol), 7-bromo-3-methyl-imidazo[4,5-c] pyridine (100 mg, 0.47 mmol), potassium acetate (139 mg, 1.41 mmol), and bis(pinacolato)diboron (240 mg, 0.94 mmol) were combined in a microwave vial, which was evacuated and backfilled three times with nitrogen. DMF (3 mL) was added. The resulting mixture was stirred at 80° C. for 20 hours. The reaction was then allowed to cool to room temperature and set aside.

Pd(dppf)$Cl_2$ (35 mg, 0.05 mmol), CsF (107 mg, 0.710 mmol), and methyl 3-amino-6-chloro-5-(cyclopropylamino) pyrazine-2-carboxylate (114 mg, 0.470 mmol) were combined in a microwave vial, which was evacuated and backfilled three times with nitrogen. The borylation mixture was added via syringe. The resulting mixture was heated at 100° C. for 2 hours. The reaction was then concentrated. The resulting residue was purified by silica gel chromatography, using 0-70% MeOH-DCM as eluent, to afford methyl 3-amino-5-(cyclopropylamino)-6-(3-methylimidazo[4,5-c] pyridin-7-yl)pyrazine-2-carboxylate (80 mg, 50% yield) as an off-white powder.

(c) 5-Amino-6-(3-methylimidazo[4,5-c]pyridin-7-yl)-3-(4-morpholinoanilino)pyrazine-2-carboxamide BrettPhos Pd G3 (21 mg, 0.020 mmol) was added to a suspension of methyl 3-amino-5-(cyclopropylamino)-6-(3-methylimidazo[4,5-c]pyridin-7-yl)pyrazine-2-carboxylate (80 mg, 0.24 mmol), 4-(4-bromophenyl) morpholine (57 mg, 0.24 mmol), and cesium carbonate (154 mg, 0.470 mmol) in 1,4-dioxane (2 mL). The resulting mixture was heated at 90° C. for 4 hours. The reaction was then concentrated. The resulting residue was purified by silica gel chromatography, using 0-70% MeOH-DCM as eluent, to afford a brown solid. This material was suspended in 7 N methanolic ammonia (510 μL, 3.57 mmol). The resulting suspension was heated to 100° C. for 14 hours. The reaction was then concentrated. The resulting residue was purified by preparative HPLC using a 5 micron, 19 mm×150 mm Xbridge C18 column, 20-50% MeCN—$H_2O$ as eluent, and 0.2% $NH_4OH$ as modifier, to afford 5-amino-6-(3-methylimidazo[4,5-c]pyridin-7-yl)-3-(4-morpholinoanilino)pyrazine-2-carboxamide (2.0 mg, 1.9%); 1H NMR (500 MHZ, DMSO-d6) 2.99-3.11 (4H, m), 3.67-3.79 (4H, m), 4.00 (3H, s), 6.91 (2H, d), 7.36 (1H, br s), 7.50 (2H, br s), 7.63 (2H, d), 7.79 (1H, br s), 8.53 (1H, s), 8.80 (1H, s), 8.98 (1H, s), 11.18 (1H, s); m/z: (ES+), [M+H]+=446.3

Example 39

6-(3-Methylimidazo[4,5-c]pyridin-7-yl)-3-(4-morpholinoanilino)pyrazine-2-carboxamide

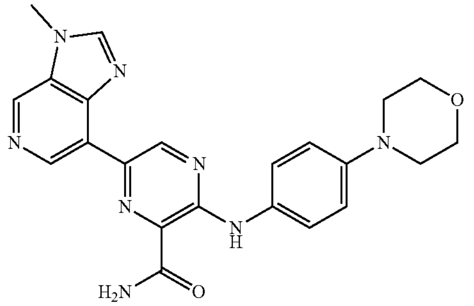 [SMILES: Cn1cnc2c(-c3cnc(Nc4ccc(N5CCOCC5)cc4)c(C(N)=O)n3)cncc21]

(a) Methyl 6-(3-methylimidazo[4,5-c]pyridin-7-yl)-3-(4-morpholinoanilino)pyrazine-2-carboxylate CataCXium A Pd G2 (17 mg, 0.03 mmol) was added to a suspension of bis(pinacolato)diboron (129 mg, 0.510 mmol), methyl 6-bromo-3-(4-morpholinoanilino)pyrazine-2-carboxylate (100 mg, 0.25 mmol), potassium acetate (75 mg, 0.76 mmol), and bis(1-adamantyl)-butyl-phosphonium tetrafluoroborate (11 mg, 0.030 mmol) in DMF (10 mL) under nitrogen. The resulting mixture was stirred at 80° C. for 16 hours. The reaction was then allowed to cool to room temperature and set aside.

A mixture of cesium fluoride (97 mg, 0.64 mmol), 7-bromo-3-methyl-imidazo[4,5-c]pyridine (54 mg, 0.25 mmol), and $PdCl_2$(dppf) (18.61 mg, 0.03 mmol) was evacuated and backfilled three times. The borylation mixture was added via syringe. The resulting mixture was stirred at 100° C. for 16 hours. The reaction was then concentrated. The resulting residue was taken up in MeOH (10 mL). Thionyl chloride (2.00 mL, 27.4 mmol) was added. The resulting mixture was stirred at 60° C. for 2 hours. The reaction was then concentrated. The resulting residue was purified by silica gel chromatography, using 0-10% MeOH-DCM as eluent, to afford methyl 6-(3-methylimidazo[4,5-c]pyridin-7-yl)-3-(4-morpholinoanilino)pyrazine-2-carboxylate (30 mg, 27%) as a yellow solid; 1H NMR (300 MHZ, DMSO-d6) δ 3.11 (4H, t), 3.72-3.81 (4H, m), 4.02 (3H, s), 4.05 (3H, s), 6.99 (2H, d), 7.55-7.63 (2H, m), 8.57 (1H, s), 9.01 (1H, s), 9.06 (1H, s), 9.82 (1H, d), 9.96 (1H, s). m/z: (ES+), [M+H]+=446.2

(b) 6-(3-Methylimidazo[4,5-c]pyridin-7-yl)-3-(4-morpholinoanilino)pyrazine-2-carboxamide 7 N Methanolic ammonia (1.0 mL, 7.0 mmol) was added to a suspension of methyl 6-(3-methylimidazo[4,5-c]pyridin-7-yl)-3-(4-morpholinoanilino)pyrazine-2-carboxylate (30 mg, 0.07 mmol) in MeOH (1 mL). The resulting mixture was stirred at 80° C. for 24 hours. The reaction was then concentrated. The resulting residue was purified by preparative HPLC, using a 5 micron, 30 mm×150 mm, Xbridge Shield RP18 OBD column, 12-22% MeCN—$H_2O$ as eluent, and 0.1% formic acid as modifier, to afford 6-(3-methylimidazo[4,5-c]pyridin-7-yl)-3-(4-morpholinoanilino)pyrazine-2-carboxamide (10 mg, 35%) as a yellow solid; 1H NMR (300 MHz, DMSO-d6) δ 3.04-3.14 (4H, m), 3.70-3.79 (4H, m), 4.02 (3H, s), 6.92-7.02 (2H, m), 7.55-7.66 (2H, m), 8.04 (1H, s), 8.55 (1H, s), 8.73 (1H, s), 9.00 (1H, s), 9.45 (1H, s), 9.90 (1H, s), 11.28 (1H, s); m/z: (ES+), [M+H]+=431.1

Example 40

5-Methoxy-6-(3-methylimidazo[4,5-c]pyridin-7-yl)-3-(4-morpholinoanilino)pyrazine-2-carboxamide

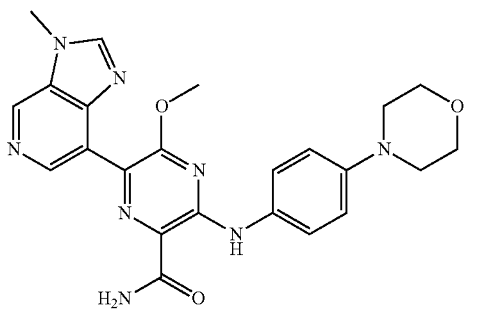 [SMILES: COc1nc(Nc2ccc(N3CCOCC3)cc2)c(C(N)=O)nc1-c1cncc2c1ncn2C]

(a) 6-Chloro-5-methoxy-3-(4-morpholinoanilino)pyrazine-2-carboxamide

7 N Methanolic ammonia (5.0 mL, 35 mmol) was added to methyl 6-chloro-5-methoxy-3-(4-morpholinoanilino)pyrazine-2-carboxylate (555 mg, 1.47 mmol). The resulting suspension was stirred at 100° C. in an Emrys microwave reactor for 2 hours. The reaction was then filtered and rinsed with MeOH. The filter cake was dried under vacuum to afford 6-chloro-5-methoxy-3-(4-morpholinoanilino)pyrazine-2-carboxamide (291 mg, 61%) as a yellow solid; 1H NMR (500 MHz, DMSO-d6) 2.99-3.10 (4H, m), 3.69-3.77 (4H, m), 3.99 (3H, s), 6.94 (2H, d), 7.43-7.57 (2H, m), 7.66 (1H, br s), 7.89 (1H, s), 11.19 (1H, s) m/z: (ES−), [M−H]−=362.3

(b) 5-Methoxy-6-(3-methylimidazo[4,5-c]pyridin-7-yl)-3-(4-morpholinoanilino)pyrazine-2-carboxamide 7-Bromo-3-methyl-imidazo[4,5-c]pyridine (100 mg, 0.47 mmol), bis(pinacolato)diboron (299 mg, 1.18 mmol), cataCXium A (17 mg, 0.050 mmol), cataCXium A Pd G3 (34 mg, 0.050 mmol), and potassium acetate (139 mg, 1.41 mmol) were combined in a microwave vial, which was evacuated and backfilled three times with nitrogen. DMF (2.3 mL) was added and the resulting mixture was stirred at 80° C. for 24 hours. The reaction mixture was allowed to cool to room temperature and set aside.

6-Chloro-5-methoxy-3-(4-morpholinoanilino)pyrazine-2-carboxamide (137 mg, 0.380 mmol), Pd(dppf)$Cl_2$ dichloromethane adduct (31 mg, 0.040 mmol), and cesium fluoride (172 mg, 1.13 mmol) were combined in a microwave vial, which was evacuated and backfilled three times with nitrogen. The borylation reaction mixture was added to the vial via syringe. The resulting mixture was stirred at 100° C. for 4 hours. The reaction was allowed to cool to room temperature, diluted with water (40 mL), and filtered. The filter cake was purified by reverse phase chromatography, using 0-50% MeCN—$H_2O$ as eluent and 0.1% trifluoroacetic acid as modifier, to afford an orange residue. The aqueous filtrate was diluted with saturated aqueous sodium bicarbonate (20 mL) and extracted three times with 3:1 DCM/IPA (30 mL each). The combined organic layers were concentrated. The resulting residue was purified by reverse phase chromatography using 0-50% MeCN—$H_2O$ as eluent and 0.1% trifluoroacetic acid as modifier, to afford an orange residue. The orange residues from the two columns were dissolved in water (20 mL), basified with saturated aqueous sodium bicarbonate (10 mL), and extracted three times with DCM (20 mL each). The combined organics were dried over magnesium sulfate, filtered, and concentrated to afford 5-methoxy-6-(3-methylimidazo[4,5-c]pyridin-7-yl)-3-(4-morpholinoanilino)pyrazine-2-carboxamide (50 mg, 29%) as a yellow solid. 1H NMR (500 MHz, DMSO-d6) 3.01-3.11 (4H, m), 3.67-3.77 (4H, m), 3.92 (3H, s), 3.97 (3H, s), 6.97 (2H, d), 7.60 (2H, d), 7.67 (1H, br s), 7.94 (1H, br s), 8.38 (1H, s), 8.60 (1H, s), 8.97 (1H, s), 11.22 (1H, s); m/z: (ES+), [M+H]+=461.3

Example 41

5-Cyclopropyl-6-(3-methylimidazo[4,5-c]pyridin-7-yl)-3-(4-morpholinoanilino)pyrazine-2-carboxamide

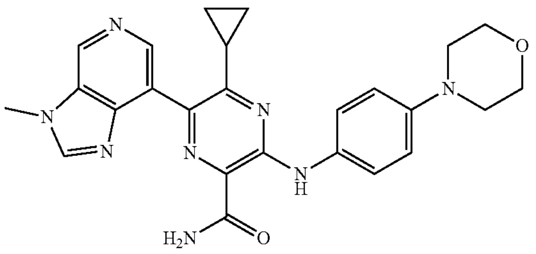 [SMILES: Cn1cnc2c(-c3nc(C(N)=O)c(Nc4ccc(N5CCOCC5)cc4)nc3C3CC3)cncc21]

(a) Methyl 6-chloro-5-cyclopropyl-3-fluoro-pyrazine-2-carboxylate

Sodium nitrite (68.4 mg, 0.990 mmol) was added to a solution of methyl 3-amino-6-chloro-5-cyclopropyl-pyrazine-2-carboxylate (215 mg, 0.940 mmol) in HF-pyridine (3.0 mL, 87 mmol) at 0° C. The reaction was stirred at 25° C. for 30 minutes. The reaction was then diluted with DCM (5 mL) and quenched with water (20 mL). The layers were separated and the aqueous layer was extracted with DCM (10 mL). The combined organic layers were dried over sodium sulfate, filtered, and concentrated to afford methyl 6-chloro-5-cyclopropyl-3-fluoro-pyrazine-2-carboxylate (0.233 g, quantitative) as a yellow oil; 1H NMR (500 MHZ, DMSO-d6) 1.03-1.13 (2H, m), 1.25-1.34 (2H, m), 2.50-2.56 (1H, m), 3.89 (3H, s); m/z: (ES+), [M+H]+=231.1

(b) Methyl 6-chloro-5-cyclopropyl-3-(4-morpholinoanilino)pyrazine-2-carboxylate

DIPEA (0.180 mL, 1.03 mmol) was added was added to a solution of methyl 6-chloro-5-cyclopropyl-3-fluoro-pyrazine-2-carboxylate (0.217 g, 0.940 mmol) and 4-morpholinoaniline (0.176 g, 0.990 mmol) in DMF (3 mL). The reaction was stirred at 100° C. for 40 minutes. The reaction was then allowed to cool to room temperature, diluted with water (80 mL), and extracted three times with EtOAc (25 mL each). The combined organic layers were washed once with 5% aqueous lithium chloride (15 mL), then dried over sodium sulfate, filtered, and concentrated. The resulting red solid was purified by silica gel chromatography, using 0-80% EtOAc-hexanes as eluent, to afford methyl 6-chloro-5-cyclopropyl-3-(4-morpholinoanilino)pyrazine-2-carboxylate (0.213 g, 58%) as an orange solid; 1H NMR (500 MHz, DMSO-d6) 0.95-1.09 (2H, m), 1.11-1.22 (2H, m), 2.39-2.44 (1H, m), 2.97-3.15 (4H, m), 3.66-3.77 (4H, m), 3.89 (3H, s), 6.93 (2H, d), 7.40 (2H, d), 9.75 (1H, s); m/z: (ES−), [M−H]−=387.2

(c) Methyl 5-cyclopropyl-6-(3-methylimidazo[4,5-c]pyridin-7-yl)-3 (4-morpholinoanilino)pyrazine-2-carboxylate Methyl 6-chloro-5-cyclopropyl-3-(4-morpholinoanilino)pyrazine-2-carboxylate (107 mg, 0.270 mmol), 2-(3-methylimidazo[4,5-c]pyridin-7-yl)-1,3,6,2-dioxazaborocane (99 mg, 82 wt %, 0.33 mmol), Pd(dppf)$Cl_2$ (23 mg, 0.030 mmol), and CsF (125 mg, 0.820 mmol) were combined in a microwave vial, which was evacuated and backfilled three times with nitrogen. MeOH (1.7 mL) was added and the resulting mixture was stirred at 100° C. for 2 hours in a Biotage microwave reactor. The reaction was then concentrated. The resulting red residue was purified by silica gel chromatography, using 0-10% methanol-DCM as eluent and 0-1% ammonia as modifier, to afford methyl 5-cyclopropyl-6-(3-methylimidazo[4,5-c]pyridin-7-yl)-3-(4-morpholinoanilino)pyrazine-2-carboxylate (0.061 g, 46%) as an orange solid; 1H NMR (500 MHZ, DMSO-d6) 0.84-0.94 (2H, m), 0.97-1.08 (2H, m), 1.79-1.88 (1H, m), 2.98-3.14 (4H, m), 3.65-3.78 (4H, m), 3.87 (3H, s), 3.99 (3H, s), 6.96 (2H, d), 7.51 (2H, d), 8.39 (1H, s), 8.42 (1H, s), 9.05 (1H, s), 9.90 (1H, s); m/z: (ES+), [M+H]+=486.2.

(d) 5-Cyclopropyl-6-(3-methylimidazo[4,5-c]pyridin-7-yl)-3-(4-morpholinoanilino)pyrazine-2-carboxamide 7 N Methanolic ammonia (2.0 mL, 14 mmol) was added to methyl 5-cyclopropyl-6-(3-methylimidazo[4,5-c]pyridin-7-yl)-3-(4-morpholinoanilino)pyrazine-2-carboxylate (61 mg, 0.13 mmol). The resulting suspension was stirred at 100° C. for 1 hour in a Biotage microwave reactor. Additional 7 N methanolic ammonia (1.0 mL, 7.0 mmol) was added and the reaction was stirred at 100° C. for 1 h in a Biotage microwave reactor. The reaction was then filtered and rinsed with methanol to afford 5-cyclopropyl-6-(3-methylimidazo[4,5-c]pyridin-7-yl)-3-(4-morpholinoanilino)pyrazine-2-carboxamide (0.036 g, 61%) as a yellow ochre solid; 1H NMR (500 MHz, DMSO-d6) 0.83-0.97 (2H, m), 0.99-1.12 (2H, m), 1.86-1.98 (1H, m), 3.01-3.12 (4H, m), 3.66-3.82 (4H, m), 4.00 (3H, s), 6.97 (2H, d), 7.54 (2H, d), 7.80 (1H, br s), 8.06 (1H, s), 8.45 (1H, s), 8.54 (1H, s), 9.05 (1H, s), 11.08 (1H, s)

Example 42

5-(Difluoromethyl)-6-(3-methylimidazo[4,5-c]pyridin-7-yl)-3-(4-morpholinoanilino)pyrazine-2-carboxamide

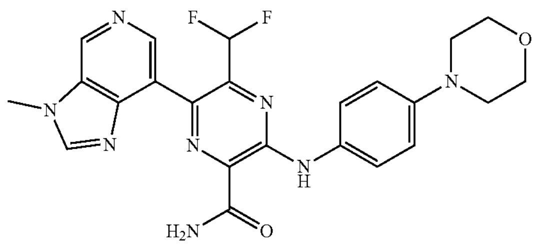 [SMILES: Cn1cnc2c(-c3nc(C(N)=O)c(Nc4ccc(N5CCOCC5)cc4)nc3C(F)F)cncc21]

(a) Methyl 3-amino-6-bromo-pyrazine-2-carboxylate

Acetonitrile (100 mL) was added to a mixture of methyl 3-aminopyrazine-2-carboxylate (5.00 g, 32.7 mmol) and N-bromosuccinimide (5.81 g, 32.7 mmol). The resulting solution was stirred at 80° C. for 45 minutes. The reaction was then concentrated. The resulting red solid was triturated in isopropanol (100 mL) and filtered to afford a red solid. The filtrate was concentrated to a red solid and recombined with the filtercake, which was dissolved in DCM (60 mL) and washed once with saturated aqueous sodium thiosulfate (50 mL) and three times with saturated aqueous sodium bicarbonate (25 mL each). The organic layer was then dried over magnesium sulfate, filtered, and concentrated to afford a red solid, which was divided into two portions. One portion was purified by silica gel chromatography using 0-40% EtOAc-hexanes as eluent to afford methyl 3-amino-6-bromopyrazine-2-carboxylate (1.33 g, 18%) as an off-white solid. The other portion was suspended in MeOH, then filtered, rinsing copiously with MeOH, to afford methyl 3-amino-6-bromopyrazine-2-carboxylate (2.89 g, 38%) as a beige microcrystalline solid; 1H NMR (500 MHZ, DMSO-d6) 3.84 (3H, s), 7.53 (2H, br s), 8.41 (1H, s); m/z: (ES+), [M+H]+=232.0

(b) Methyl 3-amino-6-bromo-5-(difluoromethyl)pyrazine-2-carboxylate

TFA (0.66 mL, 8.6 mmol) was added to a suspension of methyl 3-amino-6-bromo-pyrazine-2-carboxylate (1.00 g, 4.31 mmol) and zinc difluoromethanesulfinate (2.55 g, 8.62 mmol) in DCM (10 mL) and water (4 mL). 70 wt % aqueous tert-butyl hydroperoxide (1.80 mL, 13.1 mmol) was added dropwise to the reaction mixture. The reaction mixture was stirred at 25° C. for 16 hours. Additional zinc difluoromethanesulfinate (2.55 g, 8.62 mmol) and 70 wt % aqueous tert-butyl hydroperoxide (1.80 mL, 13.1 mmol) were added and the reaction was stirred at 25° C. for 2 days. The reaction was then quenched with saturated aqueous sodium bicarbonate (50 mL) and diluted with DCM (50 mL) and saturated aqueous ammonium chloride (20 mL). The layers were separated and the aqueous layer was extracted twice with DCM (20 mL each). The combined organics were dried over sodium sulfate, filtered, and concentrated. The resulting pale yellow solid, which was purified by silica gel chromatography, using 0-35% EtOAc-hexanes as eluent, to afford methyl 3-amino-6-bromo-5-(difluoromethyl)pyrazine-2-carboxylate (0.16 g, 13%) as a pale yellow solid; 1H NMR (500 MHz, DMSO-d6) 3.87 (3H, s), 7.03 (1H, t), 7.34-8.32 (2H, br s); m/z: (ES+), [M+H]+=282.0

(c) Methyl 6-bromo-5-(difluoromethyl)-3-(4-morpholinoanilino)pyrazine-2-carboxylate Sodium nitrite (63 mg, 0.91 mmol) was added to a solution of methyl 3-amino-6-bromo-5-(difluoromethyl) pyrazine-2-carboxylate (245 mg, 0.870 mmol) in HF-pyridine (3.0 mL, 87 mmol) at 0° C. The reaction was stirred at 25° C. for 15 minutes. The reaction was then diluted with DCM (5 mL) and quenched with water (20 mL). The layers were separated and the aqueous layer was extracted twice with DCM (10 mL each). The combined organics were dried over sodium sulfate, filtered, and concentrated to afford a pale yellow oil. 4-morpholinoaniline (0.163 g, 0.910 mmol) was added to the oil and the resulting mixture was dissolved in DMF (2 mL). DIPEA (0.17 mL, 0.97 mmol) was added to the reaction mixture. The resulting solution was stirred at 100° C. for 30 minutes. The reaction was allowed to cool to room temperature, then diluted with water (70 mL). The resulting suspension was filtered. The filter cake was dried under vacuum to afford methyl 6-bromo-5-(difluoromethyl)-3-(4-morpholinoanilino)pyrazine-2-carboxylate (0.337 g, 87%) as a brick red solid; 1H NMR (500 MHz, DMSO-d6) 3.00-3.13 (4H, m), 3.65-3.77 (4H, m), 3.94 (3H, s), 6.95 (2H, d), 7.08 (1H, t), 7.53 (2H, d), 9.89 (1H, s); m/z: (ES+), [M+H]+=443.1

(d) Methyl 5_(difluoromethyl)-6-(3-methylimidazo [4,5-c]pyridin-7-yl)-3-(4-morpholinoanilino)pyrazine-2-carboxylate 7-Bromo-3-methyl-imidazo[4,5-c]pyridine (176 mg, 0.830 mmol), cataCXium A Pd G3 (60 mg, 0.08 mmol), cataCXium A (30 mg, 0.08 mmol), bis(pinacolato)diboron (527 mg, 2.08 mmol), and potassium acetate (244 mg, 2.49 mmol) were combined in a microwave vial, which was then evacuated and backfilled three times with nitrogen. DMF (3.5 mL) was added and the reaction mixture was stirred at 80° C. for 24 hours. The reaction was then allowed to cool to room temperature and set aside.

Separately, methyl 6-bromo-5-(difluoromethyl)-3-(4-morpholinoanilino)pyrazine-2-carboxylate (337 mg, 0.760 mmol), Pd(dppf) C12 (61 mg, 0.081 mmol), and CsF (378 mg, 2.49 mmol) were combined in a microwave vial, which was evacuated and backfilled three times with nitrogen. The reaction mixture from the borylation step was added via syringe. The resulting mixture was stirred at 100° C. for 4 hours. The reaction was then allowed to cool to room temperature, diluted with water (30 mL), and extracted three times with 3:1 chloroform/isopropanol (30 mL each). The combined organic layers were washed once with 5% aqueous lithium chloride, then dried over sodium sulfate, filtered, and concentrated. The resulting red residue was purified by silica gel chromatography, using 0-5% methanol-DCM as eluent and 0-0.5% ammonia as modifier, to afford methyl 5-(difluoromethyl)-6-(3-methylimidazo[4,5-c]pyridin-7-yl)-3-(4-morpholinoanilino)pyrazine-2-carboxylate (0.12 g, 29%) as a dark red solid; 1H NMR (500 MHZ, DMSO-d6) 3.07-3.13 (4H, m), 3.72-3.77 (4H, m), 3.93 (3H, s), 4.01 (3H, s), 6.90-7.14 (3H, m), 7.66 (2H, d), 8.48 (2H, d), 9.08 (1H, s), 9.99 (1H, s); m/z: (ES+), [M+H]+=496.1

(e) 5-(Difluoromethyl)-6-(3-methylimidazo[4,5-c] pyridin-7-yl)-3-(4-morpholinoanilino)pyrazine-2-carboxamide 7 N Methanolic ammonia (2.00 mL, 14.0 mmol) was added to methyl 5-(difluoromethyl)-6-(3-methylimidazo[4,5-c]pyridin-7-yl)-3-(4-morpholinoanilino)pyrazine-2-carboxylate (120 mg, 0.24 mmol). The resulting suspension was stirred at 100° C. for 1 hour in a Biotage microwave reactor. The resulting suspension was filtered, rinsing sparingly with methanol, to afford 5-(difluoromethyl)-6-(3-methylimidazo[4,5-c]pyridin-7-yl)-3-(4-morpholinoanilino) pyrazine-2-carboxamide (0.060 g, 52%) as an orange solid; 1H NMR (500 MHz, DMSO-d6) 3.00-3.18 (4H, m), 3.67-3.83 (4H, m), 4.00 (3H, s), 6.99 (2H, d), 7.11 (1H, t), 7.67 (2H, d), 8.10 (1H, br s), 8.40 (1H, br s), 8.50 (1H, s), 8.69 (1H, s), 9.07 (1H, s), 11.24 (1H, s); m/z: (ES+), [M+H]+=481.3

Example 43

5-Methyl-6-(1-methylimidazo[4,5-d]pyridazin-4-yl)-3-(4-morpholinoanilino)pyrazine-2-carboxamide

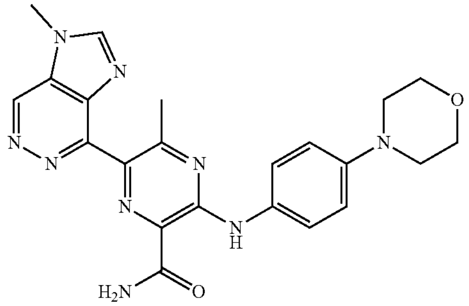 [SMILES: Cc1nc(Nc2ccc(N3CCOCC3)cc2)c(C(N)=O)nc1-c1nncc2c1ncn2C]

(a) Methyl 6-bromo-3-fluoro-5-methyl-pyrazine-2-carboxylate

Sodium nitrite (1.750 g, 25.36 mmol) was added portionwise to a solution of methyl 3-amino-6-bromo-5-methyl-pyrazine-2-carboxylate (1.56 g, 6.34 mmol) in pyridine*HF (20.0 mL, 583 mmol) at −10° C. The resulting mixture was stirred at −10° C. for 2.5 hours. The reaction was then neutralized with saturated aqueous sodium bicarbonate (450 mL), then extracted with EtOAc. The organic layer was washed with brine, dried over magnesium sulfate, filtered, and concentrated to afford methyl 6-bromo-3-fluoro-5-methyl-pyrazine-2-carboxylate (1.400 g, 89%). 1H NMR (500 MHZ, DMSO-d6) δ 2.63 (3H, s), 3.90 (3H, s). m/z: (ES+), [M+2+H]=251.0

(b) Methyl 6-bromo-5-methyl-3-(4-morpholinoanilino)pyrazine-2-carboxylate

DIPEA (0.926 mL, 5.30 mmol) was added to a solution of 4-morpholinoaniline (1.01 g, 5.64 mmol) and methyl 6-bromo-3-fluoro-5-methyl-pyrazine-2-carboxylate (1.32 g, 5.30 mmol) in DMF (10 mL). The resulting mixture was stirred at 110° C. for 1 hour in a Biotage microwave reactor. The reaction mixture was concentrated and used directly in the next step, assuming 100% yield.

(c) 6-Bromo-5-methyl-3-(4-morpholinoanilino)pyrazine-2-carboxamide

7 N Methanolic ammonia (20 mL, 140 mmol) was added to methyl 6-bromo-5-methyl-3-(4-morpholinoanilino)pyrazine-2-carboxylate (2.29 g, 5.63 mmol). The resulting suspension was stirred at 25° C. for 3 days. The reaction was then concentrated. The resulting residue was suspended in DCM (10 mL) and 7 N methanolic ammonia (40 mL, 280 mmol) was added. The resulting mixture was stirred at 25° C. for 16 hours. The resulting suspension was filtered, washed with MeOH and water, and dried under vacuum to afford 6-bromo-5-methyl-3-(4-morpholinoanilino)pyrazine-2-carboxamide (1.92 g, 87%) as an orange solid; 1H NMR (500 MHz, DMSO-d6) 2.50 (3H, s), 2.99-3.14 (4H, m), 3.66-3.80 (4H, m), 6.85-6.99 (2H, m), 7.42-7.54 (2H, m), 7.89 (1H, s), 8.11 (1H, s), 10.93 (1H, s). m/z: (ES+), [M+2+H]=394.1

(d) 3-Methyl-6H-imidazo[4,5-d]pyridazin-7-one

Hydrazine hydrate (0.267 mL, 3.52 mmol) was added to a solution of ethyl 5-formyl-1-methyl-imidazole-4-carboxylate (0.534 g, 2.93 mmol) in ethanol (20 mL). The resulting mixture was stirred at 25° C. for 90 minutes. Acetic acid (0.839 mL, 14.7 mmol) was then added. The resulting mixture was stirred at 100° C. for 19 hours. The reaction mixture was then concentrated. The resulting residue was suspended in EtOH, filtered, washed with EtOH, and dried under vacuum to afford 3-methyl-6H-imidazo[4,5-d]pyridazin-7-one (0.355 g, 81%) as a white solid; 1H NMR (500 MHz, DMSO-d6) 3.88 (3H, s), 8.23 (1H, s), 8.45 (1H, s), 12.63 (1H, br s). m/z: (ES+), [M+$H_3$O]+=169.2

(e) 4-Chloro-1-methyl-imidazo[4,5-d]pyridazine

Phosphoryl trichloride (6.00 mL, 64.4 mmol) was added to 1-methyl-1,5-dihydro-4H-imidazo[4,5-d]pyridazin-4-one (0.210 g, 1.40 mmol). The reaction mixture was stirred at 100° C. for 5.5 hours. The reaction mixture was then concentrated. The residue was treated with ice-water, basified with saturated aqueous sodium bicarbonate, and extracted with 5:1

DCM/IPA. The organic layer was dried over magnesium sulfate, filtered, concentrated to afford 4-chloro-1-methyl-imidazo[4,5-d]pyridazine (0.208 g, 88%) as a yellow solid; 1H NMR (500 MHz, DMSO-d6) 4.00 (3H, s), 8.68 (1H, s), 9.71 (1H, s); m/z: (ES+), [M+H]+=169.1

(f) 5-Methyl-6-(1-methylimidazo[4,5-d]pyridazin-4-yl)-3-(4-morpholinoanilino)pyrazine-2-carboxamide 1,4-Dioxane (1.5 mL) was added to a mixture of bis (pinacolato)diboron (0.040 g, 0.16 mmol), 6-bromo-5-methyl-3-(4-morpholinoanilino)pyrazine-2-carboxamide (0.052 g, 0.13 mmol), $PdCl_2$(dppf) (9.70 mg, 0.01 mmol), and potassium acetate (0.026 g, 0.27 mmol). The resulting mixture was evacuated and backfilled with nitrogen, then stirred at 80° C. for 3 hours. The reaction was allowed to cool to room temperature and set aside.

MeOH (1 mL) was added to a mixture of 4-chloro-1-methyl-imidazo[4,5-d]pyridazine (0.044 g, 0.26 mmol), $PdCl_2$(dppf) (9.5 mg, 0.010 mmol), and potassium phosphate (0.055 g, 0.26 mmol). The borylation mixture was added via syringe. The resulting mixture was evacuated and backfilled with nitrogen, then stirred at 100° C. for 4 hours. The reaction mixture was diluted with water and the resulting suspension was filtered. The filtrate was extracted with DCM. The organic layer was concentrated. The resulting residue was combined with the filter cake and purified by silica gel chromatography, using 0-15% MeOH-DCM, to afford a yellow solid. This material was purified further by reverse phase chromatography, C18, using 0-20% MeCN—$H_2O$ as eluent and 0.1% formic acid as modifier, to afford 5-methyl-6-(1-methylimidazo[4,5-d]pyridazin-4-yl)-3-(4-morpholinoanilino)pyrazine-2-carboxamide (0.018 g, 31%) as a yellow solid; 1H NMR (500 MHz, DMSO-d6) 2.51 (3H, s), 3.04-3.12 (4H, m), 3.69-3.78 (4H, m), 4.03 (3H, s), 6.98 (2H, d), 7.64 (2H, d), 7.93 (1H, s), 8.05 (1H, s), 8.62 (1H, s), 9.73 (1H, s), 11.08 (1H, s). m/z: (ES+), [M+H]+=446.3

Example 44

5-Methyl-6-(7-methylimidazo[4,5-c]pyridazin-4-yl)-3-(4-morpholinoanilino)pyrazine-2-carboxamide

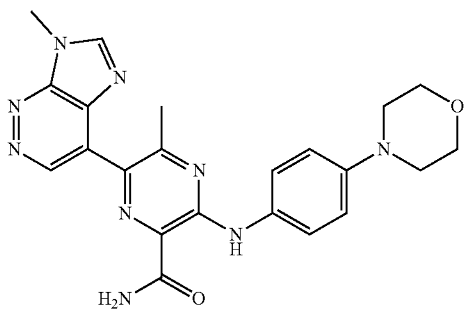 [SMILES: Cc1nc(Nc2ccc(N3CCOCC3)cc2)c(C(N)=O)nc1-c1cnnc2c1ncn2C]

(a) 5-Chloro-N3-methyl-pyridazine-3.4 diamine 40 wt % Aqueous methanamine (10.0 mL, 116 mmol) was added to 3,5-dichloropyridazin-4-amine (0.525 g, 3.20 mmol). The resulting mixture was stirred at 100° C. for 2 hours in a Biotage microwave reactor. The reaction was then concentrated to half its original volume, diluted with water, filtered, washed with water, and dried under vacuum to afford 5-chloro-N3-methyl-pyridazine-3,4-diamine (0.360 g, 71%) as a white solid; 1H NMR (500 MHZ, DMSO-d6) 2.91 (3H, d), 6.09 (2H, br s), 6.23 (1H, br d), 8.12 (1H, s); m/z: (ES+), [M+H]=159.0

(b) 4-Chloro-7-methyl-imidazo[4,5-c]pyridazine

Triethyl orthoformate (10 mL, 60 mmol) was added to 5-chloro-N3-methyl-pyridazine-3,4-diamine (0.333 g, 2.10 mmol). The resulting mixture was stirred at 150° C. for 90 minutes. The reaction was then concentrated. The resulting residue was treated with saturated aqueous sodium bicarbonate, then extracted three times with 5:1 DCM/IPA. The combined organic layers were dried over magnesium sulfate, filtered, and concentrated to afford 4-chloro-7-methyl-imidazo[4,5-c]pyridazine (0.310 g, 88%) as a beige solid;

1H NMR (500 MHZ, DMSO-d6) 4.01 (3H, s), 8.84 (1H, s), 9.24 (1H, s). m/z: (ES+), [M+H]=169.0

(c) 5-Methyl-3-(4-morpholinoanilino)-6-(4,4,5,5-tetramethyl-1,3,2-dioxaborolan-2-yl)pyrazine-2-carboxamide 1,4-Dioxane (1.0 mL) was added to a mixture of bis(pinacolato)diboron (0.031 g, 0.12 mmol), 6-bromo-5-methyl-3-(4-morpholinoanilino)pyrazine-2-carboxamide (0.040 g, 0.10 mmol), $PdCl_2$(dppf) (7.5 mg, 0.01 mmol) and potassium acetate (0.020 g, 0.20 mmol). The resulting mixture was evacuated and backfilled with nitrogen, then stirred at 80° C. for 4 hours. The reaction mixture was then allowed to cool to room temperature and used directly in the next step, assuming 100% yield.

(d) 5-Methyl-6-(7-methylimidazo[4,5-c]pyridazin-4-yl)-3-(4-morpholinoanilino)pyrazine-2-carboxamide MeOH (1.0 mL) was added to a mixture of 4-chloro-7-methyl-imidazo[4,5-c]pyridazine (0.034 g, 0.20 mmol), $PdCl_2$(dppf) (7.3 mg, 0.010 mmol) and potassium phosphate (0.042 g, 0.20 mmol). The borylation reaction mixture from the previous step was added to the vial via syringe. The vial was evacuated and backfilled with nitrogen. The resulting mixture was stirred at 100° C. for 2 hours in a Biotage microwave reactor. The reaction mixture was then diluted with water, filtered, and dried under vacuum. The resulting solid was purified twice by silica gel chromatography, each time using 0-10% MeOH-DCM as eluent, to afford 5-methyl-6-(7-methylimidazo[4,5-c]pyridazin-4-yl)-3-(4-morpholinoanilino)pyrazine-2-carboxamide (0.013 g, 29%) as a yellow solid; 1H NMR (500 MHz, DMSO-d6) 3.01-3.12 (4H, m), 3.64-3.79 (4H, m), 4.04 (3H, s), 6.97 (2H, d), 7.62 (2H, d), 7.91 (1H, s), 8.33 (1H, s), 8.79 (1H, s), 9.41 (1H, s), 11.17 (1H, s); the pyrazine methyl group signal was buried under the DMSO peak; m/z: (ES+), [M+H]=446.4

Example 45

5-(Methylamino)-6-(7-methylimidazo[4,5-c]pyridazin-4-yl)-3-(4-morpholinoanilino)pyrazine-2-carboxamide

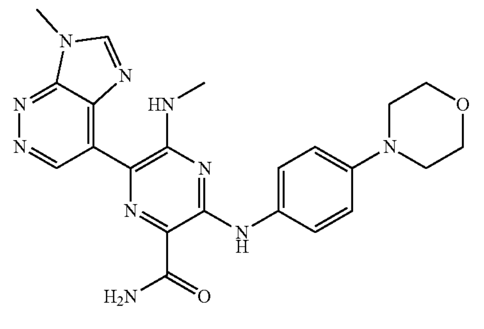 [SMILES: CNc1nc(Nc2ccc(N3CCOCC3)cc2)c(C(N)=O)nc1-c1cnnc2c1ncn2C]

(a) 6-Chloro-5_(methylamino)-3-(4-morpholinoanilino)pyrazine-2-carboxamide

7 N Methanolic (10 mL, 70 mmol) was added to methyl 6-chloro-5-(methylamino)-3-(4-morpholinoanilino)pyrazine-2-carboxylate (1.86 g, 4.92 mmol). The resulting mixture was stirred at 80° C. for 4 days in a Biotage microwave reactor. The reaction was then allowed to cool to room temperature and filtered. The resulting precipitate was collected and washed with MeOH, then dried under vacuum to afford 6-chloro-5-(methylamino)-3-(4-morpholinoanilino)pyrazine-2-carboxamide (1.576 g, 88% yield) as a yellow solid. 1H NMR (500 MHz, DMSO-d6) δ 2.91 (3H, d), 3.01-3.07 (4H, m), 3.69-3.74 (4H, m), 6.91 (2H, d), 7.29 (1H, br s), 7.48-7.58 (4H, m), 11.16 (1H, s). m/z: (ES+), [M+H]=363.1

(b) 5-(Methylamino)-6-(7-methylimidazo[4,5-c]pyridazin-4-yl)-3-(4-morpholinoanilino)pyrazine-2-carboxamide 4-Chloro-7-methyl-imidazo[4,5-c]pyridazine (0.035 g, 0.21 mmol), bis(pinacolato)diboron (0.072 g, 0.28 mmol), potassium acetate (0.062 g, 0.63 mmol), cataCXium A Pd G3 (0.015 g, 0.020 mmol), and cataCXium A (7.5 mg, 0.020 mmol) were combined in a microwave vial, which was evacuated and backfilled three times with nitrogen. DMF (2.0 mL) was added. The resulting mixture was stirred at 100° C. for 5 hours. The reaction was then allowed to cool to room temperature and set aside.

6-chloro-5-(methylamino)-3-(4-morpholinoanilino)pyrazine-2-carboxamide (0.050 g, 0.14 mmol), Pd(dppf) C12 DCM adduct (10 mg, 0.01 mmol), and cesium fluoride (0.063 g, 0.41 mmol) were combined in a microwave vial, which was evacuated and backfilled three times with nitrogen. The borylation mixture was added via syringe. The resulting mixture was stirred at 100° C. for 1 hour in a Biotage microwave reactor. The reaction was allowed to cool to room temperature, then treated with saturated aqueous sodium bicarbonate. The resulting precipitate was filtered, washed with water, and dried under vacuum. The resulting solid was purified twice by silica gel chromatography, using 0-10% MeOH in DCM as eluent each time. The resulting residue was purified further by C18 reverse phase chromatography, using 0-60% MeCN—$H_2O$ as eluent and 0.1% formic acid as modifier, to afford 5-(methylamino)-6-(7-methylimidazo[4,5-c]pyridazin-4-yl)-3-(4-morpholinoanilino)pyrazine-2-carboxamide (3.0 mg, 4.7%) as an orange solid; 1H NMR (500 MHz, DMSO-d6) 3.03 (3H, d), 3.05-3.09 (4H, m), 3.70-3.76 (4H, m), 4.03 (3H, s), 6.96 (2H, d), 7.46 (1H, s), 7.67 (2H, d), 8.09 (1H, s), 8.82 (1H, s), 9.72 (1H, q), 9.87 (1H, s), 11.52 (1H, s); m/z: (ES+), [M+H]+=461.

Example 46

6-(3-Ethylimidazo[4,5-c]pyridin-7-yl)-5-(methylamino)-3-(4-morpholinoanilino)pyrazine-2-carboxamide

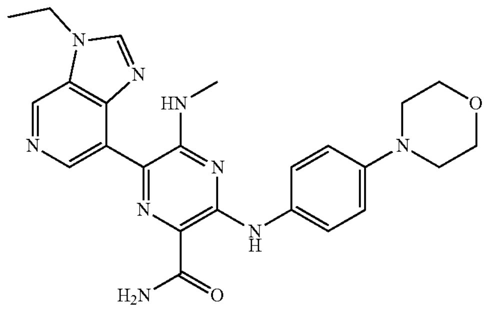 [SMILES: CCn1cnc2c(-c3nc(C(N)=O)c(Nc4ccc(N5CCOCC5)cc4)nc3NC)cncc21]

(a) 7-Bromo-3-ethyl-imidazo[4,5-c]pyridine 1,1-Diethoxy-N,N-dimethyl-methanamine (7.43 g, 50.5 mmol) was added to a solution of 7-bromo-3H-imidazo[4,5-c]pyridine (2.00 g, 10.1 mmol) in DMF (30 mL). The resulting mixture was stirred at 80° C. for 4 hours. The resulting residue was purified by C18 reverse phase chromatography, using 0-60% MeCN-4:1 MeOH/water as eluent and 0.1% ammonium bicarbonate as modifier, to afford 7-bromo-3-ethyl-imidazo[4,5-c]pyridine (800 mg, 35%) as a white solid; 1H NMR (400 MHZ, DMSO-d6) δ 1.44 (3H, t), 4.38 (2H, q), 8.46 (1H, s), 8.57 (1H, s), 9.00 (1H, s); m/z: (ES+), [M+2+H]+=228.1

(b) Methyl 3-amino-6-(3-ethylimidazo[4,5-c]pyridin-7-yl)-5-(methylamino) pyrazine-2-carboxylate CataCXium A Pd G2 (236 mg, 0.350 mmol) was added to a mixture of cataCXium A tetrafluoroborate (158 mg, 0.350 mmol), 7-bromo-3-ethyl-imidazo[4,5-c]pyridine (400 mg, 1.77 mmol), bis(pinacolato)diboron (1.35 g, 5.31 mmol), and potassium acetate (521 mg, 5.31 mmol) in DMF (16 mL) under nitrogen. The resulting mixture was stirred at 80° C. for 16 hours. The reaction was then allowed to cool to room temperature and set aside.

Methyl 3-amino-6-chloro-5-(methylamino) pyrazine-2-carboxylate (383 mg, 1.77 mmol), cesium fluoride (806 mg, 5.31 mmol), and $PdCl_2$(dppf) (194 mg, 0.27 mmol) were combined in a microwave vial, which was evacuated and backfilled three times with nitrogen. The borylation mixture was added via syringe. The resulting mixture was stirred at 100° C. for 2 hours.

The resulting residue was purified by silica gel chromatography, using 0-20% MeOH-DCM as eluent, to afford methyl 3-amino-6-(3-ethylimidazo[4,5-c]pyridin-7-yl)-5-(methylamino) pyrazine-2-carboxylate (0.207 g, 36%) as a yellow solid; 1H NMR (400 MHZ, DMSO-d6) δ 1.50 (3H, t), 2.83 (3H, d), 3.74 (3H, s), 4.44 (2H, q), 7.26 (2H, br s), 7.49 (1H, br q), 8.45 (1H, s), 8.53 (1H, s), 9.06 (1H, s). m/z: (ES+), [M+H]+=328.1

(c) Methyl 6-(3-ethylimidazo[4,5-c]pyridin-7-yl)-5 (methylamino)-3-(4-morpholinoanilino)pyrazine-2-carboxylate Brettphos Pd G3 (55 mg, 0.060 mmol) was added to a suspension of methyl 3-amino-6-(3-ethylimidazo[4,5-c]pyridin-7-yl)-5-(methylamino) pyrazine-2-carboxylate (100 mg, 0.31 mmol), 4-(4-bromophenyl) morpholine (74 mg, 0.31 mmol), and cesium carbonate (299 mg, 0.920 mmol) in 1,4-dioxane (5 mL) under nitrogen. The resulting mixture was stirred at 100° C. for 16 hours. The reaction was then concentrated. The resulting residue was purified by silica gel chromatography, using 0-20% MeOH-DCM as eluent, to afford methyl 6-(3-ethylimidazo[4,5-c]pyridin-7-yl)-5-(methylamino)-3-(4-morpholinoanilino)pyrazine-2-carboxylate (0.107 g, 72%) as a yellow solid; 1H NMR (400 MHZ, DMSO-d6) δ 1.51 (3H, t), 2.90 (3H, d), 3.04-3.12 (4H, m), 3.71-3.78 (4H, m), 3.82 (3H, s), 4.45 (2H, q), 6.97 (2H, d), 7.67 (2H, d), 7.89 (1H, br q), 8.52 (1H, s), 8.56 (1H, s), 9.08 (1H, s), 10.26 (1H, s). m/z: (ES+), [M+H]+=489.4

(d) 6-(3-Ethylimidazo[4,5-c]pyridin-7-yl)-5-(methylamino)-3-(4-morpholinoanilino)pyrazine-2-carboxamide 7 N Methanolic ammonia (5.0 mL, 35 mmol) was added to methyl 6-(3-ethylimidazo[4,5-c]pyridin-7-yl)-5-(methylamino)-3-(4-morpholinoanilino)pyrazine-2-carboxylate (92 mg, 0.19 mmol). The resulting suspension was stirred at 80° C. for 40 hours. The reaction was then concentrated. The resulting residue was purified by preparative HPLC, using a 5 micron, 50 mm×100 mm, XSelect CSH Prep C18 OBD column, decreasingly polar mixtures of MeCN—$H_2O$ as eluent, and 0.1% formic acid as modifier, to afford 6-(3-ethylimidazo[4,5-c]pyridin-7-yl)-5-(methylamino)-3-(4-morpholinoanilino)pyrazine-2-carboxamide (20 mg, 22%) as a yellow solid; 1H NMR (400 MHZ, DMSO-d6) δ 1.51 (3H, t), 2.93 (3H, d), 3.07 (4H, t), 3.74 (4H, t), 4.45 (2H, q), 6.95 (2H, d), 7.30 (1H, s), 7.66 (2H, d), 7.69 (1H, s), 7.96 (1H, br q), 8.58 (1H, s), 8.70 (1H, s), 9.06 (1H, s), 11.29 (1H, s); m/z: (ES+), [M+H]+=474.2

Example 47

6-(3-Cyclopropylimidazo[4,5-c]pyridin-7-yl)-5-(methylamino)-3-(4-morpholinoanilino)pyrazine-2-carboxamide

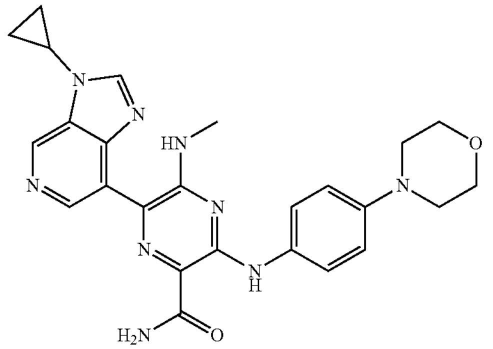 [SMILES: CNc1nc(Nc2ccc(N3CCOCC3)cc2)c(C(N)=O)nc1-c1cncc2c1ncn2C1CC1]

(a) 7-Bromo-3-cyclopropyl-imidazo[4,5-c]pyridine

Copper (II) acetate (0.532 g, 2.93 mmol) and 2,2'-bipyridine (0.457 g, 2.93 mmol) were added to a mixture of cyclopropylboronic acid (0.55 g, 6.4 mmol), 7-bromo-3H-imidazo[4,5-c]pyridine (0.580 g, 2.93 mmol), and sodium carbonate (0.621 g, 5.86 mmol) in DCE (15 mL). The resulting mixture was stirred at 70° C. for 23 hours. The reaction was then allowed to cool to room temperature, treated with saturated aqueous ammonium chloride, and extracted with DCM. The organic layer was dried over magnesium sulfate, filtered, and concentrated. The resulting residue was purified by flash silica chromatography, using 0-10% MeOH-DCM as eluent, to afford a mixture of 2 regio-isomers. The isomers were separated by preparative HPLC, using a 5 micron, 30 mm×100 mm XSelect CSH C18 OBD column, 20-40% MeCN—$H_2O$ as eluent, and 0.1% ammonium hydroxide as modifier, to afford 7-bromo-3-cyclopropyl-imidazo[4,5-c]pyridine (0.085 g, 12%). 1H NMR (500 MHz, DMSO-d6) 1.07-1.18 (4H, m), 3.61-3.71 (1H, m), 8.50 (1H, s), 8.56 (1H, s), 8.97 (1H, s); m/z: (ES+), [M+H]+=237.6

(b) 6-(3-Cyclopropylimidazo[4,5-c]pyridin-7-yl)-5-(methylamino)-3 (4-morpholinoanilino)pyrazine-2-carboxamide A mixture of 7-bromo-3-cyclopropyl-3H-imidazo[4,5-c]pyridine (0.050 g, 0.21 mmol), bis(pinacolato)diboron (0.080 g, 0.32 mmol), potassium acetate (0.062 g, 0.63 mmol), cataCXium A Pd G3 (0.015 g, 0.020 mmol), and cataCXium A (7.5 mg, 0.020 mmol) in DMF (2.0 mL) was evacuated and backfilled three times with nitrogen. The reaction mixture was stirred at 100° C. for 18.5 hours. The reaction was then allowed to cool to room temperature and set aside.

6-chloro-5-(methylamino)-3-(4-morpholinoanilino)pyrazine-2-carboxamide (0.050 g, 0.14 mmol), $PdCl_2$(dppf) (10 mg, 0.01 mmol), and cesium fluoride (0.063 g, 0.41 mmol) were combined in a microwave vial, which was evacuated and backfilled with nitrogen three times. The borylation mixture was added. The resulting mixture was stirred at 100° C. for 1 hour in a Biotage microwave reactor. The reaction was then concentrated. The resulting residue was purified by flash silica chromatography, using 0-10% MeOH-DCM as eluent. The resulting material was further purified by C18 chromatography, using 10-40% MeCN-water as eluent, and 0.2% ammonium hydroxide as modifier. The resulting material was further purified by C18 chromatography, using 0-30% MeCN—$H_2O$ as eluent, and 0.1% formic acid as modifier, to afford 6-(3-cyclopropylimidazo[4,5-c]pyridin-7-yl)-5-(methylamino)-3-(4-morpholinoanilino)pyrazine-2-carboxamide (10 mg, 15%) as a yellow solid; 1H NMR (500 MHz, DMSO-d6) δ 1.08-1.22 (4H, m), 2.91 (3H, d), 3.01-3.09 (4H, m), 3.66-3.71 (1H, m), 3.71-3.75 (4H, m), 6.94 (2H, d), 7.29 (1H, br s), 7.65 (2H, d), 7.67 (1H, br s), 7.84 (1H, br q), 8.55 (1H, s), 8.71 (1H, s), 9.02 (1H, s), 11.28 (1H, s); m/z: (ES+), [M+H]+=486.2

Example 48

6-[3-(Difluoromethyl) imidazo[4,5-c]pyridin-7-yl]-5-(methylamino)-3-(4-morpholinoanilino)pyrazine-2-carboxamide

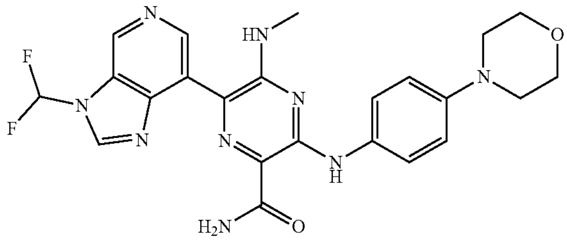 [SMILES: CNc1nc(Nc2ccc(N3CCOCC3)cc2)c(C(N)=O)nc1-c1cncc2c1ncn2C(F)F]

(a) 7-Bromo-3-(difluoromethyl) imidazo[4,5-c]pyridine

1-[[Bromo (difluoro)methyl]-ethoxy-phosphoryl]oxyethane (0.731 mL, 4.11 mmol) was added to a solution of 7-bromo-3H-imidazo[4,5-c]pyridine (0.543 g, 2.74 mmol) and potassium hydroxide (0.923 g, 16.5 mmol) in acetonitrile (8.0 mL) and water (8.0 mL). The resulting mixture was stirred at room temperature for 1 hour. The reaction was then extracted with 2-methyltetrahydrofuran. The organic layer was dried over magnesium sulfate, filtered, and concentrated. The resulting residue was purified by silica gel chromatography, using 0 to 15% MeOH-DCM as eluent. The resulting material was further purified by chiral SFC, using a 5 micron, 4.6×100 mm ChiralPak OD column, using isocratic 20% MeOH-$sCO_2$ as eluent, and 0.2% ammonium hydroxide as modifier, to afford 7-bromo-3-(difluoromethyl)-3H-imidazo[4,5-c]pyridine (0.050 g, 7.4% yield) as a yellow solid. 1H NMR (500 MHz, DMSO-d6) 8.17 (1H, t), 8.67 (1H, s), 8.94 (1H, s), 9.06 (1H, s). m/z: (ES+), [M+H]+= 247.9

(b) 6-[3-(Difluoromethyl) imidazo[4,5-c]pyridin-7-yl]-5-(methylamino)-3-(4-morpholinoanilino)pyrazine-2-carboxamide A mixture of bis(pinacolato)diboron (0.070 g, 0.28 mmol), 6-chloro-5-(methylamino)-3-(4-morpholinoanilino) pyrazine-2-carboxamide (0.067 g, 0.18 mmol), $PdCl_2$(dppf) (0.014 g, 0.020 mmol), and potassium acetate (0.054 g, 0.55 mmol) in 1,4-dioxane (2.0 mL) was degassed and purged with nitrogen. The resulting mixture was heated at 80° C. for 2 hours. The reaction was then allowed to cool to room temperature. A solution of 7-bromo-3-(difluoromethyl) imidazo[4,5-c]pyridine (0.046 g, 0.19 mmol) in dioxane (1.5 mL) and 2 M aqueous potassium phosphate (0.277 mL, 0.554 mmol) was added. The resulting mixture was degassed, purged with nitrogen, and stirred at 80° C. for 2 hours. The reaction was then concentrated. The resulting residue was diluted with water. The resulting precipitate was collected and washed with water and dried under vacuum. The resulting solid was purified by silica gel chromatography, using 0 to 10% MeOH-DCM as eluent. The resulting material was further purified by reverse phase C18 chromatography, using 0 to 30% MeCN-water as eluent, and 0.1% formic acid as modifier, to afford 6-[3-(difluoromethyl) imidazo[4,5-c]pyridin-7-yl]-5-(methylamino)-3-(4-morpholinoanilino)pyrazine-2-carboxamide (0.030 g, 33% yield) as an orange solid. 1H NMR (500 MHz, DMSO-d6) δ 2.87 (3H, d), 3.01-3.12 (4H, m), 3.70-3.77 (4H, m), 6.96 (2H, br d), 7.12 (1H, br s), 7.28 (1H, br s), 7.58-7.72 (3H, m), 8.23 (1H, t), 8.75 (1H, s), 8.92 (1H, s), 9.14 (1H, s), 11.31 (1H, s). 19F NMR (471 MHz, DMSO-d6)-94.27. m/z: (ES+), [M+H]+=495.9

Example 49

6-(7-Chloro-1-methyl-benzimidazol-4-yl)-5-(methylamino)-3-(4-morpholinoanilino)pyrazine-2-carboxamide

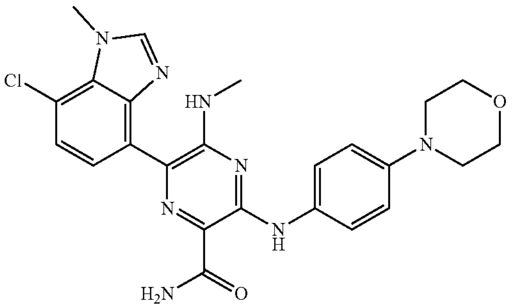 [SMILES: CNc1nc(Nc2ccc(N3CCOCC3)cc2)c(C(N)=O)nc1-c1ccc(Cl)c2c1ncn2C]

(a) 4-Bromo-7-chloro-1H-benzimidazole

A mixture of 3-bromo-6-chloro-benzene-1,2-diamine (1.18 g, 5.32 mmol) and formic acid (10 mL, 260 mmol) was stirred at 100° C. for 2 hours. The reaction was then concentrated. The resulting residue was treated with saturated aqueous sodium bicarbonate. The resulting precipitate was collected via filtration, washed with water, and dried under vacuum to afford 4-bromo-7-chloro-1H-benzimidazole (1.188 g, 96%) as a beige solid; 1H NMR (500 MHZ, DMSO-d6) 7.24 (1H, br d), 7.42 (1H, dd), 8.39 (1H, s), 13.28 (1H, br s); m/z: (ES+), [M+H]+=231.0

(b) 4-Bromo-7-chloro-1-methyl-benzimidazole 60 wt % Sodium hydride in oil (0.246 g, 6.16 mmol) was added to a solution of 4-bromo-7-chloro-1H-benzimidazole (1.188 g, 5.130 mmol) in DMF (20 mL) at 0° C. The reaction mixture was stirred at 25 C for 35 minutes. Iodomethane (0.353 mL, 5.65 mmol) was added. The reaction mixture was stirred at 25 C for 90 minutes. The reaction was then quenched with water at 0° C. The resulting precipitate was collected by filtration and washed with water. The resulting solid was purified further by preparative SFC, using a 5 micron, 21 mm×250 mm Lux amylose 2 column and 12% EtOH-$sCO_2$ as eluent, to afford 4-bromo-7-chloro-1-methyl-benzimidazole (0.198 g, 16%); 1H NMR (500 MHz, DMSO-d6) 4.08 (3H, s), 7.22 (1H, d), 7.42 (1H, d), 8.33 (1H, s); m/z: (ES+), [M+H]+=245.0

(c) (7-Chloro-1-methyl-benzimidazol-4-yl) boronic acid

A mixture of bis(pinacolato)diboron (0.159 g, 0.630 mmol), 4-bromo-7-chloro-1-methyl-benzimidazole (0.077 g, 0.31 mmol), Pd(dppf)$Cl_2$ (0.023 g, 0.030 mmol), and potassium acetate (0.092 g, 0.94 mmol) in 1,4-dioxane (2.0 mL) was sparged with nitrogen. The resulting mixture was heated at 100° C. for 40 hours. The reaction mixture was filtered through Celite and washed with EtOAc. The filtrate was concentrated. The resulting residue was purified by C18 reverse phase chromatography, using 0-15% MeCN—$H_2O$ as eluent and 0.1% formic acid as modifier, to afford (7-chloro-1-methyl-benzimidazol-4-yl) boronic acid (0.023 g, 35%) as a white solid; 1H NMR (500 MHz, DMSO-d6) 4.11 (3H, s), 7.31 (1H, d), 7.59 (1H, d), 8.40 (1H, s), 8.63 (2H, s); m/z: (ES+), [M+H]+=211.0

(d) 6-(7-Chloro-1-methyl-benzimidazol-4-yl)-5-(methylamino)-3-(4-morpholinoanilino)pyrazine-2-carboxamide (7-Chloro-1-methyl-benzimidazol-4-yl) boronic acid (0.037 g, 0.18 mmol), 6-chloro-5-(methylamino)-3-(4-morpholinoanilino)pyrazine-2-carboxamide (0.050 g, 0.14 mmol), Pd(dppf)$Cl_2$ (10 mg, 0.010 mmol), and cesium fluoride (0.063 g, 0.41 mmol) were combined in a microwave vial, which was evacuated and backfilled three times with nitrogen. MeOH (2.0 mL) was added. The resulting mixture was stirred at 100° C. for 1 hour in a Biotage microwave reactor. The reaction was then allowed to cool to room temperature and diluted with water. The resulting precipitate was collected via filtration, washed with water, and dried under vacuum. The resulting solid was purified by silica gel chromatography, using 0-10% MeOH-DCM as eluent. The resulting residue was further purified by C18 reverse phase chromatography, using 10-60% MeCN—$H_2O$ as eluent and 0.2% $NH_4OH$ as modifier, to afford 6-(7-chloro-1-methyl-benzimidazol-4-yl)-5-(methylamino)-3-(4-morpholinoanilino)pyrazine-2-carboxamide (10 mg, 15%) as a yellow solid; 1H NMR (500 MHZ, DMSO-d6) 2.87 (3H, d), 3.00-3.11 (4H, m), 3.67-3.79 (4H, m), 4.13 (3H, s), 6.93 (2H, br d), 7.26 (1H, br s), 7.37 (1H, d), 7.43 (1H, br q), 7.47 (1H, d), 7.55 (1H, br s), 7.64 (2H, br d), 8.32 (1H, s), 11.23 (1H, s); m/z: (ES+), [M+H]+=493.1

Example 50

6-(7-Cyano-1-methyl-benzimidazol-4-yl)-5-(methylamino)-3-(4-morpholinoanilino)pyrazine-2-carboxamide

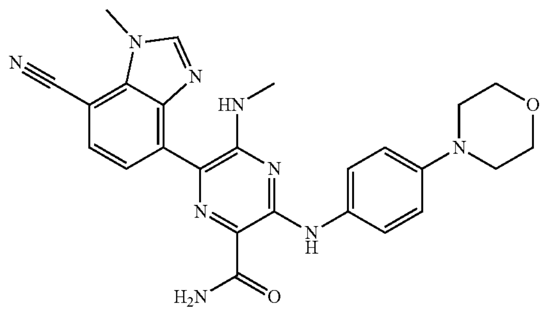 [SMILES: CNc1nc(Nc2ccc(N3CCOCC3)cc2)c(C(N)=O)nc1-c1ccc(C#N)c2c1ncn2C]

(a) 4-Bromo-7-chloro-1H-benzo[d]imidazole

A mixture of 3-bromo-6-chlorobenzene-1,2-diamine (1.18 g, 5.32 mmol) and formic acid (10 mL, 260 mmol) was stirred at 100° C. for 2 hours. The reaction was then concentrated. The resulting residue was treated with saturated aqueous sodium bicarbonate. The resulting precipitate was collected via filtration and washed with water, then dried under air to afford 4-bromo-7-chloro-1H-benzo[d]imidazole (1.19 g, 96% yield) as a beige solid. 1H NMR (500 MHz, DMSO-d6) δ 7.24 (1H, br d), 7.42 (1H, dd), 8.39 (1H, s), 13.27 (1H, br s). m/z: (ES+), [M+H]+=231.0

(b) 4-Bromo-7-chloro-1-methyl-benzimidazole and 7-bromo-4-chloro-1-methyl-benzimidazole 60 wt % Sodium hydride in mineral oil (0.246 g, 6.16 mmol) was added to a solution of 4-bromo-7-chloro-1H-benzimidazole (1.19 g, 5.13 mmol) in DMF (20 mL) at 0° C. The resulting mixture was stirred at 25° C. for 35 minutes. Iodomethane (0.353 mL, 5.65 mmol) was added. The resulting mixture was stirred at 25° C. for 90 minutes. The reaction was then cooled to 0° C. and then quenched with water. The resulting precipitate was collected by filtration, washed with water, and dried under vacuum to afford a mixture of 4-bromo-7-chloro-1-methyl-benzimidazole and 7-bromo-4-chloro-1-methyl-benzimidazole as a beige solid (1.09 g, 87%); 1H NMR (500 MHz, DMSO-d6) δ 3.99-4.15 (3H, m), 7.12-7.30 (1H, m), 7.34-7.50 (1H, m), 8.26-8.43 (1H, m); m/z: (ES+), [M+H]+=245.0

(c) 7-Chloro-3-methyl-benzimidazole-4-carbonitrile

A mixture of 4-bromo-7-chloro-1-methyl-benzimidazole and 7-bromo-4-chloro-1-methyl-benzimidazole (0.427 g, 1.74 mmol), zinc cyanide (0.204 g, 1.74 mmol) and tetrakis (triphenylphosphine) palladium (0) (0.402 g, 0.350 mmol) in DMF (5 mL) was evacuated and backfilled with nitrogen three times. The reaction mixture was stirred at 90° C. for 4 hours. The reaction was then concentrated. The resulting residue was purified by flash silica chromatography, using 0-10% MeOH-DCM as eluent. The resulting mixture of two regio-isomers was separated by preparative HPLC, using a 5 micron, 19 mm×250 mm XBridge c18 column, 20-50% MeCN—$H_2O$ as eluent, and 0.2% ammonium hydroxide as modifier, to afford 7-chloro-3-methyl-benzimidazole-4-carbonitrile (0.076 g, 18%). 1H NMR (500 MHz, DMSO-d6) δ 4.08 (3H, s), 7.47 (1H, d), 7.77 (1H, d), 8.47 (1H, s); m/z: (ES+), [M+H]+=192.0

(d) 6-(7-Cyano-1-methyl-benzimidazol-4-yl)-5-(methylamino)-3-(4-morpholinoanilino)pyrazine-2-carboxamide A mixture of 7-chloro-3-methyl-benzimidazole-4-carbonitrile (0.040 g, 0.21 mmol), bis(pinacolato)diboron (0.080 g, 0.32 mmol), potassium acetate (0.062 g, 0.63 mmol), cataCXium A Pd G3 (0.015 g, 0.020 mmol) and cataCXium A (7.5 mg, 0.020 mmol) in DMF (2.0 mL) was evacuated and backfilled three times with nitrogen. The resulting mixture was stirred at 100° C. for 18.5 hours. The reaction was then allowed to cool to room temperature and was set aside.

6-Chloro-5-(methylamino)-3-(4-morpholinoanilino)pyrazine-2-carboxamide (0.050 g, 0.14 mmol), $PdCl_2$(dppf) (10 mg, 0.01 mmol), and cesium fluoride (0.063 g, 0.41 mmol) were combined in a microwave vial, which was evacuated and backfilled three times with nitrogen. The borylation mixture was added. The resulting mixture was stirred at 100° C. for 1 hour in a Biotage microwave reactor. The reaction was then concentrated. The resulting residue was purified by flash silica chromatography, using 0-5% MeOH-DCM as eluent. The product was further purified by reverse phase C18 flash chromatography, using 0-45% MeCN—$H_2O$ as eluent, and 0.1% formic acid as modifier, to afford 6-(7-cyano-1-methyl-benzimidazol-4-yl)-5-(methylamino)-3-(4-morpholinoanilino)pyrazine-2-carboxamide (6.0 mg, 9.0%) as a yellow solid. 1H NMR (500 MHz, DMSO-d6) δ 2.90 (3H, d), 3.02-3.09 (4H, m), 3.67-3.78 (4H, m), 4.13 (3H, s), 6.60 (1H, br s), 6.94 (2H, d), 7.34 (1H, br s), 7.65 (2H, br d), 7.74 (1H, d), 7.83 (1H, d), 7.89 (1H, br q), 8.49 (1H, s), 11.30 (1H, s). m/z: (ES+), [M+H]+=484.2

Example 51

6-(3,4-Dimethylimidazo[4,5-c]pyridin-7-yl)-5-(methylamino)-3-(4-morpholinoanilino)pyrazine-2-carboxamide

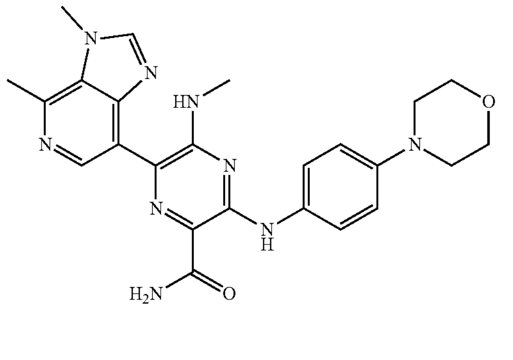 [SMILES: CNc1nc(Nc2ccc(N3CCOCC3)cc2)c(C(N)=O)nc1-c1cnc(C)c2c1ncn2C]

(a) 5-Bromo-2-methyl-pyridine-3,4-diamine 2,5-Dibromopyridine-3,4-diamine (5.00 g, 18.7 mmol) and bis(triphenylphosphine) palladium (II) chloride (1.32 g, 1.87 mmol) were combined in a multineck flask, which was evacuated and backfilled three times with nitrogen. 1,4-dioxane (10 mL) was added. Dimethylzinc (13 mL, 26 mmol) was added as a 2 M solution in toluene. The reaction was stirred at 80° C. for 60 hours. The reaction was allowed to cool to room temperature, then quenched with water (50 mL), extracted once with EtOAc (30 mL) and twice with 3:1 DCM/IPA (20 mL each). The combined organics were dried over magnesium sulfate, filtered, and concentrated. The resulting residue was purified by silica gel chromatography, using an isocratic mixture of 3:1 EtOAc-EtOH as eluent, to afford 5-bromo-2-methyl-pyridine-3,4-diamine (0.533 g, 14%) as a brown solid; 1H NMR (500 MHz, DMSO-d6) δ 2.17 (3H, s), 4.61 (2H, br s), 5.48 (2H, br s), 7.58 (1H, s); m/z: (ES+), [M+H]+=202.0

(b) 5-Bromo-N3,2-dimethylpyridine-3,4-diamine 25 wt % Methanolic sodium methoxide (3.80 mL, 16.6 mmol) was added to a suspension of 5-bromo-2-methyl-pyridine-3,4-diamine (818 mg, 4.05 mmol) and paraformaldehyde (182 mg, 6.07 mmol) in MeOH (10 mL). The reaction was stirred at 25° C. for 4 hours. Sodium borohydride (245 mg, 6.48 mmol) was added and the resulting mixture was stirred at 60° C. for 1 hour. The reaction was then concentrated to an off-white sludge, which was suspended in water (20 mL), then extracted with ethyl acetate (4×15 mL). The combined organic layers were dried over magnesium sulfate, filtered, and concentrated to a brown oil, which was a mixture of several components, including starting material and desired product. This mixture was carried forward to the next step without isolation.

(c) 7-Bromo-3,4-dimethyl-imidazo[4,5-c]pyridine

Triethyl orthoformate (15 mL, 90.1 mmol) was added to crude 5-bromo-N3,2-dimethylpyridine-3,4-diamine (0.875 g, 4.05 mmol). The resulting suspension was stirred at 145° C. for 40 minutes. The reaction was then concentrated. The resulting brown solid was purified by silica gel chromatography, using 0-10% MeOH-DCM as eluent, to afford 7-bromo-3,4-dimethyl-imidazo[4,5-c]pyridine (0.126 g, 14%) as a white solid; 1H NMR (500 MHz, DMSO-d6) δ 2.83 (3H, s), 4.08 (3H, s), 8.26 (1H, s), 8.40 (1H, s); m/z: (ES+), [M+H]+=226.0

(d) 6-(3,4-Dimethylimidazo[4,5-c]pyridin-7-yl)-5-(methylamino)-3-(4-morpholinoanilino)pyrazine-2-carboxamide A mixture of 7-bromo-3,4-dimethyl-imidazo[4,5-c]pyridine (0.050 g, 0.22 mmol), bis(pinacolato)diboron (0.084 g, 0.33 mmol), potassium acetate (0.065 g, 0.66 mmol), cataCXium A Pd G3 (0.016 g, 0.020 mmol) and cataCXium A (7.9 mg, 0.020 mmol) in DMF (2.0 mL) was evacuated and backfilled three times with nitrogen. The reaction mixture was stirred at 100° C. for 20 hours. The reaction was then allowed to cool to room temperature and set aside.

6-Chloro-5-(methylamino)-3-(4-morpholinoanilino)pyrazine-2-carboxamide (0.050 g, 0.14 mmol), $PdCl_2$(dppf) (10 mg, 0.01 mmol), and cesium fluoride (0.063 g, 0.41 mmol) were combined in a microwave vial, which was evacuated and backfilled three times with nitrogen. The borylation mixture was added. The resulting mixture was stirred at 100° C. for 1 hour in a Biotage microwave reactor. The reaction was then concentrated. The resulting residue was purified by silica gel chromatography, using 0-10% MeOH-DCM as eluent. The resulting material was further purified by alumina chromatography, using 0-5% MeOH-DCM as eluent. The resulting material was further purified by c18 reverse phase chromatography, using 0-20% MeCN—$H_2O$ as eluent and 0.1% formic acid as modifier, to afford 6-(3,4-dimethylimidazo[4,5-c]pyridin-7-yl)-5-(methylamino)-3-(4-morpholinoanilino)pyrazine-2-carboxamide (18 mg, 28%) as a yellow solid; 1H NMR (500 MHz, DMSO-d6) δ 2.90 (3H, d), 2.93 (3H, s), 3.03-3.07 (4H, m), 3.71-3.75 (4H, m), 4.14 (3H, s), 6.94 (2H, d), 7.27 (1H, br s), 7.63 (1H, br s), 7.64 (2H, d), 7.79 (1H, br q), 8.40 (1H, s), 8.46 (1H, s), 11.24 (1H, s); m/z: (ES+), [M+H]+=474.2

Example 52

3-(2-Fluoro-4-morpholino-anilino)-5-(methylamino)-6-(3-methylimidazo[4,5-c]pyridin-7-yl)pyrazine-2-carboxamide

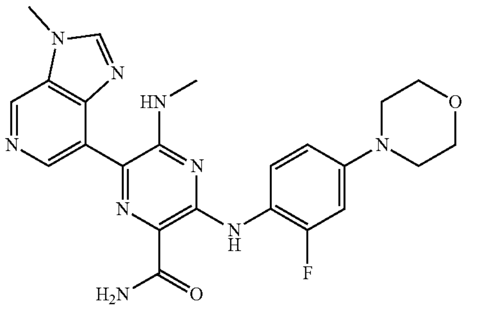 [SMILES: CNc1nc(Nc2ccc(N3CCOCC3)cc2F)c(C(N)=O)nc1-c1cncc2c1ncn2C]

(a) Methyl 3-amino-5-(methylamino)-6-(3-methylimidazo[4,5-c]pyridin-7-yl)pyrazine-2-carboxylate A mixture of methyl 3-amino-6-chloro-5-(methylamino) pyrazine-2-carboxylate (2.17 g, 10.0 mmol), 2-(3-methylimidazo[4,5-c]pyridin-7-yl)-1,3,6,2-dioxazaborocane (3.08 g, 12.5 mmol), Pd(dppf) C12 dichloromethane adduct (0.817 g, 1.00 mmol), and cesium fluoride (4.56 g, 30.0 mmol) was evacuated and backfilled three times with nitrogen. 1,4-Dioxane (91 mL) and water (9.1 mL) were added. The resulting mixture was allowed to stir at 90° C. for 3 hours. The reaction was allowed to cool to room temperature, then cooled to 0° C., then diluted with water (100 mL). The resulting precipitate was collected by filtration, rinsed with water and diethyl ether, and dried under vacuum, to afford methyl 3-amino-5-(methylamino)-6-(3-methylimidazo[4,5-c]pyridin-7-yl)pyrazine-2-carboxylate (3.095 g, 99% yield) as a gray solid. 1H NMR (500 MHZ, DMSO-d6) 2.81 (3H, d), 3.73 (3H, s), 3.99 (3H, s), 7.23 (2H, br s), 7.50 (1H, br q), 8.45 (2H, s), 8.99 (1H, s). m/z: (ES+), [M+H]+=314.4

(b) Methyl 3-(2-fluoro-4-morpholino-anilino)-5-(methylamino)-6-(3-methylimidazo[4,5-c]pyridin-7-yl)pyrazine-2-carboxylate Brettphos Pd G3 (23 mg, 0.030 mmol) was added to a suspension of methyl 3-amino-5-(methylamino)-6-(3-methylimidazo[4,5-c]pyridin-7-yl)pyrazine-2-carboxylate (80 mg, 0.26 mmol), 4-(4-bromo-3-fluoro-phenyl) morpholine (66 mg, 0.26 mmol), and cesium carbonate (250 mg, 0.77 mmol) in 1,4-dioxane (6 mL) under nitrogen. The resulting mixture was stirred at 100° C. for 16 hours. The reaction was then concentrated. The resulting residue was purified by silica gel chromatography, using 0-20% MeOH-DCM as eluent, to afford methyl 3-(2-fluoro-4-morpholino-anilino)-5-(methylamino)-6-(3-methylimidazo[4,5-c]pyridin-7-yl) pyrazine-2-carboxylate (0.100 g, 80% yield) as a brown solid; 1H NMR (400 MHZ, DMSO-d6) δ 2.85 (3H, d), 3.01-3.21 (4H, m), 3.62-3.86 (7H, m), 4.01 (3H, s), 6.80 (1H, d), 6.89-7.03 (1H, m), 7.92 (1H, s), 8.36 (1H, t), 8.45-8.58 (2H, m), 9.04 (1H, s), 10.35 (1H, s). m/z: (ES−), [M−H]−=491.2

(c) 3-(2-Fluoro-4-morpholino-anilino)-5-(methylamino)-6-(3-methylimidazo[4,5-c]pyridin-7-yl)pyrazine-2-carboxamide 7 N Methanolic ammonia (8.0 mL, 56 mmol) was added to methyl 3-(2-fluoro-4-morpholino-anilino)-5-(methylamino)-6-(3-methylimidazo[4,5-c]pyridin-7-yl)pyrazine-2-carboxylate (80 mg, 0.16 mmol). The resulting suspension was stirred at 80° C. for 16 hours. The reaction was then concentrated. The resulting residue was purified by preparative HPLC, using a 5 micron, 30 mm×150 mm Xselect CSH OBD column, 15-35% MeCN/H2O as eluent, and 0.1% formic acid as modifier, to afford 3-(2-fluoro-4-morpholino-anilino)-5-(methylamino)-6-(3-methylimidazo[4,5-c]pyridin-7-yl)pyrazine-2-carboxamide (4.3 mg, 5.5%) as a yellow solid; 1H NMR (400 MHZ, DMSO-d6) δ 2.92 (3H, d), 3.06-3.13 (4H, m), 3.73 (4H, m), 4.01 (3H, s), 6.79 (1H, d), 6.93 (1H, dd), 7.31 (1H, s), 7.71 (1H, s), 8.00 (1H, br q), 8.44 (1H, t), 8.47 (1H, s), 8.73 (1H, s), 9.02 (1H, s), 11.37 (1H, s). m/z: (ES+), [M+H]+=478.2

Example 53

3-(2,3-Difluoro-4-morpholino-anilino)-5-(methylamino)-6-(3-methylimidazo[4,5-c]pyridin-7-yl)pyrazine-2-carboxamide

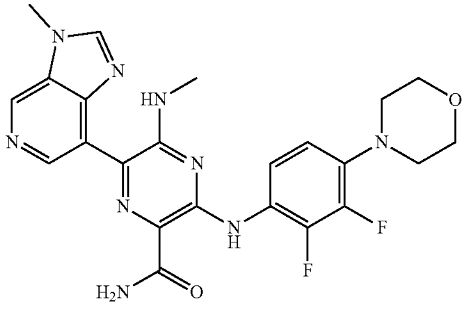 [SMILES: CNc1nc(Nc2ccc(N3CCOCC3)c(F)c2F)c(C(N)=O)nc1-c1cncc2c1ncn2C]

(a) 4-(4-Bromo-2,3-difluoro-phenyl) morpholine (rac)-BINAP (1.95 g, 3.14 mmol) and palladium (II) acetate (0.704 g, 3.14 mmol) were added to a mixture of 1-bromo-2,3-difluoro-4-iodo-benzene (1.00 g, 3.14 mmol), morpholine (0.273 g, 3.14 mmol), and cesium carbonate (1.02 g, 3.14 mmol) in toluene (15 mL) under nitrogen. The resulting mixture was stirred at 100° C. for 1 hour. The reaction was then concentrated. The resulting residue was purified by reverse phase C18 chromatography, using 0 to 60% MeCN-water as eluent, and 0.05% formic acid as modifier, to afford 4-(4-bromo-2,3-difluoro-phenyl) morpholine (300 mg, 34% yield) as a yellow solid. 1H NMR (400 MHZ, DMSO-d6) δ 2.94-3.04 (4H, m), 3.71-3.77 (4H, m), 6.95-6.99 (1H, m), 7.59-7.67 (1H, m). m/z: (ES+), [M+2+H]+=280.0

(b) Methyl 3-(2,3-difluoro-4-morpholino-anilino)-5-(methylamino)-6-(3-methylimidazo[4,5-c]pyridin-7-yl)pyrazine-2-carboxylate BrettPhos Pd G3 (289 mg, 0.320 mmol) was added to methyl 3-amino-5-(methylamino)-6-(3-methylimidazo[4,5-c]pyridin-7-yl)pyrazine-2-carboxylate (100 mg, 0.32 mmol), 4-(4-bromo-2,3-difluoro-phenyl) morpholine (89 mg, 0.32 mmol), and cesium carbonate (104 mg, 0.320 mmol) in 1,4-dioxane (15 mL) under nitrogen. The resulting mixture was stirred at 100° C. for 13 hours. The reaction was then concentrated. The resulting residue was purified by silica gel chromatography, using 0-10% MeOH-DCM as eluent, to afford methyl 3-(2,3-difluoro-4-morpholino-anilino)-5-(methylamino)-6-(3-methylimidazo[4,5-c]pyridin-7-yl)pyrazine-2-carboxylate (0.050 g, 31%) as a yellow solid; 1H NMR (400 MHZ, DMSO-d6) δ 2.88 (3H, d), 3.02 (4H, t), 3.76 (4H, t), 3.84 (3H, s), 4.01 (3H, s), 6.91 (1H, t), 7.94 (1H, s), 8.26 (1H, t), 8.51 (2H, d), 9.05 (1H, s), 10.50 (1H, s); m/z: (ES+), [M+H]+=511.2

(c) 3-(2,3-Difluoro-4-morpholino-anilino)-5-(methylamino)-6-(3-methylimidazo[4,5-c]pyridin-7-yl) pyrazine-2-carboxamide 7 N Methanolic ammonia (8.0 mL, 56 mmol) was added to methyl 3-(2,3-difluoro-4-morpholino-anilino)-5-(methylamino)-6-(3-methylimidazo[4,5-c]pyridin-7-yl)pyrazine-2-carboxylate (40 mg, 0.08 mmol). The resulting suspension was stirred at 80° C. for 19 hours. The reaction was then concentrated. The resulting residue was purified by preparative HPLC using a 5 micron, 19 mm×250 mm XSelect CSH Prep C18 OBD column, 30-40% MeCN—$H_2O$ as eluent, and 0.1% formic acid as modifier, to afford 3-(2,3-difluoro-4-morpholino-anilino)-5-(methylamino)-6-(3-methylimidazo[4,5-c]pyridin-7-yl)pyrazine-2-carboxamide (3.0 mg, 7.7%) as a yellow solid; 1H NMR (300 MHz, DMSO-d6) δ 2.99 (3H, d), 2.96-3.03 (4H, m), 3.72-3.80 (4H, m), 4.00 (3H, s), 6.85-7.93 (1H, m), 7.39 (1H, s), 7.76 (1H, s), 8.02 (1H, br q) 8.30-8.39 (1H, m), 8.50 (1H, s), 8.71 (1H, s), 9.02 (1H, s), 11.63 (1H, s); m/z: (ES+), [M+H]+=496.2

Example 54

3-(2-Fluoro-3-methyl-4-morpholino-anilino)-5-(methylamino)-6-(3-methylimidazo[4,5-c]pyridin-7-yl)pyrazine-2-carboxamide

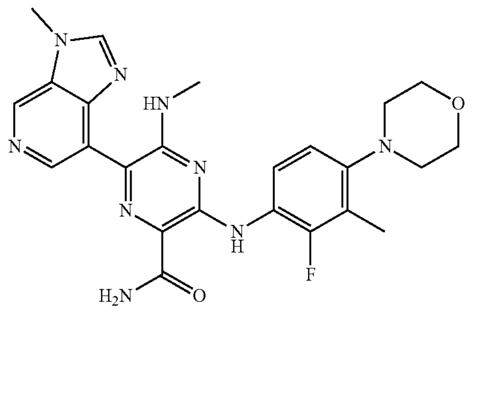 [SMILES: CNc1nc(Nc2ccc(N3CCOCC3)c(C)c2F)c(C(N)=O)nc1-c1cncc2c1ncn2C]

(a) 4-(4-Bromo-3-fluoro-2-methyl-phenyl) morpholine

Pd(OAc) 2 (0.071 g, 0.32 mmol) was added to a mixture of 1-bromo-2-fluoro-4-iodo-3-methyl-benzene (1.00 g, 3.18 mmol), morpholine (0.553 g, 6.35 mmol), rac-BINAP (0.198 g, 0.320 mmol), and potassium tert-butoxide (1.07 g, 9.53 mmol) in toluene (15 mL) under nitrogen. The resulting mixture was stirred at 100° C. for 2 hours. The reaction was then concentrated. The resulting residue was purified by silica gel chromatography, using 0-10% EtOH-DCM as eluent, to afford 4-(4-bromo-3-fluoro-2-methyl-phenyl) morpholine (0.300 g, 35%) as a brown solid; 1H NMR (400 MHZ, DMSO-d6) δ 2.19 (3H, dd), 2.80-2.87 (4H, m), 3.66-3.77 (4H, m), 6.84 (1H, dd), 7.46 (1H, t); m/z: (ES+), [M+H]+=274.

(b) Methyl 3-(2-fluoro-3-methyl-4-morpholino-anilino)-5-(methylamino)-6-(3-methylimidazo[4,5-c] pyridin-7-yl)pyrazine-2-carboxylate BrettPhos Pd G3 (376 mg, 0.410 mmol) was added to methyl 3-amino-5-(methylamino)-6-(3-methylimidazo[4,5-c]pyridin-7-yl)pyrazine-2-carboxylate (130 mg, 0.41 mmol), 4-(4-bromo-3-fluoro-2-methyl-phenyl) morpholine (114 mg, 0.410 mmol), and cesium carbonate (135 mg, 0.410 mmol) in 1,4-dioxane (15 mL) under nitrogen. The resulting mixture was stirred at 100° C. for 13 hours. The reaction was then concentrated. The resulting residue was purified by silica gel chromatography, using 0-10% MeOH-DCM as eluent, to afford methyl 3-(2-fluoro-3-methyl-4-morpholino-anilino)-5-(methylamino)-6-(3-methylimidazo [4,5-c]pyridin-7-yl)pyrazine-2-carboxylate (0.090 g, 43%) as a yellow solid; 1H NMR (300 MHz, DMSO-d6) δ 2.25 (3H, s), 2.82-2.88 (4H, m), 2.93 (3H, d), 3.73-3.77 (4H, m), 3.84 (3H, s), 4.02 (3H, s), 6.93 (1H, d), 7.84-8.04 (1H, m), 8.44-8.48 (1H, m), 8.50 (1H, s), 8.54 (1H, s), 9.06 (1H, s), 10.60 (1H, s); m/z: (ES+), [M+H]+=507.3

(c) 3-(2-Fluoro-3-methyl-4-morpholino-anilino)-5-(methylamino)-6-(3-methylimidazo[4,5-c]pyridin-7-yl)pyrazine-2-carboxamide 7 N Methanolic ammonia (8.0 mL, 56 mmol) was added to methyl 3-(2-fluoro-3-methyl-4-morpholino-anilino)-5-(methylamino)-6-(3-methylimidazo[4,5-c]pyridin-7-yl) pyrazine-2-carboxylate (50 mg, 0.10 mmol). The resulting mixture was stirred at 80° C. for 20 hours. The reaction was then concentrated. The resulting residue was purified by preparative HPLC using a 5 micron, 30×150 mm Sunfire prep C18 column, 20-30% MeCN—$H_2O$ as eluent, and 0.1% formic acid as modifier, to afford 3-(2-fluoro-3-methyl-4-morpholino-anilino)-5-(methylamino)-6-(3-methylimidazo[4,5-c]pyridin-7-yl)pyrazine-2-carboxamide (20 mg, 40%) as a yellow solid; 1H NMR (400 MHZ, DMSO-d6) δ 2.23 (3H, d), 2.83 (4H, t), 2.95 (3H, d), 3.74 (4H, t), 4.01 (3H, s), 6.90 (1H, d), 7.38 (1H, s), 7.75 (1H, s), 8.00 (1H, br q), 8.47-8.56 (2H, m), 8.73 (1H, s), 9.03 (1H, s), 11.62 (1H, d); m/z: (ES+), [M+H]+=492.2

Example 55

3-(3-Chloro-2-fluoro-4-morpholino-anilino)-5-(methylamino)-6-(3-methylimidazo[4,5-c]pyridin-7-yl)pyrazine-2-carboxamide

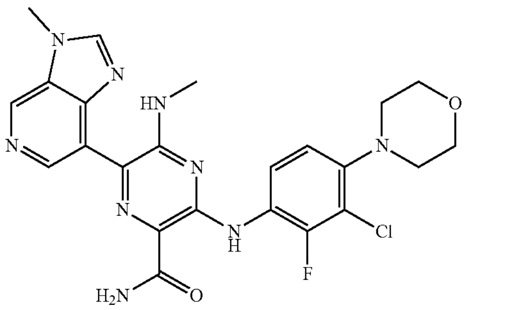 [SMILES: CNc1nc(Nc2ccc(N3CCOCC3)c(Cl)c2F)c(C(N)=O)nc1-c1cncc2c1ncn2C]

(a) Methyl 3-(3-chloro-2-fluoro-4-morpholino-anilino)-5-(methylamino)-6-(3-methylimidazo[4,5-c]pyridin-7-yl)pyrazine-2-carboxylate BrettPhos Pd G3 (29 mg, 0.030 mmol) was added to a suspension of methyl 3-amino-5-(methylamino)-6-(3-methylimidazo[4,5-c]pyridin-7-yl)pyrazine-2-carboxylate (100 mg, 0.32 mmol), 4-(4-bromo-2-chloro-3-fluoro-phenyl) morpholine (94 mg, 0.32 mmol), and cesium carbonate (312 mg, 0.960 mmol) in 1,4-dioxane (10 mL) under nitrogen. The resulting mixture was stirred at 100° C. for 12 hours. The reaction was then concentrated. The resulting residue was purified by silica gel chromatography, using 0-10% MeOH-DCM as eluent to afford methyl 3-(3-chloro-2-fluoro-4-morpholino-anilino)-5-(methylamino)-6-(3-methylimidazo[4,5-c]pyridin-7-yl)pyrazine-2-carboxylate (0.060 g, 36%) as a brown solid; 1H NMR (400 MHZ, DMSO-d6) δ 2.90 (3H, d), 2.99 (4H, t), 3.72-3.79 (4H, m), 3.84 (3H, s), 4.01 (3H, s), 7.06 (1H, dd), 7.97 (1H, br q), 8.44-8.56 (3H, m), 9.05 (1H, s), 10.56 (1H, d); m/z: (ES+), [M+H]+=527.2

(b) 3-(3-Chloro-2-fluoro-4-morpholino-anilino)-5-(methylamino)-6-(3-methylimidazo[4,5-c]pyridin-7-yl)pyrazine-2-carboxamide 7 N Methanolic ammonia (8.0 mL, 56 mmol) was added to methyl 3-(3-chloro-2-fluoro-4-morpholino-anilino)-5-(methylamino)-6-(3-methylimidazo[4,5-c]pyridin-7-yl) pyrazine-2-carboxylate (60 mg, 0.11 mmol). The resulting suspension was stirred at 80° C. for 18 hours. The reaction was then concentrated. The resulting residue was purified by preparative HPLC using a 5 micron, 30×150 mm, Xselect CSH OBD column, 22-38% MeCN—$H_2O$ as eluent, and 0.1% formic acid as a modifier, to afford 3-(3-chloro-2-fluoro-4-morpholino-anilino)-5-(methylamino)-6-(3-methylimidazo[4,5-c]pyridin-7-yl)pyrazine-2-carboxamide (34 mg, 58%) as a yellow solid; 1H NMR (300 MHz DMSO-d6) δ 2.91-3.03 (7H, m), 3.76 (4H, d), 4.02 (3H, s), 7.06 (1H, d), 7.45 (1H, s), 7.81 (1H, s), 8.02 (1H, br q), 8.53 (1H, s), 8.63 (1H, t), 8.73 (1H, s), 9.05 (1H, s), 11.74 (1H, d); m/z: (ES+), [M+H]+=512.2

Example 56

5-(Methylamino)-6-(3-methylimidazo[4,5-c]pyridin-7-yl)-3-(2,3,5-trifluoro-4-morpholino-anilino)pyrazine-2-carboxamide

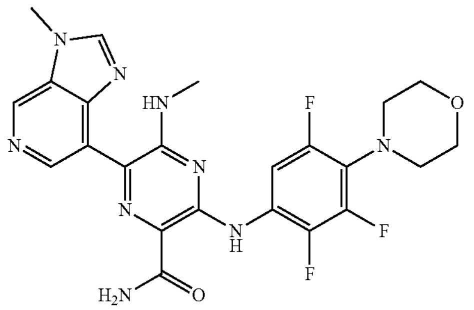 [SMILES: CNc1nc(Nc2cc(F)c(N3CCOCC3)c(F)c2F)c(C(N)=O)nc1-c1cncc2c1ncn2C]

(a) 4-(2,3,6-Trifluoro-4-nitro-phenyl) morpholine 1,2,3,4-Tetrafluoro-5-nitrobenzene (1.00 g, 5.13 mmol) was added to a solution of DIPEA (0.179 mL, 1.03 mmol), morpholine (0.0890 g, 1.03 mmol) in acetonitrile (10 mL). The resulting mixture was stirred at room temperature for 1 hour. The reaction was then concentrated. The resulting residue was purified by silica gel chromatography, using 0-5% DCM-(1:10 EtOAc/petroleum ether) as eluent, to afford 4-(2,3,6-trifluoro-4-nitro-phenyl) morpholine (0.200 g, 15%) as a yellow solid. 1H NMR (DMSO, 300 MHz) δ 3.36-3.43 (4H, m), 3.67-3.76 (4H, m), 7.91-8.03 (1H, m); m/z: (ES+), [M+H]+=263.1

(b) 2,3,5-Trifluoro-4-morpholinoaniline 4-(2,3,6-Trifluoro-4-nitro-phenyl) morpholine (100 mg, 0.38 mmol) was added to tin (II) chloride (289 mg, 1.53 mmol) in ethanol (10 mL). The resulting mixture was stirred at 60° C. for 2 hours. The reaction was then concentrated. The resulting residue was redissolved in ethyl acetate (100 mL) and washed three times with saturated aqueous sodium bicarbonate (100 mL each). The organic layer was dried over sodium sulfate, filtered, and concentrated to afford 2,3,5-trifluoro-4-morpholinoaniline (0.080 g, 90%) as a solid. 1H NMR (DMSO, 400 MHz) δ 2.88-3.00 (4H, m), 3.58-3.68 (4H, m), 5.54 (2H, s), 6.30-6.38 (1H, m); m/z: (ES+), [M+H]+=233.1

(c) 4-(4-Bromo-2,3,6-trifluorophenyl) morpholine 2,3,5-Trifluoro-4-morpholinoaniline (70 mg, 0.30 mmol) was added to a mixture of bromotrimethylsilane (0.059 mL, 0.45 mmol), tert-butyl nitrite (47 mg, 0.45 mmol) in dibromomethane (1.00 mL, 14.3 mmol) under nitrogen. The resulting mixture was stirred at 25 C for 16 hours. The reaction was then concentrated. The resulting residue was purified by silica gel chromatography, using 0-20% EtOAc-petroleum ether as eluent, to afford 4-(4-bromo-2,3,6-trifluorophenyl) morpholine (0.060 g, 67%) as a yellow solid. 1H NMR (DMSO, 300 MHz) δ 3.10-3.20 (4H, m), 3.64-3.75 (4H, m), 7.53-7.63 (1H, m); m/z: (ES+), [M+H]+=296.0

(d) Methyl 5-(methylamino)-6-(3-methylimidazo[4,5-c]pyridin-7-yl)-3-(2,3,5-trifluoro-4-morpholino-anilino)pyrazine-2-carboxylate 4-(4-Bromo-2,3,6-trifluorophenyl) morpholine (60 mg, 0.20 mmol) was added to a suspension of methyl 3-amino- 5-(methylamino)-6-(3-methylimidazo[4,5-c]pyridin-7-yl) pyrazine-2-carboxylate (64 mg, 0.20 mmol), cesium carbonate (198 mg, 0.610 mmol), and BrettPhos Pd G3 (18.4 mg, 0.0200 mmol) in 1,4-dioxane (10 mL) under nitrogen. The resulting mixture was stirred at 100° C. for 16 hours. The reaction was then concentrated. The resulting residue was purified by silica gel chromatography, using 0-10% MeOH-DCM as eluent, to afford methyl 5-(methylamino)-6-(3-methylimidazo[4,5-c]pyridin-7-yl)-3-(2,3,5-trifluoro-4-morpholino-anilino)pyrazine-2-carboxylate (0.060 g, 56%) as a yellow solid; 1H NMR (DMSO, 300 MHz) δ 2.93 (3H, d), 3.05-3.18 (4H, m), 3.66-3.74 (4H, s), 3.85 (3H, s), 4.03 (3H, s), 8.06 (1H, br q), 8.38-8.46 (1H, m), 8.49-8.57 (2H, m), 9.08 (1H, s), 10.78 (1H, s); m/z: (ES+), [M+H]+=529.3

(e) 5-(Methylamino)-6-(3-methylimidazo[4,5-c]pyridin-7-yl)-3-(2,3,5-trifluoro-4-morpholino-anilino)pyrazine-2-carboxamide 7 N Methanolic ammonia (10 mL, 70 mmol) was added to methyl 5-(methylamino)-6-(3-methylimidazo[4,5-c]pyridin-7-yl)-3-(2,3,5-trifluoro-4-morpholino-anilino)pyrazine-2-carboxylate (60 mg, 0.11 mmol). The resulting mixture was stirred at 80° C. for 24 hours. The reaction was then concentrated. The resulting residue was purified by preparative HPLC, using a 5 micron, 30 mm×150 mm, Xselect CSH OBD column, decreasingly polar mixtures of MeCN—$H_2O$ as eluent, and 0.1% formic acid as modifier, to afford 5-(methylamino)-6-(3-methylimidazo[4,5-c]pyridin-7-yl)-3-(2,3,5-trifluoro-4-morpholino-anilino)pyrazine-2-carboxamide (14 mg, 24%) as a yellow solid; 1H NMR (DMSO, 300 MHz) δ 2.96 (3H, d), 3.06-3.16 (4H, m), 3.66-3.76 (4H, m), 4.02 (3H, s), 7.50 (1H, s), 7.85 (1H, s), 8.10 (1H, br q), 8.42-8.52 (1H, m), 8.54 (1H, s), 8.73 (1H, s), 9.05 (1H, s), 11.99 (1H, s); m/z: (ES+), [M+H]+=514.4

Example 57

3-(2-Fluoro-5-methyl-4-morpholino-anilino)-5-(methylamino)-6-(3-methylimidazo[4,5-c]pyridin-7-yl)pyrazine-2-carboxamide

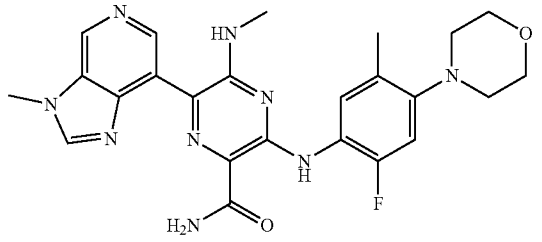 [SMILES: CNc1nc(Nc2cc(C)c(N3CCOCC3)cc2F)c(C(N)=O)nc1-c1cncc2c1ncn2C]

(a) 4-(4-Bromo-5-fluoro-2-methyl-phenyl) morpholine

1-Bromo-2-fluoro-4-iodo-5-methyl-benzene (500 mg, 1.59 mmol) was added to a mixture of morpholine (138 mg, 1.59 mmol), cesium carbonate (1.55 g, 4.76 mmol) and Xantphos Pd G3 (151 mg, 0.16 mmol) in 1,4-dioxane (10 mL) under nitrogen. The resulting mixture was stirred at 100° C. for 16 hours. The reaction was then concentrated. The resulting residue was purified by preparative HPLC, using a 5 micron, 30 mm×100 mm, XBridge Prep C18 OBD column, decreasingly polar mixtures of MeCN—$H_2O$ as eluent, and 0.1% ammonium bicarbonate as modifier, to afford 4-(4-bromo-5-fluoro-2-methyl-phenyl) morpholine (0.160 g, 37%) as a red solid; 1H NMR (DMSO, 300 MHZ) δ 2.22 (3H, s), 2.79-2.88 (4H, m), 3.68-3.78 (4H, m), 7.01 (1H, d), 7.48 (1H, d); m/z: (ES+), [M+H]+=274.0

(b) Methyl 3-(2-fluoro-5-methyl-4-morpholino-anilino)-5-(methylamino)-6-(3-methylimidazo[4,5-c]pyridin-7-yl)pyrazine-2-carboxylate 4-(4-Bromo-5-fluoro-2-methylphenyl) morpholine (150 mg, 0.55 mmol) was added to methyl 3-amino-6-(3-methyl-3H-imidazo[4,5-c]pyridin-7-yl)-5-(methylamino) pyrazine-2-carboxylate (171 mg, 0.550 mmol), cesium carbonate (535 mg, 1.64 mmol) and BrettPhos Pd G3 (50 mg, 0.05 mmol) in 1,4-dioxane (1 mL) under nitrogen. The resulting mixture was stirred at 100° C. for 3 hours. The reaction was then concentrated. The resulting residue was purified by silica gel chromatography, using 0-10% MeOH-DCM as eluent, to afford methyl 3-(2-fluoro-5-methyl-4-morpholino-anilino)-5-(methylamino)-6-(3-methylimidazo[4,5-c]pyridin-7-yl) pyrazine-2-carboxylate (0.150 g, 54%) as a yellow solid; 1H NMR (DMSO, 300 MHZ) δ 2.27 (3H, s), 2.79-2.87 (4H, m), 2.94 (3H, d), 3.69-3.78 (4H, m), 3.84 (3H, s), 4.02 (3H, s), 7.03 (1H, d), 8.01 (1H, br q), 8.44-8.58 (3H, m), 9.05 (1H, s), 10.50 (1H, d); m/z: (ES+), [M+H]+=507.3

(c) 3-(2-Fluoro-5-methyl-4-morpholino-anilino)-5-(methylamino)-6 (3-methylimidazo[4,5-c]pyridin-7-yl)pyrazine-2-carboxamide 7 N Methanolic ammonia (10 mL, 70 mmol) was added to methyl 3-(2-fluoro-5-methyl-4-morpholino-anilino)-5-(methylamino)-6-(3-methylimidazo[4,5-c]pyridin-7-yl) pyrazine-2-carboxylate (100 mg, 0.20 mmol). The resulting mixture was stirred at 80° C. for 16 hours. The reaction was then concentrated. The resulting residue was purified by preparative HPLC, using a 5 micron, 30 mm×150 mm, Sunfire prep C18 column, decreasingly polar mixtures of MeCN—$H_2O$ as eluent, and 0.1% formic acid as modifier, to afford 3-(2-fluoro-5-methyl-4-morpholino-anilino)-5-(methylamino)-6-(3-methylimidazo[4,5-c]pyridin-7-yl) pyrazine-2-carboxamide (21 mg, 22%) as a yellow solid; 1H NMR (DMSO, 300 MHZ) δ 2.27 (3H, s), 2.78-2.86 (4H, m), 2.98 (3H, d), 3.70-3.79 (4H, m), 4.02 (3H, s), 7.01 (1H, d), 7.36 (1H, s), 7.76 (1H, s), 8.07 (1H, br q), 8.53 (1H, s), 8.61 (1H, d), 8.74 (1H, s), 9.03 (1H, s), 11.52 (1H, d); m/z: (ES+), [M+H]+=492.2

Example 58

3-(3,5-Difluoro-4-morpholino-anilino)-5-(methylamino)-6-(3-methylimidazo[4,5-c]pyridin-7-yl)pyrazine-2-carboxamide

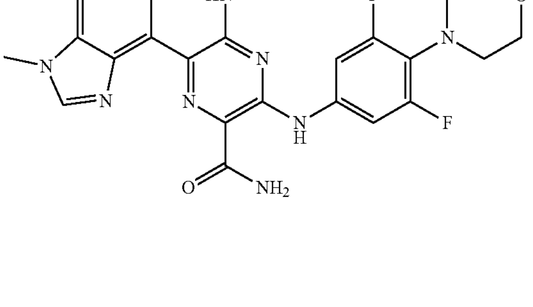

(a) Methyl 3-(3,5-difluoro-4-morpholino-anilino)-5-(methylamino)-6-(3-methylimidazo[4,5-c]pyridin-7-yl)pyrazine-2-carboxylate BrettPhos Pd G3 (23 mg, 0.030 mmol) was added to methyl 3-amino-5-(methylamino)-6-(3-methylimidazo[4,5-c]pyridin-7-yl)pyrazine-2-carboxylate (80 mg, 0.26 mmol), 4-(4-bromo-2,6-difluoro-phenyl) morpholine (142 mg, 0.51 mmol), and cesium carbonate (250 mg, 0.77 mmol) in 1,4-dioxane (10 mL) under nitrogen. The resulting mixture was stirred at 100° C. for 3 hours. The reaction was then concentrated. The resulting residue was purified by silica gel chromatography, using 0-10% MeOH-DCM as eluent, to afford methyl 3-(3,5-difluoro-4-morpholino-anilino)-5-(methylamino)-6-(3-methylimidazo[4,5-c]pyridin-7-yl) pyrazine-2-carboxylate (0.060 g, 46%) as a yellow solid; 1H NMR (300 MHz, DMSO-d6) δ 2.93 (3H, d), 3.08 (4H, t), 3.70 (4H, t), 3.84 (3H, s), 4.03 (3H, s), 7.65 (2H, d), 8.01 (1H, br q), 8.55 (2H, s), 9.10 (1H, s), 10.49 (1H, s); m/z: (ES+), [M+H]+=511.3

(b) 3-(3,5-Difluoro-4-morpholino-anilino)-5-(methylamino)-6-(3-methylimidazo[4,5-c]pyridin-7-yl) pyrazine-2-carboxamide 7 N Methanolic ammonia (1.50 mL, 10.5 mmol) was added to methyl 3-(3,5-difluoro-4-morpholino-anilino)-5-(methylamino)-6-(3-methylimidazo[4,5-c]pyridin-7-yl) pyrazine-2-carboxylate (55 mg, 0.11 mmol). The resulting suspension was stirred at 80° C. for 3 hours. The reaction was then concentrated. The resulting residue was purified by preparative HPLC, using a 5 micron, 30 mm×150 mm Sunfire prep C18 column, 20-32% MeCN—$H_2O$ as eluent, and 0.1% formic acid as modifier, to afford 3-(3,5-difluoro-4-morpholino-anilino)-5-(methylamino)-6-(3-methylimidazo[4,5-c]pyridin-7-yl)pyrazine-2-carboxamide (14 mg, 26%) as a yellow solid; 1H NMR (300 MHz, DMSO-d6) δ 2.96 (3H, d), 3.07 (4H, m), 3.69 (4H, m), 4.02 (3H, s), 7.46 (1H, s), 7.58 (1H, s), 7.59 (1H, s) 7.81 (1H, s), 8.07 (1H, br q), 8.53 (1H, s), 8.73 (1H, s), 9.04 (1H, s), 11.69 (1H, s); m/z: (ES+), [M+H]+=496.2

Example 59

3-(3-Chloro-4-morpholino-anilino)-5-(methylamino)-6-(1-methylbenzimidazol-4-yl)pyrazine-2-carboxamide

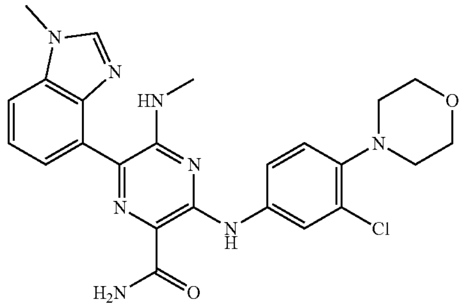 [SMILES: CNc1nc(Nc2ccc(N3CCOCC3)c(Cl)c2)c(C(N)=O)nc1-c1cccc2c1ncn2C]

N-Chlorosuccinimide (66 mg, 0.49 mmol) was added to a suspension of methyl 3-(3-chloro-4-morpholino-anilino)-5-(methylamino)-6-(1-methylbenzimidazol-4-yl)pyrazine-2-carboxylate (150 mg, 0.33 mmol) in MeCN (2 mL). The reaction was stirred at 82° C. for 20 hours. The reaction was then concentrated. The resulting residue was purified by silica gel chromatography, using 0-5% MeOH-DCM as eluent and 0-0.5% ammonia as modifier, to afford a yellow solid. This solid was dissolved in DCM (20 mL) and washed three times with saturated aqueous sodium bicarbonate (10 mL each). The organic layer was then dried over magnesium sulfate, filtered, and concentrated to afford 3-(3-chloro-4-morpholino-anilino)-5-(methylamino)-6-(1-methylbenzimidazol-4-yl)pyrazine-2-carboxamide (57 mg, 35%) as a yellow solid; 1H NMR (500 MHz, DMSO-d6) 2.89-2.95 (4H, m), 2.96 (3H, d), 3.65-3.80 (4H, m), 3.90 (3H, s), 7.15 (1H, d), 7.34-7.43 (2H, m), 7.46 (1H, dd), 7.58-7.71 (3H, m), 8.18-8.29 (2H, m), 8.34 (1H, s), 11.46 (1H, s; m/z: (ES+), [M+H]+=493.4

Example 60

3-(3-Chloro-4-morpholino-anilino)-5-(methylamino)-6-(3-methylimidazo[4,5-c]pyridin-7-yl)pyrazine-2-carboxamide

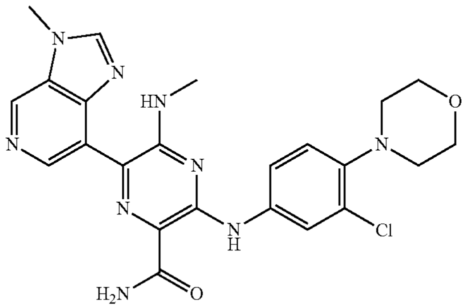 [SMILES: CNc1nc(Nc2ccc(N3CCOCC3)c(Cl)c2)c(C(N)=O)nc1-c1cncc2c1ncn2C]

Acetonitrile (2 mL) was added to a mixture of 5-(methylamino)-6-(3-methylimidazo[4,5-c]pyridin-7-yl)-3-(4-morpholinoanilino)pyrazine-2-carboxamide (42 mg, 0.090 mmol) and N-chlorosuccinimide (34 mg, 0.25 mmol). The resulting suspension was stirred at 80° C. for 16 hours. The reaction was then concentrated. The resulting orange-brown solid was taken up in 3:1 chloroform/IPA (20 mL) and washed three times with saturated aqueous sodium bicarbonate (20 mL each). The organic layer was dried over sodium sulfate, filtered, and loaded onto celite, then purified by silica gel chromatography, using 0-10% MeOH-DCM as eluent and 0-1% ammonia as modifier, to afford 3-(3-chloro-4-morpholino-anilino)-5-(methylamino)-6-(3-methylimidazo[4,5-c]pyridin-7-yl)pyrazine-2-carboxamide (14 mg, 31%) as a yellow solid; 1H NMR (500 MHZ, DMSO-d6) 2.89-2.99 (7H, m), 3.70-3.78 (4H, m), 4.00 (3H, s), 7.16 (1H, d), 7.39 (1H, br s), 7.47 (1H, dd), 7.76 (1H, br s), 8.00-8.13 (1H, m), 8.25 (1H, d), 8.51 (1H, s), 8.72 (1H, s), 9.01 (1H, s), 11.52 (1H, s); m/z: (ES+), [M+H]+=494.5

Example 61

5-(Methylamino)-6-(3-methylimidazo[4,5-c]pyridin-7-yl)-3-(3-methyl-4-morpholino-anilino)pyrazine-2-carboxamide

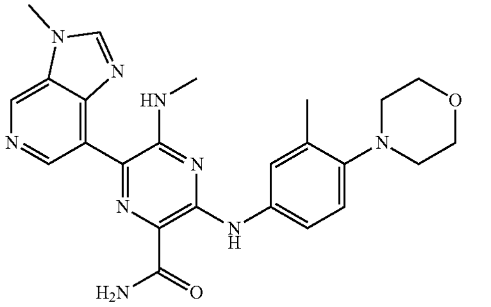 [SMILES: CNc1nc(Nc2ccc(N3CCOCC3)c(C)c2)c(C(N)=O)nc1-c1cncc2c1ncn2C]

(a) Methyl 5-(methylamino)-6-(3-methylimidazo[4,5-c]pyridin-7-yl)-3-(3-methyl-4-morpholino-anilino) pyrazine-2-carboxylate BrettPhos Pd G3 (23 mg, 0.030 mmol) was added to 4-(4-bromo-2-methyl-phenyl) morpholine (131 mg, 0.510 mmol), methyl 3-amino-5-(methylamino)-6-(3-methylimidazo[4,5-c]pyridin-7-yl)pyrazine-2-carboxylate (80 mg, 0.26 mmol), and cesium carbonate (250 mg, 0.77 mmol) in 1,4-dioxane (2 mL) under nitrogen. The resulting mixture was stirred at 100° C. for 3 hours. The reaction was then concentrated. The resulting residue was purified by silica gel chromatography, using 0-10% MeOH-DCM as eluent, to afford methyl 5-(methylamino)-6-(3-methylimidazo[4,5-c]pyridin-7-yl)-3-(3-methyl-4-morpholino-anilino)pyrazine-2-carboxylate (0.030 g, 24%) as a yellow solid; 1H NMR (300 MHz, DMSO-d6) δ 2.30 (3H, s), 2.83 (4H, t), 2.94 (3H, d), 3.70-3.78 (4H, m), 3.83 (3H, s), 4.02 (3H, s), 7.05 (1H, d), 7.59-7.73 (2H, m), 7.94 (1H, br q), 8.51 (1H, s), 8.54 (1H, s), 9.05 (1H, s), 10.36 (1H, s); m/z: (ES+), [M+H]+=489.3

(b) 5-(Methylamino)-6-(3-methylimidazo[4,5-c]pyridin-7-yl)-3-(3-methyl-4-morpholino-anilino) pyrazine-2-carboxamide 7 N Methanolic ammonia (1.0 mL, 7.0 mmol) was added to methyl 5-(methylamino)-6-(3-methylimidazo[4,5-c]pyridin-7-yl)-3-(3-methyl-4-morpholino-anilino)pyrazine-2-carboxylate (35 mg, 0.07 mmol). The resulting suspension was stirred at 80° C. for 24 hours. The reaction was then concentrated. The resulting residue was purified by preparative HPLC, using a 5 micron, 30 mm×150 mm Xselect CSH OBD column, 8-38% MeCN—$H_2O$ as eluent, and 0.1% formic acid as modifier, to afford 5-(methylamino)-6-(3-methylimidazo[4,5-c]pyridin-7-yl)-3-(3-methyl-4-morpholino-anilino)pyrazine-2-carboxamide (12 mg, 35%) as a yellow solid; 1H NMR (300 MHz, DMSO-d6) δ 2.29 (3H, s), 2.82 (4H, t), 2.97 (3H, d), 3.74 (4H, t), 4.02 (3H, s), 7.04 (1H, d), 7.35 (1H, s), 7.59-7.68 (2H, m) 7.74 (1H, s), 8.02 (1H, br q), 8.53 (1H, s), 8.74 (1H, s), 9.02 (1H, s), 11.39 (1H, s); m/z: (ES+), [M+H]+=474.3

Example 62

3-(3,5-Dimethyl-4-morpholino-anilino)-5-(methylamino)-6-(3-methylimidazo[4,5-c]pyridin-7-yl)pyrazine-2-carboxamide

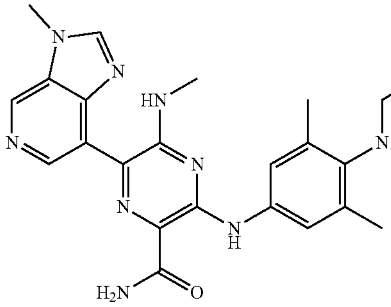

(a) Methyl 3-(3,5-dimethyl-4-morpholino-anilino)-5-(methylamino)-6-(3-methylimidazo[4,5-c]pyridin-7-yl)pyrazine-2-carboxylate BrettPhos Pd G3 (29 mg, 0.030 mmol) was added to a suspension of cesium carbonate (312 mg, 0.960 mmol), methyl 3-amino-5-(methylamino)-6-(3-methylimidazo[4,5-c]pyridin-7-yl)pyrazine-2-carboxylate (100 mg, 0.32 mmol) and 4-(4-bromo-2,6-dimethyl-phenyl) morpholine (172 mg, 0.640 mmol) in 1,4-dioxane (1.5 mL) under nitrogen. The resulting mixture was stirred at 100° C. for 10 hours. The reaction was then concentrated. The resulting residue was purified by silica gel chromatography, using 0-10% MeOH-DCM as eluent, to afford methyl 3-(3,5-dimethyl-4-morpholino-anilino)-5-(methylamino)-6-(3-methylimidazo[4,5-c]pyridin-7-yl)pyrazine-2-carboxylate (0.080 g, 50%) as a yellow solid; 1H NMR (300 MHz, DMSO-d6) δ 2.32 (6H, s), 2.95 (3H, d), 3.01 (4H, t), 3.64-3.74 (4H, t), 3.83 (3H, s), 4.02 (3H, s), 7.52 (2H, s), 7.97 (1H, br q), 8.50 (1H, s), 8.54 (1H, s), 9.05 (1H, s), 10.35 (1H, s); m/z: (ES+), [M+H]+=503.3

(b) 3-(3,5-Dimethyl-4-morpholino-anilino)-5-(methylamino)-6-(3-methylimidazo[4,5-c]pyridin-7-yl) pyrazine-2-carboxamide 7 N Methanolic ammonia (10 mL, 70 mmol) was added to methyl 3-(3,5-dimethyl-4-morpholino-anilino)-5-(methylamino)-6-(3-methylimidazo[4,5-c]pyridin-7-yl)pyrazine-2-carboxylate (75 mg, 0.15 mmol). The resulting suspension was stirred at 80° C. for 16 hours. The reaction was then concentrated. The resulting residue was purified by preparative HPLC, using a 5 micron, 30 mm×150 mm, Xselect CSH OBD column, 25-40% MeCN—$H_2O$ as eluent, and 0.1% formic acid as modifier, to afford 3-(3,5-dimethyl-4-morpholino-anilino)-5-(methylamino)-6-(3-methylimidazo[4,5-c]pyridin-7-yl)pyrazine-2-carboxamide (36 mg, 48%) as a yellow solid; 1H NMR (300 MHz, DMSO-d6) δ 2.32 (6H, s), 3.00 (7H, m), 3.69 (4H, t), 4.02 (3H, s), 7.37 (1H, s), 7.49 (2H, s), 7.75 (1H, s), 8.03 (1H, br q), 8.53 (1H, s), 8.73 (1H, s), 9.03 (1H, s), 11.38 (1H, s); m/z: (ES+), [M+H]+=488.2

Example 63

3-(3-Cyano-4-morpholino-anilino)-5-(methylamino)-6-(3-methylimidazo[4,5-c]pyridin-7-yl)pyrazine-2-carboxamide

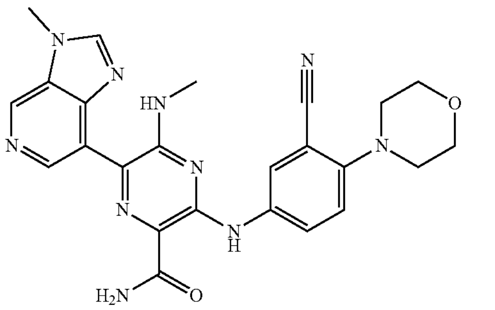 [SMILES: CNc1nc(Nc2ccc(N3CCOCC3)c(C#N)c2)c(C(N)=O)nc1-c1cncc2c1ncn2C]

(a) Methyl 3-(3-cyano-4-morpholino-anilino)-5-(methylamino)-6-(3-methylimidazo[4,5-c]pyridin-7-yl)pyrazine-2-carboxylate BrettPhos Pd G3 (22 mg, 0.020 mmol) was added to 5-bromo-2-morpholino-benzonitrile (128 mg, 0.480 mmol), methyl 3-amino-5-(methylamino)-6-(3-methylimidazo[4,5-c]pyridin-7-yl)pyrazine-2-carboxylate (75 mg, 0.24 mmol), and cesium carbonate (234 mg, 0.720 mmol) in 1,4-dioxane (10 mL) under nitrogen. The resulting mixture was stirred at 100° C. for 3 hours. The reaction was then concentrated. The resulting residue was purified by silica gel chromatography, using 0-10% MeOH-DCM as eluent, to afford methyl 3-(3-cyano-4-morpholino-anilino)-5-(methylamino)-6-(3-methylimidazo[4,5-c]pyridin-7-yl)pyrazine-2-carboxylate (0.060 g, 50%) as a yellow solid; 1H NMR (DMSO, 300 MHz) δ 2.92 (3H, d), 3.11 (4H, t), 3.78 (4H, t), 3.84 (3H, s), 4.02 (3H, s), 7.22 (1H, d), 7.90 (1H, d), 8.01 (1H, br q), 8.42 (1H, d), 8.49-8.54 (1H, m), 8.55 (1H, s), 9.07 (1H, d), 10.40 (1H, s); m/z: (ES+), [M+H]+=500.2

(b) 3-(3-Cyano-4-morpholino-anilino)-5-(methylamino)-6-(3-methylimidazo[4,5-c]pyridin-7-yl)pyrazine-2-carboxamide 7 N Methanolic ammonia (1.0 mL, 7.0 mmol) was added to methyl 3-(3-cyano-4-morpholino-anilino)-5-(methylamino)-6-(3-methylimidazo[4,5-c]pyridin-7-yl)pyrazine-2-carboxylate (55 mg, 0.11 mmol). The resulting suspension was stirred at 80° C. for 24 hours. The reaction was then concentrated. The resulting residue was purified by preparative HPLC, using a 5 micron, 30 mm×150 mm Sunfire prep C18 column, 17-30% MeCN—$H_2O$ as eluent, and 0.1% formic acid as modifier, to afford 3-(3-cyano-4-morpholino-anilino)-5-(methylamino)-6-(3-methylimidazo[4,5-c]pyridin-7-yl)pyrazine-2-carboxamide (28 mg, 53%) as a yellow solid; 1H NMR (300 MHz, DMSO-d6) δ 2.96 (3H, d), 3.04-3.11 (4H, m), 3.73-3.80 (4H, m), 4.02 (3H, s), 7.21 (1H, d), 7.43 (1H, s), 7.80 (1H, s), 7.83 (1H, d), 8.10 (1H, br q), 8.45 (1H, d), 8.53 (1H, s), 8.74 (1H, s), 9.04 (1H, s), 11.57 (1H, s); m/z: (ES+), [M+H]+=485.1

Example 64

3-(3-Methoxy-4-morpholino-anilino)-5-(methylamino)-6-(3-methylimidazo[4,5-c]pyridin-7-yl)pyrazine-2-carboxamide

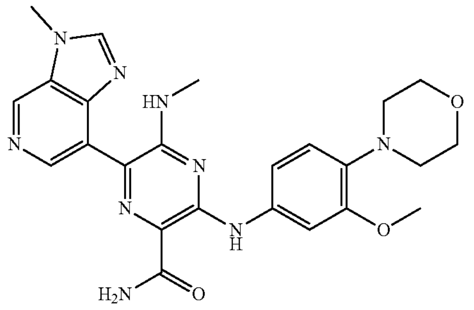 [SMILES: CNc1nc(Nc2ccc(N3CCOCC3)c(OC)c2)c(C(N)=O)nc1-c1cncc2c1ncn2C]

(a) 4-(4-Bromo-2-methoxy-phenyl) morpholine

4-Bromo-1-iodo-2-methoxy-benzene (120 mg, 0.38 mmol) was added to a mixture of morpholine (50 mg, 0.58 mmol), Xantphos Pd G3 (36 mg, 0.040 mmol), and cesium carbonate (375 mg, 1.15 mmol) in 1,4-dioxane (10 mL) under nitrogen. The resulting mixture was stirred at 100° C. for 16 hours. The reaction was then concentrated. The resulting residue was purified by preparative HPLC, using a 5 micron, 30 mm×100 mm, XBridge Prep C18 OBD column, decreasingly polar mixtures of MeCN—$H_2O$ as eluent, and 0.1% ammonium bicarbonate as modifier, to afford 4-(4-bromo-2-methoxy-phenyl) morpholine (0.080 g, 77%) as a yellow solid. 1H NMR (DMSO, 300 MHz) δ 2.90-2.98 (4H, m), 3.66-3.75 (4H, m), 3.80 (3H, s), 6.82 (1H, d), 7.02-7.10 (2H, m); m/z: (ES+), [M+H]+=272.0

(b) Methyl 3-(3-methoxy-4-morpholino-anilino)-5-(methylamino)-6-(3-methylimidazo[45-c]pyridin-7-yl)pyrazine-2-carboxylate BrettPhos Pd G3 (40 mg, 0.04 mmol) was added to a suspension of cesium carbonate (431 mg, 1.32 mmol), 4-(4-bromo-2-methoxy-phenyl) morpholine (120 mg, 0.44 mmol) and methyl 3-amino-5-(methylamino)-6-(3-methylimidazo[4,5-c]pyridin-7-yl)pyrazine-2-carboxylate (138 mg, 0.440 mmol) in 1,4-dioxane (11 mL) under nitrogen. The resulting mixture was stirred at 100° C. for 16 hours. The reaction was then concentrated. The resulting residue was purified by silica gel chromatography, using 0-10% MeOH-DCM as eluent, to afford methyl 3-(3-methoxy-4-morpholino-anilino)-5-(methylamino)-6-(3-methylimidazo[4,5-c]pyridin-7-yl)pyrazine-2-carboxylate (0.100 g, 45%) as a yellow solid. 1H NMR (DMSO, 300 MHz) δ 2.90-3.00 (7H, m), 3.67-3.77 (4H, m), 3.83 (3H, s), 3.84 (3H, s), 4.02 (3H, s), 6.89 (1H, d), 7.16-7.24 (1H, m), 7.63 (1H, d), 7.92 (1H, br q), 8.49 (1H, s), 8.53 (1H, s), 9.04 (1H, s), 10.43 (1H, s); m/z: (ES+), [M+H]+=505.3

(c) 3-(3-Methoxy-4-morpholino-anilino)-5-(methylamino)-6-(3-methylimidazo[4,5-c]pyridin-7-yl)pyrazine-2-carboxamide 7 N Methanolic ammonia (1.0 mL, 7.0 mmol) was added to methyl 3-(3-methoxy-4-morpholino-anilino)-5-(methylamino)-6-(3-methylimidazo[4,5-c]pyridin-7-yl)pyrazine-2-carboxylate (80 mg, 0.16 mmol). The resulting mixture was stirred at 80° C. for 16 hours. The reaction was then concentrated. The resulting residue was purified by preparative HPLC, using a 5 micron, 30 mm×150 mm, Xselect CSH OBD column, decreasingly polar mixtures of MeCN—$H_2O$ as eluent, and 0.1% formic acid as modifier, to afford 3-(3-methoxy-4-morpholino-anilino)-5-(methylamino)-6-(3-methylimidazo[4,5-c]pyridin-7-yl)pyrazine-2-carboxamide (25 mg, 31%) as a yellow solid; 1H NMR (DMSO, 400 MHZ) δ 2.88-2.94 (4H, m), 2.97 (3H, d), 3.68-3.74 (4H, m), 3.83 (3H, s), 4.00 (3H, s), 6.87 (1H, d), 7.08-7.14 (1H, m), 7.32 (1H, s), 7.65 (1H, d), 7.72

Example 65

3-[3-(Difluoromethyl)-4-morpholino-anilino]-5-(methylamino)-6-(3-methylimidazo[4,5-c]pyridin-7-yl)pyrazine-2-carboxamide

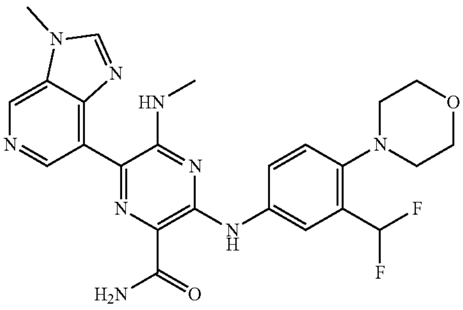 [SMILES: CNc1nc(Nc2ccc(N3CCOCC3)c(C(F)F)c2)c(C(N)=O)nc1-c1cncc2c1ncn2C]

(a) 4-Bromo-2-(difluoromethyl)-1-iodo-benzene

2-Methoxy-N-(2-methoxyethyl)-N-(trifluoro-24-sulfanyl) ethanamine (712 μL, 3.86 mmol) was added to a solution of 5-bromo-2-iodo-benzaldehyde (600 mg, 1.93 mmol) in DCM (10 mL) under nitrogen. The resulting mixture was stirred at 25 C for 16 hours. The reaction was then diluted with DCM (200 mL) and washed sequentially with saturated aqueous sodium bicarbonate (100 mL) and brine (50 mL). The organic layer was dried over $Na_2SO_4$, filtered, and concentrated. The resulting residue was purified by silica gel chromatography, using 0-20% EtOAc-petroleum ether as eluent, to afford 4-bromo-2-(difluoromethyl)-1-iodo-benzene (0.400 g, 62%) as a colorless oil; 1H NMR (400 MHZ, $CDCl_3$) δ 6.72 (1H, t), 7.30-7.37 (1H, m), 7.71-7.78 (2H, m); poor ionization by LCMS (b) 4-[4-Bromo-2-(difluoromethyl)phenyl]morpholine Pd(OAc) 2 (27.6 mg, 0.12 mmol) was added to morpholine (129 μl, 1.48 mmol), 4-bromo-2-(difluoromethyl)-1-iodobenzene (410 mg, 1.23 mmol), Cesium carbonate (1.20 g, 3.69 mmol), and rac-BINAP (77 mg, 0.12 mmol) in 1,4-dioxane (16 mL) under nitrogen. The resulting mixture was stirred at 100° C. for 16 hours. The reaction was then concentrated. The resulting residue was purified by silica gel chromatography, using 0-10% MeOH-DCM as eluent, to afford 4-[4-bromo-2-(difluoromethyl)phenyl]morpholine (0.160 g, 45%) as a yellow oil; 1H NMR (300 MHz, $CDCl_3$) δ 2.90-2.99 (4H, m), 3.82-3.91 (4H, m), 6.79-7.24 (2H, m), 7.55-7.64 (1H, m), 7.79 (1H, d).

(c) Methyl 3-[3-(difluoromethyl)-4-morpholino-anilino]-5-(methylamino)-6-(3-methylimidazo[4,5-c]pyridin-7-yl)pyrazine-2-carboxylate BrettPhos Pd G3 (32 mg, 0.040 mmol) was added to a suspension of 4-[4-bromo-2-(difluoromethyl)phenyl]morpholine (154 mg, 0.530 mmol), methyl 3-amino-5-(methylamino)-6-(3-methylimidazo[4,5-c]pyridin-7-yl)pyrazine-2-carboxylate (110 mg, 0.35 mmol), and cesium carbonate (343 mg, 1.05 mmol) in 1,4-dioxane (20 mL) under nitrogen. The resulting mixture was stirred at 100° C. for 4 hours. The reaction was then filtered and the filtrate was concentrated. The resulting residue was purified by silica gel chromatography, using 0-20% MeOH-DCM as eluent, to afford methyl 3-[3-(difluoromethyl)-4-morpholino-anilino]-5-(methylamino)-6-(3-methylimidazo[4,5-c]pyridin-7-yl) pyrazine-2-carboxylate (0.100 g, 54% yield) as a yellow solid. 1H NMR (300 MHz, DMSO-d6) δ 2.82-2.91 (4H, m), 2.94 (3H, d), 3.71-3.80 (4H, m), 3.85 (3H, s), 4.02 (3H, s), 7.26 (1H, t), 7.38 (1H, d), 7.61-7.71 (1H, m), 7.92-8.06 (1H, m), 8.50 (1H, s), 8.51 (1H, s), 8.54 (1H, s), 9.05 (1H, s), 10.51 (1H, s). m/z: (ES+), [M+H]+=525.1

(d) 3-[3-(Difluoromethyl)-4-morpholino-anilino]-5-(methylamino)-6-(3-methylimidazo[4,5-c]pyridin-7-yl)pyrazine-2-carboxamide 7 N Methanolic ammonia (12 mL, 84 mmol) was added to methyl 3-[3-(difluoromethyl)-4-morpholino-anilino]-5-(methylamino)-6-(3-methylimidazo[4,5-c]pyridin-7-yl) pyrazine-2-carboxylate (90 mg, 0.17 mmol). The resulting mixture was stirred at 80° C. for 16 hours. The reaction was then concentrated. The resulting residue was purified by preparative HPLC using a 5 micron, 30×150 mm Xselect CSH OBD column, 25-35% MeCN—$H_2O$ as eluent, and 0.1% formic acid as modifier, to afford 3-[3-(difluoromethyl)-4-morpholino-anilino]-5-(methylamino)-6-(3-methylimidazo[4,5-c]pyridin-7-yl)pyrazine-2-carboxamide (22 mg, 25%) as a yellow solid; 1H NMR (300 MHz, DMSO-d6) δ 2.81-2.90 (4H, m), 2.97 (3H, d), 3.71-3.80 (4H, m), 4.02 (3H, s), 7.04-7.39 (2H, m), 7.43 (1H, d), 7.56-7.66 (1H, m), 7.79 (1H, s), 8.01-8.12 (1H, m), 8.50 (1H, d), 8.53 (1H, s), 8.74 (1H, s), 9.03 (1H, s), 11.62 (1H, s); m/z: (ES+), [M+H]+=510.2

Example 66

5-(Methylamino)-6-(3-methylimidazo[4,5-c]pyridin-7-yl)-3-(2-methyl-4-morpholino-anilino)pyrazine-2-carboxamide

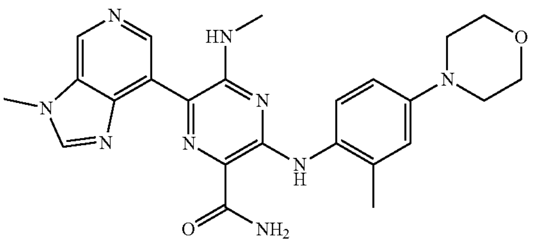 [SMILES: CNc1nc(Nc2ccc(N3CCOCC3)cc2C)c(C(N)=O)nc1-c1cncc2c1ncn2C]

(a) Methyl 5_(methylamino)-6-(3-methylimidazo[4,5-c]pyridin-7-yl)-3-(2-methyl-4-morpholino-anilino)pyrazine-2-carboxylate BrettPhos Pd G3 (58 mg, 0.060 mmol) was added to a suspension of methyl 3-amino-5-(methylamino)-6-(3-methylimidazo[4,5-c]pyridin-7-yl)pyrazine-2-carboxylate (200 mg, 0.64 mmol), 4-(4-bromo-3-methyl-phenyl) morpholine (327 mg, 1.28 mmol), and cesium carbonate (624 mg, 1.91 mmol) in 1,4-dioxane (15 mL) under nitrogen. The resulting mixture was stirred at 100° C. for 2 hours. The reaction was then concentrated. The resulting residue was purified by silica gel chromatography, using 0-10% MeOH-DCM as eluent, to afford methyl 5-(methylamino)-6-(3-methylimidazo[4,5-c]pyridin-7-yl)-3-(2-methyl-4-morpholino-anilino)pyrazine-2-carboxylate (0.080 g, 26%) as a yellow solid; 1H NMR (300 MHZ, DMSO-d6) δ 2.33 (3H, s), 2.85 (3H, d), 3.09 (4H, m), 3.75 (4H, m), 3.83 (3H, s), 4.02 (3H, s), 6.83 (1H, m), 6.90 (1H, d), 7.88 (1H, br q), 8.16 (1H, d), 8.49 (1H, s), 8.54 (1H, s), 9.04 (1H, s), 10.12 (1H, s); m/z: (ES+), [M+H]+=489.2

5-(Methylamino)-6-(3-methylimidazo[4,5-c]pyridin-7-yl)-3-(2-methyl-4-morpholino-anilino)pyrazine-2-carboxamide 7 N Methanolic ammonia (10 mL, 70 mmol) was added to methyl 5-(methylamino)-6-(3-methylimidazo[4,5-c]pyridin-7-yl)-3-(2-methyl-4-morpholino-anilino)pyrazine-2-carboxylate (80 mg, 0.16 mmol). The resulting suspension was stirred at 100° C. for 3 days. The reaction was then concentrated. The resulting residue was purified by preparative HPLC, using a 5 micron, 30 mm×150 mm, Xselect CSH OBD column, 10-35% MeCN—$H_2O$ as eluent, and 0.1% formic acid as modifier, to afford 5-(methylamino)-6-(3-methylimidazo[4,5-c]pyridin-7-yl)-3-(2-methyl-4-morpholino-anilino)pyrazine-2-carboxamide (40 mg, 50%) as a yellow solid; 1H NMR (300 MHz, DMSO-d6) δ 2.32 (3H, s), 2.90 (3H, d), 3.07 (4H, m), 3.74 (4H, m), 4.02 (3H, s), 6.82 (1H, m), 6.88 (1H, d), 7.29 (1H, s), 7.72 (1H, s), 7.96 (1H, br q), 8.30 (1H, m), 8.55 (1H, s), 8.75 (1H, s), 9.04 (1H, s), 11.18 (1H, s); m/z: (ES+), [M+H]+=474.2

Example 67

3-(2-Methoxy-4-morpholino-anilino)-5-(methylamino)-6-(3-methylimidazo[4,5-c]pyridin-7-yl)pyrazine-2-carboxamide

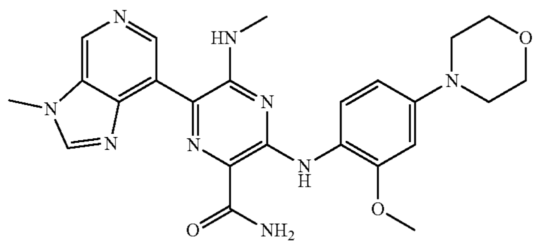 [SMILES: CNc1nc(Nc2ccc(N3CCOCC3)cc2OC)c(C(N)=O)nc1-c1cncc2c1ncn2C]

(a) Methyl 3-(2-methoxy-4-morpholino-anilino)-5-(methylamino)-6-(3-methylimidazo[4,5-c]pyridin-7-yl)pyrazine-2-carboxylate BrettPhos Pd G3 (116 mg, 0.130 mmol) was added to a suspension of methyl 3-amino-5-(methylamino)-6-(3-methylimidazo[4,5-c]pyridin-7-yl)pyrazine-2-carboxylate (200 mg, 0.64 mmol), 4-(4-bromo-3-methoxy-phenyl) morpholine (174 mg, 0.640 mmol), and cesium carbonate (416 mg, 1.28 mmol) in 1,4-dioxane (15 mL) under nitrogen. The resulting mixture was stirred at 100° C. for 16 hours. The reaction was then concentrated. The resulting residue was purified by silica gel chromatography, using 0-10% MeOH-DCM as eluent, to afford methyl 3-(2-methoxy-4-morpholino-anilino)-5-(methylamino)-6-(3-methylimidazo[4,5-c]pyridin-7-yl)pyrazine-2-carboxylate (0.120 g, 37%) as a brown solid; 1H NMR (300 MHZ, DMSO-d6) δ 2.93 (3H, d), 3.07-3.14 (4H, m), 3.72-3.81 (4H, m), 3.82 (3H, s), 3.92 (3H, s), 4.01 (3H, s), 6.53 (1H, d), 6.72 (1H, s), 7.96 (1H, br q), 8.45-8.52 (2H, m), 8.55 (1H, s), 9.03 (1H, s), 10.60 (1H, s) m/z: (ES+), [M+H]+=505.3

(b) 3-(2-Methoxy-4-morpholino-anilino)-5-(methylamino)-6-(3-methylimidazo[4,5-c]pyridin-7-yl)pyrazine-2-carboxamide 7 N Methanolic ammonia (10 mL, 70 mmol) was added to methyl 3-(2-methoxy-4-morpholino-anilino)-5-(methylamino)-6-(3-methylimidazo[4,5-c]pyridin-7-yl)pyrazine-2-carboxylate (120 mg, 0.24 mmol). The resulting mixture was stirred at 80° C. for 1 day. The reaction was then concentrated. The resulting residue was purified by preparative HPLC Column using a 5 micron, 30×150 mm Sunfire prep C18 column, 12-30% MeCN—$H_2O$ as eluent, and 0.1% formic acid as modifier, to afford 3-(2-methoxy-4-morpholino-anilino)-5-(methylamino)-6-(3-methylimidazo[4,5-c]pyridin-7-yl)pyrazine-2-carboxamide (30 mg, 25%) as a brown solid; 1H NMR (400 MHZ, DMSO-d6) δ 2.95 (3H, d), 3.10 (4H, t), 3.75 (4H, t), 3.89 (3H, s), 4.01 (3H, s), 6.48-6.55 (1H, m), 6.69 (1H, d), 7.17 (1H, s), 7.65 (1H, s), 8.01 (1H, br q), 8.52 (1H, s), 8.53 (1H, s), 8.73 (1H, s), 9.00 (1H, s), 11.42 (1H, s); m/z: (ES+), [M+H]+=490.1

Example 68

3-(2-Chloro-4-morpholino-anilino)-5-(methylamino)-6-(3-methylimidazo[4,5-c]pyridin-7-yl)pyrazine-2-carboxamide

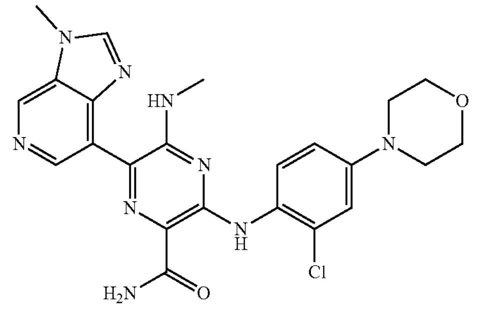 [SMILES: CNc1nc(Nc2ccc(N3CCOCC3)cc2Cl)c(C(N)=O)nc1-c1cncc2c1ncn2C]

(a) Methyl 3-(2-chloro-4-morpholino-anilino)-5-(methylamino)-6-(3-methylimidazo[4,5-c]pyridin-7-yl)pyrazine-2-carboxylate Brettphos Pd G3 (116 mg, 0.130 mmol) was added to a suspension of methyl 3-amino-5-(methylamino)-6-(3-methylimidazo[4,5-c]pyridin-7-yl)pyrazine-2-carboxylate (200 mg, 0.64 mmol), 4-(4-bromo-3-chloro-phenyl) morpholine (177 mg, 0.640 mmol), and cesium carbonate (624 mg, 1.91 mmol) in 1,4-dioxane (1 mL) under nitrogen. The resulting mixture was stirred at 100° C. for 16 hours. The reaction was then concentrated. The resulting residue was purified by silica gel chromatography, using 0 to 12% MeOH-DCM as eluent, to afford methyl 3-(2-chloro-4-morpholino-anilino)-5-(methylamino)-6-(3-methylimidazo[4,5-c]pyridin-7-yl) pyrazine-2-carboxylate (137 mg, 42% yield). 1H NMR (400 MHZ, DMSO-d6) δ 2.87 (3H, d), 3.09-3.14 (4H, m), 3.71-3.75 (4H, m), 3.82 (3H, s), 4.01 (3H, s), 6.99 (1H, dd), 7.09 (1H, d), 7.92 (1H, br q), 8.46-8.53 (2H, m), 8.54 (1H, s), 9.05 (1H, s), 10.55 (1H, s). m/z: (ES+), [M+H]+=509.3

(b) 3-(2-Chloro-4-morpholino-anilino)-5-(methylamino)-6-(3-methylimidazo[4,5-c]pyridin-7-yl)pyrazine-2-carboxylic acid Sodium hydroxide (44.0 mg, 1.10 mmol) was added to a suspension of methyl 3-(2-chloro-4-morpholino-anilino)-5-(methylamino)-6-(3-methylimidazo[4,5-c]pyridin-7-yl) pyrazine-2-carboxylate (112 mg, 0.220 mmol) in MeOH (0.5 mL) and water (0.5 mL). The resulting mixture was stirred at 80° C. for 16 hours. The reaction was then concentrated. The resulting residue was acidified with 2 M HCl, and the resulting solid was filtered to afford 3-(2-chloro-4-morpholino-anilino)-5-(methylamino)-6-(3-methylimidazo[4,5-c]pyridin-7-yl)pyrazine-2-carboxylic acid (105 mg, 96%) as a yellow solid. 1H NMR (400 MHZ, DMSO-d6) δ 2.87 (3H, d), 3.08-3.15 (4H, m), 3.71-3.77 (4H, m), 4.08 (3H, s), 7.00 (1H, dd), 7.10 (1H, d), 7.81 (1H, br q), 8.48 (1H, d), 8.76 (1H, s), 8.82 (1H, s), 9.37 (1H, s), 10.82 (1H, s). m/z: (ES−), [M−H]−=494.2

(c) 3-(2-Chloro-4-morpholino-anilino)-5-(methylamino)-6-(3-methylimidazo[4,5-c]pyridin-7-yl)pyrazine-2-carboxamide HATU (104 mg, 0.270 mmol) was added to a mixture of 3-(2-chloro-4-morpholino-anilino)-5-(methylamino)-6-(3-methylimidazo[4,5-c]pyridin-7-yl)pyrazine-2-carboxylic acid (90 mg, 0.18 mmol) and DIPEA (95 μL, 0.55 mmol) in DMF (5 mL). The resulting solution was stirred at 25° C. for 30 minutes. Ammonium chloride (49 mg, 0.91 mmol) was added. The resulting mixture was stirred at 25° C. for 16 hours. The reaction was then poured into water. The resulting suspension was filtered, washed with water (10 mL), and dried under vacuum. The resulting solid was purified by preparative HPLC, using a 5 micron, 50 mm×100 mm, XSelect CSH Prep C18 OBD column, decreasingly polar mixtures of MeCN—$H_2O$ as eluent, and 0.1% formic acid as modifier, to afford 3-(2-chloro-4-morpholino-anilino)-5-(methylamino)-6-(3-methylimidazo[4,5-c]pyridin-7-yl) pyrazine-2-carboxamide (30 mg, 33%) as a yellow solid; 1H NMR (400 MHZ, DMSO-d6) δ 2.91 (3H, d), 3.06-3.16 (4H, m), 3.66-3.79 (4H, m), 4.01 (3H, s), 6.98 (1H, dd), 7.07 (1H, d), 7.30 (1H, s), 7.72 (1H, s), 8.01 (1H, br q), 8.52 (1H, s), 8.56 (1H, d), 8.73 (1H, s), 9.02 (1H, s), 11.55 (1H, s); m/z: (ES+), [M+H]+=494.2

Example 69

5-(Methylamino)-6-(3-methylimidazo[4,5-c]pyridin-7-yl)-3-[(5-methyl-6-morpholino-3-pyridyl)amino] pyrazine-2-carboxamide

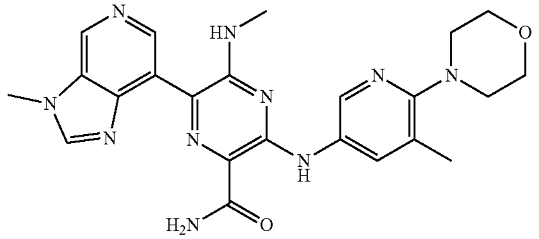 [SMILES: CNc1nc(Nc2cnc(N3CCOCC3)c(C)c2)c(C(N)=O)nc1-c1cncc2c1ncn2C]

(a) 4-(3-Methyl-5-nitro-2-pyridyl) morpholine

DIPEA (0.40 mL, 2.3 mmol) was added to a mixture of 2-chloro-3-methyl-5-nitro-pyridine (200 mg, 1.16 mmol) and morpholine (121 mg, 1.39 mmol) in THF (5 mL). The resulting mixture was stirred at 80° C. for 21 hours. The reaction was then concentrated. The resulting residue was treated with water. The resulting suspension was filtered to afford 4-(3-methyl-5-nitro-2-pyridyl) morpholine.

(b) 5-Methyl-6-morpholino-pyridin-3-amine

A mixture of 10 wt % palladium on carbon (238 mg, 2.24 mmol) and 4-(3-methyl-5-nitro-2-pyridyl) morpholine (500 mg, 2.24 mmol) in MeOH (10 mL) was stirred under a hydrogen atmosphere at 25 C for 12 hours. The reaction was then filtered through sand and Celite and washed with methanol. The resulting filtrate was concentrated to afford 5-methyl-6-morpholino-pyridin-3-amine (430 mg, 99%) as an off-white solid. m/z: (ES+), [M+H]+=194.2

(c) Methyl 6-chloro-5-(methylamino)-3-[(5-methyl-6-morpholino-3-pyridyl)amino]pyrazine-2-carboxylate DIPEA (0.254 mL, 1.45 mmol) was added to solution of 5-methyl-6-morpholino-pyridin-3-amine (187 mg, 0.97 mmol) and methyl 6-chloro-3-fluoro-5-(methylamino) pyrazine-2-carboxylate (213 mg, 0.970 mmol) in DMF (5 mL). The resulting mixture was stirred at 150° C. for 13 hours in a Biotage microwave reactor. The reaction was then concentrated. The resulting residue was purified by silica gel chromatography, using 0-100% EtOAc-hexanes and then isocratic 10% MeOH-DCM, to afford methyl 6-chloro-5-(methylamino)-3-[(5-methyl-6-morpholino-3-pyridyl) amino]pyrazine-2-carboxylate (153 mg, 40%) as a pale yellow solid. m/z: (ES+), [M+H]+=393.3

(d) Methyl 5-(methylamino)-6-(3-methylimidazo[4,5-c]pyridin-7-yl)-3-[(5-methyl-6-morpholino-3-pyridyl)amino]pyrazine-2-carboxylate CatacXium A Pd G3 (34 mg, 0.050 mmol), bis(pinacolato)diboron (240 mg, 0.94 mmol), potassium acetate (139 mg, 1.41 mmol), 7-bromo-3-methyl-imidazo[4,5-c]pyridine (100 mg, 0.47 mmol), and cataCXium A (17 mg, 0.050 mmol) were combined in a microwave vial, which was evacuated and backfilled three times with nitrogen. DMF (2.5 mL) was added. The resulting mixture was stirred at 90 C for 14 hours. The reaction was allowed to cool to room temperature and set aside.

$PdCl_2$(dppf) (31 mg, 0.040 mmol), methyl 6-chloro-5-(methylamino)-3-[(5-methyl-6-morpholino-3-pyridyl)amino]pyrazine-2-carboxylate (166 mg, 0.420 mmol), and cesium fluoride (193 mg, 1.27 mmol) were combined in a microwave vial, which was evacuated and backfilled three times with nitrogen. DMF (1.5 mL) and the borylation mixture were sequentially added by syringe. The resulting mixture was stirred at 120° C. for 1 hour in a Biotage microwave reactor. The reaction was then concentrated. The resulting residue was partitioned between ethyl acetate and water. The organic layer was separated, dried over sodium sulfate, filtered, and concentrated to afford methyl 5-(methylamino)-6-(3-methylimidazo[4,5-c]pyridin-7-yl)-3-[(5-methyl-6-morpholino-3-pyridyl)amino]pyrazine-2-carboxylate (50 mg, 24% yield) as a brown solid. m/z: (ES+), [M+H]+=490.4

(e) 5-(Methylamino)-6-(3-methylimidazo[4,5-c]pyridin-7-yl)-3-[(5-methyl-6-morpholino-3-pyridyl)amino]pyrazine-2-carboxamide Lithium hydroxide (24.5 mg, 1.02 mmol) was added to a suspension of methyl 5-(methylamino)-6-(3-methylimidazo[4,5-c]pyridin-7-yl)-3-[(5-methyl-6-morpholino-3-pyridyl)amino]pyrazine-2-carboxylate (50 mg, 0.10 mmol) in water (0.500 mL) and MeOH (0.500 mL). The resulting mixture was stirred at 100° C. for 1 hour. The reaction was then concentrated. The resulting residue was redissolved in DMF (3 mL). Ammonium chloride (15 mg, 0.29 mmol), HATU (72 mg, 0.19 mmol), and DIPEA (0.050 mL, 0.29 mmol) were sequentially added. The resulting mixture was stirred at 25 C for 12 hours. The reaction was then quenched with water and diluted with ethyl acetate. The layers were separated and the aqueous layer was extracted with ethyl acetate. The combined organic layers were dried over anhydrous sodium sulfate, filtered, and concentrated. The resulting residue was purified by silica gel chromatography, using 0-100% MeOH-DCM as eluent. The resulting material was further purified by preparative HPLC, using 0-70% MeCN—$H_2O$ as eluent, and 0.1% trifluoroacetic acid as modifier, to afford 5-(methylamino)-6-(3-methylimidazo[4,5-c]pyridin-7-yl)-3-[(5-methyl-6-morpholino-3-pyridyl)amino]pyrazine-2-carboxamide (15 mg, 33% yield) as a pale yellow solid; 1H NMR (500 MHz, DMSO-d6) 2.29 (3H, s), 2.95 (3H, d), 2.98-3.06 (4H, m), 3.71-3.79 (4H, m), 4.02 (3H, s), 7.38 (1H, br s), 7.76 (1H, br s), 7.98-8.11 (2H, m), 8.53 (1H, s), 8.58 (1H, d), 8.73 (1H, s), 9.03 (1H, s), 11.36 (1H, s); m/z: (ES+), [M+H]+=475.5

Example 70

5-(Methylamino)-6-(3-methylimidazo[4,5-c]pyridin-7-yl)-3-[[5-methyl-6-[(3S)-3-methylmorpholin-4-yl]-3-pyridyl]amino]pyrazine-2-carboxamide

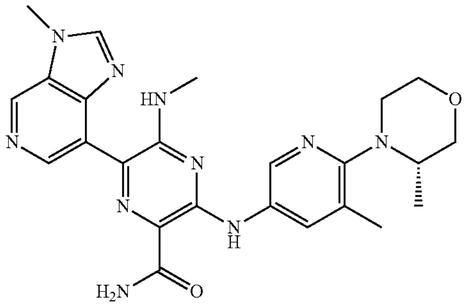 [SMILES: CNc1nc(Nc2cnc(N3CCOC[C@@H]3C)c(C)c2)c(C(N)=O)nc1-c1cncc2c1ncn2C]

(a) (3S)-4-(5-Bromo-3-methyl-2-pyridyl)-3-methyl-morpholine (3S)-3-Methylmorpholine (10.65 g, 105.3 mmol) was added to 5-bromo-2-fluoro-3-methyl-pyridine (2.00 g, 10.5 mmol). The resulting mixture was stirred at 140° C. for 14 days. The reaction was then concentrated, diluted with EtOAc (50 mL), and washed three times with brine (50 mL each). The organic layer was dried over sodium, filtered, and concentrated. The resulting residue was purified by silica gel chromatography, using 0-50% EtOAc-petroleum ether as eluent, to afford (3S)-4-(5-bromo-3-methyl-2-pyridyl)-3-methyl-morpholine (1.10 g, 39%) as a colorless oil; 1H NMR (300 MHz, DMSO-d6) δ 0.84 (3H, d), 2.22 (3H, s), 2.69-2.82 (1H, m), 3.02-3.16 (1H, m), 3.26-3.40 (1H, m), 3.42-3.54 (1H, m), 3.68 (2H, dd), 3.74 (1H, dd), 7.78 (1H, dd), 8.24 (1H, dd). m/z: (ES+), [M+2+H]+=273.0

(b) Methyl 5-(methylamino)-6-(3-methylimidazo[4,5-c]pyridin-7-yl)-3-[[5-methyl-6-[(3S)-3-methylmorpholin-4-yl]-3-pyridyl]amino]pyrazine-2-carboxylate Cesium carbonate (218 mg, 0.670 mmol) was added to a mixture of methyl 3-amino-5-(methylamino)-6-(3-methylimidazo[4,5-c]pyridin-7-yl)pyrazine-2-carboxylate (70 mg, 0.22 mmol), (3S)-4-(5-bromo-3-methyl-2-pyridyl)-3-methyl-morpholine (61 mg, 0.22 mmol), and BrettPhos Pd G3 (31 mg, 0.030 mmol) in 1,4-dioxane (5 mL) under nitrogen. The resulting mixture was stirred at 100° C. for 16 hours. The reaction was then concentrated. The resulting residue was purified by silica gel chromatography, using 0-100% MeOH-DCM as eluent to afford methyl 5-(methylamino)-6-(3-methylimidazo[4,5-c]pyridin-7-yl)-3-[[5-methyl-6-[(3S)-3-methylmorpholin-4-yl]-3-pyridyl]amino]pyrazine-2-carboxylate (50 mg, 44% yield) as a yellow solid. m/z: (ES+), [M+H]+=504.3

(c) 5-(Methylamino)-6-(3-methylimidazo[4,5-c]pyridin-7-yl)-3-[[5-methyl-6-[(3S)-3-methylmorpholin-4-yl]-3-pyridyl]amino]pyrazine-2-carboxamide 7N Methanolic ammonia (8.0 mL, 56 mmol) was added to methyl 5-(methylamino)-6-(3-methylimidazo[4,5-c]pyridin-7-yl)-3-[[5-methyl-6-[(3S)-3-methylmorpholin-4-yl]-3-pyridyl]amino]pyrazine-2-carboxylate (90 mg, 0.18 mmol).

The resulting suspension was stirred at 80° C. for 16 hours. The reaction was then concentrated. The resulting residue was purified by preparative HPLC, using a 5 micron, 19 mm×250 mm, XSelect CSH Prep C18 OBD column, 10% to 20% MeCN—$H_2O$ as eluent, and 0.1% formic acid as modifier, to afford 5-(methylamino)-6-(3-methylimidazo[4,5-c]pyridin-7-yl)-3-[[5-methyl-6-[(3S)-3-methylmorpholin-4-yl]-3-pyridyl]amino]pyrazine-2-carboxamide (32 mg, 36%) as a yellow solid; 1H NMR (400 MHZ, DMSO-d6) δ 0.80 (3H, d), 2.29 (3H, s), 2.75 (1H, ddd), 2.94-3.04 (4H, m), 3.32 (1H, dd), 3.41-3.50 (1H, m), 3.65-3.73 (1H, m), 3.73-3.84 (2H, m), 4.02 (3H, s), 7.40 (1H, s), 7.77 (1H, s), 8.05 (1H, d), 8.14 (1H, d), 8.53 (1H, s), 8.60 (1H, d), 8.74 (1H, s), 9.03 (1H, s), 11.43 (1H, s); m/z: (ES+), [M+H]+=489.2

Example 71

5-(Methylamino)-6-(3-methylimidazo[4,5-c]pyridin-7-yl)-3-[[5-methyl-6-[(2S)-2-methylmorpholin-4-yl]-3-pyridyl]amino]pyrazine-2-carboxamide

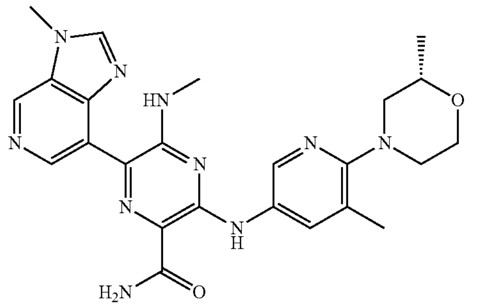 [SMILES: CNc1nc(Nc2cnc(N3CCO[C@@H](C)C3)c(C)c2)c(C(N)=O)nc1-c1cncc2c1ncn2C]

(a) (2S)-4-(5-Bromo-3-methyl-2-pyridyl)-2-methylmorpholine

DIPEA (1.38 mL, 7.89 mmol) was added to a solution of 5-bromo-2-fluoro-3-methyl-pyridine (0.500 g, 2.63 mmol) and (2S)-2-methylmorpholine (0.399 g, 3.95 mmol) in DMSO (15 mL). The resulting mixture was stirred at 100° C. for 4 days. The reaction was then diluted with EtOAc and washed sequentially with water. The organic layer was dried over sodium sulfate, filtered, and concentrated. The resulting residue was purified by silica gel chromatography, using 0-30% EtOAc-petroleum ether as eluent, to afford (2S)-4-(5-bromo-3-methyl-2-pyridyl)-2-methyl-morpholine (0.520 g, 73%) as a yellow oil; 1H NMR (300 MHz, DMSO-d6) δ 1.12 (3H, d), 2.24 (3H, d), 2.53 (1H, d), 2.72-2.87 (1H, m), 3.17-3.32 (2H, m), 3.60-3.76 (2H, m), 3.80-3.91 (1H, m), 7.75 (1H, dd), 8.19 (1H, dd); m/z: (ES+), [M+H]+=270.9

(b) Methyl 5-(methylamino)-6-(3-methylimidazo[4,5-c]pyridin-7-yl)-3-[[5-methyl-6-[(2S)-2-methylmorpholin-4-yl]-3-pyridyl]amino]pyrazine-2-carboxylate Brettphos Pd G3 (46 mg, 0.050 mmol) was added to a suspension of methyl 3-amino-5-(methylamino)-6-(3-methylimidazo[4,5-c]pyridin-7-yl)pyrazine-2-carboxylate (80 mg, 0.26 mmol), (2S)-4-(5-bromo-3-methyl-2-pyridyl)-2-methyl-morpholine (69 mg, 0.26 mmol), and cesium carbonate (250 mg, 0.77 mmol) in 1,4-dioxane (10 mL) under nitrogen. The resulting mixture was stirred at 100° C. for 16 hours. The reaction was then concentrated. The resulting residue was purified by silica gel chromatography, using 0-10% MeOH-DCM as eluent to afford methyl 5-(methylamino)-6-(3-methylimidazo[4,5-c]pyridin-7-yl)-3-[[5-methyl-6-[(2S)-2-methylmorpholin-4-yl]-3-pyridyl]amino]pyrazine-2-carboxylate (85 mg, 66%) as a brown solid; 1H NMR (400 MHZ, DMSO-d6) δ 1.13 (3H, d), 2.29 (3H, s), 2.52-2.58 (1H, m), 2.80 (1H, d), 2.90 (3H, d), 3.16-3.22 (2H, m), 3.62-3.77 (2H, m), 3.83 (3H, s), 3.85-3.90 (1H, m), 4.01 (3H, s), 7.96 (1H, br s), 8.06 (1H, s), 8.44-8.52 (1H, m), 8.54 (2H, d), 9.05 (1H, s), 10.25 (1H, s); m/z: (ES+), [M+H]+=504.3

(c) 5_(Methylamino)-6-(3-methylimidazo[4,5-c]pyridin-7-yl)-3-[[5-methyl-6-[(2S)-2-methylmorpholin-4-yl]-3-pyridyl]amino]pyrazine-2-carboxamide 7 N Methanolic ammonia (8.0 mL, 56 mmol) was added to methyl 5-(methylamino)-6-(3-methylimidazo[4,5-c]pyridin-7-yl)-3-[[5-methyl-6-[(2S)-2-methylmorpholin-4-yl]-3-pyridyl]amino]pyrazine-2-carboxylate (80 mg, 0.16 mmol). The resulting suspension was stirred at 80° C. for 16 hours. The reaction was then concentrated. The resulting residue was purified by preparative HPLC, using a 5 micron, 30 mm×150 mm, XBridge Shield RP18 OBD column, 11%-21% MeCN—$H_2O$ as eluent, and 0.1% formic acid as modifier, to afford 5-(methylamino)-6-(3-methylimidazo[4,5-c]pyridin-7-yl)-3-[[5-methyl-6-[(2S)-2-methylmorpholin-4-yl]-3-pyridyl]amino]pyrazine-2-carboxamide (21 mg, 27%) as a yellow solid; 1H NMR (400 MHZ, DMSO-d6) δ 1.13 (3H, d), 2.28 (3H, s), 2.55 (1H, s), 2.72-2.82 (1H, m), 2.94 (3H, d), 3.16 (2H, dd), 3.65-3.74 (2H, m), 3.81-3.88 (1H, m), 4.01 (3H, s), 7.39 (1H, s), 7.76 (1H, s), 7.94-8.07 (2H, m), 8.50-8.58 (2H, m), 8.72 (1H, s), 9.02 (1H, s), 11.35 (1H, s). m/z: (ES+), [M+H]+=489.3

Example 72

5-Cyclopropyl-6-(3-methylimidazo[4,5-c]pyridin-7-yl)-3-[[6-[(3R)-3-methylmorpholin-4-yl]-3-pyridyl]amino]pyrazine-2-carboxamide

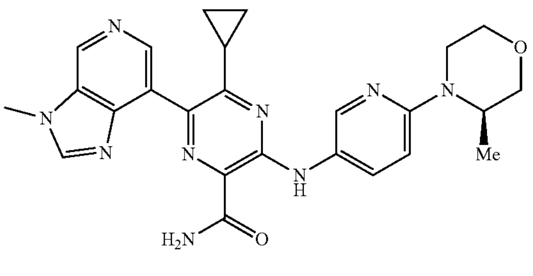 [SMILES: C[C@@H]1COCCN1c1ccc(Nc2nc(C3CC3)c(-c3cncc4c3ncn4C)nc2C(N)=O)cn1]

(a) (3R)-3-Methyl-4-(5-nitro-2-pyridyl) morpholine

DIPEA (1.9 mL, 10.90 mmol) was slowly added to a solution of (3R)-3-methylmorpholine hydrochloride (500 mg, 3.63 mmol) and 2-chloro-5-nitropyridine (1.15 mg, 7.27 mmol) in DMF (15 mL). The resulting mixture was stirred at 100° C. for 1 hour. The reaction was then allowed to cool to room temperature, quenched with water (50 mL), and extracted three times with EtOAc (50 mL each). The combined organic layers were washed twice with 5% aqueous LiCl solution and once with brine, dried over sodium sulfate, filtered, and concentrated. The resulting residue was purified by silica gel chromatography, using 0-40% EtOAc-hexanes as eluent, to afford (3R)-3-methyl-4-(5-nitro-2-pyridyl) morpholine (0.321 g, 40%) as a yellow oil; 1H NMR (500 MHZ, CHLOROFORM-d) 1.36 (3H, d), 3.38 (1H, td), 3.62 (1H, td), 3.77 (1H, dd), 3.85 (1H, d), 4.07 (1H, dd), 4.12-4.21 (1H, m), 4.48 (1H, br dd), 6.56 (1H, d), 8.26 (1H, dd), 9.09 (1H, d); m/z: (ES+), [M+H]+=224.1

(b) Methyl 6-chloro-5-cyclopropyl-3-[[6-[(3R)-3-methylmorpholin-4-yl]-3-pyridyl]amino]pyrazine-2-carboxylate A mixture of 10 wt % palladium on carbon (32 mg, 0.030 mmol) and (3R)-3-methyl-4-(5-nitro-2-pyridyl) morpholine (321 mg, 1.44 mmol) in MeOH (9.6 mL) was stirred under a hydrogen atmosphere at 25 C for 18 hours. The reaction was then filtered, and the filtrate was concentrated. The resulting residue was dissolved in DMF (6.5 mL). Methyl 6-chloro-5-cyclopropyl-3-fluoro-pyrazine-2-carboxylate (0.365 g, 1.58 mmol) and DIPEA (0.755 mL, 4.32 mmol) were sequentially added. The resulting mixture was stirred at 100° C. for 60 hours. The reaction was then allowed to cool to room temperature, diluted with water, and extracted three times with EtOAc (30 mL each). The combined organic layers were washed twice with 5% aqueous LiCl and once with brine, dried over sodium sulfate, filtered, and concentrated. The resulting residue was purified by silica gel chromatography, using 0-10% MeOH-DCM as eluent, to afford methyl 6-chloro-5-cyclopropyl-3-[[6-[(3R)-3-methylmorpholin-4-yl]-3-pyridyl]amino]pyrazine-2-carboxylate (0.254 g, 44%) as a dark orange solid; 1H NMR (500 MHz, CHLOROFORM-d) δ 1.06-1.20 (2H, m), 1.22-1.28 (5H, m), 2.46-2.55 (1H, m), 3.18-3.29 (1H, m), 3.62-3.70 (1H, m), 3.72-3.81 (2H, m), 3.91-3.97 (1H, m), 4.00 (3H, s), 4.02-4.07 (1H, m), 4.23-4.34 (1H, m), 6.60 (1H, br d), 7.68 (1H, br d), 8.30 (1H, br s), 9.76 (1H, br s); m/z: (ES+), [M+H]+=404.1

(c) Methyl 5-cyclopropyl-6-(3-methylimidazo[4,5-c] pyridin-7-yl)-3_ [[6-[(3R)-3-methylmorpholin-4-yl]-3-pyridyl]amino]pyrazine-2-carboxylate 7-Bromo-3-methyl-imidazo[4,5-c]pyridine (200 mg, 0.94 mmol), bis(pinacolato)diboron (479 mg, 1.89 mmol), cataCXium A Pd G3 (68.7 mg, 0.09 mmol), cataCXium A (33.8 mg, 0.09 mmol), and potassium acetate (185 mg, 1.89 mmol) were combined in a microwave vial, which was evacuated and backfilled three times with nitrogen. DMF (4.2 mL) was added. The resulting mixture was stirred at 80° C. for 24 hours. The reaction was then allowed to cool to room temperature and set aside.

Methyl 6-chloro-5-cyclopropyl-3-[[6-[(3R)-3-methylmorpholin-4-yl]-3-pyridyl]amino]pyrazine-2-carboxylate (254 mg, 0.630 mmol), Pd(dppf) Cl2*CH2C12 complex (51 mg, 0.060 mmol), and cesium fluoride (287 mg, 1.89 mmol) were combined in a microwave vial, which was evacuated and backfilled three times with nitrogen. The borylation mixture was added. The resulting mixture was stirred at 100° C. for 5 hours. The reaction was then allowed to cool to room temperature, treated with water, and extracted three times with 4:1 DCM/IPA. The combined organic layers were washed once with 5% aqueous LiCl solution and once with brine, dried over sodium sulfate, filtered, and concentrated. The resulting residue was purified by silica gel chromatography, using 0-10% MeOH-DCM as eluent, and 1% ammonia as modifier, to afford methyl 5-cyclopropyl-6-(3-methylimidazo[4,5-c]pyridin-7-yl)-3-[[6-[(3R)-3-methylmorpholin-4-yl]-3-pyridyl]amino]pyrazine-2-carboxylate (0.122 g, 39%) as a brown film. m/z: (ES+), [M+H]+=501.2

(d) 5-Cyclopropyl-6-(3-methylimidazo[4,5-c]pyridin-7-yl)-3-[[6-[(3R)-3-methylmorpholin-4-yl]-3-pyridyl]amino]pyrazine-2-carboxamide 7 N Methanolic ammonia (2.0 mL, 14 mmol) was added to a solution of methyl (R)-5-cyclopropyl-6-(3-methyl-3H-imidazo[4,5-c]pyridin-7-yl)-3-((6-(3-methylmorpholino) pyridin-3-yl)amino) pyrazine-2-carboxylate (122 mg, 0.240 mmol) in methanol (2.0 mL). The resulting suspension was stirred at 80° C. for 2 hours. The reaction was then concentrated. The resulting residue was purified by silica gel chromatography, using 0-10% MeOH-DCM as eluent, and 1% ammonia as modifier, to afford 5-cyclopropyl-6-(3-methylimidazo[4,5-c]pyridin-7-yl)-3-[[6-[(3R)-3-methylmorpholin-4-yl]-3-pyridyl]amino]pyrazine-2-carboxamide (57 mg, 48%) as a dark yellow film. 1H NMR (500 MHz, CHLOROFORM-d) 0.88-0.99 (2H, m), 1.15-1.32 (5H, m), 1.91-2.05 (1H, m), 3.25 (1H, td), 3.67 (1H, td), 3.73-3.87 (3H, m), 3.99-4.06 (4H, m), 4.29 (1H, q), 5.41 (1H, br d), 6.62 (1H, d), 7.80 (1H, br d), 7.87 (1H, dd), 8.04 (1H, s), 8.46 (1H, d), 8.66 (1H, s), 8.93 (1H, s), 10.57 (1H, s); m/z: (ES+), [M+H]+=486.2

Example 73

3-[(5-Cyano-6-morpholino-3-pyridyl)amino]-5-(methylamino)-6-(3-methylimidazo[4,5-c]pyridin-7-yl)pyrazine-2-carboxamide

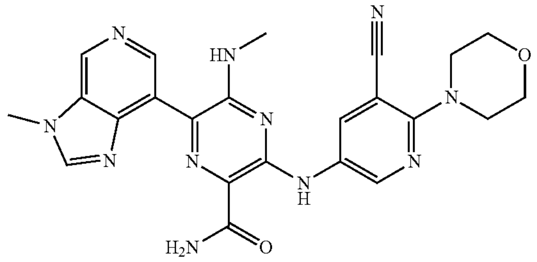 [SMILES: CNc1nc(Nc2cnc(N3CCOCC3)c(C#N)c2)c(C(N)=O)nc1-c1cncc2c1ncn2C]

(a) 5-Bromo-2-morpholino-pyridine-3-carbonitrile

DIPEA (1.21 mL, 6.90 mmol) was added to a mixture of 5-bromo-2-chloro-pyridine-3-carbonitrile (500 mg, 2.30 mmol) and morpholine (300 mg, 3.45 mmol) in MeCN (10 mL). The resulting solution was stirred at 80° C. for 2 hours. The reaction was then allowed to cool to room temperature, then poured into ice water. The resulting precipitate was collected by filtration, washed with water (25 mL), and dried under vacuum to afford 5-bromo-2-morpholino-pyridine-3-carbonitrile (0.480 g, 78%); 1H NMR (400 MHZ, $CDCl_3$) δ 3.69-3.75 (4H, m), 3.80-3.87 (4H, m), 7.86 (1H, d), 8.37 (1H, d); m/z: (ES+), [M+H]+=268.0

(b) Methyl 3-[(5-cyano-6-morpholino-3-pyridyl) amino]-5-(methylamino)-6-(3-methylimidazo[4,5-c] pyridin-7-yl)pyrazine-2-carboxylate BrettPhos Pd G3 (57.8 mg, 0.06 mmol) was added to a suspension of methyl 3-amino-5-(methylamino)-6-(3-methylimidazo[4,5-c]pyridin-7-yl)pyrazine-2-carboxylate (100 mg, 0.32 mmol), 5-bromo-2-morpholino-pyridine-3-carbonitrile (128 mg, 0.480 mmol), and cesium carbonate (312 mg, 0.96 mmol) in 1,4-dioxane (5 mL) under nitrogen. The resulting mixture was stirred at 100° C. for 15 hours. The reaction was then concentrated. The resulting residue was purified by silica gel chromatography, using 0-15% MeOH-DCM as eluent, to afford methyl 3-[(5-cyano-6-morpholino-3-pyridyl)amino]-5-(methylamino)-6-(3-methylimidazo[4,5-c]pyridin-7-yl)pyrazine-2-carboxylate (0.081 g, 51%) as a yellow solid; 1H NMR (400 MHz, DMSO-d6) δ 2.87 (3H, d), 3.48-3.53 (4H, m), 3.73-3.77 (4H, m), 3.84 (3H, s), 4.01 (3H, s), 8.02 (1H, br q), 8.50 (1H, s), 8.53 (1H, s), 8.69 (1H, d), 8.78 (1H, d), 9.05 (1H, s), 10.23 (1H, s); m/z: (ES+), [M+H]+=501.2

(c) 3-[(5-Cyano-6-morpholino-3-pyridyl)amino]-5-(methylamino)-6-(3-methylimidazo[4,5-c]pyridin-7-yl)pyrazine-2-carboxamide 7 N methanolic ammonia (10 mL, 70 mmol) was added to methyl 3-[(5-cyano-6-morpholino-3-pyridyl)amino]-5-(methylamino)-6-(3-methylimidazo[4,5-c]pyridin-7-yl) pyrazine-2-carboxylate (75 mg, 0.15 mmol). The resulting mixture was stirred at 80° C. for 50 hours. The reaction was then concentrated. The resulting residue was purified by preparative HPLC, using a 5 micron, 30 mm×150 mm, Xselect CSH OBD column, decreasingly polar mixtures of MeCN—$H_2O$ as eluent, and 0.1% formic acid as modifier, to afford 3-[(5-cyano-6-morpholino-3-pyridyl)amino]-5-(methylamino)-6-(3-methylimidazo[4,5-c]pyridin-7-yl) pyrazine-2-carboxamide (16 mg, 22%) as a yellow solid; 1H NMR (400 MHz, DMSO-d6) δ 2.91 (3H, d), 3.47 (4H, t), 3.71-3.78 (4H, m), 4.01 (3H, s), 7.40 (1H, s), 7.76 (1H, s), 8.08 (1H, br q), 8.51 (1H, s), 8.69-8.77 (3H, m), 9.02 (1H, s), 11.41 (1H, s); m/z: (ES+), [M+H]+=486.3

Example 74

3-((4-(1,4-Oxazepan-4-yl)phenyl)amino)-6-(3-methyl-3H-imidazo[4,5-c]pyridin-7-yl)-5-(methylamino) pyrazine-2-carboxamide

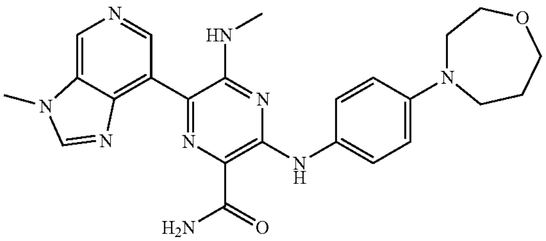 [SMILES: CNc1nc(Nc2ccc(N3CCCOCC3)cc2)c(C(N)=O)nc1-c1cncc2c1ncn2C]

(a) 4-(4-Bromophenyl)-1,4-oxazepane

Palladium (II) acetate (0.119 g, 0.530 mmol) and 1-bromo-4-iodo-benzene (1.00 g, 3.53 mmol) were added to a mixture of potassium tert-butoxide (1.19 g, 10.6 mmol), 1,4-oxazepane hydrochloride (0.486 g, 3.53 mmol), and (rac)-BINAP (0.33 g, 0.53 mmol) in toluene (20 mL) under nitrogen. The resulting mixture was stirred at 100° C. for 3 hours. The reaction was then concentrated. The resulting residue was purified by flash silica chromatography, using 0-20% EtOAc-petroleum ether, to afford 4-(4-bromophenyl)-1,4-oxazepane (0.370 g, 41%) as a red solid; 1H NMR (400 MHZ, DMSO-d6) δ 1.81-1.94 (2H, m), 3.49-3.62 (6H, m), 3.69 (2H, dd), 6.65-6.80 (2H, m), 7.22-7.30 (2H, m); m/z: (ES+), [M+H]+=256.0

(b) Methyl 5-(methylamino)-6-(3-methylimidazo[4,5-c]pyridin-7-yl)-3-[4-(1,4-oxazepan-4-yl)anilino] pyrazine-2-carboxylate 4-(4-Bromophenyl)-1,4-oxazepane (245 mg, 0.960 mmol) was added to a suspension of cesium carbonate (624 mg, 1.91 mmol), methyl 3-amino-5-(methylamino)-6-(3-methylimidazo[4,5-c]pyridin-7-yl)pyrazine-2-carboxylate (200 mg, 0.64 mmol), and BrettPhos Pd G3 (87 mg, 0.10 mmol) in 1,4-dioxane (20 mL) under nitrogen. The resulting mixture was stirred at 100° C. for 16 hours. The reaction was then concentrated. The resulting residue was purified by flash silica chromatography, using 0-20% MeOH-DCM as eluent, to afford methyl 5-(methylamino)-6-(3-methylimidazo[4,5-c]pyridin-7-yl)-3-[4-(1,4-oxazepan-4-yl)anilino] pyrazine-2-carboxylate (0.130 g, 42%) as a yellow solid. m/z: (ES+), [M+H]+=489.2

(c) 3-((4-(1,4-Oxazepan-4-yl)phenyl)amino)-6-(3-methyl-3H-imidazo[4,5-c]pyridin-7-yl)-5-(methylamino) pyrazine-2-carboxamide 7 N Methanolic ammonia (10 mL, 70 mmol) was added to methyl 5-(methylamino)-6-(3-methylimidazo[4,5-c]pyridin-7-yl)-3-[4-(1,4-oxazepan-4-yl)anilino]pyrazine-2-carboxylate (100 mg, 0.21 mmol). The resulting mixture was stirred at 80° C. for 3 days. The reaction was then concentrated. The resulting residue was purified by preparative HPLC, using a 5 micron, 30 mm×150 mm, Sunfire prep C18 column, decreasingly polar mixtures of MeCN—$H_2O$ as eluent, and 0.1% formic acid as modifier, to afford 3-((4-(1,4-oxazepan-4-yl)phenyl)amino)-6-(3-methyl-3H-imidazo[4,5-c]pyridin-7-yl)-5-(methylamino) pyrazine-2-carboxamide (56 mg, 56%) as a red solid; 1H NMR (400 MHZ, DMSO-d6) δ 1.90 (2H, p), 2.93 (3H, d), 3.51-3.61 (6H, m), 3.72 (2H, dd), 4.00 (3H, s), 6.70-6.79 (2H, m), 7.27 (1H, d), 7.54-7.63 (2H, m), 7.66-7.70 (1H, m), 8.00 (1H, br q), 8.51 (1H, s), 8.72 (1H, s), 8.99 (1H, s), 11.18 (1H, s); m/z: (ES+), [M+H]+=474.2

Example 75

5-(Methylamino)-6-(3-methylimidazo[4,5-c]pyridin-7-yl)-3-[[5-methyl-6-[(3R)-3-methylmorpholin-4-yl]-3-pyridyl]amino]pyrazine-2-carboxamide

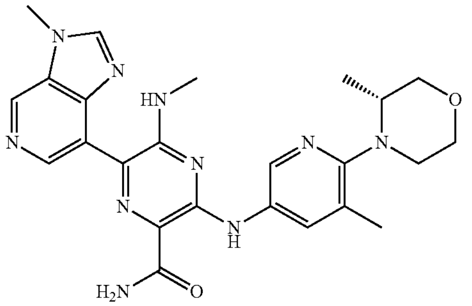 [SMILES: CNc1nc(Nc2cnc(N3CCOC[C@H]3C)c(C)c2)c(C(N)=O)nc1-c1cncc2c1ncn2C]

(a) (3R)-4-(5-Bromo-3-methyl-2-pyridyl)-3-methylmorpholine (3R)-3-Methylmorpholine (266 mg, 2.63 mmol) was added to a mixture of 5-bromo-2-fluoro-3-methyl-pyridine (500 mg, 2.63 mmol), potassium tert-butoxide (886 mg, 7.89 mmol), palladium (II) acetate (89 mg, 0.39 mmol), and (rac)-BINAP (246 mg, 0.390 mmol) in toluene (10 mL) under nitrogen. The resulting mixture was stirred at 100° C. for 2 hours. The reaction was then concentrated. The resulting residue was purified by silica gel chromatography, using 0-30% MeOH-DCM as eluent, to afford (3R)-4-(5-bromo-3-methyl-2-pyridyl)-3-methyl-morpholine (0.200 g, 28%) as a red solid; 1H NMR (300 MHz, DMSO-d6) δ 0.84 (3H, d), 2.22 (3H, s), 2.77-2.82 (1H, m), 3.03-3.15 (1H, m), 3.43-3.55 (1H, m), 3.65-3.69 (2H, m), 3.71-3.78 (1H, m), 3.78-3.89 (1H, m), 7.78 (1H, dd), 8.24 (1H, d); m/z: (ES+), [M+H]+=271.0

(b) Methyl 5-(methylamino)-6-(3-methylimidazo[4,5-c]pyridin-7-yl)-3-[[5-methyl-6-[(3R)-3-methylmorpholin-4-yl]-3-pyridyl]amino]pyrazine-2-carboxylate (3R)-4-(5-Bromo-3-methyl-2-pyridyl)-3-methyl-morpholine (104 mg, 0.38 mmol) was added to a suspension of methyl 3-amino-5-(methylamino)-6-(3-methylimidazo[4,5-c]pyridin-7-yl)pyrazine-2-carboxylate (100 mg, 0.32 mmol), cesium carbonate (312 mg, 0.96 mmol) and Brett-Phos Pd G3 (43.4 mg, 0.05 mmol) in 1,4-dioxane (10 mL) under nitrogen. The resulting mixture was stirred at 100° C. for 16 hours. The reaction was then concentrated. The resulting residue was purified by silica gel chromatography, using 0-30% MeOH-DCM as eluent, to afford methyl 5-(methylamino)-6-(3-methylimidazo[4,5-c]pyridin-7-yl)-3-[[5-methyl-6-[(3R)-3-methylmorpholin-4-yl]-3-pyridyl]amino]pyrazine-2-carboxylate (0.060 g, 37%) as a yellow solid; 1H NMR (400 MHZ, DMSO-d6) δ 0.81 (3H, d), 2.29 (3H, s), 2.74-2.81 (1H, m), 2.91 (3H, d), 2.99-3.07 (1H, m), 3.13-3.25 (1H, m), 3.42-3.50 (1H, m), 3.63-3.84 (3H, m), 3.84 (3H, s), 4.02 (3H, s), 7.96 (1H, br q), 8.17 (1H, d), 8.50 (1H, s), 8.53 (1H, s), 8.61 (1H, d), 9.06 (1H, s), 10.32 (1H, s); m/z: (ES+), [M+H]+=504.3

(c) 5-(Methylamino)-6-(3-methylimidazo[4,5-c]pyridin-7-yl)-3-[[5-methyl-6-[(3R)-3-methylmorpholin-4-yl]-3-pyridyl]amino]pyrazine-2-carboxamide 7 N Methanolic ammonia (8 mL, 56 mmol) was added to methyl 5-(methylamino)-6-(3-methylimidazo[4,5-c]pyridin-7-yl)-3-[[5-methyl-6-[(3R)-3-methylmorpholin-4-yl]-3-pyridyl]amino]pyrazine-2-carboxylate (50.0 mg, 0.10 mmol). The resulting suspension was stirred at 90° C. for 24 hours. The reaction was then concentrated. The resulting residue was purified by preparative HPLC, using a 5 micron, 30 mm×150 mm, XBridge Prep OBD C18 column, 26-36% MeCN-10 mM aqueous ammonium bicarbonate as eluent, and 0.1% ammonium hydroxide as modifier, to afford 5-(methylamino)-6-(3-methylimidazo[4,5-c]pyridin-7-yl)-3-[[5-methyl-6-[(3R)-3-methylmorpholin-4-yl]-3-pyridyl]amino]pyrazine-2-carboxamide (0.021 g, 43.1%) as a yellow solid; 1H NMR (400 MHZ, DMSO-d6) δ 0.79 (3H, d), 2.29 (3H, s), 2.69-2.80 (1H, m), 2.93-3.03 (4H, m), 3.29 (1H, s), 3.41-3.48 (1H, m), 3.68 (1H, t), 3.78 (2H, td), 4.02 (3H, s), 7.39 (1H, s), 7.77 (1H, s), 8.05 (1H, br q), 8.14 (1H, d), 8.53 (1H, s), 8.60 (1H, d), 8.73 (1H, s), 9.03 (1H, s), 11.43 (1H, s); m/z: (ES+), [M+H]+=489.2

Example 76

5-(Methylamino)-6-(3-methylimidazo[4,5-c]pyridin-7-yl)-3-[4-[(1R,4R)-2-oxa-5-azabicyclo[2.2.1]heptan-5-yl]anilino]pyrazine-2-carboxamide

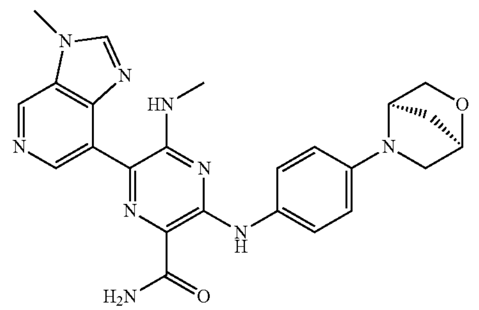 [SMILES: CNc1nc(Nc2ccc(N3C[C@H]4C[C@@H]3CO4)cc2)c(C(N)=O)nc1-c1cncc2c1ncn2C]

(a) (1R,4R)-5-(4-Bromophenyl)-2-oxa-5-azabicyclo[2.2.1]heptane (1R,4R)-2-Oxa-5-azabicyclo[2.2.1]heptane (500 mg, 5.04 mmol) was added to a mixture of 1-bromo-4-iodobenzene (1.43 g, 5.04 mmol), potassium tert-butoxide (1.70 g, 15.1 mmol), (rac)-BINAP (314 mg, 0.500 mmol), and palladium (II) acetate (113 mg, 0.500 mmol) in toluene (5 mL) at RT under nitrogen. The resulting mixture was stirred at 100° C. for 2 hours. The reaction was then concentrated. The resulting residue was purified by silica gel chromatography, using 0-50% EtOAc in petroleum ether as eluent, to afford (1R,4R)-5-(4-bromophenyl)-2-oxa-5-azabicyclo[2.2.1]heptane (0.200 g, 16%) as a red solid; 1H NMR (400 MHz, DMSO-d6) δ 1.84 (1H, ddt), 1.92 (1H, dd), 2.93 (1H, dt), 3.47 (1H, dd), 3.63 (1H, dd), 3.73 (1H, dd), 4.54 (1H, dt), 4.61 (1H, t), 6.54-6.64 (2H, m), 7.25-7.33 (2H, m). m/z: (ES+), [M+2+H]+=256.0

(b) Methyl 5-(methylamino)-6-(3-methylimidazo[4,5-c]pyridin-7-yl)-3-[4-[(1R,4R)-2-oxa-5-azabicyclo[2.2.1]heptan-5-yl]anilino]pyrazine-2-carboxylate Brettphos Pd G3 (58 mg, 0.060 mmol) was added to a suspension of methyl 3-amino-5-(methylamino)-6-(3-methylimidazo[4,5-c]pyridin-7-yl)pyrazine-2-carboxylate (100 mg, 0.32 mmol), (1R,4R)-5-(4-bromophenyl)-2-oxa-5-azabicyclo[2.2.1]heptane (81 mg, 0.32 mmol), and cesium carbonate (312 mg, 0.960 mmol) in 1,4-dioxane (5 mL) under nitrogen. The resulting mixture was stirred at 100° C. for 16 hours. The reaction was then concentrated. The resulting residue was purified by silica gel chromatography, using 0-10% MeOH-DCM as eluent, to afford methyl 5-(methylamino)-6-(3-methylimidazo[4,5-c]pyridin-7-yl)-3-[4-[(1R,4R)-2-oxa-5-azabicyclo[2.2.1]heptan-5-yl]anilino]pyrazine-2-carboxylate (0.070 g, 45% yield) as a red solid. m/z: (ES+), [M+H]+=487.2

(c) 5-(Methylamino)-6-(3-methylimidazo[4,5-c]pyridin-7-yl)-3-[4-[(1R,4R)-2-oxa-5-azabicyclo[2.2.1]heptan-5-yl]anilino]pyrazine-2-carboxamide 7 N Methanolic ammonia (5.0 mL, 35 mmol) was added to methyl 5-(methylamino)-6-(3-methylimidazo[4,5-c]pyridin-7-yl)-3-[4-[(1R,4R)-2-oxa-5-azabicyclo[2.2.1]heptan-5-yl]anilino]pyrazine-2-carboxylate (60 mg, 0.12 mmol). The resulting suspension was stirred at 80° C. for 40 hours. The reaction was then concentrated. The resulting residue was purified by preparative HPLC, using a 5 micron, 50 mm×100 mm XSelect CSH Prep C18 OBD column, decreasingly polar mixtures of MeCN—$H_2O$ as eluent, and 0.1% formic acid as modifier, to afford 5-(methylamino)-6-(3-methylimidazo[4,5-c]pyridin-7-yl)-3-[4-[(1R,4R)-2-oxa-5-azabicyclo[2.2.1]heptan-5-yl]anilino]pyrazine-2-carboxamide (7.0 mg, 12%) as a red solid; 1H NMR (400 MHZ, DMSO-d6) δ 1.83 (1H, d), 1.93 (1H, d), 2.90-2.98 (4H, m), 3.50 (1H, d), 3.69 (1H, d), 3.74 (1H, d), 4.01 (3H, s), 4.52 (1H, s), 4.59 (1H, s), 6.64 (2H, d), 7.28 (1H, s), 7.50 (2H, d), 7.69 (1H, s), 8.00 (1H, br q), 8.51 (1H, s), 8.73 (1H, s), 9.00 (1H, s), 11.19 (1H, s). m/z: (ES+), [M+H]+=472.2

Example 77

5-(Methylamino)-6-(3-methylimidazo[4,5-c]pyridin-7-yl)-3-[4-[(1S,4S)-2-oxa-5-azabicyclo[2.2.1]heptan-5-yl]anilino]pyrazine-2-carboxamide

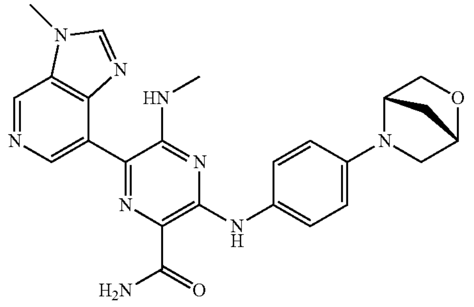 [SMILES: CNc1nc(Nc2ccc(N3C[C@@H]4C[C@H]3CO4)cc2)c(C(N)=O)nc1-c1cncc2c1ncn2C]

(a) (1S,4S)-5-(4-Bromophenyl)-2-oxa-5-azabicyclo[2.2.1]heptane (1S,4S)-2-Oxa-5-azabicyclo[2.2.1]heptane hydrochloride (500 mg, 3.69 mmol) was added to a mixture of 1-bromo-4-iodo-benzene (1043 mg, 3.69 mmol), potassium tert-butoxide (1.24 g, 11.1 mmol), palladium (II) acetate (83 mg, 0.37 mmol), and (rac)-BINAP (230 mg, 0.37 mmol) in toluene (10 mL) under nitrogen. The resulting mixture was stirred at 100° C. for 1 hour. The reaction was then concentrated. The resulting residue was purified by silica gel chromatography, using 0-50% EtOAc-petroleum ether as eluent, to afford (1S,4S)-5-(4-bromophenyl)-2-oxa-5-azabicyclo[2.2.1]heptane (97 mg, 10% yield) as a red solid; 1H NMR (400 MHZ, DMSO-d6) § 1.84 (1H, ddt), 1.92 (1H, dd), 2.93 (1H, dt), 3.47 (1H, dd), 3.63 (1H, dd), 3.73 (1H, dd), 4.54 (1H, dt), 4.61 (1H, t), 6.54-6.64 (2H, m), 7.25-7.33 (2H, m). m/z: (ES+), [M+H]+=254.1

(b) Methyl 5-(methylamino)-6-(3-methylimidazo[4,5-c]pyridin-7-yl)-3-[4-[(1S,4S)-2-oxa-5-azabicyclo[2.2.1]heptan-5-yl]anilino]pyrazine-2-carboxylate (1S,4S)-5-(4-Bromophenyl)-2-oxa-5-azabicyclo[2.2.1]heptane (97 mg, 0.38 mmol) was added to a suspension of methyl 3-amino-5-(methylamino)-6-(3-methylimidazo[4,5-c]pyridin-7-yl)pyrazine-2-carboxylate (80 mg, 0.26 mmol), cesium carbonate (250 mg, 0.77 mmol) and BrettPhos Pd G3 (34.7 mg, 0.04 mmol) in 1,4-dioxane (5 mL) under nitrogen. The resulting mixture was stirred at 100° C. for 16 hours. The reaction was then concentrated. The resulting residue was purified by silica gel chromatography, using 0-20% MeOH-DCM as eluent, to afford methyl 5-(methylamino)-6-(3-methylimidazo[4,5-c]pyridin-7-yl)-3-[4-[(1S,4S)-2-oxa-5-azabicyclo[2.2.1]heptan-5-yl]anilino]pyrazine-2-carboxylate (0.060 g, 48% yield) as a yellow solid. 1H NMR (300 MHz, DMSO-d6) δ 1.82-1.84 (1H, m), 1.87-1.93 (1H, m), 2.87 (3H, d), 2.89-2.96 (1H, m), 3.47-3.49 (1H, m), 3.64-3.71 (2H, m), 3.80 (3H, s), 3.99 (3H, s), 4.50-4.52 (1H, m), 4.55-4.61 (1H, m), 6.63 (2H, d), 7.59 (2H, d), 7.88 (1H, br q), 8.48 (1H, s), 8.52 (1H, s), 9.02 (1H, s), 10.17 (1H, s). m/z: (ES+), $[M+2H]^{2+}$=244.1

(c) 5-(Methylamino)-6-(3-methylimidazo[4,5-c]pyridin-7-yl)-3-[4-[(1S,4S)-2-oxa-5-azabicyclo[2.2.1]heptan-5-yl]anilino]pyrazine-2-carboxamide 7 N Methanolic ammonia (8.0 mL, 56 mmol) was added to methyl 5-(methylamino)-6-(3-methylimidazo[4,5-c]pyridin-7-yl)-3-[4-[(1S,4S)-2-oxa-5-azabicyclo[2.2.1]heptan-5-yl]anilino]pyrazine-2-carboxylate (50 mg, 0.10 mmol) at rt. The resulting mixture was stirred at 90° C. for 24 hours. The reaction was then concentrated. The resulting residue was purified by preparative HPLC, using a 5 micron, 30 mm×150 mm, Xselect CSH OBD column, 15-40 MeCN/H2O as eluent, and 0.1% formic acid as modifier, to afford 5-(methylamino)-6-(3-methylimidazo[4,5-c]pyridin-7-yl)-3-[4-[(1S,4S)-2-oxa-5-azabicyclo[2.2.1]heptan-5-yl]anilino]pyrazine-2-carboxamide (5.0 mg, 10%) as a brown solid; 1H NMR (300 MHZ, DMSO-d6) δ 1.83 (1H, d), 1.93 (1H, d), 2.90-3.00 (4H, m), 3.46-3.56 (1H, m), 3.66-3.79 (2H, m), 4.02 (3H, s), 4.52 (1H, s), 4.60 (1H, s), 6.65 (2H, d), 7.29 (1H, s), 7.61 (2H, d), 7.70 (1H, s), 8.00 (1H, br q), 8.52 (1H, s), 8.73 (1H, s), 9.01 (1H, s), 11.20 (1H, s). m/z: (ES+), [M+H]+=472.2

Example 78

3-[2-Fluoro-4-[(1S,4S)-2-oxa-5-azabicyclo[2.2.1]heptan-5-yl]anilino]-5-(methylamino)-6-(3-methylimidazo[4,5-c]pyridin-7-yl)pyrazine-2-carboxamide

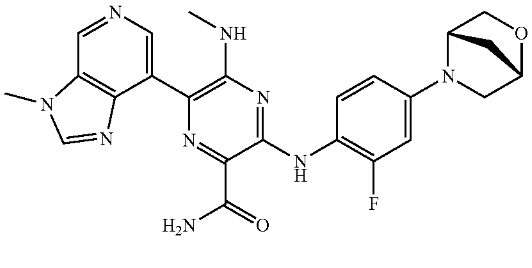 [SMILES: CNc1nc(Nc2ccc(N3C[C@@H]4C[C@H]3CO4)cc2F)c(C(N)=O)nc1-c1cncc2c1ncn2C]

(a) Methyl 3-[2-fluoro-4-[(1S,4S)-2-oxa-5-azabicyclo[2.2.1]heptan-5-yl]anilino]-5-(methylamino)-6-(3-methylimidazo[4,5-c]pyridin-7-yl)pyrazine-2-carboxylate BrettPhos Pd G3 (87 mg, 0.10 mmol) was added to a suspension of (1S,4S)-5-(4-bromo-3-fluoro-phenyl)-2-oxa-5-azabicyclo[2.2.1]heptane (347 mg, 1.28 mmol), methyl 3-amino-5-(methylamino)-6-(3-methylimidazo[4,5-c]pyridin-7-yl)pyrazine-2-carboxylate (200 mg, 0.64 mmol), and cesium carbonate (624 mg, 1.91 mmol) in 1,4-dioxane (16 mL) under nitrogen. The resulting mixture was stirred at 100° C. for 16 hours. The reaction was then concentrated. The resulting residue was purified by silica gel chromatography, using 0-25% MeOH-DCM as eluent, to afford methyl 3-[2-fluoro-4-[(1S,4S)-2-oxa-5-azabicyclo[2.2.1]heptan-5-yl]anilino]-5-(methylamino)-6-(3-methylimidazo[4,5-c]pyridin-7-yl)pyrazine-2-carboxylate (0.140 g, 44%) as a yellow solid. 1H NMR (300 MHz, DMSO-d6) δ 1.84 (1H, d), 1.93 (1H, d), 2.84 (3H, d), 2.98 (1H, d), 3.50 (1H, d), 3.69 (1H, d), 3.69 (1H, d), 3.83 (3H, s), 4.01 (3H, d), 4.61 (2H, d), 6.44-6.52 (1H, m), 6.60-6.72 (1H, m), 7.90 (1H, br q), 8.24 (1H, t), 8.43-8.56 (2H, m), 9.02 (1H, d), 10.23 (1H, d). m/z: (ES+), [M+H]+=505.2

(b) 3-[2-Fluoro-4-[(1S,4S)-2-oxa-5-azabicyclo[2.2.1]heptan-5-yl]anilino]-5-(methylamino)-6-(3-methylimidazo[4,5-c]pyridin-7-yl)pyrazine-2-carboxamide 7 N Methanolic ammonia (16.0 mL, 112 mmol) was added to methyl 3-[2-fluoro-4-[(1S,4S)-2-oxa-5-azabicyclo[2.2.1]heptan-5-yl]anilino]-5-(methylamino)-6-(3-methylimidazo[4,5-c]pyridin-7-yl)pyrazine-2-carboxylate (120 mg, 0.24 mmol). The resulting mixture was stirred at 80° C. for 16 hours. The reaction was then concentrated. The resulting residue was purified by preparative HPLC, using a 5 micron, 30 mm×150 mm, XSelect CSH OBD column, decreasingly polar mixtures of MeCN—$H_2O$ as eluent, and 0.1% formic acid as modifier, to afford 3-[2-fluoro-4-[(1S,4S)-2-oxa-5-azabicyclo[2.2.1]heptan-5-yl]anilino]-5-(methylamino)-6-(3-methylimidazo[4,5-c]pyridin-7-yl)pyrazine-2-carboxamide (0.042 g, 36%) as a yellow solid. 1H NMR (DMSO-d6, 400 MHZ) δ 1.80-1.87 (1H, m), 1.89-1.96 (1H, m), 2.91 (3H, d), 2.97 (1H, d), 3.45-3.52 (1H, m), 3.69 (1H, d), 3.74 (1H, d), 4.01 (3H, s), 4.56 (1H, s), 4.61 (1H, s), 6.42-6.50 (1H, m), 6.58-6.68 (1H, m), 7.31 (1H, d), 7.71 (1H, d), 7.99 (1H, br q), 8.34 (1H, t), 8.52 (1H, s), 8.73 (1H, s), 9.01 (1H, s), 11.24 (1H, d). 19F NMR (376 MHz, DMSO) δ −127.15, −127.39. m/z: (ES+), [M+H]+=490.2

Example 79

3-[2,3-Difluoro-4-[(1S,4S)-2-oxa-5-azabicyclo[2.2.1]heptan-5-yl]anilino]-5-(methylamino)-6-(3-methylimidazo[4,5-c]pyridin-7-yl)pyrazine-2-carboxamide

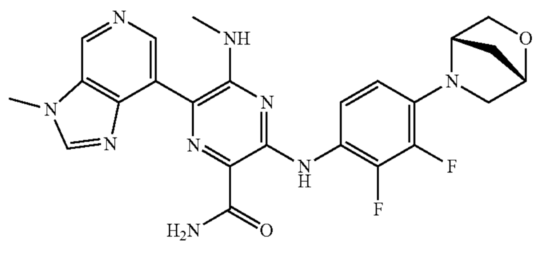 [SMILES: CNc1nc(Nc2ccc(N3C[C@@H]4C[C@H]3CO4)c(F)c2F)c(C(N)=O)nc1-c1cncc2c1ncn2C]

(a) (1S,4S)-5-(4-Bromo-2,3-difluoro-phenyl)-2-oxa-5-azabicyclo[2.2.1]heptane

Palladium (II) acetate (63 mg, 0.28 mmol) was added to a mixture of 1-bromo-2,3-difluoro-4-iodobenzene (900 mg, 2.82 mmol), (1S,4S)-2-oxa-5-azabicyclo[2.2.1]heptane hydrochloride (421 mg, 3.10 mmol), cesium carbonate (3.22 g, 9.88 mmol), and rac-BINAP (176 mg, 0.280 mmol) in 1,4-dioxane (15 mL) under nitrogen. The resulting mixture was stirred at 100° C. for 3 hours. The reaction was then concentrated. The resulting residue was purified by silica gel chromatography, using 0-40% EtOAc-petroleum ether as eluent, to afford (1S,4S)-5-(4-bromo-2,3-difluoro-phenyl)-2-oxa-5-azabicyclo[2.2.1]heptane (0.420 g, 51%) as a yellow solid; 1H NMR (300 MHz, $CDCl_3$) δ 1.91-2.10 (2H, m), 3.21-3.32 (1H, m), 3.60-3.72 (1H, m), 3.87 (1H, d), 3.97 (1H, d), 4.53 (1H, s), 4.64 (1H, s), 6.24-6.35 (1H, m), 7.04-7.16 (1H, m); m/z: (ES+), [M+H]+=290.1

(b) Methyl 3-[2,3-difluoro-4-[(1S,4S)-2-oxa-5-azabicyclo[2.2.1]heptan-5-yl]anilino]-5-(methylamino)-6-(3-methylimidazo[4,5-c]pyridin-7-yl)pyrazine-2-carboxylate BrettPhos Pd G3 (87 mg, 0.10 mmol) was added to a suspension of (1S,4S)-5-(4-bromo-2,3-difluoro-phenyl)-2-oxa-5-azabicyclo[2.2.1]heptane (278 mg, 0.960 mmol), methyl 3-amino-5-(methylamino)-6-(3-methylimidazo[4,5-c]pyridin-7-yl)pyrazine-2-carboxylate (200 mg, 0.64 mmol), and cesium carbonate (624 mg, 1.91 mmol) in 1,4-dioxane (16 mL) under nitrogen. The resulting mixture was stirred at 100° C. for 16 hours. The reaction was then concentrated. The resulting residue was purified by silica gel chromatography, using 0-20% MeOH-DCM as eluent, to afford methyl 3-[2,3-difluoro-4-[(1S,4S)-2-oxa-5-azabicyclo[2.2.1]heptan-5-yl]anilino]-5-(methylamino)-6-(3-methylimidazo[4,5-c]pyridin-7-yl)pyrazine-2-carboxylate (0.140 g, 42%) as a yellow solid; 1H NMR (DMSO-d6, 300 MHz) δ 1.76-2.02 (2H, m), 2.84 (3H, d), 3.06-3.17 (1H, m), 3.59-3.70 (1H, m), 3.72-3.89 (5H, m), 4.00 (3H, s), 4.55 (2H, d), 6.65 (1H, t), 7.96 (1H, br q), 7.99-8.14 (1H, m), 8.42-8.61 (2H, m), 9.02 (1H, d), 10.30 (1H, s); m/z: (ES+), [M+H]+=523.2

(c) 3-[2,3-Difluoro-4-[(1S,4S)-2-oxa-5-azabicyclo[2.2.1]heptan-5-yl]anilino]-5-(methylamino)-6-(3-methylimidazo[4,5-c]pyridin-7-yl)pyrazine-2-carboxamide 7 N Methanolic ammonia (12 mL, 84 mmol) was added to methyl 3-[2,3-difluoro-4-[(1S,4S)-2-oxa-5-azabicyclo[2.2.1]heptan-5-yl]anilino]-5-(methylamino)-6-(3-methylimidazo[4,5-c]pyridin-7-yl)pyrazine-2-carboxylate (120 mg, 0.23 mmol). The resulting mixture was stirred at 80° C. for 16 hours. The reaction was then concentrated. The resulting residue was purified by preparative HPLC, using a 5 micron, 30 mm×150 mm, Xselect CSH OBD column, decreasingly polar mixtures of MeCN—$H_2O$ as eluent, and 0.1% formic acid as modifier, to afford 3-[2,3-difluoro-4-[(1S,4S)-2-oxa-5-azabicyclo[2.2.1]heptan-5-yl]anilino]-5-(methylamino)-6-(3-methylimidazo[4,5-c]pyridin-7-yl)pyrazine-2-carboxamide (25 mg, 21%) as a yellow solid. 1H NMR (400 MHZ, DMSO-d6) δ 1.79-1.87 (1H, m), 1.89-1.96 (1H, m), 2.91 (3H, d), 3.06-3.14 (1H, m), 3.59-3.67 (1H, m), 3.76 (1H, d), 3.84 (1H, d), 4.01 (3H, s), 4.49 (1H, s), 4.58 (1H, s), 6.65 (1H, t), 7.38 (1H, s), 7.75 (1H, s), 7.99 (1H, br q), 8.14-8.22 (1H, m), 8.52 (1H, s), 8.73 (1H, s), 9.03 (1H, s), 11.44 (1H, d); m/z: (ES+), [M+H]+=508.3

Example 80

5-(Methylamino)-6-(3-methylimidazo[4,5-c]pyridin-7-yl)-3-[2,3,5-trifluoro-4-[(1S,4S)-2-oxa-5-azabicyclo[2.2.1]heptan-5-yl]anilino]pyrazine-2-carboxamide

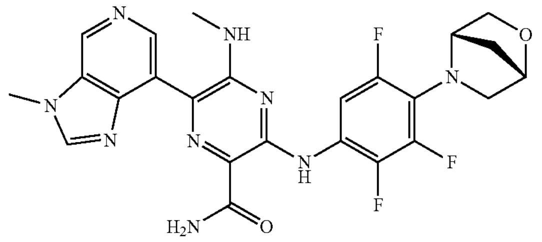 [SMILES: CNc1nc(Nc2cc(F)c(N3C[C@@H]4C[C@H]3CO4)c(F)c2F)c(C(N)=O)nc1-c1cncc2c1ncn2C]

(a) (1S,4S)-5-(2,3,6-Trifluoro-4-nitro-phenyl)-2-oxa-5-azabicyclo[2.2.1]heptane

DIPEA (1.79 mL, 10.3 mmol) was added to a solution of 1,2,3,4-tetrafluoro-5-nitro-benzene (2.00 g, 10.3 mmol) and (1S,4S)-2-oxa-5-azabicyclo[2.2.1]heptane (1.02 g, 10.3 mmol) in acetonitrile (15 mL). The resulting mixture was stirred at room temperature for 2 hours. The reaction was then concentrated. The resulting residue was purified by silica gel chromatography, using 0-20% DCM-petroleum as eluent, to afford (1S,4S)-5-(2,3,6-trifluoro-4-nitro-phenyl)-2-oxa-5-azabicyclo[2.2.1]heptane (1.70 g, 61% yield) as a yellow solid. 1H NMR (300 MHz, DMSO-d6) § 1.84-2.04 (2H, m), 3.41-3.53 (1H, m), 3.80-3.93 (3H, m), 4.65 (1H, s), 4.77-4.87 (1H, m), 7.85-7.94 (1H, m). m/z: (ES+), [M+H]+ =275.0

(b) 2,3,5-Trifluoro-4-[(1S,4S)-2-oxa-5-azabicyclo[2.2.1]heptan-5-yl]aniline

Iron powder (815 mg, 14.6 mmol) was added to a mixture of ammonium chloride (780 mg, 14.6 mmol) and (1S,4S)-5-(2,3,6-trifluoro-4-nitro-phenyl)-2-oxa-5-azabicyclo[2.2.1]heptane (800 mg, 2.92 mmol) in EtOH (7 mL) and water (7 mL) under nitrogen. The resulting mixture was stirred at 80° C. for 2 hours. The reaction was then concentrated. The resulting residue was taken into water, treated with saturated aqueous sodium bicarbonate, and extracted with dichloromethane. The extract was dried over sodium sulfate, filtered, and concentrated to afford 2,3,5-trifluoro-4-[(1S,4S)-2-oxa-5-azabicyclo[2.2.1]heptan-5-yl]aniline (0.670 g, 94% yield) as a purple solid. 1H NMR (300 MHz, DMSO-d6) δ 1.70-1.92 (2H, m), 3.13 (1H, d), 3.39-3.50 (1H, m), 3.62-3.84 (2H, m), 4.14 (1H, s), 4.52 (1H, s), 5.21 (2H, d), 6.32-6.44 (1H, m). m/z: (ES+), [M+H]+=245.2

(c) (1S,4S)-5-(4-Bromo-2,3,6-trifluoro-phenyl)-2-oxa-5-azabicyclo[2.2.1]heptane 2,3,5-Trifluoro-4-[(1S,4S)-2-oxa-5-azabicyclo[2.2.1]heptan-5-yl]aniline (300 mg, 1.23 mmol) was added to tert-butylnitrite, tech. grade (190 mg, 1.84 mmol) and trimethylbromosilane (188 mg, 1.23 mmol) in dibromomethane (5 mL) under nitrogen. The resulting mixture was stirred at room temperature for 3 hours. The reaction was then concentrated. The resulting residue was purified by silica gel chromatography, using 0-50% EtOAc-petroleum ether as eluent, to afford (1S,4S)-5-(4-bromo-2,3,6-trifluoro-phenyl)-2-oxa-5-azabicyclo[2.2.1]heptane (0.210 g, 56% yield) as a yellow solid. 1H NMR (400 MHZ, DMSO-d6) δ 1.73-2.00 (2H, m), 3.15-3.24 (1H, m), 3.66-3.91 (3H, m), 4.49-4.64 (2H, m), 7.39-7.49 (1H, m). m/z: (ES+), [M+H]+=308.0

(d) Methyl 5-(methylamino)-6-(3-methylimidazo[4,5-c]pyridin-7-yl)-3-[2,3,5-trifluoro-4-[(1S,4S)-2-oxa-5-azabicyclo[2.2.1]heptan-5-yl]anilino]pyrazine-2-carboxylate EPhos Pd G4 (67 mg, 0.070 mmol) was added to a suspension of EPhos (79 mg, 0.15 mmol), methyl 3-amino-5-(methylamino)-6-(3-methylimidazo[4,5-c]pyridin-7-yl) pyrazine-2-carboxylate (230 mg, 0.73 mmol), (1S,4S)-5-(4-bromo-2,3,6-trifluoro-phenyl)-2-oxa-5-azabicyclo[2.2.1] heptane (271 mg, 0.880 mmol), and cesium carbonate (718 mg, 2.20 mmol) in DMF (5 mL) under nitrogen. The resulting mixture was stirred at 100° C. for 3 hours. The reaction was then concentrated. The resulting residue was purified by silica gel chromatography, using 0-10% MeOH-DCM as eluent, to afford methyl 5-(methylamino)-6-(3-methylimidazo[4,5-c]pyridin-7-yl)-3-[2,3,5-trifluoro-4-[(1S,4S)-2-oxa-5-azabicyclo[2.2.1]heptan-5-yl]anilino] pyrazine-2-carboxylate (0.072 g, 18% yield) as a yellow solid. 1H NMR (300 MHz, DMSO-d6) δ 1.04-1.45 (2H, m), 1.76-1.98 (2H, m), 2.90 (3H, d), 3.76-3.90 (4H, m), 4.02 (3H, s), 4.30-4.72 (3H, m), 8.07 (1H, br q), 8.19-8.37 (1H, m), 8.43-8.56 (2H, m), 9.05 (1H, s), 10.56 (1H, s). m/z: (ES+), [M+H]+=541.2

(e) 5-(Methylamino)-6-(3-methylimidazo[4,5-c]pyridin-7-yl)-3-[2,3,5-trifluoro-4-[(1S,4S)-2-oxa-5-azabicyclo[2.2.1]heptan-5-yl]anilino]pyrazine-2-carboxamide 7 N Methanolic ammonia (10 mL, 70 mmol) was added to methyl 5-(methylamino)-6-(3-methylimidazo[4,5-c]pyridin-7-yl)-3-[2,3,5-trifluoro-4-[(1S,4S)-2-oxa-5-azabicyclo[2.2.1]heptan-5-yl]anilino]pyrazine-2-carboxylate (72 mg, 0.13 mmol). The resulting mixture was stirred at 80° C. for 16 hours. The reaction was then concentrated. The resulting residue was purified by preparative HPLC, using a 5 micron, 30 mm×150 mm, Sunfire prep C18 column, decreasingly polar mixtures of MeCN—$H_2O$ as eluent, and 0.1% formic acid as modifier, to afford 5-(methylamino)-6-(3-methylimidazo[4,5-c]pyridin-7-yl)-3-[2,3,5-trifluoro-4-[(1S,4S)-2-oxa-5-azabicyclo[2.2.1]heptan-5-yl]anilino]pyrazine-2-carboxamide (3.2 mg, 4.5% yield) as a orange solid. 1H NMR (DMSO-d6, 400 MHZ) δ 1.77-1.86 (1H, m), 1.86-1.98 (1H, m), 2.94 (3H, d), 3.19 (1H, d), 3.62-3.71 (1H, m), 3.74-3.85 (1H, m), 3.87 (1H, d), 4.01 (3H, s), 4.40-4.49 (1H, m), 4.58 (1H, d), 7.45 (1H, d), 7.80 (1H, d), 8.09 (1H, br q), 8.34-8.45 (1H, m), 8.52 (1H, s), 8.73 (1H, s), 9.04 (1H, s), 11.75 (1H, d). 19F NMR (376 MHz, DMSO) δ −127.20, −149.07-157.99. m/z: (ES+), [M+H]+=526.3

Example 81

5-(Methylamino)-6-(3-methylimidazo[4,5-c]pyridin-7-yl)-3-[4-(6-oxa-3-azabicyclo[3.1.1]heptan-3-yl)anilino]pyrazine-2-carboxamide

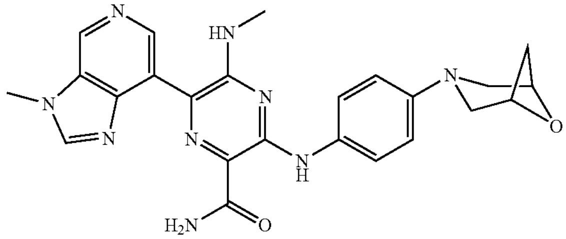 [SMILES: CNc1nc(Nc2ccc(N3CC4CC(C3)O4)cc2)c(C(N)=O)nc1-c1cncc2c1ncn2C]

(a) 3-(4-Bromophenyl)-6-oxa-3-azabicyclo[3.1.1]heptane

Potassium tert-butoxide (595 mg, 5.30 mmol) was added to a mixture of 6-oxa-3-azabicyclo[3.1.1]heptane hydrochloride (240 mg, 1.77 mmol), 1-bromo-4-iodo-benzene (500 mg, 1.77 mmol), palladium (II) acetate (40 mg, 0.18 mmol), and (rac)-BINAP (110 mg, 0.18 mmol) in toluene (5 mL) under nitrogen. The resulting mixture was stirred at 100° C. for 2 hours. The reaction was then concentrated. The resulting residue was purified by silica gel chromatography, using 0-50% EtOAc in petroleum ether as eluent, to afford 3-(4-bromophenyl)-6-oxa-3-azabicyclo[3.1.1]heptane (0.300 g, 67%) as a brown solid; 1H NMR (400 MHz, DMSO-d6) δ 1.90 (1H, dt), 3.12 (1H, dt), 3.36 (2H, dd), 3.51 (2H, d), 4.71 (2H, dd), 6.65-6.74 (2H, m), 7.32-7.40 (2H, m); m/z: (ES+), [M+H]+=254.0

(b) Methyl 5-(methylamino)-6-(3-methylimidazo[4,5-c]pyridin-7-yl)-3-[4-(6-oxa-3-azabicyclo[3.1.1]heptan-3-yl)anilino]pyrazine-2-carboxylate 3-(4-Bromophenyl)-6-oxa-3-azabicyclo[3.1.1]heptane (81 mg, 0.32 mmol) was added to a suspension of methyl 3-amino-5-(methylamino)-6-(3-methylimidazo[4,5-c]pyridin-7-yl)pyrazine-2-carboxylate (100 mg, 0.32 mmol), cesium carbonate (312 mg, 0.96 mmol), and BrettPhos Pd G3 (44 mg, 0.050 mmol) in 1,4-dioxane (5 mL) at rt under nitrogen. The resulting mixture was stirred at 100° C. for 16 hours. The reaction was then concentrated. The resulting residue was purified by silica gel chromatography, using 0-30% MeOH-DCM as eluent, to afford methyl 5-(methylamino)-6-(3-methylimidazo[4,5-c]pyridin-7-yl)-3-[4-(6-oxa-3-azabicyclo[3.1.1]heptan-3-yl)anilino]pyrazine-2-carboxylate (0.060 g, 39%) as a yellow solid; 1H NMR (300 MHz, DMSO-d6) δ 1.96 (1H, d), 2.90 (3H, d), 3.11-3.18 (1H, m), 3.36-3.44 (2H, m), 3.51-3.58 (2H, m), 3.83 (3H, s), 4.02 (3H, s), 4.73 (2H, d), 6.77 (2H, d), 7.67 (2H, d), 8.47 (1H, d), 8.50 (1H, s), 8.54 (1H, s), 9.04 (1H, s), 10.20 (1H, s); m/z: (ES+), $[M+2H]^{2+}$=486.2

(c) 5-(Methylamino)-6-(3-methylimidazo[4,5-c]pyridin-7-yl)-3-[4-(6-oxa-3-azabicyclo[3.1.1]heptan-3-yl)anilino]pyrazine-2-carboxamide 7 N Methanolic ammonia (8.0 mL, 56 mmol) was added to methyl 5-(methylamino)-6-(3-methylimidazo[4,5-c]pyridin-7-yl)-3-[4-(6-oxa-3-azabicyclo[3.1.1]heptan-3-yl)anilino]pyrazine-2-carboxylate (60.0 mg, 0.12 mmol). The resulting suspension was stirred at 90° C. for 24 hours. The reaction was then concentrated. The resulting residue was purified by preparative HPLC, using a 5 micron, 19 mm×250 mm XSelect CSH Prep C18 OBD column, 25-33% MeCN—$H_2O$ as eluent, and 0.1% formic acid as modifier, to afford 5-(methylamino)-6-(3-methylimidazo[4,5-c]pyridin-7-yl)-3-[4-(6-oxa-3-azabicyclo[3.1.1]heptan-3-yl)anilino]pyrazine-2-carboxamide (9.0 mg, 15%) as a brown solid; 1H NMR (300 MHz, DMSO-d6) δ 1.97 (1H, d), 2.94 (3H, d), 3.12 (1H, q), 3.38 (2H, d), 3.57 (2H, d), 4.02 (3H, s), 4.71 (2H, d), 6.76 (2H, d), 7.30 (1H, s), 7.62-7.73 (3H, m), 8.00 (1H, br q), 8.52 (1H, s), 8.74 (1H, s), 9.01 (1H, s), 11.20 (1H, s); m/z: (ES+), [M+H]+=472.2

Example 82

5-(Methylamino)-6-(3-methylimidazo[4,5-c]pyridin-7-yl)-3-[4-(8-oxa-3-azabicyclo[3.2.1]octan-3-yl)anilino]pyrazine-2-carboxamide

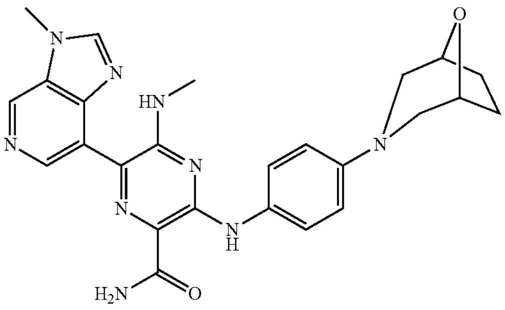 [SMILES: CNc1nc(Nc2ccc(N3CC4CCC(C3)O4)cc2)c(C(N)=O)nc1-c1cncc2c1ncn2C]

(a) 3-(4-Bromophenyl)-8-oxa-3-azabicyclo[3.2.1]octane

Potassium tert-butoxide (595 mg, 5.30 mmol) was added to a mixture of 8-oxa-3-azabicyclo[3.2.1]octane, 1-bromo-4-iodo-benzene (500 mg, 1.77 mmol), (rac)-BINAP (165 mg, 0.270 mmol), and palladium (II) acetate (59.5 mg, 0.270 mmol) in toluene (5 mL) under nitrogen. The resulting mixture was stirred at 100° C. for 2 hours. The reaction was then concentrated. The resulting residue was purified by silica gel chromatography, using 0-20% MeOH-DCM as eluent, to afford 3-(4-bromophenyl)-8-oxa-3-azabicyclo[3.2.1]octane (0.200 g, 42%) as a red solid; 1H NMR (400 MHZ, DMSO-d6) δ 1.76-1.88 (4H, m), 2.78 (2H, dd), 3.33-3.41 (2H, m), 4.42 (2H, t), 6.75-6.84 (2H, m), 7.28-7.37 (2H, m); m/z: (ES+), [M+H]+=268.0

(b) Methyl 5-(methylamino)-6-(3-methylimidazo[4,5-c]pyridin-7-yl)-3-[4-(8-oxa-3-azabicyclo[3.2.1]octan-3-yl)anilino]pyrazine-2-carboxylate Brettphos Pd G3 (58 mg, 0.060 mmol) was added to a suspension of methyl 3-amino-5-(methylamino)-6-(3-methylimidazo[4,5-c]pyridin-7-yl)pyrazine-2-carboxylate (100 mg, 0.32 mmol), (1S,5R)-3-(4-bromophenyl)-8-oxa-3-azabicyclo[3.2.1]octane (103 mg, 0.380 mmol), and Cesium carbonate (312 mg, 0.960 mmol) in 1,4-dioxane (5 mL) under nitrogen. The resulting mixture was stirred at 100° C. for 16 hours. The reaction was then concentrated. The resulting residue was purified by silica gel chromatography, using 0-10% MeOH-DCM as eluent, to afford methyl 5-(methylamino)-6-(3-methylimidazo[4,5-c]pyridin-7-yl)-3-[4-(8-oxa-3-azabicyclo[3.2.1]octan-3-yl)anilino]pyrazine-2-carboxylate (0.068 g, 43%) as a yellow solid; 1H NMR (400 MHZ, DMSO-d6) δ 1.85 (4H, s), 2.79 (2H, dd), 2.90 (3H, d), 3.37 (2H, d), 3.82 (3H, s), 4.01 (3H, s), 4.42 (2H, s), 6.86 (2H, d), 7.64 (2H, d), 7.90 (1H, br q), 8.50 (1H, s), 8.54 (1H, s), 9.04 (1H, s), 10.24 (1H, s); m/z: (ES+), $[M+2H]^{2+}$=251.1

(c) 5-(Methylamino)-6-(3-methylimidazo[4,5-c]pyridin-7-yl)-3-[4-(8-oxa-3-azabicyclo[3.2.1]octan-3-yl)anilino]pyrazine-2-carboxamide 7 N Methanolic ammonia (5.0 mL, 35 mmol) was added to methyl 5-(methylamino)-6-(3-methylimidazo[4,5-c]pyridin-7-yl)-3-[4-(8-oxa-3-azabicyclo[3.2.1]octan-3-yl)anilino]pyrazine-2-carboxylate (60 mg, 0.12 mmol). The resulting suspension was stirred at 80° C. for 40 hours. The reaction was then concentrated. The resulting residue was purified by preparative HPLC, using a 5 micron, 50 mm×100 mm XSelect CSH Prep C18 OBD column, decreasingly polar mixtures of MeCN—$H_2O$ as eluent, and 0.1% formic acid as modifier, to afford 5-(methylamino)-6-(3-methylimidazo[4,5-c]pyridin-7-yl)-3-[4-(8-oxa-3-azabicyclo[3.2.1]octan-3-yl)anilino]pyrazine-2-carboxamide (25 mg, 42%) as a orange solid; 1H NMR (400 MHZ, DMSO-d6) δ 1.76-1.92 (4H, m), 2.78 (2H, dd), 2.93 (3H, d), 3.36 (2H, d), 4.01 (3H, s), 4.41 (2H, s), 6.85 (2H, d), 7.29 (1H, s), 7.63 (2H, d), 7.70 (1H, s), 7.99 (1H, br q), 8.51 (1H, s), 8.72 (1H, s), 9.00 (1H, s), 11.25 (1H, s); m/z: (ES+), [M+H]+=486.2

Example 83

5-(Methylamino)-6-(3-methylimidazo[4,5-c]pyridin-7-yl)-3-[4-(2-oxa-6-azaspiro[3.3]heptan-6-yl)anilino]pyrazine-2-carboxamide

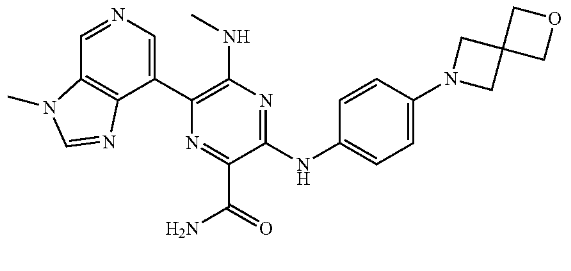 [SMILES: CNc1nc(Nc2ccc(N3CC4(COC4)C3)cc2)c(C(N)=O)nc1-c1cncc2c1ncn2C]

(a) 6-(4-Bromophenyl)-2-oxa-6-azaspiro[3 3]heptane

1-Bromo-4-iodo-benzene (500 mg, 1.77 mmol) was added to a suspension of potassium tert-butoxide (595 mg, 5.30 mmol), 2-oxa-6-azaspiro[3.3]heptane (175 mg, 1.77 mmol), (rac)-BINAP (165 mg, 0.270 mmol), and palladium (II) acetate (60 mg, 0.27 mmol) in toluene (20 mL) under nitrogen. The resulting mixture was stirred at 100° C. for 5 hours. The reaction was then concentrated. The resulting residue was purified by silica gel chromatography, using 0-50% MeOH-DCM as eluent, to afford 6-(4-bromophenyl)-2-oxa-6-azaspiro[3.3]heptane (0.250 g, 56%) as a yellow oil; 1H NMR (400 MHZ, DMSO-d6) δ 3.96 (4H, s), 4.71 (4H, s), 6.34-6.43 (2H, m), 7.26-7.34 (2H, m); m/z: (ES+) [M+H]+=254.0

(b) Methyl 5-(methylamino)-6-(3-methylimidazo[4,5-c]pyridin-7-yl)-3-[4-(2-oxa-6-azaspiro[3 3]heptan-6-yl)anilino]pyrazine-2-carboxylate 6-(4-Bromophenyl)-2-oxa-6-azaspiro[3.3]heptane (122 mg, 0.480 mmol) was added to methyl 3-amino-5-(methylamino)-6-(3-methylimidazo[4,5-c]pyridin-7-yl)pyrazine-2-carboxylate (100 mg, 0.32 mmol), cesium carbonate (312 mg, 0.960 mmol), and BrettPhos Pd G3 (43 mg, 0.050 mmol) in 1,4-dioxane (10 mL) under nitrogen. The resulting mixture was stirred at 100° C. for 16 hours. The reaction was then concentrated. The resulting residue was purified by silica gel chromatography, using 0-30% MeOH-DCM as eluent, to afford methyl 5-(methylamino)-6-(3-methylimidazo[4,5-c]pyridin-7-yl)-3-[4-(2-oxa-6-azaspiro[3.3]heptan-6-yl)anilino]pyrazine-2-carboxylate (0.080 g, 52%) as a yellow solid; 1H NMR (400 MHZ, DMSO-d6) δ 2.88 (3H, d), 3.82 (3H, s), 3.96 (4H, s), 4.01 (3H, s), 4.73 (4H, s), 6.45-6.53 (2H, m), 7.56-7.64 (2H, m), 7.90 (1H, br q), 8.50 (1H, s), 8.54 (1H, s), 9.04 (1H, s), 10.19 (1H, s); m/z: (ES+), [M+H]+=487.3

(c) 5-(Methylamino)-6-(3-methylimidazo[4,5-c]pyridin-7-yl)-3-[4-(2-oxa-6-azaspiro[3 3]heptan-6-yl)anilino]pyrazine-2-carboxamide 7 N Methanolic ammonia (7.0 mL, 49 mmol) was added to methyl 5-(methylamino)-6-(3-methylimidazo[4,5-c]pyridin-7-yl)-3-[4-(2-oxa-6-azaspiro[3.3]heptan-6-yl)anilino]pyrazine-2-carboxylate (60 mg, 0.12 mmol). The resulting suspension was stirred at 85° C. for 2 days. The reaction was then concentrated. The resulting residue was purified by c18 reverse phase chromatography, using 0-50% MeCN—$H_2O$ as eluent and 1% formic acid as modifier, to afford a yellow solid. The resulting residue was purified further by preparative HPLC, using a 5 micron, 30 mm×150 mm XBridge Shield RP18 OBD column, 27-35% MeCN—$H_2O$ as eluent, and 0.1% ammonium hydroxide as modifier, to afford 5-(methylamino)-6-(3-methylimidazo[4,5-c]pyridin-7-yl)-3-[4-(2-oxa-6-azaspiro[3.3]heptan-6-yl)anilino]pyrazine-2-carboxamide (9.0 mg, 15%) as a yellow solid; 1H NMR (400 MHz, DMSO-d6) δ 2.92 (3H, d), 3.95 (4H, s), 4.02 (3H, s), 4.72 (4H, s), 6.47 (2H, d), 7.29 (1H, s), 7.60 (2H, d), 7.70 (1H, s), 7.98 (1H, br q), 8.52 (1H, s), 8.73 (1H, s), 9.01 (1H, s), 11.21 (1H, s). m/z: (ES+), [M+H]+=472.3

Example 84

3-Anilino-5-(methylamino)-6-(3-methylimidazo[4,5-c]pyridin-7-yl)pyrazine-2-carboxamide

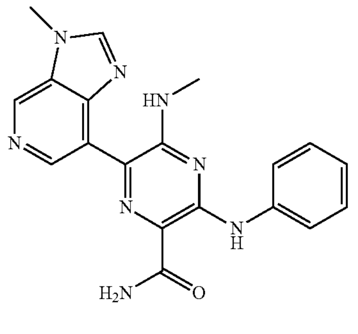 [SMILES: CNc1nc(Nc2ccccc2)c(C(N)=O)nc1-c1cncc2c1ncn2C]

(a) Methyl 3-anilino-5-(methylamino)-6-(3-methylimidazo[4,5-c]pyridin-7-yl)pyrazine-2-carboxylate Brettphos Pd G3 (58 mg, 0.060 mmol) was added to a suspension of methyl 3-amino-5-(methylamino)-6-(3-methylimidazo[4,5-c]pyridin-7-yl)pyrazine-2-carboxylate (100 mg, 0.32 mmol), bromobenzene (50 mg, 0.32 mmol), and cesium carbonate (312 mg, 0.96 mmol) in 1,4-dioxane (10 mL) under nitrogen. The resulting mixture was stirred at 100° C. for 16 hours. The reaction was then concentrated. The resulting residue was purified by silica gel chromatography, using 0-10% MeOH-DCM as eluent, to afford methyl 3-anilino-5-(methylamino)-6-(3-methylimidazo[4,5-c]pyridin-7-yl)pyrazine-2-carboxylate (0.090 g, 72%) as a brown solid. 1H NMR (DMSO-d6, 300 MHz) δ 2.92 (3H, d), 3.82 (3H, s), 4.01 (3H, s), 7.05 (1H, t), 7.37 (2H, t), 7.82 (2H, d), 7.95 (1H, br s), 8.52 (2H, d), 9.04 (1H, s), 10.45 (1H, s); m/z: (ES+), [M+H]+=390.2

(b) 3-Anilino-5-(methylamino)-6-(3-methylimidazo[4,5-c]pyridin-7-yl)pyrazine-2-carboxamide 7 N Methanolic ammonia (10 mL, 70 mmol) was added to methyl 3-anilino-5-(methylamino)-6-(3-methylimidazo[4,5-c]pyridin-7-yl)pyrazine-2-carboxylate (80 mg, 0.21 mmol). The resulting suspension was stirred at 80° C. for 16 hours. The reaction was then concentrated. The resulting residue was purified by preparative HPLC, using a 5 micron, 30 mm×150 mm, Xselect CSH OBD column, 25-40% MeCN—$H_2O$ as eluent, and 0.1% formic acid as modifier, to afford 3-anilino-5-(methylamino)-6-(3-methylimidazo[4,5-c]pyridin-7-yl)pyrazine-2-carboxamide (18 mg, 23%) as a yellow solid; 1H NMR (400 MHZ, DMSO-d6) δ 2.96 (3H, d), 4.01 (3H, s), 6.99-7.02 (1H, m), 7.31-7.41 (3H, m), 7.73-7.84 (3H, m), 8.01 (1H, d), 8.52 (1H, s), 8.73 (1H, s), 9.02 (1H, s), 11.54 (1H, s); m/z: (ES+), [M+H]+=375.2

Example 85

3-[4-(Difluoromethoxy)anilino]-5-(methylamino)-6-(3-methylimidazo[4,5-c]pyridin-7-yl)pyrazine-2-carboxamide

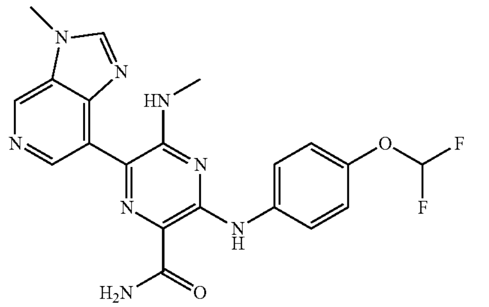 [SMILES: CNc1nc(Nc2ccc(OC(F)F)cc2)c(C(N)=O)nc1-c1cncc2c1ncn2C]

(a) Methyl 3-[4-(difluoromethoxy)anilino]-5-(methylamino)-6-(3-methylimidazo[4,5-c]pyridin-7-yl)pyrazine-2-carboxylate Methyl 3-amino-5-(methylamino)-6-(3-methylimidazo[4,5-c]pyridin-7-yl)pyrazine-2-carboxylate (140 mg, 0.45 mmol) was added to a mixture of cesium carbonate (438 mg, 1.35 mmol), 1-bromo-4-(difluoromethoxy)benzene (150 mg, 0.67 mmol), and BrettPhos Pd G3 (40 mg, 0.040 mmol) in 1,4-dioxane (10 mL) under nitrogen. The resulting mixture was stirred at 100° C. for 24 hours. The reaction was then concentrated. The resulting residue was purified by silica gel chromatography, using 0-10% MeOH-DCM as eluent, to afford methyl 3-[4-(difluoromethoxy)anilino]-5-(methylamino)-6-(3-methylimidazo[4,5-c]pyridin-7-yl)pyrazine-2-carboxylate (0.120 g, 59%) as a yellow solid; 1H NMR (400 MHZ, DMSO-d6) δ 2.91 (3H, d), 3.83 (3H, s), 4.01 (3H, s), 7.18 (1H, t), 7.19 (2H, d), 7.86 (2H, d), 7.94 (1H, br q), 8.50 (1H, s), 8.54 (1H, s), 9.05 (1H, s), 10.43 (1H, s); m/z: (ES+), [M+H]+=456.1.

(b) 3-[4-(Difluoromethoxy)anilino]-5-(methylamino)-6-(3-methylimidazo[4,5-c]pyridin-7-yl)pyrazine-2-carboxamide 7 N Methanolic ammonia (10 mL, 70 mmol) was added to methyl 3-[4-(difluoromethoxy)anilino]-5-(methylamino)-6-(3-methylimidazo[4,5-c]pyridin-7-yl)pyrazine-2-carboxylate (80 mg, 0.18 mmol). The resulting mixture was stirred at 80° C. for 2 days. The reaction was then concentrated. The resulting residue was purified by preparative HPLC using a 5 micron, 30×150 mm Xselect CSH OBD column, 18-45% MeCN—$H_2O$ as eluent, and 0.1% formic acid as modifier, to afford 3-[4-(difluoromethoxy)anilino]-5-(methylamino)-6-(3-methylimidazo[4,5-c]pyridin-7-yl)pyrazine-2-carboxamide (20 mg, 25%) as a yellow solid; 1H NMR (300 MHz, DMSO-d6) δ 2.95 (3H, d), 4.02 (3H, s), 7.17 (1H, t), 7.16-7.29 (2H, m), 7.42 (1H, s), 7.78 (1H, s), 7.82-7.88 (2H, m), 8.00 (1H, br q), 8.53 (1H, s), 8.73 (1H, s), 9.03 (1H, s), 11.57 (1H, s); m/z: (ES+), [M+H]+=441.3

Example 86

5-Cyclopropyl-3-[4-(1-hydroxy-1-methyl-ethyl)anilino]-6-(3-methylimidazo[4,5-c]pyridin-7-yl)pyrazine-2-carboxamide

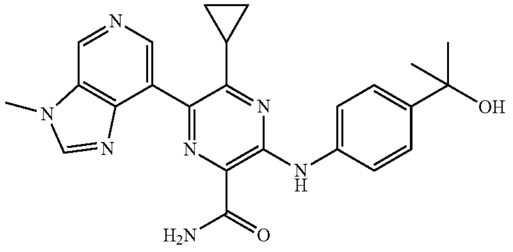

(a) Methyl 3-amino-5-cyclopropyl-6-(3-methylimidazo[4,5-c]pyridin-7-yl)pyrazine-2-carboxylate 7-Bromo-3-methyl-imidazo[4,5-c]pyridine (0.477 g, 2.25 mmol), bis(pinacolato)diboron (1.14 g, 4.50 mmol), CataCXiumA Pd G3 (0.164 g, 0.230 mmol), CataCXium A (0.081 g, 0.23 mmol), and potassium acetate (0.442 g, 4.50 mmol) were combined in a microwave vial, which was evacuated and backfilled with nitrogen 3 times. DMF (10 mL) was added and the resulting mixture was stirred at 80° C. for 24 h. The reaction was then allowed to cool to room temperature and set aside.

Methyl 3-amino-6-chloro-5-cyclopropyl-pyrazine-2-carboxylate (0.341 g, 1.50 mmol), Pd(dppf)-$CH_2Cl_2$ complex (0.122 g, 0.150 mmol), and cesium fluoride (0.684 g, 4.50 mmol) were combined in a microwave vial, which was evacuated and backfilled with nitrogen 3 times. The borylation mixture was added. The resulting mixture was stirred at 100° C. for 5 hours. The reaction was then allowed to cool to room temperature, diluted with water, and extracted with 4:1 DCM/IPA 3 times. The combined organic layers were washed once each with 5% aqueous LiCl solution and brine, dried over sodium sulfate, filtered, and concenrated. The resulting residue was purified by flash silica chromatography, using 0-10% MeOH-DCM with 0-1% ammonia as eluent. The resulting material was further purified by trituration in ethyl acetate to afford methyl 3-amino-5-cyclopropyl-6-(3-methylimidazo[4,5-c]pyridin-7-yl)pyrazine-2-carboxylate (0.105 g, 22%) as a beige solid; 1H NMR (500 MHZ, CHLOROFORM-d) δ 0.85-0.93 (2H, m), 1.14-1.23 (2H, m), 1.85-1.95 (1H, m), 3.93 (3H, s), 4.00 (3H, s), 8.00 (1H, s), 8.65 (1H, br s), 8.91 (1H, br s). The NH2 signal exchanged out in chloroform-d; m/z: (ES+), [M+H]+=325.1

(b) Methyl 5-cyclopropyl-3-[4-(1-hydroxy-1-methyl-ethyl)anilino]-6-(3-methylimidazo[4,5-c]pyridin-7-yl)pyrazine-2-carboxylate Methyl 3-amino-5-cyclopropyl-6-(3-methylimidazo[4,5-c]pyridin-7-yl)pyrazine-2-carboxylate (100 mg, 0.31 mmol), 2-(4-bromophenyl) propan-2-ol (133 mg, 0.620 mmol), BrettPhos Pd G3 (28 mg, 0.030 mmol), and cesium carbonate (300 mg, 0.92 mmol) were combined in a microwave vial, which was then evacuated and backfilled with nitrogen three times. 1,4-dioxane (3.08 mL) was added. The resulting mixture was stirred at 80° C. for 2 hours. The reaction was then allowed to cool to room temperature, diluted with water (25 mL), and extracted three times with 3:1 DCM/IPA (10 mL each). The combined organic layers were washed with water and concentrated. The resulting residue was purified by silica gel chromatography, using 0 to 10% MeOH-DCM as eluent and 0.2% ammonia as modifier to afford methyl 5-cyclopropyl-3-[4-(1-hydroxy-1-methyl-ethyl)anilino]-6-(3-methylimidazo[4,5-c]pyridin-7-yl)pyrazine-2-carboxylate (89 mg, 63% yield) as a yellow solid. 1H NMR (500 MHz, CHLOROFORM-d) δ 0.95-1.01 (2H, m), 1.28-1.33 (2H, m), 1.63 (6H, s), 1.94-2.02 (1H, m), 3.98 (3H, s), 4.01 (3H, s), 7.49 (2H, d), 7.66 (2H, d), 8.02 (1H, s), 8.67 (1H, s), 8.91 (1H, s), 10.33 (1H, s). The OH peak was broadened to the baseline. m/z: (ES+), [M+H]+=459.3

(c) 5-Cyclopropyl-3-[4-(1-hydroxy-1-methyl-ethyl)anilino]-6-(3-methylimidazo[4,5-c]pyridin-7-yl)pyrazine-2-carboxamide 7 N Methanolic ammonia (3.88 mL, 27.2 mmol) was added to methyl 5-cyclopropyl-3-[4-(1-hydroxy-1-methyl-ethyl)anilino]-6-(3-methylimidazo[4,5-c]pyridin-7-yl)pyrazine-2-carboxylate (0.089 g, 0.19 mmol). The resulting mixture was stirred at 100° C. in a Biotage microwave reactor for 2 hours. The reaction was then concentrated and dried under vacuum to afford 5-cyclopropyl-3-[4-(1-hydroxy-1-methyl-ethyl)anilino]-6-(3-methylimidazo[4,5-c]pyridin-7-yl)pyrazine-2-carboxamide (80 mg, 93% yield). 1H NMR (500 MHz, DMSO-d6) δ 0.92 (2H, br dd), 1.05-1.12 (2H, m), 1.43 (6H, s), 1.88-1.98 (1H, m), 3.99 (3H, s), 4.93 (1H, s), 7.44 (2H, br d), 7.59 (2H, br d), 7.83 (1H, br s), 8.09 (1H, br s), 8.44 (1H, s), 8.54 (1H, s), 9.04 (1H, s), 11.26 (1H, s). m/z: (ES+), [M+H]+=444.3

Example 87

3-(4-Isopropoxyanilino)-5-(methylamino)-6-(3-methylimidazo[4,5-c]pyridin-7-yl)pyrazine-2-carboxamide

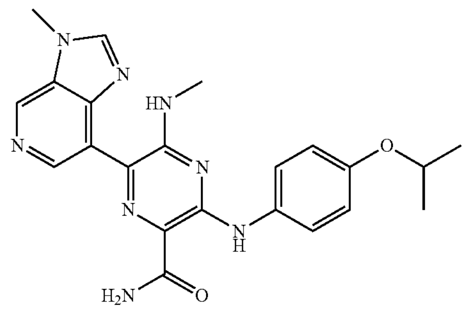 [SMILES: CNc1nc(Nc2ccc(OC(C)C)cc2)c(C(N)=O)nc1-c1cncc2c1ncn2C]

(a) Methyl 3-(4-isopropoxyanilino)-5 (methylamino)-6-(3-methylimidazo[4,5-c]pyridin-7-yl)pyrazine-2-carboxylate Methyl 3-amino-5-(methylamino)-6-(3-methylimidazo[4,5-c]pyridin-7-yl)pyrazine-2-carboxylate (100 mg, 0.32 mmol) was added to a mixture of 1-bromo-4-isopropoxybenzene (69 mg, 0.32 mmol), cesium carbonate (312 mg, 0.960 mmol), and BrettPhos Pd G3 (43 mg, 0.050 mmol) in 1,4-dioxane (10 mL) under nitrogen. The resulting mixture was stirred at 100° C. for 5 hours. The reaction was then concentrated. The resulting residue was purified by silica gel chromatography, using 0-30% MeOH-DCM as eluent, to afford methyl 3-(4-isopropoxyanilino)-5-(methylamino)-6-(3-methylimidazo[4,5-c]pyridin-7-yl)pyrazine-2-carboxylate (0.060 g, 42%) as a yellow solid; 1H NMR (300 MHz, DMSO-d6) δ 1.27 (6H, d), 2.89 (3H, d), 3.82 (3H, s), 4.01 (3H, s), 4.57 (1H, heptet), 6.92 (2H, d), 7.68 (2H, d), 7.93 (1H, br q), 8.49 (1H, s), 8.53 (1H, s), 9.03 (1H, s), 10.25 (1H, s); m/z: (ES+), [M+H]+=448.2

(b) 3-(4-Isopropoxyanilino)-5-(methylamino)-6-(3-methylimidazo[4,5-c]pyridin-7-yl)pyrazine-2-carboxamide 7 N Methanolic ammonia (7.0 mL, 49 mmol) was added to methyl 3-((4-isopropoxyphenyl)amino)-6-(3-methyl-3H-imidazo[4,5-c]pyridin-7-yl)-5-(methylamino) pyrazine-2-carboxylate (80 mg, 0.18 mmol). The resulting mixture was stirred at 85° C. for 2 days. The reaction was then concentrated. The resulting residue was purified by preparative HPLC, using a 5 micron, 30 mm×150 mm, XBridge Prep OBD C18 column, 33-53% MeCN-10 mM aqueous ammonium bicarbonate as eluent, and 0.1% ammonium hydroxide as modifier, to afford 3-(4-isopropoxyanilino)-5-(methylamino)-6-(3-methylimidazo[4,5-c]pyridin-7-yl)pyrazine-2-carboxamide (51 mg, 66%) as a yellow solid; 1H NMR (300 MHz, DMSO-d6) δ 1.25 (6H, d), 2.91 (3H, d), 4.00 (3H, s), 4.54 (1H, heptet), 6.89 (2H, d), 7.30 (1H, s), 7.65 (2H, d), 7.70 (1H, s), 7.98 (1H, br q), 8.50 (1H, s), 8.71 (1H, s), 8.99 (1H, s), 11.30 (1H, s); m/z: (ES+), [M+H]+=433.2

Example 88

[4-[[3-Carbamoyl-6-(methylamino)-5-(3-methylimidazo[4,5-c]pyridin-7-yl) pyrazin-2-yl]amino]phenyl] methanesulfonate

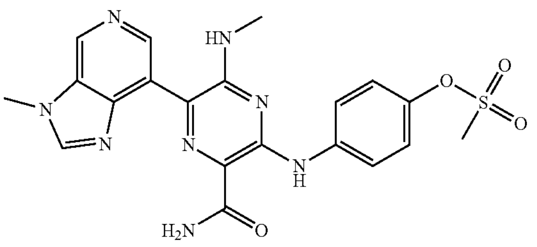 [SMILES: CNc1nc(Nc2ccc(OS(C)(=O)=O)cc2)c(C(N)=O)nc1-c1cncc2c1ncn2C]

(a) Methyl 6-chloro-5-(methylamino)-3-(4-methylsulfonyloxyanilino)pyrazine-2-carboxylate DIPEA (0.22 mL, 1.2 mmol) was added to a mixture of 4-aminophenyl methanesulfonate (78 mg, 0.41 mmol), methyl 6-chloro-3-fluoro-5-(methylamino) pyrazine-2-carboxylate (100 mg, 0.46 mmol) in DMA. The resulting mixture was stirred at 150° C. for 15 hours. The reaction was then diluted with water. The resulting precipitate was collected by filtration and dried under air to afford methyl 6-chloro-5-(methylamino)-3-(4-methylsulfonyloxyanilino) pyrazine-2-carboxylate (0.090 g, 56%) as a brown solid; 1H NMR (500 MHz, DMSO-d6) δ 2.93 (3H, d), 3.35 (3H, s), 3.81 (3H, s), 7.31 (2H, br d), 7.79 (2H, d), 7.94 (1H, br q), 10.34 (1H, s); m/z: (ES+), [M+H]+=387.1

(b) [4-[[3-Carbamoyl-5-chloro-6-(methylamino) pyrazin-2-yl]amino]phenyl]methanesulfonate 7 N Methanolic ammonia (4.0 mL, 28 mmol) was added to methyl 6-chloro-5-(methylamino)-3-(4-methylsulfonyloxyanilino)pyrazine-2-carboxylate (90 mg, 0.23 mmol). The resulting suspension was stirred at 100 C for 15 hours in a Biotage microwave reactor. The reaction was then concentrated to afford [4-[[3-carbamoyl-5-chloro-6-(methylamino) pyrazin-2-yl]amino]phenyl]methanesulfonate (0.085 g, 98%) as a brown solid; 1H NMR (500 MHz, DMSO-d6) δ 2.95 (3H, d), 3.34 (3H, s), 7.22-7.34 (2H, m), 7.41 (1H, br s), 7.62 (1H, br s), 7.66 (1H, br q), 7.73-7.81 (2H, m), 11.54 (1H, s); m/z: (ES+), [M+H]+=372.1

(c) [4-[[3-Carbamoyl-6-(methylamino)-5-(3-methylimidazo[4,5-c]pyridin-7-yl) pyrazin-2-yl]amino] phenyl]methanesulfonate CataCXium Pd G3 (47 mg, 0.060 mmol), bis(pinacolato) diboron (244 mg, 0.960 mmol), potassium acetate (189 mg, 1.92 mmol), cataCXium A (23 mg, 0.060 mmol), and 7-bromo-3-methyl-imidazo[4,5-c]pyridine (136 mg, 0.640 mmol) were combined in a microwave vial, which was evacuated and backfilled three times with nitrogen. DMF (2.5 mL) was added. The resulting mixture was stirred at 80° C. for 20 hours. The reaction was allowed to cool to room temperature and set aside.

$PdCl_2$(dppf) (47 mg, 0.060 mmol), cesium fluoride (292 mg, 1.92 mmol), and [4-[[3-carbamoyl-5-chloro-6-(methylamino) pyrazin-2-yl]amino]phenyl]methanesulfonate (238 mg, 0.640 mmol) were combined in a microwave vial, which was evacuated and backfilled three times with nitrogen. The borylation mixture was added via syringe. The resulting mixture was stirred at 100° C. for 1 hour. The reaction was then concentrated. The resulting residue was purified by silica gel chromatography, using 0-60% MeOH-DCM as eluent, to afford [4-[[3-carbamoyl-6-(methylamino)-5-(3-methylimidazo[4,5-c]pyridin-7-yl) pyrazin-2-yl]amino]phenyl]methanesulfonate (60 mg, 20%) as a pale yellow solid; 1H NMR (500 MHz, DMSO-d6) δ 2.97 (3H, d), 3.37 (3H, s), 4.02 (3H, s), 7.34 (2H, d), 7.43 (1H, br s), 7.80 (1H, br s), 7.90 (2H, d), 8.04 (1H, br q), 8.53 (1H, s), 8.74 (1H, s), 9.04 (1H, s), 11.68 (1H, s); m/z: (ES+), [M+H]+=469.2

Example 89

3-[4-(2-Methoxyethoxy)anilino]-5-(methylamino)-6-(3-methylimidazo[4,5-c]pyridin-7-yl)pyrazine-2-carboxamide

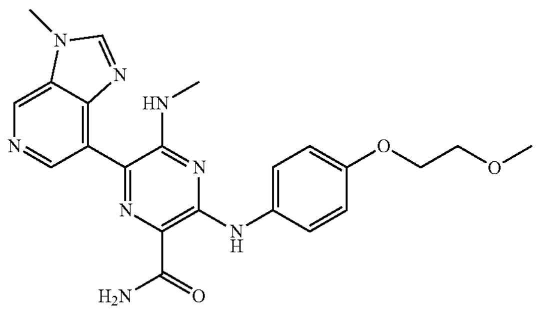

(a) Methyl 3-[4-(2-methoxyethoxy)anilino]-5-(methylamino)-6-(3-methylimidazo[4,5-c]pyridin-7-yl) pyrazine-2-carboxylate 1-Bromo-4-(2-methoxyethoxy)benzene (74 mg, 0.32 mmol) was added to methyl 3-amino-5-(methylamino)-6-(3-methylimidazo[4,5-c]pyridin-7-yl)pyrazine-2-carboxylate (100 mg, 0.32 mmol), cesium carbonate (312 mg, 0.960 mmol), and BrettPhos Pd G3 (43 mg, 0.050 mmol) in 1,4-dioxane (10 mL) under nitrogen. The resulting mixture was stirred at 100° C. for 5 hours. The reaction was then concentrated. The resulting residue was purified by silica gel chromatography, using 0-30% MeOH-DCM as eluent, to afford methyl 3-[4-(2-methoxyethoxy)anilino]-5-(methylamino)-6-(3-methylimidazo[4,5-c]pyridin-7-yl)pyrazine-2-carboxylate (0.080 g, 54%) as a yellow solid; 1H NMR (300 MHZ, DMSO-d6) δ 2.88 (3H, d), 3.63-3.68 (2H, m), 3.82 (3H, s), 4.01 (3H, s), 4.06-4.11 (2H, m), 6.95 (2H, d), 7.69 (2H, d), 7.92 (1H, br s), 8.49 (1H, s), 8.53 (1H, s), 9.03 (1H, s), 10.25 (1H, s); the ethereal methyl group signal was buried under the residual water peak; m/z: (ES+), [M+H]+=464.2

(b) 3-[4-(2-Methoxyethoxy)anilino]-5-(methylamino)-6-(3-methylimidazo[4,5-c]pyridin-7-yl)pyrazine-2-carboxamide 7 N Methanolic ammonia (7.0 mL, 49 mmol) was added to methyl 3-[4-(2-methoxyethoxy)anilino]-5-(methylamino)-6-(3-methylimidazo[4,5-c]pyridin-7-yl)pyrazine-2-carboxylate (80 mg, 0.17 mmol). The resulting mixture was stirred at 85° C. for 2 days. The reaction was then concentrated. The resulting residue was purified by preparative HPLC to afford 3-[4-(2-methoxyethoxy)anilino]-5-(methylamino)-6-(3-methylimidazo[4,5-c]pyridin-7-yl)pyrazine-2-carboxamide (56 mg, 72%) as a yellow solid; 1H NMR (300 MHz, DMSO-d6) δ 2.91 (3H, d), 3.30 (3H, s), 3.59-3.68 (2H, m), 3.99 (3H, s), 4.02-4.11 (2H, m), 6.86-6.97 (2H, m), 7.32 (1H, s), 7.61-7.74 (3H, m), 7.98 (1H, br q), 8.50 (1H, s), 8.71 (1H, s), 9.00 (1H, s), 11.31 (1H, s); m/z: (ES+), [M+H]+=449.2

Example 90

3-[4-[2-(Dimethylamino)ethoxy]anilino]-5-(methylamino)-6-(3-methylimidazo[4,5-c]pyridin-7-yl)pyrazine-2-carboxamide

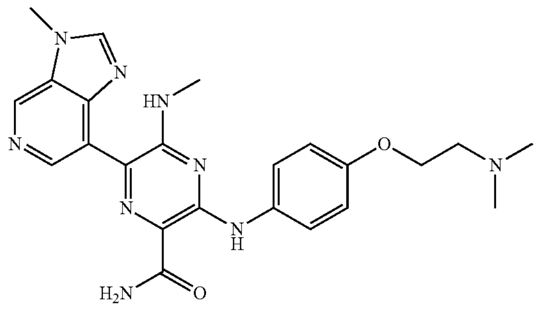 [SMILES: CNc1nc(Nc2ccc(OCCN(C)C)cc2)c(C(N)=O)nc1-c1cncc2c1ncn2C]

(a) Methyl 3-[4-[2-(dimethylamino)ethoxy]anilino]-5-(methylamino)-6-(3-methylimidazo[4,5-c]pyridin-7-yl)pyrazine-2-carboxylate 2-(4-Bromophenoxy)-N,N-dimethyl-ethanamine (94 mg, 0.38 mmol) was added to a suspension of methyl 3-amino-5-(methylamino)-6-(3-methylimidazo[4,5-c]pyridin-7-yl)pyrazine-2-carboxylate (100 mg, 0.32 mmol), cesium carbonate (312 mg, 0.96 mmol), and BrettPhos Pd G3 (43.4 mg, 0.05 mmol) in 1,4-dioxane (10 mL) under nitrogen. The resulting mixture was stirred at 100° C. for 5 hours. The reaction was then concentrated. The resulting residue was purified by silica gel chromatography, using 0-30% MeOH-DCM as eluent, to afford methyl 3-[4-[2-(dimethylamino)ethoxy]anilino]-5-(methylamino)-6-(3-methylimidazo[4,5-c]pyridin-7-yl)pyrazine-2-carboxylate (0.100 g, 66%) as a yellow solid; 1H NMR (300 MHz, DMSO-d6) δ 2.34 (6H, s), 2.78 (2H, t), 2.88 (3H, d), 3.82 (3H, s), 4.01 (3H, s), 4.09 (2H, t), 6.91-7.01 (2H, m), 7.64-7.75 (2H, m), 7.92 (1H, br q), 8.49 (1H, s), 8.53 (1H, s), 9.03 (1H, s), 10.26 (1H, s); m/z: (ES+), [M+H]+=477.2

(b) 3-[4-[2-(Dimethylamino)ethoxy]anilino]-5 (methylamino)-6-(3-methylimidazo[4,5-c]pyridin-7-yl)pyrazine-2-carboxamide 7 N Methanolic ammonia (7.0 mL, 49 mmol) was added to methyl 3-[4-[2-(dimethylamino)ethoxy]anilino]-5-(methylamino)-6-(3-methylimidazo[4,5-c]pyridin-7-yl)pyrazine-2-carboxylate (80 mg, 0.17 mmol). The resulting suspension was stirred at 85° C. for 2 days. The reaction was then concentrated. The resulting residue was purified by preparative HPLC, using a 5 micron, 30 mm×150 mm, XBridge Prep OBD C18 column, 16-43% MeCN-10 mM ammonium bicarbonate as eluent, and 0.1% ammonium hydroxide as modifier, to afford 3-[4-[2-(dimethylamino)ethoxy]anilino]-5-(methylamino)-6-(3-methylimidazo[4,5-c]pyridin-7-yl) pyrazine-2-carboxamide (40 mg, 52%) as a yellow solid; 1H NMR (300 MHz, DMSO-d6) δ 2.20 (6H, s), 2.60 (2H, t), 2.91 (3H, d), 3.96-4.06 (5H, m), 6.86-6.96 (2H, m), 7.32 (1H, s), 7.62-7.74 (3H, m), 7.98 (1H, br q), 8.50 (1H, s), 8.71 (1H, s), 9.00 (1H, s), 11.31 (1H, s); m/z: (ES+), [M+H]+=462.2

Example 91

3-[4-(2-Hydroxyethoxy)anilino]-5-(methylamino)-6-(3-methylimidazo[4,5-c]pyridin-7-yl)pyrazine-2-carboxamide

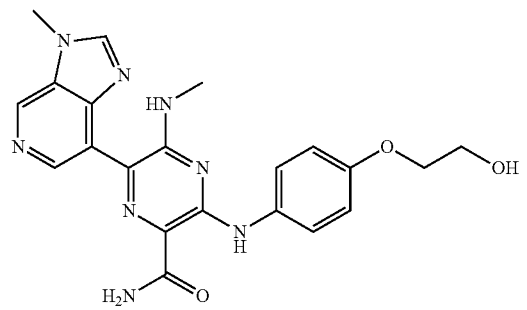 [SMILES: CNc1nc(Nc2ccc(OCCO)cc2)c(C(N)=O)nc1-c1cncc2c1ncn2C]

(a) Methyl 3-[4-(2-hydroxyethoxy)anilino]-5-(methylamino)-6-(3-methylimidazo[4,5-c]pyridin-7-yl) pyrazine-2-carboxylate 2-(4-Bromophenoxy) ethanol (83 mg, 0.38 mmol) was added to methyl 3-amino-5-(methylamino)-6-(3-methylimidazo[4,5-c]pyridin-7-yl)pyrazine-2-carboxylate (100 mg, 0.32 mmol), cesium carbonate (312 mg, 0.960 mmol), and BrettPhos Pd G3 (43 mg, 0.050 mmol) in 1,4-dioxane (10 mL) under nitrogen. The resulting mixture was stirred at 100° C. for 6 hours. The reaction was then concentrated. The resulting residue was purified by silica gel chromatography, using 0-30% MeOH-DCM as eluent, to afford methyl 3-[4-(2-hydroxyethoxy)anilino]-5-(methylamino)-6-(3-methylimidazo[4,5-c]pyridin-7-yl)pyrazine-2-carboxylate (0.080 g, 56%) as a yellow solid; 1H NMR (300 MHz, DMSO-d6) δ 2.89 (3H, d), 3.67-3.73 (2H, m), 3.82 (3H, s), 3.94-4.00 (2H, m), 4.00 (3H, s), 4.84 (1H, t), 6.96 (2H, d), 7.69 (2H, d), 7.92 (1H, br q), 8.49 (1H, s), 8.54 (1H, s), 9.05 (1H, s), 10.25 (1H, s) m/z: (ES+), [M+H]+=450.2

(b) 3-[4-(2-Hydroxyethoxy)anilino]-5-(methylamino)-6-(3-methylimidazo[4,5-c]pyridin-7-yl)pyrazine-2-carboxamide 7 N Methanolic ammonia (7.0 mL, 49 mmol) was added to methyl 3-[4-(2-hydroxyethoxy)anilino]-5-(methylamino)-6-(3-methylimidazo[4,5-c]pyridin-7-yl)pyrazine-2-carboxylate (60.0 mg, 0.13 mmol). The resulting suspension was stirred at 85° C. for 2 days. The reaction was then concentrated. The resulting residue was purified by preparative HPLC, using a 5 micron, 30 mm×150 mm Sunfire prep C18 column, 5-25% MeCN—$H_2O$ as eluent, and 0.1% formic acid as modifier, to afford 3-[4-(2-hydroxyethoxy)anilino]-5-(methylamino)-6-(3-methylimidazo[4,5-c]pyridin-7-yl)pyrazine-2-carboxamide (9.0 mg, 16%) as a yellow solid; 1H NMR (300 MHz, DMSO-d6) δ 2.91 (3H, d), 3.69 (2H, br q), 3.97 (2H, t), 4.01 (3H, s), 4.83 (1H, br t), 6.93 (2H, d), 7.32 (1H, s), 7.68 (2H, d), 7.72 (1H, s), 7.98 (1H, br q), 8.50 (1H, s), 8.71 (1H, s), 9.00 (1H, s), 11.30 (1H, s); m/z: (ES+), [M+H]+=435.2

Example 92

5-(Methylamino)-6-(3-methylimidazo[4,5-c]pyridin-7-yl)-3-[4-(2-morpholinoethoxy)anilino]pyrazine-2-carboxamide

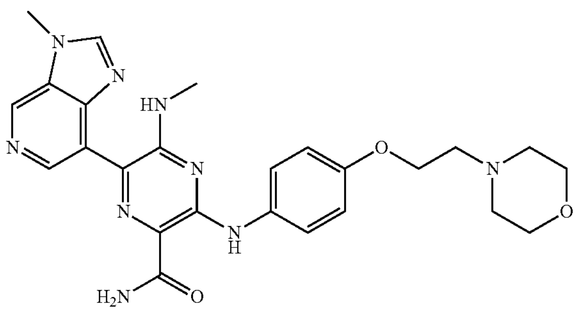 [SMILES: CNc1nc(Nc2ccc(OCCN3CCOCC3)cc2)c(C(N)=O)nc1-c1cncc2c1ncn2C]

(a) Methyl 5-(methylamino)-6-(3-methylimidazo[4,5-c]pyridin-7-yl)-3-[4-(2-morpholinoethoxy)anilino]pyrazine-2-carboxylate Methyl 3-amino-5-(methylamino)-6-(3-methylimidazo[4,5-c]pyridin-7-yl)pyrazine-2-carboxylate (100 mg, 0.32 mmol) was added to a suspension of 4-[2-(4-bromophenoxy)ethyl]morpholine (91 mg, 0.32 mmol), cesium carbonate (312 mg, 0.960 mmol), and BrettPhos Pd G3 (43 mg, 0.050 mmol) in 1,4-dioxane (10 mL) at rt under nitrogen. The resulting mixture was stirred at 100° C. for 5 hours. The reaction was then concentrated. The resulting residue was purified by silica gel chromatography, using 0-30% MeOH-DCM as eluent, to afford methyl 5-(methylamino)-6-(3-methylimidazo[4,5-c]pyridin-7-yl)-3-[4-(2-morpholinoethoxy)anilino]pyrazine-2-carboxylate (0.090 g, 54%) as a yellow solid; 1H NMR (300 MHz, DMSO-d6) δ 2.45-2.49 (2H, m), 2.69 (2H, t), 2.88 (3H, d), 3.23-3.32 (2H, m), 3.57-3.61 (4H, m), 3.82 (3H, s), 4.01 (3H, s), 4.08 (2H, t), 6.95 (2H, d), 7.69 (2H, d), 7.91 (1H, br q), 8.49 (1H, s), 8.53 (1H, s), 9.03 (1H, s), 10.26 (1H, s); m/z: (ES+), [M+H]+=519.2

(b) 5-(Methylamino)-6-(3-methylimidazo[4,5-c]pyridin-7-yl)-3-[4-(2-morpholinoethoxy)anilino]pyrazine-2-carboxamide 7 N Methanolic ammonia (7.0 mL, 49 mmol) was added to methyl 6-(3-methyl-3H-imidazo[4,5-c]pyridin-7-yl)-5-(methylamino)-3-((4-(2-morpholinoethoxy)phenyl)amino)pyrazine-2-carboxylate (60 mg, 0.12 mmol). The resulting suspension was stirred at 85° C. for 2 days. The reaction was then concentrated. The resulting residue was purified by preparative HPLC, using a 5 micron, 30 mm×150 mm, XBridge Prep OBD C18 column, 17-37% MeCN-10 mM aqueous ammonium bicarbonate as eluent, and 0.1% ammonium hydroxide as modifier, to afford 5-(methylamino)-6-(3-methylimidazo[4,5-c]pyridin-7-yl)-3-[4-(2-morpholinoethoxy)anilino]pyrazine-2-carboxamide (58 mg, 100%) as a yellow solid; 1H NMR (300 MHz, DMSO-d6) δ 2.40-2.50 (2H, m), 2.67 (2H, t), 2.91 (3H, d), 3.24-3.31 (2H, m), 3.52-3.61 (4H, m), 3.99 (3H, s), 4.06 (2H, t), 6.88-6.98 (2H, m), 7.31 (1H, s), 7.66 (2H, d), 7.70 (1H, s), 7.98 (1H, br q), 8.50 (1H, s), 8.71 (1H, s), 9.00 (1H, s), 11.30 (1H, s); m/z: (ES+), [M+H]+=504.2

Example 93

3-(4-Aminoanilino)-5-(methylamino)-6-(1-methylbenzimidazol-4-yl)pyrazine-2-carboxamide

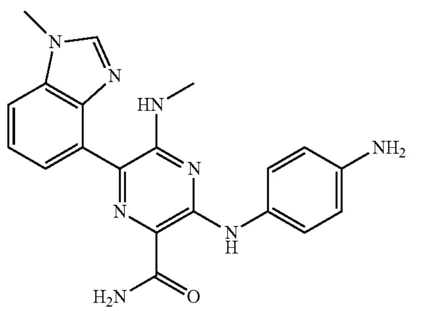 [SMILES: CNc1nc(Nc2ccc(N)cc2)c(C(N)=O)nc1-c1cccc2c1ncn2C]

(a) Methyl 3-(4-acetamidoanilino)-5-(methylamino)-6-(1-methylbenzimidazol-4-yl)pyrazine-2-carboxylate BrettPhos Pd G3 (15 mg, 0.020 mmol) was added to a suspension of cesium carbonate (156 mg, 0.480 mmol), N-(4-bromophenyl) acetamide (33 mg, 0.24 mmol), and methyl 3-amino-5-(methylamino)-6-(3-methylimidazo[4,5-c]pyridin-7-yl)pyrazine-2-carboxylate (50 mg, 0.16 mmol) in 1,4-dioxane (2 mL) under nitrogen. The resulting mixture was stirred at 100° C. for 24 hours. The resulting residue was purified by silica gel chromatography, using 0-10% MeOH-DCM as eluent, to afford methyl 3-(4-acetamidoanilino)-5-(methylamino)-6-(1-methylbenzimidazol-4-yl)pyrazine-2-carboxylate (0.060 g, 84%) as a yellow solid; 1H NMR (300 MHz, DMSO-d6) δ 2.05 (3H, s), 2.93 (3H, d), 3.83 (3H, s), 3.92 (3H, s), 7.39-7.51 (2H, m), 7.57 (2H, d), 7.60-7.78 (3H, m), 8.07 (1H, br q), 8.32 (1H, s), 9.87 (1H, s), 10.33 (1H, s). m/z: (ES+), [M+H]+=446.2

(b) 3-(4-Aminoanilino)-5-(methylamino)-6-(1-methylbenzimidazol-4-yl)pyrazine-2-carboxamide 32 wt % Aqueous HCl (5.00 mL, 165 mmol) was added to a suspension of methyl 3-(4-acetamidoanilino)-5-(methylamino)-6-(1-methylbenzimidazol-4-yl)pyrazine-2-carboxylate (45 mg, 0.10 mmol), in water (1 mL). The resulting mixture was stirred at 80° C. for 24 hours. The reaction was then filtered and the solid was dried under vacuum. 7 N methanolic ammonia (10 mL, 70 mmol) was added to a suspension of the resulting solid in MeOH (10 mL). The resulting mixture was stirred at 80° C. for 3 days. The reaction was then concentrated. The resulting residue was purified by preparative HPLC Column, using a 5 micron, 30 mm×150 mm, Xselect CSH OBD column, 5-15% MeCN—$H_2O$ as eluent, and 0.1% formic acid as modifier, to afford 3-(4-aminoanilino)-5-(methylamino)-6-(1-methylbenzimidazol-4-yl)pyrazine-2-carboxamide (6.0 mg, 15%) as a yellow solid; 1H NMR (300 MHz, DMSO-d6) δ 2.91 (3H, d), 3.91 (3H, s), 6.54-6.61 (2H, m), 7.26 (1H, s), 7.38-7.45 (3H, m), 7.58 (1H, s), 7.60-7.67 (2H, m), 8.13 (1H, br q), 8.34 (1H, s), 10.99 (1H, s); the aniline NH2 protons are broadened to the baseline. m/z: (ES+), [M+H]+=389.1

Example 94

3-[4-[2-Methoxyethyl(methyl)amino]anilino]-5-(methylamino)-6-(3-methylimidazo[4,5-c]pyridin-7-yl)pyrazine-2-carboxamide

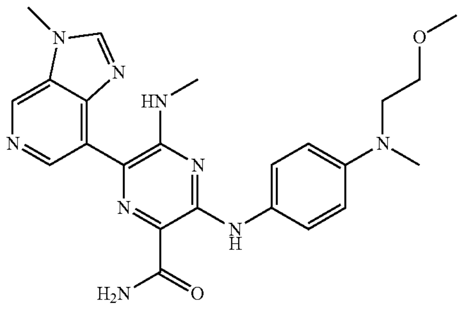

(a) Methyl 3-[4-[2-methoxyethyl(methyl)amino] anilino]-5-(methylamino)-6-(3-methylimidazo[4,5-c] pyridin-7-yl)pyrazine-2-carboxylate BrettPhos Pd G3 (58 mg, 0.060 mmol) was added to a suspension of cesium carbonate (310 mg, 0.96 mmol), 4-bromo-N-(2-methoxyethyl)-N-methyl-aniline (78 mg, 0.32 mmol) and methyl 3-amino-5-(methylamino)-6-(3-methylimidazo[4,5-c]pyridin-7-yl)pyrazine-2-carboxylate (100 mg, 0.32 mmol) in 1,4-dioxane (2 mL) under nitrogen. The resulting mixture was stirred at 100° C. for 16 hours. The reaction was then concentrated. The resulting residue was purified by silica gel chromatography, using 0-20% MeOH-DCM as eluent, to afford methyl 3-[4-[2-methoxyethyl(methyl)amino]anilino]-5-(methylamino)-6-(3-methylimidazo[4,5-c]pyridin-7-yl)pyrazine-2-carboxylate (60 mg, 39%) as a yellow solid; 1H NMR (300 MHz, DMSO-d6) δ 2.89 (3H, s), 2.91 (3H, s), 3.27 (3H, s), 3.42-3.53 (4H, m), 3.82 (3H, s), 4.02 (3H, s), 6.74 (2H, d), 7.60 (2H, d), 7.91 (1H, br q), 8.50 (1H, s), 8.55 (1H, s), 9.04 (1H, s), 10.18 (1H, s); m/z: (ES+), [M+H]+=477.2

(b) 3-[4-[2-Methoxyethyl(methyl)amino]anilino]-5-(methylamino)-6-(3-methylimidazo[4,5-c]pyridin-7-yl)pyrazine-2-carboxamide 7 N Methanolic ammonia (5.0 mL, 35 mmol) was added to a suspension of methyl 3-[4-[2-methoxyethyl(methyl) amino]anilino]-5-(methylamino)-6-(3-methylimidazo[4,5-c]pyridin-7-yl)pyrazine-2-carboxylate (80 mg, 0.17 mmol) in MeOH (10 mL). The resulting mixture was stirred at 80° C. for 3 days. The reaction was then concentrated. The resulting residue was purified by preparative HPLC, using a 5 micron, 30 mm×150 mm, Xselect CSH OBD column, 5-20% MeCN—$H_2O$ as eluent, and 0.1% formic acid as modifier, to afford 3-[4-[2-methoxyethyl(methyl)amino]anilino]-5-(methylamino)-6-(3-methylimidazo[4,5-c]pyridin-7-yl)pyrazine-2-carboxamide (32 mg, 41%) as a yellow solid; 1H NMR (300 MHz, DMSO-d6) δ 2.88-2.97 (6H, m), 3.29 (3H, s), 3.44-3.52 (4H, m), 4.02 (3H, s), 6.73 (2H, d), 7.29 (1H, s), 7.60 (2H, d), 7.70 (1H, s), 8.00 (1H, br q), 8.52 (1H, s), 8.73 (1H, s), 9.01 (1H, s), 11.19 (1H, s); m/z: (ES+), [M+H]+=462.2

Example 95

3-[4-[Bis(2-methoxyethyl)amino]anilino]-5-(methylamino)-6-(3-methylimidazo[4,5-c]pyridin-7-yl)pyrazine-2-carboxamide

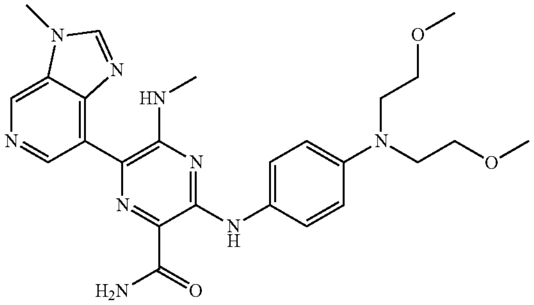 [SMILES: CNc1nc(Nc2ccc(N(CCOC)CCOC)cc2)c(C(N)=O)nc1-c1cncc2c1ncn2C]

(a) Methyl 3-[4-[bis(2-methoxyethyl)amino]anilino]-5-(methylamino)-6-(3-methylimidazo[4,5-c] pyridin-7-yl)pyrazine-2-carboxylate BrettPhos Pd G3 (29 mg, 0.030 mmol) was added to a suspension of methyl 3-amino-5-(methylamino)-6-(3-methylimidazo[4,5-c]pyridin-7-yl)pyrazine-2-carboxylate (100 mg, 0.32 mmol), 4-bromo-N,N-bis(2-methoxyethyl) aniline (184 mg, 0.640 mmol), and cesium carbonate (312 mg, 0.960 mmol) in 1,4-dioxane (15 mL) under nitrogen. The resulting mixture was stirred at 100° C. for 16 hours. The reaction was then concentrated. The resulting residue was purified by silica gel chromatography, using 0 to 10% MeOH-DCM as eluent, to afford methyl 3-[4-[bis(2-methoxyethyl)amino]anilino]-5-(methylamino)-6-(3-methylimidazo[4,5-c]pyridin-7-yl)pyrazine-2-carboxylate (0.040 g, 24%) as a brown solid; 1H NMR (400 MHZ, DMSO-d6) δ 2.89 (3H, d), 3.24-3.30 (6H, m), 3.44-3.52 (8H, m), 3.81 (3H, s), 4.01 (3H, s), 6.71 (2H, d), 7.54-7.61 (2H, m), 7.91 (1H, br q), 8.49 (1H, s), 8.54 (1H, s), 9.02 (1H, s), 10.16 (1H, s); m/z: (ES+), [M+H]+=521.2

(b) 3-[4-[Bis(2-methoxyethyl)amino]anilino]-5-(methylamino)-6-(3-methylimidazo[4,5-c]pyridin-7-yl)pyrazine-2-carboxamide 7 N Methanolic ammonia (1.0 mL, 7.0 mmol) was added to methyl 3-[4-[bis(2-methoxyethyl)amino]anilino]-5-(methylamino)-6-(3-methylimidazo[4,5-c]pyridin-7-yl) pyrazine-2-carboxylate (30 mg, 0.06 mmol). The resulting suspension was stirred at 80° C. for 30 hours. The resulting residue was purified by preparative HPLC, using a 5 micron, 30 mm×150 mm, Sunfire prep C18 column, 20-30% MeCN—$H_2O$ as eluent, and 0.1% formic acid as modifier, to afford 3-[4-[bis(2-methoxyethyl)amino]anilino]-5-(methylamino)-6-(3-methylimidazo[4,5-c]pyridin-7-yl)pyrazine-2-carboxamide (13 mg, 45% yield) as a yellow solid. 1H NMR (400 MHz, DMSO-d6) δ 2.93 (3H, d), 3.35 (6H, s), 3.48 (8H, s), 4.01 (3H, s), 6.71 (2H, d), 7.27 (1H, s), 7.57 (2H, d), 7.68 (1H, s), 8.00 (1H, br q), 8.51 (1H, s), 8.72 (1H, s), 9.00 (1H, s), 11.17 (1H, s). m/z: (ES+), $[M+2H]^{2+}$=253.8

Example 96

5-(Methylamino)-6-(3-methylimidazo[4,5-c]pyridin-7-yl)-3-[(2-methyl-4-pyridyl)amino]pyrazine-2-carboxamide formate salt

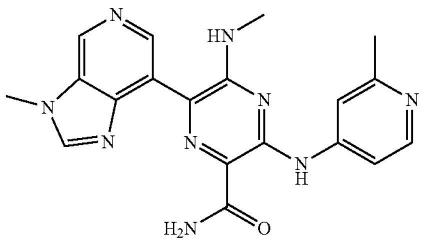 [SMILES: CNc1nc(Nc2ccnc(C)c2)c(C(N)=O)nc1-c1cncc2c1ncn2C]

(a) Methyl 5-(methylamino)-6-(3-methylimidazo[4,5-c]pyridin-7-yl)-3-[(2-methyl-4-pyridyl)amino] pyrazine-2-carboxylate XantPhos (611 mg, 1.06 mmol) was added to a suspension of methyl 3-amino-5-(methylamino)-6-(3-methylimidazo[4,5-c]pyridin-7-yl)pyrazine-2-carboxylate (110 mg, 0.35 mmol), 4-bromo-2-methyl-pyridine (61 mg, 0.35 mmol), and cesium carbonate (11.5 mg, 0.0400 mmol) in 1,4-dioxane (15 mL) under nitrogen. The resulting mixture was stirred at 100° C. for 7 hours. The reaction was then concentrated. The resulting residue was purified by silica gel chromatography, using 0-10% MeOH-DCM as eluent, to afford methyl 5-(methylamino)-6-(3-methylimidazo[4,5-c] pyridin-7-yl)-3-[(2-methyl-4-pyridyl)amino]pyrazine-2-carboxylate (0.080 g, 56%) as a brown solid; 1H NMR (300 MHZ, DMSO-d6) δ 2.45 (3H, s), 2.98 (3H, d), 3.85 (3H, s), 4.02 (3H, s), 7.68 (1H, s), 7.74 (1H, s), 8.01 (1H, br q), 8.31 (1H, d), 8.52 (2H, d), 9.08 (1H, s), 10.61 (1H, s); m/z: (ES+), [M+H]+=405.1

(b) 5-(Methylamino)-6-(3-methylimidazo[4,5-c] pyridin-7-yl)-3-[(2-methyl-4-pyridyl)amino]pyrazine-2-carboxamide formate salt 7 N Methanolic ammonia (10 mL, 70 mmol) was added to methyl 5-(methylamino)-6-(3-methylimidazo[4,5-c]pyridin-7-yl)-3-[(2-methyl-4-pyridyl)amino]pyrazine-2-carboxylate (60 mg, 0.15 mmol). The resulting suspension was stirred at 80° C. for 24 hours. The reaction was then concentrated. The resulting residue was purified by preparative HPLC using a 5 micron, 30×150 mm Sunfire prep C18 column, 2-25% MeCN—$H_2O$ as eluent, and 0.1% formic acid as modifier, to afford 5-(methylamino)-6-(3-methylimidazo[4,5-c]pyridin-7-yl)-3-[(2-methyl-4-pyridyl)amino] pyrazine-2-carboxamide formate salt (20 mg, 32%) as a yellow solid; 1H NMR (300 MHz, DMSO-d6) δ 2.44 (3H, s), 3.00 (3H, d), 4.02 (3H, s), 7.51 (1H, s), 7.59-7.64 (1H, m), 7.65-7.70 (1H, m), 7.85 (1H, s), 8.05 (1H, br q), 8.18 (1H, br s), 8.28 (1H, d), 8.53 (1H, s), 8.73 (1H, s), 9.05 (1H, s), 11.79 (1H, s); m/z: (ES+), [M+H]+=390.1

Example 97

3-[(2-Methoxy-4-pyridyl)amino]-5-(methylamino)-6-(3-methylimidazo[4,5-c]pyridin-7-yl)pyrazine-2-carboxamide

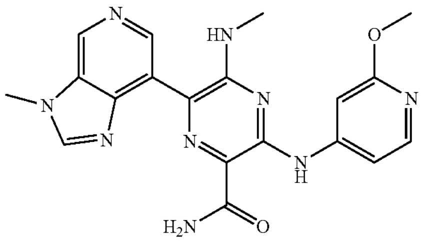

(a) Methyl 3-[(2-methoxy-4-pyridyl)amino]-5-(methylamino)-6-(3-methylimidazo[4,5-c]pyridin-7-yl)pyrazine-2-carboxylate Brettphos Pd G3 (44 mg, 0.050 mmol) was added to a suspension of methyl 3-amino-5-(methylamino)-6-(3-methylimidazo[4,5-c]pyridin-7-yl)pyrazine-2-carboxylate (150 mg, 0.48 mmol), 4-bromo-2-methoxy-pyridine (135 mg, 0.720 mmol) and cesium carbonate (469 mg, 1.44 mmol) in 1,4-dioxane (20 mL) under nitrogen. The resulting mixture was stirred at 100° C. for 16 hours. The reaction was then concentrated. The resulting residue was diluted with MeOH and filtered through celite. The resulting filtrate was concentrated. The resulting residue was purified by silica gel chromatography, using 0 to 20% MeOH-DCM as eluent, to afford methyl 3-[(2-methoxy-4-pyridyl)amino]-5-(methylamino)-6-(3-methylimidazo[4,5-c]pyridin-7-yl)pyrazine-2-carboxylate (0.115 g, 57% yield) as a yellow solid. m/z: (ES+), [M+H]+=421.2.

(b) 3-[(2-Methoxy-4-pyridyl)amino]-5-(methylamino)-6-(3-methylimidazo[4,5-c]pyridin-7-yl)pyrazine-2-carboxamide 7 N Methanolic ammonia (10 mL, 70 mmol) was added to methyl 3-[(2-methoxy-4-pyridyl)amino]-5-(methylamino)-6-(3-methylimidazo[4,5-c]pyridin-7-yl)pyrazine-2-carboxylate (80 mg, 0.19 mmol). The resulting suspension was stirred at 100° C. for 16 hours. The reaction was then concentrated. The resulting residue was purified by preparative HPLC using a 5 micron, 30 mm×150 mm, XBridge Prep OBD C18 Column, 12%-42% MeCN—$H_2O$ as eluent, and 0.1% ammonia as a modifier, to afford 3-[(2-methoxy-4-pyridyl)amino]-5-(methylamino)-6-(3-methylimidazo[4,5-c]pyridin-7-yl)pyrazine-2-carboxamide (0.019 g, 25%) as a yellow solid; 1H NMR (400 MHz, DMSO-d6) δ 2.96 (3H, d), 3.83 (3H, s), 4.00 (3H, s), 7.03-7.09 (1H, m), 7.49 (1H, s), 7.52-7.56 (1H, m), 7.84 (1H, s), 7.99 (1H, d), 8.05 (1H, br q), 8.53 (1H, s), 8.72 (1H, s), 9.05 (1H, s), 11.84 (1H, s); m/z: (ES+), [M+H]+=406.1.

Example 98

3-[(2-Methoxy-6-methyl-4-pyridyl)amino]-5-(methylamino)-6-(7-methylimidazo[4,5-c]pyridazin-4-yl) pyrazine-2-carboxamide hydrochloride

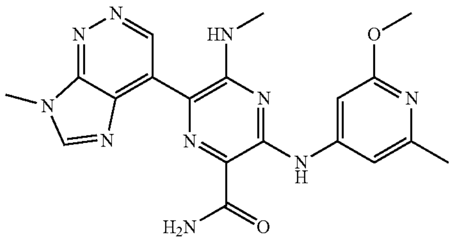

(a) Methyl 6-chloro-3-[(2-methoxy-6-methyl-4-pyridyl)amino]-5-(methylamino) pyrazine-2-carboxylate A mixture of methyl 3-amino-6-chloro-5-(methylamino) pyrazine-2-carboxylate (0.309 g, 1.43 mmol), 4-bromo-2-methoxy-6-methyl-pyridine (0.472 g, 2.34 mmol), t-BuXPhos Pd G3 (0.113 g, 0.140 mmol), t-BuXPhos (0.061 g, 0.14 mmol), and sodium tert-butoxide (0.274 g, 2.85 mmol) in THF (12 mL) was evacuated and backfilled three times with nitrogen. The resulting mixture was stirred at 40° C. for 3 hours. The reaction was then concentrated. The resulting residue was purified by silica gel chromatography, using 0-10% MeOH-DCM as eluent, to afford methyl 6-chloro-3-[(2-methoxy-6-methyl-4-pyridyl)amino]-5-(methylamino) pyrazine-2-carboxylate (0.512 g, 106%) as a brown solid. m/z: (ES−), [M−H]−=336.3

(b) 6-Chloro-3-[(2-methoxy-6-methyl-4-pyridyl) amino]-5-(methylamino) pyrazine-2-carboxamide 7 N Methanolic ammonia (10 mL, 70 mmol) was added to methyl 6-chloro-3-[(2-methoxy-6-methyl-4-pyridyl) amino]-5-(methylamino) pyrazine-2-carboxylate (0.387 g, 1.15 mmol). The resulting suspension was stirred at 100° C. for 5.5 hours. The reaction was then concentrated. The resulting residue was triturated in EtOAc. The resulting suspension was filtered. The resulting filtrate was concentrated. The resulting residue was purified by flash silica chromatography, using 0-10% MeOH-DCM as eluent, to afford 6-chloro-3-[(2-methoxy-6-methyl-4-pyridyl)amino]-5-(methylamino) pyrazine-2-carboxamide (0.247 g, 67%) as a yellow solid. m/z: (ES+), [M+H]+=323.1

(c) 3-[(2-Methoxy-6-methyl-4-pyridyl)amino]-5-(methylamino)-6-(7-methylimidazo[4,5-c]pyridazin-4-yl)pyrazine-2-carboxamide hydrochloride A mixture of 4-chloro-7-methyl-imidazo[4,5-c] pyridazine (0.037 g, 0.22 mmol), bis(pinacolato)diboron (0.084 g, 0.33 mmol), potassium acetate (0.065 g, 0.66 mmol), cataCXium A Pd G3 (0.016 g, 0.020 mmol) and cataCXium A (7.9 mg, 0.020 mmol) in DMF (2.0 mL) was evacuated and backfilled three times with nitrogen. The resulting mixture was stirred at 100° C. for 18.5 hours. The reaction was then allowed to cool to room temperature and set aside.

6-Chloro-3-[(2-methoxy-6-methyl-4-pyridyl)amino]-5-(methylamino) pyrazine-2-carboxamide (0.050 g, 0.15 mmol), $PdCl_2$(dppf) (0.011 g, 0.020 mmol), and cesium fluoride (0.071 g, 0.46 mmol) were combined in a microwave vial, which was evacuated and backfilled three times with nitrogen. The borylation mixture was added. The resulting mixture was stirred at 100° C. for 2 hours in a Biotage microwave reactor. The reaction was then concentrated. The resulting residue was purified by silica gel chromatography, using 0-10% MeOH-DCM as eluent. The resulting material was further purified by basic alumina chromatography, using 0 to 5% MeOH-DCM as eluent. The resulting material was taken up in methanol, treated with 1N HCl (20 μL), and then concentrated to afford 3-[(2-methoxy-6-methyl-4-pyridyl)amino]-5-(methylamino)-6-(7-methylimidazo[4,5-c]pyridazin-4-yl)pyrazine-2-carboxamide hydrochloride (4.0 mg, 5.7%) as an orange solid; 1H NMR (500 MHz, DMSO-d6) 2.44 (3H, br s), 3.08 (3H, d), 4.01 (3H, br s), 4.06 (3H, s), 7.23 (1H, br s), 7.72-7.84 (2H, m), 8.30 (1H, br s), 8.91 (1H, s), 9.47 (1H, br s), 9.85 (1H, s), 12.51 (1H, br s). m/z: (ES+), [M+H]+=421.2

Example 99

3-[(2,6-Dimethyl-4-pyridyl)amino]-5-(methylamino)-6-(3-methylimidazo[4,5-c]pyridin-7-yl)pyrazine-2-carboxamide

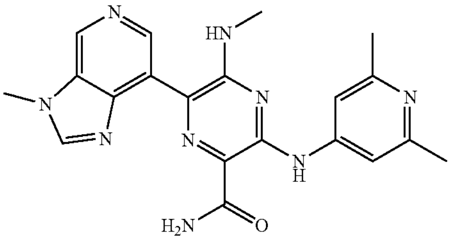

(a) Methyl 3-[(2,6-dimethyl-4-pyridyl)amino]-5-(methylamino)-6-(3-methylimidazo[4,5-c]pyridin-7-yl)pyrazine-2-carboxylate Methyl 3-amino-5-(methylamino)-6-(3-methylimidazo[4,5-c]pyridin-7-yl)pyrazine-2-carboxylate (120 mg, 0.38 mmol) was added to a mixture of 4-bromo-2,6-dimethylpyridine (143 mg, 0.770 mmol), cesium carbonate (374 mg, 1.15 mmol), and BrettPhos Pd G3 (35 mg, 0.040 mmol) in 1,4-dioxane (10 mL) under nitrogen. The resulting mixture was stirred at 80° C. for 16 hours. The reaction was then concentrated. The resulting residue was purified by silica gel chromatography, using 0-10% MeOH-DCM as eluent, to afford methyl 3-[(2,6-dimethyl-4-pyridyl)amino]-5-(methylamino)-6-(3-methylimidazo[4,5-c]pyridin-7-yl)pyrazine-2-carboxylate (0.080 g, 50%) as a yellow solid; 1H NMR (300 MHz, DMSO-d6) δ 2.42 (6H, s), 2.82 (3H, d), 3.74 (3H, s), 3.85 (3H, s), 8.03 (1H, br q), 8.46 (2H, s), 8.50 (1H, s), 8.53 (1H, s), 9.01 (1H, s), 9.07 (1H, s); m/z: (ES+), [M+H]+=419.2

(b) 3-[(2,6-Dimethyl-4-pyridyl)amino]-5-(methylamino)-6-(3-methylimidazo[4 5-c]pyridin-7-yl)pyrazine-2-carboxamide 7 N Methanolic ammonia (10 mL, 70 mmol) was added to methyl 3-[(2,6-dimethyl-4-pyridyl)amino]-5-(methylamino)-6-(3-methylimidazo[4,5-c]pyridin-7-yl)pyrazine-2-carboxylate (80 mg, 0.19 mmol). The resulting mixture was stirred at 80° C. for 16 hours. The reaction was then concentrated. The resulting residue was purified by preparative HPLC, using a 5 micron, 30 mm×150 mm Sunfire prep C18 column, 2-20% MeCN—$H_2O$ as eluent, and 0.1% formic acid as modifier, to afford 3-[(2,6-dimethyl-4-pyridyl)amino]-5-(methylamino)-6-(3-methylimidazo[4,5-c]pyridin-7-yl)pyrazine-2-carboxamide (21 mg, 25%) as a yellow solid; 1H NMR (400 MHZ, DMSO-d6) δ 2.39 (6H, s), 3.00 (3H, d), 4.02 (3H, s), 7.50 (2H, s), 7.84 (1H, s), 8.06 (1H, br q), 8.21 (1H, s), 8.53 (1H, s), 8.73 (1H, s), 9.05 (1H, s), 11.72 (1H, s); m/z: (ES+), [M+H]+=404.2

Example 100

5-Cyclopropyl-3-[(2,6-dimethyl-4-pyridyl)amino]-6-(3-methylimidazo[4,5-c]pyridin-7-yl)pyrazine-2-carboxamide

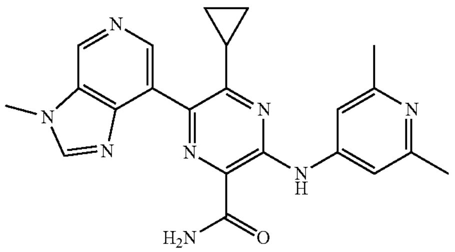

(a) Methyl 5-cyclopropyl-3-[(2,6-dimethyl-4-pyridyl)amino]-6-(3-methylimidazo[4,5-c]pyridin-7-yl)pyrazine-2-carboxylate Methyl 3-amino-5-cyclopropyl-6-(3-methylimidazo[4,5-c]pyridin-7-yl)pyrazine-2-carboxylate (100 mg, 0.31 mmol), 4-bromo-2,6-dimethyl-pyridine (69 mg, 0.37 mmol), BrettPhos Pd G3 (28 mg, 0.030 mmol), and cesium carbonate (301 mg, 0.920 mmol) were combined in a microwave vial, which was evacuated and backfilled with nitrogen three times. 1,4-Dioxane (3.1 mL) was added. The resulting mixture was stirred at 110° C. for 16 hours. The reaction was then concentrated. The resulting residue was purified by silica gel chromatography, using 0-10% MeOH-DCM with 0-1% ammonia as eluent, to afford methyl 5-cyclopropyl-3-[(2,6-dimethyl-4-pyridyl)amino]-6-(3-methylimidazo[4,5-c]pyridin-7-yl)pyrazine-2-carboxylate (0.074 g, 56%); 1H NMR (500 MHz, CHLOROFORM-d) 8.02-1.15 (2H, m), 1.32-1.41 (2H, m), 1.98-2.07 (1H, m), 2.54 (6H, s), 3.99 (3H, s), 4.01 (3H, s), 7.38 (2H, s), 8.02 (1H, s), 8.69 (1H, s), 8.93 (1H, s), 10.47 (1H, br s); m/z: (ES+), [M+H]+=430.2

(b) 5-Cyclopropyl-3-[(2,6-dimethyl-4-pyridyl)amino]-6-(3-methylimidazo[4,5-c]pyridin-7-yl)pyrazine-2-carboxamide 7 N Methanolic ammonia (2.0 mL, 14 mmol) was added to a solution of methyl 5-cyclopropyl-3-[(2,6-dimethyl-4-pyridyl)amino]-6-(3-methylimidazo[4,5-c]pyridin-7-yl) pyrazine-2-carboxylate (74 mg, 0.17 mmol) in methanol (1.5 mL). The resulting solution was stirred at 100° C. for 4 hours in a Biotage microwave reactor. The reaction was then concentrated. The resulting residue was purified by silica gel chromatography, using 0-10% MeOH-DCM as eluent, and 0-1% ammonia as modifier, to afford 5-cyclopropyl-3-[(2,6-dimethyl-4-pyridyl)amino]-6-(3-methylimidazo[4,5-c]pyridin-7-yl)pyrazine-2-carboxamide (32 mg, 45%) as a yellow solid; 1H NMR (500 MHz, CHLOROFORM-d) δ 1.00-1.14 (2H, m), 1.33-1.43 (2H, m), 2.02-2.11 (1H, m), 2.53 (6H, s), 4.03 (3H, s), 5.65 (1H, br s), 7.39 (2H, s), 7.91 (1H, br s), 8.04 (1H, s), 8.66 (1H, s), 8.94 (1H, s), 11.13 (1H, br s); m/z: (ES+), [M+H]+=415.2

Example 101

3-[(2-Methoxy-6-methyl-4-pyridyl)amino]-5-(methylamino)-6-(3-methylimidazo[4,5-c]pyridin-7-yl)pyrazine-2-carboxamide

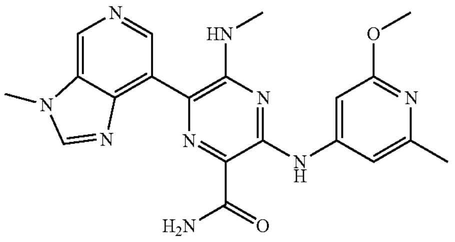

(a) 3-[(2-Methoxy-6-methyl-4-pyridyl)amino]-5-(methylamino)-6-(3-methylimidazo[4,5-c]pyridin-7-yl)pyrazine-2-carboxylic acid A mixture of methyl 3-amino-5-(methylamino)-6-(3-methylimidazo[4,5-c]pyridin-7-yl)pyrazine-2-carboxylate (45 mg, 0.14 mmol), 4-bromo-2-methoxy-6-methyl-pyridine (35 mg, 0.17 mmol), BrettPhos Pd G3 (13 mg, 0.010 mmol), and sodium tert-butoxide (41 mg, 0.43 mmol) was evacuated and backfilled three times with nitrogen. 1,4-Dioxane (1.5 mL) was added, and the mixture was evacuated and backfilled twice with nitrogen. The resulting mixture was stirred at 80° C. for 3 hours. The reaction was then concentrated. The resulting residue was acidified with 1N aqueous HCl, then washed with ethyl acetate. The aqueous layer was then concentrated. The resulting residue was used in the next step without further purification, assuming 100% yield (b) 3-[(2-Methoxy-6-methyl-4-pyridyl)amino]-5-(methylamino)-6 (3-methylimidazo[4,5-c]pyridin-7-yl)pyrazine-2-carboxamide DIPEA (0.150 mL, 0.86 mmol) was added to a suspension of 3-[(2-methoxy-6-methyl-4-pyridyl)amino]-5-(methylamino)-6-(3-methylimidazo[4,5-c]pyridin-7-yl)pyrazine-2-carboxylic acid (60 mg, 0.14 mmol), ammonium chloride (31 mg, 0.57 mmol), and HATU (109 mg, 0.290 mmol) in DMF (2 mL). The resulting mixture was stirred at 25° C. for 1 hour. The reaction was then concentrated. The resulting residue was purified by silica gel chromatography, using 0-20% MeOH-DCM as eluent, to afford a yellow solid. This material was further purified by reverse phase HPLC, using a 5 micron, 19 mm×100 mm Xbridge C18 column, 13-40% MeCN—$H_2O$ as eluent, and 0.1% trifluoroacetic acid as modifier, to afford 3-[(2-methoxy-6-methyl-4-pyridyl)

amino]-5-(methylamino)-6-(3-methylimidazo[4,5-c]pyridin-7-yl)pyrazine-2-carboxamide (0.024 g, 32%) as a light yellow solid; 1H NMR (500 MHz, DMSO-d6) δ ppm 2.42 (3H, s), 2.99 (3H, d), 3.96 (3H, s), 4.12 (3H, s), 7.12 (1H, br d), 7.69 (2H, br s), 7.89 (1H, br d), 8.03 (1H, br s), 8.93 (2H, s), 9.46 (1H, s), 12.22 (1H, br d). m/z: (ES+), [M+H]+=420.3

Example 102

3-[[2-(2-Methoxyethoxy)-6-methyl-4-pyridyl]amino]-5-(methylamino)-6-(3-methylimidazo[4,5-c]pyridin-7-yl)pyrazine-2-carboxamide

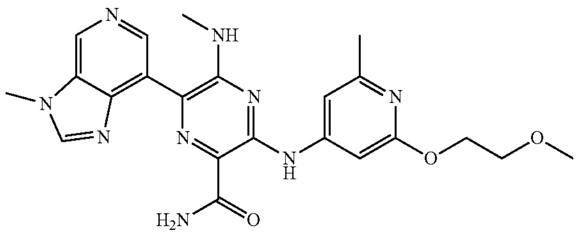

(a) 4-Bromo-2-(2-methoxyethoxy)-6-methyl-pyridine

DTBAD (3.67 g, 16.0 mmol) was added to a mixture of 4-bromo-6-methyl-pyridin-2-ol (2.00 g, 10.6 mmol), 2-methoxyethanol (1.21 g, 16.0 mmol), and triphenylphosphine (4.18 g, 15.96 mmol) in THF (50 mL) under nitrogen. The resulting mixture was stirred at room temperature for 2 hours. The reaction was then concentrated. The resulting residue was purified by C18 reverse phase chromatography, using 0-60% MeCN—$H_2O$ as eluent and 0.1% formic acid as modifier, to afford 4-bromo-2-(2-methoxyethoxy)-6-methyl-pyridine (1.40 g, 54%) as a yellow oil which crystallized on standing; 1H NMR (400 MHZ, DMSO-d6) δ 2.36 (3H, s), 3.28 (3H, s), 3.59-3.66 (2H, m), 4.32-4.39 (2H, m), 6.91 (1H, m), 7.10 (1H, m); m/z: (ES+), [M+H]+=246.0

(b) Methyl 3-[[2-(2-methoxyethoxy)-6-methyl-4-pyridyl]amino]-5_(methylamino)-6-(3-methylimidazo[4,5-c]pyridin-7-yl)pyrazine-2-carboxylate Brettphos Pd G3 (74 mg, 0.080 mmol) was added to a suspension of 4-bromo-2-(2-methoxyethoxy)-6-methyl-pyridine (100 mg, 0.41 mmol), methyl 3-amino-5-(methylamino)-6-(3-methylimidazo[4,5-c]pyridin-7-yl)pyrazine-2-carboxylate (127 mg, 0.410 mmol), and cesium carbonate (265 mg, 0.810 mmol) in 1,4-dioxane (15 mL) under nitrogen. The resulting mixture was stirred at 100° C. for 16 hours. The reaction was then concentrated. The resulting residue was purified by silica gel chromatography, using 0-10% MeOH-DCM as eluent, to afford methyl 3-[[2-(2-methoxyethoxy)-6-methyl-4-pyridyl]amino]-5-(methylamino)-6-(3-methylimidazo[4,5-c]pyridin-7-yl)pyrazine-2-carboxylate (0.080 g, 41%) as a yellow solid; 1H NMR (400 MHZ, DMSO-d6) δ 2.35 (3H, s), 2.95 (3H, d), 3.33 (3H, s), 3.74 (2H, s), 3.84 (3H, s), 4.00 (2H, s), 4.01 (3H, s), 7.15 (1H, d), 7.28 (1H, d), 8.03 (1H, d), 8.46 (1H, d), 8.53 (1H, s), 9.06 (1H, s), 10.59 (1H, s); m/z: (ES+), [M+H]+=479.2

(c) 3-[[2-(2-Methoxyethoxy)-6-methyl-4-pyridyl]amino]-5-(methylamino)-6-(3-methylimidazo[4,5-c]pyridin-7-yl)pyrazine-2-carboxamide 7 N Methanolic ammonia (8.0 mL, 56 mmol) was added to methyl 3-[[2-(2-methoxyethoxy)-6-methyl-4-pyridyl]amino]-5-(methylamino)-6-(3-methylimidazo[4,5-c]pyridin-7-yl)pyrazine-2-carboxylate (50 mg, 0.10 mmol). The resulting suspension was stirred at 80° C. for 15 hours. The reaction was then concentrated. The resulting residue was purified by preparative HPLC using a 5 micron, 30×150 mm Xselect CSH OBD column, 5-25% MeCN—$H_2O$ as eluent, and 0.1% formic acid as modifier, to afford 3-[[2-(2-methoxyethoxy)-6-methyl-4-pyridyl]amino]-5-(methylamino)-6-(3-methylimidazo[4,5-c]pyridin-7-yl)pyrazine-2-carboxamide (18 mg, 37%) as a yellow solid; 1H NMR (300 MHz, DMSO-d6) δ 2.32 (3H, s), 2.96 (3H, d), 3.58-3.67 (2H, m), 4.00 (3H, s), 4.29-4.38 (2H, m), 7.02 (1H, s), 7.26 (1H, d), 7.50 (1H, s), 7.84 (1H, s), 8.03 (1H, br q), 8.51 (1H, s), 8.71 (1H, s), 9.03 (1H, s), 11.78 (1H, s). The ethereal methyl group was obscured by the residual water peak; m/z: (ES+), [M+H]+=464.2

Example 103

3-[(2-Cyano-6-methyl-4-pyridyl)amino]-5-(methylamino)-6-(3-methylimidazo[4,5-c]pyridin-7-yl)pyrazine-2-carboxamide

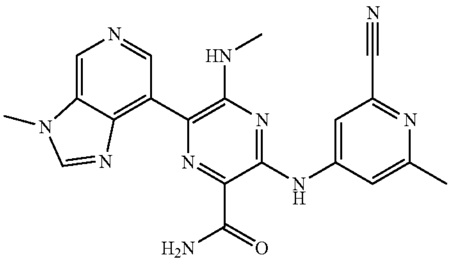

(a) 3-Amino-5-(methylamino)-6-(3-methylimidazo[4,5-c]pyridin-7-yl)pyrazine-2-carboxamide A mixture of methyl 3-amino-5-(methylamino)-6-(3-methylimidazo[4,5-c]pyridin-7-yl)pyrazine-2-carboxylate (46 mg, 0.15 mmol) and lithium hydroxide (27.0 mg, 1.13 mmol) in water (0.5 mL), MeOH (0.5 mL), and THF (0.5 mL) was stirred at 100° C. for 1 hour in a Biotage microwave reactor. The reaction mixture was then acidified with 1 N HCl and concentrated. The resulting residue was dissolved in DMF (1.5 mL). HATU (0.086 g, 0.23 mmol), ammonium chloride (0.040 g, 0.75 mmol), and triethylamine (84 μL, 0.60 mmol) were sequentially added. The resulting mixture was stirred at 25 C for 3 hours. Additional triethylamine (150 μL, 1.07 mmol) was added. The resulting mixture was stirred at 25 C for 16 hours. The reaction then was treated with saturated aqueous sodium bicarbonate. The resulting suspension was filtered. The filtrate was extracted with 5:1 DCM/IPA. The organic layer was washed with brine dried over magnesium sulfate, filtered, and concentrated to afford 3-amino-5-(methylamino)-6-(3-methylimidazo[4,5-c]pyridin-7-yl)pyrazine-2-carboxamide (0.045 g, quantitative %) as a brown solid. m/z: (ES+), [M+H]+=299.1

(b) 3-[(2-Cyano-6-methyl-4-pyridyl)amino]-5-(methylamino)-6-(3-methylimidazo[4,5-c]pyridin-7-yl)pyrazine-2-carboxamide A mixture of 4-bromo-6-methyl-pyridine-2-carbonitrile (0.035 g, 0.18 mmol), 3-amino-5-(methylamino)-6-(3-methylimidazo[4,5-c]pyridin-7-yl)pyrazine-2-carboxamide (0.045 g, 0.15 mmol), BrettPhos Pd G3 (0.027 g, 0.030 mmol), and cesium carbonate (0.147 g, 0.450 mmol) in 1,4-dioxane (2 mL) was evacuated and backfilled with nitrogen 3 times. The resulting mixture was stirred at 100° C. for 16 hours. The reaction mixture was then treated with water and filtered. The filter cake was washed with water, dried under vacuum, and purified by silica gel chromatography, using 0-15% MeOH-DCM as eluent, to afford a yellow solid. This material was further purified by C18 reverse phase chromatography, using 0-30% MeCN—$H_2O$ as eluent and 0.1% trifluoroacetic acid as modifier, to afford 3-[(2-cyano-6-methyl-4-pyridyl)amino]-5-(methylamino)-6-(3-methylimidazo[4,5-c]pyridin-7-yl)pyrazine-2-carboxamide (5.0 mg, 7.4%) as a yellow solid; 1H NMR (500 MHz, DMSO-d6) 2.99 (3H, d), 4.06 (3H, s), 7.07 (1H, t), 7.63 (1H, br s), 7.86 (1H, d), 7.95 (1H, s), 8.00 (1H, br s), 8.40 (1H, d), 8.76 (1H, br s), 8.84 (1H, s), 9.28 (1H, br s), 12.09 (1H, s); the aryl methyl group was buried under the DMSO signal; m/z: (ES+), [M+H]+=415.1

Example 104

3-[(1,5-Dimethyl-6-oxo-3-pyridyl)amino]-5-(methylamino)-6-(3-methylimidazo[4,5-c]pyridin-7-yl)pyrazine-2-carboxamide

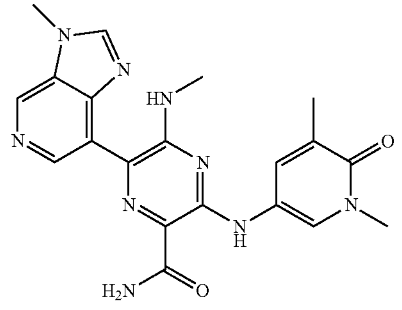 [SMILES: CNc1nc(Nc2cc(C)c(=O)n(C)c2)c(C(N)=O)nc1-c1cncc2c1ncn2C]

(a) 3-[(1,5-Dimethyl-6-oxo-3-pyridyl)amino]-5-(methylamino)-6-(3-methylimidazo[4,5

A mixture of methyl 3-amino-5-(methylamino)-6-(3-methylimidazo[4,5-c]pyridin-7-yl)pyrazine-2-carboxylate (45 mg, 0.14 mmol), 5-bromo-1,3-dimethyl-pyridin-2-one (35 mg, 0.17 mmol), BrettPhos Pd G3 (13.02 mg, 0.01 mmol) and sodium tert-butoxide (41.4 mg, 0.43 mmol) was evacuated and backfilled three times with nitrogen. 1,4-Dioxane (1.5 mL) was added, and the mixture was evacuated and backfilled twice with nitrogen. The resulting mixture was stirred at 80° C. for 3 hours. The reaction was then concentrated. The resulting residue was acidified with 1N aqueous HCl, then washed with ethyl acetate. The aqueous layer was then concentrated. The resulting residue was used in the next step without further purification, assuming 100% yield.

(b) 3-[(1,5-Dimethyl-6-oxo-3-pyridyl)amino]-5-(methylamino)-6-(3-methylimidazo[4,5-c]pyridin-7-yl)pyrazine-2-carboxamide DIPEA (0.15 mL, 0.86 mmol) was added to a suspension of 3-[(1,5-dimethyl-6-oxo-3-pyridyl)amino]-5-(methylamino)-6-(3-methylimidazo[4,5-c]pyridin-7-yl)pyrazine-2-carboxylic acid (60 mg, 0.14 mmol), ammonium chloride (31 mg, 0.57 mmol), and HATU (109 mg, 0.290 mmol) in DMF (2 mL). The resulting mixture was stirred at 25° C. for 1 hour. The reaction was then concentrated. The resulting residue was purified by silica gel chromatography, using 0-20% MeOH-DCM as eluent, to afford a yellow solid. This material was further purified by reverse phase HPLC, using a 19 mm×100 mm 5 μm Xbridge C18 column, using 13-40% MeCN—$H_2O$ as eluent and 0.1% trifluoroacetic acid as modifier, to afford 3-[(1,5-dimethyl-6-oxo-3-pyridyl)amino]-5-(methylamino)-6-(3-methylimidazo[4,5-c]pyridin-7-yl)pyrazine-2-carboxamide (3.3 mg, 5.5%) as a light yellow solid; 1H NMR (500 MHz, DMSO-d6) δ 2.40 (3H, s), 2.97 (3H, d), 3.94 (3H, s), 4.10 (3H, s), 7.11 (1H, br s), 7.67 (2H, br s), 7.83-7.94 (1H, m), 8.01 (1H, br s), 8.91 (2H, s), 9.44 (1H, s), 12.21 (1H, br s); m/z: (ES+), [M+H]+=420.3

Example 105

3-[[1-(Difluoromethyl)-6-oxo-3-pyridyl]amino]-5-(methylamino)-6-(3-methylimidazo[4,5-c]pyridin-7-yl)pyrazine-2-carboxamide

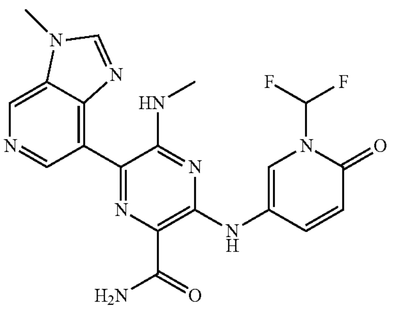 [SMILES: CNc1nc(Nc2ccc(=O)n(C(F)F)c2)c(C(N)=O)nc1-c1cncc2c1ncn2C]

(a) Methyl 3-[[1-(difluoromethyl)-6-oxo-3-pyridyl]amino]-5_(methylamino)-6-(3-methylimidazo[4,5-c]pyridin-7-yl)pyrazine-2-carboxylate Cesium carbonate (312 mg, 0.960 mmol) was added to a suspension of 5-bromo-1-(difluoromethyl) pyridin-2-one (143 mg, 0.640 mmol), BrettPhos Pd G3 (29 mg, 0.030 mmol), and methyl 3-amino-5-(methylamino)-6-(3-methylimidazo[4,5-c]pyridin-7-yl)pyrazine-2-carboxylate (100 mg, 0.32 mmol) in 1,4-dioxane (10 mL) under nitrogen. The resulting mixture was stirred at 100° C. for 16 hours. The reaction was then concentrated. The resulting residue was purified by silica gel chromatography, using 0-10% MeOH-DCM as eluent, to afford methyl 3-[[1-(difluoromethyl)-6-oxo-3-pyridyl]amino]-5-(methylamino)-6-(3-methylimidazo[4,5-c]pyridin-7-yl)pyrazine-2-carboxylate (0.060 g, 41%) as a yellow solid; 1H NMR (300 MHz, DMSO-d6) δ 2.84 (3H, d), 3.81 (3H, s), 3.99 (3H, s), 6.53-6.61 (1H, m), 7.73-7.81 (1H, m), 7.91 (1H, t), 7.96 (1H, br q), 8.48 (1H, s), 8.51 (1H, s), 8.63-8.70 (1H, m), 9.03 (1H, s), 9.96 (1H, s); m/z: (ES+), [M+H]+=457.2

(b) 3-[[1-(Difluoromethyl)-6-oxo-3-pyridyl]amino]-5-(methylamino)-6-(3-methylimidazo[4,5-c]pyridin-7-yl)pyrazine-2-carboxamide 7 N Methanolic ammonia (10 mL, 70 mmol) was added to methyl 3-[[1-(difluoromethyl)-6-oxo-3-pyridyl]amino]-5-(methylamino)-6-(3-methylimidazo[4,5-c]pyridin-7-yl) pyrazine-2-carboxylate (60 mg, 0.13 mmol). The resulting suspension was stirred at 80° C. for 24 hours. The reaction was then concentrated. The resulting residue was purified by preparative HPLC using a 5 micron, 19×250 mm XSelect CSH Prep C18 OBD column, 15-35% MeCN—$H_2O$ as eluent, and 0.1% formic acid as modifier, to afford 3-[[1-(difluoromethyl)-6-oxo-3-pyridyl]amino]-5-(methylamino)-6-(3-methylimidazo[4,5-c]pyridin-7-yl)pyrazine-2-carboxamide (8.0 mg, 14%) as a yellow solid; 1H NMR (300 MHz, DMSO-d6) δ 2.92 (3H, d), 4.02 (3H, s), 6.58 (1H, d), 7.43 (1H, s), 7.67 (1H, m), 7.79 (1H, s), 7.94 (1H, t), 8.08 (1H, br q), 8.53 (1H, s), 8.73 (1H, s), 8.83 (1H, d), 9.04 (1H, s), 11.20 (1H, s); m/z: (ES+), [M+H]+=442.1

Example 106

5-(Methylamino)-3-[4-[(1R,4R)-5-methyl-2,5-diazabicyclo[2.2.1]heptan-2-yl]anilino]-6-(3-methylimidazo[4,5-c]pyridin-7-yl)pyrazine-2-carboxamide bis-formate salt

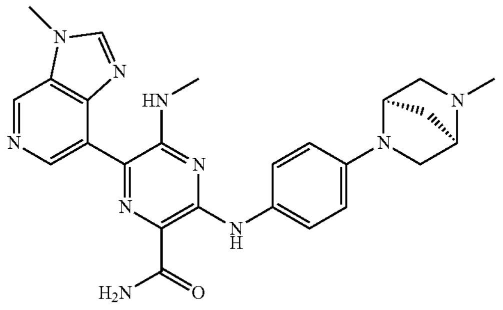 [SMILES: CNc1nc(Nc2ccc(N3C[C@H]4C[C@@H]3CN4C)cc2)c(C(N)=O)nc1-c1cncc2c1ncn2C]

(a) (1R,4R)-2-(4-Bromophenyl)-5-methyl-2,5-diazabicyclo[2.2.1]heptane

Cesium carbonate (2.30 g, 7.07 mmol) was added to a mixture of 1-bromo-4-iodo-benzene (500 mg, 1.77 mmol), (1R,4R)-2-methyl-2,5-diazabicyclo[2.2.1]heptane dihydrochloride (393 mg, 2.12 mmol), palladium (II) acetate (40 mg, 0.18 mmol), and (rac)-BINAP (110 mg, 0.18 mmol) in 1,4-dioxane (15 mL). The resulting mixture was stirred at 80° C. for 1 hour. The reaction was then concentrated. The resulting residue was purified by silica gel chromatography, using 0-10% MeOH-DCM as eluent, to afford (1R,4R)-2-(4-bromophenyl)-5-methyl-2,5-diazabicyclo[2.2.1]heptane (0.200 g, 42%) as a yellow solid; 1H NMR (300 MHz, DMSO-d6) δ 1.74 (1H, ddt), 1.86 (1H, ddt), 2.24 (3H, s), 2.43 (1H, dd), 2.76 (1H, dd), 3.10 (1H, dd), 3.28 (1H, dd), 3.41 (1H, d), 4.26 (1H, d), 6.48-6.59 (2H, m), 7.22-7.31 (2H, m). m/z: (ES+), [M+2+H]+=269.0

(b) Methyl 5-(methylamino)-3-[4-[(1R,4R)-5-methyl-2,5-diazabicyclo[2.2.1]heptan-2-yl]anilino]-6-(3-methylimidazo[4,5-c]pyridin-7-yl)pyrazine-2-carboxylate BrettPhos Pd G3 (23 mg, 0.030 mmol) was added to a suspension of cesium carbonate (250 mg, 0.77 mmol), (1R,4R)-2-(4-bromophenyl)-5-methyl-2,5-diazabicyclo [2.2.1]heptane (136 mg, 0.510 mmol) and methyl 3-amino-5-(methylamino)-6-(3-methylimidazo[4,5-c]pyridin-7-yl) pyrazine-2-carboxylate (80 mg, 0.26 mmol) in 1,4-dioxane (2 mL) under nitrogen. The resulting mixture was stirred at 100° C. for 16 hours. The reaction was then concentrated. The resulting residue was purified by silica gel chromatography, using 0-10% MeOH-DCM as eluent, to afford methyl 5-(methylamino)-3-[4-[(1R,4R)-5-methyl-2,5-diazabicyclo [2.2.1]heptan-2-yl]anilino]-6-(3-methylimidazo[4,5-c]pyridin-7-yl)pyrazine-2-carboxylate (0.060 g, 47%) as a yellow solid; 1H NMR (300 MHz, DMSO-d6) δ 1.90 (1H, d), 2.00 (2H, s), 2.43-2.49 (3H, m), 2.89 (4H, d), 3.22 (1H, d), 3.45 (1H, d), 3.70-3.78 (1H, m), 3.82 (3H, s), 4.02 (3H, d), 4.40 (1H, s), 6.64 (2H, d), 7.57-7.66 (2H, m), 7.91 (1H, d), 8.50 (1H, s), 8.54 (1H, s) 9.03 (1H, s), 10.20 (1H, s). m/z: (ES+), $[M+2H]^{2+}$=250.6

(c) 5-(Methylamino)-3-[4-[(1R,4R)-5-methyl-2,5-diazabicyclo[2.2.1]heptan-2-yl]anilino]-6-(3-methylimidazo[4,5-c]pyridin-7-yl)pyrazine-2-carboxamide bis-formate salt 7 N Methanolic ammonia (2.0 mL, 14 mmol) was added to methyl 5-(methylamino)-3-[4-[(1R,4R)-5-methyl-2,5-diazabicyclo[2.2.1]heptan-2-yl]anilino]-6-(3-methylimidazo [4,5-c]pyridin-7-yl)pyrazine-2-carboxylate (60 mg, 0.12 mmol). The resulting suspension was stirred at 80° C. for 24 hours. The resulting residue was purified by preparative HPLC Column, using a 5 micron, 19 mm×250 mm, XBridge Prep OBD C18 column, 15-35% MeCN—$H_2O$ as eluent, and 0.1% formic acid as modifier, to afford 5-(methylamino)-3-[4-[(1R,4R)-5-methyl-2,5-diazabicyclo[2.2.1] heptan-2-yl]anilino]-6-(3-methylimidazo[4,5-c]pyridin-7-yl)pyrazine-2-carboxamide bis-formate salt (9.0 mg, 13%) as a yellow solid; 1H NMR (300 MHz, DMSO-d6) δ 1.75-1.83 (1H, m), 1.86-1.95 (1H, m), 2.32 (3H, s), 2.52-2.66 (1H, m), 2.76-2.86 (1H, m), 2.93 (3H, d), 3.11-3.20 (1H, m), 3.31-3.40 (1H, m), 3.50 (1H, s), 4.02 (3H, s), 4.29 (1H, s), 6.60 (2H, d), 7.28 (1H, s), 7.59 (2H, d), 7.69 (1H, s), 8.00 (1H, br q), 8.23 (2H, s), 8.52 (1H, s), 8.73 (1H, s), 9.01 (1H, s), 11.18 (1H, s); m/z: (ES+), $[M+2H]^{2+}$=243.1

Example 107

5-(Methylamino)-3-[4-(8-methyl-3,8-diazabicyclo [3.2.1]octan-3-yl)anilino]-6-(3-methylimidazo[4,5-c] pyridin-7-yl)pyrazine-2-carboxamide

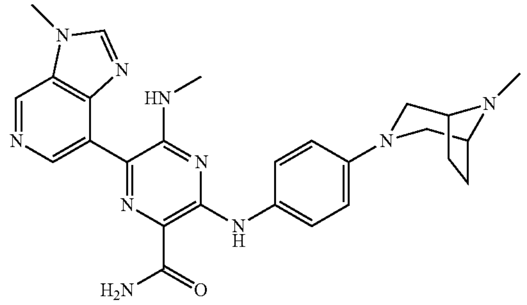 [SMILES: CNc1nc(Nc2ccc(N3CC4CCC(C3)N4C)cc2)c(C(N)=O)nc1-c1cncc2c1ncn2C]

(a) 3-(4-Bromophenyl)-8-methyl-3,8-diazabicyclo [3.2.1]octane

1-Bromo-4-iodo-benzene (500 mg, 1.77 mmol) was added to a mixture of 8-methyl-3,8-diazabicyclo[3.2.1]octane hydrochloride (287 mg, 1.77 mmol), cesium carbonate (1.73 g, 5.30 mmol), (rac)-BINAP (165 mg, 0.27 mmol), and palladium (II) acetate (60 mg, 0.27 mmol) in 1,4-dioxane (5 mL) under nitrogen. The resulting mixture was stirred at 100° C. for 2 hours. The reaction was then concentrated. The resulting residue was purified by silica gel chromatography, using 0-30% MeOH-DCM as eluent, to afford 3-(4-bromophenyl)-8-methyl-3,8-diazabicyclo[3.2.1]octane (0.200 g, 40%) as a yellow solid; 1H NMR (400 MHz, DMSO-d6) δ 1.68 (2H, d), 1.99 (2H, dd), 2.35 (3H, s), 2.82-2.97 (2H, m), 3.30-3.45 (4H, m), 6.73-6.82 (2H, m), 7.27-7.35 (2H, m); m/z: (ES+), [M+H]+=281.0

(b) Methyl 5-(methylamino)-3-[4-(8-methyl-3,8-diazabicyclo[3.2.1]octan-3-yl)anilino]-6-(3-methylimidazo[4,5-c]pyridin-7-yl)pyrazine-2-carboxylate 3-(4-Bromophenyl)-8-methyl-3,8-diazabicyclo[3.2.1]octane (90 mg, 0.32 mmol) was added to methyl 3-amino-5-(methylamino)-6-(3-methylimidazo[4,5-c]pyridin-7-yl) pyrazine-2-carboxylate (100 mg, 0.32 mmol), BrettPhos Pd G3 (43 mg, 0.050 mmol), and cesium carbonate (312 mg, 0.960 mmol) in 1,4-dioxane (5 mL) under nitrogen. The resulting mixture was stirred at 100° C. for 16 hours. The reaction was then concentrated. The resulting residue was purified by silica gel chromatography, using 0-30% MeOH-DCM as eluent, to afford methyl 5-(methylamino)-3-[4-(8-methyl-3,8-diazabicyclo[3.2.1]octan-3-yl)anilino]-6-(3-methylimidazo[4,5-c]pyridin-7-yl)pyrazine-2-carboxylate (0.060 g, 37%) as a yellow solid; 1H NMR (300 MHz, DMSO-d6) δ 1.97-1.99 (2H, m), 2.05-2.09 (2H, m), 2.90 (3H, d), 2.96-3.01 (2H, m), 3.10-3.22 (2H, m), 3.38-3.60 (2H, m), 3.82 (3H, s), 4.02 (3H, s), 6.90 (2H, d), 7.66 (2H, d), 7.90 (1H, br q), 8.50 (1H, s), 8.53 (1H, s), 9.04 (1H, s), 10.25 (1H, s); the tertiary NMe peak was obscured under the DMSO peak; m/z: (ES+), [M+H]+=514.2

(c) 5-(Methylamino)-3-[4-(8-methyl-3,8-diazabicyclo[3.2.1]octan-3-yl)anilino]-6-(3-methylimidazo[4,5-c]pyridin-7-yl)pyrazine-2-carboxamide 7 N Methanolic ammonia (8.0 mL, 56 mmol) was added to methyl 5-(methylamino)-3-[4-(8-methyl-3,8-diazabicyclo [3.2.1]octan-3-yl)anilino]-6-(3-methylimidazo[4,5-c]pyridin-7-yl)pyrazine-2-carboxylate (50 mg, 0.10 mmol). The resulting suspension was stirred at 80° C. for 24 hours. The reaction was then concentrated. The resulting residue was purified by preparative HPLC, using a 5 micron, 30 mm×150 mm, XBridge Prep OBD C18 column, 23-33% MeCN-10 mM aqueous ammonium bicarbonate as eluent, and 0.1% ammonium hydroxide as modifier, to afford 5-(methylamino)-3-[4-(8-methyl-3,8-diazabicyclo[3.2.1]octan-3-yl)anilino]-6-(3-methylimidazo[4,5-c]pyridin-7-yl) pyrazine-2-carboxamide (9.0 mg, 19%) as a yellow solid; 1H NMR (300 MHz, DMSO-d6) δ 1.60-1.70 (2H, m), 1.89-2.00 (2H, m), 2.23 (3H, s), 2.80 (2H, dd), 2.93 (3H, d), 3.20 (2H, s), 3.29 (2H, s), 4.02 (3H, s), 6.81 (2H, d), 7.30 (1H, s), 7.61 (2H, d), 7.70 (1H, s), 7.99 (1H, br q), 8.52 (1H, s), 8.73 (1H, s), 9.01 (1H, s), 11.23 (1H, s); m/z: (ES+), [M+H]+=499.3

Example 108

3-[4-[(3S,5R)-3,5-Dimethylpiperazin-1-yl]anilino]-6-(3-methylimidazo[4,5-c]pyridin-7-yl)-5-(trifluoromethyl)pyrazine-2-carboxamide

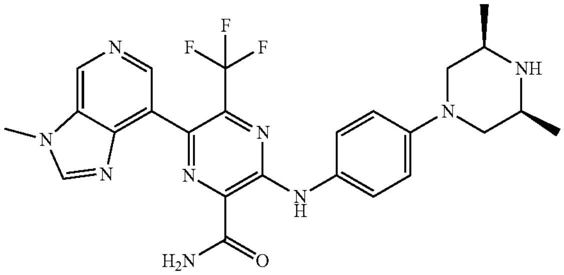

(a) (3S,5R)-1-(4-Bromophenyl)-3,5-dimethyl-piperazine

Dioxane (15 mL) was added to a mixture of 1-bromo-4-iodo-benzene (0.580 g, 2.05 mmol), (2R,6S)-2,6-dimethylpiperazine (0.351 g, 3.08 mmol), palladium (II) acetate (0.046 g, 0.21 mmol), XantPhos (0.237 g, 0.41 mmol) and sodium tert-butoxide (0.296 g, 3.08 mmol). The resulting mixture was evacuated and backfilled three times with nitrogen, then stirred at 90° C. for 6 hours. The reaction was then diluted with water and extracted with 5:1 DCM/IPA. The organic layer was concentrated. The resulting residue was purified by silica gel chromatography, using 0-10% MeOH-DCM as eluent, to afford (3S,5R)-1-(4-bromophenyl)-3,5-dimethyl-piperazine (0.372 g, 67%) as a brown solid; 1H NMR (500 MHz, DMSO-d6) δ 1.00 (6H, d), 2.08 (2H, t), 2.80 (2H, dqd), 3.16 (1H, s), 3.49 (2H, dd), 6.82-6.90 (2H, m), 7.25-7.34 (2H, m). m/z: (ES+), [M+2+H]+=271.1

(b) 3-[4-[(3S,5R)-3,5-Dimethylpiperazin-1-yl]anilino]-6-(3-methylimidazo[4,5-c]pyridin-7-yl)-5-(trifluoromethyl)pyrazine-2-carboxylic acid Dioxane (1 mL) was added to a mixture of (3S,5R)-1-(4-bromophenyl)-3,5-dimethyl-piperazine (0.037 g, 0.14 mmol), ethyl 3-amino-6-(3-methylimidazo[4,5-c]pyridin-7-yl)-5-(trifluoromethyl)pyrazine-2-carboxylate (0.042 g, 0.11 mmol), BrettPhos Pd G3 (0.021 g, 0.020 mmol), and cesium carbonate (0.112 g, 0.340 mmol). The resulting mixture was evacuated and backfilled three times with nitrogen, then stirred at 100° C. for 2.5 hours. The reaction was then concentrated. The resulting residue was treated with water and extracted with EtOAc. The aqueous layer was acidified to pH 3 with 1M HCl, then concentrated to afford 3-[4-[(3S,5R)-3,5-dimethylpiperazin-1-yl]anilino]-6-(3-methylimidazo[4,5-c]pyridin-7-yl)-5-(trifluoromethyl)pyrazine-2-carboxylic acid (0.060 g, 99%), which was used in the next step without purification.

(c) 3-[4-[(3S,5R)-3,5-Dimethylpiperazin-1-yl]anilino]-6-(3-methylimidazo[4,5-c]pyridin-7-yl)-5-(trifluoromethyl)pyrazine-2-carboxamide Triethylamine (0.061 mL, 0.44 mmol) was added to a suspension of 3-((4-((3S,5R)-3,5-dimethylpiperazin-1-yl) phenyl)amino)-6-(3-methyl-3H-imidazo[4,5-c]pyridin-7- yl)-5-(trifluoromethyl)pyrazine-2-carboxylic acid (0.058 g, 0.11 mmol), ammonium chloride (0.029 g, 0.55 mmol) and HATU (0.063 g, 0.17 mmol) in DMF (1.5 mL). The resulting mixture was stirred at 25° C. overnight. The reaction was treated with saturated aqueous sodium bicarbonate and extracted with 5:1 DCM/IPA. The organic layer was concentrated. The resulting residue was purified by C18 reverse phase chromatography, using 0-55% MeCN—$H_2O$ as eluent and 0.1% ammonium hydroxide as modifier, to afford 3-((4-((3S,5R)-3,5-dimethylpiperazin-1-yl)phenyl)amino)-6-(3-methyl-3H-imidazo[4,5-c]pyridin-7-yl)-5-(trifluoromethyl) pyrazine-2-carboxamide (0.018 g, 31%) as a yellow solid; 1H NMR (500 MHz, DMSO-d6) δ 1.15 (6H, br d), 2.31-2.43 (2H, m), 3.07-3.19 (2H, m), 3.70 (2H, br d), 3.99 (3H, s), 7.02 (2H, br d), 7.62 (2H, br d), 8.14 (1H, br d), 8.27 (1H, s), 8.40 (1H, s), 8.44 (1H, s), 9.05 (1H, s), 11.28 (1H, s). m/z: (ES+), [M+H]+=526.3

Example 109

3-[4-[(3S,5R)-3,5-Dimethylpiperazin-1-yl]-3,5-difluoro-anilino]-5-(methylamino)-6-(3-methylimidazo [4,5-c]pyridin-7-yl)pyrazine-2-carboxamide

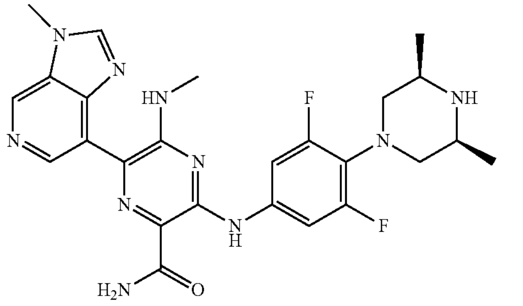 [SMILES: CNc1nc(Nc2cc(F)c(N3C[C@@H](C)N[C@@H](C)C3)c(F)c2)c(C(N)=O)nc1-c1cncc2c1ncn2C]

(a) (3S,5R)-1-(4-Bromo-2,6-difluoro-phenyl)-3,5-dimethyl-piperazine $Pd_2(dba)_3$ (288 mg, 0.320 mmol) was added to a suspension of 5-bromo-1,3-difluoro-2-iodobenzene (1.0 g, 3.14 mmol), cis-2,6-dimethylpiperazine (394 mg, 3.44 mmol), Xantphos (362 mg, 0.620 mmol), and cesium carbonate (2.04 g, 6.28 mmol) in dioxane (20 mL) under nitrogen. The resulting mixture was stirred at 100° C. for 16 hours. The reaction was then concentrated. The resulting residue was purified by silica gel chromatography, using 0-10% MeOH-DCM as eluent, to afford (3S,5R)-1-(4-bromo-2,6-difluoro-phenyl)-3,5-dimethyl-piperazine (0.300 g, 31%) as a brown oil; 1H NMR (400 MHZ, DMSO-d6) δ 0.95 (6H, d), 2.58 (2H, t), 2.75-2.90 (2H, m), 2.98 (2H, dd), 7.30-7.39 (2H, m). The NH proton was broadened to baseline. m/z: (ES+), [M+H]+=305.1

(b) 3-[4[(3S,5R)-3,5-Dimethylpiperazin-1-yl]-3,5-difluoro-anilino]-5-(methylamino)-6 (3-methylimidazo[4,5-c]pyridin-7-yl)pyrazine-2-carboxamide BrettPhos Pd G3 (23 mg, 0.030 mmol) was added to methyl 3-amino-5-(methylamino)-6-(3-methylimidazo[4,5-c]pyridin-7-yl)pyrazine-2-carboxylate (80 mg, 0.26 mmol), (3S,5R)-1-(4-bromo-2,6-difluoro-phenyl)-3,5-dimethyl-piperazine (94 mg, 0.31 mmol), and cesium carbonate (166 mg, 0.510 mmol) in dioxane (4 mL) under nitrogen. The resulting mixture was stirred at 100° C. for 16 hours. The reaction was then concentrated. The resulting residue was purified by silica gel chromatography, using 0-20% MeOH-DCM as eluent, to afford a yellow solid. This material was suspended in 7 N methanolic ammonia (7.3 mL, 51.1 mmol). The resulting mixture was stirred at 100° C. for 16 hours in a microwave reactor. The reaction was then concentrated. The resulting residue was purified by preparative HPLC Column using a 5 μm, 30 mm×150 mm SunFire C18 Prep Column, using 7-17% MeCN—$H_2O$ as eluent and 0.1% formic acid as modifier, to afford 3-[4-[(3S,5R)-3,5-dimethylpiperazin-1-yl]-3,5-difluoro-anilino]-5-(methylamino)-6-(3-methylimidazo[4,5-c]pyridin-7-yl)pyrazine-2-carboxamide (0.013 g, 9.74%) as a yellow solid; 1H NMR (400 MHZ, DMSO-d6) δ 0.97 (6H, d), 2.61 (2H, m), 2.78-2.99 (7H, m), 4.02 (3H, s), 7.43 (1H, s), 7.53 (2H, d), 7.79 (1H, s), 8.06 (1H, d), 8.52 (1H, s), 8.73 (1H, s), 9.03 (1H, s), 11.64 (1H, s); m/z: (ES+), [M+H]+=523.3

Example 110

5-(Methylamino)-3-[4-(3-methyl-3,8-diazabicyclo [3.2.1]octan-8-yl)anilino]-6-(3-methylimidazo[4,5-c] pyridin-7-yl)pyrazine-2-carboxamide formate salt

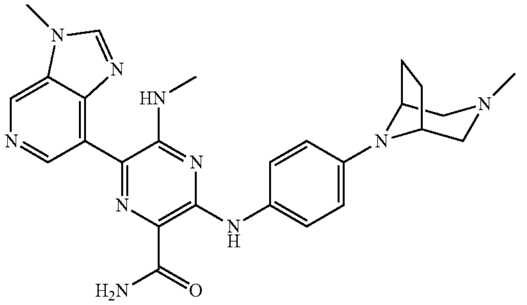 [SMILES: CNc1nc(Nc2ccc(N3C4CCC3CN(C)C4)cc2)c(C(N)=O)nc1-c1cncc2c1ncn2C]

(a) 8-(4-Bromophenyl)-3-methyl-3,8-diazabicyclo [3.2.1]octane

Palladium (II) acetate (79 mg, 0.35 mmol) was added to a mixture of (rac)-BINAP (219 mg, 0.350 mmol), 1-bromo-4-iodo-benzene (1.49 g, 5.27 mmol) and 3-methyl-3,8-diazabicyclo[3.2.1]octane dihydrochloride (700 mg, 3.52 mmol) and potassium tert-butoxide (1.18 g, 10.6 mmol) in toluene (10 mL) under nitrogen. The resulting mixture was stirred at 100° C. for 3 hours. The reaction was then concentrated. The resulting residue was purified by silica gel chromatography, using 0-10% MeOH-DCM as eluent, to afford a yellow residue. This material was further purified by preparative HPLC, using a 5 micron, 50 mm×100 mm, XBridge Prep C18 OBD column, decreasingly polar mixtures of MeCN—$H_2O$ as eluent, and 0.1% ammonium bicarbonate as modifier, to afford 8-(4-bromophenyl)-3-methyl-3,8-diazabicyclo[3.2.1]octane (0.350 g, 35%) as a yellow solid; 1H NMR (300 MHz, DMSO-d6) δ 1.86 (4H, dtd), 2.06 (3H, s), 2.23 (2H, dd), 2.44 (2H, dd), 4.20 (2H, t), 6.69-6.85 (2H, m), 7.20-7.35 (2H, m). m/z: (ES+), [M+2+H]+=283.0

(b) Methyl 5-(methylamino)-3-[4-(3-methyl-3,8-diazabicyclo[3.2.1]octan-8-yl)anilino]-6-(3-methylimidazo[4,5-c]pyridin-7-yl)pyrazine-2-carboxylate BrettPhos Pd G3 (23 mg, 0.030 mmol) was added to a suspension of cesium carbonate (250 mg, 0.77 mmol), methyl 3-amino-5-(methylamino)-6-(3-methylimidazo[4,5-c]pyridin-7-yl)pyrazine-2-carboxylate (80 mg, 0.26 mmol), and 8-(4-bromophenyl)-3-methyl-3,8-diazabicyclo[3.2.1] octane (144 mg, 0.510 mmol) in 1,4-dioxane (2 mL). The resulting mixture was stirred at 100° C. for 3 hours. The reaction was then concentrated. The resulting residue was purified by silica gel chromatography, using 0-10% MeOH-DCM as eluent, to afford methyl 5-(methylamino)-3-[4-(3-methyl-3,8-diazabicyclo[3.2.1]octan-8-yl)anilino]-6-(3-methylimidazo[4,5-c]pyridin-7-yl)pyrazine-2-carboxylate (0.080 g, 61%) as a yellow solid; 1H NMR (300 MHz, DMSO-d6) δ 1.80-1.92 (4H, m), 2.08 (3H, s), 2.24-2.38 (2H, m), 2.40-2.49 (2H, m), 2.90 (3H, d), 3.82 (3H, s), 4.02 (3H, s), 4.18-4.24 (2H, m), 6.83 (2H, d), 7.61 (2H, d), 7.92 (1H, br q), 8.50 (1H, s), 8.52 (1H, s) 9.03 (1H, s), 10.20 (1H, s). m/z: (ES+), [M+H]+=514.3

(c) 5-(Methylamino)-3-[4-(3-methyl-3,8-diazabicyclo[3 2]octan-8-yl)anilino]-6-(3-methylimidazo[4,5-c]pyridin-7-yl)pyrazine-2-carboxamide formate salt 7 N Methanolic ammonia (2.0 mL, 14 mmol) was added to methyl 5-(methylamino)-3-[4-(3-methyl-3,8-diazabicyclo[3.2.1]octan-8-yl)anilino]-6-(3-methylimidazo[4,5-c]pyridin-7-yl)pyrazine-2-carboxylate (80 mg, 0.16 mmol). The resulting suspension was stirred at 80° C. for 2 hours. The reaction was then concentrated. The resulting residue was purified by preparative HPLC, using a 5 micron, 30 mm×150 mm, Xselect CSH OBD column, 5-15

MeCN—$H_2O$ as eluent, and 0.1% formic acid as modifier, to afford 5-(methylamino)-3-[4-(3-methyl-3,8-diazabicyclo[3.2.1]octan-8-yl)anilino]-6-(3-methylimidazo[4,5-c]pyridin-7-yl)pyrazine-2-carboxamide formate salt (26 mg, 31%) as a yellow solid; 1H NMR (300 MHZ, DMSO-d6) δ 1.79-1.93 (4H, m), 2.08 (3H, s), 2.32 (2H, d), 2.44 (2H, d), 2.94 (3H, d), 4.02 (3H, s), 4.19 (2H, s), 6.82 (2H, d), 7.30 (1H, s), 7.60 (2H, d), 7.70 (1H, s), 8.01 (1H, br q), 8.16 (1H, s), 8.52 (1H, s), 8.74 (1H, s), 9.01 (1H, s), 11.22 (1H, s). m/z: (ES+), [M+H]+=499.3

Example 111

5-(Methylamino)-3-[4-[(1S,4S)-5-methyl-2,5-diazabicyclo[2.2.1]heptan-2-yl]anilino]-6-(3-methylimidazo[4,5-c]pyridin-7-yl)pyrazine-2-carboxamide

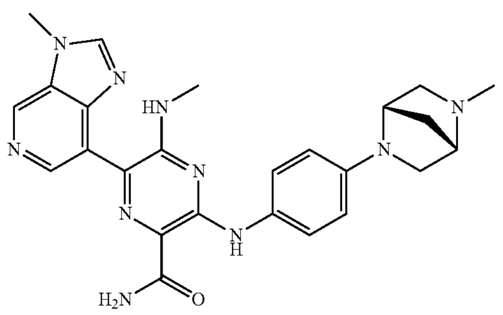 [SMILES: CNc1nc(Nc2ccc(N3C[C@@H]4C[C@H]3CN4C)cc2)c(C(N)=O)nc1-c1cncc2c1ncn2C]

(a) (1S,4S)-2-(4-Bromophenyl)-5-methyl-25-diazabicyclo[2.2.1]heptane (1S,4S)-2-Methyl-2,5-diazabicyclo[2.2.1]heptane (198 mg, 1.77 mmol) was added to 1-bromo-4-iodo-benzene (500 mg, 1.77 mmol), (rac)-BINAP (165 mg, 0.27 mmol), palladium (II) acetate (59.5 mg, 0.27 mmol), and potassium tert-butoxide (595 mg, 5.30 mmol) in toluene (10 mL) at rt under nitrogen. The resulting mixture was stirred at 100° C. for 2 hours. The reaction was then concentrated. The resulting residue was purified by silica gel chromatography, using 0-30% MeOH-DCM as eluent, to afford (1S,4S)-2-(4-bromophenyl)-5-methyl-2,5-diazabicyclo[2.2.1]heptane (0.150 g, 32%) as a yellow solid; 1H NMR (400 MHz, DMSO-d6) δ 1.98-2.05 (1H, m), 2.14-2.24 (1H, m), 2.66 (3H, br s), 2.66-2.81 (1H, m), 2.95-3.10 (2H, m), 3.23-3.28 (1H, m), 3.44-3.56 (1H, m), 3.95-4.20 (1H, m), 6.57-6.63 (2H, m), 7.30-7.35 (2H, m); m/z: (ES+), [M+2+H]+=269.0

(b) Methyl 5-(methylamino)-3-[4-[(1S,4S)-5-methyl-2,5-diazabicyclo[2.2.1]heptan-2-yl]anilino]-6-(3-methylimidazo[4,5-c]pyridin-7-yl)pyrazine-2-carboxylate (1S,4S)-2-(4-Bromophenyl)-5-methyl-2,5-diazabicyclo[2.2.1]heptane (85 mg, 0.32 mmol) was added to methyl 3-amino-5-(methylamino)-6-(3-methylimidazo[4,5-c]pyridin-7-yl)pyrazine-2-carboxylate (100 mg, 0.32 mmol), Cesium carbonate (312 mg, 0.96 mmol) and BrettPhos Pd G3 (43.4 mg, 0.05 mmol) in 1,4-dioxane (10 mL) at rt under nitrogen. The resulting mixture was stirred at 100° C. for 16 hours. The reaction was then concentrated. The resulting residue was purified by silica gel chromatography, using 0-30% MeOH-DCM as eluent, to afford methyl 5-(methylamino)-3-[4-[(1S,4S)-5-methyl-2,5-diazabicyclo[2.2.1]heptan-2-yl]anilino]-6-(3-methylimidazo[4,5-c]pyridin-7-yl) pyrazine-2-carboxylate (0.060 g, 38%) as a yellow solid; 1H NMR (400 MHZ, DMSO-d6) δ 1.71-1.79 (1H, m), 1.82-1.89 (1H, m), 2.25 (3H, s), 2.73-2.80 (1H, m), 2.89 (3H, d), 3.11-3.15 (1H, m), 3.34-3.45 (1H, m), 3.82 (3H, s), 4.01 (3H, s), 4.21-4.31 (1H, m), 6.59 (2H, d), 7.58 (2H, d), 7.91 (1H, br q), 8.50 (1H, s), 8.54 (1H, s), 9.03 (1H, s), 10.17 (1H, s); two of the bicycle protons were obscured by either residual water or the DMSO solvent peak; m/z: (ES+). [M+H]+=500.2

(c) 5-(Methylamino)-3-[4-[(1S,4S)-5-methyl-2,5-diazabicyclo[2.2.1]heptan-2-yl]anilino]-6-(3-methylimidazo[4,5-c]pyridin-7-yl)pyrazine-2-carboxamide 7 N Methanolic ammonia (8.0 mL, 56 mmol) was added to methyl 5-(methylamino)-3-[4-[(1S,4S)-5-methyl-2,5-diazabicyclo[2.2.1]heptan-2-yl]anilino]-6-(3-methylimidazo [4,5-c]pyridin-7-yl)pyrazine-2-carboxylate (50.0 mg, 0.10 mmol). The resulting suspension was stirred at 85° C. for 16 hours. The reaction was then concentrated. The resulting residue was purified by preparative HPLC, using a 5 micron, 30 mm×100 mm, XBridge Prep C18 OBD column, 15-30% MeCN-10 mM aqueous ammonium bicarbonate as eluent, and 0.1% ammonium hydroxide as modifier, to afford 5-(methylamino)-3-[4-[(1S,4S)-5-methyl-2,5-diazabicyclo [2.2.1]heptan-2-yl]anilino]-6-(3-methylimidazo[4,5-c]pyridin-7-yl)pyrazine-2-carboxamide (3.0 mg, 6.2%) as a yellow solid; 1H NMR (300 MHz, DMSO-d6) δ 1.76 (1H, d), 1.85 (1H, d), 2.25 (3H, s), 2.76 (1H, d), 2.93 (3H, d), 3.13 (1H, d), 3.29-3.31 (2H, m), 3.40 (1H, m), 4.02 (3H, s), 4.26 (1H, s), 6.59 (2H, d), 7.28 (1H, s), 7.59 (2H, d), 7.69 (1H, s), 8.01 (1H, br q), 8.52 (1H, s), 8.73 (1H, s), 9.01 (1H, s), 11.18 (1H, s); m/z: (ES+), [M+H]+=484

Example 112

3-[4-[(3S,5R)-3,5-Dimethylpiperazin-1-yl]-3,5-dimethyl-anilino]-5-(methylamino)-6-(3-methylimidazo [4,5-c]pyridin-7-yl)pyrazine-2-carboxamide

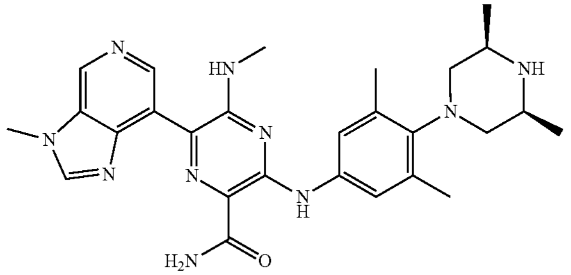

(a) (3R,5S)-1-(4-Bromo-2,6-dimethyl-phenyl)-3,5-dimethyl-piperazine

Pd-PEPPSI-IPent (128 mg, 0.160 mmol) was added to a mixture of 5-bromo-2-iodo-1,3-dimethyl-benzene (500 mg, 1.61 mmol), (2S,6R)-2,6-dimethylpiperazine (220 mg, 1.93 mmol), and cesium carbonate (1.57 g, 4.82 mmol) in DME (20 mL). The resulting mixture was stirred at 90° C. for 16 hours. The reaction was then concentrated. The resulting residue was purified by C18 reverse phase chromatography, using 0-60% MeCN—$H_2O$ as eluent, and 0.1% formic acid as modifier, to (3R,5S)-1-(4-bromo-2,6-dimethyl-phenyl)-3,5-dimethyl-piperazine (0.200 g, 31%) as a yellow oil which solidified on standing; 1H NMR (300 MHZ, DMSO-d6) δ 0.98-1.08 (6H, m), 2.22 (6H, d), 2.73-2.82 (2H, m), 2.82-2.96 (2H, m), 3.01-3.16 (2H, m), 7.13 (1H, s), 7.21 (1H, s); the NH signal was buried under either DMSO or water residual peak; m/z (ES+), [M+2+H]+=299.0

(b) Methyl 3-[4-[(3S,5R)-3,5-dimethylpiperazin-1-yl]-3,5-dimethyl-anilino]-5-(methylamino)-6-(3-methylimidazo[4,5-c]pyridin-7-yl)pyrazine-2-carboxylate Brettphos Pd G3 (61 mg, 0.070 mmol) was added to a suspension of cis-1-(4-bromo-2,6-dimethylphenyl)-3,5-dimethylpiperazine (100 mg, 0.34 mmol), methyl 3-amino-5-(methylamino)-6-(3-methylimidazo[4,5-c]pyridin-7-yl) pyrazine-2-carboxylate (105 mg, 0.34 mmol), and cesium carbonate (329 mg, 1.01 mmol) in 1,4-dioxane (15 mL) under nitrogen. The resulting mixture was stirred at 100° C. for 16 hours. The reaction was then concentrated. The crude product was purified by flash silica chromatography, using 0-10% MeOH-DCM as eluent, to afford methyl 3-[4-[(3S,5R)-3,5-dimethylpiperazin-1-yl]-3,5-dimethyl-anilino]-5-(methylamino)-6-(3-methylimidazo[4,5-c]pyridin-7-yl) pyrazine-2-carboxylate (75 mg, 42% yield) as a brown solid. This material was used directly in the next step without further purification. m/z: (ES+), [M+H]+=530.3

(c) 3-[4-[(3S,5R)-3,5-Dimethylpiperazin-1-yl]-3,5-dimethyl-anilino]-5-(methylamino)-6-(3-methylimidazo[4,5-c]pyridin-7-yl)pyrazine-2-carboxamide formate salt 7 N Methanolic ammonia (10 mL, 70 mmol) was added to methyl 3-[4-[(3S,5R)-3,5-dimethylpiperazin-1-yl]-3,5-dimethyl-anilino]-5-(methylamino)-6-(3-methylimidazo[4,5-c]pyridin-7-yl)pyrazine-2-carboxylate (70 mg, 0.13 mmol). The resulting suspension was stirred at 80° C. for 16 hours. The reaction was then concentrated. The resulting residue was purified by preparative HPLC, using a 5 micron, 30 mm×150 mm, Xselect CSH OBD column, 5-25% MeCN—$H_2O$ as eluent, and 0.1% formic acid as modifier, to afford 3-[4-[(3S,5R)-3,5-dimethylpiperazin-1-yl]-3,5-dimethyl-anilino]-5-(methylamino)-6-(3-methylimidazo[4,5-c]pyridin-7-yl)pyrazine-2-carboxamide formate salt (3.0 mg, 4.4%) as a yellow solid; 1H NMR (300 MHz, DMSO-d6) δ 1.04 (6H, d), 2.28 (6H, d), 2.76-2.92 (4H, m), 2.98 (3H, d), 3.01-3.12 (2H, m), 4.02 (3H, s), 7.38 (1H, s), 7.44 (1H, d), 7.51 (1H, d), 7.76 (1H, s), 8.02 (1H, br q), 8.26 (1H, s), 8.53 (1H, s), 8.73 (1H, s), 9.03 (1H, s), 11.37 (1H, s); the cyclic NH peak was buried under the DMSO or water peak; m/z: (ES+), [M+H]+=515.3

Example 113

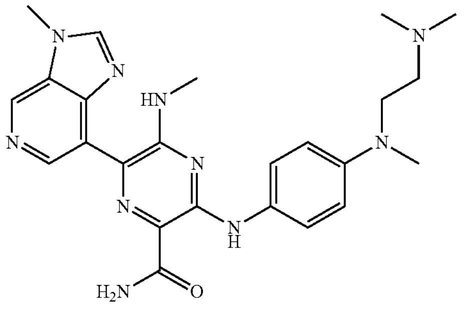 [SMILES: CNc1nc(Nc2ccc(N(C)CCN(C)C)cc2)c(C(N)=O)nc1-c1cncc2c1ncn2C]

3-[4-[2-(Dimethylamino)ethyl-methyl-amino]anilino]-5-(methylamino)-6-(3-methylimidazo[4,5-c] pyridin-7-yl)pyrazine-2-carboxamide bis-formate salt (a) N' (4-Bromophenyl)-N,N,N'-trimethyl-ethane-1,2-diamine Palladium (II) acetate (0.079 g, 0.35 mmol) was added to 1-bromo-4-iodo-benzene (1.00 g, 3.53 mmol), N,N',N'-trimethylethane-1,2-diamine (0.722 g, 7.07 mmol), potassium tert-butoxide (1.19 g, 10.6 mmol), and (rac)-BINAP (0.22 g, 0.35 mmol) in toluene (15 mL) under nitrogen. The resulting mixture was stirred at 100° C. for 2 hours. The reaction was then concentrated. The resulting residue was purified by silica gel chromatography, using 0-10% EtOH-DCM as eluent, to afford N'-(4-bromophenyl)-N,N,N'-trimethyl-ethane-1,2-diamine (0.600 g, 66%) as a brown oil; 1H NMR (300 MHz, DMSO-d6) δ 2.16 (6H, s), 2.34 (2H, t), 2.86 (3H, s), 3.38 (2H, t), 6.49-6.71 (2H, m), 7.20-7.44 (2H, m); m/z: (ES+), [M+H]+=257.0

(b) Methyl 3-[4-[2-(dimethylamino)ethyl-methyl-amino]anilino]-5 (methylamino)-6-(3-methylimidazo[4,5-c]pyridin-7-yl)pyrazine-2-carboxylate BrettPhos Pd G3 (29 mg, 0.030 mmol) was added to a suspension of N'-(4-bromophenyl)-N,N,N'-trimethyl-ethane-1,2-diamine (164 mg, 0.640 mmol), methyl 3-amino-5-(methylamino)-6-(3-methylimidazo[4,5-c]pyridin-7-yl) pyrazine-2-carboxylate (100 mg, 0.32 mmol), and cesium carbonate (312 mg, 0.960 mmol) in 1,4-dioxane (10 mL) under nitrogen. The resulting mixture was stirred at 100° C. for 16 hours. The reaction was then concentrated. The resulting residue was purified by silica gel chromatography, using 0-10% EtOH-DCM as eluent, to afford methyl 3-[4-[2-(dimethylamino)ethyl-methyl-amino]anilino]-5-(methylamino)-6-(3-methylimidazo[4,5-c]pyridin-7-yl)pyrazine-2-carboxylate (0.080 g, 51%) as a brown oil. 1H NMR (400 MHZ, DMSO-d6) δ 2.18 (6H, s), 2.34-2.42 (2H, m), 2.86-2.93 (6H, m), 3.37-3.44 (2H, m), 3.81 (3H, s), 4.01 (3H, s), 6.71 (2H, d), 7.59 (2H, d), 7.84-7.96 (1H, m), 8.49 (1H, s), 8.53 (1H, s), 9.02 (1H, s), 10.17 (1H, s); m/z: (ES+), [M+H]+=490.2

(c) 3-[4-[2-(Dimethylamino)ethyl-methyl-amino] anilino]-5-(methylamino)-6-(3-methylimidazo[4,5-c] pyridin-7-yl)pyrazine-2-carboxamide bis-formate salt 7 N Methanolic ammonia (8.0 mL, 56 mmol) was added to methyl 3-[4-[2-(dimethylamino)ethyl-methyl-amino]anilino]-5-(methylamino)-6-(3-methylimidazo[4,5-c]pyridin-7-yl)pyrazine-2-carboxylate (30 mg, 0.06 mmol). The suspension was stirred at 80° C. for 24 hours. The reaction was then concentrated. The resulting residue was purified by preparative HPLC, using a 5 micron, 6-16% MeCN—$H_2O$ as eluent, and 0.1% formic acid as modifier, to afford 3-[4-[2-(dimethylamino)ethyl-methyl-amino]anilino]-5-(methylamino)-6-(3-methylimidazo[4,5-c]pyridin-7-yl) pyrazine-2-carboxamide bis-formate salt (3.0 mg, 8.5%) as a brown solid; 1H NMR (400 MHz, DMSO-d6) δ 2.19 (6H, s), 2.39 (2H, t), 2.88 (3H, s), 2.92 (3H, d), 3.39 (2H, t), 4.01 (3H, s), 6.68-6.74 (2H, m), 7.27 (1H, s), 7.59 (2H, d), 7.68 (1H, s), 8.00 (1H, br q), 8.22 (2H, s), 8.51 (1H, s), 8.73 (1H, s), 9.00 (1H, s), 11.18 (1H, s); m/z: (ES+), [M+H]+=475.2

Example 114

3-[4-[3-(Dimethylamino) azetidin-1-yl]anilino]-5-(methylamino)-6-(3-methylimidazo[4,5-c]pyridin-7-yl)pyrazine-2-carboxamide bis-formate salt

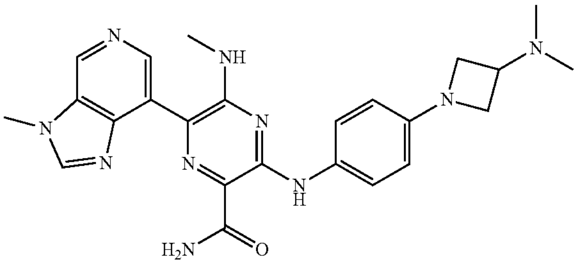

(a) 1-(4-Bromophenyl)-N, N-dimethyl-azetidin-3-amine

Palladium (II) acetate (0.079 g, 0.35 mmol) was added slowly to a mixture of 1-bromo-4-iodo-benzene (1.00 g, 3.54 mmol), N,N-dimethylazetidin-3-amine (0.709 g, 7.08 mmol), (rac)-BINAP (0.220 g, 0.35 mmol), and potassium tert-butoxide (1.19 g, 10.6 mmol) in toluene (15 mL) under nitrogen. The resulting mixture was stirred at 100° C. for 1 hour. The reaction was then concentrated. The resulting residue was purified by silica gel chromatography, using 0-10% MeOH-DCM as eluent, to afford 1-(4-bromophenyl)-N,N-dimethyl-azetidin-3-amine (0.670 g, 74%) as a brown solid; 1H NMR (300 MHz, DMSO-d6) δ 2.10 (6H, s), 3.18 (1H, td), 3.52 (2H, dd), 3.88 (2H, t), 6.32-6.43 (2H, m), 7.23-7.37 (2H, m); m/z: (ES+), [M+H]+=255.0

(b) Methyl 3-[4-[3-(dimethylamino) azetidin-1-yl] anilino]-5 (methylamino)-6-(3-methylimidazo[4,5-c] pyridin-7-yl)pyrazine-2-carboxylate BrettPhos Pd G3 (14 mg, 0.020 mmol) was added to a suspension of 1-(4-bromophenyl)-N,N-dimethyl-azetidin-3-amine (41 mg, 0.16 mmol), methyl 3-amino-5-(methylamino)-6-(3-methylimidazo[4,5-c]pyridin-7-yl)pyrazine-2-carboxylate (100 mg, 0.32 mmol), and cesium carbonate (156 mg, 0.480 mmol) in 1,4-dioxane (15 mL) under nitrogen. The resulting mixture was stirred at 100° C. for 20 hours. The reaction was then concentrated. The resulting residue was purified by silica gel chromatography, using 0-10% MeOH-DCM as eluent, to afford methyl 3-[4-[3-(dimethylamino) azetidin-1-yl]anilino]-5-(methylamino)-6-(3-methylimidazo[4,5-c]pyridin-7-yl)pyrazine-2-carboxylate (0.030 g, 39%) as a brown solid; 1H NMR (400 MHZ, DMSO-d6) δ 2.12 (6H, s), 2.88 (3H, d), 3.50-3.57 (1H, m), 3.82 (3H, s), 3.88-3.95 (2H, m), 4.01 (3H, s), 4.33-4.39 (2H, m), 6.47 (2H, d), 7.60 (2H, d), 7.91 (1H, br q), 8.49 (1H, s), 8.54 (1H, s), 9.03 (1H, s), 10.18 (1H, s); m/z: (ES+), [M+H]+=488.2

(c) 3-[4-[3-(Dimethylamino) azetidin-1-yl]anilino]-5-(methylamino)-6-(3-methylimidazo[4 5-c]pyridin-7-yl)pyrazine-2-carboxamide bis-formate salt 7 N Methanolic ammonia (8.0 mL, 56 mmol) was added to methyl 3-[4-[3-(dimethylamino) azetidin-1-yl]anilino]-5-(methylamino)-6-(3-methylimidazo[4,5-c]pyridin-7-yl) pyrazine-2-carboxylate (40 mg, 0.08 mmol) The resulting suspension was stirred at 80° C. for 25 hours. The reaction was then concentrated. The resulting residue was purified by preparative HPLC, using a 5 micron, 30 mm×150 mm, XBridge Shield RP18 OBD column, 5-16% MeCN—$H_2O$ as eluent, and 0.1% formic acid as modifier, to afford 3-[4-[3-(dimethylamino) azetidin-1-yl]anilino]-5-(methylamino)-6-(3-methylimidazo[4,5-c]pyridin-7-yl)pyrazine-2-carboxamide bis-formate salt (13 mg, 29%) as a brown solid; 1H NMR (400 MHz, DMSO-d6) δ 2.10 (6H, s), 2.92 (3H, d), 3.50 (2H, dd), 3.89 (2H, t), 4.01 (3H, s), 6.46 (2H, d), 7.28 (1H, s), 7.59 (2H, d), 7.69 (1H, s), 7.98 (1H, br q), 8.20 (2H, s), 8.51 (1H, s), 8.72 (1H, s), 9.00 (1H, s), 11.19 (1H, s); m/z: (ES+), [M+H]+=473.2

Example 115

3-[3-Cyano-4-[(3S,5R)-3,5-dimethylpiperazin-1-yl] anilino]-5-(methylamino)-6-(3-methylimidazo[4,5-c] pyridin-7-yl)pyrazine-2-carboxamide

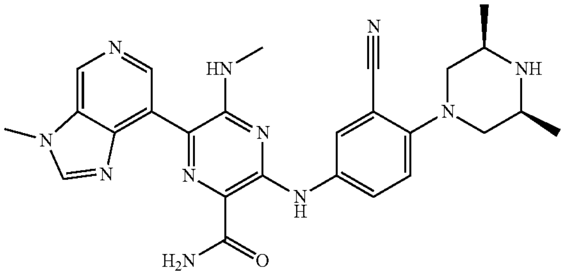

(a) tert-Butyl(2R,6S)-4-(4-bromo-2-cyano-phenyl)-2,6-dimethyl-piperazine-1-carboxylate Palladium (II) acetate (73 mg, 0.32 mmol) was added to a mixture of 5-bromo-2-iodobenzonitrile (500 mg, 1.62 mmol), tert-butyl(2S,6R)-2,6-dimethylpiperazine-1-carboxylate (348 mg, 1.62 mmol), (rac)-BINAP (202 mg, 0.320 mmol), and cesium acetate (1.59 g, 4.87 mmol) in 1,4-dioxane (10 mL) under nitrogen. The resulting mixture was stirred at 100° C. for 4 hours. The reaction was then concentrated. The resulting residue was purified by silica gel chromatography, using 0-50% EtOAc-petroleum ether as eluent, to afford tert-butyl(2R,6S)-4-(4-bromo-2-cyano-phenyl)-2,6-dimethyl-piperazine-1-carboxylate (0.510 g, 80%) as a yellow solid. 1H NMR (Chloroform-d, 400 MHz) δ 1.46-1.49 (6H, m), 1.51 (9H, s), 2.88-2.98 (2H, m), 3.29-3.38 (2H, m), 4.24-4.37 (2H, m), 6.94 (1H, d), 7.62 (1H, dd), 7.72 (1H, d); m/z: (ES+), [M+H]+=394

(b) Methyl 3-[4-[(3S,5R)-4-tert-butoxycarbonyl-3,5-dimethyl-piperazin-1-yl]-3-cyano-anilino]-5-(methylamino)-6-(3-methylimidazo[4,5-c]pyridin-7-yl)pyrazine-2-carboxylate BrettPhos Pd G3 (58 mg, 0.060 mmol) was added to a suspension of methyl 3-amino-5-(methylamino)-6-(3-methylimidazo[4,5-c]pyridin-7-yl)pyrazine-2-carboxylate (100 mg, 0.32 mmol), tert-butyl(2R,6S)-4-(4-bromo-2-cyano-phenyl)-2,6-dimethyl-piperazine-1-carboxylate (138 mg, 0.350 mmol), and cesium carbonate (312 mg, 0.960 mmol) in 1,4-dioxane (1 mL) under nitrogen. The resulting mixture was stirred at 100° C. for 15 hours. The reaction was then concentrated. The resulting residue was purified by silica gel chromatography, using 0-15% MeOH-DCM as eluent, to afford methyl 3-[4-[(3S,5R)-4-tert-butoxycarbonyl-3,5-dimethyl-piperazin-1-yl]-3-cyano-anilino]-5-(methylamino)-6-(3-methylimidazo[4,5-c]pyridin-7-yl)pyrazine-2-carboxylate (0.137 g, 69%) as a white solid. 1H NMR (400 MHz, DMSO-d6) δ 1.34-1.38 (6H, m), 1.43 (9H, s), 2.84-2.94 (5H, m), 3.17-3.23 (2H, m), 3.83 (3H, s), 4.01 (3H, s), 4.10-4.19 (2H, m), 7.24 (1H, d), 7.90 (1H, dd), 8.01 (1H, br q), 8.43 (1H, d), 8.49 (1H, s), 8.53 (1H, s), 9.04 (1H, s), 10.41 (1H, s); m/z: (ES+), [M+H]+=627.5

(c) Methyl 3-[3-cyano-4-[(3S,5R)-3,5-dimethylpiperazin-1-yl]anilino]-5-(methylamino)-6-(3-methylimidazo[4,5-c]pyridin-7-yl)pyrazine-2-carboxylate 4 N HCl in in 1,4-dioxane (3.0 mL, 12 mmol) was added to a solution of methyl 3-[4-[(3S,5R)-4-tert-butoxycarbonyl-3,5-dimethyl-piperazin-1-yl]-3-cyano-anilino]-5-(methylamino)-6-(3-methylimidazo[4,5-c]pyridin-7-yl)pyrazine-2-carboxylate (125 mg, 0.200 mmol) in DCM (5 mL). The resulting mixture was stirred at room temperature for 2 hours. The reaction was then concentrated. The resulting residue was triturated in saturated aqueous sodium bicarbonate, filtered, and dried under vacuum to afford methyl 3-[3-cyano-4-[(3S,5R)-3,5-dimethylpiperazin-1-yl]anilino]-5-(methylamino)-6-(3-methylimidazo[4,5-c]pyridin-7-yl)pyrazine-2-carboxylate (0.097 g, 92%) as a yellow solid; 1H NMR (400 MHZ, DMSO-d6) δ 1.31 (6H, d), 2.87 (3H, d), 2.92-3.00 (2H, m), 3.32-3.49 (4H, m), 3.82 (3H, s), 4.13 (3H, s), 7.29 (1H, d), 7.62 (1H, br q), 7.93 (1H, dd), 8.37-8.42 (1H, m), 8.71 (1H, s), 9.02 (1H, s), 9.64 (1H, s), 10.44 (1H, s). m/z: (ES+), [M+H]+=527.3

(d) 3-[3-Cyano-4-[(3S,5R)-3,5-dimethylpiperazin-1-yl]anilino]-5-(methylamino)-6-(3-methylimidazo[4,5-c]pyridin-7-yl)pyrazine-2-carboxamide 7 N Methanolic ammonia (10 mL, 70 mmol) was added to methyl 3-[3-cyano-4-[(3S,5R)-3,5-dimethylpiperazin-1-yl]anilino]-5-(methylamino)-6-(3-methylimidazo[4,5-c]pyridin-7-yl)pyrazine-2-carboxylate (88 mg, 0.17 mmol). The resulting mixture was stirred at 80° C. for 30 hours. The reaction was then concentrated. The resulting residue was purified by preparative HPLC, using a 5 micron, 30 mm×100 mm, Xselect CSH OBD column, decreasingly polar mixtures of MeCN—$H_2O$ as eluent, and 0.1% formic acid as modifier, to afford 3-[3-cyano-4-[(3S,5R)-3,5-dimethylpiperazin-1-yl]anilino]-5-(methylamino)-6-(3-methylimidazo[4,5-c]pyridin-7-yl)pyrazine-2-carboxamide (30 mg, 35%) as a yellow solid; 1H NMR (400 MHZ, DMSO-d6) δ 1.01 (6H, d), 2.26-2.36 (2H, m), 2.89-2.99 (5H, m), 3.25-3.32 (2H, m), 4.01 (3H, s), 7.14 (1H, d), 7.42 (1H, s), 7.70-7.83 (2H, m), 8.11 (1H, br q), 8.39 (1H, d), 8.52 (1H, s), 8.73 (1H, s), 9.02 (1H, s), 11.52 (1H, s); m/z: (ES+), [M+H]+=512.3

Example 116

3-[2,3-Difluoro-4-[4-(4-methylpiperazin-1-yl)-1-piperidyl]anilino]-5-(methylamino)-6-(3-methylimidazo[4,5-c]pyridin-7-yl)pyrazine-2-carboxamide

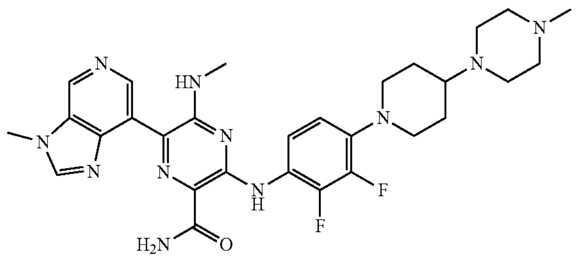

(a) 1-[1-(2,3-Difluoro-4-nitro-phenyl)-4-piperidyl]-4-methyl-piperazine

Potassium carbonate (1.382 g, 10.00 mmol) was added to a solution of 1,2,3-trifluoro-4-nitro-benzene (1.771 g, 10.00 mmol) and 1-methyl-4-(4-piperidyl) piperazine (1.833 g, 10.00 mmol) in DMSO (50 mL) at 0° C. The resulting mixture was stirred at room temperature for 2 h. The reaction was then diluted with water (300 mL) and extracted three times with EtOAc (150 mL each). The combined organic layers were washed five times with water (200 mL each), dried over sodium sulfate, and concentrated. The resulting residue was purified by silica gel chromatography, using 0 to 10% MeOH-DCM as eluent, to afford 1-[1-(2,3-difluoro-4-nitro-phenyl)-4-piperidyl]-4-methyl-piperazine (0.728 g, 21% yield) as a yellow solid. 1H NMR (500 MHz, DMSO-d6) δ 1.48 (2H, qd), 1.83 (2H, d), 2.11 (3H, s), 2.17-2.35 (4H, m), 2.36-2.48 (5H, m), 2.96 (2H, t), 3.76 (2H, d), 6.94 (1H, t), 7.87 (1H, t). 19F NMR (470 MHZ, DMSO-d6) δ −142.01, −147.27. m/z: (ES+), [M+H]+=341.8

(b) 2,3-Difluoro-4-[4-(4-methylpiperazin-1-yl)-1-piperidyl]aniline

A mixture of 1-[1-(2,3-difluoro-4-nitro-phenyl)-4-piperidyl]-4-methyl-piperazine (728 mg, 2.14 mmol) and 10 wt % palladium on carbon (228 mg, 0.210 mmol) was stirred in MeOH (10.7 mL) under a hydrogen atmosphere at room temperature for 3 hours. The reaction was then diluted with MeOH (50 mL), filtered through Celite, and concentrated to afford 2,3-difluoro-4-[4-(4-methylpiperazin-1-yl)-1-piperidyl]aniline as a brown film (0.664 g, quantitative). 1H NMR (500 MHz, DMSO-d6) 1.51 (2H, qd), 1.73-1.86 (2H, m), 2.14 (3H, s), 2.17-2.41 (6H, m), 2.51-2.58 (4H, m), 3.10-3.20 (3H, m), 4.99 (2H, s), 6.45 (1H, td), 6.59 (1H, td). m/z: (ES−), [M−H]−=309.4

(c) N-[2,3-Difluoro-4-[4-(4-methylpiperazin-1-yl)-1-piperidyl]phenyl]formamide

Formic acid (1.81 mL, 44.9 mmol) and acetic anhydride (4.44 mL, 47.1 mmol) were combined and stirred at 60° C. for 15 minutes. The resulting mixture was added dropwise to a solution of 2,3-difluoro-4-[4-(4-methylpiperazin-1-yl)-1-piperidyl]aniline (664 mg, 2.14 mmol) in THF (8 mL). The resulting mixture was stirred at room temperature for 16 h. The reaction was then concentrated. The resulting residue was purified by silica gel chromatography, using 0 to 15% MeOH-DCM as eluent, to afford N-[2,3-difluoro-4-[4-(4-methylpiperazin-1-yl)-1-piperidyl]phenyl]formamide (0.550 g, 76% yield) as an off-white solid. 1H NMR (400 MHz, DMSO-d6) δ 1.54 (2H, qd), 1.73-1.88 (2H, m), 2.16 (3H, s), 2.22-2.42 (5H, m), 2.51-2.57 (2H, m), 2.66 (2H, br t), 3.08-3.57 (4H, m), 6.81 (1H, td), 7.61 (1H, td), 8.25 (1H, d), 10.05 (1H, s). m/z: (ES+), [M+H]+=339.9

(d) Methyl 6-chloro-3-[2,3-difluoro-4-[4-(4-methylpiperazin-1-yl)-1-piperidyl]anilino]-5-(methylamino) pyrazine-2-carboxylate 60 wt % Sodium hydride in mineral oil (71.5 mg, 1.79 mmol) was added to a solution of N-[2,3-difluoro-4-[4-(4-methylpiperazin-1-yl)-1-piperidyl]phenyl]formamide (550 mg, 1.63 mmol) in DMF (8 mL). The resulting mixture was stirred at room temperature for 15 minutes. Methyl 6-chloro-3-fluoro-5-(methylamino) pyrazine-2-carboxylate (357 mg, 1.63 mmol) to the flask. The resulting mixture was stirred at 60° C. for 16 h. Potassium carbonate (1.00 g, 7.24 mmol) and MeOH (3 mL) were added. The resulting mixture was stirred at 60° C. for 1 h. The reaction was then concentrated. The resulting residue was purified by silica gel chromatography, using 0 to 15% MeOH-DCM as eluent, to afford methyl 6-chloro-3-((2,3-difluoro-4-(4-(4-methylpiperazin-1-yl) piperidin-1-yl)phenyl)amino)-5-(methylamino) pyrazine-2-carboxylate (0.366 g, 44% yield) as a beige solid. 1H NMR (400 MHz, DMSO-d6) δ 1.54 (2H, qd), 1.83 (2H, br d), 2.13 (3H, s), 2.20-2.40 (5H, m), 2.61-2.72 (2H, m), 2.89 (3H, d), 3.36 (2H, br d), 3.81 (3H, s), 6.85 (1H, td), 7.95 (1H, q), 8.01 (1H, td), 10.27 (1H, d). 4 protons were buried under the DMSO signal. m/z: (ES+), [M+H]+=509.9

(e) 6-Chloro-3-[2,3-difluoro-4-[4-(4-methylpiperazin-1-yl)-1-piperidyl]anilino]-5-(methylamino) pyrazine-2-carboxamide 7 N Methanolic ammonia (20 mL, 140 mmol) was added to methyl 6-chloro-3-[2,3-difluoro-4-[4-(4-methylpiperazin-1-yl)-1-piperidyl]anilino]-5-(methylamino) pyrazine-2-carboxylate (366 mg, 0.720 mmol). The resulting mixture was stirred at 100° C. for 1 hour in a Biotage microwave reactor. The reaction was then concentrated. The resulting residue was purified by silica gel chromatography, using 0-15% MeOH-DCM as eluent, to afford 6-chloro-3-[2,3-difluoro-4-[4-(4-methylpiperazin-1-yl)-1-piperidyl]anilino]-5-(methylamino) pyrazine-2-carboxamide (0.255 g, 72% yield) as a yellow solid. 1H NMR (400 MHZ, DMSO-d6) δ 1.54 (2H, qd), 1.83 (2H, br d), 2.18-2.40 (5H, m), 2.65 (2H, br t), 2.91 (3H, d), 3.34 (2H, br d), 6.83 (1H, dt), 7.39 (1H, br s), 7.61 (1H, br s), 7.666 (1H, br q), 8.12 (1H, dt), 11.47 (1H, d). 4 protons were buried under the DMSO signal. m/z: (ES+), [M+H]+=495.3

(f) 3-[2,3-Difluoro-4-[4-(4-methylpiperazin-1-yl)-1-piperidyl]anilino]-5 (methylamino)-6 (3-methylimidazo[4,5-c]pyridin-7-yl)pyrazine-2-carboxamide 6-Chloro-3-[2,3-difluoro-4-[4-(4-methylpiperazin-1-yl)-1-piperidyl]anilino]-5-(methylamino) pyrazine-2-carboxamide (255 mg, 0.520 mmol), 2-(3-methyl-3H-imidazo[4,5-c]pyridin-7-yl)-1,3,6,2-dioxazaborocane (158 mg, 0.640 mmol), XPhos Pd G3 (44 mg, 0.050 mmol), XPhos (25 mg, 0.050 mmol), and potassium phosphate (328 mg, 1.55 mmol) were combined. The reaction vessel was evacuated and backfilled with nitrogen. Dioxane (7.2 mL) and water (0.72 mL) were added. The resulting mixture was stirred at 60° C. for 2 hours. The reaction was then concentrated. The resulting residue was purified by silica gel chromatography on KP-Sil, using 0-20% MeOH-DCM as eluent and 1% ammonium hydroxide as modifier, afford 3-[2,3-difluoro-4-[4-(4-methylpiperazin-1-yl)-1-piperidyl]anilino]-5-(methylamino)-6-(3-methylimidazo[4,5-c]pyridin-7-yl)pyrazine-2-carboxamide (0.191 g, 63% yield) as a yellow solid. 1H NMR (500 MHz, DMSO-d6) δ 1.58 (2H, qd), 1.85 (2H, br d), 2.20 (3H, s), 2.25-2.45 (5H, m), 2.50-2.62 (4H, m), 2.68 (2H, br t), 2.93 (3H, d), 3.37 (2H, br d), 4.02 (3H, s), 6.87 (1H, td), 7.40 (1H, br s), 7.77 (1H, br s), 8.04 (1H, br q), 8.33 (1H, td), 8.52 (1H, s), 8.74 (1H, s), 9.03 (1H, s), 11.61 (1H, d). m/z: (ES+), [M+H]+=592.1

Example 117

3-[[6-(4-Isopropylpiperazin-1-yl)-5-methyl-3-pyridyl]amino]-5-(methylamino)-6-(3-methylimidazo[4,5-c]pyridin-7-yl)pyrazine-2-carboxamide

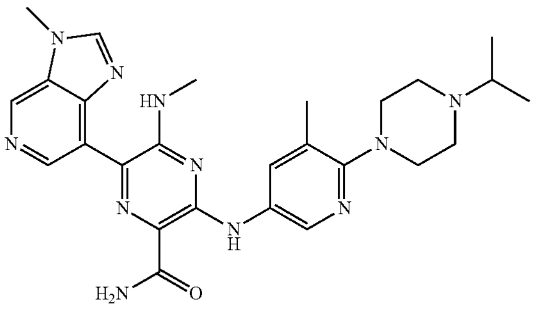 [SMILES: CNc1nc(Nc2cnc(N3CCN(C(C)C)CC3)c(C)c2)c(C(N)=O)nc1-c1cncc2c1ncn2C]

(a) 1-(5-Bromo-3-methyl-2-pyridyl)-4-isopropylpiperazine

DIPEA (4.60 mL, 26.3 mmol) was added slowly to a solution of 5-bromo-2-fluoro-3-methyl-pyridine (1.00 g, 5.26 mmol) and 1-isopropylpiperazine (0.675 g, 5.26 mmol) in DMSO (15 mL). The resulting mixture was stirred at 100° C. for 1 hour. The reaction mixture was then diluted with DCM (100 mL) and washed three times with water (100 mL each). The organic layer was dried over sodium sulfate, filtered, and concentrated. The resulting residue was purified by silica gel chromatography, using 0-20% MeOH-DCM as eluent, to afford 1-(5-bromo-3-methyl-2-pyridyl)-4-isopropyl-piperazine (0.480 g, 31%) as a beige waxy solid; 1H NMR (300 MHz, DMSO-d6) δ 0.96-1.11 (6H, m), 2.22 (3H, s), 2.47-2.62 (4H, m), 2.68 (1H, heptet), 3.00-3.09 (4H, m), 7.71 (1H, d), 8.17 (1H, d); m/z: (ES+), [M+2+H]+=300.0

(b) Methyl 3-[[6-(4-isopropylpiperazin-1-yl)-5-methyl-3-pyridyl]amino]-5 (methylamino)-6-(3-methylimidazo[4,5-c]pyridin-7-yl)pyrazine-2-carboxylate BrettPhos Pd G3 (29 mg, 0.030 mmol) was added to a suspension of 1-(5-bromo-3-methyl-2-pyridyl)-4-isopropyl-piperazine (95 mg, 0.32 mmol), methyl 3-amino-5-(methylamino)-6-(3-methylimidazo[4,5-c]pyridin-7-yl)pyrazine-2-carboxylate (100 mg, 0.32 mmol), and cesium carbonate (0.313 g, 0.960 mmol) in 1,4-dioxane (10 mL) under nitrogen. The resulting mixture was stirred at 100° C. for 15 hours. The reaction was then concentrated. The resulting residue was purified by silica gel chromatography, using 0-20% MeOH-DCM as eluent, to afford methyl 3-[[6-(4-isopropylpiperazin-1-yl)-5-methyl-3-pyridyl]amino]-5-(methylamino)-6-(3-methylimidazo[4,5-c]pyridin-7-yl) pyrazine-2-carboxylate (0.100 g, 59%) as a yellow solid; 1H NMR (300 MHz, DMSO-d6) δ 1.02 (6H, d), 2.26 (3H, s), 2.55-2.63 (4H, m), 2.65-2.76 (1H, m), 2.90 (3H, d), 2.97-3.08 (4H, m), 3.83 (3H, s), 4.01 (3H, s), 7.94 (1H, br q), 8.05 (1H, d), 8.46-8.55 (3H, m), 9.04 (1H, s), 10.23 (1H, s). m/z: (ES+), [M+H]+=531.4

(c) 3-[[6-(4-Isopropylpiperazin-1-yl)-5-methyl-3-pyridyl]amino]-5 (methylamino)-6-(3-methylimidazo[4,5-c]pyridin-7-yl)pyrazine-2-carboxamide 7 N Methanolic ammonia (20 mL, 140 mmol) was added to methyl 3-[[6-(4-isopropylpiperazin-1-yl)-5-methyl-3-pyridyl]amino]-5-(methylamino)-6-(3-methylimidazo[4,5-c]pyridin-7-yl)pyrazine-2-carboxylate (50 mg, 0.09 mmol). The resulting mixture was stirred at 80° C. for 20 hours. The reaction was then concentrated. The resulting residue was purified by preparative HPLC, using a 5 micron, 30 mm×150 mm XBridge Prep OBD C18 column, 20-50% MeCN-10 mM aqueous ammonium bicarbonate as eluent, and 0.1% ammonium hydroxide as modifier, to afford 3-[[6-(4-isopropylpiperazin-1-yl)-5-methyl-3-pyridyl]amino]-5-(methylamino)-6-(3-methylimidazo[4,5-c]pyridin-7-yl) pyrazine-2-carboxamide (10 mg, 20%) as a yellow solid; 1H NMR (400 MHZ, DMSO-d6) δ 1.02 (6H, d), 2.26 (3H, s), 2.59 (4H, t), 2.66-2.74 (1H, m), 2.94 (3H, d), 2.97-3.04 (4H, m), 4.01 (3H, s), 7.37 (1H, s), 7.74 (1H, s), 8.02 (2H, d), 8.52 (2H, s), 8.72 (1H, s), 9.02 (1H, s), 11.33 (1H, s); m/z: (ES+), [M+H]+=516.2

Example 118

3-[[5-Methoxy-6-(4-methylpiperazin-1-yl)-3-pyridyl]amino]-5-(methylamino)-6-(3-methylimidazo[4,5-c]pyridin-7-yl)pyrazine-2-carboxamide

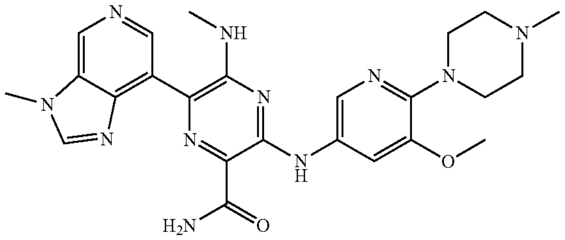

(a) 1-(5-Bromo-3-methoxy-2-pyridyl)-4-methyl-piperazine

Potassium tert-butoxide (1.07 g, 9.56 mmol) and 1-methylpiperazine (0.319 g, 3.19 mmol) were sequentially added to a mixture of 5-bromo-2-iodo-3-methoxy-pyridine (1.00 g, 3.19 mmol), rac-BINAP (0.397 g, 0.640 mmol), and palladium (II) acetate (0.143 g, 0.640 mmol) in toluene (10 mL) under nitrogen. The resulting mixture was stirred at 100° C. for 4 hours. The reaction was then concentrated. The resulting residue was purified by silica gel chromatography, using 0-30% MeOH-DCM as eluent, to afford 1-(5-bromo-3-methoxy-2-pyridyl)-4-methyl-piperazine (0.500 g, 55%) as a yellow solid; 1H NMR (400 MHZ, DMSO-d6) δ 2.19 (3H, s), 2.37-2.43 (4H, m), 3.24-3.31 (4H, m), 3.82 (3H, s), 7.41 (1H, d), 7.85 (1H, d); m/z: (ES+), [M+2+H]+=288.1

(b) Methyl 3-[[5-methoxy-6-(4-methylpiperazin-1-yl)-3-pyridyl]amino]-5-(methylamino)-6-(3-methylimidazo[4,5-c]pyridin-7-yl)pyrazine-2-carboxylate 1-(5-Bromo-3-methoxy-2-pyridyl)-4-methyl-piperazine (137 mg, 0.48 mmol) was added to a suspension of methyl 3-amino-5-(methylamino)-6-(3-methylimidazo[4,5-c]pyridin-7-yl)pyrazine-2-carboxylate (150 mg, 0.48 mmol), cesium carbonate (468 mg, 1.44 mmol), and BrettPhos Pd 3G (65 mg, 0.070 mmol) in 1,4-dioxane (10 mL) under nitrogen. The resulting mixture was stirred at 100° C. for 16 hours. The reaction was then concentrated. The resulting residue was purified by silica gel chromatography, using 0-30% MeOH-DCM as eluent, to afford methyl 3-[[5-methoxy-6-(4-methylpiperazin-1-yl)-3-pyridyl]amino]-5-(methylamino)-6-(3-methylimidazo[4,5-c]pyridin-7-yl) pyrazine-2-carboxylate (0.060 g, 24%) as a yellow solid; 1H NMR (400 MHZ, DMSO-d6) δ 2.64-2.82 (4H, m), 2.92 (3H, d), 3.04-3.18 (7H, m), 3.83 (3H, s), 3.88 (3H, s), 4.01 (3H, s), 7.90 (1H, d), 7.99 (1H, br q), 8.21 (1H, d), 8.50 (1H, s), 8.52 (1H, s), 9.05 (1H, s), 10.37 (1H, s); m/z: (ES+), [M+H]+=519.0

(c) 3-[[5-Methoxy-6-(4-methylpiperazin-1-yl)-3-pyridyl]amino]-5-(methylamino)-6 (3-methylimidazo[4,5-c]pyridin-7-yl)pyrazine-2-carboxamide 7 N Methanolic ammonia (10 mL, 70 mmol) was added to methyl 3-[[5-methoxy-6-(4-methylpiperazin-1-yl)-3-pyridyl]amino]-5-(methylamino)-6-(3-methylimidazo[4,5- c]pyridin-7-yl)pyrazine-2-carboxylate (50 mg, 0.10 mmol). The resulting suspension was stirred at 80° C. for 2 days. The reaction was then concentrated. The resulting residue was purified by preparative HPLC using a 5 micron, 30×150 mm XBridge Prep OBD C18 column, 11-41% MeCN—$H_2O$ as eluent, and 0.1% $NH_4HCO_3$ as modifier to afford 3-[[5-methoxy-6-(4-methylpiperazin-1-yl)-3-pyridyl]amino]-5-(methylamino)-6-(3-methylimidazo[4,5-c]pyridin-7-yl) pyrazine-2-carboxamide (13 mg, 27%) as a yellow solid; 1H NMR (400 MHZ, DMSO-d6) δ 2.21-2.42 (4H, m), 2.96 (3H, d), 3.25 (4H, m), 3.86 (3H, s), 4.01 (3H, s), 7.37 (1H, br s), 7.75 (1H, br s), 7.96 (1H, s), 7.98 (1H, br q), 8.09 (1H, d), 8.52 (1H, s), 8.71 (1H, s), 9.02 (1H, s), 11.42 (1H, s). The piperazine NMe protons were buried under solvent; m/z: (ES+), [M+H]+=504.2

Example 119

5-(Methylamino)-6-(3-methylimidazo[4,5-c]pyridin-7-yl)-3-[[5-methyl-6-[(1R,4R)-5-methyl-2,5-diazabicyclo[2.2.1]heptan-2-yl]-3-pyridyl]amino]pyrazine-2-carboxamide

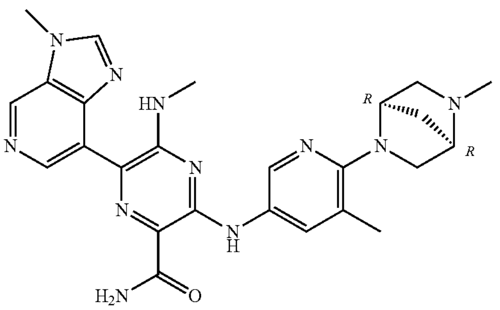

(a) tert-Butyl(1R,4R)-5-(5-bromo-3-methyl-2-pyridyl)-2 5-diazabicyclo[2.2.1]heptane-2-carboxylate 5-Bromo-2-fluoro-3-methyl-pyridine (1.00 g, 5.26 mmol) was added to a solution of tert-butyl (1R,4R)-2,5-diazabicyclo[2.2.1]heptane-2-carboxylate (1.04 g, 5.26 mmol) and DIPEA (2.76 mL, 15.8 mmol) in DMSO (1 mL). The resulting mixture was stirred at 100° C. for 16 hours. The reaction was then concentrated. The resulting residue was purified by preparative HPLC, using a 5 micron, 30×100 mm XBridge Prep C18 OBD column, decreasingly polar mixtures of MeCN—$H_2O$, and 0.5% ammonium bicarbonate as modifier, to afford tert-butyl(1R,4R)-5-(5-bromo-3-methyl-2-pyridyl)-2,5-diazabicyclo[2.2.1]heptane-2-carboxylate (0.400 g, 21%) as a yellow oil; 1H NMR (300 MHz, DMSO-d6) δ 1.37 (9H, d), 1.78-1.88 (2H, m), 2.20 (3H, s), 3.19-3.29 (1H, m), 3.30-3.33 (1H, m), 3.43-3.49 (1H, m), 3.69-3.78 (1H, m), 4.34-4.44 (1H, m), 4.60 (1H, s), 7.56-7.60 (1H, m), 8.01-8.04 (1H, m); m/z: (ES+), [M+H]+=368.1

(b) tert-Butyl(1R,4R)-5-[5-[[3-methoxycarbonyl-6-(methylamino)-5-(3-methylimidazo[4,5-c]pyridin-7-yl) pyrazin-2-yl]amino]-3-methyl-2-pyridyl]-2 5-diazabicyclo[2.2.1]heptane-2-carboxylate tert-Butyl(1R,4R)-5-(5-bromo-3-methyl-2-pyridyl)-2,5-diazabicyclo[2.2.1]heptane-2-carboxylate (250 mg, 0.68 mmol) was added to a suspension of methyl 3-amino-5-(methylamino)-6-(3-methylimidazo[4,5-c]pyridin-7-yl) pyrazine-2-carboxylate (170 mg, 0.54 mmol), cesium carbonate (664 mg, 2.04 mmol), and BrettPhos Pd G3 (62 mg, 0.070 mmol) in 1,4-dioxane (10 mL) under nitrogen. The resulting mixture was stirred at 100° C. for 16 hours. The reaction was then concentrated. The resulting residue was purified by silica gel chromatography, using 0-10% MeOH-DCM as eluent, to afford tert-butyl(1R,4R)-5-[5-[[3-methoxycarbonyl-6-(methylamino)-5-(3-methylimidazo[4,5-c]pyridin-7-yl) pyrazin-2-yl]amino]-3-methyl-2-pyridyl]-2,5-diazabicyclo[2.2.1]heptane-2-carboxylate (0.250 g, 61% yield) as a yellow solid. 1H NMR (300 MHz, DMSO-d6) δ 1.38 (9H, d), 1.75-1.92 (2H, m), 2.24 (3H, s), 2.88 (3H, d), 3.19-3.30 (1H, m), 3.32-3.41 (1H, m), 3.55 (1H, d), 3.67-3.76 (1H, m), 3.83 (3H, s), 4.02 (3H, s), 4.40 (1H, d), 4.59 (1H, s), 7.87-7.99 (2H, m), 8.38 (1H, s), 8.50 (1H, s), 8.53 (1H, s), 9.04 (1H, s), 10.12 (1H, s). m/z: (ES+), [M+H]+=601.3.

(c) 5-(Methylamino)-6-(3-methylimidazo[4,5-c]pyridin-7-yl)-3-[[5-methyl-6-[(1R,4R)-5-methyl-2,5-diazabicyclo[2.2.1]heptan-2-yl]-3-pyridyl]amino] pyrazine-2-carboxamide formate salt tert-Butyl(1R,4R)-5-[5-[[3-methoxycarbonyl-6-(methylamino)-5-(3-methylimidazo[4,5-c]pyridin-7-yl) pyrazin-2-yl]amino]-3-methyl-2-pyridyl]-2,5-diazabicyclo[2.2.1]heptane-2-carboxylate (200 mg, 0.33 mmol) was added to a solution of TFA (1.00 mL, 13.0 mmol) in DCM (10 mL). The resulting mixture was stirred at 25 C for 3 hours. The reaction was then concentrated. The resulting residue was dissolved in MeOH (10 mL). 37 wt % aqueous formaldehyde (0.028 mL, 1.00 mmol) and sodium triacetoxyborohydride (353 mg, 1.66 mmol) were added. The resulting mixture was stirred at 25 C for 2 hours. The reaction was then concentrated. The residue was suspended in 7 N methanolic ammonia (10 mL, 70 mmol). The resulting mixture was stirred at 80° C. for 16 hours. The reaction was then concentrated. The resulting residue was purified by preparative HPLC using a 5 micron, 19×250 mm XSelect CSH Prep C18 OBD column, 10-19% MeCN—$H_2O$ as eluent, and 0.1% formic acid as modifier, to afford 5-(methylamino)-6-(3-methylimidazo[4,5-c]pyridin-7-yl)-3-[[5-methyl-6-[(1R,4R)-5-methyl-2,5-diazabicyclo[2.2.1]heptan-2-yl]-3-pyridyl]amino]pyrazine-2-carboxamide formate salt (27 mg, 15%) as a yellow solid; 1H NMR (400 MHZ, DMSO-d6) δ 1.78 (1H, d), 1.93 (1H, d), 2.24 (3H, s), 2.47 (3H, s), 2.85-3.00 (4H, m), 3.11 (1H, d), 3.43-3.52 (2H, m), 3.67 (1H, s), 4.01 (3H, s), 4.46 (1H, s), 7.29-7.39 (1H, m), 7.68-7.78 (1H, m), 7.90 (1H, d), 8.01 (1H, br q), 8.26 (1H, s), 8.38 (1H, d), 8.51 (1H, s), 8.72 (1H, s), 9.01 (1H, s), 11.18 (1H, s); m/z: (ES+), [M+H]+=500.2

Example 120

3-[[5-Chloro-6-[(1R,4R)-5-methyl-2,5-diazabicyclo[2.2.1]heptan-2-yl]-3-pyridyl]amino]-5-(methylamino)-6-(3-methylimidazo[4,5-c]pyridin-7-yl)pyrazine-2-carboxamide

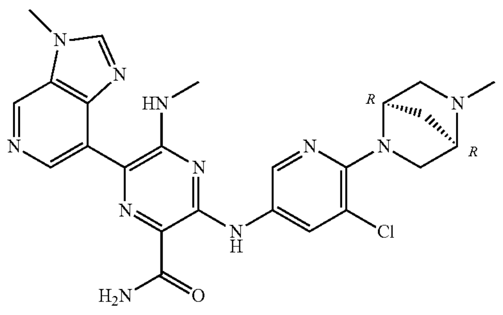

(a) tert-Butyl(1R,4R)-5-(5-bromo-3-chloro-2-pyridyl)-2 5-diazabicyclo[2.2.1]heptane-2-carboxylate tert-Butyl(1R,4R)-2,5-diazabicyclo[2.2.1]heptane-2-carboxylate (1.04 g, 5.26 mmol) was added to a solution of 5-bromo-2-fluoro-3-methyl-pyridine (1.00 g, 5.26 mmol) and DIPEA (2.76 mL, 15.8 mmol) in DMSO (20 mL). The resulting mixture was stirred at 100° C. for 24 hours. The reaction was then concentrated. The resulting residue was purified by preparative HPLC using a 5 micron, 30×100 mm XBridge Prep C18 OBD column, decreasingly polar mixtures of MeCN—$H_2O$ as eluent, and 0.1% ammonium bicarbonate as modifier, to afford tert-butyl(1R,4R)-5-(5-bromo-3-chloro-2-pyridyl)-2,5-diazabicyclo[2.2.1]heptane-2-carboxylate (1.00 g, 49%) as a yellow oil; 1H NMR (300 MHz, DMSO-d6) δ 1.37 (9H, d), 1.81-1.92 (2H, m), 3.30-3.33 (1H, m), 3.38-3.49 (2H, m), 3.86-3.96 (1H, m), 4.37-4.50 (1H, m), 4.70-4.82 (1H, m), 7.97 (1H, d), 8.18 (1H, d). m/z: (ES+), [M+H]+=388.0

(b) tert-Butyl(1R,4R)-5-[3-chloro-5-[[3-methoxycarbonyl-6-(methylamino)-5-(3-methylimidazo[4,5-c]pyridin-7-yl) pyrazin-2-yl]amino]-2-pyridyl]-2,5-diazabicyclo[2.2.1]heptane-2-carboxylate tert-Butyl(1R,4R)-5-(5-bromo-3-chloro-2-pyridyl)-2,5-diazabicyclo[2.2.1]heptane-2-carboxylate (250 mg, 0.64 mmol) was added to a suspension of methyl 3-amino-5-(methylamino)-6-(3-methylimidazo[4,5-c]pyridin-7-yl) pyrazine-2-carboxylate (161 mg, 0.510 mmol), cesium carbonate (524 mg, 1.61 mmol), and BrettPhos Pd G3 (47 mg, 0.050 mmol) in 1,4-dioxane (20 mL) under nitrogen. The resulting mixture was stirred at 100° C. for 16 hours. The reaction was then concentrated. The resulting residue was purified by silica gel chromatography, using 0-10% MeOH-DCM as eluent, to afford tert-butyl(1R,4R)-5-[3-chloro-5-[[3-methoxycarbonyl-6-(methylamino)-5-(3-methylimidazo[4,5-c]pyridin-7-yl) pyrazin-2-yl]amino]-2-pyridyl]-2,5-diazabicyclo[2.2.1]heptane-2-carboxylate (0.200 g, 50%) as a yellow solid; 1H NMR (300 MHz, DMSO-d6) δ 1.38 (9H, d), 1.86 (2H, d), 2.87 (3H, d), 3.33-3.43 (2H, m), 3.50 (1H, d), 3.83 (3H, s), 3.85-3.95 (1H, m), 4.02 (3H, s), 4.42 (1H, d), 4.74 (1H, d), 8.00 (1H, br q), 8.38 (1H, d), 8.42 (1H, d), 8.50 (1H, s), 8.54 (1H, s), 9.04 (1H, s), 10.16 (1H, s). m/z: (ES+), [M+H]+=621.3

(c) Methyl 3-[[5-chloro-6-[(1R,4R)-5-methyl-2,5-diazabicyclo[2.2.1]heptan-2-yl]-3-pyridyl]amino]-5-(methylamino)-6-(3-methylimidazo[4,5-c]pyridin-7-yl)pyrazine-2-carboxylate tert-Butyl(1R,4R)-5-[3-chloro-5-[[3-methoxycarbonyl-6-(methylamino)-5-(3-methylimidazo[4,5-c]pyridin-7-yl) pyrazin-2-yl]amino]-2-pyridyl]-2,5-diazabicyclo[2.2.1]heptane-2-carboxylate (10 mg, 0.02 mmol) was added to 4 N HCl in dioxane (1.0 mL, 4.0 mmol). The resulting mixture was stirred at room temperature for 2 hours. The reaction was then concentrated. The resulting residue was dissolved in MeOH (10 mL). 37 wt % aqueous formaldehyde (116 µL, 1.27 mmol) and sodium triacetoxyborohydride (447 mg, 2.11 mmol) were sequentially added. The resulting mixture was stirred at room temperature for 2 hours. The reaction was then concentrated. The resulting residue was diluted with DCM (50 mL) and washed three times with saturated aqueous sodium bicarbonate (50 mL each). The organic layer was dried over $Na_2SO_4$, filtered, and concentrated to afford methyl 3-[[5-chloro-6-[(1R,4R)-5-methyl-2,5-diazabicyclo[2.2.1]heptan-2-yl]-3-pyridyl]amino]-5-(methylamino)-6-(3-methylimidazo[4,5-c]pyridin-7-yl)pyrazine-2-carboxylate (0.200 g, 89%); 1H NMR (300 MHz, DMSO-d6) δ 1.63-1.71 (1H, m), 1.78-1.84 (1H, m), 2.28 (3H, s), 2.73-2.78 (3H, m), 2.88 (3H, d), 3.44-3.54 (1H, m), 3.60-3.70 (1H, m), 3.83 (3H, s), 4.01 (3H, s), 4.57 (1H, s), 8.00 (1H, br q), 8.31-8.35 (1H, m), 8.38-8.42 (1H, m), 8.50 (1H, s), 8.53 (1H, s), 9.04 (1H, s), 10.14 (1H, s); m/z: (ES+), [M+H]+=535.2

(d) 3-[[5-Chloro-6-[(1R,4R)-5-methyl-2,5-diazabicyclo[2.2.1]heptan-2-yl]-3-pyridyl]amino]-5-(methylamino)-6-(3-methylimidazo[4,5-c]pyridin-7-yl) pyrazine-2-carboxamide 7 N Methanolic ammonia (10 mL, 70 mmol) was added to methyl 3-[[5-chloro-6-[(1R,4R)-5-methyl-2,5-diazabicyclo[2.2.1]heptan-2-yl]-3-pyridyl]amino]-5-(methylamino)-6-(3-methylimidazo[4,5-c]pyridin-7-yl)pyrazine-2-carboxylate (170 mg, 0.32 mmol). The resulting suspension was stirred at 80° C. for 1 day. The reaction was then concentrated. The resulting residue was purified by preparative HPLC, using a 5 micron, 30 mm×150 mm Xselect CSH OBD column, 2-25% MeCN—$H_2O$ as eluent, and 0.1% formic acid as modifier, to afford 3-[[5-chloro-6-[(1R,4R)-5-methyl-2,5-diazabicyclo[2.2.1]heptan-2-yl]-3-pyridyl]amino]-5-(methylamino)-6-(3-methylimidazo[4,5-c]pyridin-7-yl)pyrazine-2-carboxamide (60 mg, 32%) as a yellow solid; 1H NMR (300 MHz, DMSO-d6) δ 1.72-1.80 (1H, m), 1.96-1.98 (1H, m), 2.40 (3H, s), 2.84-2.89 (1H, m), 2.92 (3H, d), 2.94-3.00 (1H, m), 3.54-3.60 (2H, m), 3.66-3.74 (1H, m), 4.02 (3H, s), 4.60 (1H, s), 7.39 (1H, s), 7.76 (1H, s), 8.06 (1H, q), 8.20 (1H, s), 8.33 (1H, d), 8.46 (1H, d), 8.52 (1H, s), 8.73 (1H, s), 9.03 (1H, s), 11.30 (1H, s); m/z: (ES+), [M+H]+=520.2

Example 121

5-(Methylamino)-3-[(6-methyl-5,7-dihydropyrrolo[3,4-b]pyridin-3-yl)amino]-6-(3-methylimidazo[4,5-c]pyridin-7-yl)pyrazine-2-carboxamide

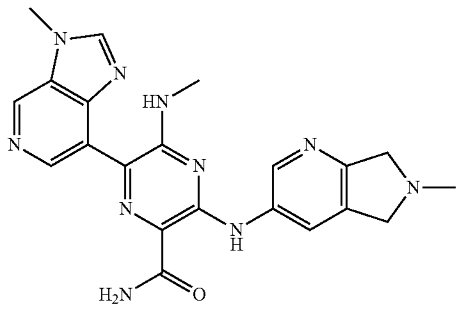 [SMILES: CNc1nc(Nc2cnc3c(c2)CN(C)C3)c(C(N)=O)nc1-c1cncc2c1ncn2C]

(a) tert-Butyl 3-bromo-5,7-dihydropyrrolo[3,4-b]pyridine-6-carboxylate

DMAP (92 mg, 0.75 mmol) was added to a solution of 3-bromo-6,7-dihydro-5H-pyrrolo[3,4-b]pyridine (500 mg, 2.51 mmol), di-tert-butyl dicarbonate (0.29 mL, 1.3 mmol), and DIPEA (1.32 mL, 7.54 mmol) in DCM (10 mL). The resulting solution was stirred at 25° C. for 1 hour. The reaction was then concentrated. The resulting residue was purified by silica gel chromatography, using 0-10% MeOH-DCM as eluent, to afford tert-butyl 3-bromo-5,7-dihydropyrrolo[3,4-b]pyridine-6-carboxylate (0.576 g, 77%) as a yellow solid; 1H NMR (300 MHz, DMSO-d6) δ 1.47 (9H, s), 4.46-4.56 (2H, m), 4.57-4.68 (2H, m), 8.01-8.10 (1H, m), 8.58 (1H, d). m/z: (ES+), [M+H]+=301.1

(b) tert-Butyl 3-[[3-methoxycarbonyl-6-(methylamino)-5-(3-methylimidazo[4,5-c]pyridin-7-yl)pyrazin-2-yl]amino]-5,7-dihydropyrrolo[3,4-b]pyridine-6-carboxylate Brettphos Pd G3 (58 mg, 0.060 mmol) was added to a suspension of tert-butyl 3-bromo-5,7-dihydropyrrolo[3,4-b]pyridine-6-carboxylate (190 mg, 0.64 mmol), methyl 3-amino-5-(methylamino)-6-(3-methylimidazo[4,5-c]pyridin-7-yl)pyrazine-2-carboxylate (100 mg, 0.32 mmol), and cesium carbonate (104 mg, 0.320 mmol) in 1,4-dioxane (5 mL) under nitrogen. The resulting mixture was stirred at 100° C. for 4 hours. The reaction was then concentrated. The resulting residue was purified by silica gel chromatography, using 0-10% MeOH-DCM as eluent, to afford tert-butyl 3-[[3-methoxycarbonyl-6-(methylamino)-5-(3-methylimidazo[4,5-c]pyridin-7-yl) pyrazin-2-yl]amino]-5,7-dihydropyrrolo[3,4-b]pyridine-6-carboxylate (0.155 g, 91%) as a yellow solid; 1H NMR (300 MHz, DMSO-d6) δ 1.48 (9H, s), 2.90 (3H, d), 3.85 (3H, s), 4.02 (3H, s), 4.54 (2H, d), 4.64 (2H, d), 7.98 (1H, s), 8.27 (1H, d), 8.50 (1H, s), 8.54 (1H, s), 8.83 (1H, d), 9.05 (1H, s), 10.42 (1H, s). m/z: (ES+), [M+H]+=532.2

(c) Methyl 3-(6,7-dihydro-5H-pyrrolo[3,4-b]pyridin-3-ylamino)-5_(methylamino)-6-(3-methylimidazo[4,5-c]pyridin-7-yl)pyrazine-2-carboxylate tert-Butyl 3-[[3-methoxycarbonyl-6-(methylamino)-5-(3-methylimidazo[4,5-c]pyridin-7-yl) pyrazin-2-yl]amino]-5,7-dihydropyrrolo[3,4-b]pyridine-6-carboxylate (147 mg, 0.280 mmol) was added to 4 M HCl in 1,4-dioxane (3.0 mL, 12 mmol). The resulting solution was stirred at 25° C. for 1 hour. The reaction was then concentrated. The resulting residue was purified by C18 reverse phase chromatography, using 5-100% MeCN-water as eluent, to afford methyl 3-(6,7-dihydro-5H-pyrrolo[3,4-b]pyridin-3-ylamino)-5-(methylamino)-6-(3-methylimidazo[4,5-c]pyridin-7-yl) pyrazine-2-carboxylate (0.115 g, 96%) as a yellow solid; 1H NMR (400 MHZ, DMSO-d6) δ 2.86 (3H, d), 3.84 (3H, s), 4.14 (3H, s), 4.46 (2H, t), 4.59 (2H, d), 7.61 (1H, d), 8.34 (1H, d), 8.72 (1H, s), 8.92 (1H, d), 9.03 (1H, s), 9.66 (1H, s), 10.14 (1H, s), 10.51 (1H, s). m/z: (ES+), [M+H]+=432.4

(d) Methyl 5-(methylamino)-3-[(6-methyl-5,7-dihydropyrrolo[3,4-b]pyridin-3-yl)amino]-6-(3-methylimidazo[4,5-c]pyridin-7-yl)pyrazine-2-carboxylate Sodium triacetoxyborohydride (248 mg, 1.17 mmol) was added to a solution of methyl 3-(6,7-dihydro-5H-pyrrolo[3,4-b]pyridin-3-ylamino)-5-(methylamino)-6-(3-methylimidazo[4,5-c]pyridin-7-yl)pyrazine-2-carboxylate (101 mg, 0.230 mmol) and 35 wt % aqueous formaldehyde (100 mg, 1.17 mmol) in MeOH (5 mL). The resulting mixture was stirred at 25° C. for 1 hour. The reaction was then concentrated. The resulting residue was purified by silica gel chromatography, using 0-20% MeOH-DCM as eluent, to afford methyl 5-(methylamino)-3-[(6-methyl-5,7-dihydropyrrolo[3,4-b]pyridin-3-yl)amino]-6-(3-methylimidazo[4,5-c]pyridin-7-yl)pyrazine-2-carboxylate (0.101 g, 97%) as a yellow solid; 1H NMR (300 MHZ, DMSO-d6) δ 2.89 (6H, br s), 3.70-3.90 (7H, m), 4.02 (3H, s), 7.96 (1H, s), 8.15 (1H, d), 8.47-8.54 (2H, m), 8.72 (1H, s), 9.06 (1H, s), 10.37 (1H, s). m/z: (ES+), [M+H]+=446.2

(e) 5-(Methylamino)-3-[(6-methyl-5,7-dihydropyrrolo[3,4-b]pyridin-3-yl)amino]-6 (3-methylimidazo[4,5-c]pyridin-7-yl)pyrazine-2-carboxamide formate salt 7 N Methanolic ammonia (5.0 mL, 35 mmol) was added to methyl 5-(methylamino)-3-[(6-methyl-5,7-dihydropyrrolo[3,4-b]pyridin-3-yl)amino]-6-(3-methylimidazo[4,5-c]pyridin-7-yl)pyrazine-2-carboxylate (83 mg, 0.19 mmol). The resulting suspension was stirred at 80° C. for 2 days. The reaction was then concentrated. The resulting residue was purified by preparative HPLC, using a 5 micron, 50 mm×100 mm, XSelect CSH Prep C18 OBD column, using decreasingly polar mixtures of MeCN—$H_2O$ as eluent and 0.1% formic acid as modifier, to afford 5-(methylamino)-3-[(6-methyl-5,7-dihydropyrrolo[3,4-b]pyridin-3-yl)amino]-6-(3-methylimidazo[4,5-c]pyridin-7-yl)pyrazine-2-carboxamide formate salt (62 mg, 71%) as a yellow solid; 1H NMR (400 MHZ, DMSO-d6) δ 2.57 (3H, s), 2.90 (3H, d), 3.88 (2H, s), 3.96 (2H, s), 4.00 (3H, s), 7.41 (1H, s), 7.77 (1H, s), 7.99 (1H, br q), 8.12 (1H, s), 8.14 (1H, s), 8.50 (1H, s), 8.71 (2H, s), 9.01 (1H, s), 11.53 (1H, s). m/z: (ES+), [M+H]+=431.3

Example 122

3-[(6-Ethyl-5,7-dihydropyrrolo[3,4-b]pyridin-3-yl)amino]-5-(methylamino)-6-(3-methylimidazo[4,5-c]pyridin-7-yl)pyrazine-2-carboxamide

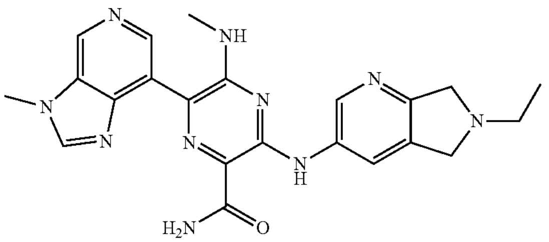 [SMILES: CCN1Cc2cc(Nc3nc(NC)c(-c4cncc5c4ncn5C)nc3C(N)=O)cnc2C1]

(a) Methyl 3-[(6-ethyl-5,7-dihydropyrrolo[3,4-b]pyridin-3-yl)amino]-5 (methylamino)-6 (3-methylimidazo[4,5-c]pyridin-7-yl)pyrazine-2-carboxylate Sodium triacetoxyborohydride (295 mg, 1.39 mmol) was added to a mixture of methyl 3-(6,7-dihydro-5H-pyrrolo[3,4-b]pyridin-3-ylamino)-5-(methylamino)-6-(3-methylimidazo[4,5-c]pyridin-7-yl)pyrazine-2-carboxylate (Example 121 (c)) (120 mg, 0.28 mmol) and 40 wt % aqueous acetaldehyde (153 mg, 1.39 mmol) in DCM (5 mL). The resulting solution was stirred at 25° C. for 16 hours. The reaction was then concentrated. The resulting residue was purified by silica gel chromatography, using 0-15% MeOH-DCM, to afford methyl 3-[(6-ethyl-5,7-dihydropyrrolo[3,4-b]pyridin-3-yl)amino]-5-(methylamino)-6-(3-methylimidazo[4,5-c]pyridin-7-yl)pyrazine-2-carboxylate (0.102 g, 80%) as a yellow solid. 1H NMR (400 MHz, DMSO-d6) δ 1.14 (3H, t), 2.73 (2H, q), 2.88 (3H, d), 3.80-3.86 (5H, m), 3.88-3.93 (2H, m), 4.01 (3H, s), 7.96 (1H, br q), 8.17 (1H, d), 8.49 (1H, s), 8.53 (1H, s), 8.70 (1H, d), 9.05 (1H, s), 10.36 (1H, s); m/z: (ES+), [M+H]+=460.3

(b) 3-[(6-Ethyl-5,7-dihydropyrrolo[3,4-b]pyridin-3-yl)amino]-5 (methylamino)-6-(3-methylimidazo[4,5-c]pyridin-7-yl)pyrazine-2-carboxamide 7 N Methanolic ammonia (1.0 mL, 7.0 mmol) was added to methyl 3-[(6-ethyl-5,7-dihydropyrrolo[3,4-b]pyridin-3-yl)amino]-5-(methylamino)-6-(3-methylimidazo[4,5-c]pyridin-7-yl)pyrazine-2-carboxylate (91 mg, 0.20 mmol). The resulting suspension was stirred at 80° C. for 40 hours. The reaction was then concentrated. The resulting residue was purified by preparative HPLC, using a 5 micron, 50 mm×100 mm, XSelect CSH Prep C18 OBD column, decreasingly polar mixtures of MeCN—$H_2O$ as eluent, and 0.1% formic acid as modifier, to afford 3-[(6-ethyl-5,7-dihydropyrrolo[3,4-b]pyridin-3-yl)amino]-5-(methylamino)-6-(3-methylimidazo[4,5-c]pyridin-7-yl)pyrazine-2-carboxamide (20 mg, 21%) as a yellow solid; 1H NMR (400 MHZ, DMSO-d6) δ 1.12 (3H, t), 2.72 (2H, q), 2.92 (3H, d), 3.81 (2H, s), 3.90 (2H, s), 4.01 (3H, s), 7.42 (1H, s), 7.78 (1H, s), 8.02 (1H, br q), 8.15 (1H, d), 8.52 (1H, s), 8.69 (1H, d), 8.73 (1H, s), 9.03 (1H, s), 11.52 (1H, s); m/z: (ES+), [M+H]+=445.2

Example 123

3-[(6-Isopropyl-5,7-dihydropyrrolo[3,4-b]pyridin-3-yl)amino]-5-(methylamino)-6-(3-methylimidazo[4,5-c]pyridin-7-yl)pyrazine-2-carboxamide formate salt

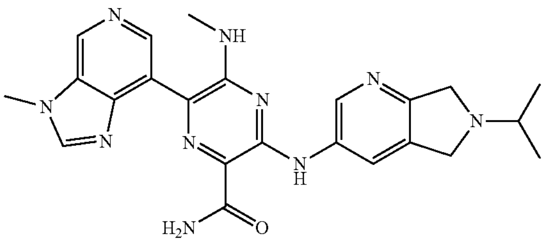 [SMILES: CNc1nc(Nc2cnc3c(c2)CN(C(C)C)C3)c(C(N)=O)nc1-c1cncc2c1ncn2C]

(a) Methyl 3-[(6-isopropyl-5,7-dihydropyrrolo[3,4-b]pyridin-3-yl)amino]-5-(methylamino)-6-(3-methylimidazo[4,5-c]pyridin-7-yl)pyrazine-2-carboxylate Sodium triacetoxyborohydride (246 mg, 1.16 mmol) was added to methyl 3-(6,7-dihydro-5H-pyrrolo[3,4-b]pyridin-3-ylamino)-5-(methylamino)-6-(3-methylimidazo[4,5-c]pyridin-7-yl)pyrazine-2-carboxylate (100 mg, 0.23 mmol) and acetone (170 μL, 2.32 mmol) in MeOH (5 mL). The resulting solution was stirred at 25° C. for 4 hours. The reaction was then concentrated. The resulting residue was purified by silica gel chromatography, using 0-15% MeOH-DCM as eluent, to afford methyl 3-[(6-isopropyl-5,7-dihydropyrrolo[3,4-b]pyridin-3-yl)amino]-5-(methylamino)-6-(3-methylimidazo[4,5-c]pyridin-7-yl)pyrazine-2-carboxylate (0.093 g, 85%) as a yellow solid. 1H NMR (400 MHZ, DMSO-d6) δ 1.15-1.22 (6H, m), 2.90 (3H, d), 3.01-3.15 (1H, m), 3.80-3.90 (5H, m), 3.92-4.12 (5H, m), 7.98 (1H, br q), 8.33 (1H, s), 8.50 (1H, s), 8.53 (1H, s), 8.84 (1H, s), 9.06 (1H, s), 10.46 (1H, s). m/z: (ES+), [M+H]+=474.4

(b) 3-[(6-Isopropyl-5,7-dihydropyrrolo[3,4-b]pyridin-3-yl)amino]-5 (methylamino)-6-(3-methylimidazo[4,5-c]pyridin-7-yl)pyrazine-2-carboxamide formate salt Methyl 3-[(6-isopropyl-5,7-dihydropyrrolo[3,4-b]pyridin-3-yl)amino]-5-(methylamino)-6-(3-methylimidazo[4,5-c]pyridin-7-yl)pyrazine-2-carboxylate (85 mg, 0.18 mmol) was added to ammonia of solution in MeOH (5 mL) at 25° C. under air. The resulting mixture was stirred at 80° C. for 40 hours. The reaction was then concentrated. The resulting residue was purified by preparative HPLC, using a 5 micron, 50 mm×100 mm, XSelect CSH Prep C18 OBD column, decreasingly polar mixtures of MeCN—$H_2O$ as eluent, and 0.1% formic acid as modifier, to afford 3-[(6-isopropyl-5,7-dihydropyrrolo[3,4-b]pyridin-3-yl)amino]-5-(methylamino)-6-(3-methylimidazo[4,5-c]pyridin-7-yl)pyrazine-2-carboxamide formate salt (20 mg, 22% yield) as a yellow solid; 1H NMR (300 MHz, DMSO-d6) δ 1.13 (6H, d), 2.72-2.82 (1H, m), 2.93 (3H, d), 3.86 (2H, s), 3.95 (2H, s), 4.02 (3H, s), 7.44 (1H, s), 7.80 (1H, s), 8.03 (1H, br q), 8.17 (2H, s), 8.53 (1H, s), 8.69 (1H, d), 8.73 (1H, s), 9.04 (1H, s), 11.54 (1H, s); m/z: (ES+), [M+H]+=459.2

Example 124

3-[4-[(Dimethylamino)methyl]anilino]-5-(methylamino)-6-(3-methylimidazo[4,5-c]pyridin-7-yl)pyrazine-2-carboxamide

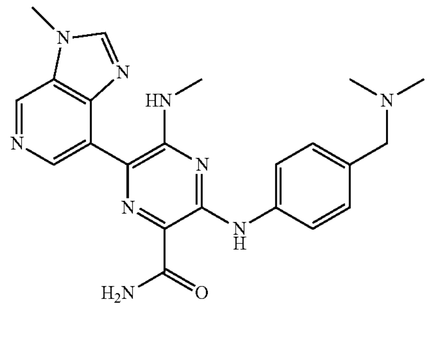 [SMILES: CNc1nc(Nc2ccc(CN(C)C)cc2)c(C(N)=O)nc1-c1cncc2c1ncn2C]

(a) N-[4-(1_3-Dioxolan-2-yl)phenyl]formamide

Formic acid (4.64 mL, 121 mmol) was added dropwise to acetic anhydride (11.4 mL, 121 mmol). The resulting solution was stirred at 50° C. for 2 hours. The reaction was allowed to cool to room temperature and then added dropwise to a solution of 4-(1,3-dioxolan-2-yl) aniline (1.66 g, 10.1 mmol) in THF (51 mL) at 0° C. The resulting mixture was stirred at 25 C for 2 hours. The reaction was then diluted with EtOAc and washed with saturated aqueous sodium bicarbonate. The layers were separated and the aqueous layer was extracted four times with EtOAc (50 mL each). The organic layers were combined, dried over $Na_2SO_4$, and concentrated to afford N-[4-(1,3-dioxolan-2-yl)phenyl]formamide (1.94 g, 100%) as a beige solid.

(b) Methyl 6-chloro-3-[4-(1_3-dioxolan-2-yl)anilino]-5-(methylamino) pyrazine-2-carboxylate 60 wt % Sodium hydride in oil (0.400 g, 10.0 mmol) was added portionwise to a solution of N-[4-(1,3-dioxolan-2-yl) phenyl]formamide (1.93 g, 10.0 mmol) in DMF (46 mL). Methyl 6-chloro-3-fluoro-5-(methylamino) pyrazine-2-carboxylate (1.50 g, 6.83 mmol) was added. The resulting mixture was stirred at 60° C. for 16 hours. The reaction was then quenched with water and concentrated. The resulting residue was dissolved in DCM, washed with water, dried over $Na_2SO_4$, filtered, and concentrated. The resulting residue was purified by silica gel chromatography, using 0-20% MeOH-DCM as eluent, to afford methyl 6-chloro-3-[4-(1, 3-dioxolan-2-yl)anilino]-5-(methylamino) pyrazine-2-carboxylate (0.810 g, 33%) as a yellow solid; 1H NMR (500 MHZ, DMSO-d6) δ 2.94 (3H, d), 3.81 (3H, s), 3.89-3.96 (2H, m), 4.01-4.07 (2H, m), 5.68 (1H, s), 7.39 (2H, d), 7.71 (2H, br d), 7.83-7.96 (1H, m), 10.33 (1H, s); m/z: (ES+), [M+H]+=365.1

(c) 6-Chloro-3-[4-(1,3-dioxolan-2-yl)anilino]-5-(methylamino) pyrazine-2-carboxamide 7 N Methanolic ammonia (5.0 mL, 35 mmol) was added to methyl 6-chloro-3-[4-(1,3-dioxolan-2-yl)anilino]-5-(methylamino) pyrazine-2-carboxylate (410 mg, 1.12 mmol). The resulting suspension was stirred at 110° C. for 16 hours. The reaction was then concentrated. The resulting residue was purified by silica gel chromatography, using 0-20% MeOH-DCM as eluent, to afford 6-chloro-3-[4-(1,3-dioxolan-2-yl)anilino]-5-(methylamino) pyrazine-2-carboxamide (0.230 g, 59%) as a yellow solid; 1H NMR (500 MHz, DMSO-d6) δ 2.94 (3H, d), 3.87-3.97 (2H, m), 3.99-4.07 (2H, m), 5.66 (1H, s), 7.31-7.42 (3H, m), 7.61 (1H, br s), 7.68 (2H, d), 7.82-7.93 (1H, m), 11.49 (1H, s); m/z: (ES+), [M+H]+=350.4

(d) 3-[4-(1,3-Dioxolan-2-yl)anilino]-5-(methylamino)-6-(3-methylimidazo[4,5-c]pyridin-7-yl)pyrazine-2-carboxamide 7-Bromo-3-methyl-imidazo[4,5-c]pyridine (0.172 g, 0.810 mmol), bis(pinacolato)diboron (0.514 g, 2.03 mmol), cataCXium A Pd G3 (0.059 g, 0.080 mmol), cataCXium A (0.029 g, 0.080 mmol), and potassium acetate (0.238 g, 2.43 mmol) were combined in a microwave vial, which was evacuated and backfilled three times with nitrogen. DMF (3.5 mL) was added and the reaction was stirred at 80° C. for 24 hours. The reaction was allowed to cool to room temperature and set aside.

6-Chloro-3-[4-(1,3-dioxolan-2-yl)anilino]-5-(methylamino) pyrazine-2-carboxamide (230 mg, 0.66 mmol), Pd(dppf)$Cl_2$ DCM complex (96 mg, 0.13 mmol), and cesium fluoride (300 mg, 1.97 mmol) were combined in a microwave vial, which was evacuated and backfilled three times with nitrogen. The borlyation mixture was added via syringe. The resulting reaction was stirred at 90° C. for 1 hour. The reaction was then concentrated. The resulting residue was diluted with DCM and washed with water. The layers were separated and the aqueous layer was extracted with 3:1 chloroform/IPA. The combined organic layers were dried over $Na_2SO_4$, and concentrated. The resulting residue was purified by silica gel chromatography, using 0-10% MeOH-DCM as eluent, to afford 3-[4-(1,3-dioxolan-2-yl) anilino]-5-(methylamino)-6-(3-methylimidazo[4,5-c]pyridin-7-yl)pyrazine-2-carboxamide (0.130 g, 44%) as an orange solid; 1H NMR (500 MHZ, DMSO-d6) 2.95 (3H, d), 3.89-3.95 (2H, m), 4.00 (3H, s), 4.03-4.10 (2H, m), 5.68 (1H, s), 7.39 (2H, br d), 7.45-7.66 (1H, m), 7.80 (2H, br d), 7.84-7.93 (1H, m), 7.96-8.09 (1H, m), 8.51 (1H, s), 8.74 (1H, s), 9.02 (1H, s), 11.60 (1H, s); m/z: (ES+), [M+H]+=447.4

(e) 3-(4-Formylanilino)-5-(methylamino)-6-(3-methylimidazo[4,5-c]pyridin-7-yl)pyrazine-2-carboxamide hydrochloride 2 N Aqueous HCl (10 mL, 20 mmol) was added to 3-[4-(1,3-dioxolan-2-yl)anilino]-5-(methylamino)-6-(3-methylimidazo[4,5-c]pyridin-7-yl)pyrazine-2-carboxamide (125 mg, 0.28 mmol). The resulting mixture was stirred for 1 hour. The reaction was then concentrated to afford 3-(4-formylanilino)-5-(methylamino)-6-(3-methylimidazo[4,5-c] pyridin-7-yl)pyrazine-2-carboxamide hydrochloride (0.120 g, 98%) as a reddish/orange solid; 1H NMR (500 MHZ, DMSO-d6) 2.99 (3H, s), 4.14 (3H, s), 7.59 (1H, br s), 7.78 (1H, br s), 7.89 (2H, d), 8.07 (3H, d), 8.98 (1H, s), 9.05 (1H, s), 9.57 (1H, s), 9.86 (1H, s), 12.07 (1H, s); m/z: (ES+), [M+H]+=403.2

(f) 3-[4-[(Dimethylamino)methyl]anilino]-5-(methylamino)-6-(3-methylimidazo[4,5-c]pyridin-7-yl) pyrazine-2-carboxamide bis-formate salt 2 M Dimethylamine in THF (270 μL, 0.54 mmol) was added to a solution of 3-(4-formylanilino)-5-(methylamino)-

6-(3-methylimidazo[4,5-c]pyridin-7-yl)pyrazine-2-carboxamide (60 mg, 0.14 mmol) in DMF (1.0 mL), MeOH (0.4 mL), and acetic acid (0.1 mL). The resulting mixture was stirred at 65° C. for 1 hour, then cooled to 0° C. Sodium triacetoxyborohydride (79 mg, 0.37 mmol) was added. The resulting mixture was stirred at 25 C for 15 minutes. The reaction was then concentrated. The resulting residue was redissolved in DMF (1.6 mL). Dimethylammonium chloride (82 mg, 1.0 mmol), DIPEA (175 μL, 1.00 mmol), and acetic acid (0.1 mL) were added. The resulting mixture was stirred at 70° C. for 1 hour. The reaction was then allowed to cool to room temperature. Sodium triacetoxyborohydride (79 mg, 0.37 mmol) was added. The resulting mixture was stirred for 5 minutes, then filtered and concentrated. The resulting residue was purified by preparative HPLC using a 5 micron, 30 mm×150 mm Xselect CSH OBD column, 5-25% MeCN—$H_2O$ as eluent, and 0.1% formic acid as modifier to afford 3-[4-[(dimethylamino)methyl]anilino]-5-(methylamino)-6-(3-methylimidazo[4,5-c]pyridin-7-yl)pyrazine-2-carboxamide bis-formate salt (28 mg, 43%); 1H NMR (500 MHZ, DMSO-d6) 2.26 (6H, s), 2.95 (3H, br d), 3.53 (2H, s), 4.00 (3H, s), 7.29 (2H, br d), 7.37 (1H, br s), 7.69-7.82 (3H, m), 7.99 (1H, br q), 8.17 (2H, s), 8.51 (1H, s), 8.72 (1H, s), 9.01 (1H, s), 11.54 (1H, s); m/z: (ES+), [M+H]+=432.3

Example 125

5-(Methylamino)-6-(3-methylimidazo[4,5-c]pyridin-7-yl)-3-[4-(pyrrolidin-1-ylmethyl)anilino]pyrazine-2-carboxamide bis-formate salt

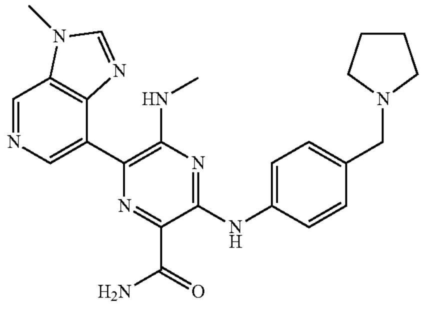 [SMILES: CNc1nc(Nc2ccc(CN3CCCC3)cc2)c(C(N)=O)nc1-c1cncc2c1ncn2C]

Pyrrolidine (41 μL, 0.50 mmol) was added to a mixture of 3-(4-formylanilino)-5-(methylamino)-6-(3-methylimidazo[4,5-c]pyridin-7-yl)pyrazine-2-carboxamide (50 mg, 0.12 mmol) and acetic acid (0.1 mL) in DCE (1.24 mL) and MeOH (0.41 mL). The resulting mixture was stirred at 65° C. for 1 hour, then cooled to 0° C. Sodium triacetoxyborohydride (79 mg, 0.37 mmol) was added. The resulting mixture was stirred at 25 C for 5 minutes. The reaction was then concentrated. The resulting residue was redissolved in DMF (1.6 mL). Additional pyrrolidine (41 μL, 0.50 mmol) and acetic acid (0.1 mL) were added. The resulting mixture was then stirred at 70° C. for 1 hour. The reaction was then allowed to cool to room temperature. Additional sodium triacetoxyborohydride (79 mg, 0.37 mmol) was added. The reaction was then filtered and the filtrate was concentrated. The resulting residue was purified by preparative HPLC, using a 5 micron, 30 mm×150 mm Xselect CSH OBD column, 5-25% MeCN—$H_2O$ as eluent, and 0.1% formic acid as modifier, to afford 5-(methylamino)-6-(3-methylimidazo[4,5-c]pyridin-7-yl)-3-[4-(pyrrolidin-1-ylmethyl)anilino]pyrazine-2-carboxamide bis-formate salt (12 mg, 22%); 1H NMR (500 MHz, DMSO-d6) 1.63-1.78 (4H, m), 2.53-2.66 (4H, m), 2.95 (3H, d), 3.67 (2H, s), 4.00 (3H, s), 7.30 (2H, br d), 7.36 (1H, s), 7.75 (3H, d), 7.99 (1H, br q), 8.25 (3H, br s), 8.51 (1H, s), 8.72 (1H, s), 9.01 (1H, s), 11.53 (1H, s); m/z: (ES+), [M+H]+=458.2

Example 126

5-(Methylamino)-6-(3-methylimidazo[4,5-c]pyridin-7-yl)-3-[4-(morpholinomethyl)anilino]pyrazine-2-carboxamide

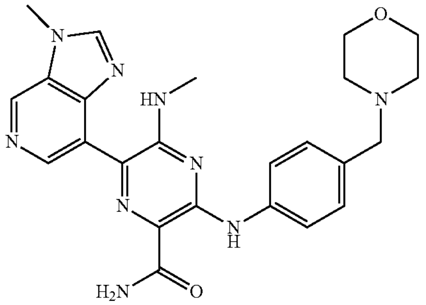 [SMILES: CNc1nc(Nc2ccc(CN3CCOCC3)cc2)c(C(N)=O)nc1-c1cncc2c1ncn2C]

(a) Methyl 5-(methylamino)-6-(3-methylimidazo[4,5-c]pyridin-7-yl)-3-[4-(morpholinomethyl)anilino]pyrazine-2-carboxylate Brettphos Pd G3 (58 mg, 0.060 mmol) was added to a suspension of methyl 3-amino-5-(methylamino)-6-(3-methylimidazo[4,5-c]pyridin-7-yl)pyrazine-2-carboxylate (100 mg, 0.32 mmol), 4-[(4-bromophenyl)methyl]morpholine (82 mg, 0.32 mmol), and cesium carbonate (313 mg, 0.960 mmol) in 1,4-dioxane (5 mL) under nitrogen. The resulting mixture was stirred at 100° C. for 16 hours. The reaction was then concentrated. The resulting residue was purified by silica gel chromatography, using 0-20% MeOH-DCM as eluent, to afford methyl 5-(methylamino)-6-(3-methylimidazo[4,5-c]pyridin-7-yl)-3-[4-(morpholinomethyl)anilino]pyrazine-2-carboxylate (0.117 g, 75%) as a yellow solid; 1H NMR (400 MHZ, DMSO-d6) δ 2.30-2.43 (4H, m), 2.93 (3H, d), 3.44 (2H, s), 3.54-3.63 (4H, m), 3.84 (3H, s), 4.02 (3H, s), 7.30 (2H, d), 7.78 (2H, d), 7.95 (1H, br q), 8.50 (1H, s), 8.54 (1H, s), 9.05 (1H, s), 10.46 (1H, s); m/z: (ES+), [M+H]+=489.2

(b) 5-(Methylamino)-6-(3-methylimidazo[4,5-c]pyridin-7-yl)-3-[4-(morpholinomethyl)anilino]pyrazine-2-carboxamide 7 N Methanolic ammonia (10 mL, 70 mmol) was added to methyl 5-(methylamino)-6-(3-methylimidazo[4,5-c]pyridin-7-yl)-3-[4-(morpholinomethyl)anilino]pyrazine-2-carboxylate (91 mg, 0.19 mmol). The resulting suspension was stirred at 80° C. for 2 days. The reaction was then concentrated. The resulting residue was purified by preparative HPLC, using a 5 micron, 50 mm×100 mm, XSelect CSH Prep C18 OBD column, decreasingly polar mixtures of MeCN—$H_2O$ as eluent, and 0.1% formic acid as modifier, to afford 6-(3-methyl-3H-imidazo[4,5-c]pyridin-7-yl)-5-(methylamino)-3-((4-(morpholinomethyl)phenyl)amino)pyrazine-2-carboxamide (30 mg, 33%) as a yellow solid; 1H NMR (400 MHZ, DMSO-d6) δ 2.36 (4H, t), 2.96 (3H, d), 3.42 (2H, s), 3.58 (4H, t), 4.01 (3H, s), 7.27 (2H, d), 7.37 (1H, s), 7.72-7.78 (3H, m), 8.00 (1H, br q), 8.52 (1H, s), 8.73 (1H, s), 9.02 (1H, s), 11.53 (1H, s); m/z: (ES+), [M+H]+=474.4

Example 127

5-(Methylamino)-6-(3-methylimidazo[4,5-c]pyridin-7-yl)-3-[4-[(4-methylpiperazin-1-yl)methyl]anilino]pyrazine-2-carboxamide

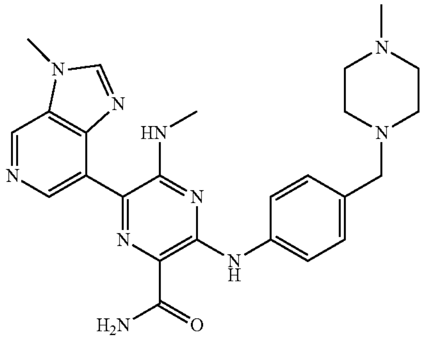 [SMILES: CNc1nc(Nc2ccc(CN3CCN(C)CC3)cc2)c(C(N)=O)nc1-c1cncc2c1ncn2C]

(a) Methyl 5-(methylamino)-6-(3-methylimidazo[4,5-c]pyridin-7-yl)-3-[4-[(4-methylpiperazin-1-yl)methyl]anilino]pyrazine-2-carboxylate Brettphos Pd G3 (58 mg, 0.060 mmol) was added to a suspension of methyl 3-amino-5-(methylamino)-6-(3-methylimidazo[4,5-c]pyridin-7-yl)pyrazine-2-carboxylate (100 mg, 0.32 mmol), 1-[(4-bromophenyl)methyl]-4-methyl-piperazine (86 mg, 0.32 mmol), and cesium carbonate (313 mg, 0.960 mmol) in 1,4-dioxane (5 mL) under nitrogen. The resulting mixture was stirred at 100° C. for 16 hours. The reaction was then concentrated. The resulting residue was purified by silica gel chromatography, using 0-25% MeOH-DCM as eluent, to afford methyl 5-(methylamino)-6-(3-methylimidazo[4,5-c]pyridin-7-yl)-3-[4-[(4-methylpiperazin-1-yl)methyl]anilino]pyrazine-2-carboxylate (0.092 g, 57% yield) as a yellow solid. 1H NMR (400 MHZ, DMSO-d6) δ 1.24 (3H, s), 2.54-2.76 (8H, m), 2.93 (3H, d), 3.32 (2H, s), 3.84 (3H, s), 4.02 (3H, s), 7.31 (2H, d), 7.81 (2H, d), 7.95 (1H, br q), 8.50 (1H, s), 8.54 (1H, s), 9.05 (1H, s), 10.48 (1H, s). m/z: (ES+), $[M+2H]^{2+}$=251.6

(b) 5-(Methylamino)-6-(3-methylimidazo[4,5-c]pyridin-7-yl)-3-[4-[(4-methylpiperazin-1-yl)methyl]anilino]pyrazine-2-carboxamide formate salt 7 N Methanolic ammonia (10 mL, 70 mmol) was added to methyl 5-(methylamino)-6-(3-methylimidazo[4,5-c]pyridin-7-yl)-3-[4-[(4-methylpiperazin-1-yl)methyl]anilino]pyrazine-2-carboxylate (70 mg, 0.14 mmol). The resulting suspension was stirred at 80° C. for 2 days. The reaction was then concentrated. The resulting residue was purified by preparative HPLC, using a 5 micron, 50 mm×100 mm, XSelect CSH Prep C18 OBD column, decreasingly polar mixtures of MeCN—$H_2O$ as eluent, and 0.1% formic acid as modifier, to afford 5-(methylamino)-6-(3-methylimidazo[4,5-c]pyridin-7-yl)-3-[4-[(4-methylpiperazin-1-yl)methyl]anilino]pyrazine-2-carboxamide formate salt (25 mg, 33%) as a yellow solid; 1H NMR (400 MHZ, DMSO-d6) δ 2.19 (3H, s), 2.25-2.53 (8H, m), 2.96 (3H, d), 3.42 (2H, s), 4.01 (3H, s), 7.25 (2H, d), 7.36 (1H, s), 7.70-7.81 (3H, m), 8.00 (1H, br q), 8.18 (1H, br s), 8.52 (1H, s), 8.73 (1H, s), 9.02 (1H, s), 11.52 (1H, s). m/z: (ES+), [M+H]+=487.4

Example 128

5-(Methylamino)-6-(3-methylimidazo[4,5-c]pyridin-7-yl)-3-[4-(2-oxa-6-azaspiro[3.3]heptan-6-ylmethyl)anilino]pyrazine-2-carboxamide

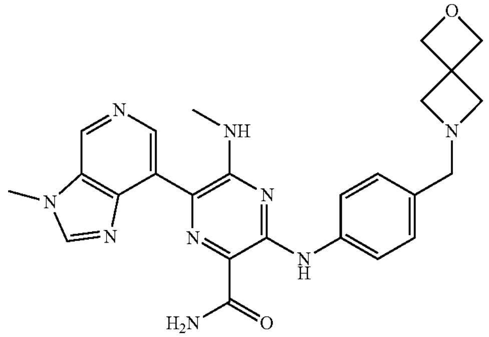 [SMILES: CNc1nc(Nc2ccc(CN3CC4(COC4)C3)cc2)c(C(N)=O)nc1-c1cncc2c1ncn2C]

(a) Methyl 5-(methylamino)-6-(3-methylimidazo[4,5-c]pyridin-7-yl)-3-[4-(2-oxa-6-azaspiro[3 3]heptan-6-ylmethyl)anilino]pyrazine-2-carboxylate BrettPhos Pd G3 (29 mg, 0.030 mmol) was added to a suspension of methyl 3-amino-5-(methylamino)-6-(3-methylimidazo[4,5-c]pyridin-7-yl)pyrazine-2-carboxylate (100 mg, 0.32 mmol), 6-(4-bromobenzyl)-2-oxa-6-azaspiro[3.3]heptane (86 mg, 0.32 mmol), and cesium carbonate (312 mg, 0.960 mmol) in 1,4-dioxane (10 mL) under nitrogen. The resulting suspension was stirred at 100° C. for 8 hours. The reaction was then concentrated. The crude product was purified by silica gel chromatography, using 0-10% MeOH-DCM as eluent, to afford methyl 5-(methylamino)-6-(3-methylimidazo[4,5-c]pyridin-7-yl)-3-[4-(2-oxa-6-azaspiro[3.3]heptan-6-ylmethyl)anilino]pyrazine-2-carboxylate (0.040 g, 25% yield) as a yellow solid. m/z: (ES+), [M+H]+= 501.3

(b) 5-(Methylamino)-6-(3-methylimidazo[4,5-c]pyridin-7-yl)-3-[4-(2-oxa-6-azaspiro[3 3]heptan-6-ylmethyl)anilino]pyrazine-2-carboxamide bis-formate salt 7 N Methanolic ammonia (10 mL, 70 mmol) was added to methyl 5-(methylamino)-6-(3-methylimidazo[4,5-c]pyridin-7-yl)-3-[4-(2-oxa-6-azaspiro[3.3]heptan-6-ylmethyl)anilino]pyrazine-2-carboxylate (60 mg, 0.12 mmol). The resulting suspension was stirred at 80° C. for 24 hour. The reaction was then concentrated. The resulting residue was purified by preparative HPLC using a 5 micron, 30×150 mm Xselect CSH OBD column, 5-20% MeCN—$H_2O$ as eluent, and 0.1% formic acid as modifier, to afford 5-(methylamino)-6-(3-methylimidazo[4,5-c]pyridin-7-yl)-3-[4-(2-oxa-6-azaspiro[3.3]heptan-6-ylmethyl)anilino]pyrazine-2-carboxamide bis-formate salt (9.0 mg, 13% yield) as a yellow solid; 1H NMR (300 MHz, DMSO-d6) δ 2.95 (3H, d), 3.31 (4H, s), 3.48 (2H, s), 4.02 (3H, s), 4.61 (4H, s), 7.21 (2H, d), 7.40 (1H, s), 7.73 (2H, d), 7.77 (1H, s), 7.99 (1H, br q), 8.18 (2H, s), 8.53 (1H, s), 8.73 (1H, s), 9.03 (1H, s), 11.53 (1H, s); m/z: (ES+), [M+H]+=486.3.

Example 129 and 130

5-(Methylamino)-6-(3-methylimidazo[4,5-c]pyridin-7-yl)-3-[4-[rel-(1R)-1-(4-methylpiperazin-1-yl)ethyl]anilino]pyrazine-2-carboxamide formate salt and 5-(methylamino)-6-(3-methylimidazo[4,5-c]pyridin-7-yl)-3-[4-[rel-(1S)-1-(4-methylpiperazin-1-yl)ethyl]anilino]pyrazine-2-carboxamide formate salt

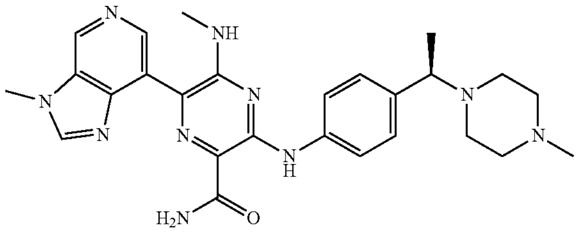

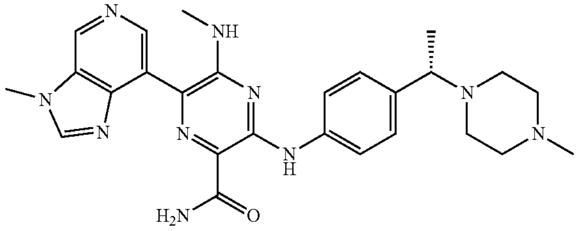

(a) 1-Methyl-4-[rel-(1R)-1-(4-bromophenyl)ethyl]piperazine and 1-methyl-4-[rel-(1S)-1-(4-bromophenyl)ethyl]piperazine Thionyl chloride (4.44 g, 37.3 mmol) was added to a solution of (4-bromophenyl) methanol (5.00 g, 24.9 mmol) in DCM (2 mL). The resulting mixture was stirred at 25° C. for 4 hours. The reaction was then concentrated. A solution of 1-methylpiperazine (4.98 g, 49.7 mmol) in MeCN (2 mL) was added to the residue. The resulting mixture was stirred at 25° C. for 24 hours. The reaction was then concentrated. The resulting residue was purified by silica gel chromatography, using 0-10% MeOH-DCM as eluent, to afford racemic 1-[1-(4-bromophenyl)ethyl]-4-methyl-piperazine (2.00 g, 28%) as a yellow oil. This material was further purified by preparative chiral HPLC, using a 5 micron, 2.12 cm×25 cm, Lux 5u Cellulose-4, AXIA packed column, using isocratic 17% MeOH-s$CO_2$ as eluent, and 2 mM ammonia as modifier, to afford 1-methyl-4-[rel-(1R)-1-(4-bromophenyl)ethyl]piperazine (0.400 g, 5.6% yield) and 1-methyl-4-[rel-(1S)-1-(4-bromophenyl)ethyl]piperazine (0.400 g, 5.6%), each as a yellow oil; 1H NMR (300 MHz, DMSO-d6) δ 1.25 (3H, d), 2.30-2.56 (11H, m), 3.41 (1H, q), 7.17-7.34 (2H, m), 7.45-7.58 (2H, m); m/z: (ES+), [M+H]+=283.1

(b1)Methyl 5-(methylamino)-6-(3-methylimidazo[4,5-c]pyridin-7-yl)-3-[4-[rel-(1R)-1-(4-methylpiperazin-1-yl)ethyl]anilino]pyrazine-2-carboxylate Methyl 3-amino-5-(methylamino)-6-(3-methylimidazo[4,5-c]pyridin-7-yl)pyrazine-2-carboxylate (111 mg, 0.350 mmol) was added to a suspension of 1-methyl-4-[rel-(1R)-1-(4-bromophenyl)ethyl]piperazine (200 mg, 0.71 mmol), cesium carbonate (690 mg, 2.12 mmol) and BrettPhos Pd G3 (64 mg, 0.070 mmol) in 1,4-dioxane (10 mL) under nitrogen. The resulting mixture was stirred at 100° C. for 3 hours. The reaction was then concentrated. The resulting residue was purified by silica gel chromatography, using 0-10% MeOH-DCM as eluent, to afford methyl 5-(methylamino)-6-(3-methylimidazo[4,5-c]pyridin-7-yl)-3-[4-[rel-(1R)-1-(4-methylpiperazin-1-yl)ethyl]anilino]pyrazine-2-carboxylate (0.080 g, 22%) as a yellow solid; 1H NMR (300 MHz, DMSO-d6) δ 1.31 (3H, d), 2.26 (3H, s), 2.25-2.47 (4H, m), 2.94 (3H, d), 3.39-3.52 (5H, m), 3.84 (3H, s), 4.02 (3H, s), 7.29 (2H, d), 7.74-7.88 (2H, m), 7.95 (1H, br q), 8.50 (1H, s), 8.54 (1H, s), 9.05 (1H, s), 10.48 (1H, s). m/z: (ES+), [M+H]+=516.3

(c1) 5-(Methylamino)-6-(3-methylimidazo[4,5-c]pyridin-7-yl)-3-[4-[rel-(1R)-1-(4-methylpiperazin-1-yl)ethyl]anilino]pyrazine-2-carboxamide formate salt 7 N Methanolic ammonia (10 mL, 70 mmol) was added to methyl 5-(methylamino)-6-(3-methylimidazo[4,5-c]pyridin-7-yl)-3-[4-[rel-(1R)-1-(4-methylpiperazin-1-yl)ethyl]anilino]pyrazine-2-carboxylate (60 mg, 0.12 mmol). The resulting suspension was stirred at 80° C. for 16 hours. The reaction was then concentrated. The resulting residue was purified by preparative HPLC, using a 5 micron, 30 mm×150 mm, Xselect CSH OBD column, 2-15% MeCN—$H_2O$ as eluent, and 0.1% formic acid as modifier, to afford 5-(methylamino)-6-(3-methylimidazo[4,5-c]pyridin-7-yl)-3-[4-[rel-(1R)-1-(4-methylpiperazin-1-yl)ethyl]anilino]pyrazine-2-carboxamide formate salt (26 mg, 39%) as a yellow solid; 1H NMR (300 MHz, DMSO-d6) δ 1.30 (3H, d), 2.19 (3H, s), 2.24-2.56 (8H, m), 2.97 (3H, d), 3.38 (1H, q), 4.02 (3H, s), 7.26 (2H, d), 7.38 (1H, s), 7.72-7.80 (3H, m), 8.02 (1H, br q), 8.17 (1H, s), 8.53 (1H, s), 8.74 (1H, s), 9.03 (1H, s), 11.54 (1H, s). m/z: (ES+), [M]+=501.5

(b2)Methyl 5-(methylamino)-6-(3-methylimidazo[4,5-c]pyridin-7-yl)-3-[4-[rel-(1R)-1-(4-methylpiperazin-1-yl)ethyl]anilino]pyrazine-2-carboxylate Cesium carbonate (345 mg, 1.06 mmol) was added to a suspension of (R)-1-(1-(4-bromophenyl)ethyl)-4-methylpiperazine (200 mg, 0.71 mmol), methyl 3-amino-6-(3-methyl-3H-imidazo[4,5-c]pyridin-7-yl)-5-(methylamino) pyrazine-2-carboxylate (111 mg, 0.35 mmol), and BrettPhos Pd G3 (32.0 mg, 0.04 mmol) in 1,4-dioxane (10 mL) under nitrogen. The resulting mixture was stirred at 100° C. for 3 hours. The reaction was then concentrated. The resulting residue was purified by silica gel chromatography, using 0-10% MeOH-DCM as eluent, to afford methyl 5-(methylamino)-6-(3-methylimidazo[4,5-c]pyridin-7-yl)-3-[4-[rel-(1S)-1-(4-methylpiperazin-1-yl)ethyl]anilino]pyrazine-2-carboxylate (0.080 g, 22%) as a yellow solid; 1H NMR (300 MHz, DMSO-d6) δ 1.31 (3H, d), 2.26 (3H, s), 2.25-2.47 (4H, m), 2.94 (3H, d), 3.39-3.52 (5H, m), 3.84 (3H, s), 4.02 (3H, s), 7.29 (2H, d), 7.74-7.88 (2H, m), 7.95 (1H, br q), 8.50 (1H, s), 8.54 (1H, s), 9.05 (1H, s), 10.48 (1H, s); m/z: (ES+), [M+H]+=516.3

(c2) 5-(methylamino)-6-(3-methylimidazo[4,5-c]pyridin-7-yl)-3-[4-[rel-(1R)-1-(4-methylpiperazin-1-yl)ethyl]anilino]pyrazine-2-carboxamide formate salt 7 N Methanolic ammonia (10 mL, 70 mmol) was added to methyl 5-(methylamino)-6-(3-methylimidazo[4,5-c]pyridin-7-yl)-3-[4-[rel-(1S)-1-(4-methylpiperazin-1-yl)ethyl]anilino]pyrazine-2-carboxylate (60 mg, 0.12 mmol). The resulting suspension was stirred at 80° C. for 16 hours. The reaction was then concentrated. The resulting residue was purified by preparative HPLC, using a 5 micron, 30 mm×150 mm Xselect CSH OBD column, 2-15% MeCN—$H_2O$ as eluent, and 0.1% formic acid as modifier, to afford 5-(methylamino)-6-(3-methylimidazo[4,5-c]pyridin-7-yl)-3-[4-[rel-(1S)-1-(4-methylpiperazin-1-yl)ethyl]anilino]pyrazine-2-carboxamide formate salt (26 mg, 39%) as a yellow solid; 1H NMR (300 MHz, DMSO-d6) δ 1.30 (3H, d), 2.19 (3H, s), 2.24-2.56 (8H, m), 2.97 (3H, d), 3.38 (1H, q), 4.02 (3H, s), 7.26 (2H, d), 7.38 (1H, s), 7.72-7.80 (3H, m), 8.02 (1H, br q), 8.17 (1H, s), 8.53 (1H, s), 8.74 (1H, s), 9.03 (1H, s), 11.54 (1H, s); m/z: (ES+), [M+H]+=501.5

Examples 131 and 132

5-(Methylamino)-6-(3-methylimidazo[4,5-c]pyridin-7-yl)-3-[4-[rel-(1R)-1-morpholinoethyl]anilino]pyrazine-2-carboxamide formate salt and 5-(methylamino)-6-(3-methylimidazo[4,5-c]pyridin-7-yl)-3-[4-[rel-(1S)-1-morpholinoethyl]anilino]pyrazine-2-carboxamide formate salt

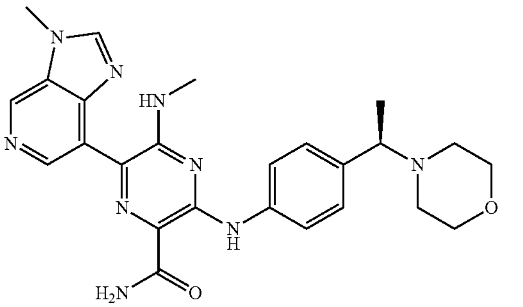

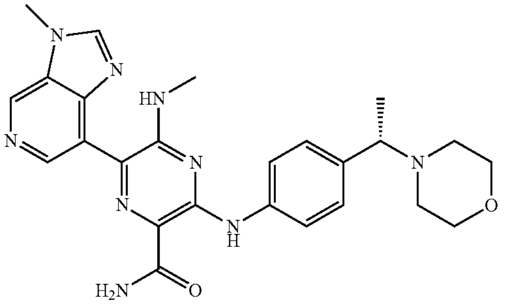

(a) 1-Bromo-4-(1-chloroethyl)benzene

Thionyl chloride (2.72 mL, 37.3 mmol) was added to a solution of 1-(4-bromophenyl) ethanol (5.00 g, 24.9 mmol) in DCM (50 mL). The resulting solution was stirred at 25° C. for 4 hours. The reaction was then concentrated. The resulting residue was redissolved in EtOAc (50 mL) and washed once with saturated aqueous sodium bicarbonate (50 mL) and twice with brine (50 mL). The organic layer was dried over $Na_2SO_4$, filtered, and concentrated to afford 1-bromo-4-(1-chloroethyl)benzene (5.1 g, 93% yield) as a colorless oil. 1H NMR (300 MHZ, Chloroform-d) δ 1.83 (3H, d), 5.04 (1H, q), 7.25-7.33 (2H, m), 7.46-7.52 (2H, m). Poor behavior by LCMS.

(b) 4-[rel-(1R)-1-(4-Bromophenyl)ethyl]morpholine and 4-[rel-(1S)-1-(4-bromophenyl)ethyl]morpholine Potassium iodide (0.113 g, 0.680 mmol) was added to a solution of 1-bromo-4-(1-chloroethyl)benzene (3.00 g, 13.7 mmol), morpholine (1.43 g, 16.4 mmol) and triethylamine (5.7 mL, 41 mmol) in MeCN (30 mL). The resulting solution was stirred at 60° C. for 50 hours. The reaction was then concentrated. The resulting residue was purified by silica gel chromatography, using 0-40% EtOAc-petroleum ether as eluent, to afford 4-[1-(4-bromophenyl)ethyl]morpholine (2.60 g, 70%) as a colorless oil. This material was purified further by chiral SFC, using a 3 micron, 4.6 mm×50 mm, ChiralPak AD3 column, isocratic 20% MeOH-$sCO_2$ as eluent, and 0.1% diethylamine as modifier, to afford 4-[rel-(1R)-1-(4-bromophenyl)ethyl]morpholine (227 mg, 27% yield) and 4-[rel-(1S)-1-(4-bromophenyl)ethyl]morpholine (231 mg, 27% yield), each as a colorless oil. 4-[rel-(1R)-1-(4-bromophenyl)ethyl]morpholine: 1H NMR (400 MHZ, Chloroform-d) δ 1.33 (3H, d), 2.28-2.44 (2H, m), 2.47-2.58 (2H, m), 3.29 (1H, q), 3.63-3.77 (4H, m), 7.18-7.27 (2H, m), 7.42-7.49 (2H, m). m/z: (ES+), [M+H]+=272.1 4-[rel-(1S)-1-(4-bromophenyl)ethyl]morpholine: 1H NMR (400 MHZ, Chloroform-d) δ 1.33 (3H, d), 2.29-2.43 (2H, m), 2.45-2.57 (2H, m), 3.29 (1H, q), 3.61-3.77 (4H, m), 7.20-7.25 (2H, m), 7.43-7.49 (2H, m). m/z: (ES+), [M+H]+=272.1

(c1)Methyl 5-(methylamino)-6-(3-methylimidazo[4,5-c]pyridin-7-yl)-3-[4-[rel-(1R)-1-morpholinoethyl]anilino]pyrazine-2-carboxylate Brettphos Pd G3 (58 mg, 0.060 mmol) was added to a suspension of methyl 3-amino-5-(methylamino)-6-(3-methylimidazo[4,5-c]pyridin-7-yl)pyrazine-2-carboxylate (100 mg, 0.32 mmol), 4-[rel-(1R)-1-(4-bromophenyl)ethyl]morpholine (103 mg, 0.380 mmol), and cesium carbonate (312 mg, 0.960 mmol) in 1,4-dioxane (5 mL) under nitrogen. The resulting mixture was stirred at 100° C. for 16 hours. The reaction was then concentrated. The resulting residue was purified by flash silica chromatography, using 0-10% MeOH-DCM as eluent, to afford methyl 5-(methylamino)-6-(3-methylimidazo[4,5-c]pyridin-7-yl)-3-[4-[rel-(1R)-1-morpholinoethyl]anilino]pyrazine-2-carboxylate (0.127 g, 79% yield) as a yellow solid. 1H NMR (300 MHz, DMSO-d6) δ 1.30 (3H, d), 2.22-2.47 (4H, m), 2.94 (3H, d), 3.33-3.42 (1H, m), 3.50-3.62 (4H, m), 3.84 (3H, s), 4.02 (3H, s), 7.29 (2H, d), 7.79 (2H, d), 7.97 (1H, br q), 8.50 (1H, s), 8.55 (1H, s), 9.05 (1H, s), 10.47 (1H, s). m/z: (ES+), [M+H]+=503.3

(d1) 5-(Methylamino)-6-(3-methylimidazo[4,5-c]pyridin-7-yl)-3-[4-[rel-(1R)-1-morpholinoethyl]anilino]pyrazine-2-carboxamide formate salt 7 N Methanolic ammonia (5.0 mL, 35 mmol) was added to methyl 5-(methylamino)-6-(3-methylimidazo[4,5-c]pyridin-7-yl)-3-[4-[rel-(1R)-1-morpholinoethyl]anilino]pyrazine-2-carboxylate (103 mg, 0.200 mmol). The resulting solution was stirred at 80 C for 20 hours. The reaction was then concentrated. The resulting residue was purified by preparative HPLC, using a 5 micron, 50 mm×100 mm, XSelect CSH Prep C18 OBD column, decreasingly polar mixtures of MeCN—$H_2O$ as eluent, and 0.1% formic acid as modifier, to afford 5-(methylamino)-6-(3-methylimidazo[4,5-c]pyridin-7-yl)-3-[4-[rel-(1R)-1-morpholinoethyl]anilino]pyrazine-2-carboxamide formate salt (18 mg, 17%) as a yellow solid; 1H NMR (400 MHZ, DMSO-d6) δ 1.29 (3H, d), 2.24-2.35 (2H, m), 2.34-2.44 (2H, m), 2.97 (3H, d), 3.34-3.37 (1H, m), 3.51-3.59 (4H, m), 4.01 (3H, s), 7.26 (2H, d), 7.37 (1H, s), 7.71-7.81 (3H, m), 8.01 (1H, br q), 8.14 (1H, s), 8.52 (1H, s), 8.73 (1H, s), 9.02 (1H, s), 11.53 (1H, s); m/z: (ES+), [M+H]+=488.4

(c2)Methyl 5-(methylamino)-6-(3-methylimidazo[4,5-c]pyridin-7-yl)-3-[4-[rel-(1S)-1-morpholinoethyl]anilino]pyrazine-2-carboxylate BrettPhos Pd G3 (58 mg, 0.060 mmol) was added to a suspension of methyl 3-amino-5-(methylamino)-6-(3-methylimidazo[4,5-c]pyridin-7-yl)pyrazine-2-carboxylate (100 mg, 0.32 mmol), 4-[rel-(1S)-1-(4-bromophenyl)ethyl]morpholine (103 mg, 0.380 mmol), and cesium carbonate (312 mg, 0.960 mmol) in 1,4-dioxane (5 mL) under nitrogen. The resulting mixture was stirred at 100° C. for 16 hours. The reaction was then concentrated. The resulting residue was purified by silica gel chromatography, using 0 to 15% MeOH-DCM, to afford methyl 5-(methylamino)-6-(3-methylimidazo[4,5-c]pyridin-7-yl)-3-[4-[rel-(1S)-1-morpholinoethyl]anilino]pyrazine-2-carboxylate (0.119 g, 74% yield) as a yellow solid. 1H NMR (300 MHz, DMSO-d6) δ 1.30 (3H, d), 2.20-2.49 (4H, m), 2.94 (3H, d), 3.33-3.41 (1H, m), 3.52-3.62 (4H, m), 3.84 (3H, s), 4.02 (3H, s), 7.29 (2H, d), 7.79 (2H, d), 7.97 (1H, br q), 8.50 (1H, s), 8.55 (1H, s), 9.05 (1H, s), 10.47 (1H, s). m/z: (ES+), [M+H]+=503.3

(d2) 5-(Methylamino)-6-(3-methylimidazo[4,5-c]pyridin-7-yl)-3-[4-[rel-(1S)-1-morpholinoethyl]anilino]pyrazine-2-carboxamide formate salt 7 N Methanolic ammonia (5.0 mL, 35 mmol) was added to methyl 5-(methylamino)-6-(3-methylimidazo[4,5-c]pyridin-7-yl)-3-[4-[rel-(1S)-1-morpholinoethyl]anilino]pyrazine-2-carboxylate (102 mg, 0.20 mmol). The resulting solution was stirred at 80° C. for 20 hours. The reaction was then concentrated. The resulting residue was purified by preparative HPLC, using a 5 micron, 50×100 mm XSelect CSH Prep C18 OBD column, decreasingly polar mixtures of MeCN—$H_2O$ as eluent, and 0.1% formic acid as modifier, to afford 5-(methylamino)-6-(3-methylimidazo[4,5-c]pyridin-7-yl)-3-[4-[rel-(1S)-1-morpholinoethyl]anilino]pyrazine-2-carboxamide (18 mg, 17%) formate salt as a yellow solid; 1H NMR (400 MHZ, DMSO-d6) δ 1.29 (3H, d), 2.25-2.33 (2H, m), 2.35-2.45 (2H, m), 2.97 (3H, d), 3.32 (1H, q), 3.50-3.60 (4H, m), 4.01 (3H, s), 7.19-7.30 (2H, m), 7.37 (1H, s), 7.66-7.83 (3H, m), 8.02 (1H, br q), 8.16 (1H, s), 8.52 (1H, s), 8.73 (1H, s), 9.02 (1H, s), 11.53 (1H, s); m/z: (ES+), [M+H]+=488.4

Example 133

5-(Methylamino)-6-(3-methylimidazo[4,5-c]pyridin-7-yl)-3-[4-[1-methyl-1-(4-methylpiperazin-1-yl)ethyl]anilino]pyrazine-2-carboxamide

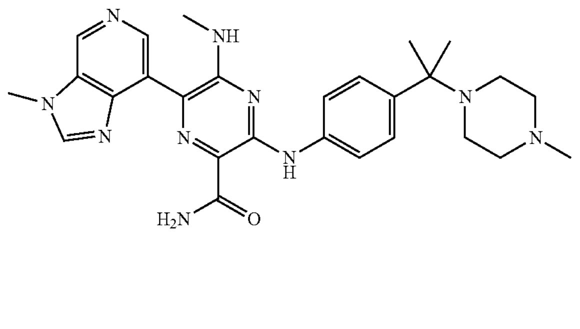

(a) 2-[[1-(4-Bromophenyl)-1-methyl-ethyl]-(2-hydroxyethyl)amino]ethanol

2-Bromoethanol (1.284 g, 10.28 mmol) was added to a solution of 2-(4-bromophenyl) propan-2-amine (1.100 g, 5.14 mmol) and DIPEA (4.50 mL, 25.7 mmol) in MeCN (40 mL). The resulting mixture was stirred at 120° C. for 16 hours. The reaction was then concentrated. The resulting residue was redissolved in DCM (200 mL) and washed twice with brine (200 mL each). The organic layer was dried over $Na_2SO_4$, filtered, and concentrated. The resulting residue was purified by silica gel chromatography, using 0-50% EtOAc-petroleum ether as eluent, to afford 2-[[1-(4-bromophenyl)-1-methyl-ethyl]-(2-hydroxyethyl)amino]ethanol (1.20 g, 77%) as a yellow solid; 1H NMR (400 MHZ, DMSO-d6) δ 1.27 (6H, s), 2.44 (4H, t), 3.31-3.36 (4H, m), 4.40 (2H, t), 7.47 (4H, s); m/z: (ES+), [M+2+H]+=303.9

(b) 1-[1-(4-Bromophenyl)-1-methyl-ethyl]-4-methyl-piperazine

Methanesulfonyl chloride (455 mg, 3.97 mmol) was added to a solution of 2-[[1-(4-bromophenyl)-1-methyl-ethyl]-(2-hydroxyethyl)amino]ethanol (600 mg, 1.99 mmol) and DIPEA (1.04 mL, 5.96 mmol) in DCM (10 mL) at 0° C. The resulting mixture was stirred at 0° C. for 1 hour. The reaction was then concentrated. The resulting residue was taken up in IPA (10 mL). tert-Butyl ammonium iodide (73 mg, 0.20 mmol) and 2M methanolic methanamine (10 mL, 20 mmol) were sequentially added. The resulting mixture was stirred at 90° C. for 16 hours. The reaction was then concentrated, redissolved in DCM (100 mL), and washed three times with brine (100 mL each). The organic layer was dried over $Na_2SO_4$, filtered, and concentrated. The resulting residue was purified by silica gel chromatography, using 0-50% EtOAc-petroleum ether as eluent, to afford 1-[1-(4-bromophenyl)-1-methyl-ethyl]-4-methyl-piperazine (0.700 g, quantitative) as a yellow oil; 1H NMR (400 MHZ, DMSO-d6) δ 1.27 (6H, s), 2.39 (3H, s), 2.45-2.50 (4H, m), 2.62-2.68 (4H, m), 7.40-7.47 (2H, m), 7.47-7.54 (2H, m); m/z: (ES+), [M+2+H]+=299.0

(c) Methyl 5-(methylamino)-6-(3-methylimidazo[4,5-c]pyridin-7-yl)-3-[4-[1-methyl-1-(4-methylpiperazin-1-yl)ethyl]anilino]pyrazine-2-carboxylate Cesium carbonate (312 mg, 0.960 mmol) was added to methyl 3-amino-5-(methylamino)-6-(3-methylimidazo[4,5-c]pyridin-7-yl)pyrazine-2-carboxylate (100 mg, 0.32 mmol), 1-[1-(4-bromophenyl)-1-methyl-ethyl]-4-methylpiperazine (95 mg, 0.32 mmol) and BrettPhos Pd G3 (43 mg, 0.050 mmol) in 1,4-dioxane (10 mL) under nitrogen. The resulting mixture was stirred at 100° C. for 16 hours. The reaction was then concentrated. The resulting residue was purified by silica gel chromatography, using 0-30% MeOH-DCM as eluent, to afford methyl 5-(methylamino)-6-(3-methylimidazo[4,5-c]pyridin-7-yl)-3-[4-[1-methyl-1-(4-methylpiperazin-1-yl)ethyl]anilino]pyrazine-2-carboxylate (0.050 g, 30% yield) as a yellow solid; 1H NMR (400 MHZ, DMSO-d6) δ 1.34 (6H, s), 2.31 (3H, s), 2.94 (3H, d), 3.83 (3H, s), 4.02 (3H, s), 7.49 (1H, s), 7.81 (2H, d), 7.96 (1H, d), 8.51 (1H, s), 8.54 (1H, s), 9.06 (1H, s), 9.93 (1H, s), 10.50 (1H, s). The piperazine CH protons were buried under solvent. m/z: (ES+), [M+H]+=430.2

(d) 5-(Methylamino)-6-(3-methylimidazo[4,5-c]pyridin-7-yl)-3-[4-[1-methyl-1-(4-methylpiperazin-1-yl)ethyl]anilino]pyrazine-2-carboxamide 7 N Methanolic ammonia (10 mL, 70 mmol) was added to methyl 5-(methylamino)-6-(3-methylimidazo[4,5-c]pyridin-7-yl)-3-[4-[1-methyl-1-(4-methylpiperazin-1-yl)ethyl] anilino]pyrazine-2-carboxylate (60 mg, 0.11 mmol). The resulting mixture was stirred at 80° C. for 2 days. The reaction was then concentrated. The resulting residue was purified by preparative HPLC using a 5 micron, 30×250 mm YMC-Actus Triart C18 column, 30-35% MeCN—$H_2O$ as eluent, and 0.1% ammonium bicarbonate as modifier to afford 5-(methylamino)-6-(3-methylimidazo[4,5-c]pyridin-7-yl)-3-[4-[1-methyl-1-(4-methylpiperazin-1-yl)ethyl]anilino]pyrazine-2-carboxamide (6.0 mg, 10%) as a yellow solid; 1H NMR (400 MHZ, DMSO-d6) δ 1.30 (6H, s), 2.14 (3H, s), 2.26-2.37 (4H, m), 2.34-2.48 (4H, m), 2.97 (3H, d), 4.02 (3H, s), 7.35 (1H, s), 7.43 (2H, d), 7.70-7.78 (2H, m), 7.75 (1H, s), 8.02 (1H, br q), 8.52 (1H, s), 8.73 (1H, s), 9.02 (1H, s), 11.51 (1H, s); m/z: (ES+), $[M-C_5H_{11}N_2]+$=415.2

Example 134

5-(Methylamino)-6-(3-methylimidazo[4,5-c]pyridin-7-yl)-3-[4-(1-methyl-1-morpholino-ethyl)anilino] pyrazine-2-carboxamide

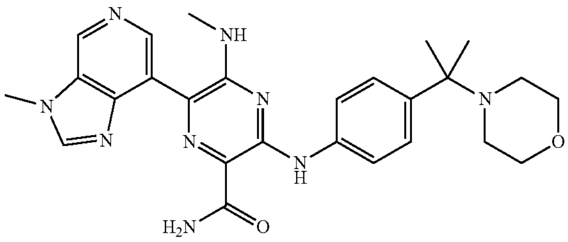 [SMILES: CNc1nc(Nc2ccc(C(C)(C)N3CCOCC3)cc2)c(C(N)=O)nc1-c1cncc2c1ncn2C]

Step 1. 4-[1-(4-Bromophenyl)-1-methyl-ethyl]morpholine

1-Bromo-2-(2-bromoethoxy) ethane (130 mg, 0.56 mmol) was added to a solution of 2-(4-bromophenyl) propan-2-amine (100 mg, 0.47 mmol), and DIPEA (250 mg, 1.93 mmol) in acetonitrile (20 mL). The resulting mixture was stirred at 120° C. for 16 hours. The reaction was then concentrated. The crude residue was purified by silica gel chromatography, using 0-80% EtOAc-petroleum ether as eluent, to afford 4-[1-(4-bromophenyl)-1-methyl-ethyl]morpholine (0.090 g, 68%) as a yellow liquid; 1H NMR (400 MHZ, $CDCl_3$) δ 1.33 (6H, s), 2.26-2.58 (4H, m), 3.65-3.71 (4H, m), 7.43 (4H, s); m/z: (ES+), [M+H]+=284.0

(b) Methyl 5-(methylamino)-6-(3-methylimidazo[4,5-c]pyridin-7-yl)-3-[4-(1-methyl-1-morpholino-ethyl)anilino]pyrazine-2-carboxylate BrettPhos Pd G3 (43 mg, 0.050 mmol) was added to a mixture of methyl 3-amino-5-(methylamino)-6-(3-methylimidazo[4,5-c]pyridin-7-yl)pyrazine-2-carboxylate (150 mg, 0.48 mmol), 4-[1-(4-bromophenyl)-1-methyl-ethyl] morpholine (204 mg, 0.720 mmol), and cesium carbonate (468 mg, 1.44 mmol) in 1,4-dioxane (20 mL) under nitrogen. The resulting mixture was stirred at 100° C. for 16 hours. The reaction was then concentrated. The resulting residue was purified by silica gel chromatography, using 0-20% MeOH-DCM as eluent, to afford methyl 5-(methylamino)-6-(3-methylimidazo[4,5-c]pyridin-7-yl)-3-[4-(1-methyl-1-morpholino-ethyl)anilino]pyrazine-2-carboxylate (0.110 g, 45%) as a yellow solid; 1H NMR (300 MHz, DMSO-d6) δ 1.32 (6H, s), 2.40 (4H, br s), 2.94 (3H, d), 3.57 (4H, br s), 3.84 (3H, s), 4.02 (3H, s), 7.49 (2H, d), 7.79 (2H, d), 7.94-8.03 (1H, m), 8.50 (1H, s), 8.55 (1H, s), 9.05 (1H, s), 10.47 (1H, s); m/z: (ES+), $[M-C_{4-8}NO]+$=430.3

(c) 5-(Methylamino)-6-(3-methylimidazo[4,5-c]pyridin-7-yl)-3-[4-(1-methyl-1-morpholino-ethyl)anilino]pyrazine-2-carboxamide 7 N Methanolic ammonia (2.0 mL, 14 mmol) was added to methyl 6-(3-methyl-3H-imidazo[4,5-c]pyridin-7-yl)-5-(methylamino)-3-((4-(2-morpholinopropan-2-yl)phenyl) amino) pyrazine-2-carboxylate (110 mg, 0.21 mmol). The resulting suspension was stirred at 100° C. for 16 hours. The reaction was then concentrated. The resulting residue was purified by C18 reverse phase chromatography, using 5-40% MeCN—$H_2O$ as eluent and 0.1% formic acid as modifier, to afford a yellow solid. This material was further purified by preparative SFC using a 5 micron, 20×250 mm DAICEL DCpak P4VP column, 0-40% MeOH-$sCO_2$ as eluent, and 0.5% ammonia as modifier, to afford 5-(methylamino)-6-(3-methylimidazo[4,5-c]pyridin-7-yl)-3-[4-(1-methyl-1-morpholino-ethyl)anilino]pyrazine-2-carboxamide (19 mg, 18%) as a yellow solid; 1H NMR (300 MHz, DMSO-d6) δ 1.31 (6H, s), 2.35-2.44 (4H, m), 2.97 (3H, d), 3.54-3.64 (4H, m), 4.02 (3H, s), 7.36 (1H, s), 7.43-7.50 (2H, m), 7.71-7.79 (3H, m), 8.01 (1H, br q), 8.52 (1H, s), 8.73 (1H, s), 9.03 (1H, s), 11.52 (1H, s); m/z: (ES+), $[M-C_4H_8NO]+$=415.2

Example 135

(R)-3-((4-((3-Fluoropyrrolidin-1-yl)methyl)phenyl) amino)-6-(3-methyl-3H-imidazo[4,5-c]pyridin-7-yl)-5-(methylamino) pyrazine-2-carboxamide formate salt

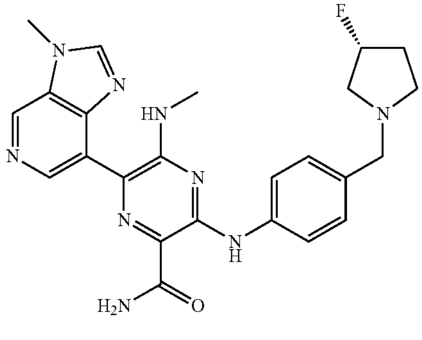 [SMILES: CNc1nc(Nc2ccc(CN3CC[C@@H](F)C3)cc2)c(C(N)=O)nc1-c1cncc2c1ncn2C]

A mixture of 3-(4-formylanilino)-5-(methylamino)-6-(3-methylimidazo[4,5-c]pyridin-7-yl)pyrazine-2-carboxamide (50 mg, 0.12 mmol), (R)-3-fluoropyrrolidine (33 mg, 0.37 mmol), and acetic acid (two drops) in DMF (1.5 mL) and MeOH (0.5 mL) was stirred at 65° C. for 1 hour. The reaction was then cooled to 0° C. Sodium triacetoxyborohydride (87 mg, 0.41 mmol) was added. The resulting mixture was stirred at 25° C. for 16 hours. The reaction was then filtered. The filtrate was purified by preparative HPLC, using a 5 micron, 30 mm×100 mm XSelect CSH C18 column, decreasingly polar mixtures of MeCN—$H_2O$ as eluent, and 0.1% formic acid as modifier, to afford 3-[4-

[[(3R)-3-fluoropyrrolidin-1-yl]methyl]anilino]-5-(methylamino)-6-(3-methylimidazo[4,5-c]pyridin-7-yl)pyrazine-2-carboxamide formate salt (4.0 mg, 6.2%) as a yellow solid; 1H NMR (500 MHz, DMSO-d6) δ 1.74-1.96 (1H, m), 2.07-2.22 (1H, m), 2.27-2.34 (1H, m), 2.56 (1H, br dd), 2.69-2.81 (2H, m), 2.95 (3H, d), 4.00 (3H, s), 5.10-5.27 (1H, m), 6.60 (2H, br s), 7.26 (2H, d), 7.35 (1H, br s), 7.68-7.80 (3H, m), 7.99 (1H, br q), 8.35 (1H, s), 8.51 (1H, s), 8.72 (1H, s), 9.01 (1H, s), 11.50 (1H, s); m/z: (ES+), [M+H]+=476.1

Example 136

3-[4-[[(3S)-3-Fluoropyrrolidin-1-yl]methyl]anilino]-5-(methylamino)-6-(3-methylimidazo[4,5-c]pyridin-7-yl)pyrazine-2-carboxamide formate salt

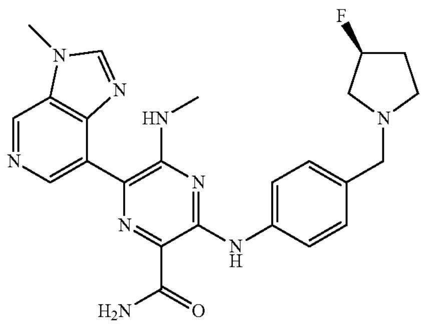 [SMILES: CNc1nc(Nc2ccc(CN3CC[C@H](F)C3)cc2)c(C(N)=O)nc1-c1cncc2c1ncn2C]

A mixture of 3-(4-formylanilino)-5-(methylamino)-6-(3-methylimidazo[4,5-c]pyridin-7-yl)pyrazine-2-carboxamide (50 mg, 0.12 mmol), (S)-3-fluoropyrrolidine (33 mg, 0.37 mmol) and acetic acid (two drops) in DMF (1.5 mL) and MeOH (0.5 mL) was stirred at 60° C. for 1 hour. The reaction was then cooled to 0° C. Sodium triacetoxyborohydride (79 mg, 0.37 mmol) was added. The resulting mixture was stirred at 25° C. for 16 hours. The reaction was then filtered. The filtrate was purified by preparative HPLC, using a 5 micron, 30 mm×100 mm XSelect CSH C18 column, decreasingly polar mixtures of MeCN—$H_2O$ as eluent, and 0.1% formic acid as modifier, to afford 3-[4-[[(3S)-3-fluoropyrrolidin-1-yl]methyl]anilino]-5-(methylamino)-6-(3-methylimidazo[4,5-c]pyridin-7-yl)pyrazine-2-carboxamide formate salt (3.5 mg, 5.4%) as a yellow solid; 1H NMR (500 MHz, DMSO-d6) δ 1.74-1.96 (1H, m), 2.07-2.22 (1H, m), 2.27-2.34 (1H, m), 2.56 (1H, br dd), 2.69-2.81 (2H, m), 2.95 (3H, d), 4.00 (3H, s), 5.10-5.27 (1H, m), 6.60 (2H, br s), 7.26 (2H, d), 7.35 (1H, br s), 7.68-7.80 (3H, m), 7.99 (1H, br q), 8.35 (1H, s), 8.51 (1H, s), 8.72 (1H, s), 9.01 (1H, s), 11.50 (1H, s); m/z: (ES+), [M+H]+=476.1

Example 137

3-[4-[(3,3-Difluoropyrrolidin-1-yl)methyl]anilino]-5-(methylamino)-6-(3-methylimidazo[4,5-c]pyridin-7-yl)pyrazine-2-carboxamide formate salt

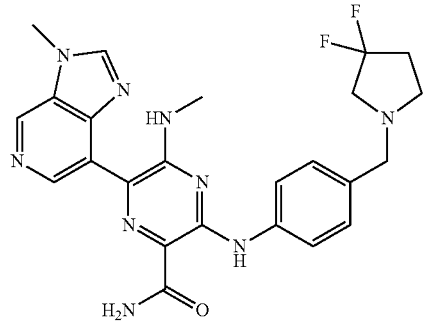 [SMILES: CNc1nc(Nc2ccc(CN3CCC(F)(F)C3)cc2)c(C(N)=O)nc1-c1cncc2c1ncn2C]

A mixture of 3-(4-formylanilino)-5-(methylamino)-6-(3-methylimidazo[4,5-c]pyridin-7-yl)pyrazine-2-carboxamide (50 mg, 0.12 mmol), 3,3-difluoropyrrolidine (40 mg, 0.37 mmol), and acetic acid (two drops) in DMF (1.5 mL) and methanol (0.500 mL) was stirred at 60° C. for 1 hour. The reaction was then cooled to 0° C. Sodium triacetoxyborohydride (79 mg, 0.37 mmol) was then added. The resulting mixture was stirred at 25 C for 16 hours. The reaction was then filtered. The filtrate was diluted with DMF (1.5 mL) and purified by preparative HPLC, using a 5 micron, 30 mm×100 mm, Xselect CSH OBD column, 5-15% MeCN—$H_2O$ as eluent, and 0.1% formic acid as modifier, to afford 3-[4-[(3,3-difluoropyrrolidin-1-yl)methyl]anilino]-5-(methylamino)-6-(3-methylimidazo[4,5-c]pyridin-7-yl)pyrazine-2-carboxamide formate salt (2.0 mg, 3.0%) as a yellow solid; 1H NMR (500 MHz, DMSO-d6) δ 2.18-2.33 (2H, m), 2.68 (2H, br t), 2.85 (2H, br t), 2.95 (3H, d), 3.57 (2H, s), 4.00 (3H, s), 7.26 (2H, d), 7.35 (1H, br s), 7.69-7.78 (3H, m), 7.98 (1H, br s), 8.49 (1H, s), 8.51 (1H, s), 8.72 (1H, s), 9.01 (1H, s), 11.52 (1H, s); m/z: (ES+), [M+H]+=494.3

Example 138

3-[4-[[(3S)-3,4-Dimethylpiperazin-1-yl]methyl]anilino]-5-(methylamino)-6-(3-methylimidazo[4,5-c]pyridin-7-yl)pyrazine-2-carboxamide tris-formate salt

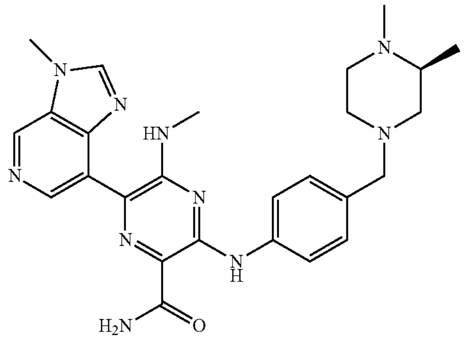 [SMILES: CNc1nc(Nc2ccc(CN3CCN(C)[C@@H](C)C3)cc2)c(C(N)=O)nc1-c1cncc2c1ncn2C]

(2S)-1,2-Dimethylpiperazine dihydrochloride (21 mg, 0.11 mmol) was added to a solution of 3-(4-formylanilino)-5-(methylamino)-6-(3-methylimidazo[4,5-c]pyridin-7-yl) pyrazine-2-carboxamide hydrochloride (50 mg, 0.11 mmol) and DIPEA (20 μL, 0.11 mmol) in DMF (1.5 mL), MeOH (0.5 mL) and THF (0.5 mL). A catalytic amount of AcOH was added to the reaction (4 drops). The resulting mixture was stirred at 60° C. for 1 h, then cooled to 0° C. Sodium triacetoxyborohydride (72 mg, 0.34 mmol) was added. The resulting mixture was stirred at room temperature for 16 h. The reaction was then concentrated and purified by MDAP, using a 5 micron, 30 mm×100 mm, Waters XSelect CSH C18 OBD Prep column, 5 to 25% MeCN-water as eluent, and 0.1% formic acid as modifier, to afford(S)-3-((4-((3,4-dimethylpiperazin-1-yl)methyl)phenyl)amino)-6-(3-methyl-3H-imidazo[4,5-c]pyridin-7-yl)-5-(methylamino) pyrazine-2-carboxamide tris-formate salt (6.0 mg, 9.6% yield) as a yellow solid. 1H NMR (500 MHz, DMSO-d6) 0.91 (3H, d), 1.74 (1H, br t), 1.93-2.03 (2H, m), 2.04-2.12 (5H, m), 2.13 (3H, s), 2.63-2.68 (1H, m), 2.95 (3H, d), 4.00 (3H, s), 7.24 (2H, d), 7.35 (1H, br s), 7.65-7.79 (3H, m), 7.99 (1H, br q), 8.31 (3H, s), 8.51 (1H, s), 8.72 (1H, s), 9.01 (1H, s), 11.50 (1H, s). m/z: (ES+), [M+H]+=501.3

Example 139

3-[4-[[(3R)-3,4-Dimethylpiperazin-1-yl]methyl]anilino]-5-(methylamino)-6-(3-methylimidazo[4,5-c]pyridin-7-yl)pyrazine-2-carboxamide formate salt

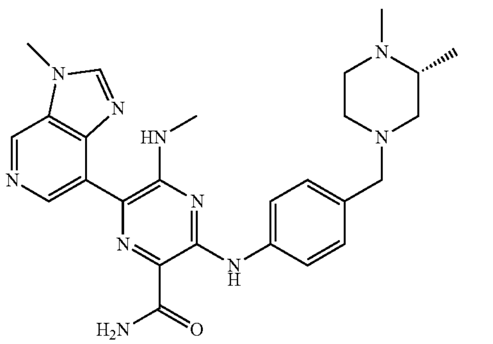 [SMILES: CNc1nc(Nc2ccc(CN3CCN(C)[C@H](C)C3)cc2)c(C(N)=O)nc1-c1cncc2c1ncn2C]

(2R)-1,2-Dimethylpiperazine (13 mg, 0.11 mmol) was added to a solution of 3-(4-formylanilino)-5-(methylamino)-6-(3-methylimidazo[4,5-c]pyridin-7-yl)pyrazine-2-carboxamide hydrochloride (50 mg, 0.11 mmol) and DIPEA (60 μL, 0.34 mmol) in DMF (1.0 mL), THF (0.5 mL), and MeOH (0.5 mL). A catalytic amount of AcOH was added (4 drops). The resulting mixture was stirred at 60° C. for 1 hour, then cooled to 0° C. Sodium triacetoxyborohydride (72 mg, 0.34 mmol) was added. The resulting mixture was stirred at room temperature for 3 days. The reaction was then filtered, concentrated, and purified by MDAP, using a 5 micron, 30 mm×100 mm, Waters XSelect CSH C18 OBD Prep column, 5 to 25% MeCN-water as eluent, and 0.1% formic acid as modifier, to afford 3-[4-[[(3R)-3,4-dimethylpiperazin-1-yl] methyl]anilino]-5-(methylamino)-6-(3-methylimidazo[4,5-c]pyridin-7-yl)pyrazine-2-carboxamide formate salt (4.0 mg, 6.4% yield) as a yellow solid. 1H NMR (500 MHz, DMSO-d6) 0.91 (3H, d), 1.69-1.79 (1H, m), 1.94-2.04 (2H, m), 2.05-2.11 (2H, m), 2.11-2.16 (4H, m), 2.94 (3H, d), 4.00 (3H, s), 6.52 (2H, br s), 7.24 (2H, d), 7.34 (1H, s), 7.74 (3H, s), 7.99 (1H, d), 8.22 (2H, s), 8.50 (1H, s), 8.72 (1H, s), 9.01 (1H, s), 11.51 (1H, s) m/z: (ES+), [M+H]+=501.3

Example 140

5-(Methylamino)-6-(3-methylimidazo[4,5-c]pyridin-7-yl)-3-[[6-(morpholinomethyl)-3-pyridyl]amino] pyrazine-2-carboxamide formate salt

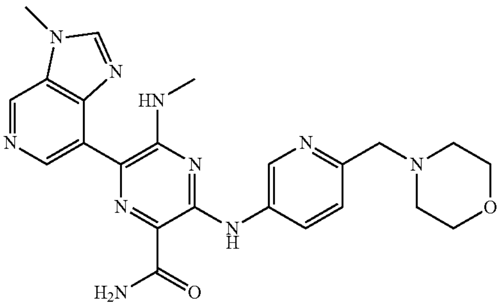 [SMILES: CNc1nc(Nc2ccc(CN3CCOCC3)nc2)c(C(N)=O)nc1-c1cncc2c1ncn2C]

(a) Methyl 5-(methylamino)-6-(3-methylimidazo[4,5-c]pyridin-7-yl)-3-[[6-(morpholinomethyl)-3-pyridyl]amino]pyrazine-2-carboxylate BrettPhos Pd G3 (100 mg, 0.32 mmol) was added to a suspension of methyl 3-amino-5-(methylamino)-6-(3-methylimidazo[4,5-c]pyridin-7-yl)pyrazine-2-carboxylate (100 mg, 0.32 mmol), 4-[(5-bromo-2-pyridyl)methyl]morpholine (164 mg, 0.640 mmol), and cesium carbonate (208 mg, 0.640 mmol) in 1,4-dioxane (10 mL) under nitrogen. The resulting mixture was stirred at 100° C. for 16 hours. The reaction was then concentrated. The resulting residue was purified by silica gel chromatography, using 0-20% MeOH-DCM as eluent, to afford methyl 5-(methylamino)-6-(3-methylimidazo[4,5-c]pyridin-7-yl)-3-[[6-(morpholinomethyl)-3-pyridyl]amino]pyrazine-2-carboxylate (0.060 g, 38% yield) as a yellow solid. 1H NMR (300 MHz, DMSO-d6) δ 2.41 (4H, t), 2.89 (3H, d), 3.55 (2H, s), 3.58 (4H, t), 3.82 (3H, s), 4.00 (3H, s), 7.41 (1H, d), 7.94 (1H, br q), 8.19-8.29 (1H, m), 8.48 (1H, s), 8.51 (1H, s), 8.89 (1H, d), 9.03 (1H, s), 10.40 (1H, s). m/z: (ES+), [M+H]+=490.2

(b) 5-(Methylamino)-6-(3-methylimidazo[4,5-c]pyridin-7-yl)-3-[[6-(morpholinomethyl)-3-pyridyl]amino]pyrazine-2-carboxylic acid Methyl 5-(methylamino)-6-(3-methylimidazo[4,5-c]pyridin-7-yl)-3-[[6-(morpholinomethyl)-3-pyridyl]amino]pyrazine-2-carboxylate (60 mg, 0.12 mmol) was added to a solution of sodium hydroxide (24.5 mg, 0.610 mmol) in water (5 mL) and MeOH (5 mL). The resulting mixture was stirred at 60° C. for 3 hours. The reaction was then concentrated. The resulting residue was purified by reverse phase chromatography, using 5 to 80% MeCN-water as eluent and 0.1% formic acid as modifier, to afford 5-(methylamino)-6-(3-methylimidazo[4,5-c]pyridin-7-yl)-3-[[6-(morpholinomethyl)-3-pyridyl]amino]pyrazine-2-carboxylic acid (0.060 g, quantitative) as a yellow solid. 1H NMR (300 MHZ, DMSO-d6) δ 2.40 (4H, s), 2.91 (3H, d), 3.52 (2H, s), 3.58 (4H, t), 3.99 (3H, s), 7.36 (1H, d), 8.11-8.31 (1H, m), 8.66

(1H, s), 8.85 (1H, s), 8.95 (1H, s), 13.52 (1H, s). The NH and COOH protons broadened into the baseline. m/z: (ES+), [M+H]+=476.2

(c) 5-(Methylamino)-6-(3-methylimidazo[4,5-c] pyridin-7-yl)-3-[[6-(morpholinomethyl)-3-pyridyl] amino]pyrazine-2-carboxamide formate salt 5-(Methylamino)-6-(3-methylimidazo[4,5-c]pyridin-7-yl)-3-[[6-(morpholinomethyl)-3-pyridyl]amino]pyrazine-2-carboxylic acid (55 mg, 0.12 mmol) was added to a mixture of HATU (88 mg, 0.23 mmol), DIPEA (100 μL, 0.58 mmol), ammonium chloride (19 mg, 0.35 mmol), DMF (20 mL). The resulting mixture was stirred at 20° C. for 2 days. The reaction was then concentrated. The resulting residue was purified by reverse phase HPLC, using a 5 micron, 19 mm×250 mm XSelect CSH Prep C18 OBD column, 2-10% MeCN-water as eluent, and 0.1% formic acid as modifier, to afford 5-(methylamino)-6-(3-methylimidazo[4,5-c]pyridin-7-yl)-3-[[6-(morpholinomethyl)-3-pyridyl]amino]pyrazine-2-carboxamide formate salt (3.4 mg, 5.8% yield) as a yellow solid. 1H NMR (300 MHz, DMSO-d6) δ 2.32-2.46 (4H, m), 2.93 (3H, d), 3.53 (2H, s), 3.56-3.60 (4H, m), 4.00 (3H, s), 7.35-7.44 (2H, m), 7.74-7.81 (1H, m), 7.98 (1H, br q), 8.17-8.26 (1H, m), 8.28 (1H, s), 8.51 (1H, s), 8.71 (1H, s), 8.88 (1H, d), 9.02 (1H, s), 11.55 (1H, s). m/z: (ES+), [M+H]+=475.3

Example 141

3-[2-Fluoro-4-[(4-methylpiperazin-1-yl)methyl]anilino]-5-(methylamino)-6-(3-methylimidazo[4,5-c] pyridin-7-yl)pyrazine-2-carboxamide

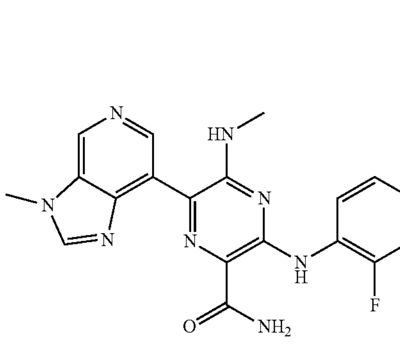

(a) 1-[(4-Bromo-3-fluoro-phenyl)methyl]-4-methyl-piperazine

Sodium triacetoxyborohydride (10.44 g, 49.26 mmol) was added to a solution of 4-bromo-3-fluoro-benzaldehyde (2.00 g, 9.85 mmol) and 1-methylpiperazine (0.987 g, 9.85 mmol) in DCE (40 mL). The resulting mixture was stirred at 25 C for 5 hours. The reaction was then concentrated. The resulting residue was redissolved in DCM (200 mL) and washed three times with saturated aqueous sodium bicarbonate (200 mL each). The organic layer was dried over $Na_2SO_4$, filtered, and concentrated to afford 1-[(4-bromo-3-fluoro-phenyl)methyl]-4-methyl-piperazine (1.00 g, 35% yield); 1H NMR (400 MHZ, DMSO-d6) δ 2.14 (3H, s), 2.17-2.52 (8H, m), 3.44 (2H, s), 7.10 (1H, dd), 7.27 (1H, dd), 7.63 (1H, dd); m/z: (ES+), [M+H]+=287.2

(b) Methyl 3-[2-fluoro-4-[(4-methylpiperazin-1-yl) methyl]anilino]-5-(methylamino)-6-(3-methylimidazo[4,5-c]pyridin-7-yl)pyrazine-2-carboxylate 1-[(4-Bromo-3-fluoro-phenyl)methyl]-4-methyl-piperazine (220 mg, 0.77 mmol) was added to a suspension of methyl 3-amino-5-(methylamino)-6-(3-methylimidazo[4,5-c]pyridin-7-yl)pyrazine-2-carboxylate (200 mg, 0.64 mmol), cesium carbonate (624 mg, 1.91 mmol), and BrettPhos Pd G3 (87 mg, 0.10 mmol) in 1,4-dioxane (20 mL) under nitrogen. The resulting mixture was stirred at 100° C. for 16 hours. The reaction was then concentrated. The resulting residue was purified by silica gel chromatography, using 0 to 30% MeOH-DCM as eluent, to afford methyl 3-[2-fluoro-4-[(4-methylpiperazin-1-yl)methyl]anilino]-5-(methylamino)-6-(3-methylimidazo[4,5-c]pyridin-7-yl) pyrazine-2-carboxylate (0.100 g, 30% yield) as a yellow solid. m/z: (ES+), [M+H]+=505.5

(c) 3-[2-Fluoro-4-[(4-methylpiperazin-1-yl)methyl] anilino]-5-(methylamino)-6-(3-methylimidazo[4,5-c] pyridin-7-yl)pyrazine-2-carboxamide 7 N Methanolic ammonia (10 mL, 70 mmol) was added to methyl 3-[2-fluoro-4-[(4-methylpiperazin-1-yl)methyl] anilino]-5-(methylamino)-6-(3-methylimidazo[4,5-c]pyridin-7-yl)pyrazine-2-carboxylate (130 mg, 0.25 mmol). The resulting mixture was stirred at 80° C. for 24 hours. The reaction was then concentrated. The resulting residue was purified by preparative HPLC Column using a 5 micron, 30×150 mm XBridge Prep OBD C18 column, 14-44% MeCN—$H_2O$ as eluent, and 0.1% ammonium bicarbonate as modifier, to afford 3-[2-fluoro-4-[(4-methylpiperazin-1-yl)methyl]anilino]-5-(methylamino)-6-(3-methylimidazo[4,5-c]pyridin-7-yl)pyrazine-2-carboxamide (55 mg, 44%) as a yellow solid; 1H NMR (400 MHZ, DMSO-d6) δ 2.15 (3H, s), 2.29-2.40 (8H, m), 2.96 (3H, d), 3.43 (2H, s), 4.02 (3H, s), 7.11 (1H, d), 7.19 (1H, d), 7.39 (1H, s), 7.77 (1H, s), 8.02 (1H, br q), 8.52 (1H, s), 8.67 (1H, t), 8.74 (1H, s), 9.03 (1H, s), 11.70 (1H, d); m/z: (ES+), [M+H]+=505.5

Example 142

3-[3-Chloro-4-[(4-methylpiperazin-1-yl)methyl]anilino]-5-(methylamino)-6-(3-methylimidazo[4,5-c] pyridin-7-yl)pyrazine-2-carboxamide formate salt

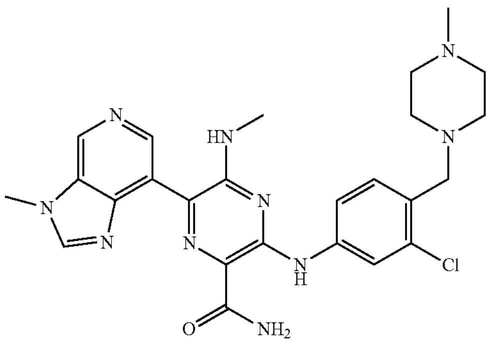 [SMILES: CNc1nc(Nc2ccc(CN3CCN(C)CC3)c(Cl)c2)c(C(N)=O)nc1-c1cncc2c1ncn2C]

(a) 1-[(4-Bromo-2-chloro-phenyl)methyl]-4-methyl-piperazine

Sodium triacetoxyborohydride (9.66 g, 45.6 mmol) was added to a solution of 4-bromo-2-chloro-benzaldehyde (2.00 g, 9.11 mmol) and 1-methylpiperazine (0.913 g, 9.11 mmol) in DCE (40 mL). The resulting mixture was stirred at 25 C for 5 hours. The reaction was then concentrated. The resulting residue was redissolved in DCM (200 mL), then washed three times with saturated aqueous sodium bicarbonate three times (200 mL each) and once with brine (200 mL). The organic layer was dried over $Na_2SO_4$, filtered, and concentrated to afford 1-[(4-bromo-2-chloro-phenyl)methyl]-4-methyl-piperazine (1.20 g, 43% yield) as an off-white solid; 1H NMR (400 MHZ, DMSO-d6) δ 2.15 (3H, s), 2.30-2.34 (4H, m), 2.39-2.43 (4H, m), 3.50 (2H, s), 7.41 (1H, d), 7.53 (1H, dd), 7.68 (1H, d); m/z: (ES+), [M+2+H]+=305.1

(b) Methyl 3-[3-chloro-4-[(4-methylpiperazin-1-yl)methyl]anilino]-5-(methylamino)-6-(3-methylimidazo[4,5-c]pyridin-7-yl)pyrazine-2-carboxylate 1-[(4-Bromo-2-chloro-phenyl)methyl]-4-methyl-piperazine (242 mg, 0.800 mmol) was added to a suspension of methyl 3-amino-5-(methylamino)-6-(3-methylimidazo[4,5-c]pyridin-7-yl)pyrazine-2-carboxylate (250 mg, 0.80 mmol), cesium carbonate (780 mg, 2.39 mmol), and BrettPhos Pd G3 (108 mg, 0.120 mmol) in 1,4-dioxane (20 mL) under nitrogen. The resulting mixture was stirred at 100° C. for 16 hours. The reaction was then concentrated. The resulting residue was purified by silica gel chromatography, using 0-30% MeOH-DCM as eluent, to afford methyl 3-[3-chloro-4-[(4-methylpiperazin-1-yl)methyl]anilino]-5-(methylamino)-6-(3-methylimidazo[4,5-c]pyridin-7-yl)pyrazine-2-carboxylate (0.130 g, 30%) as a yellow solid; 1H NMR (400 MHZ, DMSO-d6) δ 2.35-2.45 (4H, m), 2.74-2.84 (4H, m), 2.93 (3H, d), 3.65 (3H, s), 3.84 (3H, s), 4.06 (3H, s), 7.44 (1H, d), 7.57 (1H, dd), 7.86 (1H, s), 8.13 (1H, s), 8.34 (1H, d), 8.69 (1H, s), 9.27 (1H, s), 10.55 (1H, s). m/z: (ES+), [M+H]+=536.2

(c) 3-[3-Chloro-4-[(4-methylpiperazin-1-yl)methyl]anilino]-5-(methylamino)-6-(3-methylimidazo[4,5-c]pyridin-7-yl)pyrazine-2-carboxamide formate salt 7 N Methanolic ammonia (10 mL, 70 mmol) was added to methyl 3-[3-chloro-4-[(4-methylpiperazin-1-yl)methyl]anilino]-5-(methylamino)-6-(3-methylimidazo[4,5-c]pyridin-7-yl)pyrazine-2-carboxylate (120 mg, 0.22 mmol). The resulting mixture was stirred at 80° C. for 1 day. The reaction was then concentrated. The resulting residue was purified by preparative HPLC using a 5 micron, 50×100 mm XBridge Prep C18 OBD column, decreasingly polar mixtures of MeCN—$H_2O$ as eluent, and 0.5% formic acid as modifier to afford 3-[3-chloro-4-[(4-methylpiperazin-1-yl)methyl]anilino]-5-(methylamino)-6-(3-methylimidazo[4,5-c]pyridin-7-yl)pyrazine-2-carboxamide formate salt (35 mg, 28%) as a yellow solid; 1H NMR (400 MHZ, DMSO-d6) δ 2.41 (3H, s), 2.98 (3H, d), 3.56 (2H, s), 4.02 (3H, s), 7.40 (1H, d), 7.45 (2H, m), 7.82 (1H, s), 8.07 (1H, br q), 8.14 (1H, s), 8.34 (1H, d), 8.53 (1H, s), 8.73 (1H, s), 9.04 (1H, s), 11.68 (1H, s). The piperazine CH protons were buried under solvent. m/z: (ES+), [M+H]+=521.4

Example 143

3-[2-Fluoro-4-(morpholinomethyl)anilino]-5-(methylamino)-6-(3-methylimidazo[4,5-c]pyridin-7-yl)pyrazine-2-carboxamide formate salt

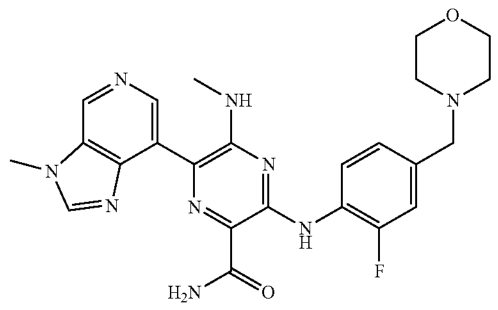 [SMILES: CNc1nc(Nc2ccc(CN3CCOCC3)cc2F)c(C(N)=O)nc1-c1cncc2c1ncn2C]

(a) Methyl 3-[2-fluoro-4-(morpholinomethyl)anilino]-5-(methylamino)-6-(3-methylimidazo[4,5-c]pyridin-7-yl)pyrazine-2-carboxylate BrettPhos Pd G3 (58 mg, 0.060 mmol) was added to a suspension of methyl 3-amino-5-(methylamino)-6-(3-methylimidazo[4,5-c]pyridin-7-yl)pyrazine-2-carboxylate (200 mg, 0.64 mmol), 4-(4-bromo-3-fluorobenzyl) morpholine (175 mg, 0.640 mmol), and cesium carbonate (624 mg, 1.91 mmol) in 1,4-dioxane (20 mL) under nitrogen. The resulting mixture was stirred at 100° C. for 16 hours. The reaction was then concentrated. The resulting residue was purified by silica gel chromatography, using 0-10% MeOH-DCM as eluent, to afford methyl 3-[2-fluoro-4-(morpholinomethyl)anilino]-5-(methylamino)-6-(3-methylimidazo[4,5-c]pyridin-7-yl)pyrazine-2-carboxylate (0.140 g, 43%) as a brown solid; 1H NMR (400 MHZ, DMSO-d6) δ 2.37 (4H, d), 2.91 (3H, d), 3.45 (2H, s), 3.57 (4H, d), 3.83 (3H, s), 4.01 (3H, s), 7.15 (1H, d), 7.25 (1H, dd), 8.41-8.49 (2H, m), 8.52 (1H, s), 8.62 (1H, t), 9.04 (1H, s), 10.66 (1H, s). m/z: (ES+), [M+H]+=507.

(b) 3-[2-Fluoro-4-(morpholinomethyl)anilino]-5-(methylamino)-6-(3-methylimidazo[4,5-c]pyridin-7-yl)pyrazine-2-carboxamide formate salt 7 N Methanolic ammonia (2.0 mL, 14 mmol) was added to methyl 3-[2-fluoro-4-(morpholinomethyl)anilino]-5-(methylamino)-6-(3-methylimidazo[4,5-c]pyridin-7-yl)pyrazine-2-carboxylate (135 mg, 0.270 mmol). The resulting mixture was stirred at 80° C. for 16 hours. The reaction was then concentrated. The resulting residue was purified by preparative HPLC, using a 5 micron, 30 mm×150 mm, Sunfire prep C18 column, decreasingly polar mixtures of MeCN—$H_2O$ as eluent, and 0.1% formic acid as modifier, to afford 3-[2-fluoro-4-(morpholinomethyl)anilino]-5-(methylamino)-6-(3-methylimidazo[4,5-c]pyridin-7-yl)pyrazine-2-carboxamide formate salt (0.060 g, 43%) as a yellow solid. 1H NMR (400 MHz, DMSO-d6) δ 2.39 (4H, t), 2.92 (3H, d), 3.47 (2H, s), 3.57 (4H, d), 3.98 (3H, s), 7.13 (1H, dd), 7.19-7.29 (2H, m), 7.73-7.83 (2H, m), 8.14 (1H, s), 8.45 (1H, s), 8.61-8.68 (2H, m), 8.99 (1H, s), 11.60 (1H, d); m/z: (ES+), [M+H]+=492.3

Example 144

3-[2,3-Difluoro-4-(morpholinomethyl)anilino]-5-(methylamino)-6-(3-methylimidazo[4,5-c]pyridin-7-yl)pyrazine-2-carboxamide

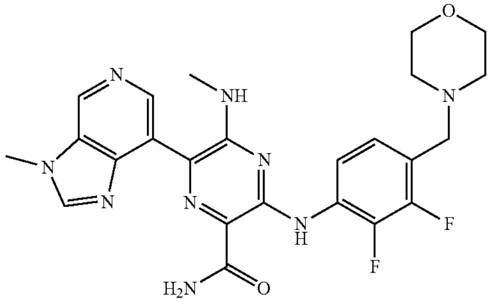 [SMILES: CNc1nc(Nc2ccc(CN3CCOCC3)c(F)c2F)c(C(N)=O)nc1-c1cncc2c1ncn2C]

(a) 4-[(4-Bromo-2,3-difluoro-phenyl)methyl]morpholine

Sodium triacetoxyborohydride (7.19 g, 33.9 mmol) was added to a solution of 4-bromo-2,3-difluoro-benzaldehyde (1.50 g, 6.79 mmol) and morpholine (0.59 g, 6.8 mmol) in 1,2-dichloroethane (10 mL). The resulting mixture was stirred at room temperature for 5 hours. The reaction was then concentrated. The resulting residue was dissolved in dichloromethane (200 mL) and washed three times with saturated aqueous sodium bicarbonate (200 mL each). The organic layer was dried over sodium sulfate, filtered, and concentrated to afford 4-[(4-bromo-2,3-difluoro-phenyl)methyl]morpholine (1.7 g, 86%). 1H NMR (300 MHz, DMSO-d6) δ 2.26-2.41 (4H, m), 3.37-3.68 (6H, m), 7.09-7.27 (1H, m), 7.39-7.54 (1H, m). m/z: (ES+), [M+H]+=292.1

(b) 3-((2,3-Difluoro-4-(morpholinomethyl)phenyl)amino)-6-(3-methyl-3H-imidazo[4,5-c]pyridin-7-yl)-5-(methylamino) pyrazine-2-carboxylic acid BrettPhos Pd G3 (28.9 mg, 0.03 mmol) was added to a suspension of methyl 3-amino-6-(3-methyl-3H-imidazo[4,5-c]pyridin-7-yl)-5-(methylamino) pyrazine-2-carboxylate (100 mg, 0.32 mmol), 4-[(4-bromo-2,3-difluoro-phenyl)methyl]morpholine (112 mg, 0.38 mmol), and cesium carbonate (310 mg, 0.96 mmol) in 1,4-dioxane (10 mL) under nitrogen. The resulting mixture was stirred at 100° C. for 3 hours. The reaction was then concentrated. The resulting residue was purified by silica gel chromatography, using 0-10% MeOH-DCM as eluent, to afford 3-((2,3-difluoro-4-(morpholinomethyl)phenyl)amino)-6-(3-methyl-3H-imidazo[4,5-c]pyridin-7-yl)-5-(methylamino) pyrazine-2-carboxylic acid (0.100 g, 61%) as a yellow solid. 1H NMR (400 MHZ, DMSO-d6) δ 2.41 (4H, d), 2.93 (3H, d), 3.50-3.62 (6H, m), 4.02 (3H, s), 7.20 (1H, t), 7.93 (1H, br q), 8.16 (1H, s), 8.51 (2H, d), 8.61 (1H, s), 9.04 (1H, s) 11.50 (1H, br s). m/z: (ES+), [M+H]+=511.2

(c) 3-[2,3-Difluoro-4-(morpholinomethyl)anilino]-5-(methylamino)-6-(3-methylimidazo[4,5-c]pyridin-7-yl)pyrazine-2-carboxamide HATU (89 mg, 0.24 mmol) was added to a solution of 3-((2,3-difluoro-4-(morpholinomethyl)phenyl)amino)-6-(3-methyl-3H-imidazo[4,5-c]pyridin-7-yl)-5-(methylamino) pyrazine-2-carboxylic acid (100 mg, 0.20 mmol) in DMF (10 mL). The resulting mixture was stirred at room temperature for 10 minutes. Ammonium chloride (31 mg, 0.59 mmol) and DIPEA (41 μL, 0.24 mmol) were added. The resulting mixture was stirred at room temperature for 16 hours. The reaction was then concentrated. The resulting residue was purified by preparative HPLC, using a 5 micron, 30 mm×150 mm, Sunfire prep C18 column, decreasingly polar mixtures of MeCN—$H_2O$ as eluent, and 0.1% formic acid as modifier, to afford 3-[2,3-difluoro-4-(morpholinomethyl)anilino]-5-(methylamino)-6-(3-methylimidazo[4,5-c]pyridin-7-yl)pyrazine-2-carboxamide (0.016 g, 16%) as a yellow solid. 1H NMR (DMSO-d6, 400 MHz) δ 2.40 (4H, s), 2.96 (3H, d), 3.53 (2H, s), 3.57 (4H, t), 4.02 (3H, s), 7.19 (1H, t), 7.47 (1H, s), 7.83 (1H, s), 8.03 (1H, br q), 8.53 (2H, s), 8.74 (1H, s), 9.05 (1H, s), 11.90 (1H, d). 19F NMR (DMSO-d6, 376 MHz) δ −155.40 (d), −143.25 (d). m/z: (ES+), [M+H]+=510.3

Example 145

3-[2-Fluoro-4-[[(1S,4S)-2-oxa-5-azabicyclo[2.2.1]heptan-5-yl]methyl]anilino]-5-(methylamino)-6-(3-methylimidazo[4,5-c]pyridin-7-yl)pyrazine-2-carboxamide

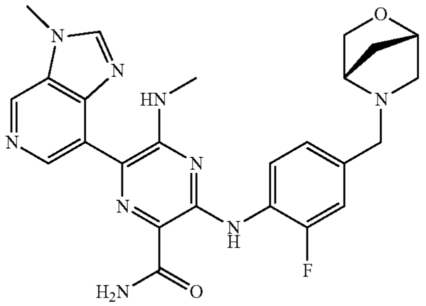 [SMILES: CNc1nc(Nc2ccc(CN3C[C@@H]4C[C@H]3CO4)cc2F)c(C(N)=O)nc1-c1cncc2c1ncn2C]

(a) (1S,4S)-5-[(4-Bromo-3-fluoro-phenyl)methyl]-2-oxa-5-azabicyclo[2.2.1]heptane (1S,4S)-2-Oxa-5-azabicyclo[2.2.1]heptane (1.50 g, 15.1 mmol) was added to a mixture of 4-bromo-3-fluoro-benzaldehyde (2.56 g, 12.6 mmol) and sodium triacetoxyborohydride (5.34 g, 25.2 mmol) in 1,2-dichloroethane (20 mL). The resulting mixture was stirred at 25° C. for 12 hours. The reaction mixture was then concentrated, diluted with dichloromethane (50 mL), and washed sequentially with saturated aqueous sodium bicarbonate and brine. The organic layer was dried over sodium sulfate, filtered, and concentrated to afford (1S,4S)-5-[(4-bromo-3-fluoro-phenyl)methyl]-2-oxa-5-azabicyclo[2.2.1]heptane (2.00 g, 55% yield) as a yellow liquid. 1H NMR (300 MHz, DMSO-d6) δ 1.55-1.86 (2H, m), 2.35-2.45 (1H, m), 2.68-2.76 (1H, m), 3.49-3.57 (1H, m), 3.64-3.78 (2H, m), 3.87-3.93 (2H, m), 4.33-4.38 (1H, m), 7.12-7.18 (1H, m), 7.29-7.35 (1H, m), 7.59-7.66 (1H, m). m/z: (ES+), [M+H]+=285.9

(b) Methyl 3-[2-fluoro-4-[[(1S,4S)-2-oxa-5-azabicyclo[2.2.1]heptan-5-yl]methyl]anilino]-5-(methylamino)-6-(3-methylimidazo[4,5-c]pyridin-7-yl)pyrazine-2-carboxylate BrettPhos Pd G3 (158 mg, 0.170 mmol) was added to a suspension of (1R,4R)-5-[(4-bromo-3-fluoro-phenyl)

methyl]-2-oxa-5-azabicyclo[2.2.1]heptane (500 mg, 1.75 mmol), methyl 3-amino-5-(methylamino)-6-(3-methylimidazo[4,5-c]pyridin-7-yl)pyrazine-2-carboxylate (547 mg, 1.75 mmol), and cesium carbonate (1.71 g, 5.24 mmol) in 1,4-dioxane (30 mL) under nitrogen. The resulting mixture was stirred at 100° C. for 12 hours. The reaction was then concentrated. The resulting residue was purified by silica gel chromatography, using 0-25% MeOH-DCM as eluent, to afford methyl 3-[2-fluoro-4-[[(1S,4S)-2-oxa-5-azabicyclo[2.2.1]heptan-5-yl]methyl]anilino]-5-(methylamino)-6-(3-methylimidazo[4,5-c]pyridin-7-yl)pyrazine-2-carboxylate (0.410 g, 45% yield) as a yellow solid. 1H NMR (300 MHz, DMSO-d6) δ 1.56-1.64 (1H, m), 1.79-1.83 (1H, m), 2.39-2.44 (1H, m), 2.71-2.79 (1H, m), 2.91 (3H, d), 3.47 (1H, s), 3.51-3.56 (1H, m), 3.69-3.72 (2H, m), 3.84 (3H, s), 3.93 (1H, d), 4.02 (3H, s), 4.31-4.39 (1H, m), 7.16-7.21 (1H, m), 7.24-7.29 (1H, m), 7.99 (1H, br q), 8.50 (1H, s), 8.54 (1H, s), 8.57-8.65 (1H, m), 9.05 (1H, s), 10.65 (1H, d). m/z: (ES+), [M+H]+=519.2

(c) 3-[2-Fluoro-4-[[(1S,4S)-2-oxa-5-azabicyclo[2 2.1]heptan-5-yl]methyl]anilino]-5-(methylamino)-6-(3-methylimidazo[4,5-c]pyridin-7-yl)pyrazine-2-carboxamide 7 N Methanolic ammonia (40 mL, 280 mmol) was added to methyl 3-[2-fluoro-4-[[(1R,4R)-2-oxa-5-azabicyclo[2.2.1]heptan-5-yl]methyl]anilino]-5-(methylamino)-6-(3-methylimidazo[4,5-c]pyridin-7-yl)pyrazine-2-carboxylate (400 mg, 0.77 mmol). The resulting mixture was stirred at 80° C. for 16 hours. The reaction was then concentrated. The resulting residue was purified by silica gel chromatography, using 0-10% MeOH-DCM as eluent, to afford 3-[2-fluoro-4-[[(1S,4S)-2-oxa-5-azabicyclo[2.2.1]heptan-5-yl]methyl]anilino]-5-(methylamino)-6-(3-methylimidazo[4,5-c]pyridin-7-yl)pyrazine-2-carboxamide (0.110 g, 28% yield) as a yellow solid. 1H NMR (400 MHZ, DMSO-d6) δ 1.56-1.63 (1H, m), 1.77-1.85 (1H, m), 2.39-2.45 (1H, m), 2.71-2.79 (1H, m), 2.95 (3H, d), 3.46 (1H, s), 3.50-3.56 (1H, m), 3.63-3.76 (2H, m), 3.90-3.95 (1H, m), 4.02 (3H, s), 4.33-4.38 (1H, m), 7.12-7.19 (1H, m), 7.20-7.28 (1H, m), 7.39 (1H, s), 7.77 (1H, s), 8.02 (1H, br q), 8.52 (1H, s), 8.62-8.70 (1H, m), 8.73 (1H, s), 9.03 (1H, s), 11.66-11.71 (1H, m). 19F NMR (376 MHZ, DMSO) δ −130.18. m/z: (ES+), [M+H]+=504.3. $[\alpha]^{25}_{D}$=+40.75°

Example 146

3-[2-Fluoro-4-[[(1R,4R)-2-oxa-5-azabicyclo[2.2.1]heptan-5-yl]methyl]anilino]-5-(methylamino)-6-(3-methylimidazo[4,5-c]pyridin-7-yl)pyrazine-2-carboxamide

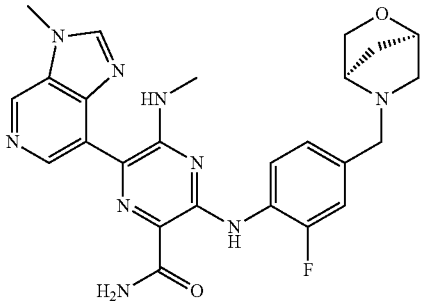 [SMILES: CNc1nc(Nc2ccc(CN3C[C@H]4C[C@@H]3CO4)cc2F)c(C(N)=O)nc1-c1cncc2c1ncn2C]

(a) (1R,4R)-5-[(4-Bromo-3-fluoro-phenyl)methyl]-2-oxa-5-azabicyclo[2.2.1]heptane DIPEA (0.175 mL, 1.00 mmol) was added to a suspension of 1-bromo-4-(bromomethyl)-2-fluoro-benzene (0.268 g, 1.00 mmol), (1R,4R)-2-oxa-5-azabicyclo[2.2.1]heptane hydrochloride (0.203 g, 1.50 mmol), and potassium carbonate (0.691 g, 5.00 mmol) in MeCN (4 mL). The resulting mixture was stirred at room temperature for 16 hours. The reaction was then diluted with saturated aqueous ammonium chloride and DCM. The layers were separated and the organic layer was washed sequentially with water and brine, then dried over sodium sulfate, filtered, and concentrated to afford (1R,4R)-5-[(4-bromo-3-fluoro-phenyl)methyl]-2-oxa-5-azabicyclo[2.2.1]heptane (0.285 g, quantitative) as a colorless oil. 1H NMR (500 MHZ, DMSO-d6) 1.58 (1H, br d), 1.79 (1H, dd), 2.39 (1H, d), 2.71 (1H, dd), 3.43 (1H, s), 3.51 (1H, dd), 3.63-3.77 (2H, m), 3.89 (1H, d), 4.33 (1H, s), 7.13 (1H, dd), 7.30 (1H, dd), 7.61 (1H, t). m/z: (ES+), [M+2+H]+=288.9

(b) Methyl 3-[2-fluoro-4-[[(1R,4R)-2-oxa-5-azabicyclo[2.2.1]heptan-5-yl]methyl]anilino]-5-(methylamino)-6-(3-methylimidazo[4,5-c]pyridin-7-yl)pyrazine-2-carboxylate BrettPhos Pd G4 (73 mg, 0.080 mmol) was added to a mixture of methyl 3-amino-5-(methylamino)-6-(3-methylimidazo[4,5-c]pyridin-7-yl)pyrazine-2-carboxylate (250 mg, 0.80 mmol), (1R,4R)-5-[(4-bromo-3-fluoro-phenyl)methyl]-2-oxa-5-azabicyclo[2.2.1]heptane (285 mg, 1.00 mmol), and cesium carbonate (780 mg, 2.39 mmol) in 1,4-dioxane (8 mL). The resulting mixture was sparged with argon for 20 minutes, then stirred at 96° C. for 2 hours under argon. The reaction was then concentrated. The resulting residue was purified by silica gel chromatography, using 0 to 10% MeOH-DCM as eluent, and 1% methanolic ammonia as modifier, to afford methyl 3-[2-fluoro-4-[[(1R,4R)-2-oxa-5-azabicyclo[2.2.1]heptan-5-yl]methyl]anilino]-5-(methylamino)-6-(3-methylimidazo[4,5-c]pyridin-7-yl)pyrazine-2-carboxylate (0.245 g, 59% yield) as an orange foam. m/z: (ES+), [M+H]+=519.3

(c) 3-[2-Fluoro-4-[[(1R,4R)-2-oxa-5-azabicyclo[2.2.1]heptan-5-yl]methyl]anilino]-5-(methylamino)-6-(3-methylimidazo[4,5-c]pyridin-7-yl)pyrazine-2-carboxamide 7 N Methanolic ammonia (8.0 mL, 56 mmol) was added to methyl 3-((4-(((1R,4R)-2-oxa-5-azabicyclo[2.2.1]heptan-5-yl)methyl)-2-fluorophenyl)amino)-6-(3-methyl-3H-imidazo[4,5-c]pyridin-7-yl)-5-(methylamino) pyrazine-2-carboxylate (245 mg, 0.47 mmol). The resulting mixture was stirred at 100° C. for 10 hours in a Biotage microwave reactor. The reaction was then concentrated. The resulting residue was purified by silica gel chromatography, using 0 to 10% MeOH-DCM as eluent and 1% ammonium hydroxide as modifier, to afford 3-((4-(((1R,4R)-2-oxa-5-azabicyclo[2.2.1]heptan-5-yl)methyl)-2-fluorophenyl)amino)-6-(3-methyl-3H-imidazo[4,5-c]pyridin-7-yl)-5-(methylamino) pyrazine-2-carboxamide (0.104 g, 44% yield) as a bright yellow solid. 1H NMR (500 MHZ, DMSO-d6) δ 1.58 (1H, d), 1.80 (1H, d), 2.41 (1H, d), 2.74 (1H, d), 2.94 (3H, d), 3.44 (1H, s), 3.52 (1H, d), 3.62-3.76 (2H, m), 3.91 (1H, d), 4.00 (3H, s), 4.34 (1H, s), 7.14 (1H, d), 7.22 (1H, d), 7.37 (1H, s), 7.75 (1H, br s), 8.02 (1H, br s), 8.51 (1H, s), 8.64 (1H, t), 8.72 (1H, s), 9.02 (1H, s), 11.66 (1H, s). m/z: (ES+), [M+H]+=504.2. $[\alpha]^{25}_{D}$=−37.60°

Example 147

3-[2,3-Difluoro-4-[[(1R,4R)-2-oxa-5-azabicyclo[2.2.1]heptan-5-yl]methyl]anilino]-5-(methylamino)-6-(3-methylimidazo[4,5-c]pyridin-7-yl)pyrazine-2-carboxamide

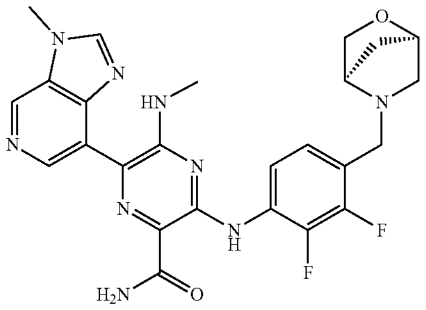 [SMILES: CNc1nc(Nc2ccc(CN3C[C@H]4C[C@@H]3CO4)c(F)c2F)c(C(N)=O)nc1-c1cncc2c1ncn2C]

(a) (1R,4R)-5-[(4-Bromo-2,3-difluoro-phenyl)methyl]-2-oxa-5-azabicyclo[2.2.1]heptane Sodium triacetoxyborohydride (2.88 g, 13.6 mmol) was added to a solution of 4-bromo-2,3-difluoro-benzaldehyde (1.50 g, 6.79 mmol) and (1R,4R)-2-oxa-5-azabicyclo[2.2.1]heptane (0.673 g, 6.79 mmol) in 1,2-dichloroethane (40 mL). The resulting mixture was stirred at room temperature for 16 hours. The reaction mixture was then concentrated, redissolved in dichloromethane, and washed with saturated aqueous sodium bicarbonate. The organic layer was dried over sodium sulfate, filtered and concentrated. The resulting residue was purified by flash C18 chromatography, using 5-100% ACN-water as eluent, and 1% formic acid as modifier, to afford (1R,4R)-5-[(4-bromo-2,3-difluoro-phenyl)methyl]-2-oxa-5-azabicyclo[2.2.1]heptane (1.20 g, 58% yield) as a white solid. 1H NMR (400 MHZ, DMSO-d6) δ 1.60 (1H, ddt), 1.79 (1H, dd), 2.47 (1H, dd), 2.75 (1H, dd), 3.47 (1H, s), 3.53 (1H, dd), 3.73-3.79 (2H, m), 3.90 (1H, dd), 4.35 (1H, t), 7.27 (1H, ddd), 7.49 (1H, ddd). m/z: (ES+), [M+H]+=303.9

(b) Methyl 3-[2,3-difluoro-4-[[(1R,4R)-2-oxa-5-azabicyclo[2.2.1]heptan-5-yl]methyl]anilino]-5-(methylamino)-6-(3-methylimidazo[4,5-c]pyridin-7-yl)pyrazine-2-carboxylate Brettphos Pd G3 (217 mg, 0.24 mmol) was added to a suspension of cesium carbonate (1.56 g, 4.79 mmol), (1R,4R)-5-[(4-bromo-2,3-difluoro-phenyl)methyl]-2-oxa-5-azabicyclo[2.2.1]heptane (485 mg, 1.60 mmol), and methyl 3-amino-5-(methylamino)-6-(3-methylimidazo[4,5-c]pyridin-7-yl)pyrazine-2-carboxylate (500 mg, 1.60 mmol) in 1,4-dioxane (50 mL) under nitrogen. The resulting mixture was stirred at 100° C. for 16 hours. The reaction was then concentrated. The resulting residue was purified by silica gel chromatography, using 0-20% MeOH-DCM as eluent, to afford methyl 3-[2,3-difluoro-4-[[(1R,4R)-2-oxa-5-azabicyclo[2.2.1]heptan-5-yl]methyl]anilino]-5-(methylamino)-6-(3-methylimidazo[4,5-c]pyridin-7-yl)pyrazine-2-carboxylate (0.300 g, 35% yield) as a yellow solid. 1H NMR (DMSO-d6, 400 MHZ) § 1.61 (1H, d), 1.80 (1H, d), 2.78 (1H, d), 2.91 (3H, d), 3.30 (1H, s), 3.49 (1H, s), 3.55 (1H, d), 3.77 (2H, s), 3.84 (3H, s), 3.93 (1H, d), 4.02 (3H, s), 4.36 (1H, s), 7.28 (1H, t), 7.97 (1H, br q), 8.42 (1H, t), 8.49 (1H, s), 8.53 (1H, s), 9.06 (1H, s), 10.70 (1H, s). m/z (ES+), [M+H]+=537.2

(c) 3-[2,3-Difluoro-4-[[(1R,4R)-2-oxa-5-azabicyclo[2.2.1]heptan-5-yl]methyl]anilino]-5-(methylamino)-6-(3-methylimidazo[4,5-c]pyridin-7-yl)pyrazine-2-carboxamide 7 N Methanolic ammonia (30 mL, 210 mmol) was added to methyl 3-[2,3-difluoro-4-[[(1R,4R)-2-oxa-5-azabicyclo[2.2.1]heptan-5-yl]methyl]anilino]-5-(methylamino)-6-(3-methylimidazo[4,5-c]pyridin-7-yl)pyrazine-2-carboxylate (300 mg, 0.56 mmol). The resulting mixture was stirred at 80° C. for 3 days. The reaction was then concentrated. The resulting residue was purified by flash C18 chromatography, using 5-100% ACN-water as eluent, and 1% formic acid as modifier, to afford 3-[2,3-difluoro-4-[[(1R,4R)-2-oxa-5-azabicyclo[2.2.1]heptan-5-yl]methyl]anilino]-5-(methylamino)-6-(3-methylimidazo[4,5-c]pyridin-7-yl)pyrazine-2-carboxamide (0.113 g, 39% yield) as a yellow solid. 1H NMR (DMSO-d6, 400 MHz) § 1.60 (1H, d), 1.76-1.83 (1H, m), 2.78 (1H, dd), 2.95 (3H, d), 3.31 (1H, s), 3.48 (1H, s), 3.54 (1H, dd), 3.70-3.81 (2H, m), 3.92 (1H, d), 4.02 (3H, s), 4.36 (1H, s), 7.24 (1H, t), 7.45 (1H, s), 7.81 (1H, s), 8.02 (1H, br q), 8.51 (2H, d), 8.73 (1H, s), 9.04 (1H, s), 11.85 (1H, d). 19F NMR (376 MHz, DMSO) δ −144.155, −155.523. m/z (ES+), [M+H]+=522.3

Example 148

3-[2-Chloro-4-(2-oxa-6-azaspiro[3.3]heptan-6-ylmethyl)anilino]-5-(methylamino)-6-(3-methylimidazo[4,5-c]pyridin-7-yl)pyrazine-2-carboxamide formate salt

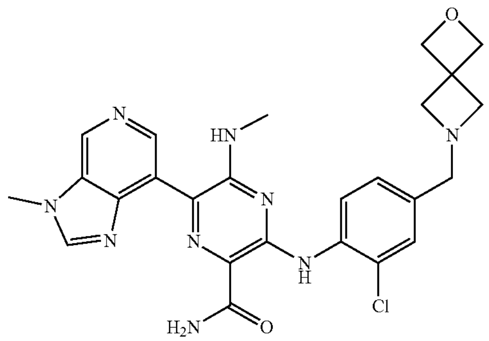 [SMILES: CNc1nc(Nc2ccc(CN3CC4(COC4)C3)cc2Cl)c(C(N)=O)nc1-c1cncc2c1ncn2C]

(a) 6-[(4-Bromo-3-chloro-phenyl)methyl]-2-oxa-6-azaspiro[3 3]heptane

Sodium triacetoxyborohydride (2.90 g, 13.7 mmol) was added to a solution of 4-bromo-3-chloro-benzaldehyde (1.00 g, 4.56 mmol) and 2-oxa-6-azaspiro[3.3]heptane hemioxalate (0.657 g, 4.56 mmol) in DCE (40 mL). The resulting mixture was stirred at room temperature for 2 hours. The reaction was then concentrated. The resulting residue was redissolved in DCM and washed sequentially with saturated aqueous sodium bicarbonate and brine. The organic layer was dried over sodium sulfate, filtered, and concentrated.

The resulting residue was purified by silica gel chromatography, using 0 to 100% EtOAc-petroleum ether as eluent, to afford 6-[(4-bromo-3-chloro-phenyl)methyl]-2-oxa-6-azaspiro[3.3]heptane (0.800 g, 58% yield) as a yellow oil. 1H NMR (400 MHZ, DMSO-d6) δ 3.28 (4H, s), 3.46 (2H, s), 4.59 (4H, s), 7.15 (1H, dd), 7.46 (1H, d), 7.68 (1H, d). m/z: (ES+), [M+2+H]+=304.0

(b) Methyl 3-[2-chloro-4-(2-oxa-6-azaspiro[3 3]heptan-6-ylmethyl)anilino]-5-(methylamino)-6-(3-methylimidazo[4,5-c]pyridin-7-yl)pyrazine-2-carboxylate Brettphos Pd G3 (30 mg, 0.03 mmol) was added to a suspension of 6-[(4-bromo-3-chloro-phenyl)methyl]-2-oxa-6-azaspiro[3.3]heptane (200 mg, 0.66 mmol), methyl 3-amino-5-(methylamino)-6-(3-methylimidazo[4,5-c]pyridin-7-yl)pyrazine-2-carboxylate (104 mg, 0.330 mmol), and cesium carbonate (323 mg, 0.990 mmol) in 1,4-dioxane (10 mL) under nitrogen. The resulting mixture was stirred at 100° C. for 16 hours. The reaction was then concentration. The resulting residue was purified by silica gel chromatography, using 0 to 20% MeOH-DCM as eluent, to afford methyl 3-[2-chloro-4-(2-oxa-6-azaspiro[3.3]heptan-6-ylmethyl)anilino]-5-(methylamino)-6-(3-methylimidazo[4,5-c]pyridin-7-yl)pyrazine-2-carboxylate (0.100 g, 57% yield) as a yellow solid. 1H NMR (300 MHz, DMSO-d6) δ 2.89 (3H, d), 3.31 (4H, s), 3.46 (2H, s), 3.82 (3H, s), 4.00 (3H, s), 4.59 (4H, s), 7.22 (1H, dd), 7.38 (1H, d), 7.97 (1H, br q), 8.48 (1H, s), 8.52 (1H, s), 8.70 (1H, d), 9.04 (1H, s), 10.82 (1H, s). m/z: (ES+), [M+H]+=535.2

(c) 3-[2-Chloro-4-(2-oxa-6-azaspiro[3.3]heptan-6-ylmethyl)anilino]-5-(methylamino)-6-(3-methylimidazo[4,5-c]pyridin-7-yl)pyrazine-2-carboxamide formate salt 7 N Methanolic ammonia (20 mL, 140 mmol) was added to methyl 3-[2-chloro-4-(2-oxa-6-azaspiro[3.3]heptan-6-ylmethyl)anilino]-5-(methylamino)-6-(3-methylimidazo[4,5-c]pyridin-7-yl)pyrazine-2-carboxylate (100 mg, 0.19 mmol). The resulting mixture was stirred at 80° C. for 16 hours. The reaction was then concentrated. The resulting residue was purified by reverse phase HPLC, using a 5 micron, 30×150 mm, Xselect CSH OBD column, 2 to 13% MeCN-water as eluent, and 0.05% formic acid as modifier, to afford 3-[2-chloro-4-(2-oxa-6-azaspiro[3.3]heptan-6-ylmethyl)anilino]-5-(methylamino)-6-(3-methylimidazo[4,5-c]pyridin-7-yl)pyrazine-2-carboxamide formate salt (0.037 g, 35% yield) as a yellow solid. 1H NMR (400 MHZ, DMSO-d6) δ 2.94 (3H, d), 3.30 (4H, s), 3.46 (2H, s), 4.02 (3H, s), 4.61 (4H, s), 7.21 (1H, dd), 7.36 (2H, t), 7.77 (1H, d), 8.02 (1H, br q), 8.19 (1H, s), 8.53 (1H, s), 8.71-8.78 (2H, m), 9.04 (1H, s), 11.85 (1H, s). m/z: (ES+), [M+H]+=520.2

Example 149

5-(Methylamino)-6-(3-methylimidazo[4,5-c]pyridin-7-yl)-3-[4-(2-morpholinoethyl)anilino]pyrazine-2-carboxamide

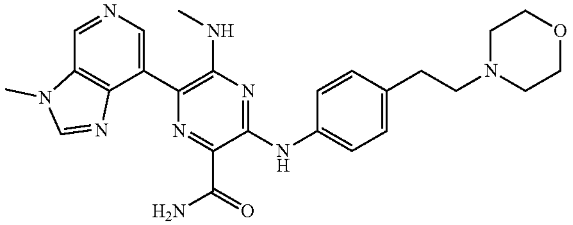 [SMILES: CNc1nc(Nc2ccc(CCN3CCOCC3)cc2)c(C(N)=O)nc1-c1cncc2c1ncn2C]

(a) 4-[2-(4-Bromophenyl)ethyl]morpholine

DIPEA (734 mg, 5.68 mmol) was added to a mixture 1-bromo-4-(2-bromoethyl)benzene (500 mg, 1.89 mmol), morpholine (248 mg, 2.84 mmol), and potassium iodide (15.72 mg, 0.09 mmol) in MeCN (10 mL). The resulting mixture was stirred at 80° C. for 2 hours. The reaction was then concentrated. The resulting residue was purified by C18 chromatography, using 5-90% MeCN—$H_2O$ as eluent, to afford 4-[2-(4-bromophenyl)ethyl]morpholine (0.410 g, 80%) as a white solid; 1H NMR (Chloroform-d, 400 MHZ) δ 2.47-2.55 (4H, m), 2.55-2.61 (2H, m), 2.71-2.81 (2H, m), 3.70-3.79 (4H, m), 7.10 (2H, d), 7.42 (2H, d); m/z: (ES+), [M+H]+=270.2

(b) Methyl 5_(methylamino)-6-(3-methylimidazo[4,5-c]pyridin-7-yl)-3-[4-(2-morpholinoethyl)anilino]pyrazine-2-carboxylate BrettPhos Pd G3 (173 mg, 0.190 mmol) was added to a suspension of methyl 3-amino-5-(methylamino)-6-(3-methylimidazo[4,5-c]pyridin-7-yl)pyrazine-2-carboxylate (300 mg, 0.96 mmol), 4-[2-(4-bromophenyl)ethyl]morpholine (259 mg, 0.960 mmol), and cesium carbonate (936 mg, 2.87 mmol) in 1,4-dioxane (10 mL) under nitrogen. The resulting mixture was stirred at 100° C. for 15 hours. The reaction was then concentrated. The resulting residue was purified by silica gel chromatography, using 0-15% MeOH-DCM as eluent, to afford methyl 5-(methylamino)-6-(3-methylimidazo[4,5-c]pyridin-7-yl)-3-[4-(2-morpholinoethyl)anilino]pyrazine-2-carboxylate (0.154 g, 32%) as a yellow solid; 1H NMR (400 MHZ, DMSO-d6) δ 2.47 (4H, s), 2.54 (2H, s), 2.73 (2H, t), 2.92 (3H, d), 3.59 (4H, t), 3.83 (3H, s), 4.01 (3H, s), 7.22 (2H, d), 7.69-7.75 (2H, m), 8.49 (1H, s), 8.53 (1H, s), 9.04 (1H, s), 10.39 (1H, s); m/z: (ES+), [M+H]+=503.2

(c) 5-(Methylamino)-6-(3-methylimidazo[4,5-c]pyridin-7-yl)-3-[4-(2-morpholinoethyl)anilino]pyrazine-2-carboxamide 7 N Methanolic ammonia (10 mL, 70 mmol) was added to methyl 5-(methylamino)-6-(3-methylimidazo[4,5-c]pyridin-7-yl)-3-[4-(2-morpholinoethyl)anilino]pyrazine-2-carboxylate (143 mg, 0.280 mmol). The resulting mixture was stirred at 80° C. for 30 hours. The reaction was then concentrated. The resulting residue was purified by preparative LCMS, using a 5 micron, 50 mm×100 mm, XSelect CSH C18 column, decreasingly polar mixtures of MeCN—$H_2O$ as eluent, and 0.1% ammonium carbonate as modifier, to afford 5-(methylamino)-6-(3-methylimidazo[4,5-c]pyridin-7-yl)-3-[4-(2-morpholinoethyl)anilino]pyrazine-2-carboxamide (50 mg, 36%) as a yellow solid. 1H NMR (400 MHZ, DMSO-d6) δ 2.38-2.46 (4H, m), 2.51-2.54 (2H, m), 2.66-2.75 (2H, m), 2.95 (3H, d), 3.53-3.62 (4H, m), 4.01 (3H, s), 7.20 (2H, d), 7.35 (1H, s), 7.70 (2H, d), 7.74 (1H, s), 8.00 (1H, br q), 8.52 (1H, s), 8.73 (1H, s), 9.02 (1H, s), 11.45 (1H, s); m/z: (ES+), [M+H]+=448.3

Example 150

5-(Methylamino)-6-(3-methylimidazo[4,5-c]pyridin-7-yl)-3-[4-[2-(4-methylpiperazin-1-yl)ethyl]anilino]pyrazine-2-carboxamide

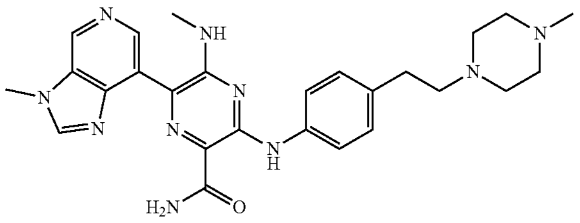

(a) 1-[2-(4-Bromophenyl)ethyl]-4-methyl-piperazine

Potassium iodide (16 mg, 0.090 mmol) was added to a solution of 1-bromo-4-(2-bromoethyl)benzene (500 mg, 1.89 mmol) and 1-methylpiperazine (949 mg, 9.47 mmol) in acetonitrile (10 mL). The resulting solution was stirred at 80° C. for 4 hours. The reaction was then concentrated. The resulting residue was purified by C18 reverse phase chromatography, using 5-90% MeCN—$H_2O$ as eluent to afford 1-[2-(4-bromophenyl)ethyl]-4-methyl-piperazine (0.317 g, 59%) as a yellow solid; 1H NMR (400 MHZ, $CDCl_3$) δ 2.32 (3H, s), 2.35-2.72 (10H, m), 2.73-2.81 (2H, m), 7.09 (2H, d), 7.41 (2H, d); m/z: (ES+), [M+H]+=283.0

(b) Methyl 5-(methylamino)-6-(3-methylimidazo[4,5-c]pyridin-7-yl)-3-[4-[2-(4-methylpiperazin-1-yl)ethyl]anilino]pyrazine-2-carboxylate BrettPhos Pd G3 (116 mg, 0.130 mmol) was added to a suspension of methyl 3-amino-5-(methylamino)-6-(3-methylimidazo[4,5-c]pyridin-7-yl)pyrazine-2-carboxylate (200 mg, 0.64 mmol), 1-[2-(4-bromophenyl)ethyl]-4-methyl-piperazine (217 mg, 0.77 mmol) and cesium carbonate (624 mg, 1.91 mmol) in 1,4-dioxane (10 mL) under nitrogen. The resulting mixture was stirred at 100° C. for 4 hours. The reaction was concentrated. The resulting residue was purified by silica gel chromatography, using 0-20% MeOH-DCM as eluent, to afford methyl 5-(methylamino)-6-(3-methylimidazo[4,5-c]pyridin-7-yl)-3-[4-[2-(4-methylpiperazin-1-yl)ethyl]anilino]pyrazine-2-carboxylate (0.105 g, 32%) as a yellow solid; 1H NMR (400 MHz, DMSO-d6) δ 2.27 (3H, s), 2.51-2.53 (8H, m), 2.54-2.58 (2H, m), 2.69-2.75 (2H, m), 2.91 (3H, d), 3.83 (3H, s), 4.01 (3H, s), 7.22 (2H, d), 7.72 (2H, d), 7.93 (1H, br q), 8.49 (1H, s), 8.53 (1H, s), 9.04 (1H, s), 10.39 (1H, s); m/z: (ES+), [M+H]+=516.4

(c) 5-(Methylamino)-6-(3-methylimidazo[4,5-c]pyridin-7-yl)-3-[4-[2-(4-methylpiperazin-1-yl)ethyl]anilino]pyrazine-2-carboxamide 7 N Methanolic ammonia (10 mL, 70 mmol) was added to methyl 5-(methylamino)-6-(3-methylimidazo[4,5-c]pyridin-7-yl)-3-[4-[2-(4-methylpiperazin-1-yl)ethyl]anilino]pyrazine-2-carboxylate (90 mg, 0.17 mmol). The resulting solution was stirred at 80° C. for 40 hours. The reaction was then concentrated. The resulting residue was purified by preparative HPLC using a 5 micron, 50×100 mm XSelect CSH Prep C18 OBD column, decreasingly polar mixtures of MeCN—$H_2O$ as eluent, and 0.1% ammonium bicarbonate as modifier, to afford 5-(methylamino)-6-(3-methylimidazo[4,5-c]pyridin-7-yl)-3-[4-[2-(4-methylpiperazin-1-yl)ethyl]anilino]pyrazine-2-carboxamide (16 mg, 18%) as a yellow solid; 1H NMR (400 MHz, DMSO-d6) δ 2.14 (3H, s), 2.22-2.37 (4H, m), 2.37-2.47 (4H, m), 2.51-2.52 (2H, m), 2.65-2.70 (2H, m), 2.94 (3H, d), 4.00 (3H, s), 7.18 (2H, d), 7.34 (1H, s), 7.68 (2H, d), 7.73 (1H, s), 7.98 (1H, br q), 8.50 (1H, s), 8.71 (1H, s), 9.01 (1H, s), 11.43 (1H, s); m/z: (ES+), [M+H]+=501.4

Example 151

5-Cyclopropyl-6-(3-methylimidazo[4,5-c]pyridin-7-yl)-3-[4-(pyrrolidin-1-ylmethyl)anilino]pyrazine-2-carboxamide

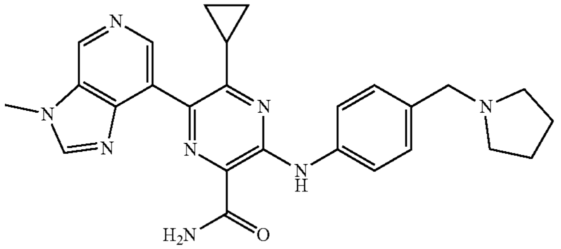 [SMILES: Cn1cnc2c(-c3nc(C(N)=O)c(Nc4ccc(CN5CCCC5)cc4)nc3C3CC3)cncc21]

(a) 1-[(4-Bromophenyl)methyl]pyrrolidine

Sodium triacetoxyborohydride (3.18 g, 15.0 mmol) was added to a mixture of 4-bromobenzaldehyde (1.85 g, 10.0 mmol) and pyrrolidine (1.67 mL, 20.0 mmol) in DCM (38 mL). The resulting mixture was stirred at 25 C for 18 hours. The reaction was then quenched by addition of 2 M aqueous NaOH solution and extracted three times with DCM (15 mL each). The combined organic layers were washed with brine, dried over sodium sulfate, filtered, and concentrated to afford 1-[(4-bromophenyl)methyl]pyrrolidine (2.45 g, 102%) as a pale yellow oil; 1H NMR (500 MHZ, CHLOROFORM-d) δ 1.79 (4H, dt), 2.42-2.56 (4H, m), 3.57 (2H, s), 7.22 (2H, d), 7.38-7.48 (2H, m); m/z: (ES+), [M+H]+=240.0

(b) Methyl 5-cyclopropyl-6-(3-methylimidazo[4,5-c]pyridin-7-yl)-3-[4-(pyrrolidin-1-ylmethyl)anilino]pyrazine-2-carboxylate Methyl 3-amino-5-cyclopropyl-6-(3-methylimidazo[4,5-c]pyridin-7-yl)pyrazine-2-carboxylate (140 mg, 0.43 mmol), 1-[(4-bromophenyl)methyl]pyrrolidine (124 mg, 0.520 mmol), BrettPhos Pd G3 (39 mg, 0.040 mmol), and cesium carbonate (422 mg, 1.29 mmol) were combined in a microwave vial, which was evacuated and backfilled three times with nitrogen. 1,4-dioxane (4.3 mL) was added. The resulting mixture was stirred at 110° C. for 20 hours. The reaction was then concentrated. The resulting residue was purified by silica gel chromatography, using 0-20% MeOH-DCM as eluent, and 1% ammonia as modifier, to afford methyl 5-cyclopropyl-6-(3-methylimidazo[4,5-c]pyridin-7-yl)-3-[4-(pyrrolidin-1-ylmethyl)anilino]pyrazine-2-carboxylate (0.078 g, 37%) as a bright yellow dry film; 1H NMR (500 MHz, CHLOROFORM-d) δ 0.90-1.03 (2H, m), 1.22-1.34 (2H, m), 1.82 (4H, br s), 1.93-2.03 (1H, m), 2.56 (4H, br s), 3.63 (2H, br s), 3.97 (3H, s), 4.01 (3H, s), 7.33 (2H, br d), 7.64 (2H, d), 8.01 (1H, s), 8.68 (1H, s), 8.91 (1H, s), 10.30 (1H, s); m/z: (ES+), [M+H]+=484.2

(c) 5-Cyclopropyl-6-(3-methylimidazo[4,5-c]pyridin-7-yl)-3-[4-(pyrrolidin-1-ylmethyl)anilino]pyrazine-2-carboxamide 7 N Methanolic ammonia (2.0 mL, 14 mmol) was added to a solution of methyl 5-cyclopropyl-6-(3-methylimidazo[4,5-c]pyridin-7-yl)-3-[4-(pyrrolidin-1-ylmethyl)anilino]pyrazine-2-carboxylate (78 mg, 0.16 mmol) in methanol (1.5 mL). The resulting mixture was stirred at 100° C. for 4 hours in a Biotage microwave reactor. The reaction was then concentrated to afford 5-cyclopropyl-6-(3-methylimidazo[4,5-c]pyridin-7-yl)-3-[4-(pyrrolidin-1-ylmethyl)anilino]pyrazine-2-carboxamide (0.063 g, 83%) as a yellow solid. 1H NMR (500 MHz, DMSO-d6) δ 0.85-0.97 (2H, m), 1.01-1.13 (2H, m), 1.71 (4H, br s), 1.88-1.98 (1H, m), 3.58 (2H, br s), 3.99 (3H, s), 7.29 (2H, br d), 7.61 (2H, br d), 7.85 (1H, br s), 8.10 (1H, br s), 8.44 (1H, s), 8.54 (1H, s), 9.04 (1H, s), 11.29 (1H, s); the 4 pyrrolidine protons alpha to the amine were buried under the DMSO-d6 solvent peak; m/z: (ES+), [M+H]+=469.2

Example 152

5-Cyclopropyl-6-(3-methylimidazo[4,5-c]pyridin-7-yl)-3-[4-[(4-methylpiperazin-1-yl)methyl]anilino]pyrazine-2-carboxamide

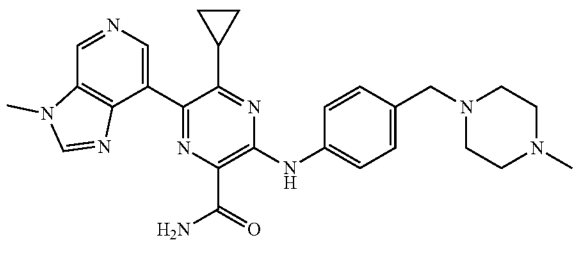

(a) Methyl 6-chloro-5-cyclopropyl-3-[4-[(4-methylpiperazin-1-yl)methyl]anilino]pyrazine-2-carboxylate DIPEA (757 μL, 4.34 mmol) was added to a solution of methyl 6-chloro-5-cyclopropyl-3-fluoro-pyrazine-2-carboxylate (7.23 mL, 2.17 mmol) and 4-[(4-methylpiperazin-1-yl)methyl]aniline (490 mg, 2.38 mmol) in DMF (8 mL). The resulting mixture was stirred at 100° C. for 1 hour. The reaction was then allowed to cool to room temperature and diluted with EtOAc (50 mL) and brine (50 mL). The layers were separated and the aqueous layer was extracted twice with EtOAc (20 mL each). The combined organic layers were dried over sodium sulfate, filtered, and concentrated. The resulting residue was purified by silica gel chromatography, using 0-20% MeOH-DCM as eluent, to afford methyl 6-chloro-5-cyclopropyl-3-[4-[(4-methylpiperazin-1-yl)methyl]anilino]pyrazine-2-carboxylate (0.425 g, 47%) as a yellow solid. 1H NMR (500 MHz, DMSO-d6) δ 1.15-1.26 (2H, m), 1.26-1.46 (4H, m), 2.29 (3H, s), 2.58 (1H, ddd), 2.62-2.72 (6H, m), 3.55 (2H, s), 4.03 (3H, s), 7.38 (2H, br d), 7.62 (2H, br d), 10.07 (1H, s); m/z: (ES+), [M+H]+=416.1

(b) Methyl 5-cyclopropyl-6-(3-methylimidazo[4,5-c]pyridin-7-yl)-3-[4-[(4-methylpiperazin-1-yl)methyl]anilino]pyrazine-2-carboxylate 7-Bromo-3-methyl-imidazo[4,5-c]pyridine (153 mg, 0.720 mmol), bis(pinacolato)diboron (366 mg, 1.44 mmol), cataCXium A Pd G3 (53 mg, 0.070 mmol), cataCXium A (26 mg, 0.070 mmol), and potassium acetate (142 mg, 1.44 mmol) were combined in a microwave vial, which was evacuated and backfilled three times with nitrogen. DMF (3.2 mL) was added. The resulting mixture was stirred at 80° C. for 20 hours. The reaction was then allowed to cool to room temperature and set aside.

Methyl 6-chloro-5-cyclopropyl-3-[4-[(4-methylpiperazin-1-yl)methyl]anilino]pyrazine-2-carboxylate (200 mg, 0.48 mmol), Pd(dppf) C12 dichloromethane complex (39 mg, 0.050 mmol), and cesium fluoride (219 mg, 1.44 mmol) were combined in a microwave vial, which was evacuated and backfilled three times with nitrogen. The borylation mixture was added. The resulting mixture was stirred at 100° C. for 2 hours. The reaction was then allowed to cool to room temperature, diluted with water, and extracted three times with 3:1 DCM/IPA. The combined organic layers were washed once with 5% aqueous LiCl solution and once with brine. The combined organic layers were dried over sodium sulfate, filtered, and concentrated. The resulting residue was purified by silica gel chromatography, using 0-10% MeOH-DCM as eluent, and 1% ammonia as modifier, to afford methyl 5-cyclopropyl-6-(3-methylimidazo[4,5-c]pyridin-7-yl)-3-[4-[(4-methylpiperazin-1-yl)methyl]anilino]pyrazine-2-carboxylate (0.116, 47%) as a glassy yellow solid; 1H NMR (500 MHz, DICHLOROMETHANE-d2) δ 0.91-0.98 (2H, m), 1.18-1.29 (2H, m), 1.87-2.00 (1H, m), 2.24 (3H, br s), 2.27-2.65 (8H, m), 3.47 (2H, s), 3.95 (3H, s), 3.97 (3H, s), 7.30 (2H, d), 7.63 (2H, d), 7.99 (1H, s), 8.53 (1H, s), 8.91 (1H, s), 10.24 (1H, s); m/z: (ES+), [M+H]+=513.2

(c) 5-Cyclopropyl-6-(3-methylimidazo[4,5-c]pyridin-7-yl)-3-[4[(4-methylpiperazin-1-yl)methyl]anilino]pyrazine-2-carboxamide 7 N Methanolic ammonia (2.0 mL, 14 mmol) was added to methyl 5-cyclopropyl-6-(3-methylimidazo[4,5-c]pyridin-7-yl)-3-[4-[(4-methylpiperazin-1-yl)methyl]anilino]pyrazine-2-carboxylate (116 mg, 0.230 mmol). The resulting suspension was stirred at 100° C. for 2 hours. The reaction was then concentrated. The resulting residue was purified by silica gel chromatography, using 0-20% MeOH-DCM as eluent, and 1% ammonia as modifier, to afford 5-cyclopropyl-6-(3-methylimidazo[4,5-c]pyridin-7-yl)-3-[4-[(4-methylpiperazin-1-yl)methyl]anilino]pyrazine-2-carboxamide (32 mg, 28%) as a bright yellow solid. 1H NMR (500 MHz, DMSO-d6) δ 0.86-0.97 (2H, m), 1.04-1.13 (2H, m), 1.87-

1.97 (1H, m), 2.14 (3H, s), 2.18-2.45 (8H, m), 3.41 (2H, s), 3.99 (3H, s), 7.26 (2H, br d), 7.61 (2H, br d), 7.87 (1H, br s), 8.10 (1H, br s), 8.44 (1H, s), 8.54 (1H, s), 9.04 (1H, s), 11.30 (1H, s); m/z: (ES+), [M+H]+=498.2

Example 153

5-Methoxy-6-(3-methylimidazo[4,5-c]pyridin-7-yl)-3-[4-[(4-methylpiperazin-1-yl)methyl]anilino]pyrazine-2-carboxamide

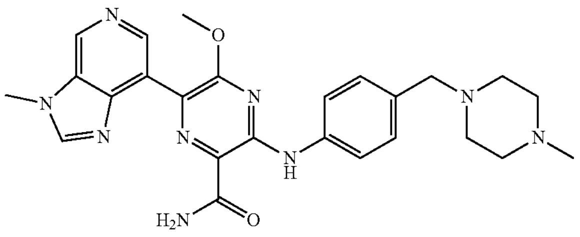

(a) Methyl 6-chloro-5-methoxy-3-[4-[(4-methylpiperazin-1-yl)methyl]anilino]pyrazine-2-carboxylate DIPEA (180 μL, 1.09 mmol) was added to a solution of 4-[(4-methylpiperazin-1-yl)methyl]aniline (205 mg, 1.00 mmol), and methyl 6-chloro-3-fluoro-5-methoxy-pyrazine-2-carboxylate (200 mg, 0.91 mmol) in DMF (0.73 mL). The resulting solution was stirred at 100° C. for 1 hour. The reaction was then allowed to cool to room temperature and diluted with brine (5 mL) and DCM (5 mL). The layers were separated and the aqueous layer was extracted three times with DCM (5 mL each). The organic layers were combined and concentrated. The resulting residue was purified by silica gel chromatography, using 0-40% DCM-MeOH as eluent, to afford methyl 6-chloro-5-methoxy-3-[4-[(4-methylpiperazin-1-yl)methyl]anilino]pyrazine-2-carboxylate (0.093 g, 25%) as a yellow solid; 1H NMR (500 MHz, DMSO-d6) 2.58-2.71 (4H, m), 2.77-3.07 (4H, m), 3.53 (2H, br s), 3.67 (3H, s), 3.89 (3H, s), 4.03 (3H, s), 7.31 (2H, br d), 7.65 (2H, br d), 10.22 (1H, s); m/z: (ES+), [M+H]+=406.2.

(b) Methyl 5-methoxy-6-(3-methylimidazo[4,5-c]pyridin-7-yl)-3-[4-[(4-methylpiperazin-1-yl)methyl]anilino]pyrazine-2-carboxylate Bis(pinacolato)diboron (449 mg, 1.77 mmol), cataCXium A (25 mg, 0.070 mmol), cataCXium A Pd G3 (52 mg, 0.070 mmol), potassium acetate (208 mg, 2.12 mmol), and 7-bromo-3-methyl-imidazo[4,5-c]pyridine (150 mg, 0.71 mmol) were combined in a microwave vial, which was evacuated and backfilled three times with nitrogen. DMF (3.5 mL) was added. The resulting mixture was stirred at 80° C. for 24 hours. The reaction was then allowed to cool to room temperature and set aside.

Cesium fluoride (104 mg, 0.69 mmol), Pd(dppf)$Cl_2$ DCM adduct (17 mg, 0.020 mmol), and methyl 6-chloro-5-methoxy-3-((4-((4-methylpiperazin-1-yl)methyl)phenyl)amino) pyrazine-2-carboxylate (92.7 mg, 0.23 mmol) were combined in a microwave vial, which was evacuated and backfilled three times with nitrogen. Half of the borylation mixture (1.75 mL) from the previous step was added by syringe. The resulting mixture was stirred at 100° C. for 3 hours. The reaction was then allowed to cool to room temperature and loaded onto celite. The resulting material was purified by silica gel chromatography, using 0-70% DCM-MeOH as eluent, to afford methyl 5-methoxy-6-(3-methylimidazo[4,5-c]pyridin-7-yl)-3-[4-[(4-methylpiperazin-1-yl)methyl]anilino]pyrazine-2-carboxylate (0.236 g) as a yellow solid that was taken forward without purification. m/z: (ES+): [M+H]+=503.3.

(c) 5-Methoxy-6-(3-methylimidazo[4,5-c]pyridin-7-yl)-3-[4-[(4-methylpiperazin-1-yl)methyl]anilino]pyrazine-2-carboxamide 7 N Methanolic ammonia (7.0 mL, 49 mmol) was added to methyl 5-methoxy-6-(3-methylimidazo[4,5-c]pyridin-7-yl)-3-[4-[(4-methylpiperazin-1-yl)methyl]anilino]pyrazine-2-carboxylate (262 mg, 0.520 mmol). The resulting mixture was stirred at 100° C. for 2 hours in a Biotage microwave reactor. The reaction was then concentrated. The resulting residue was purified by silica gel chromatography, using 0-10% MeOH-DCM as eluent and 0-1% ammonia as modifier, to afford an orange solid. This material was further purified by preparative HPLC using a 5 micron, 30 mm×150 mm Xselect CSH OBD column, 5-25% MeCN—$H_2O$ as eluent, and 0.2% ammonium hydroxide as modifier, to afford 5-methoxy-6-(3-methylimidazo[4,5-c]pyridin-7-yl)-3-[4-[(4-methylpiperazin-1-yl)methyl]anilino]pyrazine-2-carboxamide (13 mg, 5.0%) as a yellow solid; 1H NMR (500 MHZ, DMSO-d6) 2.13 (3H, s), 2.18-2.44 (8H, m), 3.41 (2H, s), 3.96 (3H, s), 3.97 (3H, s), 7.29 (2H, br d), 7.69 (2H, br d), 7.73 (1H, br s), 7.99 (1H, br s), 8.39 (1H, s), 8.62 (1H, s), 8.98 (1H, s), 11.45 (1H, s); m/z: (ES+), [M+H]+=488.3

Example 154

5-(Difluoromethyl)-6-(3-methylimidazo[4,5-c]pyridin-7-yl)-3-[4-[(4-methylpiperazin-1-yl)methyl]anilino]pyrazine-2-carboxamide

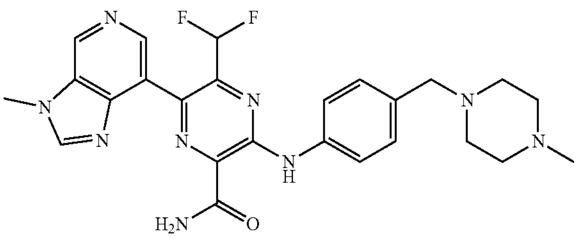

(a) Methyl 3-amino-6-chloro-5-(difluoromethyl)pyrazine-2-carboxylate

TFA (110 μL, 1.43 mmol) was added to a suspension of methyl 3-amino-6-chloro-pyrazine-2-carboxylate (250 mg, 1.33 mmol) and zinc (II) difluoromethanesulfinate (788 mg, 2.67 mmol) in DCM (3 mL) and water (1.2 mL). 70 wt % aqueous tert-butyl hydroperoxide (600 μL, 4.38 mmol) was added dropwise. The resulting mixture was stirred at 25 C for 16 hours. Additional zinc (II) difluoromethanesulfinate (711 mg, 2.41 mmol) was added and 70 wt % aqueous tert-butyl hydroperoxide (600 μL, 4.38 mmol) was added dropwise. The resulting mixture was stirred at 25 C for 60 hours. The reaction was then diluted with DCM (10 mL), quenched with saturated aqueous sodium bicarbonate (40 mL), and stirred vigorously for 2 hours. The layers were separated and the aqueous layer was extracted twice with DCM (20 mL each). The combined organic layers were dried over magnesium sulfate, filtered, and concentrated to afford methyl 3-amino-6-chloro-5-(difluoromethyl)pyrazine-2-carboxylate (0.172 g, 54%) as a yellow solid; 1H NMR (500 MHz, DMSO-d6) 3.87 (3H, s), 7.07 (1H, t), 7.80 (2H, br s); m/z: (ES+), [M+H]+=238.1

(b) Methyl 6-chloro-5-(difluoromethyl)-3-fluoro-pyrazine-2-carboxylate

Sodium nitrite (55 mg, 0.80 mmol) was added to a solution of methyl 3-amino-6-chloro-5-(difluoromethyl) pyrazine-2-carboxylate (172 mg, 0.720 mmol) in HF-pyridine (3.0 mL, 87 mmol) at −10 C. The resulting mixture was stirred at 25 C for 30 minutes. The reaction was then diluted with DCM (5 mL) and quenched with water (10 mL). The layers were separated and the aqueous layer was extracted twice with DCM (5 mL each). The combined organic layers were dried over magnesium sulfate, filtered, and concentrated to afford methyl 6-chloro-5-(difluoromethyl)-3-fluoro-pyrazine-2-carboxylate (0.147 g, 84%) as a yellow oil; 1H NMR (500 MHz, DICHLOROMETHANE-d2) 4.03 (3H, s), 6.94 (1H, t); this intermediate ionized poorly by LCMS.

(c) Methyl 6-chloro-5-(difluoromethyl)-3-[4-[(4-methylpiperazin-1-yl)methyl]anilino]pyrazine-2-carboxylate DIPEA (200 μL, 1.15 mmol) was added to a solution of methyl 6-chloro-5-(difluoromethyl)-3-fluoro-pyrazine-2-carboxylate (147 mg, 0.610 mmol) and 4-[(4-methylpiperazin-1-yl)methyl]aniline (138 mg, 0.670 mmol) in DMF (2 mL). The resulting solution was stirred at 100° C. for 1 hour. The reaction was then allowed to cool to room temperature and diluted with EtOAc (20 mL) and water (30 mL). The layers were separated and the aqueous layer was extracted twice with EtOAc (10 mL each). The combined organic layers were dried over $MgSO_4$, filtered, and concentrated. The resulting residue was purified by silica gel chromatography, using 0-20% MeOH-DCM as eluent, to afford methyl 6-chloro-5-(difluoromethyl)-3-[4-[(4-methylpiperazin-1-yl) methyl]anilino]pyrazine-2-carboxylate (0.135 g, 52%) as a yellow ochre solid; 1H NMR (500 MHz, DMSO-d6) 2.14 (3H, s), 2.20-2.44 (8H, m), 3.42 (2H, s), 3.95 (3H, s), 7.17 (1H, t), 7.28 (2H, br d), 7.60-7.68 (2H, m), 10.06 (1H, s); m/z: (ES+), [M+H]+=426.4

(d) Methyl 5-(difluoromethyl)-6-(3-methylimidazo [4,5-c]pyridin-7-yl)-3-[4-[(4-methylpiperazin-1-yl) methyl]anilino]pyrazine-2-carboxylate 7-Bromo-3-methyl-imidazo[4,5-c]pyridine (101 mg, 0.480 mmol), cataCXium A Pd G3 (35 mg, 0.050 mmol), cataCXium A (17 mg, 0.050 mmol), bis(pinacolato)diboron (183 mg, 0.720 mmol), and potassium acetate (140 mg, 1.43 mmol) were combined in a microwave vial, which was evacuated and backfilled three times with nitrogen. DMF (1.8 mL) was added. The resulting mixture was stirred at 100° C. for 20 hours. The reaction was then allowed to cool to room temperature and set aside.

In a separate microwave vial, methyl 6-chloro-5-(difluoromethyl)-3-[4-[(4-methylpiperazin-1-yl)methyl]anilino] pyrazine-2-carboxylate (135 mg, 0.320 mmol), $Pd(dppf)Cl_2$ (23 mg, 0.030 mmol), and cesium fluoride (144 mg, 0.950 mmol) were combined. The vial was evacuated and back-filled three times with nitrogen. The borylation mixture was added via syringe. The resulting mixture was stirred at 100° C. for 2 hours. The reaction was then allowed to cool to room temperature, diluted with DCM (20 mL), loaded onto Celite, and concentrated. The resulting material was purified by silica gel chromatography, using 0-10% MeOH-DCM as eluent and 0-1% ammonia as modifier, to afford methyl 5-(difluoromethyl)-6-(3-methylimidazo[4,5-c]pyridin-7-yl)-3-[4-[(4-methylpiperazin-1-yl)methyl]anilino]pyrazine-2-carboxylate as a dark yellow solid; 1H NMR (500 MHz, DMSO-d6) 2.14 (3H, s), 2.19-2.42 (8H, m), 3.44 (2H, s), 3.94 (3H, s), 4.01 (3H, s), 7.07 (1H, t), 7.30 (2H, d), 7.76 (2H, d), 8.48 (1H, s), 8.49 (1H, s), 9.10 (1H, s), 10.15 (1H, s); m/z: (ES+), [M+H]+=523.3.

(e) 5-(Difluoromethyl)-6-(3-methylimidazo[4,5-c] pyridin-7-yl)-3-[4-[(4-methylpiperazin-1-yl)methyl] anilino]pyrazine-2-carboxamide 7 N Methanolic ammonia (2.50 mL, 17.5 mmol) was added to methyl 5-(difluoromethyl)-6-(3-methylimidazo[4,5-c]pyridin-7-yl)-3-[4-[(4-methylpiperazin-1-yl)methyl]anilino]pyrazine-2-carboxylate (166 mg, 0.320 mmol). The resulting suspension was stirred at 100° C. for 1 hour in a Biotage microwave reactor. The reaction was then concentrated. The resulting residue was purified by silica gel chromatography, using 0-10% MeOH-DCM as eluent and 0-1% ammonia as modifier, to afford 5-(difluoromethyl)-6-(3-methylimidazo[4,5-c]pyridin-7-yl)-3-[4-[(4-methylpiperazin-1-yl)methyl]anilino]pyrazine-2-carboxamide (52 mg, 32%) as a yellow solid; 1H NMR (400 MHZ, DMSO-d6) 2.14 (3H, s), 2.17-2.45 (8H, m), 3.43 (2H, s), 4.01 (3H, s), 7.13 (1H, t), 7.29 (2H, d), 7.76 (2H, d), 8.15 (1H, s), 8.45 (1H, s), 8.50 (1H, s), 8.71 (1H, s), 9.08 (1H, s), 11.45 (1H, s); m/z: (ES+), [M+H]+=508.3

Example 155

5-(Difluoromethyl)-6-(3-methylimidazo[4,5-c]pyridin-7-yl)-3-[4-(morpholinomethyl)anilino]pyrazine-2-carboxamide

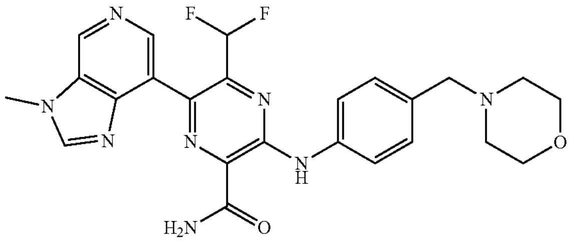 [SMILES: Cn1cnc2c(-c3nc(C(N)=O)c(Nc4ccc(CN5CCOCC5)cc4)nc3C(F)F)cncc21]

(a) Methyl 6-chloro-5-(difluoromethyl)-3-[4-(morpholinomethyl)anilino]pyrazine-2-carboxylate 1 M Lithium bis(trimethylsilyl)amide in THF (1.26 mL, 1.26 mmol) was added to a mixture of tBuXPhos Pd G3 (50 mg, 0.060 mmol), tBuXPhos (27 mg, 0.060 mmol), 4-(4-bromobenzyl) morpholine (194 mg, 0.760 mmol) and methyl 3-amino-6-chloro-5-(difluoromethyl)pyrazine-2-carboxylate (150 mg, 0.63 mmol) in 1,4-dioxane (5 mL). The resulting mixture was sparged with nitrogen for five minutes, then stirred at 50° C. for 2 hours. The reaction was then allowed to cool to room temperature and quenched with saturated aqueous ammonium chloride (5 mL). The layers were separated and the aqueous layer was extracted three times with EtOAc (5 mL each). The combined organic layers were dried over sodium sulfate, filtered, and concentrated. The resulting residue was purified by flash silica chromatography, using 0-40% MeOH-DCM as eluent, to afford methyl 6-chloro-5-(difluoromethyl)-3-[4-(morpholinomethyl)anilino]pyrazine-2-carboxylate (0.180 g, 69%) as a brown solid. m/z: (ES+), [M+H]+=413.1

(b) Methyl 5-(difluoromethyl)-6-(3-methylimidazo[4,5-c]pyridin-7-yl)-3-[4-(morpholinomethyl)anilino]pyrazine-2-carboxylate CataCXium A (21.14 mg, 0.06 mmol), bis(pinacolato)diboron (374 mg, 1.47 mmol), CataCXium A Pd G3 (43 mg, 0.060 mmol), potassium acetate (116 mg, 1.18 mmol), 7-bromo-3-methyl-imidazo[4,5-c]pyridine (125 mg, 0.590 mmol), and DMF (2.95 mL) were added to a vial. The resulting suspension was sparged with nitrogen for 5 minutes, then heated to 100° C. for 18 hours. The reaction was then cooled to room temperature and set aside. Pd(dppf) C12 DCM adduct (40 mg, 0.05 mmol), cesium fluoride (147 mg, 0.970 mmol), and methyl 6-chloro-5-(difluoromethyl)-3-[4-(morpholinomethyl)anilino]pyrazine-2-carboxylate (200 mg, 0.48 mmol) were combined in a vial. The borylation mixture was added. The resulting mixture was sparged with nitrogen for 5 minutes, then stirred at 100° C. for 45 minutes. The reaction was then concentrated onto celite. The resulting material was purified by flash silica chromatography, using 0-10% MeOH-DCM as eluent and 0-1% ammonia as modifier, to afford methyl 5-(difluoromethyl)-6-(3-methylimidazo[4,5-c]pyridin-7-yl)-3-[4-(morpholinomethyl)anilino]pyrazine-2-carboxylate (0.200 g, 81%) as a brown solid. m/z: (ES+), [M+H]+=510.3

(c) 5-(Difluoromethyl)-6-(3-methylimidazo[4,5-c]pyridin-7-yl)-3-[4-(morpholinomethyl)anilino]pyrazine-2-carboxamide 7 N Methanolic ammonia (2.0 mL, 14 mmol) was added to methyl 5-(difluoromethyl)-6-(3-methylimidazo[4,5-c]pyridin-7-yl)-3-[4-(morpholinomethyl)anilino]pyrazine-2-carboxylate (100 mg, 0.20 mmol). The resulting mixture was stirred at 100° C. in a microwave reactor for 2 hours. The reaction was then concentrated. The resulting residue was purified by preparative HPLC, using a 5 micron, 19 mm×250 mm XSelect CSH C18 column, decreasingly polar mixtures of MeCN—$H_2O$ as eluent, and 0.2% ammonium carbonate as modifier, to afford 5-(difluoromethyl)-6-(3-methylimidazo[4,5-c]pyridin-7-yl)-3-[4-(morpholinomethyl)anilino]pyrazine-2-carboxamide (0.022 g, 22%) as a yellow solid. 1H NMR (500 MHz, DMSO-d6) δ 3.46 (2H, s), 3.58 (4H, br d), 4.02 (4H, s), 7.15 (1H, s), 7.33 (2H, d), 7.78 (2H, d), 8.11-8.20 (1H, m), 8.46 (1H, s), 8.52 (1H, s), 8.72 (1H, s), 9.10 (1H, s), 11.47 (1H, s); m/z: (ES+), [M+H]+=495.2

Example 156

3-[2-Fluoro-4-(morpholinomethyl)anilino]-5-methoxy-6-(3-methylimidazo[4,5-c]pyridin-7-yl)pyrazine-2-carboxamide

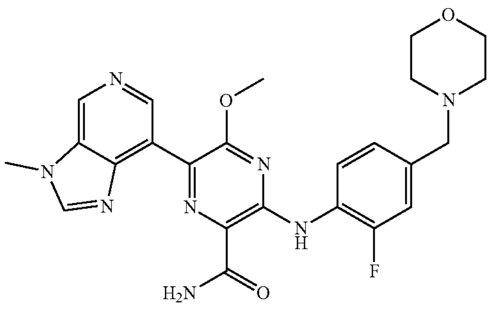 [SMILES: COc1nc(Nc2ccc(CN3CCOCC3)cc2F)c(C(N)=O)nc1-c1cncc2c1ncn2C]

(a) Methyl 3-[2-fluoro-4-(morpholinomethyl)anilino]-5-methoxy-6-(3-methylimidazo[4,5-c]pyridin-7-yl)pyrazine-2-carboxylate BrettPhos Pd G3 (43 mg, 0.050 mmol) was added to a suspension of methyl 3-amino-5-methoxy-6-(3-methylimidazo[4,5-c]pyridin-7-yl)pyrazine-2-carboxylate (150 mg, 0.48 mmol), 4-[(4-bromo-3-fluoro-phenyl)methyl]morpholine (196 mg, 0.720 mmol), and cesium carbonate (310 mg, 0.95 mmol) in 1,4-dioxane (15 mL) under nitrogen. The resulting mixture was stirred at 100° C. for 16 hours. The reaction was then concentrated. The resulting residue was purified by silica gel chromatography, using 0-10% MeOH-DCM as eluent, to afford methyl 3-[2-fluoro-4-(morpholinomethyl)anilino]-5-methoxy-6-(3-methylimidazo[4,5-c]pyridin-7-yl)pyrazine-2-carboxylate (0.150 g, 62%) as a yellow solid. 1H NMR (300 MHZ, DMSO-d6) δ 3.10-3.20 (4H, m), 3.67-3.79 (4H, m), 3.80 (3H, s), 3.91 (3H, s), 4.01 (3H, s), 4.22 (2H, s), 7.29 (1H, d), 7.40 (1H, d), 8.47-8.55 (1H, m), 8.63 (1H, s), 8.77 (1H, s), 9.29 (1H, s). m/z: (ES+), [M+H]+=508.2

(b) 3-[2-Fluoro-4-(morpholinomethyl)anilino]-5-methoxy-6-(3-methylimidazo[4,5-c]pyridin-7-yl)pyrazine-2-carboxamide 7 N Methanolic ammonia (10 mL, 70 mmol) was added to methyl 3-[2-fluoro-4-(morpholinomethyl)anilino]-5-methoxy-6-(3-methylimidazo[4,5-c]pyridin-7-yl)pyrazine-2-carboxylate (150 mg, 0.30 mmol). The resulting mixture was stirred at 80° C. for 16 hours. The reaction was then concentrated. The resulting residue was purified by preparative HPLC, using a 5 micron, 30 mm×150 mm, Sunfire C18 column, decreasingly polar mixtures of MeCN—$H_2O$ as eluent, and 0.1% formic acid as modifier, to afford 3-[2-fluoro-4-(morpholinomethyl)anilino]-5-methoxy-6-(3-methylimidazo[4,5-c]pyridin-7-yl)pyrazine-2-carboxamide (0.040 g, 27%) as a yellow solid. 1H NMR (300 MHz, DMSO-d6) δ 2.33-2.39 (4H, m), 3.45 (2H, s), 3.53-3.62 (4H, m), 3.93-4.00 (6H, m), 7.10-7.27 (2H, m), 7.77 (1H, s), 8.02 (1H, s), 8.40 (1H, s), 8.48 (1H, t), 8.61 (1H, s), 8.99

(1H, s), 11.65 (1H, s). 19F NMR (282 MHZ, DMSO) δ −129.61. m/z: (ES+), [M+H]+=493.2

Example 157

3-[2,3-Difluoro-4-(morpholinomethyl)anilino]-5-methoxy-6-(3-methylimidazo[4,5-c]pyridin-7-yl)pyrazine-2-carboxamide

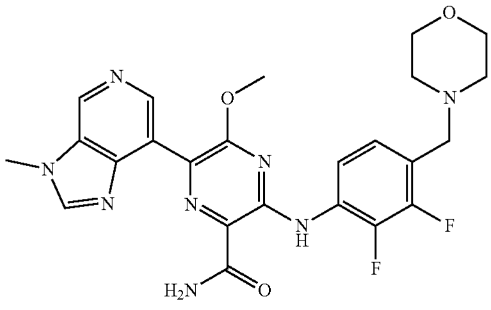 [SMILES: COc1nc(Nc2ccc(CN3CCOCC3)c(F)c2F)c(C(N)=O)nc1-c1cncc2c1ncn2C]

(a) 3-[2 3-Difluoro-4-(morpholinomethyl)anilino]-5-methoxy-6-(3-methylimidazo[4,5-c]pyridin-7-yl)pyrazine-2-carboxylic acid BrettPhos Pd G3 (43 mg, 0.050 mmol) was added to a suspension of cesium carbonate (466 mg, 1.43 mmol), 4-[(4-bromo-2,3-difluoro-phenyl)methyl]morpholine (209 mg, 0.720 mmol), and methyl 3-amino-5-methoxy-6-(3-methylimidazo[4,5-c]pyridin-7-yl)pyrazine-2-carboxylate (150 mg, 0.48 mmol) in DMF (10 mL) under nitrogen. The resulting mixture was stirred at 100° C. for 16 hours. The reaction was then concentrated. The resulting residue was purified by flash C18-flash chromatography, using 5-40% MeCN—$H_2O$ as eluent, and 0.1% formic acid as modifier, to afford 3-[2,3-difluoro-4-(morpholinomethyl)anilino]-5-methoxy-6-(3-methylimidazo[4,5-c]pyridin-7-yl)pyrazine-2-carboxylic acid, formic acid salt (0.075 g, 29%) as a yellow solid. 1H NMR (300 MHz, DMSO-d6) δ 2.40-2.44 (4H, m), 3.55-3.59 (6H, m), 3.91-4.00 (6H, m), 7.01-7.40 (1H, m), 8.12 (1H, s), 8.22-8.39 (2H, m), 8.44 (1H, s), 8.93 (1H, s). m/z: (ES+), [M+H]+=512.1

(b) 3-((2,3-Difluoro-4-(morpholinomethyl)phenyl)amino)-5-methoxy-6-(3-methyl-3H-imidazo[4,5-c]pyridin-7-yl)pyrazine-2-carboxamide Ammonium chloride (21 mg, 0.39 mmol) was added to a solution of DIPEA (110 μL, 0.64 mmol), HATU (59 mg, 0.15 mmol), and 3-[2,3-difluoro-4-(morpholinomethyl)anilino]-5-methoxy-6-(3-methylimidazo[4,5-c]pyridin-7-yl)pyrazine-2-carboxylic acid, formic acid salt (70 mg, 0.13 mmol) in DMF (15 mL). The resulting mixture was stirred at room temperature for 2 days. The reaction was then concentrated. The resulting residue was purified by preparative HPLC, using a 5 micron, 30 mm×150 mm, XBridge Prep C18 OBD column, decreasingly polar mixtures of MeCN—$H_2O$ as eluent, and 10 mmol/L ammonium bicarbonate+0.1% ammonium hydroxide as modifier, to afford 3-[2,3-difluoro-4-(morpholinomethyl)anilino]-5-methoxy-6-(3-methylimidazo[4,5-c]pyridin-7-yl)pyrazine-2-carboxamide (0.024 g, 37%) as a pale yellow solid. 1H NMR (300 MHz, DMSO-d6) δ 2.36-2.42 (4H, m), 3.50-3.60 (6H, m), 3.94-4.00 (6H, m), 7.23 (1H, t), 7.83 (1H, s), 8.07 (1H, s), 8.33 (1H, t), 8.40 (1H, s), 8.61 (1H, s), 9.00 (1H, s), 11.81 (1H, s). 19F NMR (282 MHZ, DMSO) δ −142.86, −154.39. m/z: (ES+), [M+H]+=511.2

Examples 158 and 159

5-Methyl-6-(1-methylbenzimidazol-4-yl)-3-[4-[rel-(3S)-4-methylmorpholin-3-yl]anilino]pyrazine-2-carboxamide and 5-methyl-6-(1-methylbenzimidazol-4-yl)-3-[4-[rel-(3R)-4-methylmorpholin-3-yl]anilino]pyrazine-2-carboxamide

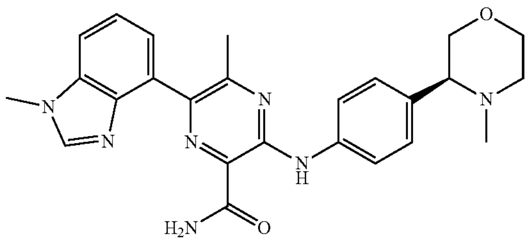

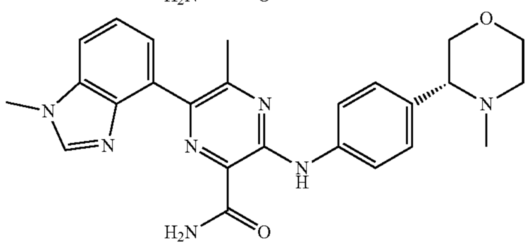

(a) Methyl 5-methyl-6-(1-methylbenzimidazol-4-yl)-3-(4-morpholin-3-ylanilino)pyrazine-2-carboxylate Brettphos Pd G3 (61 mg, 0.070 mmol) was added to a mixture of methyl 3-amino-5-methyl-6-(1-methylbenzimidazol-4-yl)pyrazine-2-carboxylate (200 mg, 0.67 mmol), 3-(4-bromophenyl) morpholine (163 mg, 0.670 mmol), and cesium carbonate (658 mg, 2.02 mmol) in 1,4-dioxane (10 mL) under nitrogen. The resulting mixture was stirred at 100° C. for 4 hours. The reaction was then concentrated. The resulting residue was purified by silica gel chromatography, using 0-20% MeOH-DCM as eluent, to afford methyl 5-methyl-6-(1-methylbenzimidazol-4-yl)-3-(4-morpholin-3-ylanilino)pyrazine-2-carboxylate (0.240 g, 78%) as a brown solid; 1H NMR (400 MHZ, DMSO-d6) δ 2.40 (3H, s), 3.23-3.27 (3H, m), 3.75-3.87 (1H, m), 3.91 (6H, s), 3.95-4.00 (2H, m), 4.36-4.44 (1H, m), 7.30 (1H, d), 7.41 (1H, t), 7.63 (2H, d), 7.70 (1H, d), 7.86 (2H, d), 8.24 (1H, s), 10.14 (1H, s), 10.25 (1H, s); m/z: (ES+), [M+H]+=459.2

(b) Methyl 5-methyl-6-(1-methylbenzimidazol-4-yl)-3-[4-(4-methylmorpholin-3-yl)anilino]pyrazine-2-carboxylate 37 wt % Aqueous formaldehyde (390 μL, 5.20 mmol) was added to methyl 5-methyl-6-(1-methylbenzimidazol-4-yl)-3-(4-morpholin-3-ylanilino)pyrazine-2-carboxylate (240 mg, 0.52 mmol) in MeOH (10 mL). The resulting mixture was stirred at 25 C for 5 minutes. Sodium triacetoxyborohydride (555 mg, 2.62 mmol) was added. The resulting mixture was stirred at 25 C for 30 minutes. The reaction was then concentrated. The resulting residue was redissolved in EtOAc, then washed sequentially with saturated aqueous sodium bicarbonate and brine. The organic layer was dried over sodium sulfate, filtered, and concentrated to afford methyl 5-methyl-6-(1-methylbenzimidazol-4-yl)-3-[4-(4-methylmorpholin-3-yl)anilino]pyrazine-2-carboxylate (0.230 g, 93%) as a yellow solid; 1H NMR (300 MHZ, DMSO-d6) δ 1.98 (3H, s), 2.17-2.32 (1H, m), 2.37 (3H, s), 2.81 (1H, d), 2.95-3.04 (1H, m), 3.20 (1H, s), 3.59 (2H, d), 3.81 (1H, d), 3.88 (6H, s), 7.28-7.45 (4H, m), 7.62-7.69 (1H, m), 7.71-7.78 (2H, m), 8.22 (1H, s), 10.07 (1H, s); m/z: (ES+), [M+H]+=473.2

(c) 5-Methyl-6-(1-methylbenzimidazol-4-yl)-3-[4-[rel-(3S)-4-methylmorpholin-3-yl]anilino]pyrazine-2-carboxamide and 5-methyl-6-(1-methylbenzimidazol-4-yl)-3-[4-[rel-(3R)-4-methylmorpholin-3-yl]anilino]pyrazine-2-carboxamide 7 N Methanolic ammonia (20 mL, 140 mmol) was added to methyl 5-methyl-6-(1-methylbenzimidazol-4-yl)-3-[4-(4-methylmorpholin-3-yl)anilino]pyrazine-2-carboxylate (220 mg, 0.47 mmol). The resulting mixture was stirred at 80° C. for 1 hour. The reaction was then concentrated. The resulting residue was purified by preparative HPLC, using a 5 micron, 30 mm×150 mm XBridge Shield RP18 OBD column, 5-20% MeCN—$H_2O$ as eluent, and 0.05% ammonium hydroxide as modifier, to afford a yellow solid. This material was further purified by preparative chiral-HPLC, using a 3 micron, 4.6 mm×100 mm CHIRAL Cellulose-SB column, isocratic 2:1:1 EtOH/hexanes/DCM as eluent, and 0.1% diethylamine as modifier, to afford 5-methyl-6-(1-methylbenzimidazol-4-yl)-3-[4-[rel-(3S)-4-methylmorpholin-3-yl]anilino]pyrazine-2-carboxamide (38 mg, 18%) and 5-methyl-6-(1-methylbenzimidazol-4-yl)-3-[4-[rel-(3R)-4-methylmorpholin-3-yl]anilino]pyrazine-2-carboxamide (40 mg, 20%), each as a yellow solid; 1H NMR (400 MHZ, DMSO-d6) δ 2.00 (3H, s), 2.27 (1H, t), 2.40 (3H, s), 2.83 (1H, d), 3.00 (1H, d), 3.20-3.31 (1H, m), 3.62 (2H, t), 3.83 (1H, d), 3.90 (3H, s), 7.33 (2H, d), 7.36-7.45 (2H, m), 7.63-7.72 (1H, m), 7.75 (2H, d), 7.89 (1H, d), 8.10 (1H, s), 8.25 (1H, s), 11.29 (1H, s); m/z: (ES+), [M+H]+=458.3

Examples 160 and 161

5-Methyl-6-(1-methylbenzimidazol-4-yl)-3-[4-[rel-(2R)-4-methylmorpholin-2-yl]anilino]pyrazine-2-carboxamide and 5-methyl-6-(1-methylbenzimidazol-4-yl)-3-[4-[rel-(2S)-4-methylmorpholin-2-yl]anilino]pyrazine-2-carboxamide

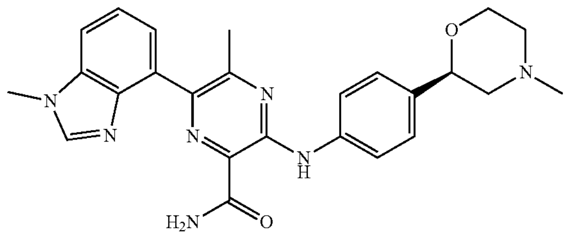

-continued

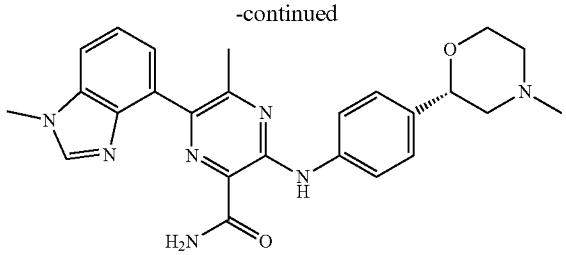

(a) Methyl 5-methyl-6-(1-methylbenzimidazol-4-yl)-3-(4-morpholin-2-ylanilino)pyrazine-2-carboxylate Brettphos Pd G3 (114 mg, 0.130 mmol) was added to a mixture of methyl 3-amino-5-methyl-6-(1-methylbenzimidazol-4-yl)pyrazine-2-carboxylate (250 mg, 0.84 mmol), 2-(4-bromophenyl) morpholine (204 mg, 0.84 mmol), and cesium carbonate (822 mg, 2.52 mmol) in 1,4-dioxane (15 mL) under nitrogen. The resulting mixture was stirred at 100° C. for 2 hours. The reaction was then concentrated. The resulting residue was purified by silica gel chromatography, using 0-10% MeOH-DCM as eluent, to afford methyl 5-methyl-6-(1-methylbenzimidazol-4-yl)-3-(4-morpholin-2-ylanilino)pyrazine-2-carboxylate (0.260 g, 67%) as a brown solid; 1H NMR (300 MHz, DMSO-d6) δ 2.30 (1H, s), 2.37 (3H, s), 3.10-3.24 (3H, m), 3.84-4.15 (8H, m), 4.75 (1H, d), 7.28 (1H, dd), 7.38 (3H, dd), 7.68 (1H, dd), 7.79 (2H, d), 8.23 (1H, s), 10.09 (1H, s); m/z: (ES+), [M+H]+=459.2

(b) Methyl 5-methyl-6-(1-methylbenzimidazol-4-yl)-3-[4-(4-methylmorpholin-2-yl)anilino]pyrazine-2-carboxylate Sodium triacetoxyborohydride (277 mg, 1.31 mmol) was added to a mixture of 37 wt % aqueous formaldehyde (36.0 μL, 1.31 mmol) and methyl 5-methyl-6-(1-methylbenzimidazol-4-yl)-3-(4-morpholin-2-ylanilino)pyrazine-2-carboxylate (200 mg, 0.44 mmol) in MeOH (20 mL). The resulting mixture was stirred at 25° C. for 1 hour. The reaction mixture was then diluted with DCM (50 mL) and washed three times with water (50 mL each). The organic layer was dried over sodium sulfate, filtered, and concentrated to afford methyl 5-methyl-6-(1-methylbenzimidazol-4-yl)-3-[4-(4-methylmorpholin-2-yl)anilino]pyrazine-2-carboxylate (0.150 g, 73%) as a yellow solid; 1H NMR (300 MHz, DMSO-d6) δ 1.85-1.97 (1H, m), 1.98-2.15 (1H, m), 2.21 (3H, s), 2.39 (3H, s), 2.64-2.74 (1H, m), 2.80-2.91 (1H, m), 3.61-3.77 (1H, m), 3.90 (3H, s), 3.91 (3H, s), 3.94-3.97 (1H, m), 4.41-4.54 (1H, m), 7.25-7.48 (4H, m), 7.72 (3H, dd), 8.24 (1H, s), 10.07 (1H, s); m/z: (ES+), [M+H]+=473.2

(c) 5-Methyl-6-(1-methylbenzimidazol-4-yl)-3-[4-[rel-(2R)-4-methylmorpholin-2-yl]anilino]pyrazine-2-carboxamide and 5-methyl-6-(1-methylbenzimidazol-4-yl)-3-[4-[rel-(2S)-4-methylmorpholin-2-yl]anilino]pyrazine-2-carboxamide 7 N Methanolic ammonia (1.50 mL, 10.5 mmol) was added to a suspension of methyl 5-methyl-6-(1-methylbenzimidazol-4-yl)-3-[4-(4-methylmorpholin-2-yl)anilino]pyrazine-2-carboxylate (200 mg, 0.42 mmol) in MeOH (1 mL). The resulting suspension was stirred at 80° C. for 24 hours. The reaction was then concentrated. The resulting residue was purified by chiral HPLC, using a 5 micron, 2 cm×25 cm ChiralPak IE column, isocratic 20% MeOH-MTBE as eluent, to afford 5-methyl-6-(1-methylbenzimidazol-4-yl)-3-[4-[rel-(2R)-4-methylmorpholin-2-yl]anilino]pyrazine-2-carboxamide (25 mg, 31%) and 5-methyl-6-(1-methylbenzimidazol-4-yl)-3-[4-[rel-(2S)-4-methylmorpholin-2-yl]anilino]pyrazine-2-carboxamide (22 mg, 28%), each as a yellow solid. 1H NMR (300 MHz, DMSO-d6) δ 1.82-2.01 (1H, m), 2.05-2.18 (1H, m), 2.24 (3H, s), 2.41 (3H, s), 2.66-2.78 (1H, m), 2.79-2.96 (1H, m), 3.59-3.76 (1H, m), 3.90 (3H, s), 3.93-3.99 (1H, m), 4.43-4.50 (1H, m), 7.34 (2H, d), 7.41 (1H, d), 7.43 (1H, s), 7.66-7.71 (1H, m), 7.71-7.78 (2H, m), 7.91 (1H, s), 8.11 (1H, s), 8.25 (1H, s), 11.29 (1H, s); m/z: (ES+), [M+H]+=458.3

Example 162

5-(Methylamino)-6-(3-methylimidazo[4,5-c]pyridin-7-yl)-3-[4-(4-piperidyloxy)anilino]pyrazine-2-carboxamide

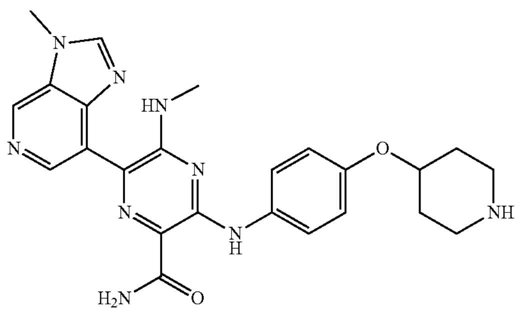 [SMILES: CNc1nc(Nc2ccc(OC3CCNCC3)cc2)c(C(N)=O)nc1-c1cncc2c1ncn2C]

(a) Methyl 5-(methylamino)-6-(3-methylimidazo[4,5-c]pyridin-7-yl)-3-[4-(4-piperidyloxy)anilino]pyrazine-2-carboxylate BrettPhos Pd G3 (104 mg, 0.110 mmol) was added to a suspension of cesium carbonate (936 mg, 2.87 mmol), tert-butyl 4-(4-bromophenoxy) piperidine-1-carboxylate (853 mg, 2.39 mmol), and methyl 3-amino-5-(methylamino)-6-(3-methylimidazo[4,5-c]pyridin-7-yl)pyrazine-2-carboxylate (300 mg, 0.96 mmol) in 1,4-dioxane (20 mL). The resulting mixture was stirred at 100° C. for 2 hours. The reaction was then concentrated. The resulting solid was added to a stirred mixture of thionyl chloride (2.00 mL, 27.4 mmol) in MeOH (20 mL). The resulting mixture was stirred at 60° C. for 10 minutes. The reaction was then concentrated. The resulting residue was purified by silica gel chromatography, using 0-20% MeOH-DCM as eluent, to afford methyl 5-(methylamino)-6-(3-methylimidazo[4,5-c]pyridin-7-yl)-3-[4-(4-piperidyloxy)anilino]pyrazine-2-carboxylate (350 mg, 75%) as a yellow solid; 1H NMR (300 MHz, DMSO-d6) δ 1.76-1.92 (2H, m), 2.02-2.18 (2H, m), 2.87 (3H, d), 3.02-3.12 (2H, m), 3.20-3.26 (2H, m) 3.82 (3H, s), 4.12 (3H, s), 4.57-4.66 (1H, m), 7.04 (2H, d), 7.59 (1H, q), 7.73 (2H, d), 8.70 (1H, s), 8.74-8.88 (1H, m) 8.95 (1H, s), 9.54 (1H, s), 10.35 (1H, s). m/z: (ES+), [M+H]+=489.3

(b) 5-(Methylamino)-6-(3-methylimidazo[4,5-c]pyridin-7-yl)-3-[4-(4-piperidyloxy)anilino]pyrazine-2-carboxamide 7 N Methanolic ammonia (1.0 mL, 7.0 mmol) was added to a suspension of methyl 6-(3-methyl-3H-imidazo[4,5-c]pyridin-7-yl)-5-(methylamino)-3-((4-(piperidin-4-yloxy)phenyl)amino) pyrazine-2-carboxylate (15 mg, 0.03 mmol) in MeOH (2 mL). The resulting mixture was stirred at 80° C. for 24 hours. The reaction was then concentrated. The resulting residue was purified by preparative HPLC Column, using a 19 mm×250 mm, 5 micron, XSelect CSH C18 OBD column, using 8-12% MeCN—$H_2O$ as eluent and 0.1% formic acid as modifier, to afford 5-(methylamino)-6-(3-methylimidazo[4,5-c]pyridin-7-yl)-3-[4-(4-piperidyloxy)anilino]pyrazine-2-carboxamide (5.0 mg, 34%) as a yellow solid; 1H NMR (300 MHz, DMSO-d6) δ 1.65-1.74 (2H, m), 2.03 (2H, m), 2.82-2.98 (5H, m), 3.09-3.19 (2H, m), 4.02 (3H, s), 4.45-4.60 (1H, m), 6.94-7.03 (2H, m), 7.30-7.37 (1H, m), 7.66-7.75 (3H, m), 8.01 (1H, br q), 8.34 (1H, s), 8.52 (1H, s), 8.73 (1H, s), 9.02 (1H, s), 11.35 (1H, s). m/z: (ES+), [M+H]+=474.3

Example 163

3-[4-[(1-Acetyl-4-piperidyl)oxy]anilino]-5-(methylamino)-6-(3-methylimidazo[4,5-c]pyridin-7-yl)pyrazine-2-carboxamide

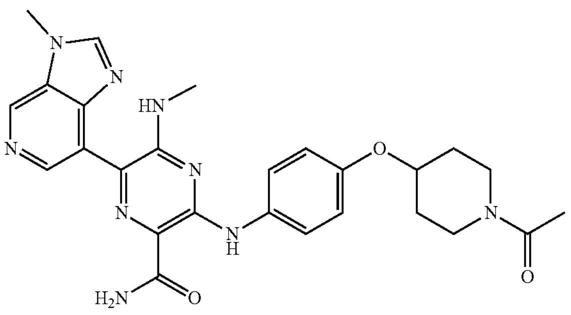 [SMILES: CNc1nc(Nc2ccc(OC3CCN(C(C)=O)CC3)cc2)c(C(N)=O)nc1-c1cncc2c1ncn2C]

(a) Methyl 3-[4-[(1-acetyl-4-piperidyl)oxy]anilino]-5-(methylamino)-6-(3-methylimidazo[4,5-c]pyridin-7-yl)pyrazine-2-carboxylate DMAP (2 mg, 0.02 mmol) was added to a solution of triethylamine (0.69 mL, 0.49 mmol), acetic anhydride (33 mg, 0.33 mmol) and methyl 5-(methylamino)-6-(3-methylimidazo[4,5-c]pyridin-7-yl)-3-[4-(4-piperidyloxy)anilino]pyrazine-2-carboxylate (80 mg, 0.16 mmol) in DCM (20 mL). The resulting mixture was stirred at 25° C. for 1 hour. The reaction was then washed three times with water (50 mL each). The organic layer was dried over sodium sulfate, filtered, and concentrated to afford methyl 3-[4-[(1-acetyl-4-piperidyl)oxy]anilino]-5-(methylamino)-6-(3-methylimidazo[4,5-c]pyridin-7-yl)pyrazine-2-carboxylate (80 mg, 92%) as a yellow solid; 1H NMR (300 MHz, DMSO-d6) δ 1.37-1.77 (2H, m), 1.88 (2H, d), 2.02 (3H, s), 2.90 (3H, d), 3.05-3.25 (1H, m), 3.31-3.35 (1H, m), 3.67 (1H, s), 3.83 (3H, s), 3.87-3.91 (1H, m), 4.02 (3H, s), 4.31-4.77 (1H, m), 7.01 (2H, d), 7.71 (2H, d), 7.93 (1H, d), 8.50 (1H, s), 8.54 (1H, s), 9.05 (1H, s), 10.29 (1H, s); m/z: (ES+), [M+H]+=531.3

(b) 3-[4-[(1-Acetyl-4-piperidyl)oxy]anilino]-5-(methylamino)-6-(3-methylimidazo[4,5-c]pyridin-7-yl)pyrazine-2-carboxamide 7 N Methanolic ammonia (5.0 mL, 35 mmol) was added to a suspension of methyl 3-[4-[(1-acetyl-4-piperidyl)oxy]

anilino]-5-(methylamino)-6-(3-methylimidazo[4,5-c]pyridin-7-yl)pyrazine-2-carboxylate (70 mg, 0.13 mmol) in MeOH (20 mL). The resulting mixture was stirred at 70° C. for 24 hours. The resulting residue was purified by preparative HPLC Column, using a 19 mm×250 mm, 5 micron, XSelect CSH C18 OBD column, using 25-35% MeCN—$H_2O$ as eluent and 0.1% formic acid as modifier, to afford 3-[4-[(1-acetyl-4-piperidyl)oxy]anilino]-5-(methylamino)-6-(3-methylimidazo[4,5-c]pyridin-7-yl)pyrazine-2-carboxamide (33 mg, 47%) as a yellow solid; 1H NMR (300 MHz, DMSO-d6) δ 1.56 (2H, m), 1.80-2.05 (5H, m), 2.94 (3H, d), 3.17-3.31 (2H, m), 3.63-3.77 (1H, m), 3.80-3.93 (1H, m), 4.02 (3H, s), 4.55 (1H, m), 6.95-7.08 (2H, m), 7.34 (1H, d), 7.66-7.78 (3H, m), 8.01 (1H, br q), 8.53 (1H, s), 8.74 (1H, s), 9.03 (1H, s), 11.36 (1H, s). m/z: (ES+), [M+H]+=516.2

Example 164

5-(Methylamino)-6-(3-methylimidazo[4,5-c]pyridin-7-yl)-3-[4-[(1-methyl-4-piperidyl)oxy]anilino]pyrazine-2-carboxamide

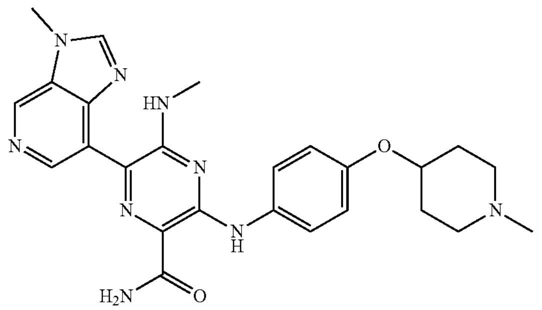 [SMILES: CNc1nc(Nc2ccc(OC3CCN(C)CC3)cc2)c(C(N)=O)nc1-c1cncc2c1ncn2C]

(a) Methyl 5-(methylamino)-6-(3-methylimidazo[4,5-c]pyridin-7-yl)-3-[4-[(1-methyl-4-piperidyl)oxy]anilino]pyrazine-2-carboxylate Sodium triacetoxyborohydride (26 mg, 0.12 mmol) was added to a solution of 35 wt % aqueous formaldehyde (19 μL, 0.25 mmol) and methyl 6-(3-methyl-3H-imidazo[4,5-c]pyridin-7-yl)-5-(methylamino)-3-((4-(piperidin-4-yloxy)phenyl)amino) pyrazine-2-carboxylate (60 mg, 0.12 mmol) in MeOH (10 mL). The resulting mixture was stirred at 25° C. for 30 minutes. The reaction was then concentrated. The resulting residue was redissolved in DCM (100 mL), and washed three times with brine (50 mL each). The organic layer was dried over sodium sulfate, filtered, and concentrated to afford methyl 5-(methylamino)-6-(3-methylimidazo[4,5-c]pyridin-7-yl)-3-[4-[(1-methyl-4-piperidyl)oxy]anilino]pyrazine-2-carboxylate (0.050 g, 81%) as a yellow solid; 1H NMR (300 MHz, DMSO-d6) δ 1.73-2.39 (4H, m), 2.77 (3H, s), 2.90 (3H, d), 3.00-3.30 (4H, m), 3.83 (3H, s), 4.02 (3H, s), 4.39-4.93 (1H, m), 7.05 (2H, d), 7.75 (2H, d), 7.92 (1H, br q), 8.50 (1H, s), 8.54 (1H, s), 9.05 (1H, s), 10.32 (1H, s); m/z: (ES+), [M+H]+=503.3

(b) 5-(Methylamino)-6-(3-methylimidazo[4,5-c]pyridin-7-yl)-3-[4-[(1-methyl-4-piperidyl)oxy]anilino]pyrazine-2-carboxamide 7 N Methanolic ammonia (1 mL, 7 mmol) was added to a suspension of methyl 5-(methylamino)-6-(3-methylimidazo[4,5-c]pyridin-7-yl)-3-[4-[(1-methyl-4-piperidyl)oxy]anilino]pyrazine-2-carboxylate (60 mg, 0.12 mmol) in MeOH (2 mL). The resulting mixture was stirred at 80° C. for 24 hours. The reaction was then concentrated. The resulting residue was purified by preparative HPLC Column, using a 19 mm×250 mm, 5 micron, XSelect CSH C18 OBD column, using 8-12% MeCN—$H_2O$ as eluent and 0.1% formic acid as modifier, to afford 5-(methylamino)-6-(3-methylimidazo[4,5-c]pyridin-7-yl)-3-[4-[(1-methyl-4-piperidyl)oxy]anilino]pyrazine-2-carboxamide (28 mg, 45%) as a yellow solid; 1H NMR (300 MHz, DMSO-d6) δ 1.69-1.83 (2H, m), 1.94-2.05 (2H, m), 2.47 (3H, s), 2.63-2.77 (2H, m), 2.84-3.02 (5H, m), 4.02 (3H, s), 4.43 (1H, m), 6.93-7.03 (2H, m), 7.34 (1H, s), 7.69-7.73 (2H, m), 8.00 (1H, m), 8.15 (1H, s), 8.52 (1H, s), 8.73 (1H, s), 9.02 (1H, s), 11.36 (1H, s); m/z: (ES+), [M+H]+=488.3

Example 165

3-[4-[[1-(2-Hydroxyacetyl)-4-piperidyl]oxy]anilino]-5-(methylamino)-6-(3-methylimidazo[4,5-c]pyridin-7-yl)pyrazine-2-carboxamide

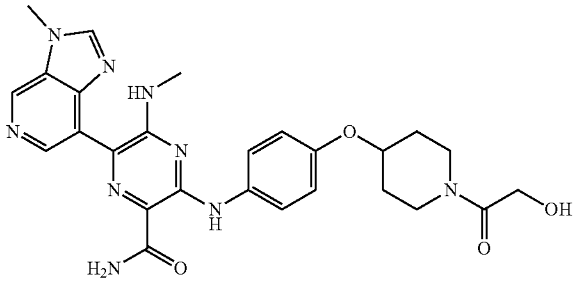 [SMILES: CNc1nc(Nc2ccc(OC3CCN(C(=O)CO)CC3)cc2)c(C(N)=O)nc1-c1cncc2c1ncn2C]

(a) Methyl 3-[4-[[1-(2-hydroxyacetyl)-4-piperidyl]oxy]anilino]-5-(methylamino)-6-(3-methylimidazo[4,5-c]pyridin-7-yl)pyrazine-2-carboxylate DMAP (2 mg, 0.02 mmol) was added to a solution of 2-hydroxyacetic acid (31 mg, 0.41 mmol), HATU (93 mg, 0.25 mmol), triethylamine (69 μL, 0.49 mmol) and methyl 6-(3-methyl-3H-imidazo[4,5-c]pyridin-7-yl)-5-(methylamino)-3-((4-(piperidin-4-yloxy)phenyl)amino) pyrazine-2-carboxylate (80 mg, 0.16 mmol) in DCM (20 mL). The resulting mixture was stirred at 25° C. for 2 hours. The reaction was washed three times with water (50 mL each). The organic layer was concentrated to afford methyl 3-[4-[[1-(2-hydroxyacetyl)-4-piperidyl]oxy]anilino]-5-(methylamino)-6-(3-methylimidazo[4,5-c]pyridin-7-yl)pyrazine-2-carboxylate (0.080 g, 89%) as a yellow solid; 1H NMR (300 MHz, DMSO-d6) δ 1.42-1.65 (2H, m), 1.90-2.00 (2H, m), 2.90 (3H, d), 3.50-3.66 (1H, m), 3.83 (3H, s), 3.85-3.92 (1H, s), 4.02 (3H, s), 4.11 (3H, s), 4.47-4.60 (2H, m), 5.76 (1H, s), 7.01 (2H, d), 7.72 (2H, d), 7.92 (1H, br q), 8.51 (1H, s), 8.55 (1H, s), 9.06 (1H, s), 10.29 (1H, s); m/z: (ES+), [M+H]+=547.3

(b) 3-[4-[[1-(2-Hydroxyacetyl)-4-piperidyl]oxy]anilino]-5-(methylamino)-6-(3-methylimidazo[4,5-c]pyridin-7-yl)pyrazine-2-carboxamide 7 N Methanolic ammonia (5.0 mL, 35 mmol) was added to a suspension of methyl 3-[4-[[1-(2-hydroxyacetyl)-4- piperidyl]oxy]anilino]-5-(methylamino)-6-(3-methylimidazo[4,5-c]pyridin-7-yl)pyrazine-2-carboxylate (70 mg, 0.13 mmol) in MeOH (5 mL). The resulting mixture was stirred at 80° C. for 24 hours. The reaction was then concentrated. The resulting residue was purified by preparative HPLC Column, using a 19 mm×250 mm, 5 micron, XSelect CSH C18 OBD column, using 23-33% MeCN—$H_2O$ as eluent and 0.1% formic acid as modifier, to afford 3-[4-[[1-(2-hydroxyacetyl)-4-piperidyl]oxy]anilino]-5-(methylamino)-6-(3-methylimidazo[4,5-c]pyridin-7-yl)pyrazine-2-carboxamide (28 mg, 41%) as a yellow solid; 1H NMR (300 MHz, DMSO-d6) δ 1.46-1.68 (2H, m), 1.86-2.03 (2H, m), 2.94 (3H, d), 3.14-3.22 (2H, m), 3.52-3.64 (1H, m), 3.82-3.93 (1H, m), 4.04 (3H, s), 4.11 (2H, s), 4.47-4.77 (2H, m), 7.00 (2H, d), 7.36 (1H, s), 7.71 (2H, d), 7.76 (1H, s), 7.98 (1H, br q), 8.61 (1H, s), 8.78 (1H, s), 9.10 (1H, s), 11.37 (1H, s); m/z: (ES+), [M+H]+=532.3

Example 166

5-Methoxy-6-(3-methylimidazo[4,5-c]pyridin-7-yl)-3-[4-[(1-methyl-4-piperidyl)oxy]anilino]pyrazine-2-carboxamide

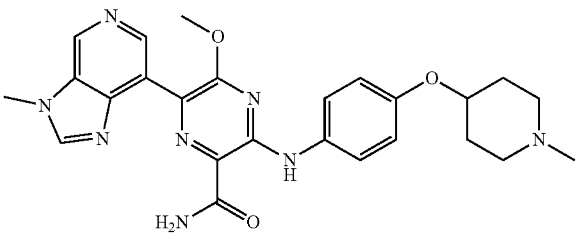

(a) Methyl 3-[4-[(1-tert-butoxycarbonyl-4-piperidyl)oxy]anilino]-6-chloro-5-methoxy-pyrazine-2-carboxylate DIPEA (410 μL, 2.5 mmol) was added to a solution of methyl 6-chloro-3-fluoro-5-methoxy-pyrazine-2-carboxylate (500 mg, 2.27 mmol) and tert-butyl 4-(4-aminophenoxy) piperidine-1-carboxylate (696 mg, 2.38 mmol) in DMF (1.9 mL). The resulting solution was stirred at 100° C. for 1 hour. It was then allowed to cool to room temperature and diluted with EtOAc (5 mL) and water (5 mL). The layers were separated and the aqueous layer was extracted three times with EtOAc (5 mL each). The combined organic layers were washed twice with brine (5 mL each), dried over sodium sulfate, and concentrated. The resulting residue was purified by silica gel chromatography, using 0-40% MeOH-DCM as eluent, to afford methyl 3-[4-[(1-tert-butoxycarbonyl-4-piperidyl)oxy]anilino]-6-chloro-5-methoxy-pyrazine-2-carboxylate (200 mg, 18% yield) as a brown solid. m/z: (ES−), [M−H]−=491.1.

(b) Methyl 3-[4-[(1-tert-butoxycarbonyl-4-piperidyl)oxy]anilino]-5-methoxy-6-(3-methylimidazo[4,5-c]pyridin-7-yl)pyrazine-2-carboxylate 7-Bromo-3-methyl-imidazo[4,5-c]pyridine (500 mg, 2.36 mmol), Bis(pinacolato)diboron (1.50 g, 5.89 mmol), cataCXium A (85 mg, 0.24 mmol), cataCXium A Pd G3 (172 mg, 0.240 mmol), and potassium acetate (694 mg, 7.07 mmol) were added to a vial. DMF (11.8 mL) was then added. The resulting mixture was sparged with nitrogen for 5 minutes, then and stirred at 80° C. for 16 hours. It was then cooled to room temperature and set aside.

A mixture of cesium fluoride (185 mg, 1.22 mmol), Pd(dppf) C12 DCM adduct (30 mg, 0.04 mmol), and methyl 3-[4-[(1-tert-butoxycarbonyl-4-piperidyl)oxy]anilino]-6-chloro-5-methoxy-pyrazine-2-carboxylate (200 mg, 0.41 mmol) was combined in a vial, which was evacuated and backfilled three times with nitrogen. A portion (2.03 mL) of the borylation mixture was added via syringe. The resulting suspension was stirred at 100° C. for 3 hours. The reaction was then allowed to cool to room temperature and diluted with $H_2O$ (30 mL) and DCM (30 mL). The layers were separated and the aqueous layer was extracted three times with DCM (30 mL each). The organic layers were combined, dried over $Na_2SO_4$, and concentrated. The resulting residue was then loaded onto celite and purified by silica gel chromatography, using 0-20% MeOH-DCM as eluent, to afford methyl 3-[4-[(1-tert-butoxycarbonyl-4-piperidyl)oxy]anilino]-5-methoxy-6-(3-methylimidazo[4,5-c]pyridin-7-yl)pyrazine-2-carboxylate (0.112 g, 47%) as a brown solid; 1H NMR (500 MHz, DMSO-d6) δ 1.40 (9H, s), 1.46-1.57 (2H, m), 1.82-1.97 (2H, m), 3.09-3.22 (2H, m), 3.61-3.72 (2H, m), 3.85 (3H, s), 3.86 (3H, s), 3.97 (3H, s), 4.41-4.62 (1H, m), 7.01 (2H, d), 7.64 (2H, d), 8.36 (1H, s), 8.36 (1H, s), 9.00 (1H, s), 10.20 (1H, s); m/z: (ES−), [M−H]−=588.2

(c) Methyl 5-methoxy-6-(3-methylimidazo[4,5-c]pyridin-7-yl)-3-[4 (4-piperidyloxy)anilino]pyrazine-2-carboxylate 2,2,2-Trifluoroacetic acid (440 μL, 5.70 mmol) was added to a solution of methyl 3-[4-[(1-tert-butoxycarbonyl-4-piperidyl)oxy]anilino]-5-methoxy-6-(3-methylimidazo[4,5-c]pyridin-7-yl)pyrazine-2-carboxylate (112 mg, 0.19 mmol) in DCM (0.51 mL). The resulting solution was stirred at room temperature for 15 minutes. The reaction was then concentrated to yield methyl 5-methoxy-6-(3-methylimidazo[4,5-c]pyridin-7-yl)-3-[4-(4-piperidyloxy)anilino]pyrazine-2-carboxylate (0.089 g, 96%) as a yellow gum. The product was used without further purification; m/z: (ES+), [M+H]+=490.3

(d) 5-Methoxy-6-(3-methylimidazo[4,5-c]pyridin-7-yl)-3-[4-[(1-methyl-4-piperidyl)oxy]anilino]pyrazine-2-carboxamide Sodium triacetoxyborohydride (58 mg, 0.28 mmol) was added portionwise to a stirred solution of methyl 5-methoxy-6-(3-methylimidazo[4,5-c]pyridin-7-yl)-3-[4-(4-piperidyloxy)anilino]pyrazine-2-carboxylate (89 mg, 0.18 mmol) and 37 wt % aqueous formaldehyde (21 μL, 0.28 mmol) in DCM (1.82 mL) under nitrogen. The resulting solution was stirred at room temperature for 1 hour. The reaction was then diluted with saturated aqueous sodium bicarbonate (5 mL) and DCM (5 mL). The layers were separated, and the aqueous layer was extracted twice with DCM (5 mL each). The combined organic layers were dried over sodium sulfate and concentrated. The resulting residue was treated with 7 N methanolic ammonia (2.0 mL, 14 mmol). The resulting mixture was stirred at 100° C. for 2 hours in a Biotage microwave reactor. The reaction was then concentrated. The resulting residue was purified by preparative HPLC using a 5 micron, 30 mm×150 mm Xselect CSH OBD column, 25-50% MeCN—$H_2O$ as eluent, and 0.2% $NH_4OH$ as modifier, to afford 5-methoxy-6-(3-methylimidazo[4,5-c]pyridin-7-yl)-3-[4-[(1-methyl-4-piperidyl)oxy]anilino]pyrazine-2-carboxamide (14 mg, 16%) as a yellow solid; 1H NMR (500 MHz, DMSO-d6) δ 1.36-1.50 (1H, m), 1.54-1.68 (1H, m), 1.83-1.97 (2H, m), 2.10-2.20 (3H, m), 2.53-2.65 (2H, m), 2.86-2.99 (1H, m), 3.92 (3H, s), 3.97 (3H, s), 4.25-4.37 (1H, m), 6.91-7.02 (2H, m), 7.56-7.65 (2H, m), 7.68 (1H, br s), 7.95 (1H, br s), 8.39 (1H, s), 8.61 (1H, s), 8.97 (1H, s), 11.24 (1H, br s); m/z: (ES+), [M+H]+=489.2

Example 167

5-Cyclopropyl-6-(3-methylimidazo[4,5-c]pyridin-7-yl)-3-[4-[(1-methyl-4-piperidyl)oxy]anilino]pyrazine-2-carboxamide

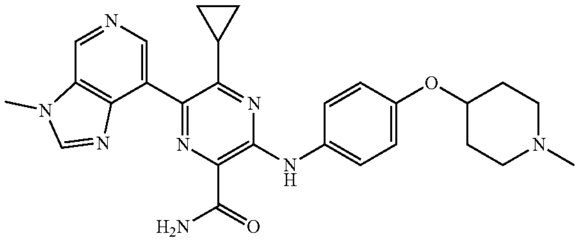

(a) Methyl 3-[4-[(1-tert-butoxycarbonyl-4-piperidyl)oxy]anilino]-6-chloro-5-cyclopropyl-pyrazine-2-carboxylate Sodium nitrite (71.0 mg, 1.03 mmol) was added to a solution of methyl 3-amino-6-chloro-5-cyclopropyl-pyrazine-2-carboxylate (223 mg, 0.980 mmol) in HF-pyridine (3.0 mL, 87 mmol) at 0 C. The reaction was stirred at 25 C for 30 minutes. Additional sodium nitrite (20 mg, 0.29 mmol) was added in two portions over two hours. The reaction was then diluted with DCM (5 mL) and quenched with water (10 mL). The layers were separated and the aqueous layer was extracted twice with DCM (10 mL each). The combined organic layers were dried over magnesium sulfate, filtered, and concentrated. The resulting residue was dissolved in DMF (3 mL). Tert-butyl 4-(4-aminophenoxy)piperidine-1-carboxylate (0.301 g, 1.03 mmol) and DIPEA (0.200 mL, 1.15 mmol) were sequentially added. The resulting mixture was stirred at 100 C for 2 hours. The reaction was then allowed to cool to room temperature, diluted with EtOAc (15 mL), and quenched with water (50 mL). The layers were separated and the aqueous layer was extracted twice with EtOAc (10 mL each). The combined organic layers were dried over sodium sulfate, filtered, and concentrated. The resulting residue was purified by silica gel chromatography, using 0-40% EtOAc-hexanes as eluent, to afford methyl 3-[4-[(1-tert-butoxycarbonyl-4-piperidyl)oxy]anilino]-6-chloro-5-cyclopropyl-pyrazine-2-carboxylate (0.247 g, 50%) as a yellow solid; 1H NMR (500 MHZ, DMSO-d6) 1.02 (2H, dt), 1.13-1.22 (2H, m), 1.40 (9H, s), 1.44-1.57 (2H, m), 1.84-1.95 (2H, m), 2.39-2.44 (1H, m), 3.15 (2H, br d), 3.58-3.73 (2H, m), 3.89 (3H, s), 4.45-4.56 (1H, m), 6.96 (2H, d), 7.42 (2H, d), 9.77 (1H, s); m/z: (ES+), [M+H]+=503.3

(b) Methyl 3-[4-[(1-tert-butoxycarbonyl-4-piperidyl)oxy]anilino]-5-cyclopropyl-6-(3-methylimidazo[4,5-c]pyridin-7-yl)pyrazine-2-carboxylate 7-Bromo-3-methyl-imidazo[4,5-c]pyridine (156 mg, 0.740 mmol), bis(pinacolato)diboron (468 mg, 1.84 mmol), cataCXium A Pd G3 (54 mg, 0.070 mmol), cataCXium A (26 mg, 0.070 mmol), and potassium acetate (217 mg, 2.21 mmol) were combined in a microwave vial, which was evacuated and backfilled three times with nitrogen. DMF (3.7 mL) was added and the reaction was stirred at 80 C for 24 hours. The reaction was then allowed to cool to room temperature and set aside.

Separately, methyl 3-[4-[(1-tert-butoxycarbonyl-4-piperidyl)oxy]anilino]-6-chloro-5-cyclopropyl-pyrazine-2-carboxylate (247 mg, 0.490 mmol), Pd(dppf) C12*dichloromethane adduct (40 mg, 0.05 mmol), and cesium fluoride (224 mg, 1.47 mmol) were combined in a scintillation vial, which was evacuated and backfilled three times with nitrogen. The borylation mixture was added by syringe. The resulting mixture was stirred at 100 C for 2 hours. The reaction mixture was then loaded directly onto celite and purified by silica gel chromatography, using 0-7% MeOH-DCM as eluent and 0-0.7% ammonia as modifier, to afford methyl 3-[4-[(1-tert-butoxycarbonyl-4-piperidyl)oxy]anilino]-5-cyclopropyl-6-(3-methylimidazo[4,5-c]pyridin-7-yl)pyrazine-2-carboxylate (0.156 g, 53%) as a dark yellow residue; 1H NMR (500 MHZ, dichloromethane-d20.87-0.94 (2H, m), 1.15-1.18 (2H, m), 1.45 (9H, s), 1.72 (2H, dtd), 1.86-1.98 (3H, m), 3.20-3.33 (2H, m), 3.68-3.78 (2H, m), 3.94 (3H, s), 3.96 (3H, s), 4.43 (1H, td), 6.93 (2H, br d), 7.56 (2H, br d), 8.01 (1H, s), 8.53 (1H, br s), 8.91 (1H, br s), 10.07 (1H, s). m/z: (ES+), [M+H]+=599.8

(c) Methyl 5-cyclopropyl-6-(3-methylimidazo[4,5-c]pyridin-7-yl)-3-[4-[(1-methyl-4-piperidyl)oxy]anilino]pyrazine-2-carboxylate TFA (0.5 mL, 6.49 mmol) was added to a solution of methyl 3-[4-[(1-tert-butoxycarbonyl-4-piperidyl)oxy]anilino]-5-cyclopropyl-6-(3-methylimidazo[4,5-c]pyridin-7-yl)pyrazine-2-carboxylate (156 mg, 0.26 mmol) in DCM (1.5 mL). The resulting solution was stirred at 25 C for 90 minutes. The reaction was then concentrated. The resulting dark yellow solid was dissolved in DCM (2 mL). 37 wt % aqueous formaldehyde (0.03 mL, 0.40 mmol) and sodium triacetoxyhydroborate (83 mg, 0.39 mmol) were sequentially added. The resulting mixture was stirred at 25 C for 30 minutes. Additional 37 wt % aqueous formaldehyde (0.100 mL, 1.20 mmol) was added and the reaction was stirred at 25 C for 30 minutes. Additional sodium triacetoxyborohydride (180 mg, 0.85 mmol) was added and the reaction was stirred at 25 C for 30 minutes. Additional sodium triacetoxyborohydride (100 mg, 0.47 mmol) was added and the reaction was stirred at 25 C for 15 minutes. The reaction was quenched with saturated aqueous sodium bicarbonate (15 mL) and extracted three times with DCM (10 mL each). The combined organic layers were dried over sodium sulfate, filtered, and concentrated. The resulting yellow residue was purified by silica gel chromatography, using 0-10% MeOH-DCM as eluent and 0-1% ammonia as modifier, to afford methyl 5-cyclopropyl-6-(3-methylimidazo[4,5-c]pyridin-7-yl)-3-[4-[(1-methyl-4-piperidyl)oxy]anilino]pyrazine-2-carboxylate (0.088 g, 66%) as a yellow solid; 1H NMR (500 MHz, DMSO-d6) 0.83-0.95 (2H, m), 0.97-1.06 (2H, m), 1.57-1.76 (2H, m), 1.83 (1H, td), 1.89-2.01 (2H, m), 2.17-2.39 (5H, m), 2.65-2.84 (2H, m), 3.87 (3H, s), 3.99 (3H, s), 4.37 (1H, br s), 6.97 (2H, d), 7.53 (2H, d), 8.39 (1H, s), 8.42 (1H, s), 9.05 (1H, s), 9.91 (1H, s); m/z: (ES+), [M+H]+=514.3

(d) 5-Cyclopropyl-6-(3-methylimidazo[4,5-c]pyridin-7-yl)-3-[4-[(1-methyl-4-piperidyl)oxy]anilino] pyrazine-2-carboxamide 7 N Methanolic ammonia (2.0 mL, 14 mmol) was added to methyl 5-cyclopropyl-6-(3-methylimidazo[4,5-c]pyridin-7-yl)-3-[4-[(1-methyl-4-piperidyl)oxy]anilino]pyrazine-2-carboxylate (88 mg, 0.17 mmol). The resulting yellow solution was stirred at 100 C for 1 h in a Biotage microwave reactor. The reaction was allowed to cool to room temperature. The resulting yellow suspension was filtered and rinsed sparingly with MeOH to afford 5-cyclopropyl-6-(3-methylimidazo[4,5-c]pyridin-7-yl)-3-[4-[(1-methyl-4-piperidyl) oxy]anilino]pyrazine-2-carboxamide (48 mg, 56%) as a yellow solid; 1H NMR (500 MHz, DMSO-d6) 0.79-0.96 (2H, m), 0.99-1.09 (2H, m), 1.54-1.70 (2H, m), 1.85-1.97 (3H, m), 2.06-2.22 (5H, m), 2.56-2.66 (2H, m), 3.99 (3H, s), 4.30 (1H, td), 6.94 (2H, d), 7.53 (2H, d), 7.79 (1H, br d), 8.05 (1H, br s), 8.43 (1H, s), 8.52 (1H, s), 9.03 (1H, s), 11.08 (1H, s); m/z: (ES+), [M+H]+=499.4

Example 168

3-[3,5-Difluoro-4-[(1-methyl-4-piperidyl)oxy]anilino]-5-(methylamino)-6-(3-methylimidazo[4,5-c] pyridin-7-yl)pyrazine-2-carboxamide

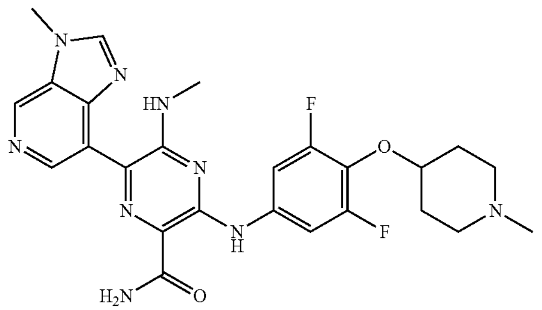 [SMILES: CNc1nc(Nc2cc(F)c(OC3CCN(C)CC3)c(F)c2)c(C(N)=O)nc1-c1cncc2c1ncn2C]

(a) tert-Butyl 4-(4-bromo-2,6-difluoro-phenoxy) piperidine-1-carboxylate

4-Bromo-2,6-difluoro-phenol (1.00 g, 4.78 mmol) and potassium carbonate (1.98 g, 14.4 mmol) were added to tert-butyl 4-methylsulfonyloxypiperidine-1-carboxylate (2.01 g, 7.18 mmol) in DMSO (20 mL). The resulting mixture was stirred at 80° C. for 2 hours. The reaction was then diluted with EtOAc (300 mL) and washed with brine three times (300 mL each). The organic layer was dried over $MgSO_4$, filtered, and concentrated. The resulting residue was purified by C18 reverse phase chromatography, using 5-100% MeCN—$H_2O$ as eluent and 0.1% formic acid as modifier to afford tert-butyl 4-(4-bromo-2,6-difluoro-phenoxy) piperidine-1-carboxylate (0.500 g, 27%) as a yellow oil; 1H NMR (400 MHZ, DMSO-d6) δ 1.41 (9H, s), 1.56 (2H, dtd), 1.86 (2H, ddd), 3.14 (2H, t), 3.65 (2H, ddd), 4.31 (1H, tt), 7.48-7.59 (2H, m); m/z: (ES+), $[M-C_5H_9O_2+H]+=$ 291.9

(b) Methyl 3-[4-[(1-tert-butoxycarbonyl-4-piperidyl) oxy]-3,5-difluoro-anilino]-5-(methylamino)-6-(3-methylimidazo[4,5-c]pyridin-7-yl)pyrazine-2-carboxylate tert-Butyl 4-(4-bromo-2,6-difluoro-phenoxy) piperidine-1-carboxylate (282 mg, 0.720 mmol) was added to a suspension of methyl 3-amino-5-(methylamino)-6-(3-methylimidazo[4,5-c]pyridin-7-yl)pyrazine-2-carboxylate (150 mg, 0.48 mmol), cesium carbonate (468 mg, 1.44 mmol), and BrettPhos Pd G3 (65 mg, 0.070 mmol) in 1,4-dioxane (15 mL) under nitrogen. The resulting mixture was stirred at 100° C. for 16 hours. The reaction was then concentrated. The resulting residue was purified by silica gel chromatography, using 0-30% MeOH-DCM as eluent, to afford methyl 3-[4-[(1-tert-butoxycarbonyl-4-piperidyl)oxy]-3,5-difluoro-anilino]-5-(methylamino)-6-(3-methylimidazo[4,5-c]pyridin-7-yl)pyrazine-2-carboxylate (0.120 g, 40%) as a yellow solid; 1H NMR (400 MHZ, DMSO-d6) δ 1.41 (9H, s), 1.54-1.63 (2H, m), 1.80-1.97 (2H, m), 2.93 (3H, d), 3.08-3.19 (2H, m), 3.63-3.73 (2H, m), 3.84 (3H, s), 4.01 (3H, s), 4.22 (1H, dt), 7.73 (2H, d), 8.05 (1H, br q), 8.50 (1H, s), 8.53 (1H, s), 9.05 (1H, s), 10.48 (1H, s); m/z: (ES+), [M+H]+= 625.3

(c) Methyl 3-[3,5-difluoro-4-(4-piperidyloxy)anilino]-5-(methylamino)-6-(3-methylimidazo[4,5-c] pyridin-7-yl)pyrazine-2-carboxylate 4 M HCl in dioxane (3.0 mL, 12 mmol) was added to methyl 3-[4-[(1-tert-butoxycarbonyl-4-piperidyl)oxy]-3,5-difluoro-anilino]-5-(methylamino)-6-(3-methylimidazo[4, 5-c]pyridin-7-yl)pyrazine-2-carboxylate (120 mg, 0.19 mmol) in MeOH (20 mL). The resulting mixture was stirred at room temperature for 2 hours. The reaction was then concentrated to afford methyl 3-[3,5-difluoro-4-(4-piperidyloxy)anilino]-5-(methylamino)-6-(3-methylimidazo[4,5-c] pyridin-7-yl)pyrazine-2-carboxylate (100 mg, 99% yield) as a yellow residue. m/z: (ES+), [M+H]+=525.4

(d) Methyl 3-[3,5-difluoro-4-[(1-methyl-4-piperidyl) oxy]anilino]-5_(methylamino)-6-(3-methylimidazo [4,5-c]pyridin-7-yl)pyrazine-2-carboxylate Paraformaldehyde (57.2 mg, 1.91 mmol) was added to a mixture of methyl 3-[3,5-difluoro-4-(4-piperidyloxy)anilino]-5-(methylamino)-6-(3-methylimidazo[4,5-c]pyridin-7-yl)pyrazine-2-carboxylate (100 mg, 0.19 mmol) and sodium triacetoxyborohydride (162 mg, 0.760 mmol) in THF (10 mL). The resulting mixture was stirred at room temperature for 16 hours. The reaction was then concentrated. The resulting residue was redissolved in DCM (10 mL) and washed twice with saturated sodium bicarbonate (10 mL each). The organic layer was dried over sodium sulfate, filtered, and concentrated to afford and evaporated to afford methyl 3-[3,5-difluoro-4-[(1-methyl-4-piperidyl)oxy] anilino]-5-(methylamino)-6-(3-methylimidazo[4,5-c]pyridin-7-yl)pyrazine-2-carboxylate as a yellow solid. 1H NMR (400 MHz, DMSO-d6) δ 1.65-1.75 (2H, m), 1.85-1.90 (2H, m), 2.08-2.12 (3H, m), 2.16 (3H, s), 2.61-2.65 (2H, m), 2.92 (3H, d), 3.83 (3H, s), 4.01 (3H, s), 7.72 (2H, d), 8.04 (1H, br q), 8.50 (1H, s), 8.53 (1H, s), 9.05 (1H, s), 10.48 (1H, s)

(e) 3-[3,5-Difluoro-4-[(1-methyl-4-piperidyl)oxy] anilino]-5-(methylamino)-6-(3-methylimidazo[4,5-c] pyridin-7-yl)pyrazine-2-carboxamide 7 N Methanolic ammonia (10 mL, 70 mmol) was added to methyl 3-[3,5-difluoro-4-[(1-methyl-4-piperidyl)oxy]anilino]-5-(methylamino)-6-(3-methylimidazo[4,5-c]pyridin-7-yl)pyrazine-2-carboxylate (60 mg, 0.11 mmol). The resulting mixture was stirred at 80° C. for 24 hours. The reaction was then concentrated. The resulting residue was purified by preparative HPLC, using a 5 micron, 30×150 mm XBridge Prep OBD C18 column, 20-50% MeCN—$H_2O$ as eluent, and 0.1% $NH_4HCO_3$ as modifier, to afford 3-[3,5-difluoro-4-[(1-methyl-4-piperidyl)oxy]anilino]-5-(methylamino)-6-(3-methylimidazo[4,5-c]pyridin-7-yl)pyrazine-2-carboxamide (57 mg, 98%) as a yellow solid; 1H NMR (400 MHZ, DMSO-d6) δ 1.60-1.77 (2H, m), 1.79-1.94 (2H, m), 2.04-2.14 (2H, m), 2.16 (3H, s), 2.60-2.72 (2H, m), 2.96 (3H, d), 3.97-4.10 (4H, m), 7.45 (1H, s), 7.60-7.69 (2H, m), 7.81 (1H, d), 8.08 (1H, br q), 8.53 (1H, s), 8.73 (1H, s), 9.04 (1H, s), 11.68 (1H, s); m/z: (ES+), [M+H]+=524.2

Example 169

3-[4-[(1-Isopropyl-4-piperidyl)oxy]anilino]-5-(methylamino)-6-(3-methylimidazo[4,5-c]pyridin-7-yl)pyrazine-2-carboxamide formate salt

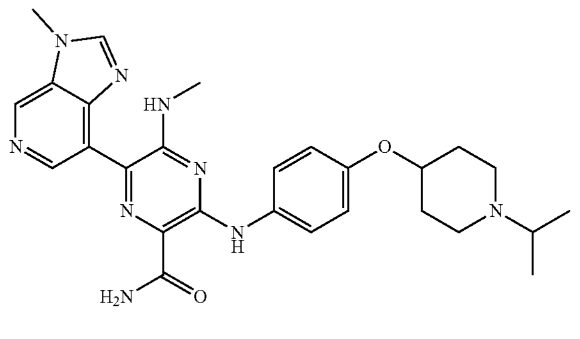 [SMILES: CNc1nc(Nc2ccc(OC3CCN(C(C)C)CC3)cc2)c(C(N)=O)nc1-c1cncc2c1ncn2C]

5-(Methylamino)-6-(3-methylimidazo[4,5-c]pyridin-7-yl)-3-[4-(4-piperidyloxy)anilino]pyrazine-2-carboxamide (120 mg, 0.25 mmol) was added to a mixture of sodium triacetoxyborohydride (537 mg, 2.53 mmol), acetone (56 µL, 0.76 mmol), and titanium isopropoxide (72 mg, 0.25 mmol) in DCM (10 mL). The resulting mixture was stirred at room temperature for 1 hour. The reaction was then concentrated. The resulting residue was purified by preparative HPLC using a 5 micron, 30×150 mm Xselect CSH OBD column, 20-30% MeCN—$H_2O$ as eluent, and 0.1% formic acid as modifier, to afford 3-[4-[(1-isopropyl-4-piperidyl)oxy]anilino]-5-(methylamino)-6-(3-methylimidazo[4,5-c]pyridin-7-yl)pyrazine-2-carboxamide formate salt (19 mg, 13%) as a yellow solid; 1H NMR (400 MHZ, DMSO-d6) δ 1.00 (6H, d), 1.54-1.65 (2H, m), 1.89-2.00 (2H, m), 2.32-2.31-2.44 (2H, m), 2.70-2.81 (3H, m), 2.93 (3H, d), 4.01 (3H, s), 4.25-4.33 (1H, m), 6.90-6.98 (2H, m), 7.32 (1H, s), 7.63-7.72 (2H, m), 7.72 (1H, s), 8.00 (1H, br q), 8.19 (1H, s), 8.52 (1H, s), 8.73 (1H, s), 9.01 (1H, s), 11.33 (1H, s); m/z: (ES+), [M+H]+=516.4

Example 170

3-[4-[[(2S,4R)-4-Hydroxy-1-methyl-pyrrolidin-2-yl]methoxy]anilino]-5-methyl-6-(1-methylbenzimidazol-4-yl)pyrazine-2-carboxamide

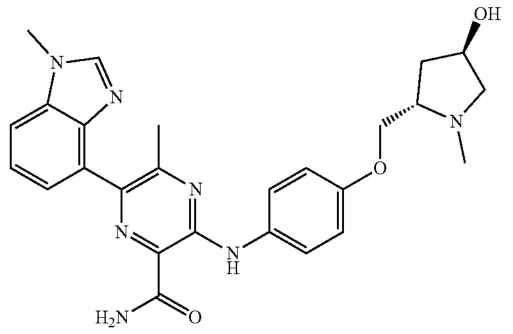 [SMILES: Cc1nc(Nc2ccc(OC[C@@H]3C[C@@H](O)CN3C)cc2)c(C(N)=O)nc1-c1cccc2c1ncn2C]

(a) Methyl (2S,4R)-4-[tert-butyl(diphenyl)silyl]oxy-1-methyl-pyrrolidine-2-carboxylate tert-Butyl-chloro-diphenyl-silane (1.27 mL, 4.90 mmol) was added to a solution of methyl (2S,4R)-4-hydroxy-1-methyl-pyrrolidine-2-carboxylate (650 mg, 4.08 mmol) and imidazole (417 mg, 6.12 mmol) in DMF (8 mL). The resulting mixture was stirred at 25 C for 16 hours. The reaction was then concentrated. The resulting residue was purified by silica gel chromatography, using 0-40% EtOAc-hexanes as eluent, to afford methyl (2S,4R)-4-[tert-butyl(diphenyl)silyl]oxy-1-methyl-pyrrolidine-2-carboxylate (1.34 g, 83%) as a colorless oil. m/z: (ES+), [M+H]+398.3

(b) [(2S,4R)-4-[tert-Butyl(diphenyl)silyl]oxy-1-methyl-pyrrolidin-2-yl]methanol

Lithium aluminum hydride (0.192 g, 5.06 mmol) was added to a solution of methyl (2S,4R)-4-[tert-butyl(diphenyl)silyl]oxy-1-methyl-pyrrolidine-2-carboxylate (1.34 g, 3.37 mmol) in THF (15 mL) at 0° C. The resulting mixture was stirred at 25 C overnight. The reaction was then diluted with ether and cooled to 0° C. Water (0.2 mL) was added dropwise. 15% aqueous sodium hydroxide (0.2 mL) was added dropwise. Additional water (0.6 mL) was added dropwise. The resulting mixture was stirred at 25 C for 15 minutes, then dried over magnesium sulfate, filtered, and concentrated. The resulting residue was purified by silica gel chromatography, using 0-20% MeOH-DCM as eluent, to afford [(2S,4R)-4-[tert-butyl(diphenyl)silyl]oxy-1-methyl-pyrrolidin-2-yl]methanol (1.032 g, 83%) as a pale yellow oil. 1H NMR (500 MHz, DMSO-d6) 0.99 (9H, s), 1.64-1.74 (1H, m), 1.76-1.85 (1H, m), 2.18-2.31 (4H, m), 2.51-2.58 (1H, m), 3.02 (1H, dd), 3.12-3.22 (1H, m), 3.31-3.36 (1H, m), 4.16-4.28 (1H, m), 4.34 (1H, br s), 7.36-7.50 (6H, m), 7.55-7.61 (4H, m); m/z: (ES+), [M+H]+=370.6

(c) (2S,4R)-4-((tert-Butyldiphenylsilyl)oxy)-1-methyl-2-((4-nitrophenoxy)methyl) pyrrolidine DIAD (253 µL, 1.30 mmol) was added to a mixture of 4-nitrophenol (166 mg, 1.19 mmol), [(2S,4R)-4-[tert-butyl(diphenyl)silyl]oxy-1-methyl-pyrrolidin-2-yl]methanol (400 mg, 1.08 mmol), and triphenylphosphine (341 mg, 1.30 mmol) in toluene (5 mL). The resulting mixture was stirred at 25 C for 1 hour. The reaction was then concentrated. The resulting residue was purified by silica gel chromatography, using 0-50% EtOAc-hexanes as eluent, to afford (2S,4R)-4-((tert-butyldiphenylsilyl)oxy)-1-methyl-2-((4-nitrophenoxy)methyl) pyrrolidine (0.717 g, 135%) as a yellow gum. This material contained residual triphenylphosphine oxide; it was carried forward to the next step without further purification. m/z: (ES+), [M+H]+=491.3

(d) (3R,5S)-1-Methyl-5-[(4-nitrophenoxy)methyl] pyrrolidin-3-ol

1 M TBAF in THF (1.19 mL, 1.19 mmol) was added to a solution of (2S,4R)-4-((tert-butyldiphenylsilyl)oxy)-1-methyl-2-((4-nitrophenoxy)methyl) pyrrolidine (531 mg, 1.08 mmol) in THF (3 mL) at 0° C. The resulting mixture was stirred at 0° C. for 1 hour. The reaction was then concentrated. The resulting residue was purified by silica gel chromatography, using 0 to 7% MeOH-DCM, to afford (3R,5S)-1-methyl-5-[(4-nitrophenoxy)methyl]pyrrolidin-3-ol (0.115 g, 42%) as a white solid; 1H NMR (500 MHZ, DMSO-d6) δ 1H NMR (500 MHz, DMSO-d6) 1.57 (1H, ddd), 1.85-1.94 (1H, m), 1.99 (1H, br dd), 2.16 (3H, s), 2.31-2.40 (1H, m), 2.55-2.65 (2H, m), 3.83 (1H, tq), 4.71 (1H, d), 4.83-4.92 (1H, m), 7.06-7.16 (2H, m), 8.11-8.22 (2H, m). m/z: (ES+), [M+H]+253.2

(e) (3R,5S)-5-[(4-Aminophenoxy)methyl]-1-methyl-pyrrolidin-3-ol

A mixture of (3R,5S)-1-methyl-5-[(4-nitrophenoxy) methyl]pyrrolidin-3-ol (50 mg, 0.20 mmol) and 10 wt % palladium on carbon (21.09 mg, 0.02 mmol) in MeOH (5 mL) was stirred under a hydrogen atmosphere at 25 C for 2 hours. The reaction was then filtered through celite and concentrated. The resulting residue was used directly in the next step without further purification, assuming 100% yield of (3R,5S)-5-[(4-aminophenoxy)methyl]-1-methyl-pyrrolidin-3-ol. m/z: (ES+), [M+H]+=223.1

(f) Methyl 6-chloro-3-[4-[[(2S,4R)-4-hydroxy-1-methyl-pyrrolidin-2-yl]methoxy]anilino]-5-methyl-pyrazine-2-carboxylate DIPEA (104 μL, 0.590 mmol) was added to a mixture of methyl 6-chloro-3-fluoro-5-methyl-pyrazine-2-carboxylate (41 mg, 0.20 mmol) and (3R,5S)-5-[(4-aminophenoxy) methyl]-1-methyl-pyrrolidin-3-ol (44 mg, 0.20 mmol) in MeCN (2 mL). The resulting mixture was stirred at 120° C. for 1 hour in a Biotage microwave reactor. The reaction was then concentrated. The resulting residue was purified by silica gel chromatography, using 0-10% MeOH-DCM as eluent, to afford methyl 6-chloro-3-[4-[[(2S,4R)-4-hydroxy-1-methyl-pyrrolidin-2-yl]methoxy]anilino]-5-methyl-pyrazine-2-carboxylate (0.046 g, 57%) as a light orange solid. m/z: (ES+), [M+H]+=407.2

(g) Methyl 3-[4-[[(2S,4R)-4-hydroxy-1-methyl-pyrrolidin-2-yl]methoxy]anilino]-5-methyl-6-(1-methylbenzimidazol-4-yl)pyrazine-2-carboxylate A mixture of methyl 6-chloro-3-[4-[[(2S,4R)-4-hydroxy-1-methyl-pyrrolidin-2-yl]methoxy]anilino]-5-methyl-pyrazine-2-carboxylate (45 mg, 0.11 mmol), 1-methyl-4-(4,4,5,5-tetramethyl-1,3,2-dioxaborolan-2-yl)benzimidazole (63 mg, 50 wt %, 0.12 mmol), $PdCl_2$(dppf)-DCM adduct (9 mg, 0.01 mmol) and cesium fluoride (34 mg, 0.22 mmol) was evacuated and backfilled three times with nitrogen. MeOH (2 mL) was added and the resulting mixture was evacuated and backfilled twice with nitrogen. The resulting mixture was stirred at 120° C. for 1 hour in a Biotage microwave reactor. The reaction was then concentrated. The resulting residue was purified by silica gel chromatography, using 0-20% MeOH-DCM as eluent, to afford methyl 3-[4-[[(2S,4R)-4-hydroxy-1-methyl-pyrrolidin-2-yl]methoxy]anilino]-5-methyl-6-(1-methylbenzimidazol-4-yl)pyrazine-2-carboxylate (0.037 g, 67%) as a light yellow solid. m/z: (ES+), [M+H]+503.3

(h) 3-[4-[[(2S,4R)-4-Hydroxy-1-methyl-pyrrolidin-2-yl] methoxy]anilino]-5-methyl-6-(1-methylbenzimidazol-4-yl) pyrazine-2-carboxamide 7 N Methanolic ammonia (1.0 mL, 7.0 mmol) was added to methyl 3-[4-[[(2S,4R)-4-hydroxy-1-methyl-pyrrolidin-2-yl]methoxy]anilino]-5-methyl-6-(1-methylbenzimidazol-4-yl)pyrazine-2-carboxylate (37 mg, 0.07 mmol). The resulting mixture was stirred at 50° C. for 16 hours. The reaction was then concentrated. The resulting residue was purified by silica gel chromatography, using 0-20% MeOH-DCM as eluent, to afford 3-[4-[[(2S,4R)-4-hydroxy-1-methyl-pyrrolidin-2-yl]methoxy]anilino]-5-methyl-6-(1-methylbenzimidazol-4-yl)pyrazine-2-carboxamide (32 mg, 89%) as a light yellow solid; 1H NMR (500 MHZ, DMSO-d6) δ 1.83 (2H, br s), 2.05-2.25 (1H, m), 2.37 (6H, s), 2.75-2.93 (1H, m), 3.23 (1H, br d), 3.79-3.93 (4H, m), 3.93-4.07 (1H, m), 4.09-4.27 (1H, m), 4.69-4.91 (1H, m), 6.96 (2H, br d), 7.41 (2H, d), 7.58-7.74 (3H, m), 7.84 (1H, br s), 8.05 (1H, br s), 8.24 (1H, s), 11.06 (1H, s); m/z: (ES+), [M+H]+488.4

Example 171

3-[4-[[(2R,4S)-4-Hydroxy-1-methyl-pyrrolidin-2-yl] methoxy]anilino]-5-methyl-6-(1-methylbenzimidazol-4-yl)pyrazine-2-carboxamide

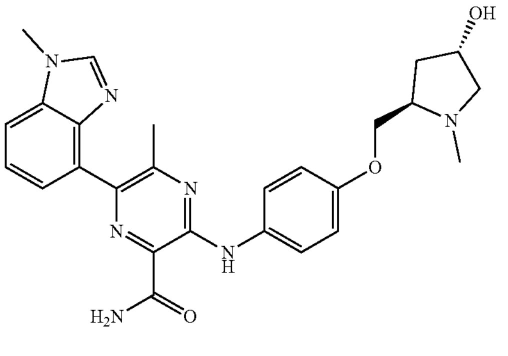 [SMILES: Cc1nc(Nc2ccc(OC[C@H]3C[C@H](O)CN3C)cc2)c(C(N)=O)nc1-c1cccc2c1ncn2C]

(a) O1-tert-Butyl O2-methyl (2R,4S)-4-[tert-butyl (diphenyl)silyl]oxypyrrolidine-1,2-dicarboxylate tert-Butyl-chloro-diphenyl-silane (1.38 mL, 5.30 mmol) was added to a solution of O1-tert-butyl O2-methyl (2R, 4S)-4-hydroxypyrrolidine-1,2-dicarboxylate (1.00 g, 4.08 mmol), and imidazole (0.555 g, 8.15 mmol) in DMF (8 mL). The resulting mixture was stirred at 25 C for 1 hour. The reaction was then concentrated. The residue was purified by silica gel chromatography, using 0-30% EtOAc in hexanes, to afford 01-tert-butyl 02-methyl (2R,4S)-4-[tert-butyl(diphenyl)silyl]oxypyrrolidine-1,2-dicarboxylate (1.97 g, 100%) as a colorless oil. m/z: (ES+), [M−C5$H_{902}$+H]+=384.3

(b) [(2R,4S)-4-[tert-Butyl(diphenyl)silyl]oxy-1-methyl-pyrrolidin-2-yl]methanol

Lithium aluminum hydride (0.464 g, 12.2 mmol) was added to a solution of 01-tert-butyl 02-methyl (2R,4S)-4-[tert-butyl(diphenyl)silyl]oxypyrrolidine-1,2-dicarboxylate (1.97 g, 4.07 mmol) in THF (15 mL) at 0° C. The resulting mixture was stirred at 25 C for 16 hours. The reaction mixture was diluted with ether and cooled to 0° C. Water (0.5 mL) was added dropwise. 15% aqueous sodium hydroxide (0.5 mL) was added dropwise. Water (1.5 mL) was added. The resulting mixture was stirred at 25 C for 15 minutes. The resulting suspension was dried over magnesium sulfate, filtered, and concentrated. The resulting residue was purified by silica gel chromatography, using 0-20% MeOH-DCM as eluent, to afford [(2R,4S)-4-[tert-butyl(diphenyl)silyl]oxy-1-methyl-pyrrolidin-2-yl]methanol (0.681 g, 45% yield) as a pale yellow oil. m/z: (ES+), [M+H]+=370.3

(c) tert-Butyl-[(3S,5R)-1-methyl-5-[(4-nitrophenoxy)methyl]pyrrolidin-3-yl]oxy-diphenyl-silane DIAD (395 μL, 2.03 mmol) was added to a mixture of 4-nitrophenol (259 mg, 1.86 mmol), [(2R,4S)-4-[tert-butyl(diphenyl)silyl]oxy-1-methyl-pyrrolidin-2-yl]methanol (625 mg, 1.69 mmol), and triphenylphosphine (532 mg, 2.03 mmol) in toluene (10 mL). The resulting mixture was stirred at 25 C for 1 hour. The reaction was then concentrated. The resulting residue was purified by silica gel chromatography, using 0-50% EtOAc-hexanes as eluent, to afford tert-butyl-[(3S,5R)-1-methyl-5-[(4-nitrophenoxy)methyl]pyrrolidin-3-yl]oxy-diphenyl-silane (0.617 g, 74%) as a yellow gum. m/z: (ES+), [M+H]+=491.4

(d) (3S,5R)-1-Methyl-5-[(4-nitrophenoxy)methyl]pyrrolidin-3-ol

1 M TBAF in THF (1.38 mL, 1.38 mmol) was added to a solution of tert-butyl-[(3S,5R)-1-methyl-5-[(4-nitrophenoxy)methyl]pyrrolidin-3-yl]oxy-diphenyl-silane (617 mg, 1.26 mmol) in THF (5 mL) at 0° C. The resulting mixture was stirred at 0° C. for 4 h. The reaction was then concentrated. The resulting residue was purified by silica gel chromatography, using 0-7% MeOH-DCM as eluent, to afford (3S,5R)-1-methyl-5-[(4-nitrophenoxy)methyl]pyrrolidin-3-ol (0.211 g, 67%) as a white solid; 1H NMR (500 MHZ, DMSO-d6) 1.59 (1H, ddd), 1.85-1.96 (1H, m), 1.96-2.10 (1H, m), 2.18 (3H, s), 2.32-2.42 (1H, m), 2.57-2.68 (2H, m), 3.85 (1H, tq), 4.74 (1H, br d), 4.89 (1H, br s), 7.08-7.21 (2H, m), 8.14-8.26 (2H, m); m/z: (ES+), [M+H]+=253.1

(e) Methyl 6-chloro-3-[4-[[(2R,4S)-4-hydroxy-1-methyl-pyrrolidin-2-yl]methoxy]anilino]-5-methyl-pyrazine-2-carboxylate A mixture of (3S,5R)-1-methyl-5-[(4-nitrophenoxy)methyl]pyrrolidin-3-ol (34 mg, 0.13 mmol) and 10 wt % palladium on carbon (14 mg, 0.010 mmol) in MeOH (5 mL) was stirred under a hydrogen atmosphere at 25 C for 2 hours. The reaction was then filtered through celite and concentrated. The resulting residue was dissolved in MeCN (1 mL). Methyl 6-chloro-3-fluoro-5-methyl-pyrazine-2-carboxylate (28 mg, 0.13 mmol) and DIPEA (71 μL, 0.40 mmol) were added to the reaction mixture. The resulting mixture was stirred at 120° C. for 1 hour in a Biotage microwave reactor. The reaction was then concentrated. The resulting residue was purified by silica gel chromatography, using 0-10% MeOH-DCM as eluent, to afford methyl 6-chloro-3-[4-[[(2R,4S)-4-hydroxy-1-methyl-pyrrolidin-2-yl]methoxy]anilino]-5-methyl-pyrazine-2-carboxylate (0.020 g, 36%) as a light yellow solid. m/z: (ES+), [M+H]+=407.2

(f) Methyl 3-[4-[[(2R,4S)-4-hydroxy-1-methyl-pyrrolidin-2-yl]methoxy]anilino]-5-methyl-6-(1-methylbenzimidazol-4-yl)pyrazine-2-carboxylate A mixture of methyl 6-chloro-3-[4-[[(2R,4S)-4-hydroxy-1-methyl-pyrrolidin-2-yl]methoxy]anilino]-5-methyl-pyrazine-2-carboxylate (20 mg, 0.05 mmol), 1-methyl-4-(4,4,5,5-tetramethyl-1,3,2-dioxaborolan-2-yl)benzimidazole (28 mg, 0.050 mmol), $PdCl_2$(dppf)-DCM adduct (4.0 mg, 4.9 μmol), and cesium fluoride (15 mg, 0.10 mmol) was evacuated and backfilled three times with nitrogen. MeOH (1 mL) was added and the resulting mixture was evacuated and backfilled twice with nitrogen. The resulting mixture was stirred at 120° C. for 1 hour in a Biotage microwave reactor. The resulting residue was purified by silica gel chromatography, using 0-20% MeOH-DCM as eluent, to afford methyl 3-[4-[[(2R,4S)-4-hydroxy-1-methyl-pyrrolidin-2-yl]methoxy]anilino]-5-methyl-6-(1-methylbenzimidazol-4-yl)pyrazine-2-carboxylate (0.022 g, 89%) as a light yellow solid. m/z: (ES+), [M+H]+=503.3

(g) 3-[4-[[(2R,4S)-4-Hydroxy-1-methyl-pyrrolidin-2-yl]methoxy]anilino]-5-methyl-6-(1-methylbenzimidazol-4-yl)pyrazine-2-carboxamide 7 N Methanolic ammonia (1.0 mL, 7.0 mmol) was added to methyl 3-[4-[[(2R,4S)-4-hydroxy-1-methyl-pyrrolidin-2-yl]methoxy]anilino]-5-methyl-6-(1-methylbenzimidazol-4-yl)pyrazine-2-carboxylate (22 mg, 0.040 mmol). The resulting suspension was stirred at 50° C. for 16 hours. The resulting residue was purified by silica gel chromatography, using 0-20% MeOH-DCM as eluent, to afford 3-[4-[[(2R,4S)-4-hydroxy-1-methyl-pyrrolidin-2-yl]methoxy]anilino]-5-methyl-6-(1-methylbenzimidazol-4-yl)pyrazine-2-carboxamide (15 mg, 68%) as a light yellow solid; 1H NMR (500 MHZ, DMSO-d6) δ 1.46-1.66 (1H, m), 1.76-1.91 (1H, m), 2.04 (1H, br dd), 2.16 (3H, s), 2.36 (3H, s), 2.37-2.42 (1H, m), 2.50-2.56 (2H, m), 3.80-3.94 (4H, m), 4.58-4.63 (1H, m), 4.64 (1H, d), 6.93 (2H, d), 7.39 (2H, d), 7.59-7.68 (3H, m), 7.82 (1H, br s), 8.03 (1H, br s), 8.22 (1H, s), 11.04 (1H, s); m/z: (ES+), [M+H]+=488.4

Example 172

3-[4-[[(2R,4S)-4-Methoxy-1-methyl-pyrrolidin-2-yl]methoxy]anilino]-5-methyl-6-(1-methylbenzimidazol-4-yl)pyrazine-2-carboxamide

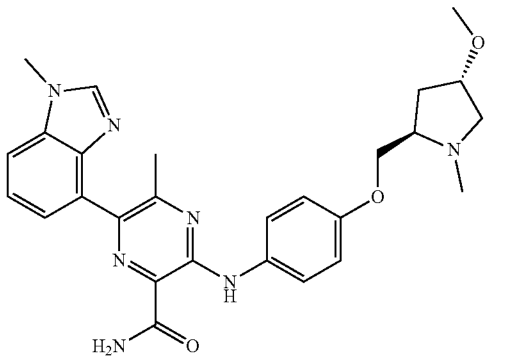 [SMILES: CO[C@H]1C[C@H](COc2ccc(Nc3nc(C)c(-c4cccc5c4ncn5C)nc3C(N)=O)cc2)N(C)C1]

(a) (2R,4S)-4-Methoxy-1-methyl-2-[(4-nitrophenoxy)methyl]pyrrolidine 60 wt % Sodium hydride in oil (9.1 mg, 0.23 mmol) was added to a solution of (3S,5R)-1-methyl-5-[(4-nitrophenoxy)methyl]pyrrolidin-3-ol (48 mg, 0.19 mmol) and iodomethane (13 µL, 0.21 mmol) in THF (2 mL). The resulting mixture was stirred at 25 C for 16 hours. The reaction was then diluted with water and extracted with EtOAc. The organic layer was concentrated to afford (2R,4S)-4-methoxy-1-methyl-2-[(4-nitrophenoxy)methyl]pyrrolidine (0.047 g, 93%) as an oil. m/z: (ES+), [M+H]+=267.2

(b) Methyl 6-chloro-3-[4-[[(2R,4S)-4-methoxy-1-methyl-pyrrolidin-2-yl]methoxy]anilino]-5-methyl-pyrazine-2-carboxylate A mixture of (2R,4S)-4-methoxy-1-methyl-2-[(4-nitrophenoxy)methyl]pyrrolidine (47 mg, 0.18 mmol) and 10 wt % palladium on carbon (19 mg, 0.020 mmol) in MeOH (5 mL) was stirred under an atmosphere of hydrogen at 25 C for 2 hours. The reaction was then filtered through celite and concentrated. The resulting residue was dissolved in MeCN (2 mL).

Methyl 6-chloro-3-fluoro-5-methyl-pyrazine-2-carboxylate (36 mg, 0.18 mmol) and DIPEA (93 µL, 0.53 mmol) were sequentially added. The resulting mixture was stirred at 120° C. for 1 hour in a Biotage microwave reactor. The reaction was then concentrated. The resulting residue was purified by silica gel chromatography, using 0-10% MeOH-DCM as eluent, to afford methyl 6-chloro-3-[4-[[(2R,4S)-4-methoxy-1-methyl-pyrrolidin-2-yl]methoxy]anilino]-5-methyl-pyrazine-2-carboxylate (0.040 g, 54%) as a light orange solid. m/z: (ES+), [M+H]+=421.2

(c) Methyl 3-((4-(((2R,4S)-4-methoxy-1-methylpyrrolidin-2-yl) methoxy)phenyl)amino)-5-methyl-6-(1-methyl-1H-benzo[d]imidazol-4-yl)pyrazine-2-carboxylate A mixture of methyl 6-chloro-3-[4-[[(2R,4S)-4-methoxy-1-methyl-pyrrolidin-2-yl]methoxy]anilino]-5-methyl-pyrazine-2-carboxylate (40 mg, 0.10 mmol), 1-methyl-4-(4,4,5,5-tetramethyl-1,3,2-dioxaborolan-2-yl)benzimidazole (54 mg, 50 wt %, 0.10 mmol), $PdCl_2$(dppf)-DCM adduct (7.8 mg, 9.5 µmol), and cesium fluoride (28.9 mg, 0.19 mmol) was evacuated and backfilled three times with nitrogen. MeOH (2 mL) was added and the reaction mixture was evacuated and backfilled twice with nitrogen. The resulting mixture was stirred at 120° C. for 1 hour. The reaction was then concentrated. The resulting residue was purified by silica gel chromatography, using 0-20% MeOH-DCM as eluent, to afford methyl 3-((4-(((2R,4S)-4-methoxy-1-methylpyrrolidin-2-yl) methoxy)phenyl)amino)-5-methyl-6-(1-methyl-1H-benzo[d]imidazol-4-yl)pyrazine-2-carboxylate (0.028 g, 57%) as a light yellow solid. m/z: (ES+), [M+H]+=517.3

(d) 3-[4-[[(2R,4S)-4-Methoxy-1-methyl-pyrrolidin-2-yl]methoxy]anilino]-5-methyl-6-(1-methylbenzimidazol-4-yl)pyrazine-2-carboxamide 7 N Methanolic ammonia (1.0 mL, 7.0 mmol) was added to methyl 3-((4-(((2R,4S)-4-methoxy-1-methylpyrrolidin-2-yl) methoxy)phenyl)amino)-5-methyl-6-(1-methyl-1H-benzo[d]imidazol-4-yl)pyrazine-2-carboxylate (28 mg, 0.050 mmol). The resulting suspension was stirred at 50° C. and stirred for 16 hours. The reaction was then concentrated. The resulting residue was purified by silica gel chromatography, using 0-20% MeOH-DCM as eluent, to afford 3-[4-[[(2R,4S)-4-methoxy-1-methyl-pyrrolidin-2-yl]methoxy]anilino]-5-methyl-6-(1-methylbenzimidazol-4-yl)pyrazine-2-carboxamide (12 mg, 45%) as a light yellow solid; 1H NMR (500 MHz, DMSO-d6) δ 1.63-1.77 (1H, m), 1.79-1.91 (1H, m), 2.18 (3H, s), 2.22 (1H, br dd), 2.36 (3H, s), 2.39-2.47 (2H, m), 2.51-2.58 (1H, m), 3.24 (3H, s), 3.56 (1H, tt), 3.88 (3H, s), 4.49-4.60 (1H, m), 6.83-7.01 (2H, m), 7.32-7.45 (2H, m), 7.59-7.69 (3H, m), 7.82 (1H, br s), 8.03 (1H, br s), 8.22 (1H, s), 11.05 (1H, s); m/z: (ES+), [M+H]+ 502.3

Example 173

3-[4-[[(2S,4R)-4-Methoxy-1-methyl-pyrrolidin-2-yl]methoxy]anilino]-5-methyl-6-(1-methylbenzimidazol-4-yl)pyrazine-2-carboxamide

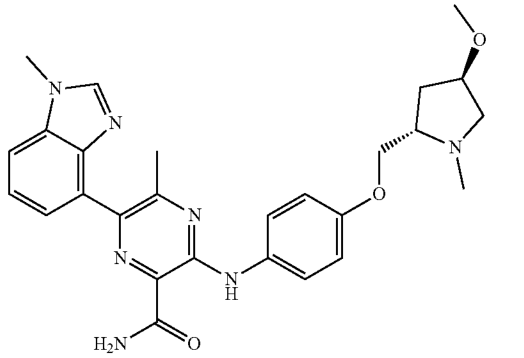 [SMILES: CO[C@@H]1C[C@@H](COc2ccc(Nc3nc(C)c(-c4cccc5c4ncn5C)nc3C(N)=O)cc2)N(C)C1]

(a) (2S,4R)-4-Methoxy-1-methyl-2-[(4-nitrophenoxy)methyl]pyrrolidine 60 wt % Sodium hydride in oil (12 mg, 0.31 mmol) was added to a solution of (3R,5S)-1-methyl-5-((4-nitrophenoxy)methyl) pyrrolidin-3-ol (65 mg, 0.26 mmol) and iodomethane (18 μL, 0.28 mmol) in THF (2 mL). The resulting mixture was stirred at 25 C for 16 hours. The reaction was then quenched with water and extracted with EtOAc. The organic layer was concentrated to afford (2S, 4R)-4-methoxy-1-methyl-2-[(4-nitrophenoxy)methyl]pyrrolidine (0.064 g, 93%) as a light amber oil. m/z: (ES+), [M+H]+=267.2

(b) Methyl 6-chloro-3-[4-[[(2S,4R)-4-methoxy-1-methyl-pyrrolidin-2-yl]methoxy]anilino]-5-methyl-pyrazine-2-carboxylate A mixture of (2S,4R)-4-methoxy-1-methyl-2-[(4-nitrophenoxy)methyl]pyrrolidine (64 mg, 0.24 mmol) and 10 wt % palladium on carbon (26 mg, 0.020 mmol) in MeOH (5 mL) was stirred under a hydrogen atmosphere at 25 C for 2 hours. The reaction was then filtered through celite and concentrated. The resulting residue was redissolved in MeCN (2 mL). Methyl 6-chloro-3-fluoro-5-methyl-pyrazine-2-carboxylate (49 mg, 0.24 mmol) and DIPEA (0.13 mL, 0.72 mmol) were sequentially added. The resulting mixture was stirred 120° C. for 1 hour in a Biotage microwave reactor. The reaction was then concentrated. The resulting residue was purified by silica gel chromatography, using 0-10% MeOH-DCM as eluent, to afford methyl 6-chloro-3-[4-[[(2S,4R)-4-methoxy-1-methyl-pyrrolidin-2-yl]methoxy] anilino]-5-methyl-pyrazine-2-carboxylate (9.0 mg, 8.9%) as a light orange solid. m/z: (ES+), [M+H]+421.2

(c) Methyl 3-[4-[[(2S,4R)-4-methoxy-1-methyl-pyrrolidin-2-yl]methoxy]anilino]-5-methyl-6-(1-methylbenzimidazol-4-yl)pyrazine-2-carboxylate A mixture of methyl 6-chloro-3-[4-[[(2S,4R)-4-methoxy-1-methyl-pyrrolidin-2-yl]methoxy]anilino]-5-methyl-pyrazine-2-carboxylate (9.0 mg, 0.020 mmol), 1-methyl-4-(4,4,5,5-tetramethyl-1,3,2-dioxaborolan-2-yl)benzimidazole (12 mg, 50 wt %, 0.020 mmol), $PdCl_2(dppf)-CH_2Cl_2$adduct (1.7 mg, 2.1 μmol), and cesium fluoride (6.5 mg, 0.040 mmol) was evacuated and backfilled three times with nitrogen. MeOH (1 mL) was added and the reaction mixture was evacuated and backfilled twice with nitrogen. The resulting mixture was subject to microwave at 120° C. for 1 h and evaporated. The residue was purified by silica gel chromatography, using 0-20% MeOH-DCM as eluent, to afford methyl 3-[4-[[(2S,4R)-4-methoxy-1-methyl-pyrrolidin-2-yl] methoxy]anilino]-5-methyl-6-(1-methylbenzimidazol-4-yl) pyrazine-2-carboxylate (5.0 mg, 45%) as a light yellow solid. m/z: (ES+), [M+H]+=517.4

(d) 3-[4-[[(2S,4R)-4-Methoxy-1-methyl-pyrrolidin-2-yl]methoxy]anilino]-5-methyl-6-(1-methylbenzimidazol-4-yl)pyrazine-2-carboxamide 7 N Methanolic ammonia (1.0 mL, 7.0 mmol) was added to methyl 3-[4-[[(2S,4R)-4-methoxy-1-methyl-pyrrolidin-2-yl]methoxy]anilino]-5-methyl-6-(1-methylbenzimidazol-4-yl)pyrazine-2-carboxylate (5.0 mg, 9.7 μmol). The resulting suspension was stirred at 50 C for 16 hours. The reaction was then concentrated. The resulting residue was purified by silica gel chromatography, using 0-20% MeOH-DCM as eluent, to afford 3-[4-[[(2S,4R)-4-methoxy-1-methyl-pyrrolidin-2-yl]methoxy]anilino]-5-methyl-6-(1-methylbenzimidazol-4-yl)pyrazine-2-carboxamide (4.3 mg, 89%) as a light yellow solid; 1H NMR (500 MHZ, DMSO-d6) δ 1.64-1.77 (1H, m), 1.79-1.91 (1H, m), 2.18 (3H, s), 2.20-2.27 (1H, m), 2.36 (3H, s), 2.39-2.45 (1H, m), 2.52-2.57 (1H, m), 3.24 (3H, s), 3.56 (1H, tt), 3.88 (3H, s), 4.51-4.59 (1H, m), 6.89-6.97 (2H, m), 7.34-7.42 (2H, m), 7.60-7.67 (3H, m), 7.82 (1H, br d), 8.04 (1H, br d), 8.22 (1H, s), 11.05 (1H, s); m/z: (ES+), [M+H]+=502.3

Example 174

5-(Methylamino)-6-(3-methylimidazo[4,5-c]pyridin-7-yl)-3-[3-(4-methylpiperazin-1-yl)anilino]pyrazine-2-carboxamide

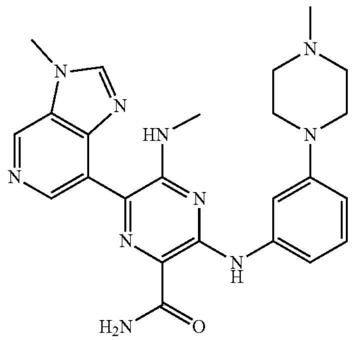 [SMILES: CNc1nc(Nc2cccc(N3CCN(C)CC3)c2)c(C(N)=O)nc1-c1cncc2c1ncn2C]

(a) Methyl 3-[3-(4-tert-butoxycarbonylpiperazin-1-yl)anilino]-5-(methylamino)-6 (3 methylimidazo[4,5-c]pyridin-7-yl)pyrazine-2-carboxylate Brettphos Pd G3 (29 mg, 0.030 mmol) was added to a suspension of methyl 3-amino-5-(methylamino)-6-(3-methylimidazo[4,5-c]pyridin-7-yl)pyrazine-2-carboxylate (100 mg, 0.32 mmol), tert-butyl 4-(3-bromophenyl) piperazine-1-carboxylate (109 mg, 0.32 mmol), and cesium carbonate (312 mg, 0.960 mmol) in 1,4-dioxane (10 mL) under nitrogen. The resulting mixture was stirred at 100° C. for 16 hours. The reaction was then concentrated. The resulting residue was purified by silica gel chromatography, using 0-10% MeOH-DCM as eluent, to afford methyl 3-[3-(4-tert-butoxycarbonylpiperazin-1-yl)anilino]-5-(methylamino)-6-(3-methylimidazo[4,5-c]pyridin-7-yl)pyrazine-2-carboxylate (0.120 g, 66% yield) as a brown solid. 1H NMR (400 MHZ, DMSO-d6) δ, 1.42 (9H, s), 2.93 (3H, d), 3.15 (4H, d), 3.46 (4H, s), 3.83 (3H, s), 4.01 (3H, s), 6.60-6.77 (1H, m), 7.12-7.29 (2H, m), 7.52 (1H, s), 7.90 (1H, br q), 8.51 (2H, d), 9.04 (1H, s), 10.46 (1H, s). m/z: (ES+), [M+H]+=574.3

(b) Methyl 5-(methylamino)-6-(3-methylimidazo[4,5-c]pyridin-7-yl)-3-(3-piperazin-1-ylanilino)pyrazine-2-carboxylate 4 M HCl in dioxane (10 mL, 40 mmol) was added to methyl 3-[3-(4-tert-butoxycarbonylpiperazin-1-yl)anilino]-5-(methylamino)-6-(3-methylimidazo[4,5-c]pyridin-7-yl)

pyrazine-2-carboxylate (120 mg, 0.21 mmol). The resulting mixture was stirred at 60° C. for 2 hours. The reaction was then concentrated. The resulting residue was purified by silica gel chromatography, using 0 to 10% MeOH-DCM as eluent and 0.1% triethylamine as modifier, to afford methyl 5-(methylamino)-6-(3-methylimidazo[4,5-c]pyridin-7-yl)-3-(3-piperazin-1-ylanilino)pyrazine-2-carboxylate (0.090 g, 91% yield) as a brown solid. 1H NMR (400 MHZ, DMSO-d6) δ 2.89 (3H, d), 3.21 (4H, s), 3.41 (4H, d), 3.82 (3H, s), 4.14 (3H, s), 6.70-6.79 (1H, m), 7.26 (1H, d), 7.45-7.55 (1H, m), 8.71 (1H, s), 9.04 (1H, s), 9.32 (2H, br s), 9.66 (1H, s), 10.51 (1H, s). m/z: (ES+), [M+H]+=474.1

(c) Methyl 5_(methylamino)-6-(3-methylimidazo[4,5-c]pyridin-7-yl)-3-[3-(4-methylpiperazin-1-yl)anilino]pyrazine-2-carboxylate Sodium triacetoxyborohydride (121 mg, 0.57 mmol) was added to a solution of methyl 5-(methylamino)-6-(3-methylimidazo[4,5-c]pyridin-7-yl)-3-(3-piperazin-1-ylanilino) pyrazine-2-carboxylate (90 mg, 0.19 mmol) and formaldehyde (132 μL, 1.90 mmol) in MeOH (10 mL). The resulting mixture was stirred at room temperature for 1 hour. The reaction was then concentrated. The resulting residue was redissolved in DCM and washed sequentially with saturated aqueous sodium bicarbonate and brine. The organic layer was dried over sodium sulfate, filtered, and concentrated to afford methyl 5-(methylamino)-6-(3-methylimidazo[4,5-c]pyridin-7-yl)-3-[3-(4-methylpiperazin-1-yl)anilino]pyrazine-2-carboxylate (0.090 g, 97% yield) as a yellow solid. 1H NMR (400 MHZ, DMSO-d6) δ 2.22 (3H, s), 2.45 (4H, t), 2.93 (3H, d), 3.17 (4H, t), 3.83 (3H, s), 4.01 (3H, s), 6.65 (1H, d), 7.07-7.27 (2H, m), 7.52 (1H, s), 7.89 (1H, br q), 8.51 (2H, d), 9.04 (1H, s), 10.45 (1H, s). m/z: (ES+), [M+H]+=488.3

(d) 5-(Methylamino)-6-(3-methylimidazo[4,5-c]pyridin-7-yl)-3-[3-(4-methylpiperazin-1-yl)anilino]pyrazine-2-carboxamide 7 N Methanolic ammonia (10 mL, 70 mmol) was added to methyl 5-(methylamino)-6-(3-methylimidazo[4,5-c]pyridin-7-yl)-3-[3-(4-methylpiperazin-1-yl)anilino]pyrazine-2-carboxylate (85 mg, 0.17 mmol). The resulting mixture was stirred at 80° C. for 16 hours. The reaction was then concentrated. The resulting residue was purified by reverse phase HPLC, using a 5 micron, 30×250 mm YMC-Actus Triart C18 column, 30-40% MeCN-water as eluent, and 10 mM ammonium bicarbonate and 0.1% ammonium hydroxide as modifier, to afford 5-(methylamino)-6-(3-methylimidazo[4,5-c]pyridin-7-yl)-3-[3-(4-methylpiperazin-1-yl)anilino]pyrazine-2-carboxamide (0.022 g, 27% yield) as a yellow solid. 1H NMR (DMSO-d6, 400 MHZ) δ 2.22 (3H, s), 2.45 (4H, t), 2.96 (3H, d), 3.16 (4H, t), 4.01 (3H, s), 6.61 (1H, dd), 7.04 (1H, dd), 7.16 (1H, t), 7.36 (1H, d), 7.57 (1H, t), 7.75 (1H, d), 7.93 (1H, br q), 8.52 (1H, s), 8.71 (1H, s), 9.02 (1H, s), 11.51 (1H, s). m/z (ES+), [M+H]+=473

Example 175

5-(Methylamino)-6-(3-methylimidazo[4,5-c]pyridin-7-yl)-3-[3-(1-methyl-4-piperidyl)anilino]pyrazine-2-carboxamide formate salt

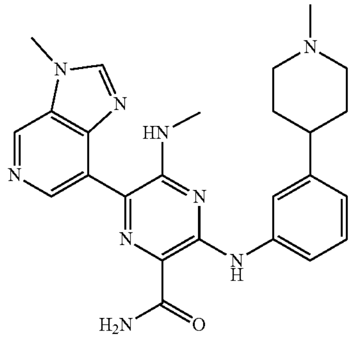

(a) Methyl 3-[3-(1-tert-butoxycarbonyl-4-piperidyl) anilino]-5 (methylamino)-6-(3-methylimidazo[4,5-c] pyridin-7-yl)pyrazine-2-carboxylate Brettphos Pd G3 (29 mg, 0.030 mmol) was added to a suspension of methyl 3-amino-5-(methylamino)-6-(3-methylimidazo[4,5-c]pyridin-7-yl)pyrazine-2-carboxylate (100 mg, 0.32 mmol), tert-butyl 4-(3-bromophenyl) piperidine-1-carboxylate (109 mg, 0.32 mmol), and cesium carbonate (310 mg, 0.96 mmol) in 1,4-dioxane (10 mL) under nitrogen. The resulting mixture was stirred at 100° C. for 16 hours. The reaction was then concentrated. The resulting residue was purified by silica gel chromatography, using 0-10% MeOH-DCM as eluent, to afford methyl 3-[3-(1-tert-butoxycarbonyl-4-piperidyl)anilino]-5-(methylamino)-6-(3-methylimidazo[4,5-c]pyridin-7-yl)pyrazine-2-carboxylate (0.130 g, 71% yield) as a brown solid. 1H NMR (400 MHZ, DMSO-d6) δ 1.19-1.26 (2H, m), 1.41 (9H, s), 1.50-1.54 (2H, m), 1.77-1.81 (1H, m), 2.73 (2H, s), 2.82 (2H, s), 2.92 (3H, d), 3.82 (3H, d), 4.01 (3H, s), 6.94 (1H, d), 7.28 (1H, t), 7.54 (1H, d), 7.86 (2H, d), 8.51 (2H, d), 9.05 (1H, s), 10.46 (1H, s). m/z: (ES+), [M+H]+=573.6

(b) Methyl 5-(methylamino)-6-(3-methylimidazo[4,5-c]pyridin-7-yl)-3-[3-(4-piperidyl)anilino]pyrazine-2-carboxylate 4 M HCl in dioxane (10 mL, 40.00 mmol) was added to methyl 3-[3-(1-tert-butoxycarbonyl-4-piperidyl)anilino]-5-(methylamino)-6-(3-methylimidazo[4,5-c]pyridin-7-yl) pyrazine-2-carboxylate (125 mg, 0.22 mmol). The resulting mixture was stirred at 60° C. for 2 hours. The reaction was then concentrated. The resulting residue was purified by silica gel chromatography, using 0 to 10% MeOH-DCM as eluent, and 0.1% triethylamine as modifier, to afford methyl 5-(methylamino)-6-(3-methylimidazo[4,5-c]pyridin-7-yl)-3-[3-(4-piperidyl)anilino]pyrazine-2-carboxylate (0.090 g, 87% yield) as a yellow solid. 1H NMR (400 MHZ, DMSO-d6) δ 2.90 (3H, d), 3.39 (2H, s), 3.57 (6H, s), 3.82 (3H, s), 3.90 (1H, s), 4.14 (3H, s), 6.96 (1H, d), 7.34 (1H, t), 7.53-7.70 (3H, m), 8.72 (1H, s), 9.03 (1H, s), 9.65 (1H, s), 10.52 (1H, s). m/z: (ES+), [M+H]+=473.3

(c) Methyl 5-(methylamino)-6-(3-methylimidazo[4,5-c]pyridin-7-yl)-3-[3-(1-methyl-4-piperidyl)anilino]pyrazine-2-carboxylate Sodium triacetoxyborohydride (121 mg, 0.570 mmol) was added to a solution of methyl 5-(methylamino)-6-(3-methylimidazo[4,5-c]pyridin-7-yl)-3-[3-(4-piperidyl)anilino]pyrazine-2-carboxylate (90 mg, 0.19 mmol) and 40% aqueous formaldehyde (131 μL, 1.90 mmol) in MeOH (10 mL). The resulting mixture was stirred at room temperature for 1 hour. The reaction was then concentrated. The resulting residue was redissolved in DCM and washed sequentially with saturated aqueous sodium bicarbonate and brine. The organic layer was dried over sodium sulfate, filtered, and concentrated to afford methyl 5-(methylamino)-6-(3-methylimidazo[4,5-c]pyridin-7-yl)-3-[3-(1-methyl-4-piperidyl)anilino]pyrazine-2-carboxylate (0.085 g, 92% yield) as a yellow solid. 1H NMR (400 MHZ, DMSO-d6) δ 2.19 (3H, s), 2.93 (3H, d), 3.28-3.32 (8H, m), 3.82 (1H, d), 3.83 (3H, s), 4.01 (3H, s), 6.94 (1H, d), 7.28 (1H, t), 7.51-7.61 (1H, m), 7.77 (1H, t), 7.91 (1H, d), 8.51 (2H, d), 9.04 (1H, s), 10.44 (1H, s). m/z: (ES+), [M+H]+=487.4

(d) 5-(Methylamino)-6-(3-methylimidazo[4,5-c]pyridin-7-yl)-3-[3-(1-methyl-4-piperidyl)anilino]pyrazine-2-carboxamide formate salt 7 N Methanolic ammonia (10 mL, 70 mmol) was added to methyl 5-(methylamino)-6-(3-methylimidazo[4,5-c]pyridin-7-yl)-3-[3-(1-methyl-4-piperidyl)anilino]pyrazine-2-carboxylate (80 mg, 0.16 mmol). The resulting mixture was stirred at 80° C. for 16 hours. The reaction was then concentrated. The resulting residue was purified by reverse phase HPLC, using 5 micron, 30×150 mm, XBridge Shield RP18 OBD column, 20-50% acetonitrile-water as eluent, and 10 mM ammonium bicarbonate and 0.1% ammonium hydroxide as modifier, to afford 5-(methylamino)-6-(3-methylimidazo[4,5-c]pyridin-7-yl)-3-[3-(1-methyl-4-piperidyl)anilino]pyrazine-2-carboxamide formate salt (0.013 g, 14% yield) as a yellow solid. 1H NMR (DMSO-d6, 400 MHZ) § 1.99 (4H, q), 2.78 (3H, s), 2.81 (1H, s), 2.97 (3H, d), 3.07 (2H, s), 3.49 (2H, d), 4.02 (3H, s), 6.89 (1H, d), 7.27-7.36 (1H, m), 7.39 (1H, d), 7.63-7.69 (2H, m), 7.78 (1H, d), 7.92 (1H, br q), 8.54 (1H, s), 8.73 (1H, s), 9.04 (1H, s), 10.1 (1H, s), 11.55 (1H, s). m/z: (ES+), [M+H]+=472.3

Example 176

5-(Methylamino)-6-(3-methylimidazo[4,5-c]pyridin-7-yl)-3-[4-(4-methylimidazol-1-yl)anilino]pyrazine-2-carboxamide

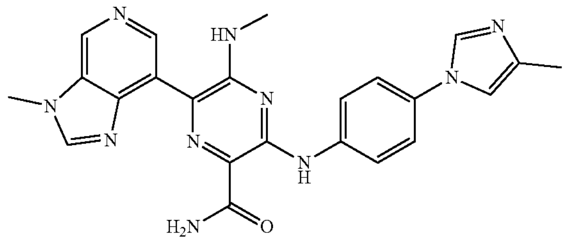

(a) Methyl 5-(methylamino)-6-(3-methylimidazo[4,5-c]pyridin-7-yl)-3-[4-(4-methylimidazol-1-yl)anilino]pyrazine-2-carboxylate 1-(4-Bromophenyl)-4-methyl-imidazole (76 mg, 0.32 mmol) was added to a suspension of methyl 3-amino-5-(methylamino)-6-(3-methylimidazo[4,5-c]pyridin-7-yl)pyrazine-2-carboxylate (100 mg, 0.32 mmol), cesium carbonate (312 mg, 0.96 mmol) and BrettPhos Pd G3 (43 mg, 0.050 mmol) in 1,4-dioxane (10 mL) under nitrogen. The resulting mixture was stirred at 100° C. for 16 hours. The reaction was then concentrated. The resulting residue was purified by silica gel chromatography, using 0-20% MeOH-DCM as eluent, to afford methyl 5-(methylamino)-6-(3-methylimidazo[4,5-c]pyridin-7-yl)-3-[4-(4-methylimidazol-1-yl)anilino]pyrazine-2-carboxylate (0.100 g, 67%) as a yellow solid. m/z: (ES+), [M+H]+=470.2

(b) 5-(Methylamino)-6-(3-methylimidazo[4,5-c]pyridin-7-yl)-3-[4-(4-methylimidazol-1-yl)anilino]pyrazine-2-carboxamide 7 N Methanolic ammonia (14 mL, 98 mmol) was added to methyl 5-(methylamino)-6-(3-methylimidazo[4,5-c]pyridin-7-yl)-3-[4-(4-methylimidazol-1-yl)anilino]pyrazine-2-carboxylate (100 mg, 0.21 mmol). The resulting mixture was stirred at 80° C. for 3 days. The reaction was then concentrated. The resulting residue was purified by preparative HPLC, using a 5 micron, 19 mm×250 mm, XBridge Prep OBD C18 column, decreasingly polar mixtures of MeCN—$H_2O$ as eluent, and 0.05% trifluoroacetic acid as modifier, to afford 5-(methylamino)-6-(3-methylimidazo[4,5-c]pyridin-7-yl)-3-[4-(4-methylimidazol-1-yl)anilino]pyrazine-2-carboxamide (20 mg, 21%) as a yellow solid; 1H NMR (400 MHZ, DMSO-d6) δ 2.33 (3H, s), 2.97 (3H, d), 4.07 (3H, s), 7.51 (1H, br s), 7.69-7.77 (2H, m), 7.91 (2H, d), 7.96 (1H, d), 7.99-8.08 (2H, m), 8.78 (1H, s), 8.87 (1H, s), 9.30 (1H, s), 9.44 (1H, d), 11.84 (1H, s). m/z: (ES+), [M+H]+=455.3

Example 177

5-(Methylamino)-6-(3-methylimidazo[4,5-c]pyridin-7-yl)-3-([1,2,4]triazolo[4,3-a]pyridin-6-ylamino)pyrazine-2-carboxamide

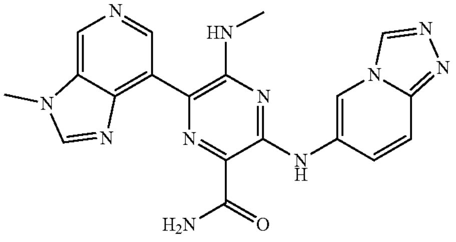 [SMILES: CNc1nc(Nc2ccc3nncn3c2)c(C(N)=O)nc1-c1cncc2c1ncn2C]

(a) Methyl 5-(methylamino)-6-(3-methylimidazo[4,5-c]pyridin-7-yl)-3-([1,2 4]triazolo[4,3-a]pyridin-6-ylamino) pyrazine-2-carboxylate XantPhos Pd G4 (37 mg, 0.040 mmol) was added to a suspension of XantPhos (44 mg, 0.080 mmol), methyl 3-amino-5-(methylamino)-6-(3-methylimidazo[4,5-c]pyridin-7-yl)pyrazine-2-carboxylate (120 mg, 0.38 mmol), 6-bromo-[1,2,4]triazolo[4,3-a]pyridine (152 mg, 0.770 mmol), and potassium phosphate (325 mg, 1.53 mmol) in DMF (20 mL) under nitrogen. The resulting mixture was stirred at 100° C. for 16 hours. The reaction was then concentrated. The resulting residue was purified by silica gel chromatography, using 0-20% MeOH-DCM as eluent, to afford methyl 5-(methylamino)-6-(3-methylimidazo[4,5-c]pyridin-7-yl)-3-([1,2,4]triazolo[4,3-a]pyridin-6-ylamino) pyrazine-2-carboxylate (0.060 g, 36% yield) as a yellow solid. m/z: (ES+), [M+H]+=431.2

(b) 5-(Methylamino)-6-(3-methylimidazo[4,5-c]pyridin-7-yl)-3-([1,2,4]triazolo[4 3-a]pyridin-6-ylamino) pyrazine-2-carboxamide 7 N Methanolic ammonia (12 mL, 84 mmol) was added to methyl 5-(methylamino)-6-(3-methylimidazo[4,5-c]pyridin-7-yl)-3-([1,2,4]triazolo[4,3-a]pyridin-6-ylamino) pyrazine-2-carboxylate (50 mg, 0.12 mmol). The resulting mixture was stirred at 80° C. for 5 days. The reaction was then concentrated. Ammonium hydroxide (12.0 mL, 308 mmol) was added. The resulting mixture was stirred at 100° C. for 4 days. The reaction was then concentrated. The resulting residue was purified by preparative HPLC, using a 5 micron, 19 mm×250 mm, XSelect CSH Prep C18 OBD column, decreasingly polar mixtures of MeCN—$H_2O$ as eluent, and 0.1% formic acid as modifier, to afford 5-(methylamino)-6-(3-methylimidazo[4,5-c]pyridin-7-yl)-3-([1,2,4]triazolo[4,3-a]pyridin-6-ylamino) pyrazine-2-carboxamide (1.960 mg, 4.0% yield) as a yellow solid. 1H NMR (300 MHz, DMSO-d6) δ 3.03 (3H, d), 4.03 (3H, s), 7.36-7.56 (2H, m), 7.71-7.87 (2H, m), 8.09 (1H, br q), 8.54 (1H, s), 8.75 (1H, s), 9.05 (1H, s), 9.28 (1H, s), 9.42 (1H, s), 11.56 (1H, s). m/z: (ES+), [M+H]+=416.2

Example 178

3-[4-(1-Hydroxy-1-methyl-ethyl)anilino]-5-(methylamino)-6-(3-methylimidazo[4,5-c]pyridin-7-yl)pyrazine-2-carboxamide

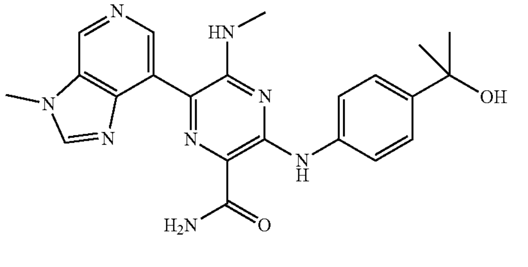 [SMILES: CNc1nc(Nc2ccc(C(C)(C)O)cc2)c(C(N)=O)nc1-c1cncc2c1ncn2C]

(a) Methyl 3-[4-(1-hydroxy-1-methyl-ethyl)anilino]-5 (methylamino)-6-(3-methylimidazo[4,5-c]pyridin-7-yl)pyrazine-2-carboxylate A mixture of methyl 3-amino-5-(methylamino)-6-(3-methylimidazo[4,5-c]pyridin-7-yl)pyrazine-2-carboxylate (150 mg, 0.48 mmol), 2-(4-bromophenyl) propan-2-ol (206 mg, 0.960 mmol), BrettPhos Pd G3 (43 mg, 0.050 mmol), and cesium carbonate (468 mg, 1.44 mmol) was evacuated and backfilled three times with nitrogen. 1,4-Dioxane (4.8 mL) was added. The resulting slurry was evacuated and backfilled three times with nitrogen, then stirred at 80° C. for 2 hours. The reaction was then concentrated. The resulting residue was purified by silica gel chromatography, using 0 to 10% MeOH-DCM as eluent, and 0 to 0.2% methanolic ammonia as modifier, to afford methyl 3-[4-(1-hydroxy-1-methyl-ethyl)anilino]-5-(methylamino)-6-(3-methylimidazo[4,5-c]pyridin-7-yl)pyrazine-2-carboxylate (164 mg, 77% yield) as a yellow solid. 1H NMR (500 MHZ, DMSO-d6): δ 1.43 (6H, s), 2.92 (3H, d), 3.82 (3H, s), 4.00 (3H, s), 4.93 (1H, s), 7.44 (2H, d), 7.73 (2H, d), 7.92 (1H, br q), 8.48 (1H, s), 8.53 (1H, s), 9.03 (1H, s), 10.42 (1H, s). m/z: (ES+), [M+H]+=448.3

(b) 3-[4-(1-Hydroxy-1-methyl-ethyl)anilino]-5-(methylamino)-6-(3-methylimidazo[4,5-c]pyridin-7-yl)pyrazine-2-carboxamide 7 N Methanolic ammonia (6.9 mL, 48 mmol) was added to methyl 3-[4-(1-hydroxy-1-methyl-ethyl)anilino]-5-(methylamino)-6-(3-methylimidazo[4,5-c]pyridin-7-yl)pyrazine-2-carboxylate (145 mg, 0.320 mmol). The resulting mixture was stirred at 100° C. for 20 hours in a Biotage microwave reactor. The reaction was then concentrated. The resulting residue was purified by reverse phase C18 chromatography, using 0 to 100% MeCN—$H_2O$ as eluent, and 0.2% ammonium hydroxide as modifier, to afford 3-[4-(1-hydroxy-1-methyl-ethyl)anilino]-5-(methylamino)-6-(3-methylimidazo[4,5-c]pyridin-7-yl)pyrazine-2-carboxamide (105 mg, 75% yield) as a yellow solid. 1H NMR (500 MHz, DMSO-d6): δ 1.42 (6H, s), 2.95 (3H, d), 4.00 (3H, s), 4.90 (1H, s), 7.34 (1H, br s), 7.42 (2H, d), 7.71 (2H, d), 7.72-7.75 (1H, m), 7.98 (1H, br q), 8.51 (1H, s), 8.72 (1H, s), 9.01 (1H, s), 11.46 (1H, s). m/z: (ES+), [M+H]+=433.3

Example 179

5-Cyclopropyl-3-[[6-(1-hydroxy-1-methyl-ethyl)-3-pyridyl]amino]-6-(3-methylimidazo[4,5-c]pyridin-7-yl)pyrazine-2-carboxamide

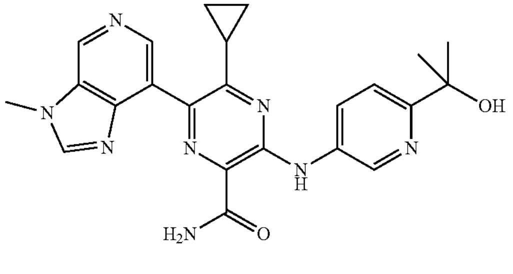 [SMILES: Cn1cnc2c(-c3nc(C(N)=O)c(Nc4ccc(C(C)(C)O)nc4)nc3C3CC3)cncc21]

(a) 2-(5-Bromo-2-pyridyl) propan-2-ol 1.4 M Methylmagnesium bromide in 3:1 THF/toluene (5.36 mL, 7.50 mmol) was added to a solution of 1-(5-bromo-2-pyridyl) ethanone (1.00 g, 5.00 mmol) in THF (19.6 mL) at 0° C. The resulting mixture was stirred at 1 hour while the ice bath expired. The reaction was then cooled to 0° C., then quenched by slow addition of saturated aqueous ammonium chloride (25 mL). The resulting mixture was stirred at room temperature for 15 minutes. The layers were separated and the aqueous layer was extracted three times with EtOAc. The combined organic layers were washed sequentially with saturated aqueous ammonium chloride and brine, then dried over sodium sulfate, filtered, and concentrated. The resulting residue was purified by silica gel chromatography, using 0 to 20% EtOAc-hexanes as eluent, to afford 2-(5-bromo-2-pyridyl) propan-2-ol (575 mg, 53% yield) as a yellow oil. 1H NMR (500 MHZ, Chloroform-d): δ 1.54 (6H, s), 4.40 (1H, s), 7.32 (1H, d), 7.82 (1H, dd), 8.58 (1H, d). m/z: (ES+), [M+H]+=216.0

(b) 5-Cyclopropyl-3-[[6-(1-hydroxy-1-methyl-ethyl)-3-pyridyl]amino]-6-(3-methylimidazo[4,5-c]pyridin-7-yl)pyrazine-2-carboxylic acid A mixture of methyl 3-amino-5-cyclopropyl-6-(3-methylimidazo[4,5-c]pyridin-7-yl)pyrazine-2-carboxylate (100 mg, 0.31 mmol), 2-(5-bromopyridin-2-yl) propan-2-ol (133 mg, 0.620 mmol), XantPhos Pd G3 (30 mg, 0.03 mmol), and cesium carbonate (301 mg, 0.920 mmol) was evacuated and backfilled three times with nitrogen. 1,4-Dioxane (3.08 mL) was added, and the resulting slurry was evacuated and backfilled three times with nitrogen, then stirred at 100° C. for 4 hours, then at 80° C. for 48 hours. The reaction mixture was then allowed to cool to room temperature, filtered through Celite, and concentrated. The resulting residue was purified by reverse phase C18 chromatography, using 0 to 50% MeCN—$H_2O$ as eluent, and 0.1% formic acid as modifier, to afford 5-cyclopropyl-3-[[6-(1-hydroxy-1-methyl-ethyl)-3-pyridyl]amino]-6-(3-methylimidazo[4,5-c]pyridin-7-yl)pyrazine-2-carboxylic acid (0.082 g, 60% yield) as an off-white solid. 1H NMR (500 MHZ, DMSO-d6): δ 0.89-0.96 (2H, m), 1.05 (2H, dt), 1.45 (6H, s), 1.83-1.93 (1H, m), 3.99 (3H, s), 5.15 (1H, br s), 7.63 (1H, d), 8.04 (1H, dd), 8.43 (1H, s), 8.44 (1H, s), 8.76 (1H, d), 9.05 (1H, s), 10.50 (1H, br s). m/z: (ES+), [M+H]+=446.2.

(c) 5-Cyclopropyl-3-[[6-(1-hydroxy-1-methyl-ethyl)-3-pyridyl]amino]-6 (3-methylimidazo[4,5-c]pyridin-7-yl)pyrazine-2-carboxamide DIPEA (157 μL, 0.90 mmol) was added to a solution of 5-cyclopropyl-3-[[6-(1-hydroxy-1-methyl-ethyl)-3-pyridyl]amino]-6-(3-methylimidazo[4,5-c]pyridin-7-yl)pyrazine-2-carboxylic acid (80 mg, 0.18 mmol) in DMF (1.7 mL). Ammonium chloride (96 mg, 1.8 mmol) and HATU (137 mg, 0.360 mmol) were sequentially added. The resulting mixture was stirred at room temperature for 20 hours. Additional ammonium chloride (96 mg, 1.80 mmol) and HATU (137 mg, 0.36 mmol) were added. The resulting mixture was stirred at room temperature for 1 hour. The reaction was then filtered, and the filtrate was concentrated. The resulting residue was-purified by reverse phase C18 chromatography, using 0 to 100% MeCN-water as eluent, and 0 to 0.2% ammonium hydroxide as modifier, to afford an off-white solid. This material was further purified silica gel chromatography, using 0 to 10% MeOH-DCM as eluent, and 0.2% methanolic ammonia as modifier, to afford 5-cyclopropyl-3-[[6-(1-hydroxy-1-methyl-ethyl)-3-pyridyl]amino]-6-(3-methylimidazo[4,5-c]pyridin-7-yl)pyrazine-2-carboxamide (0.036 g, 45% yield) as an off-white solid. 1H NMR (500 MHZ, DMSO-d6): δ 0.90-0.97 (2H, m), 1.04-1.11 (2H, m), 1.44 (6H, s), 1.87-1.98 (1H, m), 3.99 (3H, s), 5.14 (1H, s), 7.62 (1H, d), 7.88 (1H, br s), 8.04 (1H, dd), 8.13 (1H, br s), 8.44 (1H, s), 8.54 (1H, s), 8.77 (1H, d), 9.05 (1H, s), 11.28 (1H, s)

Example 180

3-[(2-Imino-2-oxo-1,3-dihydro-2-benzothiophen-5-yl)amino]-5-methyl-6-(1-methylbenzimidazol-4-yl)pyrazine-2-carboxamide

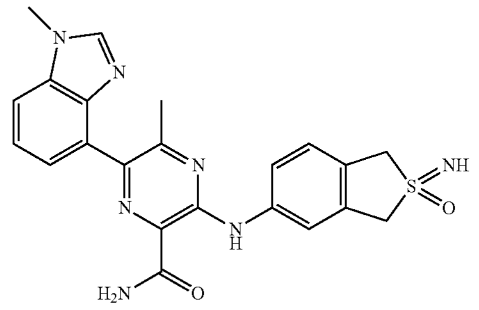 [SMILES: Cc1nc(Nc2ccc3c(c2)CS(=N)(=O)C3)c(C(N)=O)nc1-c1cccc2c1ncn2C]

(a) 5-Bromo-1,3-dihydro-2-benzothiophene

Sodium sulfide (9.10 g, 117 mmol) was added to a solution of 4-bromo-1,2-bis(bromomethyl)benzene (10.0 g, 29.2 mmol) in EtOH (25 mL). The resulting mixture was stirred at 50° C. for 1 hour. The reaction was then concentrated. The resulting residue was purified by silica gel chromatography, using 0-10% DCM-petroleum ether as eluent, to afford 5-bromo-1,3-dihydro-2-benzothiophene (3.10 g, 49%) as a white solid; 1H NMR (300 MHZ, DMSO-d6) δ 4.17 (2H, s), 4.22 (2H, s), 7.27 (1H, d), 7.41 (1H, dd), 7.53 (1H, d); m/z: Poor ionization by LCMS.

(b) Methyl 3-(1,3-dihydro-2-benzothiophen-5-ylamino)-5-methyl-6-(1-methylbenzimidazol-4-yl)pyrazine-2-carboxylate Brettphos Pd G3 (122 mg, 0.130 mmol) was added to a suspension of methyl 3-amino-5-(methylamino)-6-(3-methylimidazo[4,5-c]pyridin-7-yl)pyrazine-2-carboxylate (200 mg, 0.67 mmol), 5-bromo-1,3-dihydro-2-benzothiophene (145 mg, 0.670 mmol), and cesium carbonate (658 mg, 2.02 mmol) in 1,4-dioxane (1 mL) under nitrogen. The resulting mixture was stirred at 100° C. for 3 hours. The reaction was then concentrated. The resulting residue was purified by silica gel chromatography, using 0-20% MeOH-DCM as eluent, to afford methyl 3-(1,3-dihydro-2-benzothiophen-5-ylamino)-5-methyl-6-(1-methylbenzimidazol-4-yl)pyrazine-2-carboxylate (0.240 g, 83%) as a yellow solid; 1H NMR (300 MHZ, DMSO-d6) δ 2.39 (3H, s), 3.91 (3H, s), 3.92 (3H, s), 4.22 (2H, d), 4.26 (2H, s), 7.26-7.34 (2H, m), 7.43 (1H, t), 7.58-7.65 (1H, m), 7.68-7.73 (1H, m), 7.76 (1H, s), 8.28 (1H, s), 10.07 (1H, s); m/z: (ES+), [M+H]+=432.1

(c) Methyl 3-[(2-imino-2-oxo-1,3-dihydro-2-benzothiophen-5-yl)amino]-5-methyl-6-(1-methylbenzimidazol-4-yl)pyrazine-2-carboxylate Ammonium carbamate (109 mg, 1.39 mmol) was added to a mixture of methyl 3-(1,3-dihydro-2-benzothiophen-5-ylamino)-5-methyl-6-(1-methylbenzimidazol-4-yl)pyrazine-2-carboxylate (240 mg, 0.56 mmol) and [acetoxy (phenyl)-23-iodanyl](537 mg, 1.67 mmol) in MeOH (5 mL). The resulting mixture was stirred at 25° C. for 16 hours. The reaction was then concentrated. The resulting residue was purified by silica gel chromatography, using 0-20% MeOH-DCM as eluent, to afford methyl 3-[(2-imino-2-oxo-1,3-dihydro-2-benzothiophen-5-yl)amino]-5-methyl-6-(1-methylbenzimidazol-4-yl)pyrazine-2-carboxylate (0.079 g, 31%) as a yellow solid; 1H NMR (400 MHZ, DMSO-d6) δ 2.38 (3H, s), 3.88 (3H, s), 3.89 (4H, s), 4.34 (2H, s), 4.40 (2H, d), 7.27-7.34 (2H, m), 7.40 (1H, t), 7.64-7.71 (2H, m), 7.82 (1H, s), 8.27 (1H, s), 10.08 (1H, s); m/z: (ES+), [M+H]+=463.2

(d) 3-[(2-Imino-2-oxo-1,3-dihydro-2-benzothiophen-5-yl)amino]-5-methyl-6-(1-methylbenzimidazol-4-yl)pyrazine-2-carboxamide 7 N Methanolic ammonia (3.0 mL, 21 mmol) was added to methyl 3-[(2-imino-2-oxo-1,3-dihydro-2-benzothiophen-5-yl)amino]-5-methyl-6-(1-methylbenzimidazol-4-yl)pyrazine-2-carboxylate (62 mg, 0.13 mmol). The resulting suspension was stirred at 60° C. for 2 hours. The reaction was then concentrated. The resulting residue was purified by preparative HPLC, using a 5 micron, 50 mm×100 mm, XSelect CSH Prep C18 OBD column, decreasingly polar mixtures of MeCN—$H_2O$ as eluent, and 0.1% trifluoroacetic acid as modifier, to afford 3-[(2-imino-2-oxo-1,3-dihydro-2-benzothiophen-5-yl)amino]-5-methyl-6-(1-methylbenzimidazol-4-yl)pyrazine-2-carboxamide (17 mg, 28%) as a yellow solid; 1H NMR (400 MHz, DMSO-d6) δ 2.48 (3H, s), 4.06 (4H, s), 4.52 (2H, s), 4.58 (2H, s), 7.37 (1H, d), 7.61-7.73 (2H, m), 7.73-7.80 (1H, m), 7.87 (1H, s), 7.95 (1H, d), 8.00 (1H, s), 8.14 (1H, s), 9.23 (1H, s), 11.48 (1H, s); m/z: (ES+), [M+H]+=448.1

Examples 181 and 182 rel-(R)-3-[4-(Ethylsulfonimidoyl)-3,5-dimethyl-anilino]-5-methyl-6-(1-methylbenzimidazol-4-yl)pyrazine-2-carboxamide and rel-(S)-3-[4-(ethylsulfonimidoyl)-3,5-dimethyl-anilino]-5-methyl-6-(1-methylbenzimidazol-4-yl)pyrazine-2-carboxamide

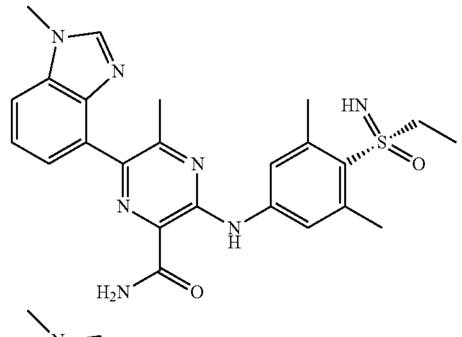

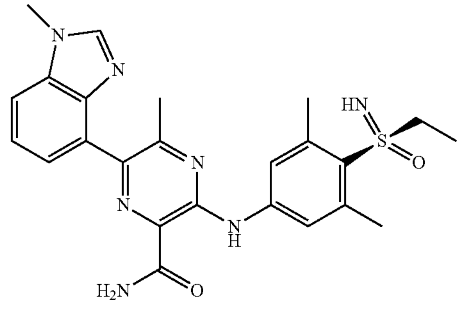

(a) 5-Bromo-2-ethylsulfanyl-1,3-dimethyl-benzene

Triethylamine (3.27 mL, 23.5 mmol) was added to a solution of 4-bromo-2,6-dimethyl-benzenethiol (1.70 g, 7.83 mmol) and bromoethane (1.02 g, 9.40 mmol) in acetonitrile (50 mL). The resulting mixture was stirred at 25° C. for 2 hours. The reaction was then concentrated. The reaction mixture was diluted with EtOAc (250 mL), and washed three times with brine (250 mL each). The organic layer was dried over sodium sulfate, filtered, and concentrated to afford 5-bromo-2-ethylsulfanyl-1,3-dimethyl-benzene (1.8 g, 94% yield) as a solid; 1H NMR (400 MHZ, DMSO-d6) δ 1.09 (3H, t), 2.47 (6H, s), 2.68 (2H, q), 7.39 (2H, s). Poor ioniziation by LCMS.

(b) (4-Bromo-2,6-dimethyl-phenyl)-ethyl-imino-oxo-16-sulfane

Ammonium carbamate (1.21 g, 15.5 mmol) was added to a mixture of 5-bromo-2-ethylsulfanyl-1,3-dimethyl-benzene (1.900 g, 7.75 mmol) and [acetoxy (phenyl)-23-iodanyl] acetate (6.24 g, 19.4 mmol) in MeOH (50 mL). The resulting mixture was stirred at 25° C. for 3 hours. The reaction was then concentrated. The resulting residue was purified by silica gel chromatography, using 0-50% EtOAc-petroleum ether as eluent, to afford (4-bromo-2,6-dimethyl-phenyl)-ethyl-imino-oxo-6-sulfane (1.38 g, 65%) as a white solid; 1H NMR (400 MHz, DMSO-d6) δ 1.13 (3H, t), 2.66 (6H, s), 3.15 (2H, qd), 4.48 (1H, s), 7.47 (2H, s). m/z: (ES+), [M+H]+=275.9

(c) Methyl 3-[4-(ethylsulfonimidoyl)-3,5-dimethyl-anilino]-5-methyl-6-(1-methylbenzimidazol-4-yl) pyrazine-2-carboxylate (4-Bromo-2,6-dimethyl-phenyl)-ethyl-imino-oxo-26-sulfane (418 mg, 1.51 mmol) was added to a suspension of methyl 3-amino-5-(methylamino)-6-(3-methylimidazo[4,5-c]pyridin-7-yl)pyrazine-2-carboxylate (300 mg, 1.01 mmol), Cesium carbonate (986 mg, 3.03 mmol) and Brett-Phos Pd G3 (183 mg, 0.200 mmol) in 1,4-dioxane (5 mL) under nitrogen. The resulting mixture was stirred at 100° C. for 16 hours. The reaction was then concentrated. Thionyl chloride (2.00 mL, 27.4 mmol) was added dropwise to a suspension of the resulting residue in MeOH (20 mL) at 0° C. The resulting mixture was stirred at 60° C. for 1 hour. The reaction was then concentrated. The resulting residue was purified by silica gel chromatography, using 0-50% MeOH-DCM as eluent, to afford methyl 3-[4-(ethylsulfonimidoyl)-3,5-dimethyl-anilino]-5-methyl-6-(1-methylbenzimidazol-4-yl)pyrazine-2-carboxylate (0.096 g, 19%) as a yellow solid; 1H NMR (400 MHZ, DMSO-d6) δ 1.17 (3H, dt), 2.44 (3H, s), 2.71 (6H, s), 3.05-3.22 (2H, m), 3.91 (6H, s), 4.25 (1H, s), 7.31 (1H, d), 7.43 (1H, t), 7.71 (3H, d), 8.25 (1H, s), 10.19 (1H, s). m/z: (ES+), [M+H]+=493.2

(d) rel-(R)-3-[4-(Ethylsulfonimidoyl)-3,5-dimethyl-anilino]-5-methyl-6-(1-methylbenzimidazol-4-yl) pyrazine-2-carboxamide and rel-(S)-3-[4-(ethylsulfonimidoyl)-3,5-dimethyl-anilino]-5-methyl-6-(1-methylbenzimidazol-4-yl)pyrazine-2-carboxamide 7 N Methanolic ammonia (8.0 mL, 56 mmol) was added to (rac)-methyl 3-[4-(ethylsulfonimidoyl)-3,5-dimethyl-anilino]-5-methyl-6-(1-methylbenzimidazol-4-yl)pyrazine-2-carboxylate (94 mg, 0.19 mmol). The resulting suspension was stirred at 70° C. for 1 hour. The reaction was then concentrated. The resulting residue was purified by preparative chiral-HPLC, using a 3 micron, 4.6 mm×100 mm, CHIRAL ART Cellulose-SB column, and isocratic 1:1 methyl tert-butyl ether-MeCN as eluent, to afford rel-(R)-3-[4-(ethylsulfonimidoyl)-3,5-dimethyl-anilino]-5-methyl-6-(1-methylbenzimidazol-4-yl)pyrazine-2-carboxamide (26 mg, 29%) and rel-(S)-3-[4-(ethylsulfonimidoyl)-3,5-dimethyl-anilino]-5-methyl-6-(1-methylbenzimidazol-4-yl) pyrazine-2-carboxamide (24 mg, 26% yield), each as a yellow solid; 1H NMR (400 MHZ, DMSO-d6) δ 1.16 (3H, t), 2.46 (3H, s), 2.70 (6H, s), 3.05-3.23 (2H, m), 3.91 (3H, s), 4.26 (1H, s), 7.38-7.47 (2H, m), 7.69 (3H, s), 7.99 (1H, d), 8.19 (1H, s), 8.27 (1H, s), 11.48 (1H, s). m/z: (ES+), [M+H]+=478.3

Example 183

3-[(2,2-Dioxo-1,3-dihydro-2-benzothiophen-5-yl) amino]-5-(methylamino)-6-(3-methylimidazo[4,5-c] pyridin-7-yl)pyrazine-2-carboxamide

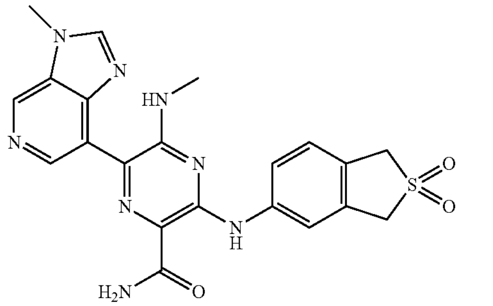 [SMILES: CNc1nc(Nc2ccc3c(c2)CS(=O)(=O)C3)c(C(N)=O)nc1-c1cncc2c1ncn2C]

(a) Methyl 6-chloro-3-[(2,2-dioxo-1,3-dihydro-2-benzothiophen-5-yl)amino]-5-(methylamino) pyrazine-2-carboxylate DIPEA (600 μL, 3.42 mmol) was added to a mixture of 2,2-dioxo-1,3-dihydro-2-benzothiophen-5-amine (626 mg, 3.42 mmol) and methyl 6-chloro-3-fluoro-5-(methylamino) pyrazine-2-carboxylate (250 mg, 1.14 mmol) in NMP (3 mL). The resulting mixture was heated at 150° C. for 20 hours. The reaction was then diluted with water. The resulting precipitate was collected by filtration and dried under air to afford methyl 6-chloro-3-[(2,2-dioxo-1,3-dihydro-2-benzothiophen-5-yl)amino]-5-(methylamino) pyrazine-2-carboxylate (0.169 g, 39%) as a brown solid. m/z: (ES+), [M+H]=383.1

(b) 6-Chloro-3-[(2,2-dioxo-1,3-dihydro-2-benzothiophen-5-yl)amino]-5-(methylamino) pyrazine-2-carboxamide 7 N Methanolic ammonia (5.0 mL, 35 mmol) was added to methyl 6-chloro-3-[(2,2-dioxo-1,3-dihydro-2-benzothiophen-5-yl)amino]-5-(methylamino) pyrazine-2-carboxylate (85 mg, 0.22 mmol). The resulting suspension was stirred at 100° C. for 20 hours. The reaction was then concentrated. The resulting residue was diluted with MeCN, then reconcentrated, to afford 6-chloro-3-((2,2-dioxido-1,3-dihydrobenzo[c]thiophen-5-yl)amino)-5-(methylamino) pyrazine-2-carboxamide (78 mg, 46% yield) as a brown solid.

(c) 3-[(2,2-Dioxo-1,3-dihydro-2-benzothiophen-5-yl)amino]-5-(methylamino)-6-(3-methylimidazo[4,5-c]pyridin-7-yl)pyrazine-2-carboxamide CataCXium A Pd G3 (15 mg, 0.020 mmol), bis(pinacolato)diboron (108 mg, 0.420 mmol), 7-bromo-3-methylimidazo[4,5-c]pyridine (45 mg, 0.21 mmol), potassium acetate (63 mg, 0.64 mmol), and cataCXium A (7.6 mg, 0.020 mmol) were combined in a microwave vial, which was evacuated and backfilled three times with nitrogen. DMF (2.5 mL) was added. The resulting mixture was stirred at 80° C. for 20 hours. The reaction was then allowed to cool to room temperature and set aside.

Pd(dppf)$Cl_2$ (16 mg, 0.020 mmol), cesium fluoride (97 mg, 0.64 mmol), and 6-chloro-3-[(2,2-dioxo-1,3-dihydro-2-benzothiophen-5-yl)amino]-5-(methylamino) pyrazine-2-carboxamide (78 mg, 0.21 mmol) were combined in a microwave vial, which was evacuated and backfilled three times with nitrogen. The borylation mixture was added via syringe. The resulting mixture was stirred at 100° C. for 1 hour. The reaction was then concentrated. The resulting residue was purified by silica gel chromatography, using 0-60% MeOH-DCM as eluent, to afford 3-[(2,2-dioxo-1,3-dihydro-2-benzothiophen-5-yl)amino]-5-(methylamino)-6-(3-methylimidazo[4,5-c]pyridin-7-yl)pyrazine-2-carboxamide (25 mg, 25%) as a pale yellow solid; 1H NMR (500 MHz, DMSO-d6) δ 2.94 (3H, br d), 4.08 (3H, s), 4.44 (2H, s), 4.51 (2H, s), 7.34 (1H, d), 7.49 (1H, br s), 7.66-7.74 (1H, m), 7.87 (2H, br s), 7.93 (1H, s), 8.85 (1H, br s), 8.90 (1H, s), 9.34 (1H, br s), 11.68 (1H, s); m/z: (ES+), [M+H]+=465.2

Example 184

5-(Methylamino)-3-[(1-methyl-2,2-dioxo-3H-2,1-benzothiazol-5-yl)amino]-6-(3-methylimidazo[4,5-c] pyridin-7-yl)pyrazine-2-carboxamide

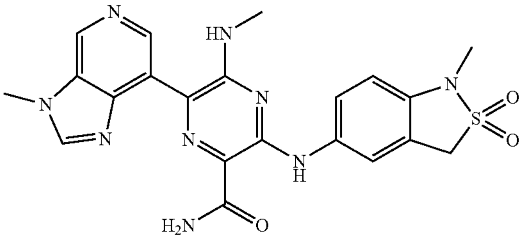 [SMILES: CNc1nc(Nc2ccc3c(c2)CS(=O)(=O)N3C)c(C(N)=O)nc1-c1cncc2c1ncn2C]

(a) Methyl 6-chloro-5-(methylamino)-3-[(1-methyl-2,2-dioxo-3H-2,1-benzothiazol-5-yl)amino]pyrazine-2-carboxylate DIPEA (0.240 mL, 1.37 mmol) was added to a mixture of methyl 6-chloro-3-fluoro-5-(methylamino) pyrazine-2-carboxylate (100 mg, 0.46 mmol) and 1-methyl-2,2-dioxo-3H-2,1-benzothiazol-5-amine (108 mg, 0.55 mmol) in DMA (3 mL). The resulting mixture was stirred at 120° C. for 20 hours. The reaction was then diluted with water (50 mL). The resulting precipitate was collected by filtration and dried under vacuum to afford methyl 6-chloro-5-(methylamino)-3-[(1-methyl-2,2-dioxo-3H-2,1-benzothiazol-5-yl)amino] pyrazine-2-carboxylate (0.130 g, 72%) as a brown solid; 1H NMR (500 MHz, DMSO-d6) δ 2.89 (3H, d), 3.02 (3H, s), 3.80 (3H, s), 4.64 (2H, s), 6.92 (1H, d), 7.62 (1H, dd), 7.72 (1H, d), 7.87 (1H, br q), 10.16 (1H, s) m/z: (ES+), [M+H]+ =398.2

(b) 6-Chloro-5-(methylamino)-3-[[(1-methyl-2,2-dioxo-3H-2,1-benzothiazol-5-yl]amino]pyrazine-2-carboxamide Methanolic ammonia (5.0 mL, 35 mmol) was added to methyl 6-chloro-5-(methylamino)-3-[(1-methyl-2,2-dioxo-3H-2,1-benzothiazol-5-yl)amino]pyrazine-2-carboxylate (120 mg, 0.30 mmol). The resulting suspension was stirred at 100° C. for 15 hours in a Biotage microwave reactor. The reaction was then concentrated to afford 6-chloro-5-(methylamino)-3-[(1-methyl-2,2-dioxo-3H-2,1-benzothiazol-5-yl)amino]pyrazine-2-carboxamide (0.115 g, 100%) as a brown solid; (500 MHz, DMSO-d6) δ 2.92 (3H, d), 3.01 (3H, s), 4.63 (2H, s), 6.91 (1H, d), 7.35 (1H, br s), 7.52-7.61 (2H, m), 7.63 (1H, dd), 7.69 (1H, d), 11.32 (1H, s); m/z: (ES+), [M+H]+=383.1

(c) 5-(Methylamino)-3-[(1-methyl-2,2-dioxo-3H-2,1-benzothiazol-5-yl)amino]-6-(3-methylimidazo[4,5-c]pyridin-7-yl)pyrazine-2-carboxamide CataCXium A Pd G3 (34 mg, 0.050 mmol), bis(pinacolato)diboron (180 mg, 0.71 mmol), 7-bromo-3-methyl-imidazo[4,5-c]pyridine (100 mg, 0.47 mmol), potassium acetate (139 mg, 1.41 mmol) and cataCXium A (17 mg, 0.050 mmol) were combined in a microwave vial, which was evacuated and backfilled three times with nitrogen. DMF (2.5 mL) was added. The resulting mixture was stirred at 80° C. for 20 hours. The reaction was then allowed to cool to room temperature and set aside.

$PdCl_2$(dppf) (35 mg, 0.050 mmol), cesium fluoride (215 mg, 1.41 mmol), and 6-chloro-5-(methylamino)-3-[(1-methyl-2,2-dioxo-3H-2,1-benzothiazol-5-yl)amino]pyrazine-2-carboxamide (181 mg, 0.470 mmol) were combined in a microwave vial, which was evacuated and backfilled three times with nitrogen. The borylation mixture was added via syringe. The resulting mixture was stirred at 100° C. for 1 hour. The reaction was then concentrated. The resulting residue was purified by silica gel chromatography, using 0-60% MeOH-DCM as eluent, to afford 5-(methylamino)-3-[(1-methyl-2,2-dioxo-3H-2,1-benzothiazol-5-yl)amino]-6-(3-methylimidazo[4,5-c]pyridin-7-yl)pyrazine-2-carboxamide (40 mg, 18%) as a pale yellow solid; 1H NMR (500 MHz, DMSO-d6) δ 2.93 (3H, d), 3.02 (3H, s), 4.00 (3H, s), 4.66 (2H, s), 6.94 (1H, d), 7.36 (1H, br s), 7.66-7.77 (2H, m), 7.83 (1H, s), 8.01 (1H, br q), 8.51 (1H, s), 8.72 (1H, s), 9.01 (1H, s), 11.45 (1H, s); m/z (ES+), [M+H]+=480.1

Example 185

5-Cyclopropyl-3-[(1-methyl-2,2-dioxo-3H-2,1-benzothiazol-5-yl)amino]-6-(3-methylimidazo[4,5-c]pyridin-7-yl)pyrazine-2-carboxamide

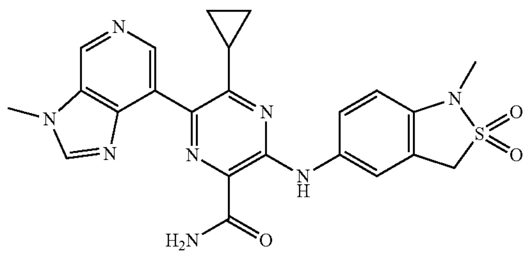 [SMILES: CN1c2ccc(Nc3nc(C4CC4)c(-c4cncc5c4ncn5C)nc3C(N)=O)cc2CS1(=O)=O]

(a) Methyl 6-chloro-5-cyclopropyl-3_ [(1-methyl-2 2-dioxo-3H-2,1-benzothiazol-5-yl)amino]pyrazine-2-carboxylate DIPEA (0.523 mL, 3.00 mmol) was slowly added to a solution of methyl 6-chloro-5-cyclopropyl-3-fluoro-pyrazine-2-carboxylate (0.231 g, 1.00 mmol) and 1-methyl-2,2-dioxo-3H-2,1-benzothiazol-5-amine (0.238 g, 1.20 mmol) in DMF (4.5 mL). The resulting mixture was stirred at 120° C. for 2 h under microwave irradiation. The reaction was then concentrated. The resulting residue was purified by silica gel chromatography, using 0-20% MeOH-DCM as eluent, to afford methyl 6-chloro-5-cyclopropyl-3-[(1-methyl-2,2-dioxo-3H-2,1-benzothiazol-5-yl)amino]pyrazine-2-carboxylate (0.261 g, 64%) as a flaky, bright orange solid. 1H NMR (500 MHZ, CHLOROFORM-d) 1.09-1.16 (2H, m), 1.18-1.25 (2H, m), 2.48-2.60 (1H, m), 3.16 (3H, s), 4.01 (3H, s), 4.35 (2H, s), 6.72 (1H, d), 7.46 (1H, dd), 7.53 (1H, s), 10.04 (1H, s). m/z: (ES+), [M+H]+=409.0

(b) 5-Cyclopropyl-3-[(1-methyl-2 2-dioxo-3H-2,1-benzothiazol-5-yl)amino]-6-(3-methylimidazo[4,5-c]pyridin-7-yl)pyrazine-2-carboxylic acid A mixture of methyl 6-chloro-5-cyclopropyl-3-[(1-methyl-2,2-dioxo-3H-2,1-benzothiazol-5-yl)amino]pyrazine-2-carboxylate (100 mg, 0.24 mmol), 2-(3-methyl-3H-imidazo[4,5-c]pyridin-7-yl)-1,3,6,2-dioxazaborocane (90 mg, 0.37 mmol), and Pd(dppf) C12-dichloromethane complex (20 mg, 0.02 mmol) was evacuated and backfilled with nitrogen 3 times. 1,4-dioxane (2.1 mL) was then added, followed by degassed 2 M aqueous potassium phosphate (370 μL, 0.73 mmol). The resulting mixture was stirred at 100° C. for 2 hours under microwave irradiation. The reaction was then diluted with 4:1 dichloromethane/isopropanol, washed with saturated ammonium chloride, dried over sodium sulfate, filtered, and concenrated. The resulting residue was stirred overnight in a mixture of aqueous lithium chloride solution and dichloromethane (2 mL), and catalytic tetrabutylammonium iodide. The mixture was then acidified to pH 6 with 1 M HCl and extracted with dichloromethane. The extract was washed with brine, dried over sodium sulfate, filtered, and concentrated. The resulting residue was used in the next step without further purification.

(c) 5-Cyclopropyl-3-[(1-methyl-2,2-dioxo-3H-2,1-benzothiazol-5-yl)amino]-6-(3-methylimidazo[4,5-c]pyridin-7-yl)pyrazine-2-carboxamide HATU (111 mg, 0.290 mmol) was added to a solution of 5-cyclopropyl-3-[(1-methyl-2,2-dioxo-3H-2,1-benzothiazol-5-yl)amino]-6-(3-methylimidazo[4,5-c]pyridin-7-yl)pyrazine-2-carboxylic acid (120 mg, 0.24 mmol) in DMF (2 mL). DIPEA (213 μL, 1.22 mmol) was added and the mixture was stirred for 15 minutes. Ammonium chloride (65.3 mg, 1.22 mmol) was then added, and the resulting mixture was stirred for 90 minutes. The reaction was then concentrated. The resulting residue was purified by silica gel chromatography, using 0-10% MeOH-DCM as eluent, and 1% ammonia as a modifier. The resulting material was dissolved in dichloromethane (50 mL), washed sequentially with saturated ammonium chloride, saturated sodium bicarbonate, 5% lithium chloride, and brine, dried over sodium sulfate, filtered, and concentrated. The resulting residue was purified by silica gel chromatography, using 0-20% MeOH-DCM as eluent, to afford 5-cyclopropyl-3-[(1-methyl-2,2-dioxo-3H-2,1-benzothiazol-5-yl)amino]-6-(3-methylimidazo[4,5-c]pyridin-7-yl)pyrazine-2-carboxamide (0.044 g, 37%) as a yellow solid. 1H NMR (500 MHz, CHLOROFORM-d) 0.88-1.03 (2H, m), 1.11-1.25 (2H, m), 1.97-2.08 (1H, m), 3.15 (3H, s), 4.04 (3H, s), 4.36 (2H, s), 5.46 (1H, br s), 6.73 (1H, d), 7.59 (1H, dd), 7.72 (1H, s), 7.84 (1H, br d), 8.04 (1H, s), 8.66 (1H, s), 8.94 (1H, s), 10.85 (1H, s). m/z: (ES+), [M+H]+=491.0

Example 186

5-Methoxy-3-[(1-methyl-2,2-dioxo-3H-2,1-benzothiazol-5-yl)amino]-6-(3-methylimidazo[4,5-c]pyridin-7-yl)pyrazine-2-carboxamide

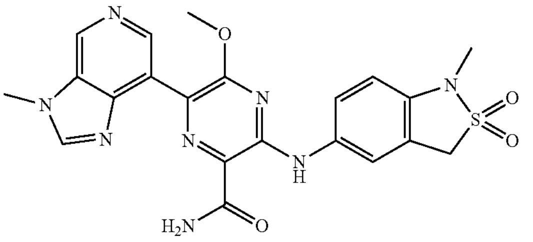 [SMILES: COc1nc(Nc2ccc3c(c2)CS(=O)(=O)N3C)c(C(N)=O)nc1-c1cncc2c1ncn2C]

(a) Methyl 6-chloro-5-methoxy-3-[(1-methyl-2,2-dioxo-3H-2,1-benzothiazol-5-yl)amino]pyrazine-2-carboxylate DIPEA (180 μL, 1.09 mmol) was added to a solution of 1-methyl-2,2-dioxo-3H-2,1-benzothiazol-5-amine (198 mg, 1.00 mmol), and methyl 6-chloro-3-fluoro-5-methoxy-pyrazine-2-carboxylate (200 mg, 0.91 mmol) in DMF (0.73 mL). The resulting solution was stirred at 100° C. for 1 hour. The reaction was then allowed to cool to room temperature. The resulting precipitate was collected by filtration to afford methyl 6-chloro-5-methoxy-3-[(1-methyl-2,2-dioxo-3H-2,1-benzothiazol-5-yl)amino]pyrazine-2-carboxylate (0.145 g, 40%) as a yellow solid; 1H NMR (500 MHz, DMSO-d6) 3.05 (3H, s), 3.89 (3H, s), 4.00 (3H, s), 4.70 (2H, s), 6.97 (1H, d), 7.59 (1H, dd), 7.70 (1H, s), 10.09 (1H, s); m/z: (ES+), [M+H]+=399.2.

(b) Methyl 5-methoxy-3-[(1-methyl-2,2-dioxo-3H-2,1-benzothiazol-5-yl)amino]-6-(3-methylimidazo[4,5-c]pyridin-7-yl)pyrazine-2-carboxylate Bis(pinacolato)diboron (449 mg, 1.77 mmol), cataCXium A (25 mg, 0.070 mmol), cataCXium A Pd G3 (52 mg, 0.070 mmol), potassium acetate (208 mg, 2.12 mmol), and 7-bromo-3-methyl-imidazo[4,5-c]pyridine (150 mg, 0.71 mmol) were combined in a microwave vial, which was evacuated and backfilled three times with nitrogen. DMF (3.5 mL) was added. The resulting mixture was stirred at 80° C. for 24 hours. The reaction was then allowed to cool to room temperature and set aside.

Cesium fluoride (166 mg, 1.09 mmol), Pd(dppf)$Cl_2$ DCM adduct (27 mg, 0.040 mmol), and methyl 6-chloro-5-methoxy-3-[(1-methyl-2,2-dioxo-3H-2,1-benzothiazol-5-yl)amino]pyrazine-2-carboxylate (145 mg, 0.360 mmol) were combined in a microwave vial, which was evacuated and backfilled three times with nitrogen. The borylation mixture from the previous step was added by syringe. The resulting suspension was sparged with nitrogen for 5 minutes then stirred at 100° C. for 2 hours. The reaction was then allowed to cool to room temperature, diluted with DCM (5 mL), and loaded onto celite. The resulting material was purified by silica gel chromatography, using 0-50% MeOH-DCM as eluent, to afford methyl 5-methoxy-3-[(1-methyl-2,2-dioxo-3H-2,1-benzothiazol-5-yl)amino]-6-(3-methylimidazo[4,5-c]pyridin-7-yl)pyrazine-2-carboxylate as a brown solid. m/z: (ES+), [M+H]+=496.2.

(c) 5-Methoxy-3-[(1-methyl-2,2-dioxo-3H-2,1-benzothiazol-5-yl)amino]-6-(3-methylimidazo[4,5-c]pyridin-7-yl)pyrazine-2-carboxamide 7 N Methanolic ammonia (2.0 mL, 14 mmol) was added to methyl 5-methoxy-3-[(1-methyl-2,2-dioxo-3H-2,1-benzothiazol-5-yl)amino]-6-(3-methylimidazo[4,5-c]pyridin-7-yl)pyrazine-2-carboxylate (125 mg, 0.25 mmol). The reaction was stirred at 100° C. for 3 hours in a Biotage microwave reactor. The reaction was then concentrated. The resulting residue was purified by silica gel chromatography, using 0-50% MeOH-DCM as eluent, to afford 5-methoxy-3-[(1-methyl-2,2-dioxo-3H-2,1-benzothiazol-5-yl)amino]-6-(3-methylimidazo[4,5-c]pyridin-7-yl)pyrazine-2-carboxamide (27 mg, 22%) as a yellow solid; 1H NMR (500 MHZ, DMSO-d6) 3.05 (3H, s), 3.95 (3H, s), 3.99 (3H, s), 4.69-4.73 (2H, m), 6.99 (1H, d), 7.69 (1H, dd), 7.74 (1H, br d), 7.81 (1H, s), 8.00 (1H, br d), 8.41 (1H, s), 8.63 (1H, s), 9.00 (1H, s), 11.37 (1H, s); m/z: (ES+), [M+H]+=481.2.

Example 187

3-[4-(1,1-Dioxo-1,4-thiazinan-4-yl)anilino]-5-(methylamino)-6-(3-methylimidazo[4,5-c]pyridin-7-yl)pyrazine-2-carboxamide

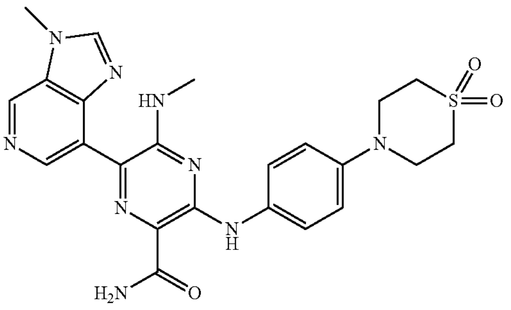 [SMILES: CNc1nc(Nc2ccc(N3CCS(=O)(=O)CC3)cc2)c(C(N)=O)nc1-c1cncc2c1ncn2C]

(a) Methyl 3-[4-(1,1-dioxo-1,4-thiazinan-4-yl)anilino]-5-(methylamino)-6 (3-methylimidazo[4,5-c]pyridin-7-yl)pyrazine-2-carboxylate Brettphos Pd G3 (58 mg, 0.060 mmol) was added to a suspension of methyl 3-amino-5-(methylamino)-6-(3-methylimidazo[4,5-c]pyridin-7-yl)pyrazine-2-carboxylate (100 mg, 0.32 mmol), 4-(4-bromophenyl)-1,4-thiazinane 1,1-dioxide (93 mg, 0.32 mmol), and cesium carbonate (313 mg, 0.960 mmol) in 1,4-dioxane (5 mL) under nitrogen. The resulting mixture was stirred at 100° C. for 16 hours. The reaction was then concentrated. The resulting residue was purified by silica gel chromatography, using 0-10% MeOH-DCM as eluent, to afford methyl 3-[4-(1,1-dioxo-1,4-thiazinan-4-yl)anilino]-5-(methylamino)-6-(3-methylimidazo[4,5-c]pyridin-7-yl)pyrazine-2-carboxylate (0.073 g, 44%) as a yellow solid; 1H NMR (300 MHZ, DMSO-d6) δ 2.91 (3H, d), 3.16 (4H, m), 3.74 (4H, m), 3.83 (3H, s), 4.02 (3H, s), 7.06 (2H, d), 7.72 (2H, d), 7.93 (1H, s), 8.51 (1H, s), 8.54 (1H, s), 9.04 (1H, d), 10.31 (1H, s). m/z: (ES+), [M+H]+=523.1

(b) 3-[4-(1,1-Dioxo-1,4-thiazinan-4-yl)anilino]-5-(methylamino)-6-(3-methylimidazo[4,5-c]pyridin-7-yl)pyrazine-2-carboxamide 7 N Methanolic ammonia (5.0 mL, 35 mmol) was added to methyl 3-[4-(1,1-dioxo-1,4-thiazinan-4-yl)anilino]-5-(methylamino)-6-(3-methylimidazo[4,5-c]pyridin-7-yl) pyrazine-2-carboxylate (55 mg, 0.11 mmol). The resulting suspension was stirred at 80° C. for 16 hours. The reaction was then concentrated. The resulting residue was purified by preparative HPLC, using a 5 micron, 50 mm×100 mm XSelect CSH Prep C18 OBD column, decreasingly polar mixtures of MeCN—$H_2O$ as eluent, and 0.1% formic acid as modifier, to afford 3-[4-(1,1-dioxo-1,4-thiazinan-4-yl)anilino]-5-(methylamino)-6-(3-methylimidazo[4,5-c]pyridin-7-yl)pyrazine-2-carboxamide (28 mg, 51%) as a yellow solid; 1H NMR (400 MHZ, DMSO-d6) δ 2.92 (3H, d), 3.10-3.19 (4H, m), 3.68-3.75 (4H, m), 3.99 (3H, s), 7.03 (2H, d), 7.31 (1H, s), 7.68 (2H, d), 7.70 (1H, s), 7.99 (1H, br q), 8.50 (1H, s), 8.71 (1H, s), 8.99 (1H, s), 11.33 (1H, s); m/z: (ES+), [M+H]+=508.2

Example 188

3-[4-[[Dimethyl(oxo)-$\lambda^6$-sulfanylidene]amino]anilino]-5-(methylamino)-6-(3-methylimidazo[4,5-c]pyridin-7-yl)pyrazine-2-carboxamide

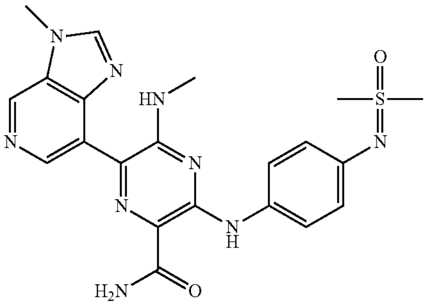 [SMILES: CNc1nc(Nc2ccc(N=S(C)(C)=O)cc2)c(C(N)=O)nc1-c1cncc2c1ncn2C]

(a) Methyl 3-[4-[[dimethyl(oxo)-16-sulfanylidene]amino]anilino]-5_(methylamino)-6-(3-methylimidazo[4,5-c]pyridin-7-yl)pyrazine-2-carboxylate BrettPhos Pd G3 (58 mg, 0.060 mmol) was added to a suspension of methyl 3-amino-5-(methylamino)-6-(3-methylimidazo[4,5-c]pyridin-7-yl)pyrazine-2-carboxylate (100 mg, 0.32 mmol), cesium carbonate (312 mg, 0.96 mmol), and (4-bromophenyl)imino-dimethyl-oxo-16-sulfane (10 mg, 0.04 mmol) in 1,4-dioxane (2 mL) under nitrogen. The resulting mixture was stirred at 100° C. for 16 hours. The reaction was then concentrated. The resulting residue was purified by silica gel chromatography, using 0-20% MeOH-DCM as eluent, to afford methyl 3-[4-[[dimethyl(oxo)-$\lambda^6$-sulfanylidene]amino]anilino]-5-(methylamino)-6-(3-methylimidazo[4,5-c]pyridin-7-yl)pyrazine-2-carboxylate (0.070 g, 46% yield) as a yellow solid. m/z: (ES+), [M+H]+=481.2

(b) 3-[4-[[Dimethyl(oxo)-$\lambda^6$-sulfanylidene]amino]anilino]-5-(methylamino)-6-(3-methylimidazo[4,5-c]pyridin-7-yl)pyrazine-2-carboxamide 7 N Methanolic ammonia (1.0 mL, 7.0 mmol) was added to a suspension of methyl 3-[4-[[dimethyl(oxo)-$\lambda^6$-sulfanylidene]amino]anilino]-5-(methylamino)-6-(3-methylimidazo[4,5-c]pyridin-7-yl)pyrazine-2-carboxylate (55 mg, 0.11 mmol) in MeOH (0.1 mL). The resulting mixture was stirred at 80° C. for 3 days. The reaction was then concentrated. The resulting residue was purified by preparative HPLC, using a 5 micron, 30 mm×150 mm, Xselect CSH OBD column, 10-30% MeCN—$H_2O$ as eluent, and 0.1% formic acid as modifier, to afford 3-[4-[[dimethyl(oxo)-$\lambda^6$-sulfanylidene]amino]anilino]-5-(methylamino)-6-(3-methylimidazo[4,5-c]pyridin-7-yl)pyrazine-2-carboxamide (17 mg, 32% yield) as a yellow solid; 1H NMR (300 MHz, DMSO-d6) δ 2.95 (3H, d), 3.20 (6H, s), 4.04 (3H, s), 6.93 (2H, d), 7.36 (1H, s), 7.62 (2H, d), 7.76 (1H, s), 7.97 (1H, br q), 8.65 (1H, s), 8.80 (1H, s), 9.13 (1H, s), 11.35 (1H, s); m/z: (ES+), [M+H]+=466.1

Example 189

3-[4-[[Dimethyl(oxo)-$\lambda^6$-sulfanylidene]amino]-2-fluoro-anilino]-5-(methylamino)-6-(3-methylimidazo[4,5-c]pyridin-7-yl)pyrazine-2-carboxamide

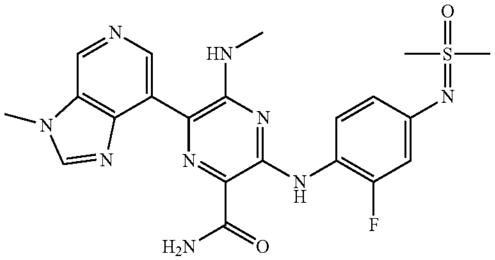

(a) (4-Bromo-3-fluoro-phenyl)imino-dimethyl-oxo-16-sulfane $Pd_2(dba)_3$ (152 mg, 0.170 mmol) was added to a suspension of Xantphos (96 mg, 0.17 mmol), 1-bromo-2-fluoro-4-iodo-benzene (500 mg, 1.66 mmol), imino-dimethyl-oxo-26-sulfane (155 mg, 1.66 mmol), and cesium carbonate (1.62 mg, 4.99 mmol) in 1,4-dioxane (20 mL) under nitrogen. The resulting mixture was stirred at 100° C. for 16 hours. The reaction was then concentrated. The resulting residue was purified by silica gel chromatography, using 0-10% MeOH-DCM as eluent, to afford (4-bromo-3-fluoro-phenyl)imino-dimethyl-oxo-26-sulfane (0.340 g, 77% yield) as a brown solid. 1H NMR (400 MHZ, DMSO-d6) δ 3.26 (6H, s), 6.69-6.76 (1H, m), 6.82-6.93 (1H, m), 7.44 (1H, t). m/z: (ES+), [M+H]+=266.0

(b) Methyl 3-[4-[[dimethyl(oxo)-16-sulfanylidene]amino]-2-fluoro-anilino]-5-(methylamino)-6-(3-methylimidazo[4,5-c]pyridin-7-yl)pyrazine-2-carboxylate Brettphos Pd G3 (34 mg, 0.040 mmol) was added to (4-bromo-3-fluoro-phenyl)imino-dimethyl-oxo-26-sulfane (100 mg, 0.38 mmol), methyl 3-amino-5-(methylamino)-6-

(3-methylimidazo[4,5-c]pyridin-7-yl)pyrazine-2-carboxylate (118 mg, 0.38 mmol), and cesium carbonate (367 mg, 1.13 mmol) in 1,4-dioxane (15 mL) under nitrogen. The resulting mixture was stirred at 100° C. for 16 hours. The reaction was then concentrated. The resulting residue was purified by silica gel chromatography, using 0-25% MeOH-DCM as eluent, to afford methyl 3-[4-[[dimethyl(oxo)-λ$^6$-sulfanylidene]amino]-2-fluoro-anilino]-5-(methylamino)-6-(3-methylimidazo[4,5-c]pyridin-7-yl)pyrazine-2-carboxylate (0.085 g, 45% yield) as a brown solid. 1H NMR (400 MHZ, DMSO-d6) δ 2.82 (3H, d), 3.25 (6H, d), 3.74 (3H, s), 4.00 (3H, s), 6.70-6.80 (1H, m), 6.80-6.88 (1H, m), 7.51 (1H, d), 7.96 (1H, br q) 8.35 (1H, td), 8.46 (1H, s), 9.01 (1H, s), 10.44 (1H, s). m/z: (ES+), [M+H]+=499.2

(c) 3-[4-[[Dimethyl(oxo)-16-sulfanylidene]amino]-2-fluoro-anilino]-5-(methylamino)-6-(3-methylimidazo[4,5-c]pyridin-7-yl)pyrazine-2-carboxamide 7 N Methanolic ammonia (10 mL, 70 mmol) was added to methyl 3-[4-[[dimethyl(oxo)-λ$^6$-sulfanylidene]amino]-2-fluoro-anilino]-5-(methylamino)-6-(3-methylimidazo[4,5-c]pyridin-7-yl)pyrazine-2-carboxylate (80 mg, 0.16 mmol). The resulting mixture was stirred at 80° C. for 16 hours. The reaction was then concentrated. The resulting residue was purified by preparative HPLC, using a 5 micron, 30 mm×150 mm, Sunfire prep C18 column, decreasingly polar mixtures of MeCN—$H_2O$ as eluent, and 0.1% formic acid as modifier, to afford 3-[4-[[dimethyl(oxo)-λ$^6$-sulfanylidene]amino]-2-fluoro-anilino]-5-(methylamino)-6-(3-methylimidazo[4,5-c]pyridin-7-yl)pyrazine-2-carboxamide (0.016 g, 20% yield) as a yellow solid. 1H NMR (400 MHZ, DMSO-d6) δ 2.93 (3H, d), 3.23 (6H, s), 4.01 (3H, s), 6.75-6.84 (2H, m), 7.34 (1H, s), 7.73 (1H, s), 8.01 (1H, br q), 8.44 (1H, t), 8.52 (1H, s), 8.73 (1H, s), 9.02 (1H, s), 11.44 (1H, d). 19F NMR (376 MHz, DMSO) δ −128.26. m/z: (ES+), [M+H]+=484.2

Example 190

3-[4-[[Dimethyl(oxo)-λ$^6$-sulfanylidene]amino]-2,3-difluoro-anilino]-5-(methylamino)-6-(3-methylimidazo[4,5-c]pyridin-7-yl)pyrazine-2-carboxamide formate salt

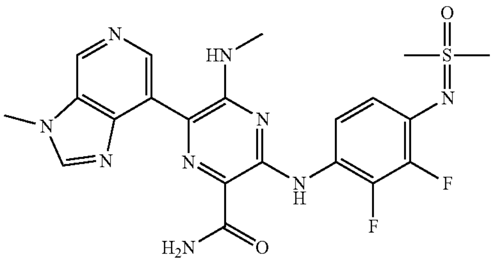

(a) (4-Bromo-2,3-difluoro-phenyl)imino-dimethyl-oxo-λ$^6$-sulfane $Pd_2(dba)_3$ (144 mg, 0.160 mmol) was added to a suspension of Xantphos (91 mg, 0.16 mmol), 1-bromo-2,3-difluoro-4-iodo-benzene (500 mg, 1.57 mmol), imino-dimethyl-oxo-26-sulfane (146 mg, 1.57 mmol), and cesium carbonate (1.53 g, 4.70 mmol) in 1,4-dioxane (25 mL) under nitrogen. The resulting mixture was stirred at 100° C. for 3 hours. The reaction was then concentrated. The resulting residue was purified by silica gel chromatography, using 0-10% MeOH-DCM as eluent, to afford (4-bromo-2,3-difluoro-phenyl)imino-dimethyl-oxo-26-sulfane (0.360 g, 81% yield) as a yellow solid. 1H NMR (400 MHZ, DMSO-d6) δ 3.32 (6H, s), 6.92-6.98 (1H, m), 7.24-7.32 (1H, m). m/z: (ES+), [M+H]+=283.9

(b) Methyl 3-[4-[[dimethyl(oxo)-λ$^6$-sulfanylidene]amino]-2,3-difluoro-anilino]-5-(methylamino)-6-(3-methylimidazo[4,5-c]pyridin-7-yl)pyrazine-2-carboxylate Brettphos Pd G3 (28.9 mg, 0.03 mmol) was added to a suspension of (4-bromo-2,3-difluoro-phenyl)imino-dimethyl-oxo-16-sulfane (100 mg, 0.35 mmol), methyl 3-amino-5-(methylamino)-6-(3-methylimidazo[4,5-c]pyridin-7-yl)pyrazine-2-carboxylate (100 mg, 0.32 mmol), and cesium carbonate (312 mg, 0.960 mmol) in 1,4-dioxane (15 mL) under nitrogen. The resulting mixture was stirred at 100° C. for 16 hours. The reaction was then concentrated. The resulting residue was purified by silica gel chromatography, using 0-20% MeOH-DCM as eluent, to afford methyl 3-[4-[[dimethyl(oxo)-λ$^6$-sulfanylidene]amino]-2,3-difluoro-anilino]-5-(methylamino)-6-(3-methylimidazo[4,5-c]pyridin-7-yl)pyrazine-2-carboxylate (0.080 g, 49%) as a brown solid. 1H NMR (400 MHZ, DMSO-d6) δ 2.82 (3H, d), 2.88 (3H, d), 3.74 (3H, s), 4.00 (3H, s), 4.01 (3H, s), 6.98 (1H, d), 8.14 (1H, br q) 8.39-8.54 (2H, m), 9.01 (1H, s), 9.05 (1H, s), 10.44 (1H, d). m/z: (ES+), [M+H]+=517.2

(c) 3-[4-[[Dimethyl(oxo)-λ$^6$-sulfanylidene]amino]-2 3-difluoro-anilino]-5-(methylamino)-6-(3-methylimidazo[4,5-c]pyridin-7-yl)pyrazine-2-carboxamide formate salt 7 N Methanolic ammonia (10 mL, 70 mmol) was added to methyl 3-[4-[[dimethyl(oxo)-λ$^6$-sulfanylidene]amino]-2,3-difluoro-anilino]-5-(methylamino)-6-(3-methylimidazo[4,5-c]pyridin-7-yl)pyrazine-2-carboxylate (80 mg, 0.15 mmol). The resulting mixture was stirred at 80° C. for 16 hours. The reaction was then concentrated. The resulting residue was purified by preparative HPLC, using a 5 micron, 30 mm×150 mm, Sunfire prep C18 column, decreasingly polar mixtures of MeCN—$H_2O$ as eluent, and 0.1% formic acid as modifier, to afford 3-[4-[[dimethyl(oxo)-λ$^6$-sulfanylidene]amino]-2,3-difluoro-anilino]-5-(methylamino)-6-(3-methylimidazo[4,5-c]pyridin-7-yl)pyrazine-2-carboxamide formate salt (0.018 g, 22% yield) as a yellow solid. 1H NMR (400 MHZ, DMSO-d6) δ 2.93 (3H, d), 3.27 (6H, s), 4.01 (3H, s), 6.97 (1H, td), 7.39 (1H, s), 7.77 (1H, s), 8.01 (1H, br q), 8.17 (1H, br s), 8.25 (1H, td), 8.52 (1H, s), 8.73 (1H, s), 9.03 (1H, s), 11.58 (1H, d). m/z: (ES+), [M+H]+=502.2

Example 191

3-[4-(1,1-Dioxo-1,2-thiazolidin-2-yl)anilino]-5-(methylamino)-6-(3-methylimidazo[4,5-c]pyridin-7-yl)pyrazine-2-carboxamide

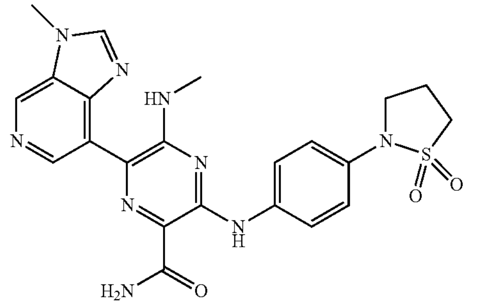 [SMILES: CNc1nc(Nc2ccc(N3CCCS3(=O)=O)cc2)c(C(N)=O)nc1-c1cncc2c1ncn2C]

(a) Methyl 3-[4-(1,1-dioxo-1,2-thiazolidin-2-yl)anilino]-5 (methylamino)-6 (3-methylimidazo[4,5-c]pyridin-7-yl)pyrazine-2-carboxylate BrettPhos Pd G3 (58 mg, 0.060 mmol) was added to a suspension of cesium carbonate (312 mg, 0.960 mmol), 2-(4-bromophenyl)-1,2-thiazolidine 1,1-dioxide (106 mg, 0.380 mmol) and methyl 3-amino-5-(methylamino)-6-(3-methylimidazo[4,5-c]pyridin-7-yl)pyrazine-2-carboxylate (100 mg, 0.32 mmol) in 1,4-dioxane (10 mL) under nitrogen. The resulting mixture was stirred at 100° C. for 16 hours. The reaction was then concentrated. The resulting residue was purified by silica gel chromatography, using 0-20% MeOH-DCM as eluent, to afford methyl 3-[4-(1,1-dioxo-1,2-thiazolidin-2-yl)anilino]-5-(methylamino)-6-(3-methylimidazo[4,5-c]pyridin-7-yl)pyrazine-2-carboxylate (80 mg, 49%) as a yellow solid; 1H NMR (300 MHz, DMSO-d6) δ 2.41 (2H, p), 2.92 (3H, d), 3.51 (2H, t), 3.75 (2H, t), 3.84 (3H, s), 4.03 (3H, s), 7.20-7.30 (2H, m), 7.85 (2H, d), 7.92 (1H, d), 8.53 (2H, d), 9.06 (1H, s), 10.44 (1H, s). m/z: (ES+), [M+H]+=509.2

(b) 3-[4-(1,1-Dioxo-1,2-thiazolidin-2-yl)anilino]-5_ (methylamino)-6-(3-methylimidazo[4,5-c]pyridin-7-yl)pyrazine-2-carboxamide 7 N Methanolic ammonia (10 mL, 70.00 mmol) was added to a suspension methyl 3-[4-(1,1-dioxo-1,2-thiazolidin-2-yl)anilino]-5-(methylamino)-6-(3-methylimidazo[4,5-c]pyridin-7-yl)pyrazine-2-carboxylate (60 mg, 0.12 mmol) in MeOH (10 mL). The resulting mixture was stirred at 80° C. for 3 days. The reaction was then concentrated. The resulting residue was purified by preparative HPLC, using a 5 micron, 30 mm×150 mm, Xselect CSH OBD column, 5-30% MeCN—$H_2O$ as eluent, and 0.1% formic acid as modifier to afford 3-[4-(1,1-dioxo-1,2-thiazolidin-2-yl)anilino]-5-(methylamino)-6-(3-methylimidazo[4,5-c]pyridin-7-yl)pyrazine-2-carboxamide (22 mg, 38%) as a yellow solid; 1H NMR (300 MHz, DMSO-d6) δ2.35-2.44 (2H, m), 2.96 (3H, d), 3.49 (2H, t), 3.74 (2H, t), 4.02 (3H, s), 7.19-7.30 (2H, m), 7.40 (1H, s), 7.81 (3H, m), 8.01 (1H, d), 8.53 (1H, s), 8.74 (1H, s), 9.03 (1H, s), 11.52 (1H, s); m/z: (ES+), [M+H]+=494.3

Example 192

3-[4-(1,1-Dioxothiazinan-2-yl)anilino]-5-(methylamino)-6-(3-methylimidazo[4,5-c]pyridin-7-yl)pyrazine-2-carboxamide

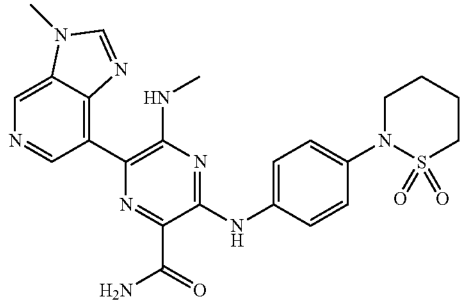 [SMILES: CNc1nc(Nc2ccc(N3CCCCS3(=O)=O)cc2)c(C(N)=O)nc1-c1cncc2c1ncn2C]

(a) Methyl 3-[4-(1,1-dioxothiazinan-2-yl)anilino]-5-(methylamino)-6-(3-methylimidazo[4,5-c]pyridin-7-yl)pyrazine-2-carboxylate Brettphos Pd G3 (58 mg, 0.060 mmol) was added to a suspension of methyl 3-amino-5-(methylamino)-6-(3-methylimidazo[4,5-c]pyridin-7-yl)pyrazine-2-carboxylate (100 mg, 0.32 mmol), 2-(4-bromophenyl) thiazinane 1,1-dioxide (93 mg, 0.32 mmol), and cesium carbonate (312 mg, 0.960 mmol) in 1,4-dioxane (5 mL) under nitrogen. The resulting mixture was stirred at 100° C. for 16 hours. The reaction was then concentrated. The resulting residue was purified by silica gel chromatography, using 0-10% MeOH-DCM as eluent, to afford methyl 3-[4-(1,1-dioxothiazinan-2-yl)anilino]-5-(methylamino)-6-(3-methylimidazo[4,5-c]pyridin-7-yl)pyrazine-2-carboxylate (0.107 g, 64%) as a yellow solid; 1H NMR (400 MHZ, DMSO-d6) δ 1.77-1.87 (2H, m), 2.11-2.21 (2H, m), 2.94 (3H, d), 3.25-3.29 (2H, m), 3.59-3.67 (2H, m), 3.84 (3H, s), 4.01 (3H, s), 7.31 (2H, d), 7.84 (2H, d), 7.96 (1H, br q), 8.50 (1H, s), 8.54 (1H, s), 9.05 (1H, s), 10.50 (1H, s); m/z: (ES+), [M+H]+=523.2

(b) 3-[4-(1,1-Dioxothiazinan-2-yl)anilino]-5-(methylamino)-6-(3-methylimidazo[4,5-c]pyridin-7-yl) pyrazine-2-carboxamide 7 N Methanolic ammonia (10 mL, 70 mmol) was added to methyl 3-[4-(1,1-dioxothiazinan-2-yl)anilino]-5-(methylamino)-6-(3-methylimidazo[4,5-c]pyridin-7-yl)pyrazine-2-carboxylate (89 mg, 0.17 mmol). The resulting suspension was stirred at 80° C. for 2 days. The reaction was then concentrated. The resulting residue was purified by preparative HPLC, using a 5 micron, 50 mm×100 mm, XSelect CSH Prep C18 OBD column, decreasingly polar mixtures of MeCN—$H_2O$ as eluent, and 0.1% formic acid as modifier, to afford 3-[4-(1,1-dioxothiazinan-2-yl)anilino]-5-(methylamino)-6-(3-methylimidazo[4,5-c]pyridin-7-yl)pyrazine-2-carboxamide (22 mg, 26%) as a yellow solid; 1H NMR (300 MHz, DMSO-d6) δ 1.73-1.89 (2H, m), 2.08-2.23 (2H, m), 2.97 (3H, d), 3.23-3.32 (2H, m), 3.56-3.68 (2H, m), 4.01 (3H, s), 7.29 (2H, d), 7.40 (1H, s), 7.78 (1H, s), 7.81 (2H, d), 8.02 (1H, br q), 8.52 (1H, s), 8.73 (1H, s), 9.02 (1H, s), 11.61 (1H, s); m/z: (ES+), [M+H]+=508.2

Example 193

3-(2-Fluoro-4-methylsulfonyl-anilino)-5-(methylamino)-6-(3-methylimidazo[4,5-c]pyridin-7-yl)pyrazine-2-carboxamide

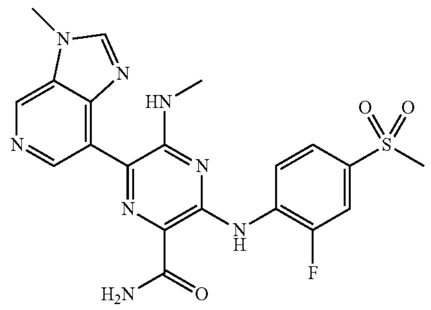 [SMILES: CNc1nc(Nc2ccc(S(C)(=O)=O)cc2F)c(C(N)=O)nc1-c1cncc2c1ncn2C]

(a) N-(2-Fluoro-4-methylsulfonyl-phenyl) formamide

Formic acid (2.00 mL, 52.2 mmol) was added to acetic anhydride (2.00 mL, 21.2 mmol). The resulting colorless solution was stirred at 25 C for 30 minutes. 2-fluoro-4-methylsulfonyl-aniline (190 mg, 1.00 mmol) was added. The resulting pale yellow solution was stirred at 25 C for 24 hours. The reaction was concentrated to a colorless oil, then diluted with EtOAc (15 mL) and quenched with saturated aqueous sodium bicarbonate (30 mL). The resulting mixture was stirred for 30 minutes, then separated. The aqueous layer was extracted twice with EtOAc (10 mL each). The combined organic layers were dried over magnesium sulfate, filtered, and concentrated to afford N-(2-fluoro-4-methylsulfonyl-phenyl) formamide (0.206 g, 94%) as a white solid; 1H NMR (500 MHz, DMSO-d6) 3.22 (3H, s), 7.74 (1H, br d), 7.83 (1H, dd), 8.40 (1H, br s), 8.45 (1H, br s), 10.55 (1H, br s). m/z: (ES−), [M−H]+=216.

(b) Methyl 6-chloro-3-(2-fluoro-4-methylsulfonyl-anilino)-5-(methylamino) pyrazine-2-carboxylate and methyl 6-chloro-3-(2-fluoro-N-formyl-4-methylsulfonyl-anilino)-5-(methylamino) pyrazine-2-carboxylate 60 wt % Sodium hydride in oil (38 mg, 0.95 mmol) was added to a solution of N-(2-fluoro-4-methylsulfonyl-phenyl) formamide (206 mg, 0.95 mmol) in DMF (3 mL). The reaction was stirred at 25 C for 20 minutes. methyl 6-chloro-3-fluoro-5-(methylamino) pyrazine-2-carboxylate (186 mg, 0.85 mmol) was added as a solution in DMF (4 mL). The reaction was stirred at 25 C for 16 hours. The reaction was then stirred at 60 C for 2 hours. The reaction was allowed to cool to room temperature, then quenched with water (50 mL). The resulting suspension was filtered to afford a 3:1 mixture of methyl 6-chloro-3-(2-fluoro-4-methylsulfonyl-anilino)-5-(methylamino) pyrazine-2-carboxylate and methyl 6-chloro-3-(2-fluoro-N-formyl-4-methylsulfonyl-anilino)-5-(methylamino) pyrazine-2-carboxylate (0.192 g, 54%) as a pale yellow solid. This mixture was carried forward directly to the next step.

Major product: 1H NMR (500 MHz, DMSO-d6, 27° C.) 2.99 (3H, d), 3.84 (3H, s), 7.72-7.97 (2H, m), 8.14 (1H, br q), 8.84 (1H, t), 10.90 (1H, d). m/z: (ES+), [M+H]+=389.0

Minor product: 1H NMR (500 MHz, DMSO-d6, 27° C.) 3.24 (3H, d), 3.97 (3H, s), 7.72-7.97 (2H, m), 8.48 (1H, t), 8.88 (1H, br d), 10.62 (1H, d). m/z: (ES+), [M+H]+=417.0

(c) Methyl 3-(2-fluoro-4-methylsulfonyl-anilino)-5-(methylamino)-6-(3-methylimidazo[4,5-c]pyridin-7-yl)pyrazine-2-carboxylate 7-Bromo-3-methyl-imidazo[4,5-c]pyridine (0.159 g, 0.750 mmol), bis(pinacolato)diboron (0.476 g, 1.88 mmol), cataCXium A Pd G3 (0.055 g, 0.080 mmol), cataCXium A (0.027 g, 0.080 mmol), and potassium acetate (0.221 g, 2.25 mmol) were combined in a microwave vial, which was evacuated and backfilled three times with nitrogen. DMF (3.5 mL) was added and the resulting mixture was stirred at 80 C for 24 hours. The reaction was then allowed to cool to room temperature at set aside.

Methyl 6-chloro-3-(2-fluoro-4-methylsulfonyl-anilino)-5-(methylamino) pyrazine-2-carboxylate (0.192 g, 0.460 mmol), Pd(dppf) C12*dichloromethane adduct (0.038 g, 0.050 mmol), and cesium fluoride (0.210 g, 1.38 mmol) were combined in a microwave vial, which was evacuated and backfilled three times with nitrogen. The borylation reaction mixture was added via syringe. The resulting mixture was stirred at 100 C for 2 hours. The reaction was then diluted with DCM (25 mL) and loaded onto Celite, then purified by silica gel chromatography, using 0-10% MeOH-DCM as eluent and 0-1% ammonia as modifier, to afford methyl 3-(2-fluoro-4-methylsulfonyl-anilino)-5-(methylamino)-6-(3-methylimidazo[4,5-c]pyridin-7-yl)pyrazine-2-carboxylate (0.108 g, 48%) as a pale yellow solid; 1H NMR (500 MHz, DMSO-d6, 27° C.) 2.96 (3H, d), 3.24 (3H, s), 3.85 (3H, s), 4.01 (3H, s), 7.81 (1H, dd), 7.87 (1H, dd), 8.04 (1H, br q), 8.49 (1H, s), 8.53 (1H, s), 9.03 (1H, t), 9.07 (1H, s), 11.08 (1H, d). m/z: (ES+), [M+H]+=486.0

(d) 3-(2-Fluoro-4-methylsulfonyl-anilino)-5_(methylamino)-6-(3-methylimidazo[4,5-c]pyridin-7-yl) pyrazine-2-carboxamide Lithium hydroxide monohydrate (93 mg, 2.22 mmol) was added to a suspension of methyl 3-(2-fluoro-4-methylsulfonyl-anilino)-5-(methylamino)-6-(3-methylimidazo[4,5-c] pyridin-7-yl)pyrazine-2-carboxylate (108 mg, 0.22 mmol) in MeOH (1 mL), THF (1 mL), and water (1 mL). The resulting suspension was stirred at 50 C for 1 hour. The reaction was allowed to cool to room temperature, then treated with 2 M aqueous HCl (1.3 mL, 2.6 mmol). The reaction was then concentrated. The resulting residue was dissolved in DMF (2 mL). HATU (0.100 g, 0.26 mmol), ammonium chloride (0.118 g, 2.20 mmol), and DIPEA (0.1 mL, 0.57 mmol) were sequentially added to the reaction mixture. The resulting orange solution was stirred at 25 C for 24 hours. Additional HATU (0.167 g, 0.44 mmol) and DIPEA (0.15 mL, 0.86 mmol) were added and the reaction was stirred at 25 C for 60 hours. The reaction was diluted with water (50 mL), then extracted three times with 3:1 chloroform-isopropanol. The combined organic layers were dried over magnesium sulfate, filtered, and concentrated onto Celite. This material was purified by silica gel chromatography, using 0-10% MeOH-DCM as eluent and 0-1% ammonia as modifier, to afford a yellow solid. This material was then suspended in MeOH (5 mL), filtered, and rinsed with MeOH (5 mL), to afford 3-(2-fluoro-4-methylsulfonyl-anilino)-5-(methylamino)-6-(3-methylimidazo[4,5-c]pyridin-7-yl)pyrazine-2-carboxamide (19 mg, 18%) as a yellow solid; 1H NMR (500 MHz, DMSO-d6, 27° C.) 2.99 (3H, br d), 3.23 (3H, s), 4.01 (3H, s), 7.52 (1H, br s), 7.72-7.84 (2H, m), 7.87 (1H, br s), 8.08 (1H, br q), 8.52 (1H, s), 8.73 (1H, s), 8.94-9.11 (2H, m), 12.25 (1H, br d). m/z: (ES+), [M+H]+=471.1

Example 194

(R)-3-[4-(Ethylsulfonimidoyl)anilino]-5-(methylamino)-6-(3-methylimidazo[4,5-c]pyridin-7-yl)pyrazine-2-carboxamide

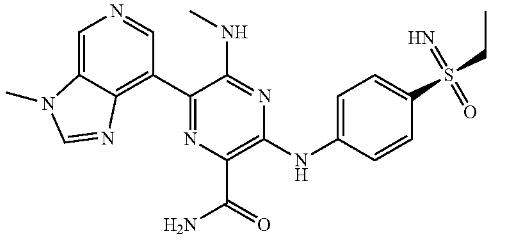 [SMILES: CC[S@@](=N)(=O)c1ccc(Nc2nc(NC)c(-c3cncc4c3ncn4C)nc2C(N)=O)cc1]

(a) tert-Butyl(R)—N-[(4-bromophenyl)-ethyl-oxo-16-sulfanylidene]carbamate

DIPEA (1.69 mL, 9.67 mmol) was added to a solution of DMAP (79 mg, 0.64 mmol), di-tert-butyl dicarbonate (1.50 mL, 6.45 mmol), and (R)-(4-bromophenyl)-ethyl-imino-oxo-26-sulfane in THF (2 mL). The resulting mixture was stirred at 60° C. for 16 hours. The reaction was then concentrated. The resulting residue was purified by silica gel chromatography, using 0-20% EtOAc-petroleum ether as eluent, to afford tert-butyl(R)—N-[(4-bromophenyl)-ethyl-oxo-26-sulfanylidene]carbamate (300 mg, 26.7%) as a white solid; 1H NMR (300 MHZ, DMSO-d6) δ 1.09 (3H, t), 1.25 (9H, s), 3.45-3.61 (2H, m), 7.76-7.86 (2H, m), 7.87-7.97 (2H, m). Did not ionize on LCMS.

(b) Methyl (R)-3-[4-(ethylsulfonimidoyl)anilino]-5-(methylamino)-6-(3-methylimidazo[4,5-c]pyridin-7-yl)pyrazine-2-carboxylate BrettPhos Pd G3 (29 mg, 0.030 mmol) was added to a suspension of cesium carbonate (312 mg, 0.960 mmol), tert-butyl(R)—N-[(4-bromophenyl)-ethyl-oxo-26-sulfanylidene]carbamate (333 mg, 0.960 mmol), and methyl 3-amino-5-(methylamino)-6-(3-methylimidazo[4,5-c]pyridin-7-yl)pyrazine-2-carboxylate (100 mg, 0.320 mmol) in 1,4-dioxane (15 mL). The resulting mixture was stirred at 100° C. for 16 hours. The reaction was then concentrated. The resulting was residue was taken up in MeOH (10 mL). Thionyl chloride (2.00 mL, 27.4 mmol) was added and the resulting mixture was stirred at 60° C. for 2 hours. The resulting residue was purified by silica gel chromatography, using 0-20% MeOH-DCM, to afford methyl (R)-3-[4-(ethylsulfonimidoyl)anilino]-5-(methylamino)-6-(3-methylimidazo[4,5-c]pyridin-7-yl)pyrazine-2-carboxylate (60 mg, 39%) as a yellow solid; 1H NMR (300 MHZ, DMSO-d6) δ 1.24 (3H, t), 2.94 (3H, d), 3.86 (3H, s), 3.95 (3H, q), 4.15 (3H, s), 7.69-7.77 (1H, m), 8.04 (2H, d), 8.26 (2H, d), 8.73 (1H, s), 9.01 (1H, s), 9.65 (1H, s), 10.97 (1H, s); m/z: (ES+), [M+H]+=481.2

(c) (R)-3-[4-(Ethylsulfonimidoyl)anilino]-5-(methylamino)-6-(3-methylimidazo[4,5-c]pyridin-7-yl)pyrazine-2-carboxamide 7 N Methanolic ammonia (10 mL, 70 mmol) was added to a suspension of methyl (R)-3-[4-(ethylsulfonimidoyl)anilino]-5-(methylamino)-6-(3-methylimidazo[4,5-c]pyridin-7-yl)pyrazine-2-carboxylate (60 mg, 0.12 mmol) in MeOH (10 mL). The resulting mixture was stirred at 60° C. for 16 hours. The reaction was then concentrated. The resulting residue was purified by preparative HPLC, using a 100 Å, 5 μm, 19 mm×250 mm SunFire C18 OBD Prep Column, using 10-19% MeCN—$H_2O$ as eluent and 0.1% formic acid as modifier, to afford (R)-3-[4-(ethylsulfonimidoyl)anilino]-5-(methylamino)-6-(3-methylimidazo[4,5-c]pyridin-7-yl)pyrazine-2-carboxamide (28 mg, 48%) as a yellow solid; 1H NMR (300 MHZ, DMSO-d6) δ 1.09 (3H, t), 2.99 (3H, d), 3.11 (2H, q), 4.03 (4H, s), 7.52 (1H, s), 7.84 (3H, m), 7.96-8.11 (3H, m), 8.54 (1H, s), 8.74 (1H, s), 9.05 (1H, s), 11.96 (1H, s). (ES+) [M+H]+=466.1

Example 195

(S)-3-[4-(Ethylsulfonimidoyl)anilino]-5-(methylamino)-6-(3-methylimidazo[4,5-c]pyridin-7-yl)pyrazine-2-carboxamide

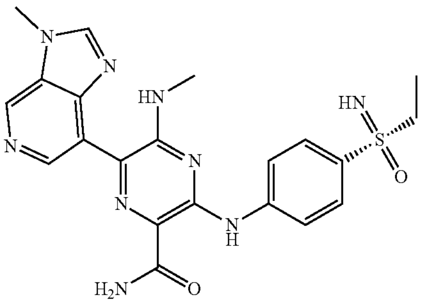 [SMILES: CC[S@](=N)(=O)c1ccc(Nc2nc(NC)c(-c3cncc4c3ncn4C)nc2C(N)=O)cc1]

(a) tert-Butyl(S)—N-[(4-bromophenyl)-ethyl-oxo-16-sulfanylidene]carbamate

DMAP (79 mg, 0.64 mmol) was added to a solution of di-tert-butyl carbonate (1.50 mL, 6.45 mmol), (S)-(4-bromophenyl)-ethyl-imino-oxo-26-sulfane (800 mg, 3.22 mmol), and DIPEA (1.69 mL, 9.67 mmol) in THF (2 mL). The resulting mixture was stirred at 60° C. for 16 hours. The reaction was then concentrated. The resulting residue was purified by silica gel chromatography, using 0-40% EtOAc-petroleum ether, to afford tert-butyl(S)—N-[(4-bromophenyl)-ethyl-oxo-26-sulfanylidene]carbamate (350 mg, 31%) as a white solid; 1H NMR (300 MHz, DMSO-d6) δ 1.09 (3H, t), 1.25 (9H, s), 3.54 (2H, qd), 7.78-7.84 (2H, m), 7.90-7.95 (2H, m); Did not ionize on LCMS.

(b) Methyl(S)-3-[4-(ethylsulfonimidoyl)anilino]-5-(methylamino)-6-(3-methylimidazo[4,5-c]pyridin-7-yl)pyrazine-2-carboxylate BrettPhos G3 Pd (29 mg, 0.030 mmol) was added to a suspension of cesium carbonate (310 mg, 0.96 mmol), tert-butyl(S)—N-[(4-bromophenyl)-ethyl-oxo-26-sulfanylidene]carbamate (330 mg, 0.96 mmol), and methyl 3-amino-5-(methylamino)-6-(3-methylimidazo[4,5-c]pyridin-7-yl)pyrazine-2-carboxylate (100 mg, 0.32 mmol) in 1,4-dioxane (10 mL). The resulting mixture was stirred at 100° C. for 3 hours. The reaction was then concentrated. The resulting residue was taken up in MeOH (8 mL) and thionyl chloride (2.00 mL, 27.4 mmol) was added. The resulting mixture was stirred at 60° C. for 2 hours. The reaction was then concentrated. The resulting residue was purified by silica gel chromatography, using 0-20% MeOH-DCM, to afford methyl (R)-3-[4-(ethylsulfonimidoyl)anilino]-5-(methylamino)-6-(3-methylimidazo[4,5-c]pyridin-7-yl) pyrazine-2-carboxylate (70 mg, 46%) as a yellow solid; 1H NMR (300 MHz, DMSO-d6) δ 1.22-1.26 (3H, m), 2.94 (3H, d), 3.86 (3H, s), 3.95 (2H, t), 4.15 (3H, s), 7.73 (1H, q), 8.05 (2H, d), 8.27 (2H, d), 8.73 (1H, s), 9.01 (1H, s), 9.65 (1H, s), 10.98 (1H, s); imidoyl NH signal buried under broad residual water peak; m/z: (ES+), [M+H]+481.2

(c) (S)-3-[4-(Ethylsulfonimidoyl)anilino]-5-(methylamino)-6-(3-methylimidazo[4,5-c]pyridin-7-yl)pyrazine-2-carboxamide 7 N Methanolic ammonia (2.0 mL, 14 mmol) was added to methyl(S)-3-[4-(ethylsulfonimidoyl)anilino]-5-(methylamino)-6-(3-methylimidazo[4,5-c]pyridin-7-yl)pyrazine-2-carboxylate (65 mg, 0.14 mmol). The resulting mixture was stirred at 60° C. for 16 hours. The reaction was then concentrated. The resulting residue was purified by preparative HPLC, using a 100 Å, 5 μm, 30 mm×150 mm SunFire C18 Prep Column, using 5-15% MeCN—$H_2O$ as eluent and 0.1% formic acid as modifier, to afford(S)-3-[4-(ethylsulfonimidoyl)anilino]-5-(methylamino)-6-(3-methylimidazo[4,5-c]pyridin-7-yl)pyrazine-2-carboxamide (17 mg, 27%) as a yellow solid; 1H NMR (300 MHz, DMSO-d6) δ 1.09 (3H, t), 2.99 (3H, d), 3.11 (2H, m), 3.99-4.20 (4H, m), 7.52 (1H, s), 7.84 (3H, m), 7.96-8.11 (3H, m), 8.54 (1H, s), 8.74 (1H, s), 9.05 (1H, s), 11.96 (1H, s); m/z: (ES+) [M+H]+466.1

Examples 196 and 197 rel-(R)-3-[4-(Isopropylsulfonimidoyl)anilino]-5-(methylamino)-6-(3-methylimidazo[4,5-c]pyridin-7-yl)pyrazine-2-carboxamide and rel-(S)-3-[4-(isopropylsulfonimidoyl)anilino]-5-(methylamino)-6-(3-methylimidazo[4,5-c]pyridin-7-yl)pyrazine-2-carboxamide

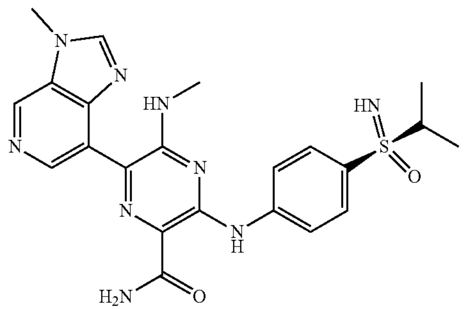

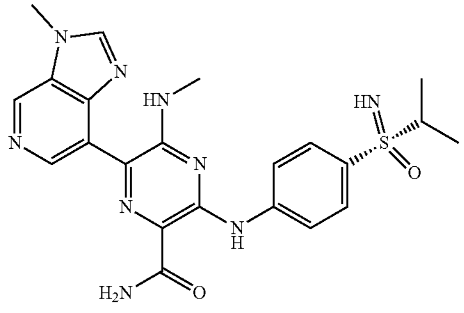

(a) (4-Bromophenyl)-imino-isopropyl-oxo-16-sulfane

Ammonium carbamate (0.844 g, 10.8 mmol) was added to a solution of 1-bromo-4-isopropylsulfanyl-benzene (1.00 g, 4.33 mmol) and [acetoxy (phenyl)-23-iodanyl]acetate (4.18 g, 13.0 mmol) in MeOH (10 mL). The resulting solution was stirred at 25° C. for 3 hours. The resulting residue was purified by C18 reverse phase chromatography, using 5-90% MeCN—$H_2O$ as eluent, to afford (4-bromophenyl)-imino-isopropyl-oxo-26-sulfane (0.900 g, 79%) as a yellow oil. 1H NMR (400 MHZ, DMSO-d6) δ 1.01-1.18 (6H, m), 3.16-3.28 (1H, m), 4.26 (1H, s), 7.77 (2H, d), 7.82 (2H, d); m/z: (ES+), [M+H]+=262.0

(b) tert-Butyl N-[(4-bromophenyl)-isopropyl-oxo-16-sulfanylidene]carbamate

DMAP (0.350 g, 2.86 mmol) was added to a solution of (4-bromophenyl)-imino-isopropyl-oxo-26-sulfane (1.50 g, 5.72 mmol), di-tert-butyl dicarbonate (2.66 mL, 11.4 mmol), and DIPEA (3.00 mL, 17.16 mmol) in DCM (15 mL). The resulting solution was stirred at 25° C. for 18 hours. The reaction was then concentrated. The resulting residue was purified by silica gel chromatography, using 0-40% EtOAc-petroleum ether as eluent, to afford tert-butyl N-[(4-bromophenyl)-isopropyl-oxo-26-sulfanylidene]carbamate (0.875 g, 42%) as a white solid; 1H NMR (400 MHZ, DMSO-d6) δ 1.09 (3H, d), 1.22 (9H, s), 1.27 (3H, d), 3.60-3.70 (1H, m), 7.74 (2H, d), 7.92 (2H, d). m/z: (ES+), [M+H]+=362.2

(c) Methyl 3-[4-(N-tert-butoxycarbonyl-S-isopropyl-sulfonimidoyl)anilino]-5 (methylamino)-6-(3-methylimidazo[4,5-c]pyridin-7-yl)pyrazine-2-carboxylate Brettphos Pd G3 (87 mg, 0.10 mmol) was added to a suspension of methyl 3-amino-6-(3-methyl-3H-imidazo[4,5-c]pyridin-7-yl)-5-(methylamino) pyrazine-2-carboxylate (150 mg, 0.48 mmol), tert-butyl N-[(4-bromophenyl)-isopropyl-oxo-26-sulfanylidene]carbamate (347 mg, 0.96 mmol), and cesium carbonate (468 mg, 1.44 mmol) in 1,4-dioxane (8 mL) under nitrogen. The resulting mixture was stirred at 100° C. for 16 hours. The reaction was then concentrated. The resulting residue was purified by silica gel chromatography, using 0-20% MeOH-DCM as eluent, to afford methyl 3-[4-(N-tert-butoxycarbonyl-S-isopropyl-sulfonimidoyl)anilino]-5-(methylamino)-6-(3-methylimidazo[4,5-c]pyridin-7-yl)pyrazine-2-carboxylate (0.153 g, 54%) as a yellow solid; 1H NMR (300 MHZ, DMSO-d6) δ 1.14 (3H, d), 1.25 (9H, s), 1.28 (3H, d), 2.95 (3H, d), 3.64 (1H, heptet), 3.86 (3H, s), 4.02 (3H, s), 7.77 (2H, d), 8.01 (1H, br q), 8.14 (2H, d), 8.51 (1H, s), 8.54 (1H, s), 9.07 (1H, s), 10.80 (1H, s). m/z: (ES+), [M+H]+=595.6

(d) Methyl 3-[4-(isopropylsulfonimidoyl)anilino]-5-(methylamino)-6-(3-methylimidazo[4,5-c]pyridin-7-yl)pyrazine-2-carboxylate 4 M HCl in 1,4-dioxane (3.0 mL, 12 mmol) was added to a suspension of methyl 3-[4-(N-tert-butoxycarbonyl-S-isopropyl-sulfonimidoyl)anilino]-5-(methylamino)-6-(3-methylimidazo[4,5-c]pyridin-7-yl)pyrazine-2-carboxylate (140 mg, 0.24 mmol) in MeOH (3 mL). The resulting mixture was stirred at 25° C. for 2 hours. The reaction was then concentrated to afford methyl 3-[4-(isopropylsulfonimidoyl)anilino]-5-(methylamino)-6-(3-methylimidazo[4,5-c]pyridin-7-yl)pyrazine-2-carboxylate (0.112 g, 96%) as a yellow solid. 1H NMR (300 MHz, DMSO-d6) δ 1.30 (3H, d), 1.39 (3H, d), 2.95 (3H, d), 3.86 (4H, s), 4.15 (3H, s), 4.18-4.26 (1H, m), 7.73 (1H, br q), 8.02 (2H, d), 8.28 (2H, d), 8.74 (1H, s), 9.03 (1H, s), 9.68 (1H, s), 10.99 (1H, s); m/z: (ES+), [M+H]+=495.2

(e) rel-(R)-3-[4-(Isopropylsulfonimidoyl)anilino]-5-(methylamino)-6-(3-methylimidazo[4,5-c]pyridin-7-yl)pyrazine-2-carboxamide and rel-(S)-3-[4-(isopropylsulfonimidoyl)anilino]-5-(methylamino)-6-(3-methylimidazo[4,5-c]pyridin-7-yl)pyrazine-2-carboxamide 7 N Methanolic ammonia (5.0 mL, 35 mmol) was added to methyl 3-[4-(isopropylsulfonimidoyl)anilino]-5-(methylamino)-6-(3-methylimidazo[4,5-c]pyridin-7-yl)pyrazine-2-carboxylate (92 mg, 0.19 mmol). The resulting mixture was stirred at 80° C. for 20 hours. The reaction was then concentrated. The resulting residue was purified by preparative HPLC, using a 5 micron, 50 mm×150 mm XSelect CSH Prep C18 OBD column, decreasingly polar mixtures of MeCN—$H_2O$ as eluent, and 0.1% formic acid as modifier, to afford a yellow solid. This material was further purified by preparative chiral HPLC, using a Chiralpak IH3 column, isocratic 1:1 MeOH-IPA as eluent, and ammonia as modifier, to afford rel-(R)-3-[4-(isopropylsulfonimidoyl)anilino]-5-(methylamino)-6-(3-methylimidazo[4,5-c]pyridin-7-yl) pyrazine-2-carboxamide (7.5 mg, 8.2%) and rel-(S)-3-[4-(isopropylsulfonimidoyl)anilino]-5-(methylamino)-6-(3-methylimidazo[4,5-c]pyridin-7-yl)pyrazine-2-carboxamide (18 mg, 20%), each as a yellow solid; 1H NMR (400 MHZ, DMSO-d6) δ 1.11-1.19 (6H, m), 2.99 (3H, d), 3.12-3.23 (1H, m), 3.94 (1H, s), 4.02 (3H, s), 7.49 (1H, s), 7.74-7.82 (2H, m), 7.84 (1H, s), 7.98-8.07 (3H, m), 8.53 (1H, s), 8.74 (1H, s), 9.04 (1H, s), 11.95 (1H, s); m/z: (ES+), [M+H]+= 480.1

Example 198

3-[4-(tert-Butylsulfonimidoyl)anilino]-5-(methylamino)-6-(3-methylimidazo[4,5-c]pyridin-7-yl)pyrazine-2-carboxamide

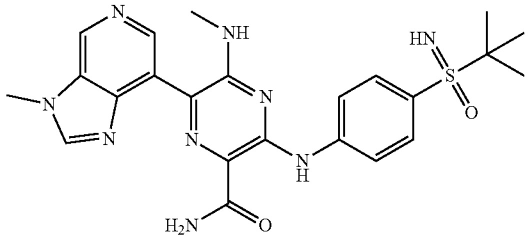 [SMILES: CNc1nc(Nc2ccc(S(=N)(=O)C(C)(C)C)cc2)c(C(N)=O)nc1-c1cncc2c1ncn2C]

(a) Methyl 3-(4-tert-butylsulfanylanilino)-5-(methylamino)-6-(3-methylimidazo[4,5-c]pyridin-7-yl)pyrazine-2-carboxylate BrettPhos Pd G3 (130 mg, 0.15 mmol) was added to a mixture of cesium carbonate (312 mg, 0.960 mmol), 1-bromo-4-tert-butylsulfanyl-benzene (352 mg, 1.44 mmol) and methyl 3-amino-5-(methylamino)-6-(3-methylimidazo [4,5-c]pyridin-7-yl)pyrazine-2-carboxylate (300 mg, 0.96 mmol) in 1,4-dioxane (40 mL) under nitrogen. The resulting mixture was stirred at 100° C. for 2 hours. The reaction was then concentrated. The resulting residue was purified by silica gel chromatography, using 0-10% MeOH-DCM as eluent, to afford methyl 3-(4-tert-butylsulfanylanilino)-5-(methylamino)-6-(3-methylimidazo[4,5-c]pyridin-7-yl) pyrazine-2-carboxylate (0.250 g, 55%) as a yellow solid; 1H NMR (300 MHz, DMSO-d6) δ 1.26 (9H, s), 2.95 (3H, d), 3.85 (3H, s), 4.02 (3H, s), 7.44-7.54 (2H, m), 7.83-7.93 (2H, m), 7.99 (1H, br q), 8.51 (1H, s), 8.55 (1H, s), 9.06 (1H, s), 10.57 (1H, s); m/z: (ES+), [M+H]+=478.2

(b) Methyl 3-[4-(tert-butylsulfonimidoyl)anilino]-5-(methylamino)-6-(3-methylimidazo[4,5-c]pyridin-7-yl)pyrazine-2-carboxylate Ammonium carbamate (82.0 mg, 1.05 mmol) was added to a suspension of [acetoxy (phenyl)-23-iodanyl]acetate (405 mg, 1.26 mmol), methyl 3-(4-tert-butylsulfanylanilino)-5-(methylamino)-6-(3-methylimidazo[4,5-c] pyridin-7-yl)pyrazine-2-carboxylate (200 mg, 0.42 mmol) in MeOH (20 mL). The resulting mixture was stirred at 25° C. for 3 hours. The resulting residue was purified by silica gel chromatography, using 0-10% MeOH-DCM as eluent, to afford methyl 3-[4-(tert-butylsulfonimidoyl)anilino]-5-(methylamino)-6-(3-methylimidazo[4,5-c]pyridin-7-yl) pyrazine-2-carboxylate (0.070 g, 33%) as a yellow solid; 1H NMR (300 MHz, DMSO-d6) δ 1.25 (9H, s), 2.95 (3H, d), 3.86 (3H, s), 3.91-4.00 (1H, m), 4.02 (3H, s), 7.79-7.83 (2H, m), 7.99-8.03 (1H, m), 8.04-8.12 (2H, m), 8.51 (1H, s), 8.55 (1H, s), 9.07 (1H, s), 10.77 (1H, s); m/z: (ES+), $[M+2H]^{2+}$ =255.2

(c) 3-[4-(tert-Butylsulfonimidoyl)anilino]-5-(methylamino)-6-(3-methylimidazo[4,5-c]pyridin-7-yl)pyrazine-2-carboxamide 7 N Methanolic ammonia (1.0 mL, 7.0 mmol) was added to methyl 3-[4-(tert-butylsulfonimidoyl)anilino]-5-(methylamino)-6-(3-methylimidazo[4,5-c]pyridin-7-yl)pyrazine-2-carboxylate (60 mg, 0.12 mmol) in MeOH (10 mL). The resulting suspension was stirred at 80° C. for 10 hours. The reaction was then concentrated. The resulting residue was purified by preparative SFC, using a 5 micron, 20 mm×250 mm, Triart Diol-NP column, isocratic 35% MeOH-$sCO_2$ as eluent, and 8 mM ammonia as modifier, to afford 3-[4-(tert-butylsulfonimidoyl)anilino]-5-(methylamino)-6-(3-methylimidazo[4,5-c]pyridin-7-yl)pyrazine-2-carboxamide (12 mg, 21%) as a yellow solid; 1H NMR (300 MHz, DMSO-d6) δ 1.25 (9H, s), 3.00 (3H, d), 3.90 (1H, s), 4.03 (3H, s), 7.51 (1H, d), 7.76-7.82 (2H, d), 7.86 (1H, s), 7.96-8.15 (3H, m), 8.54 (1H, s), 8.74 (1H, s), 9.05 (1H, s), 11.97 (1H, s); m/z: (ES+), [M+H]+=494.3

Example 199

5-(Methylamino)-6-(3-methylimidazo[4,5-c]pyridin-7-yl)-3-[4-(1-methylsulfonylcyclopropyl)anilino] pyrazine-2-carboxamide

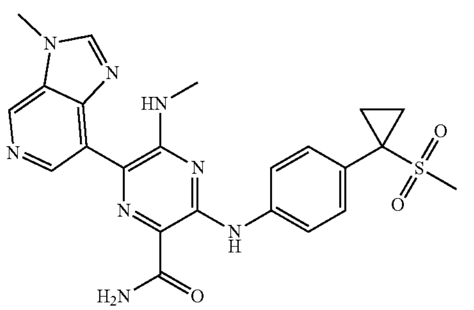 [SMILES: CNc1nc(Nc2ccc(C3(S(C)(=O)=O)CC3)cc2)c(C(N)=O)nc1-c1cncc2c1ncn2C]

(a) 5-(Methylamino)-6-(3-methylimidazo[4,5-c] pyridin-7-yl)-3-[4-(1-methylsulfonylcyclopropyl) anilino]pyrazine-2-carboxylic acid A mixture of methyl 3-amino-6-(3-methyl-3H-imidazo[4,5-c]pyridin-7-yl)-5-(methylamino) pyrazine-2-carboxylate (75 mg, 0.24 mmol), 1-bromo-4-(1-methylsulfonylcyclopropyl)benzene (79 mg, 0.29 mmol), BrettPhos Pd G3 (22 mg, 0.020 mmol) and sodium tert-butoxide (69 mg, 0.72 mmol) was evacuated and backfilled three times with nitrogen. 1,4-Dioxane (2 mL) was added, and the mixture was evacuated and backfilled twice with nitrogen. The resulting mixture was stirred at 80° C. for 3 hours. The reaction was then concentrated. The resulting residue was acidified with 1N HCl, then washed with ethyl acetate. The aqueous layer was concentrated. The resulting residue was used in the next step without further purification, assuming 100% yield.

(b) 5-(Methylamino)-6-(3-methylimidazo[4,5-c] pyridin-7-yl)-3-[4-(1-methylsulfonylcyclopropyl) anilino]pyrazine-2-carboxamide DIPEA (0.25 mL, 1.4 mmol) was added to a suspension of 5-(methylamino)-6-(3-methylimidazo[4,5-c]pyridin-7-yl)-3-[4-(1-methylsulfonylcyclopropyl)anilino]pyrazine-2-carboxylic acid (118 mg, 0.240 mmol), ammonium chloride (51.2 mg, 0.96 mmol), and HATU (180 mg, 0.48 mmol) in DMF (2 mL). The resulting mixture was stirred at 25° C. for 1 hour. The reaction was then concentrated. The resulting residue was purified by silica gel chromatography, using 0-8% MeOH-DCM, to afford 5-(methylamino)-6-(3-methylimidazo[4,5-c]pyridin-7-yl)-3-[4-(1-methylsulfonylcyclopropyl)anilino]pyrazine-2-carboxamide (32 mg, 27%) as a light yellow solid; 1H NMR (500 MHZ, DMSO-d6) δ ppm 1.23-1.36 (2H, m), 1.56-1.68 (2H, m), 2.87 (3H, s), 2.98 (3H, d), 4.03 (3H, s), 7.42 (1H, br s), 7.53 (2H, d), 7.79 (1H, br s), 7.85 (2H, d), 8.03 (1H, br q), 8.53 (1H, s), 8.74 (1H, s), 9.04 (1H, s), 11.70 (1H, s; m/z: (ES+), [M+H]+493.3

Example 200

5-Methoxy-6-(3-methylimidazo[4,5-c]pyridin-7-yl)-3-[4-(1-methylsulfonylcyclopropyl)anilino]pyrazine-2-carboxamide

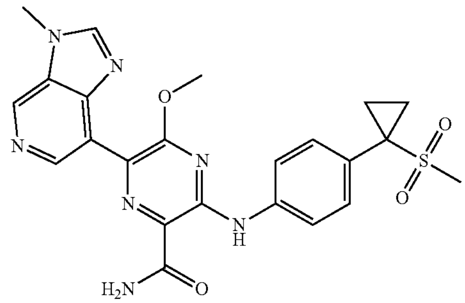 [SMILES: COc1nc(Nc2ccc(C3(S(C)(=O)=O)CC3)cc2)c(C(N)=O)nc1-c1cncc2c1ncn2C]

(a) Methyl 3-amino-5-methoxy-6-(3-methylimidazo [4,5-c]pyridin-7-yl)pyrazine-2-carboxylate 7-Bromo-3-methyl-imidazo[4,5-c]pyridine (200 mg, 0.94 mmol), bis(pinacolato)diboron (359 mg, 1.41 mmol), potassium acetate (278 mg, 2.83 mmol), cataCXium A Pd G3 (69 mg, 0.090 mmol), and cataCXium A (34 mg, 0.090 mmol) were combined in a microwave vial, which was evacuated and backfilled three times with nitrogen. DMF (5 mL) was added and the reaction was heated to 80° C. for 20 hours. The mixture was allowed to cool to room temperature and set aside.

A mixture of methyl 3-amino-6-chloro-5-methoxy-pyrazine-2-carboxylate (410 mg, 1.88 mmol), $PdCl_2$(dppf)-DCM adduct (77 mg, 0.090 mmol) and cesium fluoride (286 mg, 1.88 mmol) was evacuated and backfilled three times with nitrogen. The borylation reaction mixture was added to the vial via syringe. The vial was evacuated and backfilled twice with nitrogen. The resulting mixture was stirred at 100° C. for 2 hours. The reaction was then concentrated. The resulting residue was purified by silica gel chromatography, using 0-10% MeOH-DCM as eluent, to afford methyl 3-amino-5-methoxy-6-(3-methylimidazo[4,5-c]pyridin-7-yl)pyrazine-2-carboxylate (158 mg, 53%) as a light brown solid; 1H NMR (500 MHz, METHANOL-d4) δ ppm 3.88-3.92 (3H, m), 3.93 (3H, s), 4.07 (3H, s), 8.37 (1H, s), 8.44 (1H, s), 8.98 (1H, s). The NH2 peak exchanged out; m/z: (ES+), [M+H]+315.2

(b) 5-Methoxy-6-(3-methylimidazo[4,5-c]pyridin-7-yl)-3-[4-(1-methylsulfonylcyclopropyl)anilino]pyrazine-2-carboxylic acid A mixture of methyl 3-amino-5-methoxy-6-(3-methylimidazo[4,5-c]pyridin-7-yl)pyrazine-2-carboxylate (60 mg, 0.19 mmol), 1-bromo-4-(1-methylsulfonylcyclopropyl)benzene (63 mg, 0.23 mmol), BrettPhos Pd G3 (17 mg, 0.020 mmol) and sodium tert-butoxide (55.0 mg, 0.57 mmol) was evacuated and backfilled three times with nitrogen. 1,4-Dioxane (2 mL) was added, and the mixture was evacuated and backfilled twice with nitrogen. The resulting mixture was stirred at 80° C. for 3 hours. The reaction was then concentrated. The resulting residue was acidified with 1N aqueous HCl, then washed with ethyl acetate. The aqueous layer was then concentrated. The resulting residue was used directly in the next step without further purification, assuming 100% yield.

(c) 5-Methoxy-6-(3-methylimidazo[4,5-c]pyridin-7-yl)-3-[4-(1-methylsulfonylcyclopropyl)anilino]pyrazine-2-carboxamide DIPEA (0.199 mL, 1.14 mmol) was added to a suspension of 5-methoxy-6-(3-methylimidazo[4,5-c]pyridin-7-yl)-3-[4-(1-methylsulfonylcyclopropyl)anilino]pyrazine-2-carboxylic acid (94 mg, 0.19 mmol), ammonium chloride (41 mg, 0.76 mmol), and HATU (145 mg, 0.380 mmol) in DMF (2 mL). The resulting mixture was stirred at 25° C. for 1 hour. The reaction was then concentrated. The resulting residue was purified by silica gel chromatography, using 0-8% MeOH-DCM, to afford 5-methoxy-6-(3-methylimidazo[4,5-c]pyridin-7-yl)-3-[4-(1-methylsulfonylcyclopropyl)anilino]pyrazine-2-carboxamide (4 mg, 4.3%) as a light yellow solid; 1H NMR (500 MHz, DMSO-d6) δ ppm 1.24-1.32 (2H, m), 1.57-1.64 (2H, m), 2.86 (3H, s), 3.97 (3H, s), 3.99 (3H, s), 7.55 (2H, d), 7.74-7.83 (3H, m), 8.03 (1H, br s), 8.40 (1H, s), 8.62 (1H, s), 8.99 (1H, s), 11.61 (1H, s). m/z: (ES+), [M+H]+494.4

Example 201

5-Methoxy-6-(3-methylimidazo[4,5-c]pyridin-7-yl)-3-[(1-methylpyrazol-4-yl)amino]pyrazine-2-carboxamide

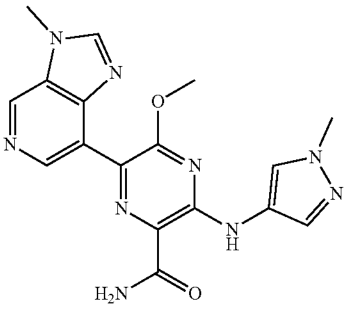 [SMILES: COc1nc(Nc2cnn(C)c2)c(C(N)=O)nc1-c1cncc2c1ncn2C]

(a) Methyl 6-chloro-5-methoxy-3-[(1-methylpyrazol-4-yl)amino]pyrazine-2-carboxylate 1-Methylpyrazol-4-amine (106 mg, 1.09 mmol) was added to a solution of methyl 6-chloro-3-fluoro-5-methoxypyrazine-2-carboxylate (200 mg, 0.91 mmol) and DIPEA (0.475 mL, 2.72 mmol) in DMF (15 mL). The resulting mixture was stirred at 100° C. for 2 hours. The reaction was then concentrated to afford methyl 6-chloro-5-methoxy-3-[(1-methylpyrazol-4-yl)amino]pyrazine-2-carboxylate (250 mg, 93%) as a yellow solid; 1H NMR (300 MHz, DMSO-d6) δ 3.82 (3H, s), 3.84 (3H, s), 4.07 (3H, s), 7.67-7.75 (1H, m), 7.99 (1H, d), 9.92 (1H, s). m/z: (ES+), [M+H]+298.1

(b) Methyl 5-methoxy-6-(3-methylimidazo[4,5-c]pyridin-7-yl)-3_ [(1-methylpyrazol-4-yl)amino]pyrazine-2-carboxylate $PdCl_2$(dppf) (49.2 mg, 0.07 mmol) was added to a suspension of (3-methylimidazo[4,5-c]pyridin-7-yl) boronic acid (143 mg, 0.81 mmol) cesium fluoride (204 mg, 1.34 mmol) and methyl 6-chloro-5-methoxy-3-[(1-methylpyrazol-4-yl)amino]pyrazine-2-carboxylate (200 mg, 0.67 mmol) in DMF (5 mL). The resulting mixture was stirred at 100° C. for 1 hour. The reaction was then concentrated. The resulting residue was purified by silica gel chromatography, using 0-10% MeOH-DCM as eluent, to afford methyl 5-methoxy-6-(3-methylimidazo[4,5-c]pyridin-7-yl)-3-[(1-methylpyrazol-4-yl)amino]pyrazine-2-carboxylate (150 mg, 57%) as a yellow solid. 1H NMR (300 MHz, DMSO-d6) δ 3.85 (3H, s), 3.86 (3H, s), 3.96 (3H, s), 3.98 (3H, s), 7.79 (1H, s), 8.11 (1H, s), 8.38 (2H, s), 9.01 (1H, s), 10.08 (1H, s). m/z: (ES+), [M+H]+=395.2

(c) 5-Methoxy-6-(3-methylimidazo[4,5-c]pyridin-7-yl)-3-[(1-methylpyrazol-4-yl)amino]pyrazine-2-carboxamide 7 N Methanolic ammonia (0.714 mL, 5.00 mmol) was added to a suspension of methyl 5-methoxy-6-(3-methylimidazo[4,5-c]pyridin-7-yl)-3-[(1-methylpyrazol-4-yl)amino]pyrazine-2-carboxylate (110 mg, 0.28 mmol) in MeOH (10 mL). The resulting mixture was stirred at 70° C. for 16 hours. The reaction was then concentrated. The resulting residue was purified by preparative HPLC, using a 5 micron, 30 mm×150 mm C18 column, 5 to 20% MeCN-water as eluent, and 0.1% formic acid as modifier, to afford 5-methoxy-6-(3-methylimidazo[4,5-c]pyridin-7-yl)-3-[(1-methylpyrazol-4-yl)amino]pyrazine-2-carboxamide (45 mg, 41% yield) as a yellow solid. 1H NMR (300 MHz, DMSO-d6) δ 3.86 (3H, s), 3.99 (3H, s), 4.00 (3H, s), 7.69 (1H, s), 7.74 (1H, d), 7.92 (1H, s), 8.12 (1H, d), 8.41 (1H, s), 8.60 (1H, s), 9.00 (1H, s), 11.00 (1H, s) m/z: (ES+), [M+H]+=380.2

Example 202

5-(Methylamino)-6-(3-methylimidazo[4,5-c]pyridin-7-yl)-3-[(1-tetrahydropyran-4-ylpyrazol-4-yl)amino]pyrazine-2-carboxamide

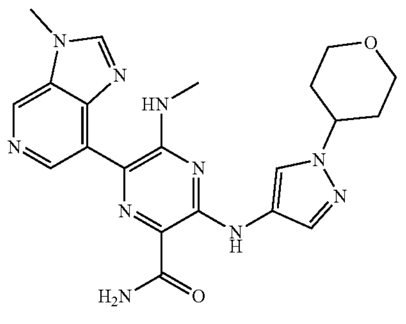 [SMILES: CNc1nc(Nc2cnn(C3CCOCC3)c2)c(C(N)=O)nc1-c1cncc2c1ncn2C]

(a) Methyl 6-chloro-5-(methylamino)-3-[(1-tetrahydropyran-4-ylpyrazol-4-yl)amino]pyrazine-2-carboxylate DIPEA (0.24 mL, 1.4 mmol) was added to a mixture of methyl 6-chloro-3-fluoro-5-(methylamino) pyrazine-2-carboxylate (60 mg, 0.27 mmol) and 1-tetrahydropyran-4-ylpyrazol-4-amine (55 mg, 0.33 mmol) in acetonitrile (2 mL). The resulting mixture was stirred at 120° C. for 3 hours in a Biotage microwave reactor. The reaction was then concentrated. The resulting residue was purified by silica gel chromatography, using 0-100% EtOAc-hexanes as eluent, to afford methyl 6-chloro-5-(methylamino)-3-[(1-tetrahydro-pyran-4-ylpyrazol-4-yl)amino]pyrazine-2-carboxylate (83 mg, 83%) as a yellow solid. m/z: (ES+), [M+H]+=367.2

(b) Methyl 5-(methylamino)-6-(3-methylimidazo[4,5-c]pyridin-7-yl)-3-[(1-tetrahydropyran-4-ylpyrazol-4-yl)amino]pyrazine-2-carboxylate 7-Bromo-3-methyl-imidazo[4,5-c]pyridine (60 mg, 0.28 mmol), bis(pinacolato)diboron (79 mg, 0.31 mmol), potassium acetate (83 mg, 0.85 mmol), cataCXium A Pd G3 (21 mg, 0.030 mmol), and cataCXium A (10 mg, 0.030 mmol) were combined in a microwave vial, which was then evacuated and backfilled three times with nitrogen. DMF (2 mL) was added and the resulting mixture was stirred at 80 C for 20 hours. The mixture was allowed to cool to room temperature and set aside.

Methyl 6-chloro-5-(methylamino)-3-[(1-tetrahydropyran-4-ylpyrazol-4-yl)amino]pyrazine-2-carboxylate (103 mg, 0.280 mmol), $PdCl_2$(dppf)-DCM adduct (23 mg, 0.030 mmol) and cesium fluoride (86 mg, 0.56 mmol) were combined in a microwave vial, which was evacuated and backfilled three times with nitrogen. The borylation reaction mixture was added to the vial via syringe. The vial was evacuated and backfilled twice with nitrogen. The resulting mixture was stirred at 100° C. for 2 hours. The reaction was then concentrated. The resulting residue was purified by silica gel chromatography, using 0-10% MeOH-DCM as eluent, to afford methyl 5-(methylamino)-6-(3-methylimidazo[4,5-c]pyridin-7-yl)-3-[(1-tetrahydropyran-4-ylpyrazol-4-yl)amino]pyrazine-2-carboxylate (37 mg, 28%) as a light brown solid. m/z: (ES+), [M+H]+=464.4

(c) 5-(Methylamino)-6-(3-methylimidazo[4,5-c]pyridin-7-yl)-3_ [(1-tetrahydropyran-4-ylpyrazol-4-yl)amino]pyrazine-2-carboxamide 7 N Methanolic ammonia (2 mL, 14 mmol) was added to methyl 5-(methylamino)-6-(3-methylimidazo[4,5-c]pyridin-7-yl)-3-[(1-tetrahydropyran-4-ylpyrazol-4-yl)amino]pyrazine-2-carboxylate (37 mg, 0.080 mmol). The resulting mixture was stirred at 120° C. for 3 hours, then at 140° C. for 1 hour. The reaction was concentrated. The resulting residue was suspended in 2M aqueous KOH (0.50 mL, 1.0 mmol), MeOH (1 mL), and THF (1 mL). The resulting mixture was stirred at 25° C. for 16 hours. The reaction was then quenched with 1M aqueous HCl (1.2 mL, 1.2 mmol). The resulting mixture was concentrated, then taken up in DMF (1 mL). Ammonium chloride (17 mg, 0.32 mmol), HATU (61 mg, 0.16 mmol), and DIPEA (0.084 mL, 0.48 mmol) were sequentially added. The resulting mixture was stirred at 25° C. for 1 hour. The reaction was concentrated. The resulting residue was purified by silica gel chromatography, using 0-8% MeOH-DCM, to afford 5-(methylamino)-6-(3-methylimidazo[4,5-c]pyridin-7-yl)-3-[(1-tetrahydropyran-4-ylpyrazol-4-yl)amino]pyrazine-2-carboxamide (22 mg, 61%) as a yellow solid; 1H NMR (500 MHZ, DMSO-d6) δ ppm 1.88-2.07 (4H, m), 3.00 (3H, d), 3.49 (2H, td), 3.93-4.00 (2H, m), 4.02 (3H, s), 4.32-4.43 (1H, m), 7.29 (1H, br s), 7.67 (1H, br s), 7.77 (1H, s), 8.01 (1H, br q), 8.18 (1H, s), 8.52 (1H, s), 8.72 (1H, s), 9.01 (1H, s), 11.01 (1H, s); m/z: (ES+), [M+H]+=449.3

Example 203

3-[(1-Isopropylpyrazol-4-yl)amino]-5-(methylamino)-6-(3-methylimidazo[4,5-c]pyridin-7-yl)pyrazine-2-carboxamide

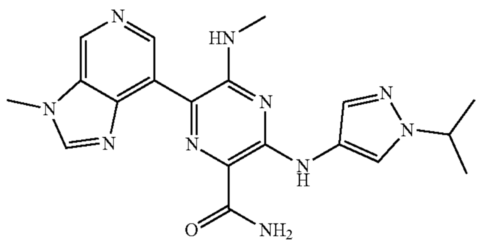 [SMILES: CNc1nc(Nc2cnn(C(C)C)c2)c(C(N)=O)nc1-c1cncc2c1ncn2C]

(a) Methyl 3-fluoro-5-(methylamino)-6-(3-methylimidazo[4,5-c]pyridin-7-yl)pyrazine-2-carboxylate CataCXium A Pd G2 (2.52 g, 3.77 mmol) was added to a mixture of 7-bromo-3-methyl-imidazo[4,5-c]pyridine (4.00 g, 18.9 mmol), potassium acetate (5.55 g, 56.6 mmol), bis(pinacolato)diboron (9.58 g, 37.7 mmol), and bis(1-adamantyl)-butyl-phosphonium tetrafluoroborate (1.68 g, 3.77 mmol) in 1,4-dioxane (1 mL) under nitrogen. The resulting mixture was stirred at 80° C. for 16 hours. The reaction was then allowed to cool to room temperature. Methyl 6-chloro-3-fluoro-5-(methylamino) pyrazine-2-carboxylate (4.14 g, 18.9 mmol), and cesium fluoride (8.60 g, 56.6 mmol) were added to the reaction mixture under nitrogen. The resulting mixture was stirred at 100° C. for 4 hours. The reaction was then concentrated. The resulting residue was purified by silica gel chromatography, using 0-15% MeOH-DCM as eluent, to afford methyl 3-fluoro-5-(methylamino)-6-(3-methylimidazo[4,5-c]pyridin-7-yl)pyrazine-2-carboxylate (1.90 g, 32%) as an orange solid; 1H NMR (300 MHZ, DMSO-d6) δ 2.83 (3H, d), 3.81 (3H, s), 4.02 (3H, s), 7.89 (1H, br q), 8.48 (1H, s), 8.50 (1H, s), 9.12 (1H, s); m/z: (ES+), [M+H]+=317.0

(b) Methyl 3-[(1-isopropylpyrazol-4-yl)amino]-5-(methylamino)-6-(3-methylimidazo[4,5-c]pyridin-7-yl)pyrazine-2-carboxylate Methyl 3-fluoro-5-(methylamino)-6-(3-methylimidazo[4,5-c]pyridin-7-yl)pyrazine-2-carboxylate (100 mg, 0.32 mmol) was added to a solution of 1-isopropylpyrazol-4-amine (79 mg, 0.63 mmol) and DIPEA (170 μL, 0.95 mmol) in DMSO (10 mL). The resulting mixture was stirred at 100° C. for 3 hours. The reaction was then concentrated. The resulting residue was purified by silica gel chromatography, using 0-10% MeOH-DCM as eluent, to afford methyl 3-[(1-isopropylpyrazol-4-yl)amino]-5-(methylamino)-6-(3-methylimidazo[4,5-c]pyridin-7-yl)pyrazine-2-carboxylate (0.090 g, 68%) as a yellow solid; 1H NMR (300 MHZ, DMSO-d6) δ 1.44 (6H, d), 2.97 (3H, d), 3.82 (3H, s), 4.02 (3H, s), 4.42-4.54 (1H, m), 7.78 (1H, s), 7.92 (1H, br q), 8.19 (1H, s), 8.49 (1H, s), 8.53 (1H, s), 9.03 (1H, s), 10.07 (1H, s); m/z: (ES+), [M+H]+=422.2

(c) 3-[(1-Isopropylpyrazol-4-yl)amino]-5-(methylamino)-6-(3-methylimidazo[4,5-c]pyridin-7-yl)pyrazine-2-carboxamide 7 N Methanolic ammonia (1.0 mL, 7.0 mmol) was added to methyl 3-[(1-isopropylpyrazol-4-yl)amino]-5-(methylamino)-6-(3-methylimidazo[4,5-c]pyridin-7-yl)pyrazine-2-carboxylate (70 mg, 0.17 mmol). The resulting mixture was stirred at 80° C. for 4 hours. The reaction was then concentrated. The resulting residue was purified by preparative HPLC using a 5 micron, 30 mm×150 mm Xselect CSH OBD column, 2-25% MeCN—$H_2O$ as eluent, and 0.1% formic acid as modifier, to afford 3-[(1-isopropylpyrazol-4-yl)amino]-5-(methylamino)-6-(3-methylimidazo[4,5-c]pyridin-7-yl)pyrazine-2-carboxamide (27 mg, 40%) as a yellow solid; 1H NMR (400 MHZ, DMSO-d6) δ 1.43 (6H, d), 2.98 (3H, d), 4.00 (3H, s), 4.40-4.52 (1H, m), 7.27 (1H, s), 7.65 (1H, s), 7.72 (1H, s), 7.98 (1H, br q), 8.14 (1H, s), 8.51 (1H, s), 8.71 (1H, s), 9.00 (1H, s), 10.97 (1H, s); m/z: (ES+), [M+H]+=407.2

Example 204

3-[[1-(1,1-Dioxothian-4-yl)pyrazol-4-yl]amino]-5-(methylamino)-6-(3-methylimidazo[4,5-c]pyridin-7-yl)pyrazine-2-carboxamide

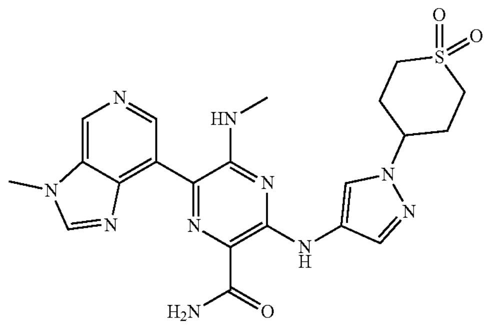 [SMILES: CNc1nc(Nc2cnn(C3CCS(=O)(=O)CC3)c2)c(C(N)=O)nc1-c1cncc2c1ncn2C]

(a) Methyl 3-bromo-6-chloro-5-(methylamino) pyrazine-2-carboxylate tert-Butyl nitrite (143 mg, 1.38 mmol) was added to a mixture of bromotrimethylsilane (120 μL, 0.92 mmol) and methyl 3-amino-6-chloro-5-(methylamino) pyrazine-2-carboxylate (100 mg, 0.46 mmol) in dibromomethane (10 mL) under nitrogen. The resulting mixture was stirred at 60° C. for 2 hours. The reaction was then concentrated. The resulting residue was purified by silica gel chromatography, using 0-20% EtOAc-petroleum ether, to afford methyl 3-bromo-6-chloro-5-(methylamino) pyrazine-2-carboxylate (0.060 g, 47% yield) as a yellow solid; 1H NMR (300 MHz, DMSO-d6) δ 2.91 (3H, d), 3.80 (3H, s), 8.20 (1H, q); m/z (ES+), [M+2+H]+=281.9

(b) Methyl 6-chloro-3-[[1-(1,1-dioxothian-4-yl) pyrazol-4-yl]amino]-5-(methylamino) pyrazine-2-carboxylate Cesium carbonate (232 mg, 0.710 mmol) was added to a suspension of methyl 3-bromo-6-chloro-5-(methylamino) pyrazine-2-carboxylate (100 mg, 0.36 mmol), 1-(1,1-dioxothian-4-yl)pyrazol-4-amine (115 mg, 0.530 mmol) and XantPhos Pd G3 (68 mg, 0.070 mmol) in 1,4-dioxane (10 mL). The resulting mixture was stirred at 80° C. for 1 hour. The reaction was then concentrated. The resulting residue was purified by silica gel chromatography, using 0-10% MeOH-DCM as eluent, to afford methyl 6-chloro-3-[[1-(1,1-dioxothian-4-yl)pyrazol-4-yl]amino]-5-(methylamino) pyrazine-2-carboxylate (0.080 g, 54%) as a brown solid; 1H NMR (300 MHz, DMSO-d6) δ 2.20-2.49 (4H, m), 2.83-3.04 (4H, m), 3.18 (3H, br d), 3.78 (3H, s), 4.56 (1H, dt), 7.80 (1H, s), 7.83-7.94 (1H, m), 8.09 (1H, s), 9.93 (1H, s); m/z: (ES+), [M+H]+=415.0

(c) Methyl 3-[[1-(1,1-dioxothian-4-yl)pyrazol-4-yl] amino]-5-(methylamino)-6-(3-methylimidazo[4,5-c] pyridin-7-yl)pyrazine-2-carboxylate 7-Bromo-3-methyl-imidazo[4,5-c]pyridine (41 mg, 0.19 mmol) was added to a mixture of bic(pinacolato)diboron (122 mg, 0.480 mmol), cataCXium A tetrafluoroborate (13 mg, 0.020 mmol), CataCXium A Pd G2 (8.6 mg, 0.020 mmol), and potassium acetate (57 mg, 0.58 mmol) in DMF (10 mL) under nitrogen. The resulting mixture was stirred at 80° C. for 24 hours. The reaction was then allowed to cool to room temperature. To this reaction mixture, Pd(dppf)$Cl_2$ DCM adduct (14 mg, 0.020 mmol), cesium fluoride (88 mg, 0.58 mmol), and methyl 6-chloro-3-[[1-(1,1-dioxothian-4-yl)pyrazol-4-yl]amino]-5-(methylamino) pyrazine-2-carboxylate (80 mg, 0.19 mmol) were added. The resulting mixture was stirred at 80° C. for 3 hours. The reaction was then concentrated. The resulting residue was purified by silica gel chromatography, using 0-10% MeOH-DCM as eluent, to afford methyl 3-[[1-(1,1-dioxothian-4-yl)pyrazol-4-yl]amino]-5-(methylamino)-6-(3-methylimidazo[4,5-c] pyridin-7-yl)pyrazine-2-carboxylate (0.060 g, 61%) as a yellow solid; 1H NMR (400 MHZ, DMSO-d6) δ 2.24-2.46 (4H, m), 2.91 (3H, d), 3.14-3.19 (2H, m), 3.21-3.43 (2H, m), 3.74 (3H, s), 4.00 (3H, s), 4.55-4.67 (1H, m), 7.88 (1H, s), 8.20 (1H, s), 8.52 (1H, s), 8.98 (1H, s), 9.05 (1H, s). The two NH protons were broadened to baseline.

(d) 3-[[1-(1,1-Dioxothian-4-yl)pyrazol-4-yl]amino]-5-(methylamino)-6-(3-methylimidazo[4,5-c]pyridin-7-yl)pyrazine-2-carboxamide 7 N Methanolic ammonia (10 mL, 70 mmol) was added to methyl 3-[[1-(1,1-dioxothian-4-yl)pyrazol-4-yl]amino]-5-(methylamino)-6-(3-methylimidazo[4,5-c]pyridin-7-yl) pyrazine-2-carboxylate (55 mg, 0.11 mmol). The resulting mixture was stirred at 80° C. for 16 hours. The reaction was then concentrated. The resulting residue was purified by preparative HPLC using a 5 micron, 19 mm×250 mm XSelect CSH Prep C18 OBD column, 2-24% MeCN—$H_2O$ as eluent, and 0.1% formic acid as modifier, to afford 3-[[1-(1,1-dioxothian-4-yl)pyrazol-4-yl]amino]-5-(methylamino)-6-(3-methylimidazo[4,5-c]pyridin-7-yl)pyrazine-2-carboxamide (1.2 mg, 2.1%) as a yellow solid; 1H NMR (400 MHz, DMSO-d6) δ 2.29-2.43 (4H, m), 2.98 (3H, d), 3.19-3.51 (4H, m), 4.01 (3H, s), 4.54-4.64 (1H, m), 7.29 (1H, s), 7.67 (1H, s), 7.82 (1H, s), 8.01 (1H, br q), 8.18 (1H, s), 8.52 (1H, s), 8.72 (1H, s), 9.01 (1H, s), 11.02 (1H, s); m/z: (ES+), [M+H]+=497.2

Example 205

5-(Methylamino)-6-(3-methylimidazo[4,5-c]pyridin-7-yl)-3-[[1-(1-methyl-4-piperidyl)pyrazol-4-yl]amino]pyrazine-2-carboxamide

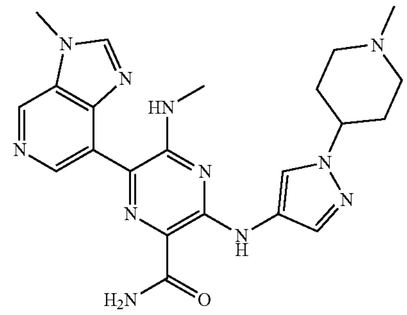 [SMILES: CNc1nc(Nc2cnn(C3CCN(C)CC3)c2)c(C(N)=O)nc1-c1cncc2c1ncn2C]

(a) Methyl 5-(methylamino)-6-(3-methylimidazo[4,5-c]pyridin-7-yl)-3-[[1-(1-methyl-4-piperidyl)pyrazol-4-yl]amino]pyrazine-2-carboxylate DIPEA (221 μL, 1.26 mmol) was added to a solution of 1-(1-methyl-4-piperidyl)pyrazol-4-amine (91 mg, 0.51 mmol) and methyl 3-fluoro-5-(methylamino)-6-(3-methylimidazo[4,5-c]pyridin-7-yl)pyrazine-2-carboxylate (80 mg, 0.25 mmol) in DMSO (8 mL). The resulting mixture was stirred at 100° C. for 16 hours. The reaction was then diluted with DCM and washed sequentially with water and brine. The organic layer was dried over sodium sulfate, filtered, and concentrated to afford methyl 5-(methylamino)-6-(3-methylimidazo[4,5-c]pyridin-7-yl)-3-[[1-(1-methyl-4-piperidyl)pyrazol-4-yl]amino]pyrazine-2-carboxylate (0.075 g, 62% yield) as a yellow solid. 1H NMR (400 MHz, DMSO-d6) δ 2.24 (7H, d), 2.49 (4H, s), 2.96 (3H, d). 3.27 (1H, s), 3.81 (3H, s), 4.01 (3H, s), 6.97 (1H, dd), 7.91 (1H, br q), 8.18 (1H, s), 8.50 (2H, d), 9.03 (1H, s), 10.08 (1H, s). m/z: (ES+), [M+H]+=477.3

(b) 5-(Methylamino)-6-(3-methylimidazo[4,5-c]pyridin-7-yl)-3-[[1-(1-methyl-4-piperidyl)pyrazol-4-yl]amino]pyrazine-2-carboxamide 7 N Methanolic ammonia (10 mL, 70 mmol) was added to methyl 5-(methylamino)-6-(3-methylimidazo[4,5-c]pyridin-7-yl)-3-[[1-(1-methyl-4-piperidyl)pyrazol-4-yl]amino]pyrazine-2-carboxylate (75 mg, 0.16 mmol). The resulting mixture was stirred at 80° C. for 16 hours. The reaction was then concentrated. The resulting residue was purified by reverse phase HPLC, using a 5 micron, 30×250 mm, YMC-Actus Triart C18 as column, 20-35% MeCN-water as eluent, and 10 mM ammonium carbonate and 0.1% ammonium hydroxide as modifier, to afford 5-(methylamino)-6-(3-methylimidazo[4,5-c]pyridin-7-yl)-3-[[1-(1-methyl-4-piperidyl)pyrazol-4-yl]amino]pyrazine-2-carboxamide (0.016 g, 22% yield) as a yellow solid. 1H NMR (DMSO-d6, 400 MHz) § 1.92 (2H, qd), 2.04 (4H, td), 2.20 (3H, s), 2.84 (2H, d), 2.98 (3H, d), 4.01 (3H, s), 4.08 (1H, dd), 7.29 (1H, s), 7.67 (1H, d), 7.74 (1H, s), 8.00 (1H, br q), 8.15 (1H, s), 8.52 (1H, s), 8.71 (1H, s), 9.00 (1H, s), 10.99 (1H, s). m/z: (ES+), [M+H]+=462.3

Example 206

5-(Methylamino)-6-(1-methylbenzimidazol-4-yl)-3-[[3-methyl-1-(1-methyl-4-piperidyl)pyrazol-4-yl]amino]pyrazine-2-carboxamide formate salt

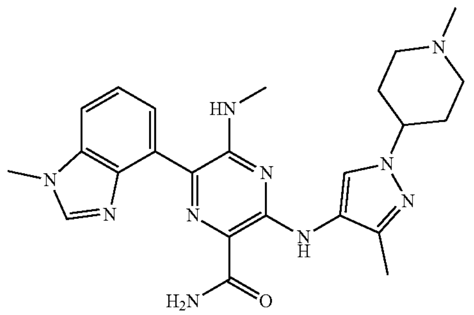 [SMILES: CNc1nc(Nc2cn(C3CCN(C)CC3)nc2C)c(C(N)=O)nc1-c1cccc2c1ncn2C]

(a) tert-Butyl 4-(3-methyl-4-nitro-pyrazol-1-yl) piperidine-1-carboxylate

3-Methyl-4-nitro-1H-pyrazole (2.00 g, 15.7 mmol) was added to a solution of tert-butyl 4-hydroxypiperidine-1-carboxylate (2.00 g, 9.94 mmol), triphenylphosphine (3.91 g, 14.9 mmol), and DTBAD (3.43 g, 14.9 mmol) in THF (40 mL). The resulting mixture was stirred at 25° C. for 16 hours. The reaction was then concentrated. The resulting residue was purified by silica gel chromatography, using 0 to 50% EtOAc-petroleum ether, to afford a 1:1 mixture of tert-butyl 4-(3-methyl-4-nitro-pyrazol-1-yl) piperidine-1-carboxylate and tert-butyl 4-(5-methyl-4-nitro-pyrazol-1-yl) piperidine-1-carboxylate (1.50 g, 24% yield) as a yellow solid. 1H NMR (300 MHz, DMSO-d6) δ 1.42 (9H, s), 1.75-1.89 (4H, m), 2.43 (3H, s), 2.82-2.90 (2H, m), 3.97-4.06 (2H, m), 4.29-4.44 (1H, m), 8.86 (1H, s). m/z: (ES+), [M-tBu+H]+=255.1

(b) tert-Butyl 4-(4-amino-3-methyl-pyrazol-1-yl) piperidine-1-carboxylate

A mixture of 1:1 tert-butyl 4-(3-methyl-4-nitro-pyrazol-1-yl) piperidine-1-carboxylate and tert-butyl 4-(5-methyl-4-nitro-pyrazol-1-yl) piperidine-1-carboxylate (2.00 g, 3.22 mmol) and 10 wt % palladium on carbon (0.171 g, 0.161 mmol) in MeOH (15 mL) was stirred under a hydrogen atmosphere at 25° C. for 2 hours. The reaction was then filtered through celite. The resulting residue was purified by silica gel chromatography to afford a 1:1 mixture of tert-butyl 4-(4-amino-3-methyl-pyrazol-1-yl) piperidine-1-carboxylate and tert-butyl 4-(4-amino-5-methyl-pyrazol-1-yl) piperidine-1-carboxylate (1.500 g, 83%) as a yellow solid. 1H NMR (300 MHz, DMSO-d6) δ 1.41 (9H, s), 1.69-1.89 (4H, m), 1.99 (3H, s), 2.85 (2H, br s), 3.92-4.15 (5H, m), 7.01 (1H, s). m/z: (ES+), [M+H]+=281.2

(c) Methyl 3-[[1-(1-tert-butoxycarbonyl-4-piperidyl)-3-methyl-pyrazol-4-yl]amino]-6-chloro-5-(methylamino) pyrazine-2-carboxylate A 1:1 mixture of tert-butyl 4-(4-amino-3-methyl-pyrazol-1-yl) piperidine-1-carboxylate and tert-butyl 4-(4-amino-5-methyl-pyrazol-1-yl) piperidine-1-carboxylate (1.50 g, 2.68 mmol) was added to a solution of methyl 6-chloro-3-fluoro- 5-(methylamino) pyrazine-2-carboxylate (0.705 g, 3.21 mmol) and DIPEA (1.40 mL, 8.03 mmol) in DMSO (20 mL). The resulting mixture was stirred at 100° C. for 3 hours. The reaction was then concentrated. The resulting residue was purified by silica gel chromatography, using 0 to 50% EtOAc-petroleum ether as eluent, to afford a mixture of regioisomers. This material was further purified by reverse phase HPLC, using a 5 micron, 2 cm×25 cm DAICEL DCpak P4VP column, isocratic 28% IPA in $sCO_2$ as eluent, and 0.5% 2M methanolic ammonia as modifier, to afford methyl 3-[[1-(1-tert-butoxycarbonyl-4-piperidyl)-3-methyl-pyrazol-4-yl]amino]-6-chloro-5-(methylamino) pyrazine-2-carboxylate (0.300 g, 23% yield) as a yellow solid. 1H NMR (400 MHz, DMSO-d6) δ 1.41 (9H, s), 1.64-1.79 (2H, m), 1.94-2.04 (2H, m), 2.15 (3H, s), 2.82-2.92 (2H, m), 2.94 (3H, d), 3.79 (3H, s), 3.96-4.09 (2H, m), 4.19-4.29 (1H, m), 7.85 (1H, br q), 8.04 (1H, s), 9.84 (1H, s). m/z: (ES+), [M+H]+=480.2

(d) Methyl 3-[[1-(1-tert-butoxycarbonyl-4-piperidyl)-3-methyl-pyrazol-4-yl]amino]-5-(methylamino)-6-(1-methylbenzimidazol-4-yl)pyrazine-2-carboxylate $PdCl_2$(dppf) (23 mg, 0.030 mmol) was added to a suspension of methyl 3-[[1-(1-tert-butoxycarbonyl-4-piperidyl)-3-methyl-pyrazol-4-yl]amino]-6-chloro-5-(methylamino) pyrazine-2-carboxylate (150 mg, 0.31 mmol), (1-methylbenzimidazol-4-yl) boronic acid (110 mg, 0.63 mmol), and cesium fluoride (142 mg, 0.94 mmol) in 1,4-dioxane (10 mL) under nitrogen. The resulting mixture was stirred at 100° C. for 16 hours. The reaction was then concentrated. The resulting residue was purified by silica gel chromatography, using 0 to 20% MeOH-DCM as eluent, to afford methyl 3-[[1-(1-tert-butoxycarbonyl-4-piperidyl)-3-methyl-pyrazol-4-yl]amino]-5-(methylamino)-6-(1-methylbenzimidazol-4-yl)pyrazine-2-carboxylate (0.120 g, 67% yield) as a yellow solid. 1H NMR (300 MHz, DMSO-d6) δ 1.42 (9H, s), 1.66-1.78 (2H, m), 1.95-2.05 (2H, m), 2.23 (3H, s), 2.82-2.90 (2H, m), 2.95 (3H, d), 3.82 (3H, s), 3.92 (3H, s), 3.98-4.07 (2H, m), 4.22-4.35 (1H, m), 7.40-7.49 (2H, m), 7.64-7.72 (1H, m), 8.03 (1H, br q), 8.21 (1H, s), 8.35 (1H, s), 10.00 (1H, s). m/z: (ES+), [M+H]+=576.4

(e) Methyl 5_(methylamino)-6-(1-methylbenzimidazol-4-yl)-3-[[3-methyl-1-(4-piperidyl)pyrazol-4-yl]amino]pyrazine-2-carboxylate trifluoroacetate Methyl 3-[[1-(1-tert-butoxycarbonyl-4-piperidyl)-3-methyl-pyrazol-4-yl]amino]-5-(methylamino)-6-(1-methylbenzimidazol-4-yl)pyrazine-2-carboxylate (120 mg, 0.21 mmol) was added to a solution of TFA (2.0 mL, 26 mmol) in DCM (10 mL). The resulting mixture was stirred at 25° C. for 3 hours. The reaction was then concentrated. The resulting solid was collected by filtration, washed with petroleum ether (100 mL), and dried under vacuum to afford methyl 5-(methylamino)-6-(1-methylbenzimidazol-4-yl)-3-[[3-methyl-1-(4-piperidyl)pyrazol-4-yl]amino]pyrazine-2-carboxylate trifluoroacetate (0.090 g, 73% yield) as a yellow solid. 1H NMR (400 MHZ, DMSO-d6) δ 2.02-2.13 (2H, m), 2.15-2.21 (2H, m), 2.25 (3H, s), 2.93 (3H, d), 3.12 (2H, q), 3.38 (2H, d), 3.81 (3H, s), 4.04 (3H, s), 4.39-4.46 (1H, m), 7.53 (1H, s), 7.58-7.65 (2H, m), 7.91 (1H, br q), 8.20 (1H, s), 8.42-8.50 (1H, m), 8.58-8.67 (1H, m), 10.07 (1H, s). The piperidine NH signal was broadened to baseline. m/z: (ES+), [M+H]+=476.3

(f) Methyl 5-(methylamino)-6-(1-methylbenzimidazol-4-yl)-3-[[3-methyl-1-(1-methyl-4-piperidyl)pyrazol-4-yl]amino]pyrazine-2-carboxylate 37% Aqueous formaldehyde (23 μL, 0.31 mmol) was added to a mixture of sodium triacetoxyborohydride (194 mg, 0.920 mmol) and methyl 5-(methylamino)-6-(1-methylbenzimidazol-4-yl)-3-[[3-methyl-1-(4-piperidyl)pyrazol-4-yl]amino]pyrazine-2-carboxylate trifluoroacetate (90 mg, 0.15 mmol) in DCM (10 mL). The resulting mixture was stirred at 25° C. for 3 hours. The reaction was then diluted with DCM (50 mL) and washed twice with saturated aqueous sodium bicarbonate (50 mL each). The organic layer was dried over sodium sulfate, filtered, and concentrated to afford methyl 5-(methylamino)-6-(1-methylbenzimidazol-4-yl)-3-[[3-methyl-1-(1-methyl-4-piperidyl)pyrazol-4-yl]amino]pyrazine-2-carboxylate (0.080 g, quantitative) as a yellow solid. 1H NMR (400 MHz, DMSO-d6) δ 1.85-1.93 (2H, m), 1.98-2.07 (4H, m), 2.19 (3H, s), 2.22 (3H, s), 2.79-2.87 (2H, m), 2.96 (3H, d), 3.81 (3H, s), 3.91 (3H, s), 3.98-4.07 (1H, m), 7.37-7.48 (2H, m), 7.64-7.70 (1H, m), 8.08 (1H, br q), 8.21 (1H, s), 8.31 (1H, s), 9.99 (1H, s). m/z: (ES+), [M+H]+=490.3

(g) 5-(Methylamino)-6-(1-methylbenzimidazol-4-yl)-3-[[3-methyl-1-(1-methyl-4-piperidyl)pyrazol-4-yl]amino]pyrazine-2-carboxamide formate salt 7 N Methanolic ammonia (10 mL, 70 mmol) was added to methyl 5-(methylamino)-6-(1-methylbenzimidazol-4-yl)-3-[[3-methyl-1-(1-methyl-4-piperidyl)pyrazol-4-yl]amino]pyrazine-2-carboxylate (100 mg, 0.20 mmoL). The resulting mixture was stirred at 80° C. for 2 days. The reaction was then concentrated. The resulting residue was purified by reverse phase HPLC, using a 5 micron, 30 mm×150 mm Sunfire prep C18 column, 2-15% MeCN-water as eluent, and 0.1% formic acid as modifier, to afford 5-(methylamino)-6-(1-methylbenzimidazol-4-yl)-3-[[3-methyl-1-(1-methyl-4-piperidyl)pyrazol-4-yl]amino]pyrazine-2-carboxamide formate salt (0.034 g, 31% yield) as a yellow solid. 1H NMR (300 MHz, DMSO-d6) δ 1.83-2.05 (4H, m), 2.10-2.17 (2H, m), 2.21 (3H, s), 2.26 (3H, s), 2.55-2.95 (2H, m), 2.99 (3H, d), 3.92 (3H, s), 4.00-4.11 (1H, m), 7.29 (1H, s), 7.41 (1H, t), 7.60 (1H, s), 7.60-7.68 (2H, m), 8.19-8.24 (2H, m), 8.26 (1H, s), 8.35 (1H, s), 10.97 (1H, s). m/z: (ES+), [M+H]+=475.2

Example 207

3-[(1,3-Dimethylpyrazol-4-yl)amino]-5-(methylamino)-6-(3-methylimidazo[4,5-c]pyridin-7-yl)pyrazine-2-carboxamide

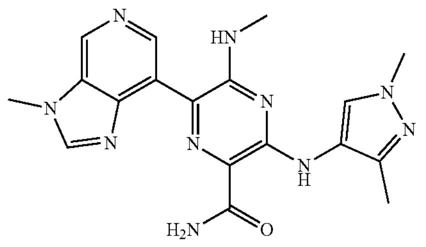 [SMILES: CNc1nc(Nc2cn(C)nc2C)c(C(N)=O)nc1-c1cncc2c1ncn2C]

(a) Methyl 3-[(1,3-dimethylpyrazol-4-yl)amino]-5-(methylamino)-6-(3-methylimidazo[4,5-c]pyridin-7-yl)pyrazine-2-carboxylate DIPEA (248 μL, 1.42 mmol) was added to a solution of 3-fluoro-5-(methylamino)-6-(3-methylimidazo[4,5-c]pyridin-7-yl)pyrazine-2-carboxamide (150 mg, 0.47 mmol) and 1,3-dimethylpyrazol-4-amine (105 mg, 0.95 mmol) in DMSO (10 mL). The resulting mixture was stirred at 120° C. for 16 hours. The reaction was then allowed to cool to room temperature, diluted with ice water, and filtered. The filter cake was collected to afford methyl 3-[(1,3-dimethylpyrazol-4-yl)amino]-5-(methylamino)-6-(3-methylimidazo[4,5-c]pyridin-7-yl)pyrazine-2-carboxylate (0.160 g, 83% yield) as brown solid. 1H NMR (400 MHZ, DMSO-d6) δ 2.22 (3H, s), 2.95 (3H, d), 3.79 (3H, s), 3.83 (3H, s), 4.02 (3H, s), 7.92 (1H, br q), 8.09 (1H, s), 8.49 (1H, s), 8.53 (1H, s), 9.03 (1H, s), 10.02 (1H, s). m/z: (ES+), [M+H]+=408.2

(b) 3-[(1,3-Dimethylpyrazol-4-yl)amino]-5-(methylamino)-6-(3-methylimidazo[4,5-c]pyridin-7-yl)pyrazine-2-carboxamide 7 N Methanolic ammonia (12 mL, 84 mmol) was added to methyl 3-[(1,3-dimethylpyrazol-4-yl)amino]-5-(methylamino)-6-(3-methylimidazo[4,5-c]pyridin-7-yl)pyrazine-2-carboxylate (160 mg, 0.39 mmol). The resulting mixture was stirred at 80° C. for 16 hours. The reaction was then concentrated. The resulting residue was purified by preparative HPLC, using a 5 micron, 30 mm×150 mm, Xselect CSH OBD column, decreasingly polar mixtures of MeCN—$H_2O$ as eluent, and 0.1% formic acid as modifier, to afford 3-[(1,3-dimethylpyrazol-4-yl)amino]-5-(methylamino)-6-(3-methylimidazo[4,5-c]pyridin-7-yl)pyrazine-2-carboxamide (0.039 g, 25% yield) as a yellow solid. 1H NMR (400 MHZ, DMSO-d6) δ 2.19 (3H, s), 2.97 (3H, d), 3.78 (3H, s), 4.01 (3H, s), 7.28 (1H, br s), 7.68 (1H, br s), 8.00 (1H, br q), 8.08 (1H, s), 8.52 (1H, s), 8.72 (1H, s), 9.01 (1H, s), 11.04 (1H, s). m/z: (ES+), [M+H]+=393.3

Example 208

5-(Methylamino)-6-(3-methylimidazo[4,5-c]pyridin-7-yl)-3-[[3-methyl-1-(2,2,2-trifluoroethyl)pyrazol-4-yl]amino]pyrazine-2-carboxamide

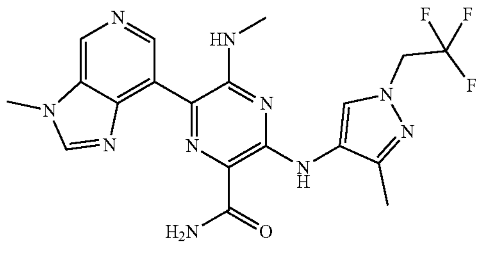 [SMILES: CNc1nc(Nc2cn(CC(F)(F)F)nc2C)c(C(N)=O)nc1-c1cncc2c1ncn2C]

(a) Methyl 3-bromo-6-chloro-5-(methylamino) pyrazine-2-carboxylate tert-Butyl nitrite (1.428 g, 13.85 mmol) was added portionwise to a solution of methyl 3-amino-6-chloro-5-(methylamino) pyrazine-2-carboxylate (1.00 g, 4.62 mmol) in dibromomethane (10 mL) at 0° C. Bromo (trimethyl) silane (1.20 mL, 9.23 mmol) was added. The resulting mixture was stirred at 60° C. for 2 hours under nitrogen. The resulting precipitate was dried under vacuum. The resulting material was purified by silica gel chromatography, using 0 to 50% EtOAc-petroleum ether as eluent, to afford methyl 3-bromo-6-chloro-5-(methylamino) pyrazine-2-carboxylate (1.200 g, 93% yield) as a yellow solid. 1H NMR (400 MHZ, DMSO-d6) δ 2.90 (3H, d), 3.79 (3H, s), 8.18 (1H, br q). m/z: (ES+), [M+2+H]+=282.1

(b) Methyl 6-chloro-5-(methylamino)-3-[[3-methyl-1-(2,2,2-trifluoroethyl)pyrazol-4-yl]amino]pyrazine-2-carboxylate Methyl 3-bromo-6-chloro-5-(methylamino) pyrazine-2-carboxylate (400 mg, 1.43 mmol) was added to a suspension of cesium carbonate (1.39 g, 4.28 mmol), 3-methyl-1-(2,2,2-trifluoroethyl)pyrazol-4-amine (255 mg, 1.43 mmol), and Pd(dppf) C12 (156 mg, 0.210 mmol) in 1,4-dioxane (40 mL) under nitrogen. The resulting mixture was stirred at 100° C. for 16 hours. The reaction was then concentrated. The resulting residue was purified by silica gel chromatography, using 0 to 100% EtOAc-petroleum ether as eluent, to afford methyl 6-chloro-5-(methylamino)-3-[[3-methyl-1-(2,2,2-trifluoroethyl)pyrazol-4-yl]amino]pyrazine-2-carboxylate (0.240 g, 44% yield) as a yellow solid. 1H NMR (400 MHZ, DMSO-d6) δ 2.20 (3H, s), 2.96 (3H, d), 3.81 (3H, s), 5.07 (2H, q), 7.93 (1H, br q), 8.17 (1H, s), 9.92 (1H, s). m/z: (ES+), [M+H]+=379.1

(c) Methyl 5-(methylamino)-6-(3-methylimidazo[4,5-c]pyridin-7-yl)-3-[[3-methyl-1-(2,2,2-trifluoroethyl)pyrazol-4-yl]amino]pyrazine-2-carboxylate Methyl 6-chloro-5-(methylamino)-3-[[3-methyl-1-(2,2,2-trifluoroethyl)pyrazol-4-yl]amino]pyrazine-2-carboxylate (240 mg, 0.63 mmol) was added to a suspension of cesium fluoride (289 mg, 1.90 mmol), 2-(3-methyl-3H-imidazo[4,5-c]pyridin-7-yl)-1,3,6,2-dioxazaborocane (155 mg, 0.630 mmol), and Pd(dppf) C12 (70 mg, 0.10 mmol) in 1,4-dioxane (30 mL) under nitrogen. The resulting mixture was stirred at 100° C. for 16 hours. The reaction was then concentrated. The resulting residue was purified by silica gel chromatography, using 0 to 10% MeOH-DCM as eluent, to afford methyl 5-(methylamino)-6-(3-methylimidazo[4,5-c]pyridin-7-yl)-3-[[3-methyl-1-(2,2,2-trifluoroethyl)pyrazol-4-yl]amino]pyrazine-2-carboxylate (130 mg, 42% yield) as a yellow solid. 1H NMR (DMSO-d6, 400 MHZ) δ 2.26 (3H, s), 2.94 (3H, d), 3.83 (3H, s), 4.01 (3H, s), 5.09 (2H, q), 7.92 (1H, br q), 8.29 (1H, s), 8.49 (1H, s), 8.52 (1H, s), 9.05 (1H, s), 10.07 (1H, s). m/z: (ES+), [M+H]+=476.3

(d) 5-(Methylamino)-6-(3-methylimidazo[4,5-c]pyridin-7-yl)-3-[[3-methyl-1-(2,2,2-trifluoroethyl)pyrazol-4-yl]amino]pyrazine-2-carboxamide 7 N Methanolic ammonia (10 mL, 70 mmol) was added to methyl 5-(methylamino)-6-(3-methylimidazo[4,5-c]pyridin-7-yl)-3-[[3-methyl-1-(2,2,2-trifluoroethyl)pyrazol-4-yl]amino]pyrazine-2-carboxylate (130 mg, 0.27 mmol). The resulting mixture was stirred at 80° C. for 16 hours. The reaction was then concentrated. The resulting residue was purified by reverse phase HPLC, using a 5 micron, 30 mm×150 mm, Xselect CSH OBD column, 13 to 24% MeCN-water as eluent, and 0.1% formic acid as modifier, to afford 5-(methylamino)-6-(3-methylimidazo[4,5-c]pyridin-7-yl)-3-[[3-methyl-1-(2,2,2-trifluoroethyl)pyrazol-4-yl]

amino]pyrazine-2-carboxamide (0.099 g, 77% yield) as a yellow solid. 1H NMR (400 MHz, DMSO-d6) δ 2.23 (3H, s), 2.98 (3H, s), 4.01 (3H, s), 4.98 (2H, q), 7.25 (1H, br), 7.99 (1H, br s), 8.23 (1H, s), 8.47 (1H, s), 8.74 (1H, s), 9.00 (1H, s), 10.94 (1H, s). The carboxamide NH2 protons were exchanged to baseline, the methylamino NH was a broad singlet, and the methylamino CH3 was a singlet. 19F NMR (376 MHZ, DMSO) δ −70.40. m/z: (ES+), [M+H]+=461.3

Example 209

3-[[1-(2,2-Difluoroethyl)-3-methyl-pyrazol-4-yl]amino]-5-(methylamino)-6-(3-methylimidazo[4,5-c]pyridin-7-yl)pyrazine-2-carboxamide

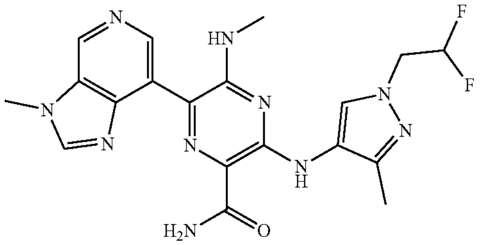 [SMILES: CNc1nc(Nc2cn(CC(F)F)nc2C)c(C(N)=O)nc1-c1cncc2c1ncn2C]

(a) 1-(2,2-Difluoroethyl)-3-methyl-4-nitro-pyrazole and 1-(2,2-difluoroethyl)-5-methyl-4-nitro-pyrazole 3-Methyl-4-nitro-1H-pyrazole (3.00 g, 23.6 mmol) was added to a solution of 2,2-difluoroethane-1-ol (2.90 g, 35.4 mmol), DTBAD (6.52 g, 28.3 mmol), and triphenylphosphine (7.43 g, 28.3 mmol) in THF (50 mL) under nitrogen. The resulting mixture was stirred at 25° C. for 3 hours. The reaction was then concentrated. The resulting residue was purified by silica gel chromatography, using 0 to 30% EtOAc-petroleum ether as eluent, to afford a 2:1 mixture of 1-(2,2-difluoroethyl)-3-methyl-4-nitro-pyrazole and 1-(2,2-difluoroethyl)-5-methyl-4-nitro-pyrazole (2.00 g, 22% yield) as a white solid. This material was further purified by chiral HPLC, using a 3 micron, 3×100 mm, CHIRALPAK IC-3 column, using isocratic 5% MeOH-s$CO_2$ as eluent, and 0.1% diethylamine as modifier, to afford 1-(2,2-difluoroethyl)-3-methyl-4-nitro-pyrazole (0.400 g, 60% yield) as a yellow oil and 1-(2,2-difluoroethyl)-5-methyl-4-nitro-1H-pyrazole (0.200 g, 60% yield) as a yellow oil. 1-(2,2-difluoroethyl)-3-methyl-4-nitro-pyrazole. 1H NMR (400 MHz, DMSO-d6) δ 2.44 (3H, s), 4.66 (2H, td), 6.43 (1H, tt), 8.86 (1H, s). m/z: (ES+), [M+H]+=192.0 1-(2,2-difluoroethyl)-5-methyl-4-nitro-1H-pyrazole. 1H NMR (400 MHZ, DMSO-d6) δ 2.63 (3H, s), 4.76 (2H, td), 6.42 (1H, tt), 8.31 (1H, s). m/z: (ES+), [M+H]+=192.0

(b) 1-(2,2-Difluoroethyl)-3-methyl-pyrazol-4-amine

A mixture of 1-(2,2-difluoroethyl)-3-methyl-4-nitro-1H-pyrazole (400 mg, 2.09 mmol) and 10 wt % palladium on carbon (4.22 mg, 2.09 mmol) in MeOH (10 mL) was stirred under a hydrogen atmosphere at 25° C. for 24 hours. The reaction was then filtered through Celite and concentrated to afford 1-(2,2-difluoroethyl)-3-methyl-pyrazol-4-amine (0.320 g, 95% yield) as a brown oil. 1H NMR (400 MHZ, DMSO) δ 2.00 (3H, s), 3.81 (2H, br s), 4.31 (2H, td), 6.20 (1H, tt), 7.00 (1H, s). m/z: (ES+), [M+H]+=162.1

(c) Methyl 3-[[1-(2,2-difluoroethyl)-3-methyl-pyrazol-4-yl]amino]-5-(methylamino)-6-(3-methylimidazo[4,5-c]pyridin-7-yl)pyrazine-2-carboxylate DIPEA (488 μL, 2.79 mmol) was added to a solution of 1-(2,2-difluoroethyl)-3-methyl-pyrazol-4-amine (150 mg, 0.93 mmol) and methyl 3-fluoro-5-(methylamino)-6-(3-methylimidazo[4,5-c]pyridin-7-yl)pyrazine-2-carboxylate (294 mg, 0.93 mmol) in DMSO (10 mL). The resulting mixture was stirred at 100° C. for 24 h. The reaction was then concentrated. The resulting residue was purified by silica gel chromatography, using 0 to 10% MeOH-DCM as eluent, to afford methyl 3-[[1-(2,2-difluoroethyl)-3-methyl-pyrazol-4-yl]amino]-5-(methylamino)-6-(3-methylimidazo[4,5-c]pyridin-7-yl)pyrazine-2-carboxylate (0.150 g, 35% yield) as a yellow solid. 1H NMR (400 MHZ, DMSO) δ 2.25 (3H, s), 2.94 (3H, d), 3.83 (3H, s), 4.01 (3H, s), 4.58 (2H, td), 6.33 (1H, tt), 7.91 (1H, br q), 8.24 (1H, s), 8.51 (1H, s), 8.53 (1H, s), 9.05 (1H, s), 10.05 (1H, s). m/z: (ES+), [M+H]+=458.2

(d) 3-[[1-(2,2-Difluoroethyl)-3-methyl-pyrazol-4-yl]amino]-5 (methylamino)-6-(3-methylimidazo[4,5-c]pyridin-7-yl)pyrazine-2-carboxamide 7 N Methanolic ammonia (20 mL, 140 mmol) was added to methyl 3-[[1-(2,2-difluoroethyl)-3-methyl-pyrazol-4-yl]amino]-5-(methylamino)-6-(3-methylimidazo[4,5-c]pyridin-7-yl)pyrazine-2-carboxylate (140 mg, 0.31 mmol). The resulting mixture was stirred at 80° C. for 3 hours. The reaction was then concentrated. The resulting residue was purified by reverse phase HPLC, using a 5 micron, 30×150 mm, Xselect CSH OBD column, 6 to 25% MeCN-water as eluent, and 0.1% formic acid as modifier, to afford 3-[[1-(2,2-difluoroethyl)-3-methyl-pyrazol-4-yl]amino]-5-(methylamino)-6-(3-methylimidazo[4,5-c]pyridin-7-yl)pyrazine-2-carboxamide (0.059 g, 42% yield) as a yellow solid. 1H NMR (400 MHZ, DMSO) δ 2.22 (3H, s), 2.97 (3H, d), 4.01 (3H, s), 4.56 (2H, td), 6.33 (1H, tt), 7.31 (1H, s), 7.70 (1H, s), 8.02 (1H, br q), 8.23 (1H, s), 8.52 (1H, s), 8.72 (1H, s), 9.01 (1H, s), 11.09 (1H, s). 19F NMR (376 MHz, DMSO) δ −122.49. m/z: (ES+), [M+H]+=443.2

Example 210

3-[[1-(2,2-Difluoroethyl)-5-methyl-pyrazol-4-yl]amino]-5-(methylamino)-6-(3-methylimidazo[4,5-c]pyridin-7-yl)pyrazine-2-carboxamide

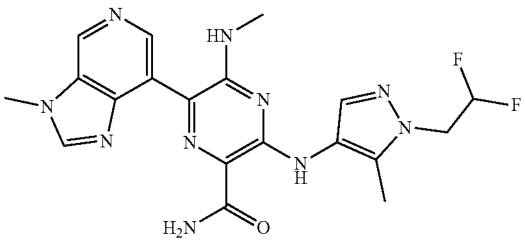 [SMILES: CNc1nc(Nc2cnn(CC(F)F)c2C)c(C(N)=O)nc1-c1cncc2c1ncn2C]

(a) 1-(2,2-Difluoroethyl)-5-methyl-pyrazol-4-amine

A mixture of 1-(2,2-difluoroethyl)-5-methyl-4-nitro-1H-pyrazole (200 mg, 1.05 mmol) and 10 wt % palladium on carbon (22.3 mg, 0.210 mmol) in MeOH (10 mL) was stirred under a hydrogen atmosphere at 25° C. for 24 hours. The reaction was then filtered through Celite and concentrated to afford 1-(2,2-difluoroethyl)-5-methyl-pyrazol-4-amine (0.120 g, 71% yield) as a yellow oil. 1H NMR (400 MHZ, DMSO-d6) δ 2.09 (3H, s), 3.89 (2H, br s), 4.39 (2H, td), 6.22 (1H, tt), 6.97 (1H, s). m/z: (ES+), [M+H]+=162.1

(b) Methyl 3-[[1-(2,2-difluoroethyl)-5-methyl-pyrazol-4-yl]amino]-5-(methylamino)-6-(3-methylimidazo[4,5-c]pyridin-7-yl)pyrazine-2-carboxylate 1-(2,2-Difluoroethyl)-5-methyl-pyrazol-4-amine (102 mg, 0.63 mmol) was added to a solution of methyl 3-fluoro-5-(methylamino)-6-(3-methylimidazo[4,5-c]pyridin-7-yl) pyrazine-2-carboxylate (100 mg, 0.32 mmol) and DIPEA (55 μL, 0.32 mmol) in DMSO (10 mL). The resulting mixture was stirred at 100° C. for 24 hours. The reaction was then concentrated. The resulting residue was purified by silica gel chromatography, using 0 to 10% MeOH-DCM as eluent, to afford methyl 3-[[1-(2,2-difluoroethyl)-5-methyl-pyrazol-4-yl]amino]-5-(methylamino)-6-(3-methylimidazo [4,5-c]pyridin-7-yl)pyrazine-2-carboxylate (0.080 g, 55% yield) as a yellow solid. 1H NMR (400 MHZ, DMSO) & 2.30 (3H, s), 2.85 (3H, d), 3.82 (3H, s), 4.01 (3H, s), 4.59 (2H, td), 6.35 (1H, tt), 7.78 (1H, br q), 8.01 (1H, s), 8.50 (1H, s), 8.51 (1H, s), 9.05 (1H, s), 9.81 (1H, s). m/z: (ES+), [M+H]+=458.2

(c) 3-[[1-(2,2-Difluoroethyl)-5-methyl-pyrazol-4-yl] amino]-5 (methylamino)-6-(3-methylimidazo[4,5-c] pyridin-7-yl)pyrazine-2-carboxamide 7 N Methanolic ammonia (10 mL, 70 mmol) was added to methyl 3-[[1-(2,2-difluoroethyl)-5-methyl-pyrazol-4-yl] amino]-5-(methylamino)-6-(3-methylimidazo[4,5-c]pyridin-7-yl)pyrazine-2-carboxylate (80 mg, 0.17 mmol). The resulting mixture was stirred at 80° C. for 2 days. The reaction was then concentrated. The resulting residue was purified by reverse phase HPLC, using a 5 micron, 30×150 mm, Xselect CSH OBD column, using 8 to 20% MeCN-water as eluent, and 0.1% formic acid as modifier, to afford 3-[[1-(2,2-difluoroethyl)-5-methyl-pyrazol-4-yl]amino]-5-(methylamino)-6-(3-methylimidazo[4,5-c]pyridin-7-yl) pyrazine-2-carboxamide (0.020 g, 25% yield) as a yellow solid. 1H NMR (DMSO, 400 MHz) δ 2.29 (3H, s), 2.89 (3H, d), 4.01 (3H, s), 4.58 (2H, td), 6.35 (1H, tt), 7.29 (1H, br s), 7.68 (1H, br s), 7.89 (1H, br q), 8.06 (1H, s), 8.51 (1H, s), 8.70 (1H, s), 9.01 (1H, s), 10.87 (1H, s). 19F NMR (376 MHz, DMSO) δ −122.10. m/z: (ES+), [M+H]+=443.2

Example 211

3-[[1-(1-Cyano-1-methyl-ethyl)-3-methyl-pyrazol-4-yl]amino]-5-(methylamino)-6-(3-methylimidazo[4,5-c]pyridin-7-yl)pyrazine-2-carboxamide

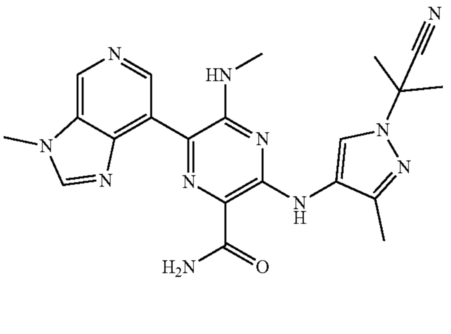 [SMILES: CNc1nc(Nc2cn(C(C)(C)C#N)nc2C)c(C(N)=O)nc1-c1cncc2c1ncn2C]

(a) Methyl 6-chloro-3-[[1-(1-cyano-1-methyl-ethyl)-3-methyl-pyrazol-4-yl]amino]-5-(methylamino) pyrazine-2-carboxylate DIPEA (1.53 mL, 8.88 mmol) was added to a solution of 2-(4-amino-3-methyl-pyrazol-1-yl)-2-methyl-propanenitrile (1.35 g, 8.20 mmol) and methyl 6-chloro-3-fluoro-5-(methylamino) pyrazine-2-carboxylate (1.50 g, 6.83 mmol) in DMF (32.6 mL). The resulting mixture was stirred at 100° C. for 18 hours. The reaction was then allowed to cool to room temperature and diluted with DCM and water (40 mL each). The layers were separated and the aqueous layer was extracted three times with DCM (40 mL each). The combined organic layers were dried over sodium sulfate, filtered, and concentrated to afford methyl 6-chloro-3-[[1-(1-cyano-1-methyl-ethyl)-3-methyl-pyrazol-4-yl]amino]-5-(methylamino) pyrazine-2-carboxylate as a brown solid, which was carried forward assuming 100% yield. m/z: (ES+), [M+H]+= 363.8

(b) Methyl 3-[[1-(1-cyano-1-methyl-ethyl)-3-methyl-pyrazol-4-yl]amino]-5-(methylamino)-6-(3-methylimidazo[4,5-c]pyridin-7-yl)pyrazine-2-carboxylate A suspension of cesium fluoride (2.088 g, 13.74 mmol), $PdCl_2$(dppf) (0.561 g, 0.69 mmol), 2-(3-methyl-3H-imidazo [4,5-c]pyridin-7-yl)-1,3,6,2-dioxazaborocane (2.02 g, 8.25 mmol), and methyl 6-chloro-3-[[1-(1-cyano-1-methyl-ethyl)-3-methyl-pyrazol-4-yl]amino]-5-(methylamino) pyrazine-2-carboxylate (2.50 g, 6.87 mmol) in water (3.12 mL) and 1,4-dioxane (31.2 mL) was sparged with nitrogen for 10 minutes. The resulting mixture was then stirred at 100° C. for 2 hours. The reaction was then allowed to cool to room temperature and dry-loaded onto celite. The resulting material was purified by silica gel chromatography, using 0 to 20% MeOH-DCM as eluent, to afford methyl 3-[[1-(1-cyano-1-methyl-ethyl)-3-methyl-pyrazol-4-yl] amino]-5-(methylamino)-6-(3-methylimidazo[4,5-c]pyridin-7-yl)pyrazine-2-carboxylate as a brown solid, which was carried forward assuming 100% yield. m/z: (ES+), [M+H]+=460.7

(c) 3-[[1-(1-Cyano-1-methyl-ethyl)-3-methyl-pyrazol-4-yl]amino]-5-(methylamino)-6-(3-methylimidazo[4,5-c]pyridin-7-yl)pyrazine-2-carboxamide 7 N Methanolic ammonia (8.0 mL, 56 mmol) was added to methyl 3-[[1-(1-cyano-1-methyl-ethyl)-3-methyl-pyrazol-4-yl]amino]-5-(methylamino)-6-(3-methylimidazo[4,5-c]pyridin-7-yl)pyrazine-2-carboxylate (450 mg, 0.98 mmol). The resulting mixture was stirred at 80° C. for 24 hours. The reaction was then allowed to cool to room temperature. The resulting solid was filtered, rinsed with methanol (10 mL), and air-dried. Separately, 7 N methanolic ammonia (40 mL, 280 mmol) was added to methyl 3-[[1-(1-cyano-1-methyl-ethyl)-3-methyl-pyrazol-4-yl]amino]-5-(methylamino)-6-(3-methylimidazo[4,5-c]pyridin-7-yl) pyrazine-2-carboxylate (3.10 g, 6.73 mmol). The resulting mixture was stirred at 80° C. for 48 hours. The reaction was then allowed to cool to room temperature. The resulting solid was filtered, rinsed with methanol (80 mL), and air-dried. These two solids were combined and dry-loaded onto celite. The resulting material was purified by silica gel chromatography, using 0 to 20% MeOH-DCM as eluent, to afford 3-[[1-(1-cyano-1-methyl-ethyl)-3-methyl-pyrazol-4-yl]amino]-5-(methylamino)-6-(3-methylimidazo[4,5-c]

pyridin-7-yl)pyrazine-2-carboxamide (0.354 g, 10% yield over three steps) as a yellow solid. 1H NMR (500 MHz, DMSO-d6) 1.97 (6H, s), 2.28 (3H, s), 3.00 (3H, d), 4.02 (3H, s), 7.33 (1H, br s), 7.72 (1H, br s), 8.02 (1H, br q), 8.48 (1H, s), 8.54 (1H, s), 8.74 (1H, s), 9.03 (1H, s), 11.14 (1H, s). m/z: (ES+), [M+H]+=446.3

Example 212

5-Cyclopropyl-3-[(1,3-dimethylpyrazol-4-yl)amino]-6-(3-methylimidazo[4,5-c]pyridin-7-yl)pyrazine-2-carboxamide

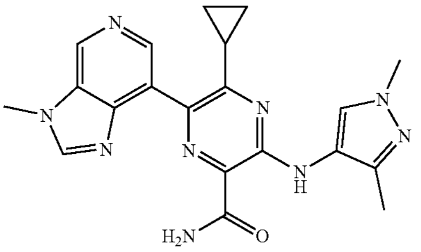 [SMILES: Cc1nn(C)cc1Nc1nc(C2CC2)c(-c2cncc3c2ncn3C)nc1C(N)=O]

(a) Methyl 6-chloro-5-cyclopropyl-3-[(1,3-dimethylpyrazol-4-yl)amino]pyrazine-2-carboxylate DIPEA (3.91 mL, 22.4 mmol) was added to a mixture of methyl 6-chloro-5-cyclopropyl-3-fluoro-pyrazine-2-carboxylate (1.035 g, 4.490 mmol) and 1,3-dimethylpyrazol-4-amine dihydrochloride (0.991 g, 5.39 mmol) in DMF (14 mL). The resulting mixture was allowed to stir at 100° C. for 2 h. The reaction was then concentrated. The resulting residue was purified by silica gel chromatography, using 0 to 10% MeOH-DCM as eluent, and 0 to 0.2% methanolic ammonia as modifier, to afford methyl 6-chloro-5-cyclopropyl-3-[(1,3-dimethyl-1H-pyrazol-4-yl)amino]pyrazine-2-carboxylate (1.247 g, 86% yield) as an orange solid. 1H NMR (500 MHz, Chloroform-d): δ 1.15-1.36 (4H, m), 2.29 (3H, s), 2.49-2.63 (1H, m), 3.85 (3H, s), 3.99 (3H, s), 7.69 (1H, s), 9.73 (1H, s). m/z: (ES+), [M+H]+=322.1

(b) Methyl 5-cyclopropyl-3-[(1,3-dimethylpyrazol-4-yl)amino]-6-(3-methylimidazo[4,5-c]pyridin-7-yl)pyrazine-2-carboxylate A mixture of methyl 6-chloro-5-cyclopropyl-3-[(1,3-dimethyl-1H-pyrazol-4-yl)amino]pyrazine-2-carboxylate (1.24 g, 3.85 mmol), 2-(3-methyl-3H-imidazo[4,5-c]pyridin-7-yl)-1,3,6,2-dioxazaborocane (1.04 g, 4.24 mmol), Pd(dppf)$Cl_2$ dichloromethane adduct (0.315 g, 0.390 mmol), and cesium fluoride (1.76 g, 11.6 mmol) was evacuated and backfilled three times with nitrogen. 1,4-Dioxane (17.5 mL) and water (1.75 mL) were added. The resulting mixture was evacuated and backfilled three times with nitrogen, then stirred at 80° C. for 2 hours. The reaction was then concentrated. The resulting residue was purified by silica gel chromatography, using 0 to 20% MeOH-DCM as eluent, and 0 to 0.4% methanolic ammonia as modifier. The resulting dark orange solid was stirred in MeOH at 40° C. for 16 hours. The resulting slurry was then allowed to cool to room temperature, filtered, rinsed with diethyl ether, and dried under air to afford methyl 5-cyclopropyl-3-[(1,3-dimethylpyrazol-4-yl)amino]-6-(3-methylimidazo[4,5-c]pyridin-7-yl)pyrazine-2-carboxylate (0.970 g, 60% yield) as a yellow solid. 1H NMR (500 MHz, DMSO-d6): δ 0.88-0.97 (2H, m), 1.09 (2H, dt), 1.80-1.89 (1H, m), 2.18 (3H, s), 3.79 (3H, s), 3.87 (3H, s), 3.99 (3H, s), 7.85 (1H, s), 8.39 (1H, s), 8.42 (1H, s), 9.05 (1H, s), 9.67 (1H, s). m/z: (ES+), [M+H]+=419.2

(c) 5-Cyclopropyl-3-[(1,3-dimethylpyrazol-4-yl)amino]-6-(3-methylimidazo[4,5-c]pyridin-7-yl)pyrazine-2-carboxamide 7 N Methanolic ammonia (13 mL, 91 mmol) was added to methyl 5-cyclopropyl-3-[(1,3-dimethyl-pyrazol-4-yl)amino]-6-(3-methylimidazo[4,5-c]pyridin-7-yl)pyrazine-2-carboxylate (960 mg, 2.29 mmol). The resulting mixture was stirred at 100° C. for 1 hour in a Biotage microwave reactor. The reaction was then allowed to cool to room temperature and left standing for 16 hours. The resulting yellow precipitate was collected by filtration, rinsed with diethyl ether, and dried under vacuum to afford 5-cyclopropyl-3-[(1,3-dimethylpyrazol-4-yl)amino]-6-(3-methylimidazo[4,5-c]pyridin-7-yl)pyrazine-2-carboxamide (911 mg, 98% yield). 1H NMR (500 MHZ, DMSO-d6): δ 0.86-0.97 (2H, m), 1.06-1.15 (2H, m), 1.82-1.95 (1H, m), 2.17 (3H, s), 3.78 (3H, s), 3.99 (3H, s), 7.76 (1H, br s), 7.85 (1H, s), 8.02 (1H, br s), 8.42 (1H, s), 8.51 (1H, s), 9.03 (1H, s), 10.81 (1H, s). m/z: (ES+), [M+H]+=404.2

Examples 213 and 214

5-Cyclopropyl-6-(3-methylimidazo[4,5-c]pyridin-7-yl)-3-[[3-methyl-1-(2,2,2-trifluoroethyl)pyrazol-4-yl]amino]pyrazine-2-carboxamide and 5-cyclopropyl-6-(3-methylimidazo[4,5-c]pyridin-7-yl)-3-[[5-methyl-1-(2,2,2-trifluoroethyl)pyrazol-4-yl]amino]pyrazine-2-carboxamide

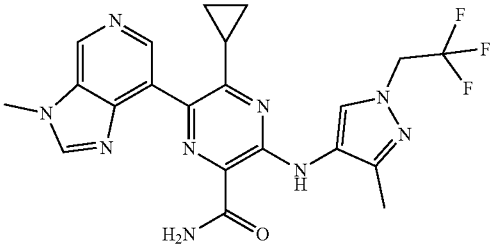

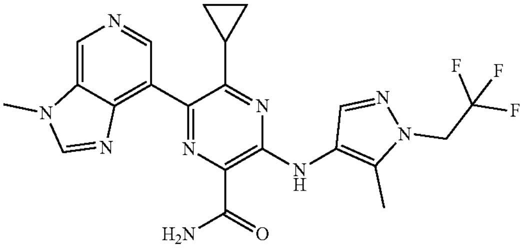

(a) 3-Methyl-4-nitro-1-(2,2,2-trifluoroethyl)pyrazole and 5-methyl-4-nitro-1-(2,2,2-trifluoroethyl)pyrazole Potassium carbonate (2.18 g, 15.7 mmol) was added to a solution of 1,1,1-trifluoro-2-iodo-ethane (1.15 mL, 11.8 mmol) and 3-methyl-4-nitro-1H-pyrazole (1.00 g, 7.87 mmol) in DMF (18.5 mL). The resulting mixture was stirred at 100° C. for 4 hours. The reaction was then allowed to cool to room temperature and diluted with EtOAc and water (50 mL each). The layers were separated and the aqueous layer was extracted three times with EtOAc (50 mL each). The combined organic layers were dried over sodium sulfate, filtered, and concentrated. The resulting residue was purified by silica gel chromatography, using 0 to 40% EtOAc-hexanes as eluent, to afford a 3:1 mixture of 3-methyl-4-nitro-1-(2,2,2-trifluoroethyl)pyrazole and 5-methyl-4-nitro-1-(2,2,2-trifluoroethyl)pyrazole (1.03 g, 63% yield) as a brown oil. 3-methyl-4-nitro-1-(2,2,2-trifluoroethyl)pyrazole: 1H NMR (500 MHZ, DMSO-d6) 2.44 (3H, s), 5.17 (2H, q), 8.92 (1H, s) m/z: (ES+), [M+H]+=209.8.

5-methyl-4-nitro-1-(2,2,2-trifluoroethyl)pyrazole: 1H NMR (500 MHz, DMSO-d6) 2.65 (3H, s), 5.30 (2H, q), 8.35 (1H, s) m/z: (ES+), [M+H]+=209.8.

(b) 3-Methyl-1-(2,2,2-trifluoroethyl)pyrazol-4-amine and 5-methyl-1-(2,2,2-trifluoroethyl)pyrazol-4-amine Iron powder (1.10 g, 19.7 mmol) was added to a suspension of ammonium chloride (1.05 g, 19.7 mmol) and a 3:1 mixture of 3-methyl-4-nitro-1-(2,2,2-trifluoroethyl)pyrazole and 5-methyl-4-nitro-1-(2,2,2-trifluoroethyl)pyrazole (1.03 g, 4.93 mmol) in water (12.3 mL) and ethanol (12.3 mL). The resulting mixture was stirred at 60° C. for 1 hour. The reaction was then allowed to cool to room temperature and diluted with DCM (5 mL). The aqueous layer was extracted twice with DCM (5 mL). The combined organics layers were dried over sodium sulfate, filtered, and concentrated to afford a 3:1 mixture of 3-methyl-1-(2,2,2-trifluoroethyl)pyrazol-4-amine and 5-methyl-1-(2,2,2-trifluoroethyl)pyrazol-4-amine as a brown oil, which was carried forward assuming 100% yield. m/z: (ES+), [M+H]+=179.9

(c) Methyl 6-chloro-5-cyclopropyl-3-[[3-methyl-1-(2,2,2-trifluoroethyl)pyrazol-4-yl]amino]pyrazine-2-carboxylate and methyl 6-chloro-5-cyclopropyl-3-[[5-methyl-1-(2,2,2-trifluoroethyl)pyrazol-4-yl]amino]pyrazine-2-carboxylate DIPEA (888 μL, 5.15 mmol) was added to a solution of methyl 6-chloro-5-cyclopropyl-3-fluoro-pyrazine-2-carboxylate (792 mg, 3.44 mmol), and a 3:1 mixture of 3-methyl-1-(2,2,2-trifluoroethyl)pyrazol-4-amine and 5-methyl-1-(2,2,2-trifluoroethyl)pyrazol-4-amine (800 mg, 4.47 mmol) in 1,4-dioxane (21.4 mL). The resulting mixture was stirred at 100° C. for 1 hour. The reaction was then allowed to cool to room temperature and concentrated. The resulting residue was purified by silica gel chromatography, using 0 to 20% MeOH-DCM as eluent, to afford a 3:1 mixture of methyl 6-chloro-5-cyclopropyl-3-[[3-methyl-1-(2,2,2-trifluoroethyl)pyrazol-4-yl]amino]pyrazine-2-carboxylate and methyl 6-chloro-5-cyclopropyl-3-[[5-methyl-1-(2,2,2-trifluoroethyl)pyrazol-4-yl]amino]pyrazine-2-carboxylate (1.20 g, 90% yield) as a brown solid. m/z: (ES+), [M+H]+=390.1.

(d) Methyl 5-cyclopropyl-6-(3-methylimidazo[4,5-c]pyridin-7-yl)-3-[[3-methyl-1-(2,2,2-trifluoroethyl)pyrazol-4-yl]amino]pyrazine-2-carboxylate and methyl 5-cyclopropyl-6-(3-methylimidazo[4,5-c]pyridin-7-yl)-3-[[5-methyl-1-(2,2,2-trifluoroethyl)pyrazol-4-yl]amino]pyrazine-2-carboxylate A suspension of a 3:1 mixture of methyl 6-chloro-5-cyclopropyl-3-[[3-methyl-1-(2,2,2-trifluoroethyl)pyrazol-4-yl]amino]pyrazine-2-carboxylate and methyl 6-chloro-5-cyclopropyl-3-[[5-methyl-1-(2,2,2-trifluoroethyl)pyrazol-4-yl]amino]pyrazine-2-carboxylate (1.20 g, 3.08 mmol), cesium fluoride (935 mg, 6.16 mmol), $PdCl_2$(dppf) (250 mg, 0.31 mmol), and 2-(3-methyl-3H-imidazo[4,5-c]pyridin-7-yl)-1,3,6,2-dioxazaborocane (905 mg, 3.69 mmol) in 1,4-dioxane (28 mL) and water (2.8 mL) was sparged with nitrogen for 10 minutes. The resulting mixture was stirred at 90° C. for 1 hour. The reaction was then allowed to room temperature and diluted with DCM and water (40 mL each). The layers were separated and the aqueous layer was extracted three times with DCM (40 mL each). The combined organic layers were dried over sodium sulfate, filtered, and concentrated. The resulting residue was purified by silica gel chromatography, using 0 to 20% MeOH-DCM as eluent, to afford methyl 5-cyclopropyl-6-(3-methylimidazo[4,5-c]pyridin-7-yl)-3-[[3-methyl-1-(2,2,2-trifluoroethyl)pyrazol-4-yl]amino]pyrazine-2-carboxylate and methyl 5-cyclopropyl-6-(3-methylimidazo[4,5-c]pyridin-7-yl)-3-[[5-methyl-1-(2,2,2-trifluoroethyl)pyrazol-4-yl]amino]pyrazine-2-carboxylate (250 mg, 17% yield) as a brown solid. m/z: (ES−), [M−H]−=485.2

(e) 5-Cyclopropyl-6-(3-methylimidazo[4,5-c]pyridin-7-yl)-3-[[3-methyl-1-(2 2,2-trifluoroethyl)pyrazol-4-yl]amino]pyrazine-2-carboxamide and 5-cyclopropyl-6-(3-methylimidazo[4,5-c]pyridin-7-yl)-3-[[5-methyl-1-(2,2,2-trifluoroethyl)pyrazol-4-yl]amino]pyrazine-2-carboxamide 7 N Methanolic ammonia (5.0 mL, 35 mmol) was added to a 3:1 mixture of methyl 5-cyclopropyl-6-(3-methylimidazo[4,5-c]pyridin-7-yl)-3-[[3-methyl-1-(2,2,2-trifluoroethyl)pyrazol-4-yl]amino]pyrazine-2-carboxylate and methyl 5-cyclopropyl-6-(3-methylimidazo[4,5-c]pyridin-7-yl)-3-[[5-methyl-1-(2,2,2-trifluoroethyl)pyrazol-4-yl]amino]pyrazine-2-carboxylate (250 mg, 0.534 mmol). The resulting mixture was stirred at 60° C. for 1 hour. The reaction was then concentrated. The resulting residue was purified by silica gel chromatography, using 0 to 20% MeOH-DCM as eluent. The resulting material was further purified by preparative SFC, using a 5 micron, 21 mm×250 mm Chiralpak ID column, isocratic 30% MeOH-$sCO_2$ as eluent, and 0.2% ammonium hydroxide as modifier, to afford 5-cyclopropyl-6-(3-methylimidazo[4,5-c]pyridin-7-yl)-3-[[3-methyl-1-(2,2,2-trifluoroethyl)pyrazol-4-yl]amino]pyrazine-2-carboxamide (140 mg, 56% yield) as a yellow solid and 5-cyclopropyl-6-(3-methylimidazo[4,5-c]pyridin-7-yl)-3-[[5-methyl-1-(2,2,2-trifluoroethyl)pyrazol-4-yl]amino]pyrazine-2-carboxamide (44.8 mg, 18% yield) as a yellow solid.

5-cyclopropyl-6-(3-methylimidazo[4,5-c]pyridin-7-yl)-3-[[3-methyl-1-(2,2,2-trifluoroethyl)pyrazol-4-yl]amino]pyrazine-2-carboxamide: 1H NMR (500 MHZ, DMSO-d6) δ 0.86-0.97 (2H, m), 1.04-1.16 (2H, m), 1.85-1.95 (1H, m), 2.22 (3H, s), 3.99 (3H, s), 5.08 (2H, q), 7.80 (1H, br s), 7.98-8.11 (2H, m), 8.43 (1H, s), 8.52 (1H, s), 9.03 (1H, s), 10.90 (1H, s). m/z: (ES−), [M−H]−=470.2 5-cyclopropyl-6-(3-methylimidazo[4,5-c]pyridin-7-yl)-3-[[5-methyl-1-(2,2,2-trifluoroethyl)pyrazol-4-yl]amino]pyrazine-2-carboxamide: 1H NMR (500 MHz, DMSO-d6) δ 0.76-0.90 (2H, m), 0.92-1.04 (2H, m), 1.79-1.93 (1H, m), 2.27 (3H, s), 3.98 (3H, s), 5.09 (2H, q), 7.76 (1H, br s), 7.84 (1H, s), 8.02 (1H, br s), 8.42 (1H, s), 8.50 (1H, s), 9.02 (1H, s), 10.56 (1H, s). m/z: (ES−), [M−H]−=470.2

Example 213, Alternative Preparation

5-Cyclopropyl-6-(3-methylimidazo[4,5-c]pyridin-7-yl)-3-[[3-methyl-1-(2,2,2-trifluoroethyl)pyrazol-4-yl]amino]pyrazine-2-carboxamide

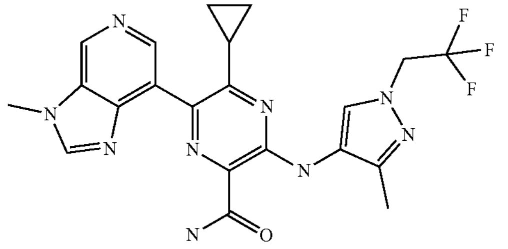 [SMILES: Cc1nn(CC(F)(F)F)cc1Nc1nc(C2CC2)c(-c2cncc3c2ncn3C)nc1C(N)=O]

(a) 3-Methyl-4-nitro-1-(2 2 2-trifluoroethyl)pyrazole and 5-methyl-4-nitro-1-(2,2,2-trifluoroethyl)pyrazole 1,1,1-Trifluoro-2-iodo-ethane (24.0 mL, 244 mmol) was added to a mixture of 3-methyl-4-nitro-1H-pyrazole (23.7 g, 186 mmol) and cesium carbonate (72.9 g, 224 mmol) in DMF (200 mL). The resulting mixture was stirred at 80° C. for 2.5 hours, then at 100° C. for 2.5 hours. Additional 1,1,1-trifluoro-2-iodoethane (7.0 mL, 71 mmol) was added and the resulting mixture was stirred at 110° C. for 90 minutes, then at room temperature for 84 hours. The reaction was then filtered through a silica pad, rinsing copiously with EtOAc. The resulting filtrate was concentrated to a volume of ~80 mL and then diluted with saturated aqueous ammonium chloride (300 mL) and EtOAc (100 mL). The layers were separated and the aqueous layer was extracted three times with EtOAc (50 mL each). The combined organics were washed twice with 5% aqueous LiCl (100 mL each), then dried over sodium sulfate, filtered, and concentrated. The resulting residue was purified by silica gel chromatography, using 0-40% EtOAc-hexanes as eluent, to afford a yellow solid. This material was further purified by SFC, using a 30 mm×250 mm, 5 micron, IG column, isocratic 10% MeOH/s$CO_2$ as eluent, and 0.2% ammonium hydroxide as modifier, to afford 3-methyl-4-nitro-1-(2,2,2-trifluoroethyl)pyrazole (13.93 g, 36% yield) and 55-methyl-4-nitro-1-(2,2,2-trifluoroethyl)pyrazole (5.77 g, 15% yield), each as a beige solid. 3-Methyl-4-nitro-1-(2,2,2-trifluoroethyl)pyrazole: 1H NMR (500 MHZ, DMSO-d6) δ 2.44 (3H, s), 5.17 (2H, q), 8.92 (1H, s). m/z: (ES+), [M+H]=210.1 5-Methyl-4-nitro-1-(2,2,2-trifluoroethyl)pyrazole: 1H NMR (500 MHZ, DMSO-d6) δ 2.65 (3H, s), 5.31 (2H, q), 8.36 (1H, s). m/z: (ES+), [M+H]=210.1

(b) 3-Methyl-1-(2,2,2-trifluoroethyl)pyrazol-4-amine

A mixture of 3-methyl-4-nitro-1-(2,2,2-trifluoroethyl)pyrazole (13.9 g, 66.5 mmol) and 10 wt % palladium on carbon (2.55 g, 2.40 mmol) in MeOH (133 mL) was stirred at room temperature for 3 hours under a hydrogen atmosphere. Acetic acid (1.0 mL, 18 mmol) and additional 10 wt % palladium on carbon (1.0 g, 0.94 mmol) were added and the hydrogen atmosphere was refreshed. The resulting mixture was stirred at room temperature for 21 hours. The reaction was then filtered through Celite, rinsing copiously with DCM. The filtrate was concentrated to afford 3-methyl-1-(2,2,2-trifluoroethyl)pyrazol-4-amine (12.6 g, quantitative) as a dark purple oil. 1H NMR (500 MHZ, CHLOROFORM-d) δ 2.19 (3H, s), 3.30 (2H, br s), 4.52 (2H, q), 7.04 (1H, s). 19F NMR (471 MHz, CHLOROFORM-d) −72.00. m/z: (ES+), $[M+H]^+$=180.0

(c) Methyl 6-chloro-5-cyclopropyl-3-[[3-methyl-1-(2 2,2-trifluoroethyl)pyrazol-4-yl]amino]pyrazine-2-carboxylate DIPEA (27.2 mL, 156 mmol) was added to a solution of 3-methyl-1-(2,2,2-trifluoroethyl)pyrazol-4-amine (11.9 g, 66.6 mmol) and methyl 6-chloro-5-cyclopropyl-3-fluoropyrazine-2-carboxylate (12.0 g, 52.0 mmol) in DMF (200 mL). The resulting mixture was stirred at 100° C. for 3 hours under nitrogen. The reaction was then allowed to cool to room temperature and concentrated. The resulting residue was taken up in MeOH (100 mL) and stirred at 50° C. for 2 hours. The resulting slurry was allowed to cool to room temperature, then filtered. The filter cake was rinsed with minimal MeOH and set aside. The filtrate was concentrated, and the slurrying/filtration procedure was carried out twice more. The filter cakes from these three operations were combined to afford methyl 6-chloro-5-cyclopropyl-3-[[3-methyl-1-(2,2,2-trifluoroethyl)pyrazol-4-yl]amino]pyrazine-2-carboxylate (8.72 g, 43% yield) as a yellow-orange solid. 1H NMR (500 MHz, CHLOROFORM-d) δ 1.18-1.23 (2H, m), 1.23-1.30 (2H, m), 2.34 (3H, s), 2.53-2.63 (1H, m), 4.01 (3H, s), 4.65 (2H, q), 7.92 (1H, s), 9.83 (1H, s). 19F NMR (471 MHZ, CHLOROFORM-d)-71.86. m/z: (ES+), $[M+H]^+$=390.1

(d) Methyl 5-cyclopropyl-6-(3-methylimidazo[4,5-c]pyridin-7-yl)-3-[[3-methyl-1-(2,2,2-trifluoroethyl)pyrazol-4-yl]amino]pyrazine-2-carboxylate Methyl 6-chloro-5-cyclopropyl-3-[[3-methyl-1-(2,2,2-trifluoroethyl)pyrazol-4-yl]amino]pyrazine-2-carboxylate (8.60 g, 22.1 mmol), 2-(3-methylimidazo[4,5-c]pyridin-7-yl)-1,3,6,2-dioxazaborocane (8.14 g, 33.1 mmol), Pd(dppf) C12 dichloromethane adduct (1.80 g, 2.21 mmol), and cesium fluoride (10.1 g, 66.2 mol) were combined. 1,4-Dioxane (100 mL) and water (10 mL) were added and the resulting mixture was stirred as the reaction vessel was evacuated and backfilled with nitrogen five times. The resulting mixture was then stirred at 80° C. for 3 hours. The reaction was then allowed to cool to room temperature and concentrated. The resulting residue was taken up in 4:1 MeOH/water and stirred at 50° C. for 2 hours. The resulting slurry was allowed to cool to room temperature and filtered, rinsing sequentially with water, MeOH, and diethyl ether. The filter cake was set aside. The filtrate was concentrated. The resulting residue was taken up in 5:1 DCM/MeOH and filtered through Celite, rinsing copiously with DCM. The Celite-containing filter cake was discarded. The resulting filtrate was concentrated, and the resulting residue was purified by silica gel chromatography, using 0-10% MeOH-DCM as eluent, and 0-0.2% methanolic ammonia as modifier, to afford a dark yellow foam. This material was taken up in 5:1 MeOH/diethyl ether and stirred at 50° C. for 1 hour. The resulting suspension was allowed to cool to room temperature and filtered, rinsing sparingly with diethyl ether. The filter cake was set aside. This slurrying/filtration/concentration process was repeated four additional times. The six filter cakes were combined to afford methyl 5-cyclopropyl-6-(3-methylimidazo[4,5-c]pyridin-7-yl)-3-[[3-methyl-1-(2,2,2-trifluoroethyl)pyrazol-4-yl]amino]pyrazine-2-carboxylate (9.26 g, 86% yield) as a yellow solid. 1H NMR (500 MHZ, CHLOROFORM-d) & 1.02 (2H, br dd), 1.25-1.30 (2H, m), 1.97-2.05 (1H, m), 2.39 (3H, s), 4.00 (3H, s), 4.01 (3H, s), 4.66 (2H, q), 8.01 (1H, s), 8.06 (1H, s), 8.68 (1H, s), 8.92 (1H, s), 9.98 (1H, s). 19F NMR (471 MHZ, CHLOROFORM-d)-71.86. m/z: (ES+), [M+H]==487.2

(e) 5-Cyclopropyl-6-(3-methylimidazo[4,5-c]pyridin-7-yl)-3_ [[3-methyl-1-(2,2,2-trifluoroethyl)pyrazol-4-yl]amino]pyrazine-2-carboxamide 7 N Methanolic ammonia (106 mL, 740 mmol) was added to methyl 5-cyclopropyl-6-(3-methylimidazo[4,5-c]pyridin-7-yl)-3-[[3-methyl-1-(2,2,2-trifluoroethyl)pyrazol-4-yl] amino]pyrazine-2-carboxylate (9.00 g, 18.5 mmol). The resulting suspension was stirred at 100° C. for 2 hours in a sealed pressure flask. The reaction was then allowed to cool to room temperature, then cooled to 0° C. The resulting precipitate was collected by filtration, rinsing with cold MeOH and copious diethyl ether. The filter cake was set aside. The filtrate was concentrated. The resulting residue was taken up in 4:1 MeOH/diethyl ether and stirred at 0° C. for 30 minutes. The resulting precipitate was collected by filtration, rinsing copiously with diethyl ether. The filter cake was set aside. This slurrying/filtration/concentration procedure was carried out twice more. The four filter cakes were then taken up together in 3:1 MeOH/diethyl ether and stirred at 50° C. for 16 hours. The resulting slurry was allowed to cool to room temperature, then cooled to 0° C., then filtered, rinsing with cold MeOH and diethyl ether. The resulting filter cake was dried under vacuum to afford 5-cyclopropyl-6-(3-methylimidazo[4,5-c]pyridin-7-yl)-3-[[3-methyl-1-(2,2,2-trifluoroethyl)pyrazol-4-yl]amino]pyrazine-2-carboxamide (7.66 g, 88% yield) as a bright yellow solid. 1H NMR (500 MHz, DMSO-d6) δ 0.91 (2H, br dd), 1.11 (2H, br s), 1.85-1.93 (1H, m), 2.22 (3H, s), 3.99 (3H, s), 5.09 (2H, q), 7.82 (1H, br s), 8.05 (1H, s), 8.08 (1H, br s), 8.43 (1H, s), 8.52 (1H, s), 9.03 (1H, s), 10.92 (1H, s). 19F NMR (471 MHz, DMSO-d6)-70.46 (1F, s). m/z: (ES+), $[M+H]^+$=472.2

Figure 11:
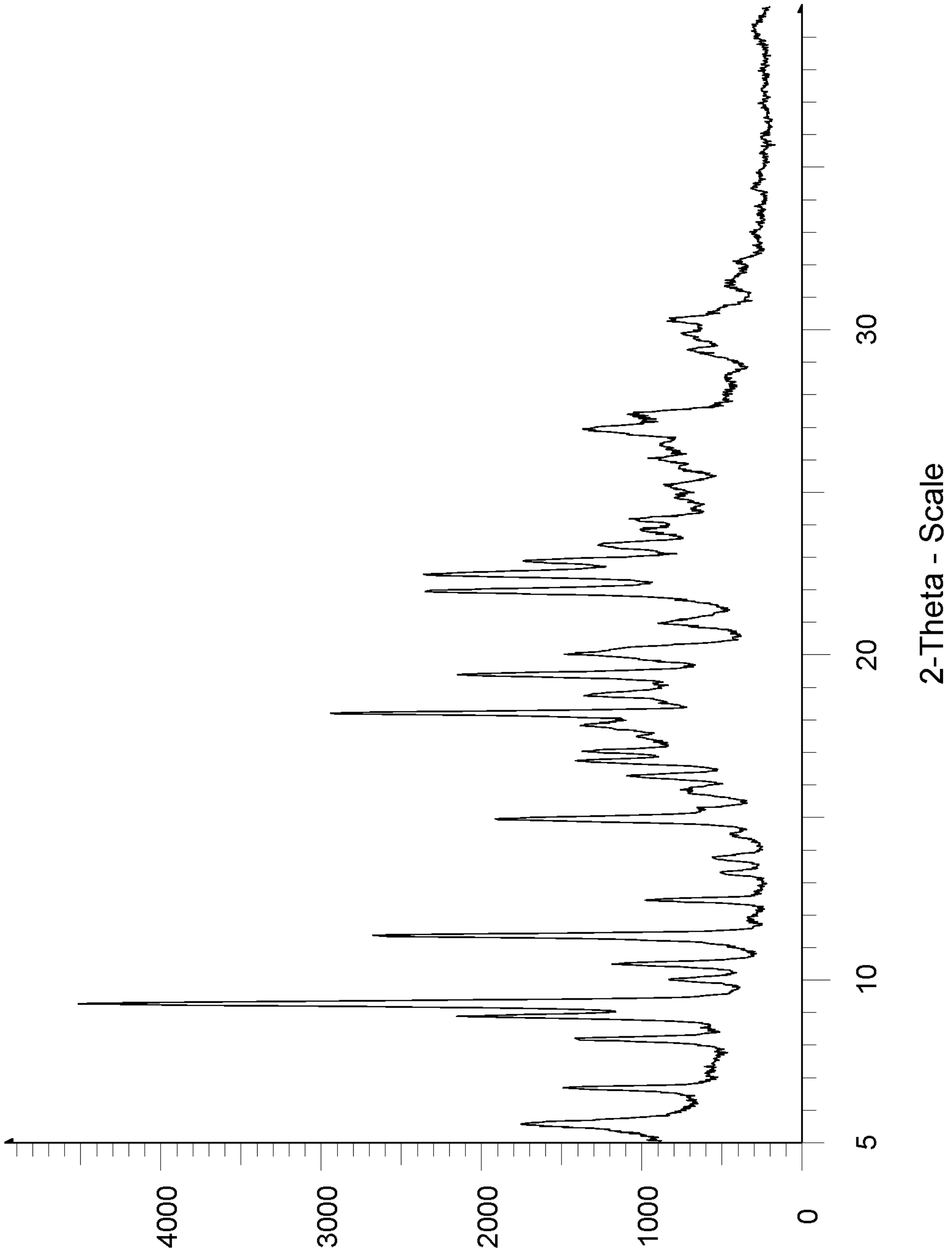
FIG. 11 shows the X-ray powder diffraction pattern for Example 213, form A: 5-Cyclopropyl-6-(3-methylimidazo[4,5-c]pyridin-7-yl)-3-[[3-methyl-1-(2,2,2-trifluoroethyl)pyrazol-4-yl]amino]pyrazine-2-carboxamide.

The solid residue was found to be crystalline by XRPD (form A) and a typical diffractogram is displayed in FIG. 11. Characteristic peak positions are listed below in Tables 11 and 12.

TABLE 11

Five peaks characteristic for Example 213, form A

| °2-theta | Relative intensity |
|---|---|
| 9.3 | vs |
| 11.4 | s |
| 18.2 | s |
| 22.0 | s |
| 22.5 | s |

TABLE 12

Peaks characteristic for Example 213, form A

| °2-theta | Relative intensity |
|---|---|
| 5.5 | m |
| 6.6 | m |
| 8.2 | m |
| 8.9 | s |
| 9.3 | vs |
| 10.0 | w |
| 10.5 | m |
| 11.4 | s |
| 12.4 | m |
| 13.3 | w |
| 13.7 | w |
| 14.5 | w |
| 14.9 | s |
| 15.3 | w |
| 15.8 | w |
| 16.3 | m |
| 16.7 | m |
| 17.0 | m |
| 17.8 | m |
| 18.2 | s |
| 18.8 | m |
| 19.4 | s |
| 20.0 | s |
| 21.0 | m |
| 22.0 | s |
| 22.5 | s |
| 22.9 | m |
| 23.4 | m |
| 23.8 | m |
| 24.2 | m |
| 24.9 | w |
| 25.2 | w |
| 25.8 | w |
| 26.1 | m |
| 27.0 | m |
| 27.4 | m |
| 28.6 | w |
| 29.4 | w |
| 29.9 | w |
| 30.3 | w |
| 31.4 | w |
| 32.1 | vw |
| 34.4 | vw |

Figure 12:
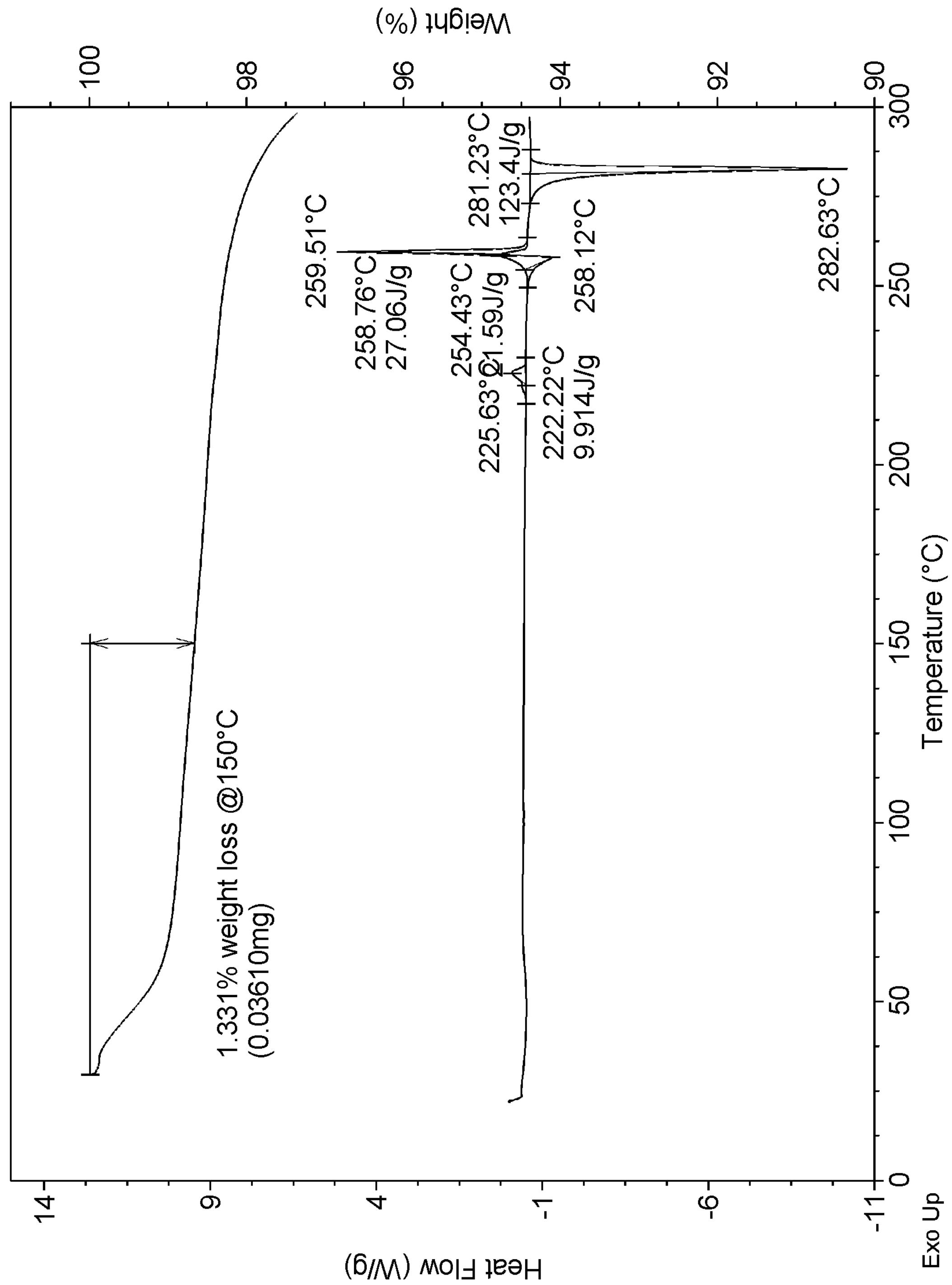
FIG. 12 shows a DSC/TGA thermogram of Example 213, form A: 5-Cyclopropyl-6-(3-methylimidazo[4,5-c]pyridin-7-yl)-3-[[3-methyl-1-(2,2,2-trifluoroethyl)pyrazol-4-yl]amino]pyrazine-2-carboxamide.

Form A was further analyzed by thermal techniques. DSC analysis shows several thermal events from 200° C. to 300° C. Form A has an exothermic event with an onset at 222° C. and a peak at 226° C., and then an endothermic with an onset at 254° C. and a peak at 258° C., followed by an exothermic event with an onset at 259° C. and a peak at 260° C. The final material has a melting/decomposition temperature with an onset at 281° C. and a peak at 283° C. TGA indicated that Form A exhibits a mass loss of about 1.3% upon heating from about 25° C. to about 150° C. A representative DSC/TGA thermogram of Form A is shown in FIG. 12.

5-6 mg of Example 213, Form A was suspended in 0.5 ml of EtOH (or ACN), and the yellow slurry was stirred at the room temperature for 1 day. 4-5 mg of yellow solid of Form B was obtained after filtration and air-dried.

Figure 13:
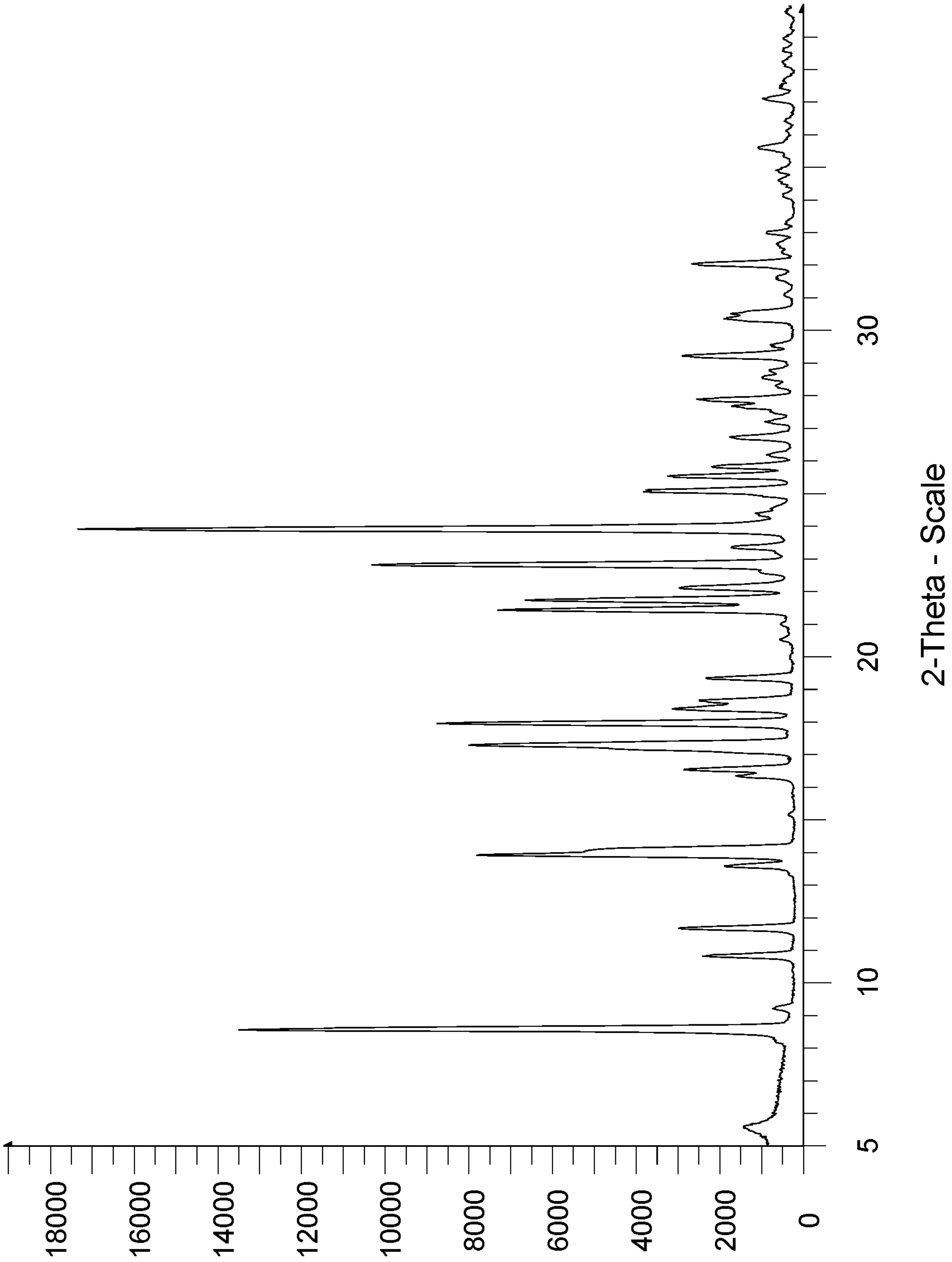
FIG. 13 shows the X-ray powder diffraction pattern for Example 213, form B: 5-Cyclopropyl-6-(3-methylimidazo[4,5-c]pyridin-7-yl)-3-[[3-methyl-1-(2,2,2-trifluoroethyl)pyrazol-4-yl]amino]pyrazine-2-carboxamide.

The solid residue was found to be crystalline by XRPD (form B) and a typical diffractogram is displayed in FIG. 13. Characteristic peak positions are listed below in Tables 13 and 14.

TABLE 13

Five peaks characteristic for Example 213, form B

| °2-theta | Relative intensity |
|---|---|
| 8.6 | s |
| 17.3 | s |
| 18.0 | s |
| 22.8 | s |
| 23.9 | vs |

TABLE 14

| Peaks characteristic for Example 213, form B | |
|---|---|
| °2-theta | Relative intensity |
| 5.5 | vw |
| 8.6 | s |
| 9.2 | vw |
| 10.8 | w |
| 11.7 | w |
| 13.6 | w |
| 14.0 | m |
| 15.1 | vw |
| 16.5 | w |
| 17.3 | s |
| 18.0 | s |
| 18.4 | w |
| 19.3 | w |
| 20.5 | vw |
| 21.4 | s |
| 21.8 | m |
| 22.1 | w |
| 22.8 | s |
| 23.3 | vw |
| 23.9 | vs |
| 24.4 | vw |
| 25.1 | m |
| 25.5 | w |
| 25.8 | w |
| 26.2 | vw |
| 26.8 | vw |
| 27.2 | vw |
| 27.9 | w |
| 28.6 | vw |
| 29.3 | w |
| 30.5 | vw |
| 31.1 | vw |
| 31.6 | vw |
| 32.1 | w |
| 32.7 | vw |
| 33.0 | vw |
| 34.2 | vw |
| 34.6 | vw |
| 35.0 | vw |
| 35.6 | vw |
| 37.1 | vw |
| 37.6 | vw |
| 38.3 | vw |
| 39.0 | vw |

Figure 14:
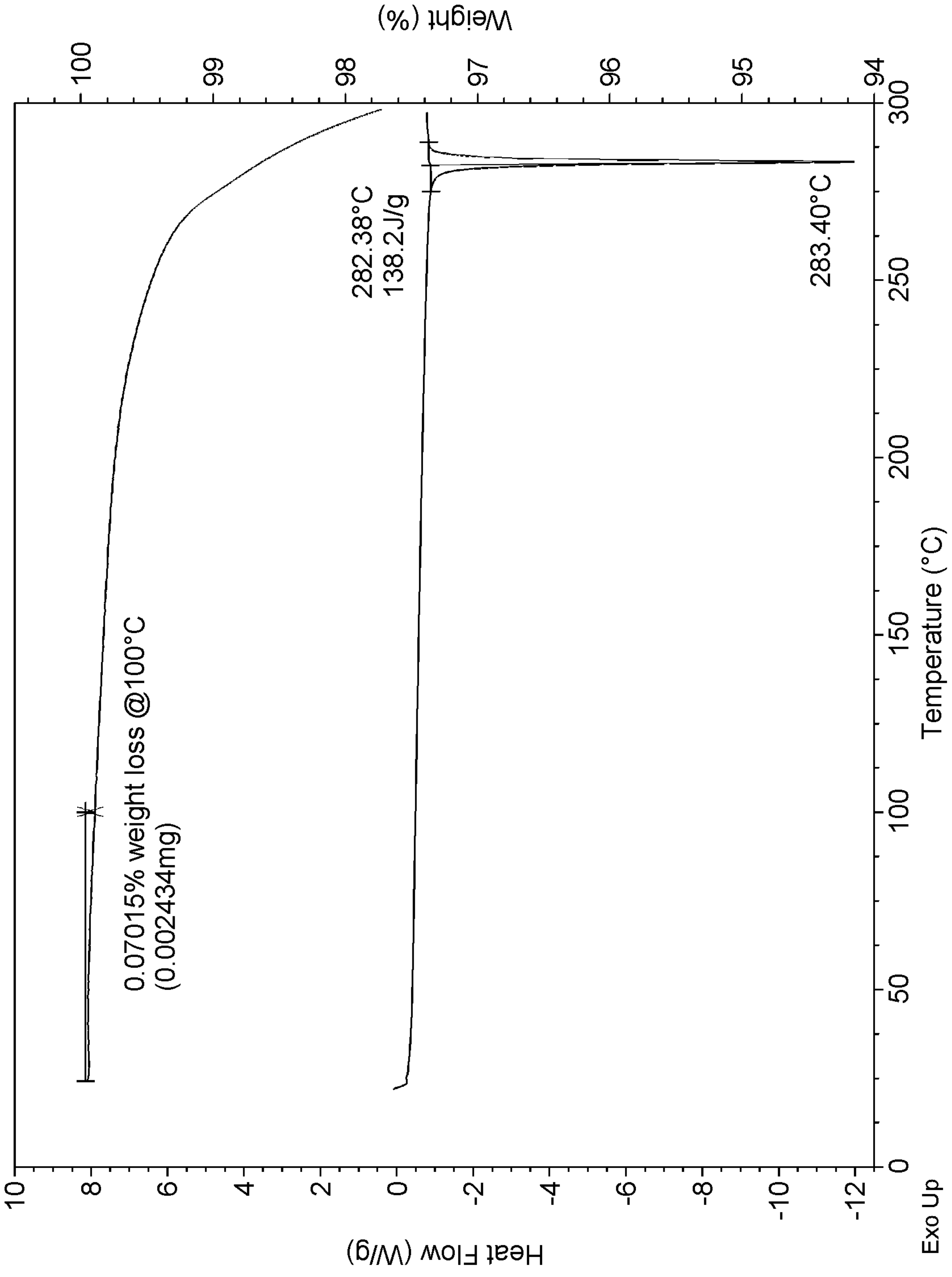
FIG. 14 shows a DSC/TGA thermogram of Example 213, form B: 5-Cyclopropyl-6-(3-methylimidazo[4,5-c]pyridin-7-yl)-3-[[3-methyl-1-(2,2,2-trifluoroethyl)pyrazol-4-yl]amino]pyrazine-2-carboxamide.

Form A was further analyzed by thermal techniques. DSC analysis indicated that Form B has a melting/decomposition temperature with an onset at 282° C. and a peak at 283° C. TGA indicated that Form B exhibits a mass loss of about 0.1% upon heating from about 25° C. to about 100° C. A representative DSC/TGA thermogram of Form B is shown in FIG. 14.

20 mg of Example 213, Form B was suspended in 1.0 ml of H2O and 0.4 ml of EtOH. The yellow slurry was stirred at the room temperature for 3 days. 17 mg of yellow solid of Form C was obtained after filtration and air-dried.

Figure 15:
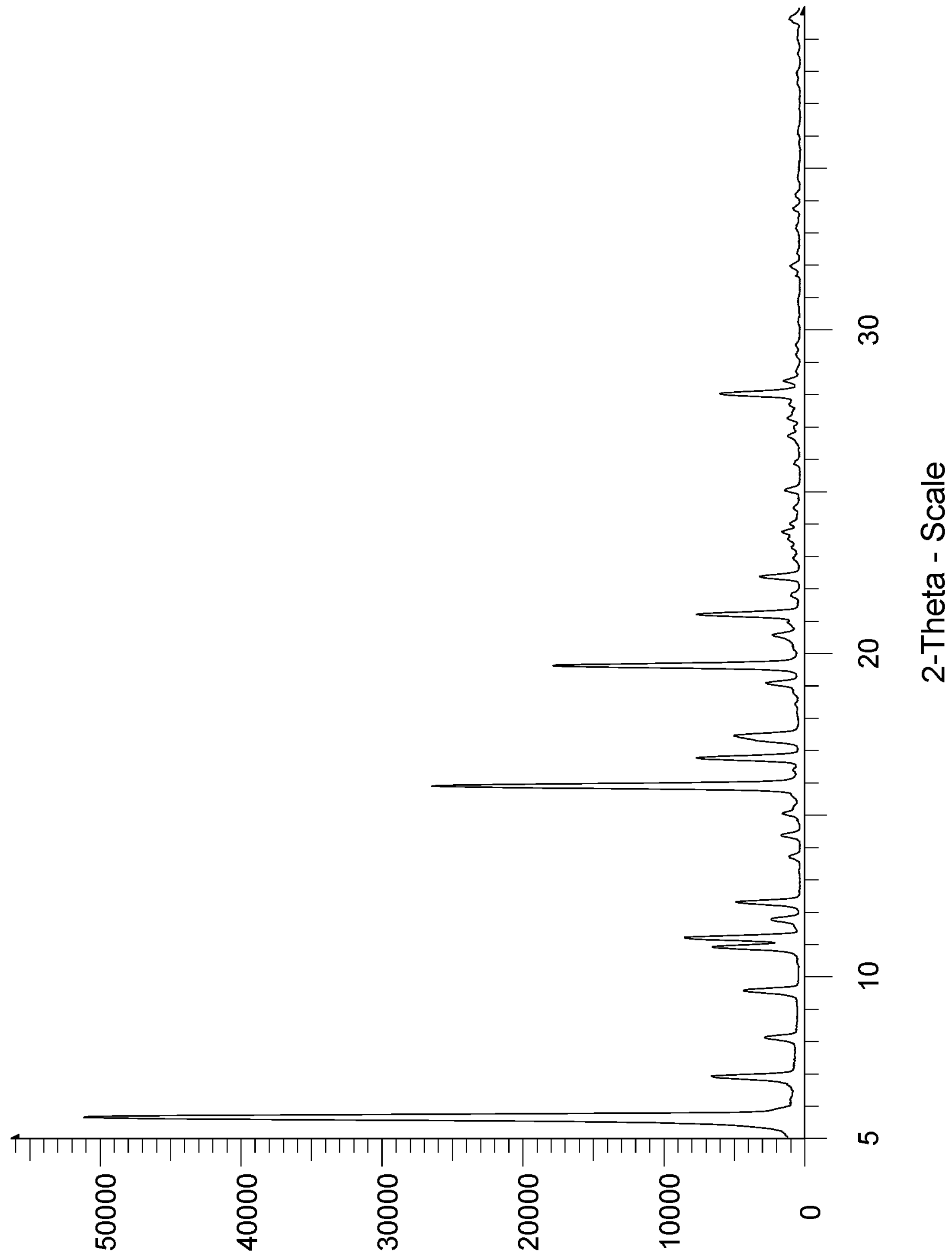
FIG. 15 shows the X-ray powder diffraction pattern for Example 213, form C: 5-Cyclopropyl-6-(3-methylimidazo[4,5-c]pyridin-7-yl)-3-[[3-methyl-1-(2,2,2-trifluoroethyl)pyrazol-4-yl]amino]pyrazine-2-carboxamide.

The solid residue was found to be crystalline by XRPD (form C) and a typical diffractogram is displayed in FIG. 15. Characteristic peak positions are listed below in Tables 15 and 16.

TABLE 15

| Five peaks characteristic for Example 213, form C | |
|---|---|
| °2-theta | Relative intensity |
| 5.6 | vs |
| 11.2 | w |
| 15.9 | s |
| 19.6 | m |
| 21.2 | w |

TABLE 16

| Peaks characteristic for Example 213, form C | |
|---|---|
| °2-theta | Relative intensity |
| 5.6 | vs |
| 6.9 | w |
| 8.1 | vw |
| 9.5 | vw |
| 10.9 | w |
| 11.2 | w |
| 11.7 | vw |
| 12.3 | vw |
| 13.7 | vw |
| 14.4 | vw |
| 15.1 | vw |
| 15.9 | s |
| 16.7 | w |
| 17.4 | vw |
| 19.1 | vw |
| 19.6 | m |
| 20.5 | vw |
| 21.2 | w |
| 21.8 | vw |
| 22.4 | vw |
| 22.9 | vw |
| 23.7 | vw |
| 24.5 | vw |
| 25.1 | vw |
| 25.9 | vw |
| 26.7 | vw |
| 27.3 | vw |
| 28.0 | w |
| 28.4 | vw |
| 30.9 | vw |
| 32.0 | vw |
| 33.2 | vw |
| 33.8 | vw |
| 34.2 | vw |
| 38.0 | vw |
| 39.7 | vw |

Figure 16:
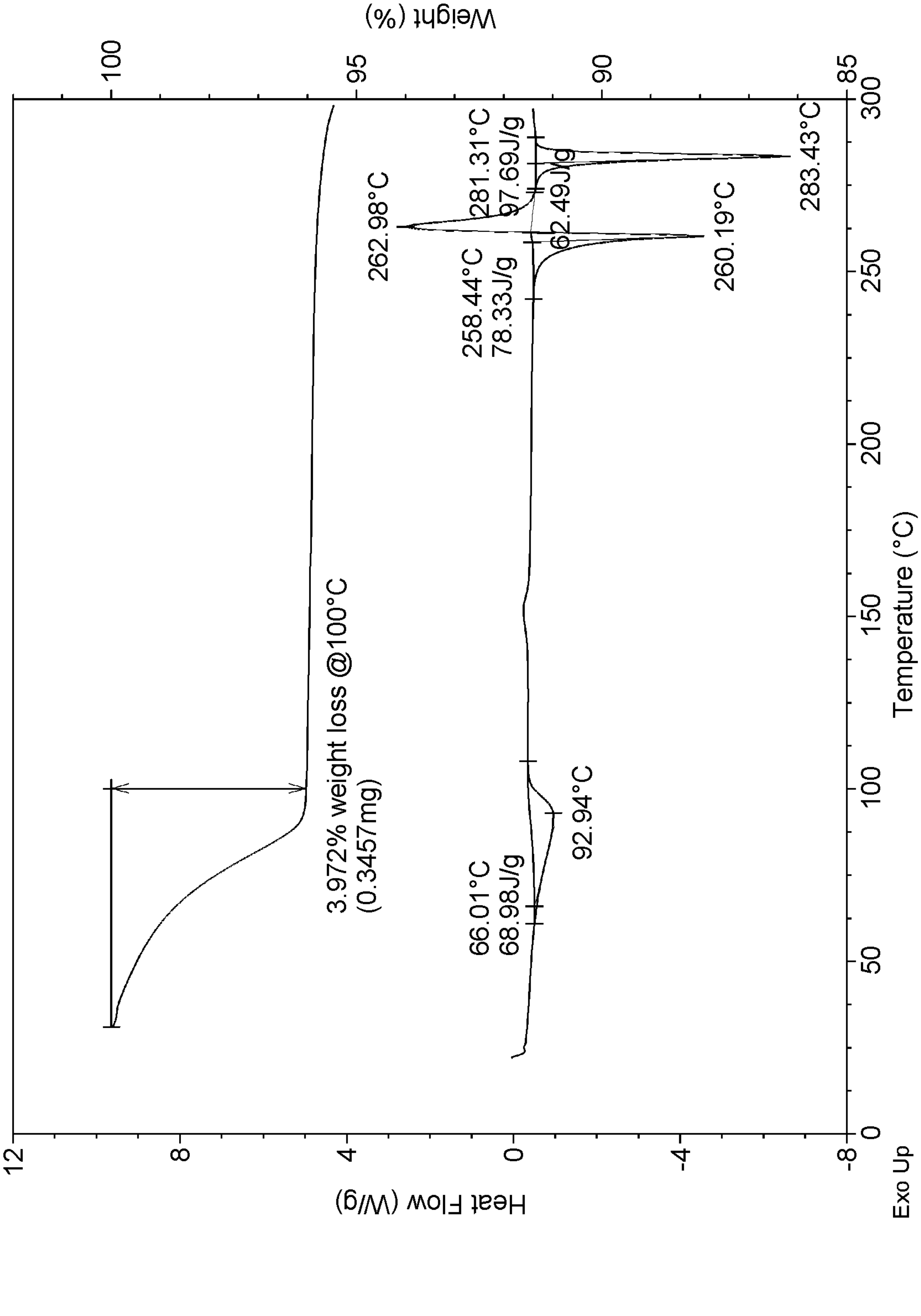
FIG. 16 shows a DSC/TGA thermogram of Example 213, form C: 5-Cyclopropyl-6-(3-methylimidazo[4,5-c]pyridin-7-yl)-3-[[3-methyl-1-(2,2,2-trifluoroethyl)pyrazol-4-yl]amino]pyrazine-2-carboxamide.

Form C was further analyzed by thermal techniques. DSC analysis indicated that Form C starts to de-solvate with an onset at 66° C. and a peak at 93° C., the de-hydrated form then has an endothermic with an onset at 258° C. and a peak at 260° C., followed by an exothermic event with a peak at 263° C. The final material has a melting/decomposition temperature with an onset at 281° C. and a peak at 283° C. TGA indicated that Form C exhibits a mass loss of about 4.0% upon heating from about 25° C. to about 100° C. A representative DSC/TGA thermogram of Form C is shown in FIG. 16.

Figure 17:
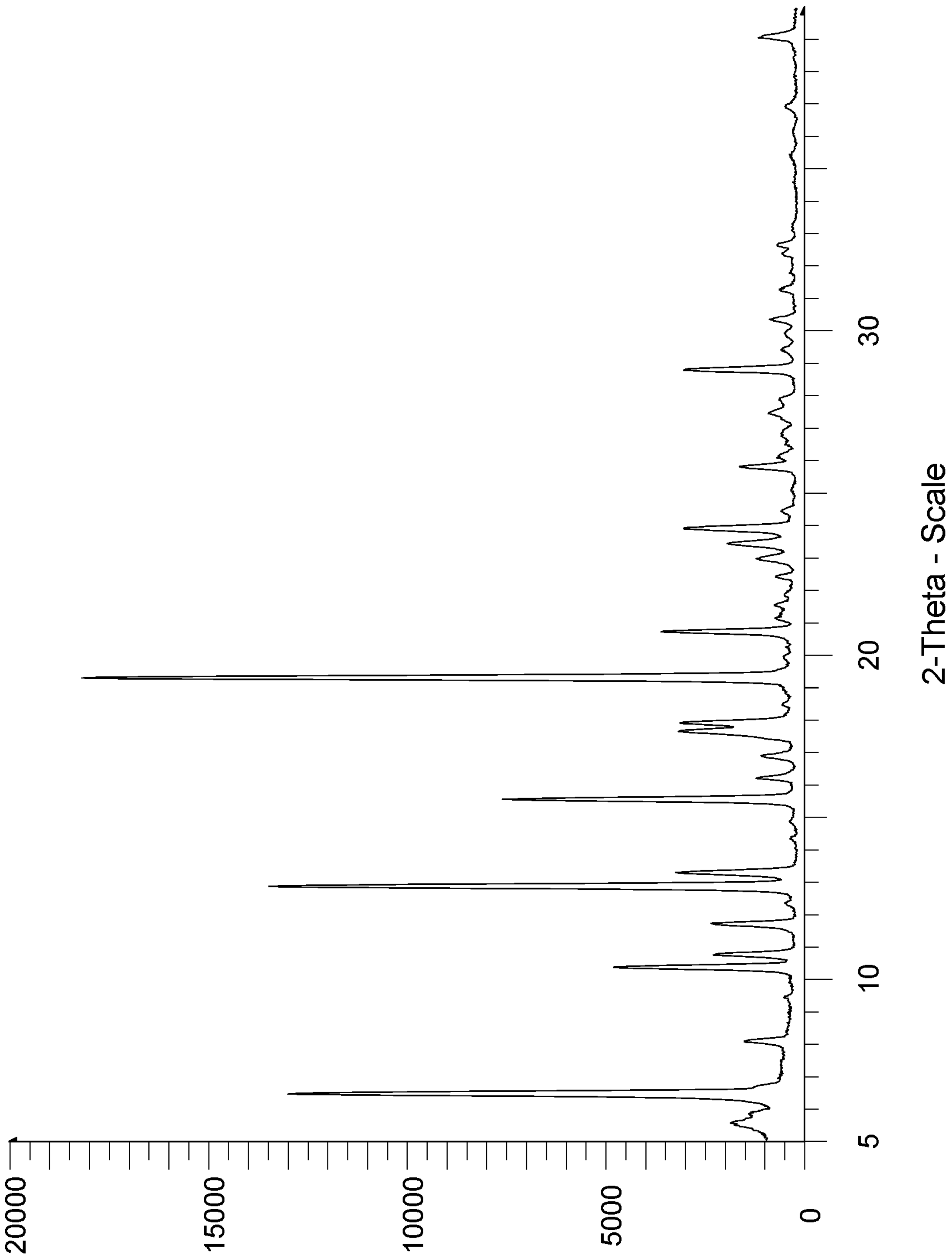
FIG. 17 shows the X-ray powder diffraction pattern for Example 213, form D: 5-Cyclopropyl-6-(3-methylimidazo[4,5-c]pyridin-7-yl)-3-[[3-methyl-1-(2,2,2-trifluoroethyl)pyrazol-4-yl]amino]pyrazine-2-carboxamide.

2-5 mg of Example 213, Form C was placed to a DSC pan and heated to 150° C. at a rate of 10/min, then cooled down to the room temperature. The solid residue was found to be crystalline by XRPD (form D) and a typical diffractogram is displayed in FIG. 17. Characteristic peak positions are listed below in Tables 17 and 18.

TABLE 17

| Five peaks characteristic for Example 213, form D | |
|---|---|
| °2-theta | Relative intensity |
| 6.4 | s |
| 10.4 | m |
| 12.9 | s |
| 15.5 | m |
| 19.3 | vs |

TABLE 18

| Peaks characteristic for Example 213, form D | |
|---|---|
| °2-theta | Relative intensity |
| 5.5 | w |
| 6.4 | s |
| 8.1 | vw |
| 9.4 | vw |
| 10.4 | m |
| 10.7 | w |
| 11.7 | w |
| 12.3 | vw |
| 12.9 | s |
| 13.3 | w |
| 14.3 | vw |
| 14.9 | vw |
| 15.5 | m |
| 16.2 | vw |
| 16.9 | vw |
| 17.6 | w |
| 17.9 | w |
| 18.5 | vw |
| 19.3 | vs |
| 19.9 | vw |
| 20.7 | w |
| 21.2 | vw |
| 21.5 | vw |
| 22.4 | vw |
| 23.0 | vw |
| 23.4 | w |
| 23.9 | w |
| 24.5 | vw |
| 25.8 | vw |
| 26.2 | vw |
| 26.8 | vw |
| 27.5 | vw |
| 27.9 | vw |
| 28.8 | w |
| 29.4 | vw |
| 29.9 | vw |
| 30.4 | vw |
| 31.3 | vw |
| 32.4 | vw |
| 32.7 | vw |
| 35.4 | vw |

Figure 18:
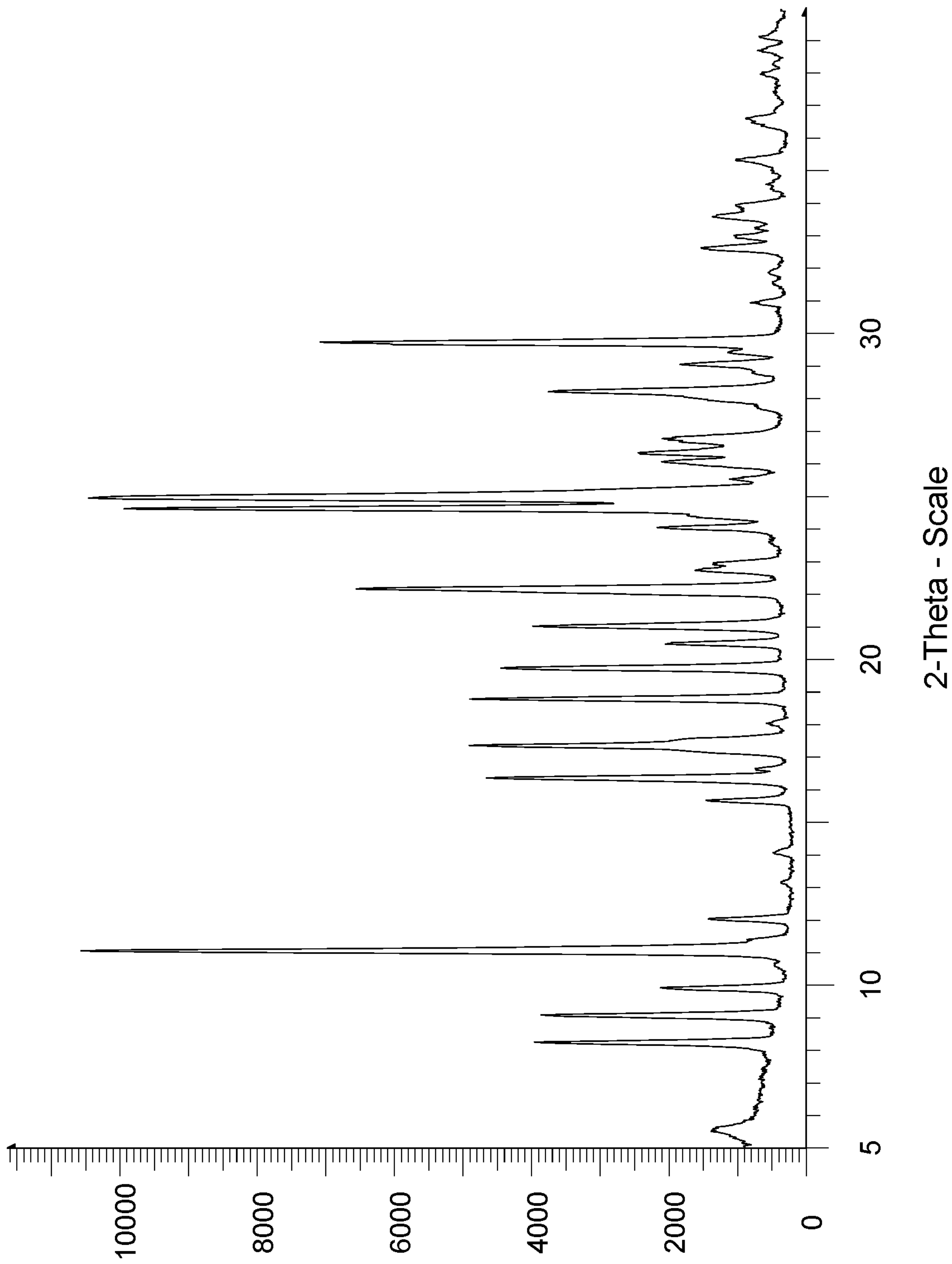
FIG. 18 shows the X-ray powder diffraction pattern for Example 213, form A, HCl salt: 5-Cyclopropyl-6-(3-methylimidazo[4,5-c]pyridin-7-yl)-3-[[3-methyl-1-(2,2,2-trifluoroethyl)pyrazol-4-yl]amino]pyrazine-2-carboxamide.

24 mg of Example 213 was suspended in 1.0 ml of MeOH. 55 ul of 1N HCl aqueous solution was added to the suspension, the solid was partially dissolved. After 20 minutes, extra 55 ul of 1N HCl aqueous solution was added, yellow solid started to precipitate and formed a wet cake. 1.0 ml of EtOH was added and the slurry was stirred at the room temperature for 5 days. The yellow suspension was filtrated and air-dried. 25 mg of yellow solid of HCl salt of Form A was obtained. The solid residue was found to be crystalline by XRPD (Form A, HCl salt) and a typical diffractogram is displayed in FIG. 18. Characteristic peak positions are listed below in Tables 19 and 20.

TABLE 19

| Five peaks characteristics for Example 213, Form A, HCl salt | |
|---|---|
| °2-theta | Relative intensity |
| 11.0 | vs |
| 22.2 | s |
| 24.6 | vs |
| 25.0 | vs |
| 29.8 | s |

TABLE 20

| Peaks characteristic for Example 213, Form A, HCl salt | |
|---|---|
| °2-theta | Relative intensity |
| 5.5 | w |
| 8.2 | m |
| 9.0 | m |
| 9.9 | w |
| 11.0 | vs |
| 12.0 | w |
| 13.1 | vw |
| 14.1 | vw |
| 15.7 | w |
| 16.3 | m |
| 17.3 | m |
| 18.0 | vw |
| 18.8 | m |
| 19.7 | m |
| 20.5 | w |
| 21.0 | m |
| 22.2 | s |
| 22.8 | w |
| 24.0 | w |
| 24.6 | vs |
| 25.0 | vs |
| 26.0 | w |
| 26.4 | m |
| 26.8 | w |
| 28.2 | m |
| 29.1 | w |
| 29.8 | s |
| 31.0 | vw |
| 32.6 | w |
| 33.0 | vw |
| 33.6 | w |
| 33.9 | vw |
| 34.6 | vw |
| 35.4 | vw |
| 36.6 | vw |
| 38.0 | vw |

Figure 19:
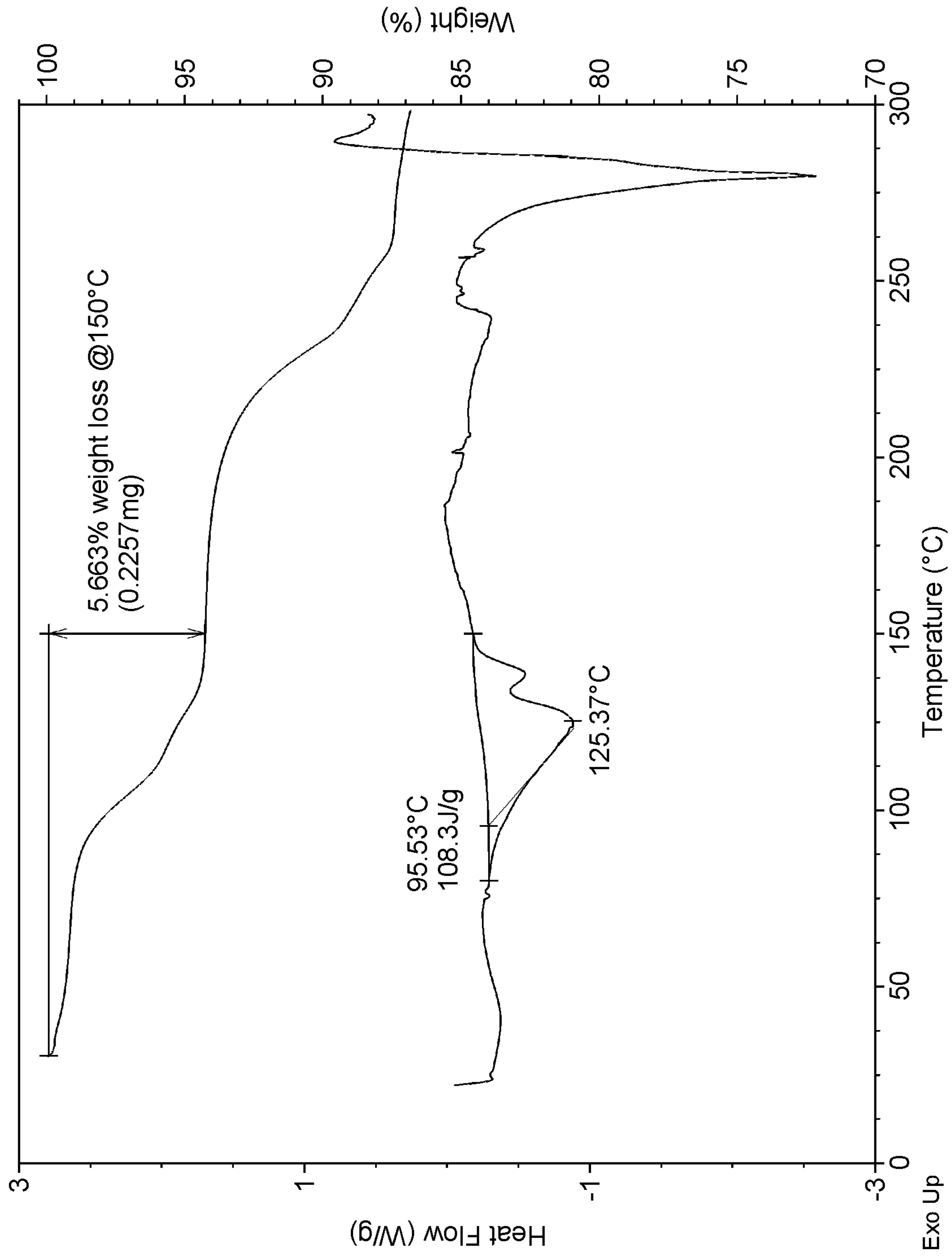
FIG. 19 shows a DSC/TGA thermogram of Example 213, form A, HCl salt: 5-Cyclopropyl-6-(3-methylimidazo[4,5-c]pyridin-7-yl)-3-[[3-methyl-1-(2,2,2-trifluoroethyl)pyrazol-4-yl]amino]pyrazine-2-carboxamide.

Form A, HCl salt was further analyzed by thermal techniques. DSC analysis indicated that Form A, HCl salt starts to de-solvate with an onset at 96° C. and a peak at 125° C. The de-hydrated solid starts to decompose at about 200° C. TGA indicated that Form A, HCl salt exhibits a mass loss of about 5.7% upon heating from about 25° C. to about 150° C. A representative DSC/TGA thermogram of Form A, HCl salt is shown in FIG. 19.

Figure 20:
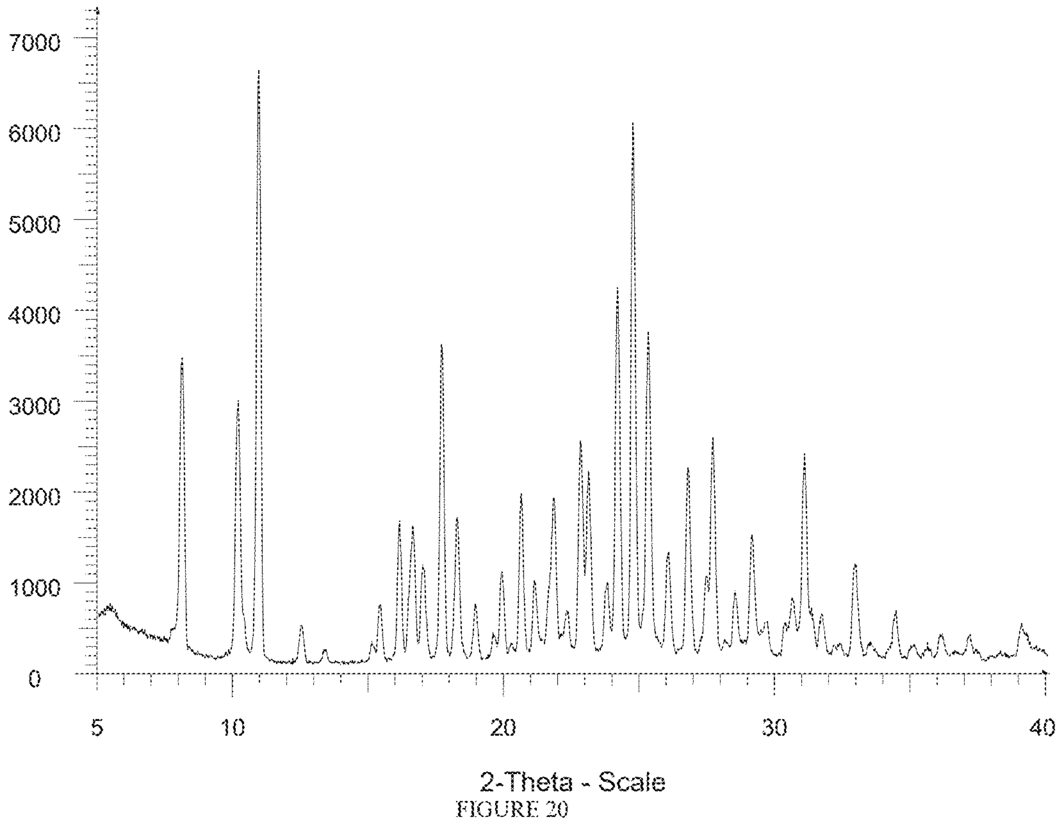
FIG. 20 shows the X-ray powder diffraction pattern for Example 213, form B, HCl salt: 5-Cyclopropyl-6-(3-methylimidazo[4,5-c]pyridin-7-yl)-3-[[3-methyl-1-(2,2,2-trifluoroethyl)pyrazol-4-yl]amino]pyrazine-2-carboxamide.

196 mg of Example 213 was suspended in 6.0 ml of EtOH. 0.44 ml of 1N HCl aqueous solution was added to the suspension. The slurry was stirred at the room temperature for 1 day and then heated to 75° C. and stirred at 75° C. for 1 hour. The yellow suspension was cooled down and filtered. The yellow solid was dried at 50° C. in vacuum for 1 hour. 186 mg of yellow solid of HCl salt of Form B was obtained. The solid residue was found to be crystalline by XRPD (Form B, HCl salt) and a typical diffractogram is displayed in FIG. 20. Characteristic peak positions are listed below in Tables 21 and 22.

TABLE 21

| Five peaks characteristic for Example 213, Form B, HCl salt | |
|---|---|
| °2-theta | Relative intensity |
| 10.9 | vs |
| 17.7 | s |
| 24.2 | s |
| 24.8 | s |
| 25.4 | s |

TABLE 22

| Peaks characteristic for Example 213, Form B, HCl salt | |
|---|---|
| °2-theta | Relative intensity |
| 8.1 | s |
| 10.2 | s |
| 10.9 | vs |
| 12.5 | vw |
| 15.1 | vw |
| 15.4 | w |
| 16.2 | m |
| 16.6 | m |
| 17.0 | w |
| 17.7 | s |
| 18.3 | m |
| 19.0 | w |
| 19.6 | vw |
| 19.9 | w |
| 20.7 | m |
| 21.2 | w |
| 21.9 | m |
| 22.3 | w |
| 22.9 | m |
| 23.2 | m |
| 23.8 | w |
| 24.2 | s |
| 24.8 | vs |
| 25.4 | s |
| 26.1 | w |
| 26.8 | m |
| 27.5 | w |
| 27.7 | m |
| 28.6 | w |
| 29.2 | m |
| 29.7 | vw |
| 30.4 | vw |
| 30.7 | w |
| 31.1 | m |
| 31.4 | vw |
| 31.8 | vw |
| 33.0 | w |
| 33.6 | vw |
| 34.5 | vw |
| 35.2 | vw |
| 35.7 | vw |
| 36.2 | vw |
| 37.2 | vw |

Figure 21:
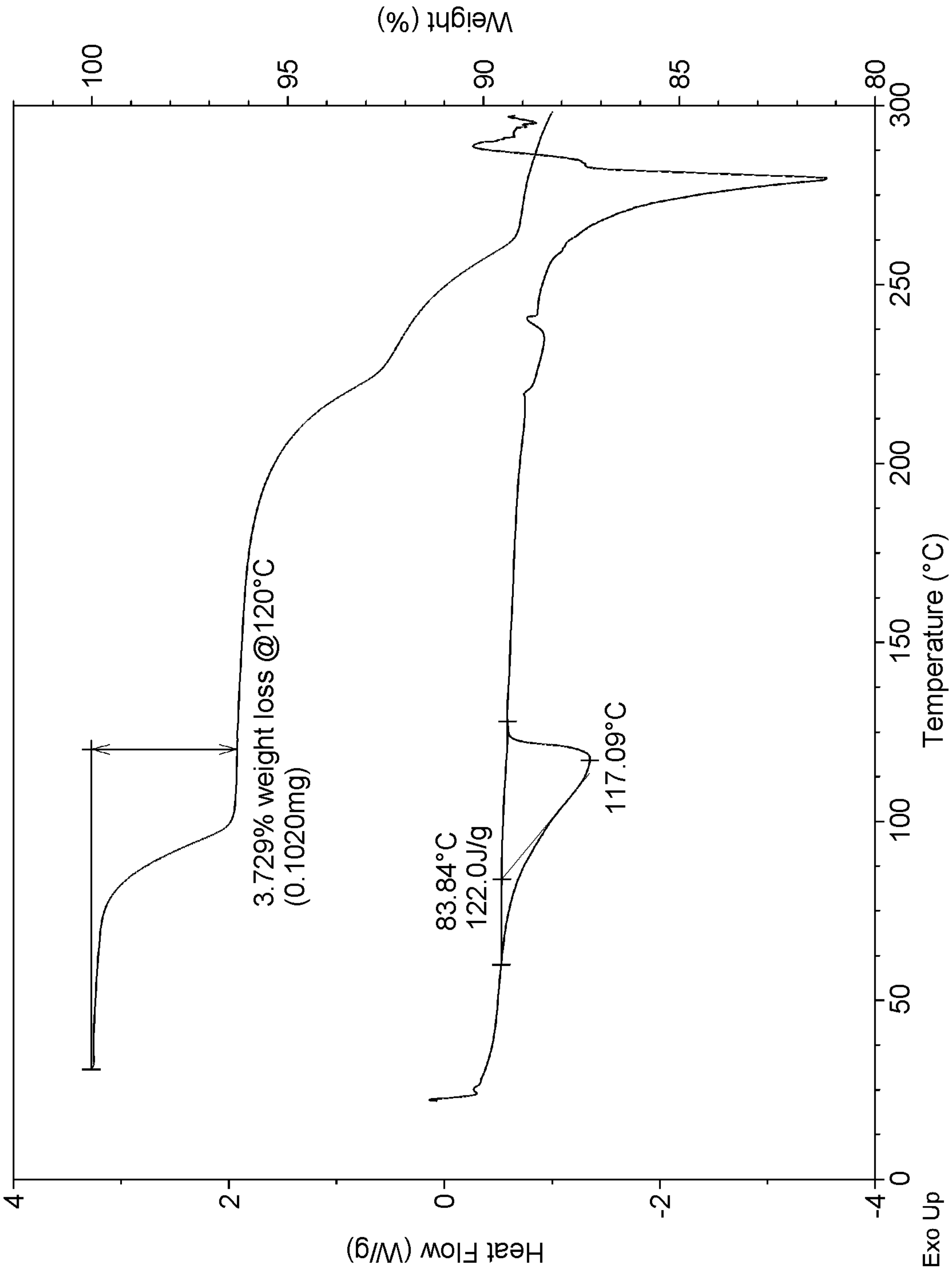
FIG. 21 shows a DSC/TGA thermogram of Example 213, form B, HCl salt: 5-Cyclopropyl-6-(3-methylimidazo[4,5-c]pyridin-7-yl)-3-[[3-methyl-1-(2,2,2-trifluoroethyl)pyrazol-4-yl]amino]pyrazine-2-carboxamide.

Form B, HCl salt was further analyzed by thermal techniques. DSC analysis indicated that Form B, HCl salt starts to de-solvate with an onset at 84° C. and a peak at 117° C. The de-hydrated solid starts to decompose at about 200° C. TGA indicated that Form B, HCl salt exhibits a mass loss of about 3.7% upon heating from about 25° C. to about 120° C. A representative DSC/TGA thermogram of Form B, HCl salt is shown in FIG. 21.

Figure 22:
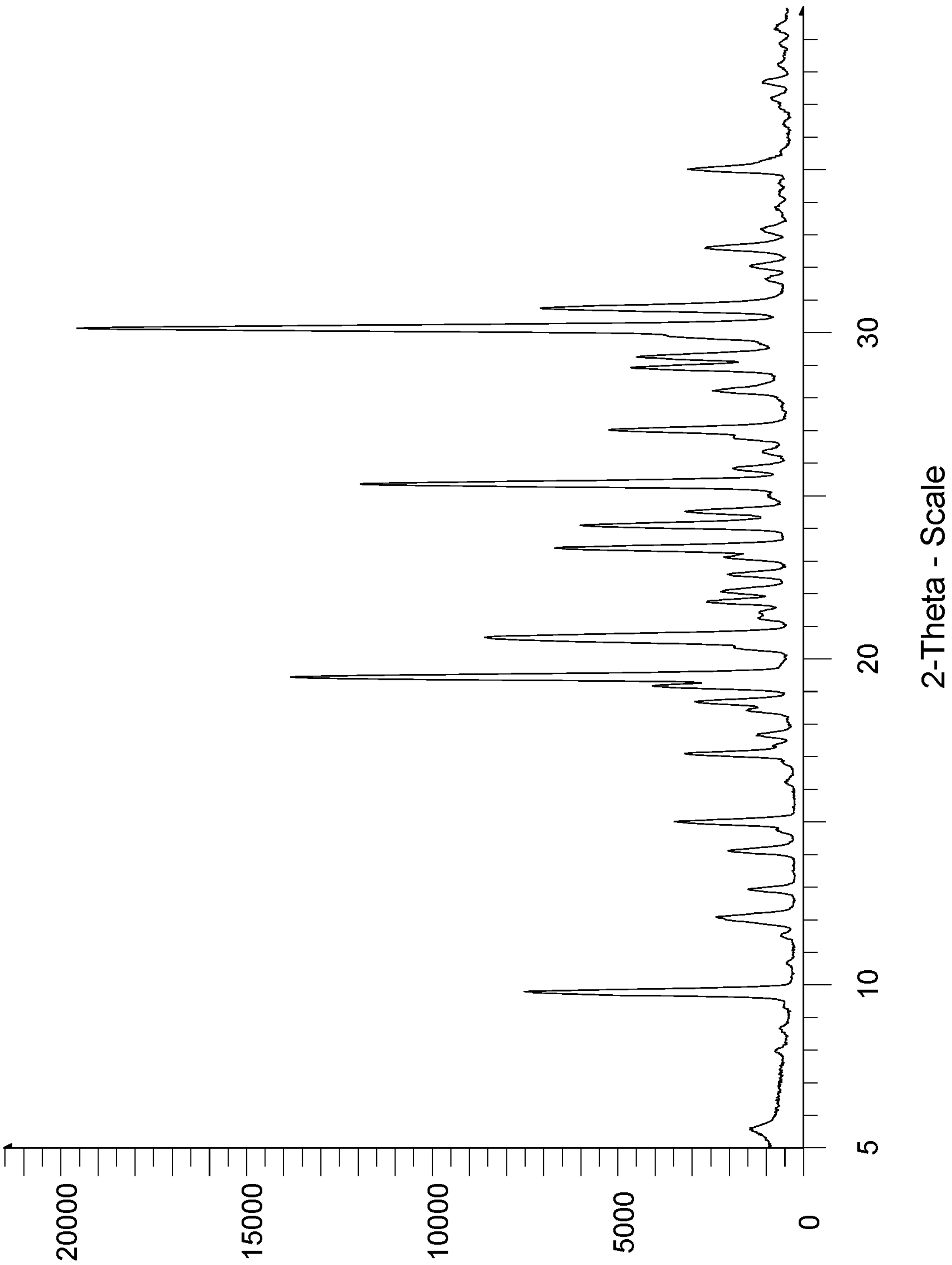
FIG. 22 shows the X-ray powder diffraction pattern for Example 213, form A, methane sulfonic acid salt: 5-Cyclopropyl-6-(3-methylimidazo[4,5-c]pyridin-7-yl)-3-[[3-methyl-1-(2,2,2-trifluoroethyl)pyrazol-4-yl]amino]pyrazine-2-carboxamide.

191 mg of Example 213 was suspended in 4.0 ml of EtOH. 0.44 ml of 1N methane sulfonic acid aqueous solution was added to the suspension, a wet cake was formed in about 15 minutes. 2.0 ml of EtOH was added and the resulting slurry was stirred at the room temperature for 1 day. The solid was isolated and dried in air. 208 mg of yellow solid of Form A, methane sulfonic acid was obtained. The solid residue was found to be crystalline by XRPD (Form A, methane sulfonic acid salt) and a typical diffractogram is displayed in FIG. 22. Characteristic peak positions are listed below in Tables 23 and 24.

TABLE 23

| Five peaks characteristic for Example 213, Form A, methane sulfonic acid salt | |
|---|---|
| °2-theta | Relative intensity |
| 9.7 | m |
| 19.4 | s |
| 20.6 | m |
| 25.4 | s |
| 30.2 | vs |

TABLE 24

| Peaks characteristic for Example 213, Form A, methane sulfonic acid salt | |
|---|---|
| °2-theta | Relative intensity |
| 5.5 | vw |
| 7.9 | vw |
| 8.6 | vw |
| 9.7 | m |
| 10.6 | vw |
| 11.5 | vw |
| 12.0 | w |
| 12.9 | vw |
| 14.1 | w |
| 15.0 | w |
| 16.2 | vw |
| 17.1 | w |
| 17.7 | vw |
| 18.7 | w |
| 19.1 | w |
| 19.4 | s |
| 20.6 | m |
| 21.3 | vw |
| 21.8 | w |
| 22.1 | w |
| 22.6 | w |
| 23.4 | m |
| 24.1 | m |
| 24.5 | w |
| 25.4 | s |
| 25.8 | vw |
| 26.4 | vw |
| 27.0 | m |
| 28.2 | w |
| 28.9 | m |
| 29.3 | m |
| 30.2 | vs |
| 30.8 | m |
| 31.7 | vw |
| 32.1 | vw |
| 32.6 | w |
| 33.2 | vw |
| 33.9 | vw |
| 35.1 | w |
| 36.5 | vw |
| 37.2 | vw |
| 37.7 | vw |
| 38.3 | vw |

TABLE 24-continued

| Peaks characteristic for Example 213, Form A, methane sulfonic acid salt | |
|---|---|
| °2-theta | Relative intensity |
| 38.9 | vw |
| 39.4 | vw |

Figure 23:
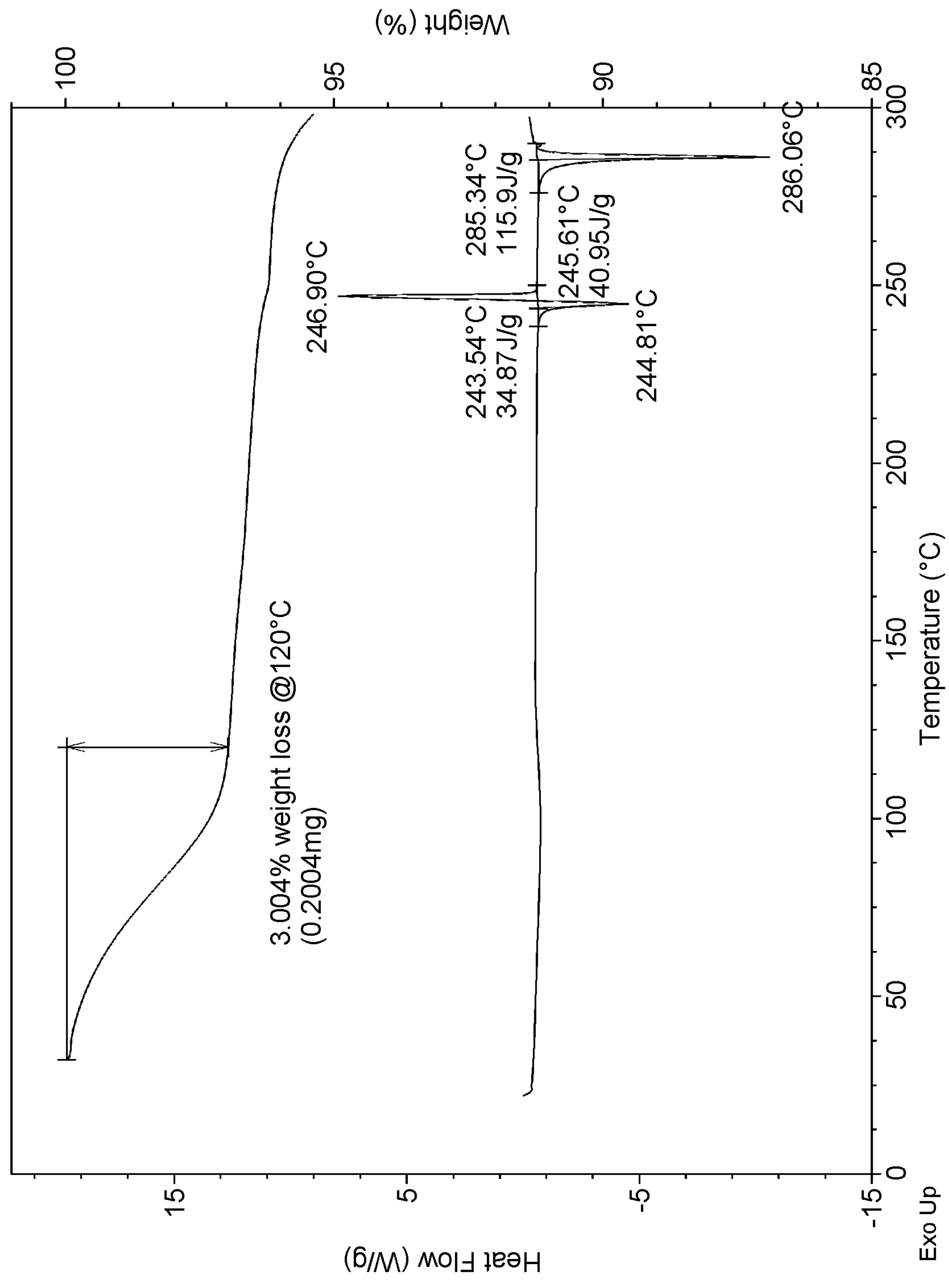
FIG. 23 shows a DSC/TGA thermogram of Example 213, form A, methane sulfonic acid salt: 5-Cyclopropyl-6-(3-methylimidazo[4,5-c]pyridin-7-yl)-3-[[3-methyl-1-(2,2,2-trifluoroethyl)pyrazol-4-yl]amino]pyrazine-2-carboxamide.

Form A, methane sulfonic acid salt was further analyzed by thermal techniques. DSC analysis indicated that a broad endothermic de-solvent from about 25° C. to about 120° C. the de-hydrated solid has an endothermic with an onset at 244° C. and a peak at 245° C., followed by an exothermic event with an onset at 246° C. and a peak at 247° C. The final material has a melting/decomposition temperature with an onset at 285° C. and a peak at 286° C. TGA indicated that Form A, methane sulfonic acid salt exhibits a mass loss of about 3.0% upon heating from about 25° C. to about 120° C. A representative DSC/TGA thermogram of Form A, methane sulfonic acid salt is shown in FIG. 23.

Figure 24:
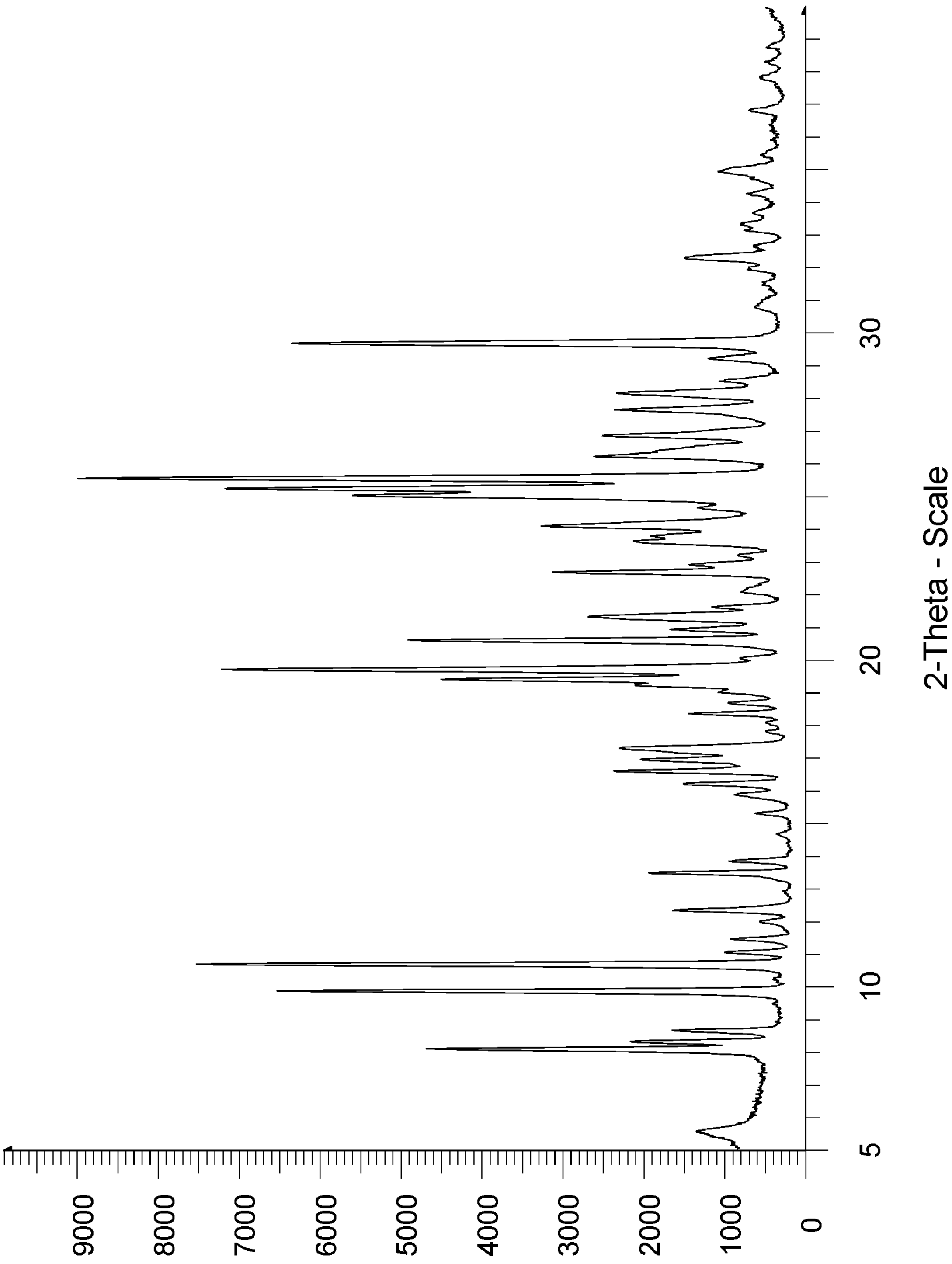
FIG. 24 shows the X-ray powder diffraction pattern for Example 213, form B, methane sulfonic acid salt: 5-Cyclopropyl-6-(3-methylimidazo[4,5-c]pyridin-7-yl)-3-[[3-methyl-1-(2,2,2-trifluoroethyl)pyrazol-4-yl]amino]pyrazine-2-carboxamide.

2-5 mg of Form A, methane sulfonic acid salt was placed to a DSC pan and heated to 275° C. at a rate of 10/min, then cooled down to the room temperature. A yellow solid was obtained. The solid residue was found to be crystalline by XRPD (Form B, methane sulfonic acid salt) and a typical diffractogram is displayed in FIG. 24. Characteristic peak positions are listed below in Tables 25 and 26.

TABLE 25

| Five peaks characteristic for Example 213, Form B, methane sulfonic acid salt | |
|---|---|
| °2-theta | Relative intensity |
| 9.8 | s |
| 10.7 | vs |
| 19.7 | s |
| 25.6 | vs |
| 29.7 | s |

TABLE 26

| Peaks characteristic for Example 213, Form B, methane sulfonic acid salt | |
|---|---|
| °2-theta | Relative intensity |
| 5.5 | w |
| 8.1 | s |
| 8.6 | w |
| 9.8 | s |
| 10.7 | vs |
| 11.0 | w |
| 11.4 | w |
| 12.0 | vw |
| 12.3 | w |
| 13.5 | m |
| 13.8 | w |
| 14.7 | vw |
| 15.3 | vw |
| 15.8 | vw |
| 16.2 | w |
| 16.6 | m |
| 16.9 | m |
| 17.3 | m |
| 18.4 | w |
| 18.7 | w |
| 19.4 | s |

TABLE 26-continued

| Peaks characteristic for Example 213, Form B, methane sulfonic acid salt | |
|---|---|
| °2-theta | Relative intensity |
| 19.7 | s |
| 20.6 | s |
| 20.9 | w |
| 21.3 | m |
| 22.1 | vw |
| 22.7 | m |
| 23.7 | m |
| 24.1 | m |
| 25.1 | s |
| 25.6 | vs |
| 26.3 | m |
| 26.9 | m |
| 27.7 | m |
| 28.2 | m |
| 28.5 | w |
| 29.2 | w |
| 29.7 | s |
| 30.8 | vw |
| 32.3 | w |
| 33.4 | vw |
| 34.3 | vw |
| 35.0 | w |
| 36.9 | vw |
| 37.9 | vw |

Figure 25:
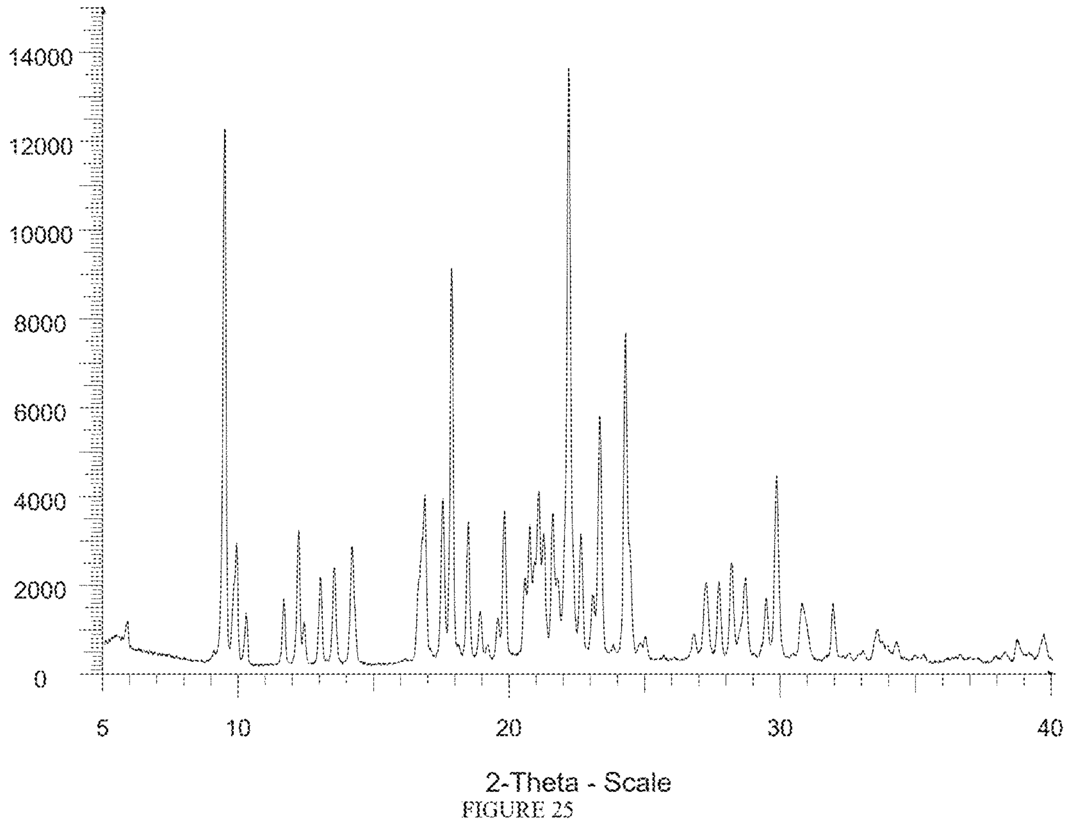
FIG. 25 shows a DSC/TGA thermogram of Example 213, form B, methane sulfonic acid salt: 5-Cyclopropyl-6-(3-methylimidazo[4,5-c]pyridin-7-yl)-3-[[3-methyl-1-(2,2,2-trifluoroethyl)pyrazol-4-yl]amino]pyrazine-2-carboxamide.

197 mg of Example 213 was suspended in 6.0 ml of EtOH. 0.44 ml of 1N methane sulfonic acid aqueous solution was added to the suspension. The slurry was stirred at the room temperature for 1 day. The slurry was heated to 75° C. and stirred at 75° C. for 1 hour. The resulting suspension was cooled down to the room temperature and filtered. The resulting solid is dried at 50° C. in vacuum for 1 hour. 203 mg was obtained. The solid residue was found to be crystalline by XRPD (Form C, methane sulfonic acid salt) and a typical diffractogram is displayed in FIG. 25. Characteristic peak positions are listed below in Tables 27 and 28.

TABLE 27

| Five peaks characteristic for Example 213, Form C, methane sulfonic acid salt | |
|---|---|
| °2-theta | Relative intensity |
| 9.4 | vs |
| 17.8 | s |
| 22.2 | vs |
| 23.4 | s |
| 24.3 | s |

TABLE 28

| Peaks characteristic for Example 213, Form C, methane sulfonic acid salt | |
|---|---|
| °2-theta | Relative intensity |
| 5.8 | vw |
| 9.4 | vs |
| 9.9 | w |
| 10.2 | vw |
| 11.7 | w |
| 12.2 | m |
| 13.0 | w |
| 13.5 | w |
| 14.2 | w |
| 16.8 | m |
| 17.5 | m |
| 17.8 | s |

TABLE 28-continued

| Peaks characteristic for Example 213, Form C, methane sulfonic acid salt | |
|---|---|
| °2-theta | Relative intensity |
| 18.5 | m |
| 18.9 | w |
| 19.8 | m |
| 20.8 | m |
| 21.1 | m |
| 21.6 | m |
| 22.2 | vs |
| 22.6 | m |
| 23.4 | m |
| 24.3 | s |
| 25.0 | vw |
| 26.8 | vw |
| 27.3 | w |
| 27.7 | w |
| 28.2 | w |
| 28.7 | w |
| 29.5 | w |
| 29.9 | m |
| 30.9 | w |
| 32.0 | w |
| 33.0 | vw |
| 33.6 | vw |
| 34.3 | vw |
| 38.3 | vw |
| 38.8 | vw |
| 39.8 | vw |

Figure 26:
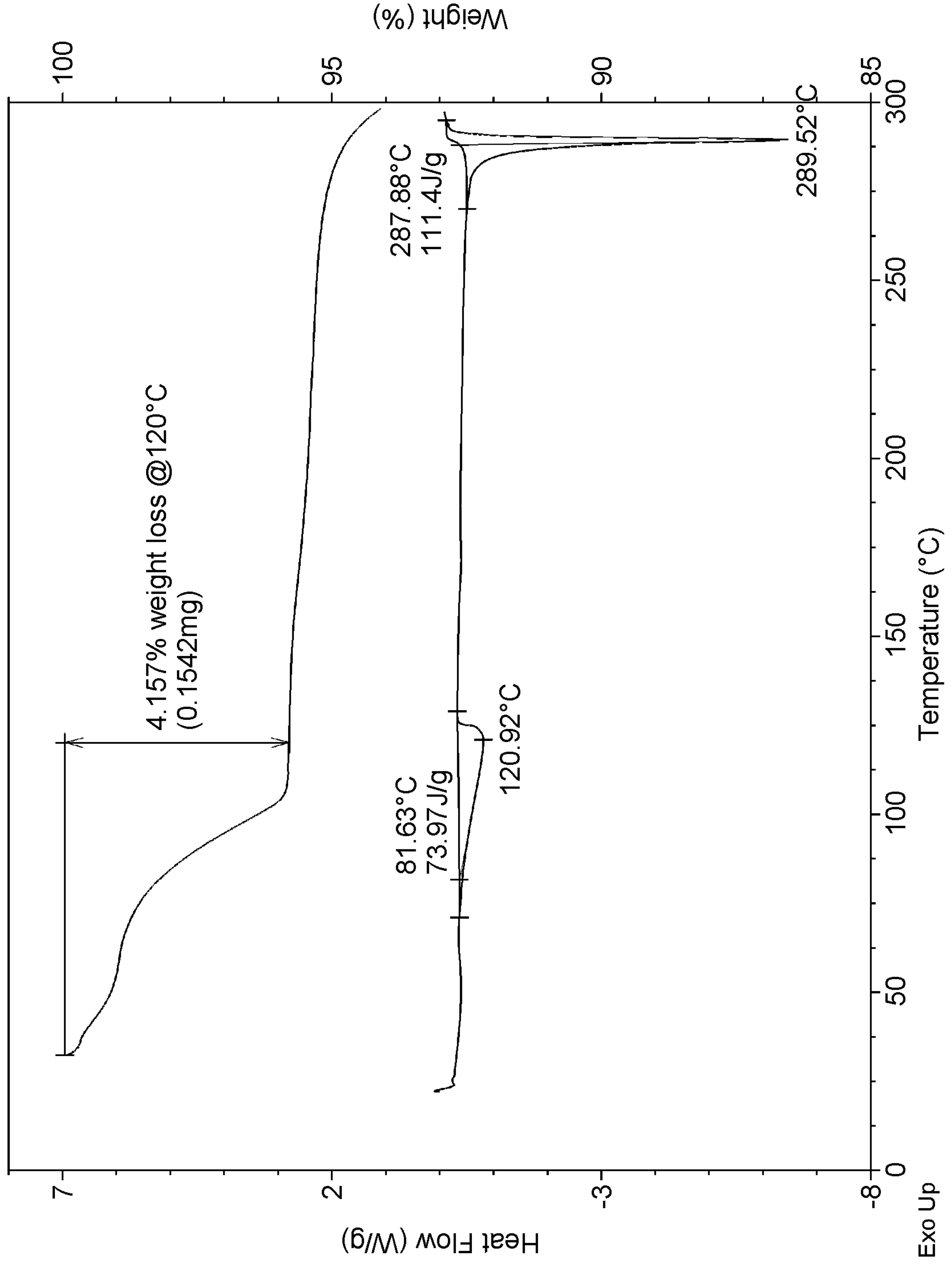
FIG. 26 shows a DSC/TGA thermogram of Example 213, form C, methane sulfonic acid salt: 5-Cyclopropyl-6-(3-methylimidazo[4,5-c]pyridin-7-yl)-3-[[3-methyl-1-(2,2,2-trifluoroethyl)pyrazol-4-yl]amino]pyrazine-2-carboxamide.

Form C, methane sulfonic acid salt was further analyzed by thermal techniques. DSC analysis indicated that Form C, methane sulfonic acid salt starts to de-solvate with an onset at 82° C. and a peak at 121° C. The de-solvated form has a melting/decomposition temperature with an onset at 288° C. and a peak at 290° C. TGA indicated that Form C, methane sulfonic acid salt exhibits a mass loss of about 4.2% upon heating from about 25° C. to about 120° C. A representative DSC/TGA thermogram of Form C, methane sulfonic acid salt is shown in FIG. 26.

Alternative Preparation of methyl 6-chloro-5-cyclopropyl-3-[[3-methyl-1-(2,2,2-trifluoroethyl)pyrazol-4-yl]amino]pyrazine-2-carboxylate a) Ethyl N-(2,2,2-trifluoroethylamino) carbamate Pyridine (116.5 g, 1473 mmol) was added to a mixture of 70 wt % aqueous 2,2,2-trifluoroethylhydrazine (80 g, 490 mmol) in 2-methyltetrahydrofuran (880 mL) at 0° C. DMAP (4.30 g, 24.5 mmol) was added. Ethyl chloroformate (58.6 g, 540 mmol) was added dropwise and the ice bath was removed. The resulting mixture was stirred at room temperature for 20 h. The reaction was then poured into water (200 mL) and stirred at room temperature for 30 min. The layers were separated and the aqueous layer was extracted twice with EtOAc (400 mL each). The combined organics were washed twice with brine (400 mL each), dried over sodium sulfate, filtered, and concentrated. The resulting solid was triturated in ice-cold pentane (450 mL), then filtered, rinsing with ice-cold pentane (50 mL). The resulting filter cake was dried under vacuum at 40° C., to afford ethyl N-(2,2,2-trifluoroethylamino) carbamate (74.9 g, 402 mmol, 82% yield) as a white solid. 1H NMR (400 MHZ, DMSO-d6) δ 1.16 (3H, t), 3.39 (2H, qd), 4.02 (2H, q), 5.33 (1H, q), 8.74 (1H, s).

b) 3-Methyl-1-(2,2,2-trifluoroethyl)pyrazole-4-carboxylic acid

Ethyl 2-(ethoxymethylene)-3-oxo-butanoate (77.7 g, 417 mmol) was added to a solution of ethyl N-(2,2,2-trifluoroethylamino) carbamate (74.0 g, 398 mmol) and AcOH (2.40 g, 39.8 mmol) in EtOH (296 mL). The resulting mixture was stirred at 80° C. for 18 h. 2M aqueous NaOH (596 mL, 1190 mmol) was added dropwise at 80° C. The resulting mixture was stirred at 80° C. for 4 h. The reaction was then cooled to room temperature, diluted with water (1 L), and washed three times with MTBE (500 mL each). The aqueous layer was acidified to pH 3 with 2 M aqueous HCl, then extracted three times with EtOAc (500 mL each). This second batch of combined organics was washed with brine (500 mL), dried over sodium sulfate, filtered, and concentrated. The resulting solid was suspended in heptane (500 mL) and the resulting suspension was stirred at 50° C. for 1 h. This mixture was then stirred at room temperature for 16 h, then filtered. The resulting filter cake was washed with heptane, then dried under vacuum at 40° C., to afford 3-methyl-1-(2,2,2-trifluoroethyl)pyrazole-4-carboxylic acid (68.6 g, 330 mmol, 83% yield) as a beige solid. 1H NMR (400 MHZ, DMSO-d6) δ 2.34 (3H, s), 5.10 (2H, q), 8.27 (1H, s), 12.41 (1H, s). m/z: (ES+), $[M+H]^+$=209.0 c) Benzyl N-[3-methyl-1-(2,2,2-trifluoroethyl)pyrazol-4-yl]carbamate

DPPA (111.6 g, 405.4 mmol) was added to a solution of 3-methyl-1-(2,2,2-trifluoroethyl)pyrazole-4-carboxylic acid and triethylamine (44.0 g, 435 mmol) in toluene (686 mL). The resulting mixture was stirred at room temperature for 3 h. Benzyl alcohol (130.8 g, 1210 mmol) was added and the resulting mixture was stirred at 100° C. for 3 h. The reaction was then allowed to cool to room temperature and quenched with saturated aqueous sodium bicarbonate (1 L). The layers were separated, and the organic layer was washed three times with saturated aqueous sodium bicarbonate (500 mL each). The organic layer was then dried over sodium sulfate, filtered, and concentrated. The resulting solid was stirred in petroleum ether (1 L) for 1 h. The resulting suspension was filtered. The filter cake was washed with petroleum ether (100 mL), then dried under vacuum at 40° C., to afford benzyl N-[3-methyl-1-(2,2,2-trifluoroethyl)pyrazol-4-yl]carbamate (85.6 g, 273 mmol, 83% yield) as a white solid. 1H (400 MHZ, DMSO-d6) δ 2.09 (3H, s), 4.96 (2H, q), 5.12 (2H, s), 7.30-7.43 (5H, m), 7.83 (1H, s), 9.15 (1H, s). m/z: (ES+), $[M+H]^+$=314.1 d) 3-Methyl-1-(2,2,2-trifluoroethyl)pyrazol-4-amine

A mixture of benzyl N-[3-methyl-1-(2,2,2-trifluoroethyl)pyrazol-4-yl]carbamate (85.6 g, 273 mmol) and 20 wt % palladium on carbon (14.5 g, 137 mmol) in MeOH (770 mL) was stirred under a hydrogen atmosphere at room temperature for 16 h. The reaction was then filtered through Celite. The filtrate was concentrated to afford 3-methyl-1-(2,2,2-trifluoroethyl)pyrazol-4-amine (48.4 g, 270 mmol, 99% yield) as a light tan solid. 1H (400 MHz, DMSO-d6) δ 2.01 (3H, s), 3.78 (2H, s), 4.79 (2H, q), 7.03 (1H, s). m/z: (ES+), $[M+H]^+$=180.2 e) Methyl 5-chloro-6-cyclopropyl-2-oxo-1H-pyrazine-3-carboxylate

Sodium nitrite (78.2 g, 1130 mmol) in water (1.3 L) was added dropwise into a solution of methyl 3-amino-6-chloro-5-cyclopropyl-pyrazine-2-carboxylate (129 g, 567 mmol) and 80% aqueous sulfuric acid (1.29 L) in MeCN (1.3 L). The resulting mixture was stirred at room temperature for 1 h. The reaction was then poured into ice water (1.3 L). The resulting slurry was filtered and rinsed three times with water (650 mL each). The resulting filter cake was dried under vacuum at 40° C. to afford methyl 5-chloro-6-cyclopropyl-2-oxo-1H-pyrazine-3-carboxylate (117 g, 512 mmol, 90% yield) as a light yellow solid. 1H (400 MHZ, DMSO-d6) δ 1.08 (2H, dt), 1.19 (2H, dt), 2.42 (1H, tt), 3.84 (3H, s). m/z: (ES+), [M+H]=229.0 f) Methyl 6-chloro-5-cyclopropyl-3-(trifluoromethylsulfonyloxy) pyrazine-2-carboxylate Triflic anhydride (131.7 g, 466.7 mmol) was added dropwise to a solution of methyl 5-chloro-6-cyclopropyl-2-oxo-1H-pyrazine-3-carboxylate (97.0 g, 424 mmol) and DIPEA (109.7 g, 848.5 mmol) at 0° C. in DCM (1.4 L). The resulting mixture was stirred at 0° C. for 30 min. The reaction was then poured into heptane (1.45 L) and stirred at room temperature for 30 min. The resulting slurry was filtered and washed with heptane (500 mL). The filtrate was washed three times with water (700 mL each) and once with brine (700 mL). The organic phase was then dried over sodium sulfate, filtered, and concentrated to afford methyl 6-chloro-5-cyclopropyl-3-(trifluoromethylsulfonyloxy) pyrazine-2-carboxylate (142 g, 88 wt %, 82% yield) as a yellow solid. 1H (400 MHZ, DMSO-d6) δ 1.10-1.03 (2H, m), 1.39 (2H, dq), 2.61 (1H, tt), 3.49 (3H, s). m/z: (ES+), [M+H]=360.9 g) Methyl 6-chloro-5-cyclopropyl-3-[[3-methyl-1-(2 2,2-trifluoroethyl)pyrazol-4-yl]amino]pyrazine-2-carboxylate DIPEA (93.3 g, 722 mmol) was added to a solution of methyl 6-chloro-5-cyclopropyl-3-(trifluoromethylsulfonyloxy) pyrazine-2-carboxylate (86.8 g, 212 mmol (88 wt %)) and 3-methyl-1-(2,2,2-trifluoroethyl)pyrazol-4-amine (47.0 g, 262 mmol) in DMF (1.2 L). The resulting mixture was stirred at 100° C. for 5 h. The reaction was then cooled to room temperature, then poured into water (2.4 L) and stirred for 30 min. The resulting slurry was filtered, and the filter cake was rinsed three times with water (500 mL each). The filter cake was dried under vacuum at 40° C. to afford methyl 6-chloro-5-cyclopropyl-3-[[3-methyl-1-(2,2,2-trifluoroethyl)pyrazol-4-yl]amino]pyrazine-2-carboxylate (90.1 g, 88 wt %, 203 mmol, 96% yield as a light yellow solid. 1H (400 MHZ, DMSO-d6) δ 1.23-1.16 (2H, m), 1.25 (2H, dt), 2.33 (3H, s), 2.58 (1H, tt), 4.01 (3H, s), 4.64 (2H, q), 7.91 (1H, s), 9.82 (1H, s). m/z: (ES+), $[M+H]^+$=390.1

Alternative Preparation of methyl 6-chloro-5-cyclopropyl-3-[[3-methyl-1-(2,2,2-trifluoroethyl)pyrazol-4-yl]amino]pyrazine-2-carboxylate a) tert-Butyl N-[3-methyl-1-(2,2,2-trifluoroethyl) pyrazol-4-yl]carbamate Triethylamine (93.0 mL, 664 mmol) was added to a solution of 3-methyl-1-(2,2,2-trifluoroethyl)pyrazole-4-carboxylic acid (39.5 g, 190 mmol) in toluene (400 mL) and tert-butanol (72.6 mL, 759 mmol). The resulting mixture was stirred at 90° C. for 45 min. A solution of DPPA (42.8 mL, 199 mmol) in toluene (100 mL) was added at 1 mL/min to the reaction mixture at 90° C. Following the addition, the resulting mixture was stirred at 90° C. for 50 min, then at 25° C. for 30 min. The reaction was then quenched with saturated aqueous sodium bicarbonate (400 mL). The layers were then separated and the organic layer was washed once with aqueous sodium bicarbonate (200 mL), once with a mixture of saturated aqueous potassium bisulfate (200 mL) and water (400 mL), and once with 30% brine (20 mL). The organic layer was then dried over sodium sulfate, filtered through Celite, and concentrated to remove 70% of the toluene. The resulting mixture was heated to 60° C., seeded with 10 mg of tert-butyl N-[3-methyl-1-(2,2,2-trifluoroethyl)pyrazol-4-yl]carbamate, and heptane (360 mL) was added dropwise. The resulting suspension was cooled to 20° C. over 1 h, then filtered, rinsing with 3:1 heptane/toluene (160 mL). The resulting filter cake was dried under air for 5 min and then dried under vacuum for 3 d, to afford tert-butyl N-[3-methyl-1-(2,2,2-trifluoroethyl)pyrazol-4-yl]carbamate (31.7 g, 60% yield) as a tan solid. 1H (400 MHZ, DMSO-d6) δ 1.45 (9H, s), 2.08 (3H, s), 4.94 (2H, q), 7.79 (1H, s), 8.72 (1H, s). m/z: (ES+), [M+H]=280.1 b) 3-Methyl-1-(2,2,2-trifluoroethyl)pyrazol-4-amine tosylate 4-methylbenzenesulfonic acid hydrate (25.3 g, 133 mmol) was added to a solution of tert-butyl N-[3-methyl-1-(2,2,2-trifluoroethyl)pyrazol-4-yl]carbamate (31.0 g, 111 mmol) in EtOAc (300 mL). The resulting mixture was stirred at 60° C. for 3 h. Stirring was ceased and the reaction mixture was seeded with 10 mg of 3-methyl-1-(2,2,2-trifluoroethyl)pyrazol-4-amine tosylate and cooled to 20° C. over 5 h, then left to stand at 20° C. for 22 h. The resulting mixture was filtered, rinsing twice with EtOAc (60 mL each). The resulting filter cake was collected, dried under air for 5 min, and dried under vacuum for 18 h, to afford 3-methyl-1-(2,2-trifluoroethyl)pyrazol-4-amine tosylate (33 g, 85% yield) as a white, crystalline solid. 1H (500 MHZ, DMSO-d6) δ 2.19 (3H, s), 2.30 (3H, s), 5.10 (2H, q), 7.14 (2H, d), 7.45-7.58 (2H, m), 7.98 (1H, s), 9.86 (3H, s).

c) Methyl 6-chloro-5-cyclopropyl-3-[[3-methyl-1-(2,2,2-trifluoroethyl)pyrazol-4-yl]amino]pyrazine-2-carboxylate DIPEA (19.9 mL, 114 mmol) was added to a solution of methyl 6-chloro-5-cyclopropyl-3-(trifluoromethylsulfonyloxy) pyrazine-2-carboxylate (14.75 g, 38.04 mmol) and 3-methyl-1-(2,2,2-trifluoroethyl)pyrazol-4-amine tosylate (15.0 g, 41.8 mmol) in IPA (120 mL). The resulting mixture was stirred at 60° C. for 16 h. The reaction was then stirred at 10° C. for 1 h. The resulting suspension was filtered, rinsing twice with IPA (20 mL each), twice with water (40 mL each), and once again with IPA (20 mL). The resulting filter cake was dried under vacuum at 50° C. for 16 h, to afford methyl 6-chloro-5-cyclopropyl-3-[[3-methyl-1-(2,2,2-trifluoroethyl)pyrazol-4-yl]amino]pyrazine-2-carboxylate (11.0 g, 74% yield) as a bright yellow solid. 1H (400 MHZ, DMSO-d6) δ 1.23-1.16 (2H, m), 1.25 (2H, dt), 2.33 (3H, s), 2.58 (1H, tt), 4.01 (3H, s), 4.64 (2H, q), 7.91 (1H, s), 9.82 (1H, s). m/z: (ES+), [M+H]+=390.1

Example 215

5-Cyclopropyl-3-[[1-(2,2-difluoroethyl)-3-methyl-pyrazol-4-yl]amino]-6-(3-methylimidazo[4,5-c]pyridin-7-yl)pyrazine-2-carboxamide

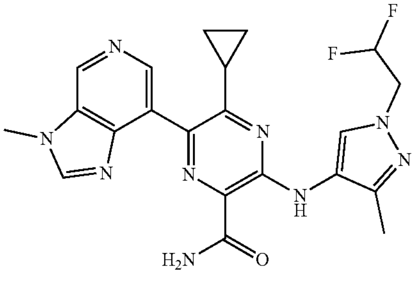 [SMILES: Cc1nn(CC(F)F)cc1Nc1nc(C2CC2)c(-c2cncc3c2ncn3C)nc1C(N)=O]

(a) 1-(2,2-Difluoroethyl)-3-methyl-4-nitro-pyrazole

A mixture of 3-methyl-4-nitro-1H-pyrazole (5.00 g, 39.3 mmol) and cesium carbonate (15.38 g, 47.21 mmol) was suspended in DMF (39.3 mL). 1,1-difluoro-2-iodoethane (9.82 g, 51.1 mmol). The resulting mixture was stirred at 80° C. for 2 hours. The reaction was then allowed to cool to room temperature and diluted with water. The aqueous layer was extracted three times with EtOAc. The combined organic layers were washed three times with 5% aqueous LiCl and once with brine, then dried over sodium sulfate, filtered, and concentrated. The resulting residue was purified by preparative SFC, using a 5 micron, 21 mm×250 mm, ChiralPak IG column, 5% MeOH-s$CO_2$ as eluent, and 0.2% ammonium hydroxide as modifier, to afford 1-(2,2-difluoroethyl)-3-methyl-4-nitro-1H-pyrazole (4.17 g, 55% yield) as a pale yellow oil. 1H NMR (400 MHZ, Chloroform-d): 8 2.55 (3H, s), 4.43 (2H, td), 6.13 (1H, tt), 8.22 (1H, s). 19F NMR (377 MHz, Chloroform-d): δ −122.89. m/z: (ES+), [M+H]+=192.0

(b) 1-(2,2-Difluoroethyl)-3-methyl-pyrazol-4-amine

A mixture of 1-(2,2-difluoroethyl)-3-methyl-4-nitro-1H-pyrazole (4.165 g, 21.79 mmol), 10 wt % palladium on carbon (0.835 g, 0.784 mmol) in MeOH (43.6 mL) was stirred under a hydrogen atmosphere at room temperature for 16 h. The reaction was then filtered through Celite and rinsed with DCM. The resulting filtrate was concentrated to afford 1-(2,2-difluoroethyl)-3-methyl-1H-pyrazol-4-amine (3.40 g, 97% yield) as a dark orange oily solid. 1H NMR (500 MHZ, Chloroform-d): 8 2.16 (3H, s), 2.74 (2H, br s), 4.25 (2H, td), 5.97 (1H, tt), 6.99 (1H, s). 1° F. NMR (471 MHz, $CDCl_3$): δ −122.16. m/z: (ES+), [M+H]+=162.1.

(c) Methyl 6-chloro-5-cyclopropyl-3-[[1-(2,2-difluoroethyl)-3-methyl-pyrazol-4-yl]amino]pyrazine-2-carboxylate DIPEA (5.66 mL, 32.5 mmol) was added to a solution of 1-(2,2-difluoroethyl)-3-methyl-1H-pyrazol-4-amine (2.62 g, 16.3 mmol) and methyl 6-chloro-5-cyclopropyl-3-fluoro-pyrazine-2-carboxylate (2.50 g, 10.8 mmol) in DMF (48.5 mL). The resulting mixture was stirred at 100° C. for 1 hour. The reaction was then concentrated. The resulting residue was purified by silica gel chromatography, using 0 to 5%

MeOH-DCM as eluent, and 0 to 0.1% methanolic ammonia as modifier, to afford methyl 6-chloro-5-cyclopropyl-3-[[1-(2,2-difluoroethyl)-3-methyl-pyrazol-4-yl]amino]pyrazine-2-carboxylate (3.67 g, 91% yield) as a yellow-orange solid. 1H NMR (500 MHz, Chloroform-d): δ 1.17-1.32 (4H, m), 2.32 (3H, s), 2.45-2.61 (1H, m), 4.01 (3H, s), 4.41 (2H, td), 6.06 (1H, tt), 7.87 (1H, s), 9.78 (1H, s). 19F NMR (471 MHz, $CDCl_3$): δ −122.19. m/z: (ES+), [M+H]+=372.3

(d) Methyl 5-cyclopropyl-3-[[1-(2,2-difluoroethyl)-3-methyl-pyrazol-4-yl]amino]-6 (3-methylimidazo[4,5-c]pyridin-7-yl)pyrazine-2-carboxylate 1,4-Dioxane (73.4 mL) and water (7.34 mL) were added to a mixture of methyl 6-chloro-5-cyclopropyl-3-[[1-(2,2-difluoroethyl)-3-methyl-pyrazol-4-yl]amino]pyrazine-2-carboxylate (3.00 g, 8.07 mmol), 2-(3-methylimidazo[4,5-c]pyridin-7-yl)-1,3,6,2-dioxazaborocane (2.48 g, 10.1 mmol), Pd(dppf) C12 dichloromethane adduct (0.659 g, 0.810 mmol), and cesium fluoride (3.68 g, 24.2 mmol). The resulting mixture was evacuated and backfilled three times with nitrogen, then stirred at 80° C. for 1 hour. The reaction was then concentrated. The resulting residue was purified by silica gel chromatography, using 0 to 20% MeOH-DCM as eluent, and 0 to 0.4% methanolic ammonia as modifier. The resulting dark yellow solid was slurried in 5:1 methanol/diethyl ether and stirred at 40° C. for 1 hour. The resulting suspension was then allowed to cool to room temperature, and the solid was collected by filtration and rinsed with diethyl ether. The filtrate was concentrated, and the slurrying/filtration process was repeated twice more. The combined solids were dried under vacuum to afford methyl 5-cyclopropyl-3-[[1-(2,2-difluoroethyl)-3-methyl-pyrazol-4-yl]amino]-6-(3-methylimidazo[4,5-c]pyridin-7-yl)pyrazine-2-carboxylate (2.64 g, 70% yield) as a bright yellow solid. 1H NMR (500 MHZ, DMSO-d6): δ 0.89-0.97 (2H, m), 1.07-1.13 (2H, m), 1.79-1.88 (1H, m), 2.22 (3H, s), 3.88 (3H, s), 3.99 (3H, s), 4.57 (2H, td), 6.32 (1H, tt), 7.99 (1H, s), 8.39 (1H, s), 8.42 (1H, s), 9.05 (1H, s), 9.71 (1H, s). 19F NMR (471 MHz, DMSO-d6): δ −122.68. m/z: (ES+), [M+H]+=469.2.

(e) 5-Cyclopropyl-3-[[1-(2_2-difluoroethyl)-3-methyl-pyrazol-4-yl]amino]-6-(3-methylimidazo[4,5-c]pyridin-7-yl)pyrazine-2-carboxamide 7 N Methanolic ammonia (40 mL, 280 mmol) was added to methyl 5-cyclopropyl-3-[[1-(2,2-difluoroethyl)-3-methyl-pyrazol-4-yl]amino]-6-(3-methylimidazo[4,5-c]pyridin-7-yl)pyrazine-2-carboxylate in a pressure flask. The resulting mixture was stirred at 80° C. for 1 hour. The reaction was then allowed to cool to room temperature. The resulting precipitate was collected by filtration and dried under vacuum to afford 5-cyclopropyl-3-[[1-(2,2-difluoroethyl)-3-methyl-pyrazol-4-yl]amino]-6-(3-methylimidazo[4,5-c]pyridin-7-yl)pyrazine-2-carboxamide (2.378 g, 94% yield) as a yellow solid. 1H NMR (500 MHZ, DMSO-d6): δ 0.81-0.95 (2H, m), 1.04-1.15 (2H, m), 1.84-1.95 (1H, m), 2.21 (3H, s), 3.99 (3H, s), 4.56 (2H, td), 6.32 (1H, tt), 7.79 (1H, br s), 8.00 (1H, s), 8.05 (1H, br s), 8.42 (1H, s), 8.52 (1H, s), 9.03 (1H, s), 10.87 (1H, s). 19F NMR (471 MHz, DMSO-d): δ −122.59. m/z: (ES+), [M+H]+=454.2.

Example 216

3-[[1-(1-Cyano-1-methyl-ethyl)-3-methyl-pyrazol-4-yl]amino]-5-cyclopropyl-6-(3-methylimidazo[4,5-c]pyridin-7-yl)pyrazine-2-carboxamide

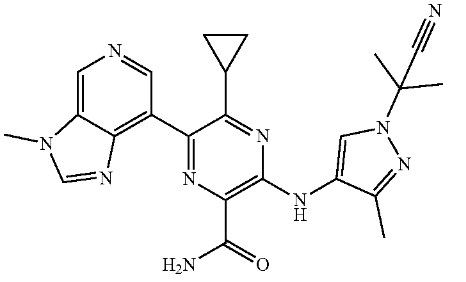 [SMILES: Cc1nn(C(C)(C)C#N)cc1Nc1nc(C2CC2)c(-c2cncc3c2ncn3C)nc1C(N)=O]

(a) Methyl 6-chloro-3-[[1-(1-cyano-1-methyl-ethyl)-3-methyl-pyrazol-4-yl]amino]-5-cyclopropyl-pyrazine-2-carboxylate DIPEA (3.00 mL, 17.3 mmol) was added to a solution of methyl 6-chloro-5-cyclopropyl-3-fluoro-pyrazine-2-carboxylate (2.00 g, 8.67 mmol), 2-(4-amino-3-methyl-pyrazol-1-yl)-2-methyl-propanenitrile (1.57 g, 9.54 mmol) in dioxane (30 mL). The resulting mixture was stirred at 100° C. for 48 hours. The reaction was then, allowed to cool to room temperature, diluted with EtOAc, and filtered. The filter cake was washed with water and dried under vacuum to afford methyl 6-chloro-3-[[1-(1-cyano-1-methyl-ethyl)-3-methyl-pyrazol-4-yl]amino]-5-cyclopropyl-pyrazine-2-carboxylate (2.78 g, 86% yield) as a yellow solid. 1H NMR (500 MHz, DMSO-d6) 1.15 (2H, quin), 1.25 (2H, dq), 1.97 (6H, s), 2.22 (3H, s), 2.46-2.48 (1H, m), 3.92 (3H, s), 8.12 (1H, s), 9.61 (1H, s). m/z: (ES+), [M+H]+=375.1

(b) Methyl 3-[[1-(1-cyano-1-methyl-ethyl)-3-methyl-pyrazol-4-yl]amino]-5-cyclopropyl-6-(3-methylimidazo[4,5-c]pyridin-7-yl)pyrazine-2-carboxylate A mixture of methyl 6-chloro-3-[[1-(1-cyano-1-methyl-ethyl)-3-methyl-pyrazol-4-yl]amino]-5-cyclopropyl-pyrazine-2-carboxylate (2.78 g, 7.42 mmol), 2-(3-methyl-3H-imidazo[4,5-c]pyridin-7-yl)-1,3,6,2-dioxazaborocane (2.56 g, 10.4 mmol), and $PdCl_2$(dppf) dichloromethane adduct (0.606 g, 0.74 mmol) in 1,4-dioxane (30 mL) and water (3 mL) was evacuated and backfilled with nitrogen 3 times. The resulting mixture was stirred at 80° C. for 2 h. The reaction was then concentrated. The resulting residue was purified by silica gel chromatography, using 0 to 15% MeOH-DCM, to afford methyl 3-[[1-(1-cyano-1-methyl-ethyl)-3-methyl-pyrazol-4-yl]amino]-5-cyclopropyl-6-(3-methylimidazo[4,5-c]pyridin-7-yl)pyrazine-2-carboxylate (3.60 g, 98% yield) as a gray solid. 1H NMR (500 MHz, DMSO-d6) 0.97 (2H, dd), 1.11-1.20 (2H, m), 1.80-1.93 (1H, m), 1.98 (6H, s), 2.28 (3H, s), 3.90 (3H, s), 4.01 (3H, s), 8.25 (1H, s), 8.41 (1H, s), 8.44 (1H, s), 9.08 (1H, s), 9.74 (1H, s). m/z: (ES+), [M+H]+=470.2

(c) 3-[[1-(1-Cyano-1-methyl-ethyl)-3-methyl-pyrazol-4-yl]amino]-5-cyclopropyl-6-(3-methylimidazo[4,5-c]pyridin-7-yl)pyrazine-2-carboxamide 7 N Methanolic ammonia (20 mL, 140 mmol) was added to methyl 3-[[1-(1-cyano-1-methyl-ethyl)-3-methyl-pyrazol-4-yl]amino]-5-cyclopropyl-6-(3-methylimidazo[4,5-c]pyridin-7-yl)pyrazine-2-carboxylate (3.44 g, 7.30 mmol). The resulting mixture was stirred at room temperature for 20 hours, then 40° C. for 20 hours, then 60° C. for 5 hours. The reaction was then allowed to cool to room temperature and filtered to afford 3-[[1-(1-cyano-1-methyl-ethyl)-3-methyl-pyrazol-4-yl]amino]-5-cyclopropyl-6-(3-methylimidazo[4,5-c]pyridin-7-yl)pyrazine-2-carboxamide (2.88 g, 86% yield) as a yellow solid. 1H NMR (500 MHZ, DMSO-d6) 0.90-1.01 (2H, m), 1.11-1.21 (2H, m), 1.89-1.94 (1H, m), 1.98 (6H, s), 2.27 (3H, s), 4.01 (3H, s), 7.83 (1H, br s), 8.09 (1H, br s), 8.26 (1H, s), 8.45 (1H, s), 8.54 (1H, s), 9.06 (1H, s), 10.93 (1H, s). m/z: (ES+), [M+H]+=457.0

Example 217

3-[[1-(1-Cyanocyclopropyl)-3-methyl-pyrazol-4-yl]amino]-5-cyclopropyl-6-(3-methylimidazo[4,5-c]pyridin-7-yl)pyrazine-2-carboxamide

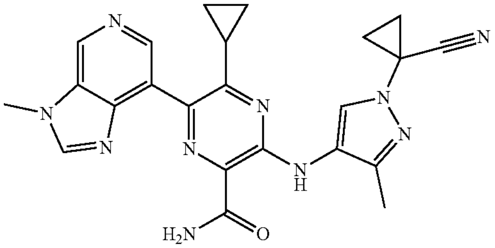 [SMILES: Cc1nn(C2(C#N)CC2)cc1Nc1nc(C2CC2)c(-c2cncc3c2ncn3C)nc1C(N)=O]

(a) Methyl 1-(3-methyl-4-nitro-pyrazol-1-yl) cyclopropanecarboxylate

Potassium carbonate (163 g, 1.18 mol) was added to a solution of 3-methyl-4-nitro-1H-pyrazole (50.0 g, 393 mmol) and methyl 2,4-dibromobutanoate (102 g, 393 mmol) in MeCN (500 mL). The resulting mixture was stirred at 60° C. for 16 hours. The reaction mixture was then filtered through celite. The resulting filtrate was concentrated to afford a 2.5:1 mixture of methyl 1-(3-methyl-4-nitro-pyrazol-1-yl) cyclopropanecarboxylate and methyl 1-(5-methyl-4-nitro-pyrazol-1-yl) cyclopropanecarboxylate (100 g, 56% yield) as a brown oil Methyl 1-(3-methyl-4-nitro-pyrazol-1-yl) cyclopropanecarboxylate: 1H NMR (400 MHZ, DMSO-d6) δ 1.73 (4H, s), 2.42 (3H, s), 3.64 (3H, s), 9.03 (1H, s). m/z: (ES+), [M+H]+=226.1

Methyl 1-(5-methyl-4-nitro-pyrazol-1-yl) cyclopropanecarboxylate: 1H NMR (400 MHZ, DMSO-d6) δ 1.77-1.89 (4H, m), 2.59 (3H, s), 3.67 (3H, s), 8.26 (1H, s). m/z: (ES+), [M+H]+=226.1

(b) 1-(3-Methyl-4-nitro-pyrazol-1-yl) cyclopropanecarboxamide

7 N Methanolic ammonia (500 mL, 3.50 mol) was added to a 2.5:1 mixture of methyl 1-(3-methyl-4-nitro-pyrazol-1-yl) cyclopropanecarboxylate and methyl 1-(5-methyl-4-nitro-pyrazol-1-yl) cyclopropanecarboxylate (50.0 g, 111 mmol). The resulting mixture was stirred at room temperature for 16 hours. The resulting precipitate was filtered, washed with MeOH (50 mL), and dried under vacuum to afford 1-(3-methyl-4-nitro-pyrazol-1-yl) cyclopropanecarboxamide (25 g, 53% yield) as a white solid. 1H NMR (400

MHZ, DMSO-d6) δ 1.43-1.50 (2H, m), 1.50-1.61 (2H, m), 2.42 (3H, s), 6.84 (1H, s), 7.40 (1H, s), 8.96 (1H, s). m/z: (ES+), [M+H]+=211.1

(c) 1-(3-Methyl-4-nitro-pyrazol-1-yl) cyclopropanecarbonitrile (Methoxycarbonylsulfamoyl)triethylammonium hydroxide, inner salt (2.26 g, 9.52 mmol) was added to a solution of 1-(3-methyl-4-nitro-pyrazol-1-yl) cyclopropanecarboxamide (1.00 g, 2.38 mmol) in THF (20 mL). The resulting mixture was stirred at room temperature for 2 hours. The reaction was then concentrated. The resulting residue was redissolved in DCM and washed sequentially with water and brine. The organic layer was dried over sodium sulfate, filtered, and concentrated to afford 1-(3-methyl-4-nitro-pyrazol-1-yl) cyclopropanecarbonitrile (700 mg, 77% yield) as a yellow oil. 1H NMR (400 MHZ, DMSO-d6) δ 1.92 (4H, s), 2.45 (3H, s), 9.15 (1H, s). m/z: (ES+), [M+H]+=193.1

(d) 1-(4-Amino-3-methyl-pyrazol-1-yl) cyclopropanecarbonitrile

Iron powder (1.627 g, 29.14 mmol) was added to a suspension of ammonium chloride (1.56 g, 29.1 mmol) and 1-(3-methyl-4-nitro-pyrazol-1-yl) cyclopropanecarbonitrile (1.40 g, 7.28 mmol) in EtOH (10.00 mL) and water (10.0 mL. The resulting mixture was stirred at 60° C. for 16 hours. The reaction was then concentrated. The resulting residue was purified by silica gel chromatography, using 0 to 10% MeOH-DCM. Pure fractions were evaporated to dryness to afford 1-(4-amino-3-methyl-pyrazol-1-yl) cyclopropanecarbonitrile (1.00 g, 85% yield) as a purple solid. 1H NMR (400 MHZ, DMSO-d6) δ 1.61-1.67 (2H, m), 1.68-1.75 (2H, m), 2.01 (3H, s), 3.89 (2H, s), 7.07 (1H, s). m/z: (ES+), [M+H]+=163.3

(e) Methyl 6-chloro-3-[[1-(1-cyanocyclopropyl)-3-methyl-pyrazol-4-yl]amino]-5-cyclopropyl-pyrazine-2-carboxylate DIPEA (2.16 mL, 12.4 mmol) was added to a solution of methyl 6-chloro-5-cyclopropyl-3-fluoro-pyrazine-2-carboxylate (0.950 g, 4.12 mmol) and 1-(4-amino-3-methyl-pyrazol-1-yl) cyclopropanecarbonitrile (0.724 g, 4.46 mmol) in DMF (25 mL). The resulting mixture was stirred at 100° C. for 5 hours. The reaction was then concentrated. The resulting residue was triturated in EtOAc and water, then filtered. The resulting solid was collected by filtration and dried under vacuum. The organic layer from the filtrate was dried over magnesium sulfate, filtered, and concentrated. The solids were combined to afford methyl 6-chloro-3-[[1-(1-cyanocyclopropyl)-3-methyl-pyrazol-4-yl]amino]-5-cyclopropyl-pyrazine-2-carboxylate (1.472 g, 96% yield) as a yellow solid. 1H NMR (500 MHZ, DMSO-d6) 1.13 (2H, quin), 1.22-1.27 (2H, m), 1.73-1.78 (2H, m), 1.86-1.91 (2H, m), 2.17 (3H, s), 2.44-2.47 (1H, m), 3.90 (3H, s), 7.98 (1H, s), 9.57 (1H, s). m/z: (ES+), [M+H]+=373.1

(f) Methyl 3-[[1-(1-cyanocyclopropyl)-3-methyl-pyrazol-4-yl]amino]-5-cyclopropyl-6-(3-methylimidazo[4,5-c]pyridin-7-yl)pyrazine-2-carboxylate A mixture of methyl 6-chloro-3-[[1-(1-cyanocyclopropyl)-3-methyl-pyrazol-4-yl]amino]-5-cyclopropyl-pyrazine-2-carboxylate (0.570 g, 1.53 mmol), 2-(3-methyl-3H-imidazo[4,5-c]pyridin-7-yl)-1,3,6,2-dioxazaborocane (0.477 g, 1.95 mmol), $PdCl_2$(dppf) (0.129 g, 0.180 mmol), and cesium fluoride (0.697 g, 4.59 mmol) in 1,4-dioxane (8 mL) and water (0.800 mL) was degassed and purged with nitrogen three times. The resulting mixture was heated at 80° C. for 2 hours. The reaction was then concentrated. The resulting residue was purified by silica gel chromatography, using 0 to 10% MeOH-DCM as eluent and 0.2% $NH_4OH$ as modifier, to afford methyl 3-[[1-(1-cyanocyclopropyl)-3-methyl-pyrazol-4-yl]amino]-5-cyclopropyl-6-(3-methylimidazo[4,5-c]pyridin-7-yl)pyrazine-2-carboxylate (0.684 g, 95% yield) as a yellow solid. m/z: (ES+), [M+H]+=470.0

(g) 3-[[1-(1-Cyanocyclopropyl)-3-methyl-pyrazol-4-yl]amino]-5-cyclopropyl-6-(3-methylimidazo[4,5-c]pyridin-7-yl)pyrazine-2-carboxamide 7 N Methanolic ammonia (30 mL, 210 mmol) was added to methyl 3-[[1-(1-cyanocyclopropyl)-3-methyl-pyrazol-4-yl]amino]-5-cyclopropyl-6-(3-methylimidazo[4,5-c]pyridin-7-yl)pyrazine-2-carboxylate (1.85 g, 3.95 mmol). The resulting mixture was stirred at room temperature for 19 hours, then 40° C. for 6 hours, then at room temperature for 2 days. The reaction was then concentrated. The resulting residue was washed with 50% EtOAc in hexanes and dried under vacuum. The resulting material was purified by silica gel chromatography, using 0 to 6% MeOH-DCM as eluent, and 0.2% ammonium hydroxide as modifier, to afford 3-[[1-(1-cyanocyclopropyl)-3-methyl-pyrazol-4-yl]amino]-5-cyclopropyl-6-(3-methylimidazo[4,5-c]pyridin-7-yl)pyrazine-2-carboxamide (1.14 g, 63% yield) as a yellow solid. 1H NMR (500 MHZ, DMSO-d6) 0.92-1.01 (2H, m), 1.11-1.20 (2H, m), 1.78-1.83 (2H, m), 1.87-1.96 (3H, m), 2.24 (3H, s), 4.01 (3H, s), 7.84 (1H, br s), 8.10 (1H, br s), 8.11 (1H, s), 8.45 (1H, s), 8.54 (1H, s), 9.06 (1H, s), 10.93 (1H, s). m/z: (ES+), [M+H]+=455.0

Example 218

5-Cyclopropyl-3-[(1,5-dimethylpyrazol-4-yl)amino]-6-(3-methylimidazo[4,5-c]pyridin-7-yl)pyrazine-2-carboxamide

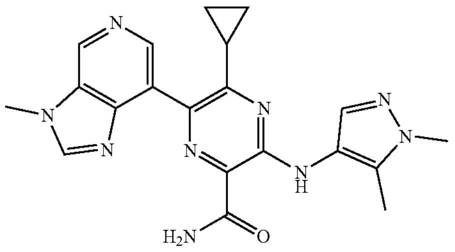

(a) Methyl 6-chloro-5-cyclopropyl-3_ [(1,5-dimethylpyrazol-4-yl)amino]pyrazine-2-carboxylate DIPEA (0.379 mL, 2.17 mmol) was added to a solution of methyl 6-chloro-5-cyclopropyl-3-fluoro-pyrazine-2-carboxylate (0.10 g, 0.43 mmol), and 1,5-dimethylpyrazol-4-amine dihydrochloride (0.160 g, 0.87 mmol) in DMF (3.0 mL). The resulting mixture was stirred at 80° C. for 2 hours. The reaction was then diluted with DCM and water. The layers were separated and the aqueous layer was extracted with DCM. The combined organic layers were dried over magnesium sulfate, filtered, and concentrated to afford methyl 6-chloro-5-cyclopropyl-3-[(1,5-dimethylpyrazol-4-yl)amino]pyrazine-2-carboxylate as a yellow solid. 1H NMR (500 MHz, DMSO-d6) δ 0.93-1.01 (2H, m), 1.12-1.18 (2H, m), 2.16 (3H, s), 2.38-2.43 (1H, m), 3.72 (3H, s), 3.88 (3H, s), 7.52 (1H, s), 9.33 (1H, s). m/z: (ES−), [M−H]−= 320.1

(b) 6-Chloro-5-cyclopropyl-3-[(1_5-dimethylpyrazol-4-yl)amino]pyrazine-2-carboxamide 7 N Methanolic ammonia (4.0 mL, 28 mmol) was added to methyl 6-chloro-5-cyclopropyl-3-[(1,5-dimethylpyrazol-4-yl)amino]pyrazine-2-carboxylate (0.138 g, 0.430 mmol). The resulting mixture was stirred at 80° C. for 2 hours. The reaction was then concentrated to afford 6-chloro-5-cyclopropyl-3-[(1,5-dimethylpyrazol-4-yl)amino]pyrazine-2-carboxamide (0.132 g, quantitative) as a yellow solid. 1H NMR (500 MHz, DMSO-d6) δ 0.96-1.05 (2H, m), 1.09-1.19 (2H, m), 2.17 (3H, s), 2.37-2.43 (1H, m), 3.71 (3H, s), 7.58 (1H, s), 7.82 (1H, s), 8.07 (1H, s), 10.50 (1H, s). m/z: (ES+), [M+H]+=306.8

(c) 5-Cyclopropyl-3-[(1,5-dimethylpyrazol-4-yl)amino]-6-(3-methylimidazo[4,5-c]pyridin-7-yl)pyrazine-2-carboxamide A mixture of 6-chloro-5-cyclopropyl-3-[(1,5-dimethylpyrazol-4-yl)amino]pyrazine-2-carboxamide (0.132 g, 0.430 mmol), 2-(3-methyl-3H-imidazo[4,5-c]pyridin-7-yl)-1,3,6,2-dioxazaborocane (0.158 g, 0.65 mmol), and $PdCl_2$(dppf) (0.063 g, 0.090 mmol) in 2 M aqueous potassium phosphate (0.645 mL, 1.29 mmol) and 1,4-dioxane (3.0 mL) was degassed and purged with nitrogen. The resulting mixture was stirred at 80° C. for 2 hours. The reaction was then concentrated. The resulting residue was triturated in water, then dried under vacuum. The resulting solid was purified by silica gel chromatography, using 0 to 10% MeOH-DCM as eluent. The resulting material was further purified by reverse phase C18 chromatography, using 0 to 25% MeCN-water as eluent, and 0.1% formic acid as modifier, to afford 5-cyclopropyl-3-[(1,5-dimethylpyrazol-4-yl)amino]-6-(3-methylimidazo[4,5-c]pyridin-7-yl)pyrazine-2-carboxamide (0.098 g, 57% yield) as a yellow solid. 1H NMR (500 MHZ, DMSO-d6) δ 0.82-0.92 (2H, m), 0.95-1.06 (2H, m), 1.83-1.90 (1H, m), 2.23 (3H, s), 3.74 (3H, s), 3.98 (3H, s), 7.70 (1H, s), 7.74 (1H, br s), 8.00 (1H, br s), 8.42 (1H, s), 8.50 (1H, s), 9.02 (1H, s), 10.59 (1H, s). m/z: (ES+), [M+H]+= 403.9

Example 219

5-Cyclopropyl-6-(3-methylimidazo[4,5-c]pyridin-7-yl)-3-[(3-methyl-1H-pyrazol-4-yl)amino]pyrazine-2-carboxamide

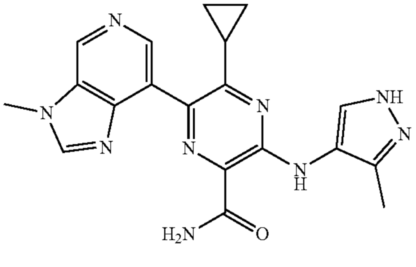 [SMILES: Cc1n[nH]cc1Nc1nc(C2CC2)c(-c2cncc3c2ncn3C)nc1C(N)=O]

(a) Methyl 3-[(1-tert-butoxycarbonyl-3-methyl-pyrazol-4-yl)amino]-6-chloro-5-cyclopropyl-pyrazine-2-carboxylate DIPEA (3.40 mL, 19.5 mmol) was added to a solution of methyl 6-chloro-5-cyclopropyl-3-fluoro-pyrazine-2-carboxylate (1.50 g, 6.50 mmol) and tert-butyl 4-amino-3-methyl-pyrazole-1-carboxylate (1.92 g, 9.76 mmol) in DMF (18.3 mL). The resulting mixture was stirred at 60° C. for 16 hours. The reaction mixture was then concentrated. The resulting residue was purified by silica gel chromatography, using 0 to 5% MeOH-DCM as eluent, and 0 to 0.1% methanolic ammonia as modifier, to afford methyl 3-[(1-tert-butoxycarbonyl-3-methyl-pyrazol-4-yl)amino]-6-chloro-5-cyclopropyl-pyrazine-2-carboxylate (2.207 g, 83% yield) as a dark orange foam. 1H NMR (500 MHz, Chloroform-d): δ 1.26-1.33 (4H, m), 1.66 (9H, s), 2.40 (3H, s), 2.54-2.63 (1H, m), 4.00 (3H, s), 8.43 (1H, s), 9.92 (1H, s). m/z: (ES+), [M+H]+=408.1

(b) Methyl 3-[(1-tert-butoxycarbonyl-3-methyl-pyrazol-4-yl)amino]-5-cyclopropyl-6 (3-methylimidazo[4,5-c]pyridin-7-yl)pyrazine-2-carboxylate A mixture of methyl 3-[(1-tert-butoxycarbonyl-3-methyl-pyrazol-4-yl)amino]-6-chloro-5-cyclopropyl-pyrazine-2-carboxylate (2.21 g, 5.41 mmol) was charged with 2-(3-methyl-3H-imidazo[4,5-c]pyridin-7-yl)-1,3,6,2-dioxazaborocane (1.47 g, 5.95 mmol), Pd(dppf) C12 dichloromethane adduct (0.442 g, 0.540 mmol), and cesium fluoride (2.466 g, 16.23 mmol) was evacuated and backfilled three times with nitrogen. 1,4-Dioxane (19.7 mL) and water (2.0 mL) were added. The resulting mixture was evacuated and backfilled three times with nitrogen, then stirred at 80° C. for 2 hours. The reaction was then concentrated. The resulting residue was purified by silica gel chromatography, using 0 to 10% MeOH-DCM as eluent, and 0 to 0.2% methanolic ammonia as modifier, to afford methyl 3-[(1-tert-butoxycarbonyl-3-methyl-pyrazol-4-yl)amino]-5-cyclopropyl-6-(3-methylimidazo[4,5-c]pyridin-7-yl)pyrazine-2-carboxylate (1.513 g, 55% yield) as a dark yellow-orange foam. 1H NMR (500 MHZ, Chloroform-d): δ 1.02-1.09 (2H, m), 1.35-1.40 (2H, m), 1.67 (9H, s), 1.96-2.10 (1H, m), 2.45 (3H, s), 3.98 (3H, s), 4.01 (3H, s), 8.01 (1H, s), 8.59 (1H, s), 8.68 (1H, s), 8.92 (1H, s), 10.09 (1H, s). m/z: (ES+), [M+H]+=505.3

(c) 5-Cyclopropyl-6-(3-methylimidazo[4,5-c]pyridin-7-yl)-3-[(3-methyl-1H-pyrazol-4-yl)amino]pyrazine-2-carboxamide 7 N Methanolic ammonia (13 mL, 91 mmol) was added to methyl 3-[(1-tert-butoxycarbonyl-3-methyl-pyrazol-4-yl)amino]-5-cyclopropyl-6-(3-methylimidazo[4,5-c]pyridin-7-yl)pyrazine-2-carboxylate (1.513 g, 3.000 mmol). The resulting mixture was stirred at 100° C. for 2 hours in a pressure flask. The reaction was then concentrated. The resulting residue was purified by silica gel chromatography, using 0 to 40% MeOH-DCM as eluent, and 0 to 0.4% methanolic ammonia as modifier. The resulting material was suspended in MeOH/diethyl ether and stirred at 40° C. for 4 hours. The resulting slurry was allowed to cool to room temperature, then filtered, rinsed with diethyl ether, and dried under vacuum to afford 5-cyclopropyl-6-(3-methylimidazo[4,5-c]pyridin-7-yl)-3-[(3-methyl-1H-pyrazol-4-yl)amino]pyrazine-2-carboxamide (0.647 g, 51% yield) as a yellow solid. The compound exists as a 2:1 mixture of pyrazole tautomers. 1H NMR (500 MHZ, DMSO-d6): δ 0.80-0.97 (2H, m), 0.97-1.12 (2H, m), 1.80-1.94 (1H, m), 2.21 (3H, s), 3.98 (3H, s), 7.69-7.96 (2H, m), 8.02 (1H, br s), 8.42 (1H, s), 8.51 (1H, s), 9.02 (1H, s), 10.45-10.94 (1H, m), 12.17-12.54 (1H, m). m/z: (ES+), [M+H]+=390.1

Examples 220-223

5-Cyclopropyl-6-(3-methylimidazo[4,5-c]pyridin-7-yl)-3-[[3-methyl-1-[rel-(2R)-2,3-difluoropropyl]pyrazol-4-yl]amino]pyrazine-2-carboxamide, 5-cyclopropyl-6-(3-methylimidazo[4,5-c]pyridin-7-yl)-3-[[3-methyl-1-[rel-(2S)-2,3-difluoropropyl]pyrazol-4-yl]amino]pyrazine-2-carboxamide, 5-cyclopropyl-6-(3-methylimidazo[4,5-c]pyridin-7-yl)-3-[[5-methyl-1-[rel-(2R)-2,3-difluoropropyl]pyrazol-4-yl]amino]pyrazine-2-carboxamide, and 5-cyclopropyl-6-(3-methylimidazo[4,5-c]pyridin-7-yl)-3-[[5-methyl-1-[rel-(2S)-2,3-difluoropropyl]pyrazol-4-yl]amino]pyrazine-2-carboxamide

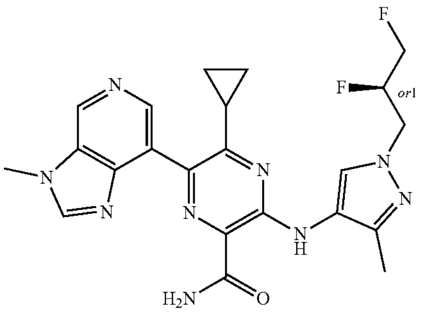

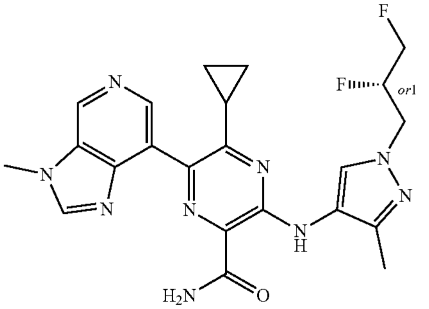

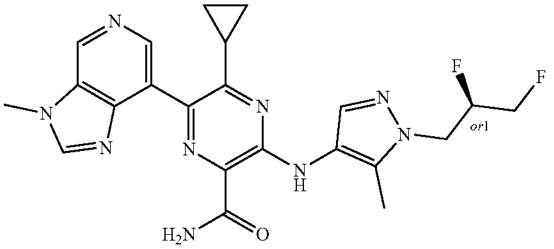

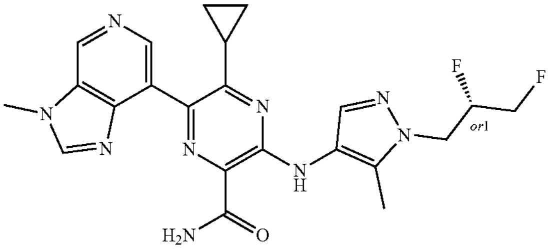

(a) 2,3-Difluoropropyl 4-methylbenzenesulfonate

4-Methylbenzenesulfonyl chloride (149 mg, 0.780 mmol) was added to a solution of 2,3-difluoropropan-1-ol (50 mg, 0.52 mmol), and triethylamine (107 μL, 0.780 mmol) in DCM (2.5 mL). The resulting mixture was stirred at room temperature for 3 hours. The reaction was then quenched with saturated aqueous ammonium chloride (3 mL). The layers were separated and the aqueous layer was extracted three times with DCM (3 mL each). The combined organic layers were dried over sodium sulfate, filtered, and concentrated. The resulting residue was carried forward assuming 100% yield. m/z: (ES+), [M+H]+=251.0

(b) 5-Cyclopropyl-6-(3-methylimidazo[4,5-c]pyridin-7-yl)-3_ [[3-methyl-1-[rel-(2R)-2,3-difluoropropyl]pyrazol-4-yl]amino]pyrazine-2-carboxamide, 5-cyclopropyl-6-(3-methylimidazo[4,5-c]pyridin-7-yl)-3-[[3-methyl-1-[rel-(2S)-2 3-difluoropropyl]pyrazol-4-yl]amino]pyrazine-2-carboxamide, 5-cyclopropyl-6-(3-methylimidazo[4,5-c]pyridin-7-yl)-3-[[5-methyl-1-[rel-(2R)-2,3-difluoropropyl]pyrazol-4-yl]amino]pyrazine-2-carboxamide, and 5-cyclopropyl-6-(3-methylimidazo[4,5-c]pyridin-7-yl)-3-[[5-methyl-1-[rel-(2S)-2,3-difluoropropyl]pyrazol-4-yl]amino]pyrazine-2-carboxamide Cesium carbonate (335 mg, 1.03 mmol) was added to a mixture of 5-cyclopropyl-6-(3-methylimidazo[4,5-c]pyridin-7-yl)-3-[(3-methyl-1H-pyrazol-4-yl)amino]pyrazine-2-carboxamide (100 mg, 0.26 mmol) and 2,3-difluoropropyl 4-methylbenzenesulfonate (129 mg, 0.510 mmol) in DMSO (0.856 mL). The resulting mixture was stirred at 100° C. for 1.5 hours. The reaction was then allowed to cool to room temperature and concentrated. The resulting residue was purified by reverse phase C18 chromatography, using 0 to 40% MeCN-water as eluent, and 0.1% formic acid as modifier. The resulting material was further purified by preparative SFC, using a 5 micron, 4.6 mm×100 mm, ChiralPak IG column, using isocratic 45% MeOH-s$CO_2$ as eluent, and 0.2% ammonium hydroxide as modifier, to afford three portions of material: 5-cyclopropyl-6-(3-methylimidazo[4,5-c]pyridin-7-yl)-3-[[5-methyl-1-[rel-(2R)-2,3-difluoropropyl]pyrazol-4-yl]amino]pyrazine-2-carboxamide (14.3 mg, 12% yield) as a yellow solid, 5-cyclopropyl-6-(3-methylimidazo[4,5-c]pyridin-7-yl)-3-[[5-methyl-1-[rel-(2S)-2,3-difluoropropyl]pyrazol-4-yl]amino]pyrazine-2-carboxamide (14.6%, 12% yield) as a yellow solid, and a yellow solid. This latter material was further purified by preparative SFC, using a 3 micron, 4.6 mm×100 mm, ChiralPak IA column, using isocratic 20% MeOH-s$CO_2$ as eluent, and 0.2% ammonium hydroxide as modifier, to afford 5-cyclopropyl-6-(3-methylimidazo[4,5-c]pyridin-7-yl)-3-[[3-methyl-1-[rel-(2R)-2,3-difluoropropyl]pyrazol-4-yl]amino]pyrazine-2-carboxamide (16.1 mg, 13% yield) as a yellow solid and 5-cyclopropyl-6-(3-methylimidazo[4,5-c]pyridin-7-yl)-3-[[3-methyl-1-[rel-(2S)-2,3-difluoropropyl]pyrazol-4-yl]amino]pyrazine-2-carboxamide (16.5 mg, 14% yield) as yellow solid.

5-Cyclopropyl-6-(3-methylimidazo[4,5-c]pyridin-7-yl)-3-[[3-methyl-1-[rel-(2R)-2,3-difluoropropyl]pyrazol-4-yl]amino]pyrazine-2-carboxamide. 1H NMR (500 MHz, DMSO-d6) 1H NMR (500 MHz, DMSO-d6) 0.80-0.97 (2H, m), 1.00-1.18 (2H, m), 1.77-1.95 (1H, m), 2.20 (3H, s), 3.99 (3H, s), 4.28-4.85 (4H, m), 4.93-5.23 (1H, m), 7.80 (1H, br s), 7.97 (1H, s), 8.06 (1H, br s), 8.43 (1H, s), 8.52 (1H, s), 9.03 (1H, s), 10.86 (1H, s). m/z: (ES+), [M+H]+=468.0

5-Cyclopropyl-6-(3-methylimidazo[4,5-c]pyridin-7-yl)-3-[[3-methyl-1-[rel-(2S)-2,3-difluoropropyl]pyrazol-4-yl]amino]pyrazine-2-carboxamide. 1H NMR (500 MHZ, DMSO-d6) 0.80-0.97 (2H, m), 1.06-1.16 (2H, m), 1.82-1.93 (1H, m), 2.20 (3H, s), 3.98 (3H, s), 4.31-4.86 (4H, m), 4.93-5.25 (1H, m), 7.80 (1H, br s), 7.97 (1H, s), 8.06 (1H, br s), 8.43 (1H, s), 8.52 (1H, s), 9.03 (1H, s), 10.85 (1H, s). m/z: (ES+), [M+H]+=468.0

5-Cyclopropyl-6-(3-methylimidazo[4,5-c]pyridin-7-yl)-3-[[5-methyl-1-[rel-(2R)-2,3-difluoropropyl]pyrazol-4-yl]amino]pyrazine-2-carboxamide. 1H NMR (500 MHZ, DMSO-d6) 0.79-0.93 (2H, m), 0.93-1.05 (2H, m), 1.80-1.92 (1H, m), 2.24 (3H, s), 3.98 (3H, s), 4.34-4.88 (4H, m), 4.99-5.24 (1H, m), 7.78 (1H, br s), 7.81 (1H, s), 8.04 (1H, br s), 8.43 (1H, s), 8.50 (1H, s), 9.03 (1H, s), 10.60 (1H, s). m/z: (ES+), [M+H]+=468.0

5-Cyclopropyl-6-(3-methylimidazo[4,5-c]pyridin-7-yl)-3-[[5-methyl-1-[rel-(2S)-2,3-difluoropropyl]pyrazol-4-yl]amino]pyrazine-2-carboxamide. 1H NMR (500 MHZ, DMSO-d6) 0.76-0.93 (2H, m), 0.93-1.06 (2H, m), 1.79-1.92 (1H, m), 2.24 (3H, s), 3.98 (3H, s), 4.32-4.87 (4H, m), 4.98-5.24 (1H, m), 7.78 (1H, br s), 7.81 (1H, s), 8.04 (1H, br s), 8.43 (1H, s), 8.50 (1H, s), 9.03 (1H, s), 10.60 (1H, s). m/z: (ES+), [M+H]+=468.0

Example 224 and 225

5-Cyclopropyl-6-(3-methylimidazo[4,5-c]pyridin-7-yl)-3-[[3-methyl-1-(oxetan-3-yl)pyrazol-4-yl]amino]pyrazine-2-carboxamide and 5-cyclopropyl-6-(3-methylimidazo[4,5-c]pyridin-7-yl)-3-[[5-methyl-1-(oxetan-3-yl)pyrazol-4-yl]amino]pyrazine-2-carboxamide

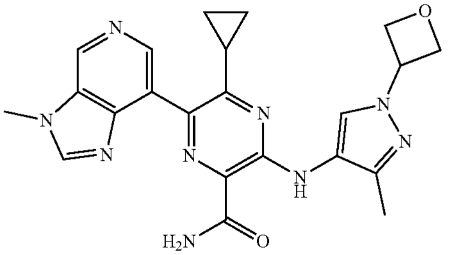

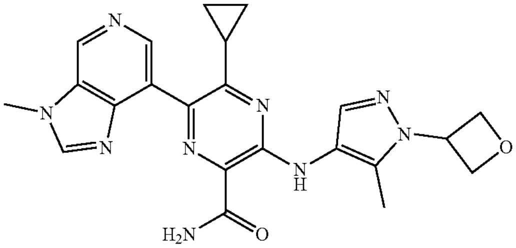

3-Iodooxetane (132 μL, 1.50 mmol) was added to a suspension of 5-cyclopropyl-6-(3-methylimidazo[4,5-c]pyridin-7-yl)-3-[(3-methyl-1H-pyrazol-4-yl)amino]pyrazine-2-carboxamide (168 mg, 0.430 mmol) and cesium carbonate (421 mg, 1.30 mmol) in DMSO (2 mL). The resulting mixture was stirred at 100° C. for 1 hour. The reaction mixture was directly purified by reverse phase C18 chromatography, using 0 to 100% MeCN/water as eluent, and 0.2% ammonium hydroxide as modifier, to afford a yellow film (128 mg). This material was further purified by preparative SFC, using a 5 micron, 21 mm×250 mm, OJ-H column, isocratic 25% MeOH-s$CO_2$ as eluent, and 0.2% ammonium hydroxide as modifier, to afford 5-cyclopropyl-6-(3-methylimidazo[4,5-c]pyridin-7-yl)-3-[[3-methyl-1-(oxetan-3-yl)pyrazol-4-yl]amino]pyrazine-2-carboxamide (55 mg, 64% yield) as a yellow solid and 5-cyclopropyl-6-(3-methylimidazo[4,5-c]pyridin-7-yl)-3-[[5-methyl-1-(oxetan-3-yl)pyrazol-4-yl]amino]pyrazine-2-carboxamide (27 mg, 32% yield) as a yellow solid.

5-Cyclopropyl-6-(3-methylimidazo[4,5-c]pyridin-7-yl)-3-[[3-methyl-1-(oxetan-3-yl)pyrazol-4-yl]amino]pyrazine-2-carboxamide: 1H NMR (500 MHZ, DMSO-d6): δ 0.86-0.96 (2H, m), 1.06-1.16 (2H, m), 1.86-1.94 (1H, m), 2.25 (3H, s), 3.99 (3H, s), 4.86 (2H, br t), 4.89-4.97 (2H, m), 5.40-5.56 (1H, m), 7.79 (1H, br s), 8.05 (1H, br s), 8.08 (1H, s), 8.42 (1H, s), 8.52 (1H, d), 9.03 (1H, d), 10.89 (1H, s). m/z: (ES+), [M+H]+=446.2

5-Cyclopropyl-6-(3-methylimidazo[4,5-c]pyridin-7-yl)-3-[[5-methyl-1-(oxetan-3-yl)pyrazol-4-yl]amino]pyrazine-2-carboxamide: 1H NMR (500 MHZ, DMSO-d6): δ 0.82-0.94 (2H, m), 1.03 (2H, dt), 1.81-1.94 (1H, m), 2.21 (3H, s), 3.98 (3H, s), 4.83-4.92 (2H, m), 4.92-4.99 (2H, m), 5.58 (1H, quin), 7.75 (1H, br s), 7.95 (1H, s), 8.02 (1H, br s), 8.42 (1H, s), 8.51 (1H, s), 9.03 (1H, s), 10.65 (1H, s). m/z: (ES+), [M+H]+=446.2

Example 226

5-Cyclopropyl-3-[[1-(2,2-difluoroethyl)-5-methyl-pyrazol-4-yl]amino]-6-(3-methylimidazo[4,5-c]pyridin-7-yl)pyrazine-2-carboxamide

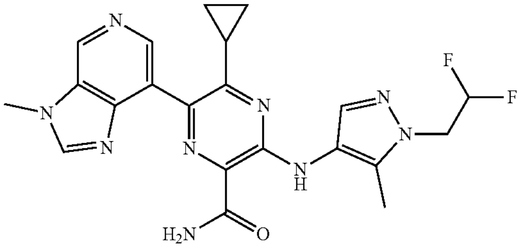 [SMILES: Cc1c(Nc2nc(C3CC3)c(-c3cncc4c3ncn4C)nc2C(N)=O)cnn1CC(F)F]

1,1-Difluoro-2-iodo-ethane (38 μL, 0.44 mmol) was added to a suspension of 5-cyclopropyl-6-(3-methylimidazo[4,5-c]pyridin-7-yl)-3-[(3-methyl-1H-pyrazol-4-yl)amino]pyrazine-2-carboxamide (85 mg, 0.22 mmol and cesium carbonate (213 mg, 0.650 mmol) in DMSO (1 mL). The resulting mixture was stirred at 100° C. for 1 hour. The reaction mixture was purified directly by reverse phase C18 chromatography, using 0 to 100% MeCN-water as eluent, and 0.2% ammonium hydroxide as modifier, to afford a yellow solid (88 mg). This material was further purified by preparative SFC, using a 5 micron, 21 mm×250 mm, IB column, isocratic 35% MeOH-s$CO_2$ as eluent, and 0.2% $NH_4OH$ as modifier, to afford 5-cyclopropyl-3-[[1-(2,2-difluoroethyl)-3-methyl-pyrazol-4-yl]amino]-6-(3-methylimidazo[4,5-c]pyridin-7-yl)pyrazine-2-carboxamide (48 mg, 49% yield) and 5-cyclopropyl-3-[[1-(2,2-difluoroethyl)-5-methyl-pyrazol-4-yl]amino]-6-(3-methylimidazo[4,5-c]pyridin-7-yl)pyrazine-2-carboxamide (23 mg, 23% yield) as yellow solids.

5-Cyclopropyl-3-[[1-(2,2-difluoroethyl)-5-methyl-pyrazol-4-yl]amino]-6-(3-methylimidazo[4,5-c]pyridin-7-yl)pyrazine-2-carboxamide: 1H NMR (500 MHz, DMSO-d6):

δ 0.76-0.94 (2H, m), 0.94-1.12 (2H, m), 1.78-1.96 (1H, m), 2.26 (3H, s), 3.98 (3H, s), 4.57 (2H, td), 6.34 (1H, tt), 7.76 (1H, br s), 7.83 (1H, s), 8.02 (1H, br s), 8.42 (1H, s), 8.51 (1H, s), 9.03 (1H, s), 10.60 (1H, s). 19F NMR (471 MHz, DMSO-d6): δ −122.12. m/z: (ES+), [M+H]+=454.2

Examples 227 and 228

5-Cyclopropyl-3-[[1-(3,3-difluoropropyl)-3-methyl-pyrazol-4-yl]amino]-6-(3-methylimidazo[4,5-c]pyridin-7-yl)pyrazine-2-carboxamide and 5-cyclopropyl-3-[[1-(3,3-difluoropropyl)-5-methyl-pyrazol-4-yl]amino]-6-(3-methylimidazo[4,5-c]pyridin-7-yl)pyrazine-2-carboxamide

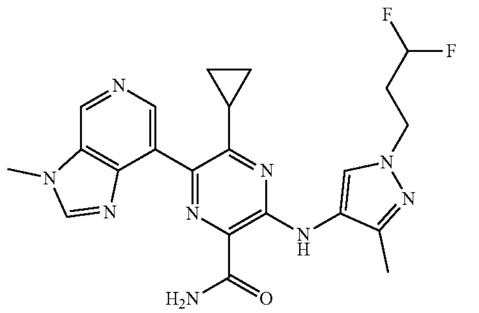

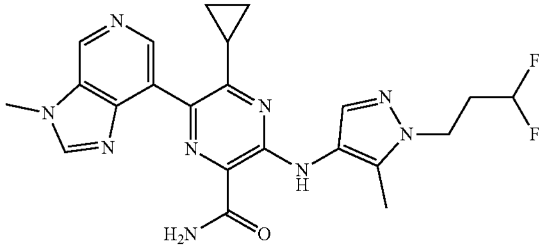

3,3-Difluoropropyl methanesulfonate (112 mg, 0.640 mmol) was added to a suspension of 5-cyclopropyl-6-(3-methylimidazo[4,5-c]pyridin-7-yl)-3-[(3-methyl-1H-pyrazol-4-yl)amino]pyrazine-2-carboxamide (100 mg, 0.26 mmol) and cesium carbonate (251 mg, 0.770 mmol) in DMSO (2.0 mL). The resulting mixture was stirred at 100° C. for 1 hour. The reaction was allowed to cool to room temperature and purified directly by reverse phase C18 chromatography, using 0 to 80% MeCN-water as eluent, and 0.2% ammonium hydroxide as modifier, to afford 116 mg of a yellow solid. This material was purified by preparative SFC using a 5 micron, 21 mm×250 mm ChiralPak IJ column, isocratic 20% MeOH-s$CO_2$ as eluent, and 0.2% ammonium as modifier, to afford 5-cyclopropyl-3-[[1-(3,3-difluoropropyl)-3-methyl-pyrazol-4-yl]amino]-6-(3-methylimidazo[4,5-c]pyridin-7-yl)pyrazine-2-carboxamide (44 mg, 37% yield) as a yellow solid and 5-cyclopropyl-3-[[1-(3,3-difluoropropyl)-5-methyl-pyrazol-4-yl]amino]-6-(3-methylimidazo[4,5-c]pyridin-7-yl)pyrazine-2-carboxamide (38 mg, 32% yield) as yellow solids.

5-Cyclopropyl-3-[[1-(3,3-difluoropropyl)-3-methyl-pyrazol-4-yl]amino]-6-(3-methylimidazo[4,5-c]pyridin-7-yl)pyrazine-2-carboxamide. 1H NMR (500 MHZ, DMSO-d6): δ 0.90 (2H, br dd), 1.10 (2H, br s), 1.85-1.92 (1H, m), 2.19 (3H, s), 2.27-2.48 (2H, m), 3.98 (3H, s), 4.21 (2H, t), 6.10 (1H, tt), 7.77 (1H, br s), 7.93 (1H, s), 8.03 (1H, br s), 8.42 (1H, s), 8.51 (1H, s), 9.03 (1H, s), 10.80 (1H, s). 19F NMR (471 MHz, DMSO-d6): δ −116.50. m/z: (ES+), [M+H]+=468.2

5-Cyclopropyl-3-[[1-(3,3-difluoropropyl)-5-methyl-pyrazol-4-yl]amino]-6-(3-methylimidazo[4,5-c]pyridin-7-yl)pyrazine-2-carboxamide. 1H NMR (500 MHz, DMSO-d6): 0.86 (2H, br dd), 1.00 (2H, br s), 1.83-1.90 (1H, m), 2.25 (3H, s), 2.28-2.41 (2H, m), 3.98 (3H, s), 4.20 (2H, br t), 6.12 (1H, tt), 7.75 (1H, br s), 7.79 (1H, s), 8.01 (1H, br s), 8.42 (1H, s), 8.50 (1H, s), 9.02 (1H, s), 10.60 (1H, s). 19F NMR (471 MHz, DMSO-d6): δ −116.48. m/z: (ES+), [M+H]+=468.2.

Example 229 and 230

5-Cyclopropyl-6-(3-methylimidazo[4,5-c]pyridin-7-yl)-3-[(3-methyl-1-tetrahydropyran-4-yl-pyrazol-4-yl)amino]pyrazine-2-carboxamide and 5-cyclopropyl-6-(3-methylimidazo[4,5-c]pyridin-7-yl)-3-[(5-methyl-1-tetrahydropyran-4-yl-pyrazol-4-yl)amino]pyrazine-2-carboxamide

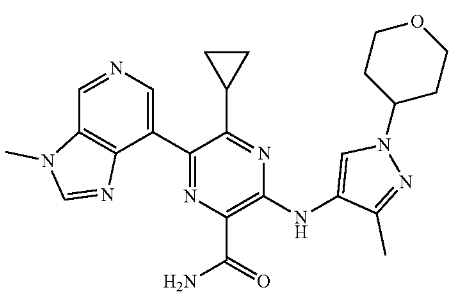

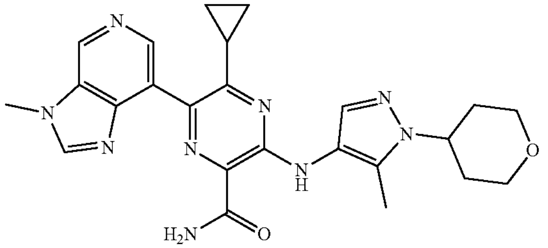

(a) 3-Methyl-4-nitro-1-tetrahydropyran-4-yl-pyrazole and 5-methyl-4-nitro-1-tetrahydropyran-4-yl-pyrazole DMF (5 mL) was added to a mixture of 3-methyl-4-nitro-1H-pyrazole (0.508 g, 4.00 mmol), tetrahydro-2H-pyran-4-yl methanesulfonate (0.865 g, 4.80 mmol), and cesium carbonate (1.56 g, 4.80 mmol). The resulting suspension was stirred at 100° C. for 18 hours. The reaction was then diluted with water (15 mL). The resulting precipitate was collected by filtration, rinsed with water, and dried under air to afford a 2:1 mixture of 3-methyl-4-nitro-1-tetrahydropyran-4-yl-pyrazole and 5-methyl-4-nitro-1-tetrahydropyran-4-yl-pyrazole (0.423 g, 50% yield) as a white, fluffy solid.

3-methyl-4-nitro-1-tetrahydropyran-4-yl-pyrazole. 1H NMR (500 MHZ, CHLOROFORM-d) 1.96-2.09 (2H, m), 2.10-2.17 (2H, m), 2.55 (3H, s), 3.48-3.60 (2H, m), 4.09-4.19 (2H, m), 4.29 (1H, tq), 8.16 (1H, s). m/z: (ES+), [M+H]+=212.0

5-methyl-4-nitro-1-tetrahydropyran-4-yl-pyrazole. 1H NMR (500 MHZ, CHLOROFORM-d) 1.77-1.91 (2H, m), 2.34 (2H, qd), 2.70 (3H, s), 3.48-3.60 (2H, m), 4.09-4.19 (2H, m), 4.29 (1H, tq), 8.11 (1H, s). m/z: (ES+), [M+H]+=212.0

(b) 3-Methyl-1-tetrahydropyran-4-yl-pyrazol-4-amine and 5-methyl-1-tetrahydropyran-4-yl-pyrazol-4-amine A mixture of 10 wt % palladium on carbon (85 mg, 0.080 mmol) and 2:1 mixture of 3-methyl-4-nitro-1-tetrahydropyran-4-yl-pyrazole and 5-methyl-4-nitro-1-tetrahydropyran-4-yl-pyrazole (423 mg, 2.00 mmol) in MeOH (8 mL) was stirred under a hydrogen atmosphere at room temperature for 4 hours. The reaction was then filtered through Celite and rinsed with DCM. The resulting filtrate was concentrated to afford a 2:1 mixture of 3-methyl-1-tetrahydropyran-4-yl-pyrazol-4-amine and 5-methyl-1-tetrahydropyran-4-yl-pyrazol-4-amine (340 mg, 94% yield) as a dark purple oil. m/z: (ES+), [M+H]+=182.8.

(c) Methyl 6-chloro-5-cyclopropyl-3-[(3-methyl-1-tetrahydropyran-4-yl-pyrazol-4-yl)amino]pyrazine-2-carboxylate and methyl 6-chloro-5-cyclopropyl-3-[(5-methyl-1-tetrahydropyran-4-yl-pyrazol-4-yl)amino]pyrazine-2-carboxylate DIPEA (0.657 mL, 3.77 mmol) was added to a solution of methyl 6-chloro-5-cyclopropyl-3-fluoro-pyrazine-2-carboxylate (290 mg, 1.26 mmol) and a 2:1 mixture of 3-methyl-1-tetrahydropyran-4-yl-pyrazol-4-amine and 5-methyl-1-tetrahydropyran-4-yl-pyrazol-4-amine (342 mg, 1.89 mmol) in DMF (5.6 mL). The resulting mixture was stirred at 100° C. for 45 minutes. The reaction was then concentrated. The resulting residue was purified by silica gel chromatography, using 0 to 5% MeOH-DCM as eluent, and 0 to 0.1% methanolic ammonia as modifier to afford a 2:1 mixture of methyl 6-chloro-5-cyclopropyl-3-[(3-methyl-1-tetrahydropyran-4-yl-pyrazol-4-yl)amino]pyrazine-2-carboxylate and methyl 6-chloro-5-cyclopropyl-3-[(5-methyl-1-tetrahydropyran-4-yl-pyrazol-4-yl)amino]pyrazine-2-carboxylate (0.420 g, 85% yield) as an orange-brown solid. 1H NMR (500 MHZ, Chloroform-d): δ 1.14-1.17 (2H, m), 1.17-1.34 (2H, m), 1.83-2.18 (3H, m), 2.25-2.39 (4H, m), 2.47-2.62 (1H, m), 3.51-3.61 (2H, m), 3.96-4.03 (3H, m), 4.11-4.18 (2H, m), 4.19-4.33 (1H, m), 7.76-7.90 (1H, m), 9.44-9.84 (1H, m). m/z: (ES+), [M+H]+=391.5

(d) Methyl 5-cyclopropyl-6-(3-methylimidazo[4,5-c]pyridin-7-yl)-3-[(3-methyl-1-tetrahydropyran-4-yl-pyrazol-4-yl)amino]pyrazine-2-carboxylate and methyl 5-cyclopropyl-6-(3-methylimidazo[4,5-c]pyridin-7-yl)-3-[(5-methyl-1-tetrahydropyran-4-yl-pyrazol-4-yl)amino]pyrazine-2-carboxylate A mixture of 2-(3-methyl-3H-imidazo[4,5-c]pyridin-7-yl)-1,3,6,2-dioxazaborocane (386 mg, 1.57 mmol) 2:1 methyl 6-chloro-5-cyclopropyl-3-[(3-methyl-1-tetrahydropyran-4-yl-pyrazol-4-yl)amino]pyrazine-2-carboxylate and methyl 6-chloro-5-cyclopropyl-3-[(5-methyl-1-tetrahydropyran-4-yl-pyrazol-4-yl)amino]pyrazine-2-carboxylate (410 mg, 1.05 mmol), Pd(dppf) C12 dichloromethane adduct (85 mg, 0.10 mmol), and cesium fluoride (477 mg, 3.14 mmol) was evacuated and backfilled three times with nitrogen. 1,4-Dioxane (9.5 mL) and water (0.95 mL) and the resulting slurry was evacuated and backfilled three times with nitrogen, then stirred at 80° C. for 20 hours. The reaction was then concentrated. The resulting residue was purified by silica gel chromatography, using 0 to 10% MeOH-DCM as eluent, and 0 to 0.2% methanolic ammonia as modifier, to afford a 2:1 mixture of methyl 5-cyclopropyl-6-(3-methylimidazo[4,5-c]pyridin-7-yl)-3-[(3-methyl-1-tetrahydropyran-4-yl-pyrazol-4-yl)amino]pyrazine-2-carboxylate and methyl 5-cyclopropyl-6-(3-methylimidazo[4,5-c]pyridin-7-yl)-3-[(5-methyl-1-tetrahydropyran-4-yl-pyrazol-4-yl)amino]pyrazine-2-carboxylate (0.157 g, 31% yield) as an orange film. m/z: (ES+), [M+H]+=489.2.

(e) 5-Cyclopropyl-6-(3-methylimidazo[4,5-c]pyridin-7-yl)-3-[(3-methyl-1-tetrahydropyran-4-yl-pyrazol-4-yl)amino]pyrazine-2-carboxamide and 5-cyclopropyl-6-(3-methylimidazo[4,5-c]pyridin-7-yl)-3_ [(5-methyl-1-tetrahydropyran-4-yl-pyrazol-4-yl)amino]pyrazine-2-carboxamide 7 N Methanolic ammonia (4.6 mL, 32 mmol) was added to a 2:1 mixture of methyl 5-cyclopropyl-6-(3-methylimidazo[4,5-c]pyridin-7-yl)-3-[(3-methyl-1-tetrahydropyran-4-yl-pyrazol-4-yl)amino]pyrazine-2-carboxylate and methyl 5-cyclopropyl-6-(3-methylimidazo[4,5-c]pyridin-7-yl)-3-[(5-methyl-1-tetrahydropyran-4-yl-pyrazol-4-yl)amino]pyrazine-2-carboxylate (157 mg, 0.320 mmol). The resulting mixture was stirred at 100° C. for 30 minutes in a Biotage microwave reactor. The reaction was then concentrated. The resulting residue was purified by reverse phase C18 chromatography, using 0 to 80% MeCN-water as eluent, and 0.2% ammonium hydroxide as modifier, to afford a yellow film. This material was further purified by preparative SFC, using a 5 micron, 21 mm×250 mm ChiralPak IJ column, isocratic 20% MeOH-s$CO_2$ as eluent, and 0.2% ammonium as modifier, to afford 5-cyclopropyl-6-(3-methylimidazo[4,5-c]pyridin-7-yl)-3-[(3-methyl-1-tetrahydropyran-4-yl-pyrazol-4-yl)amino]pyrazine-2-carboxamide (33 mg, 22% yield) as a yellow solid and 5-cyclopropyl-6-(3-methylimidazo[4,5-c]pyridin-7-yl)-3-[(5-methyl-1-tetrahydropyran-4-yl-pyrazol-4-yl)amino]pyrazine-2-carboxamide (68 mg, 45% yield) as a yellow solid.

5-cyclopropyl-6-(3-methylimidazo[4,5-c]pyridin-7-yl)-3-[(3-methyl-1-tetrahydropyran-4-yl-pyrazol-4-yl)amino]pyrazine-2-carboxamide: 1H NMR (500 MHz, DMSO-d6): δ 0.86-0.97 (2H, m), 1.06-1.15 (2H, m), 1.82-1.94 (3H, m), 2.00 (2H, br d), 2.20 (3H, s), 3.48 (2H, br t), 3.96 (2H, br d), 3.99 (3H, s), 4.25-4.37 (1H, m), 7.77 (1H, br s), 8.00 (1H, s), 8.03 (1H, br s), 8.43 (1H, s), 8.52 (1H, s), 9.03 (1H, s), 10.81 (1H, s). m/z: (ES+), [M+H]+=474.3

5-cyclopropyl-6-(3-methylimidazo[4,5-c]pyridin-7-yl)-3-[(5-methyl-1-tetrahydropyran-4-yl-pyrazol-4-yl)amino]pyrazine-2-carboxamide: 1H NMR (500 MHZ, DMSO-d6): δ 0.87 (2H, br dd), 0.99-1.06 (2H, m), 1.80 (2H, br d), 1.83-1.91 (1H, m), 1.96-2.09 (2H, m), 2.28 (3H, s), 3.49 (2H, br t), 3.92-4.02 (5H, m), 4.33-4.45 (1H, m), 7.74 (1H, br s), 7.81 (1H, s), 8.01 (1H, br s), 8.42 (1H, s), 8.51 (1H, s), 9.02 (1H, s), 10.64 (1H, s). m/z: (ES+), [M+H]+=474.2

Example 231 and 232

5-Cyclopropyl-6-(1-methylbenzimidazol-4-yl)-3-[[3-methyl-1-(1-methyl-4-piperidyl)pyrazol-4-yl]amino]pyrazine-2-carboxamide and 5-cyclopropyl-6-(1-methylbenzimidazol-4-yl)-3-[[5-methyl-1-(1-methyl-4-piperidyl)pyrazol-4-yl]amino]pyrazine-2-carboxamide

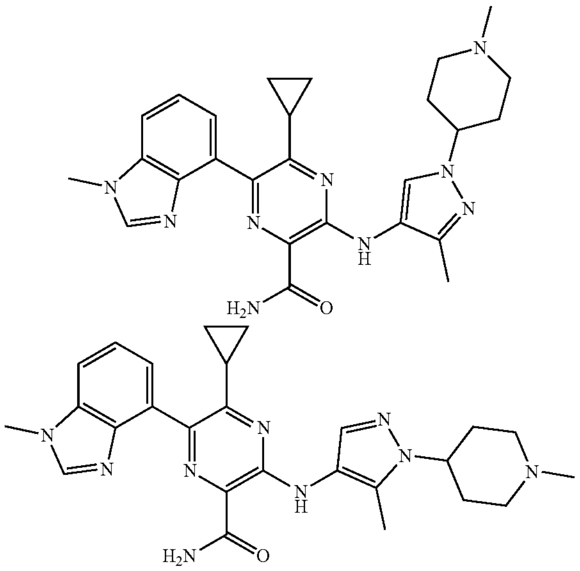

(a) tert-Butyl 4-(3-methyl-4-nitro-pyrazol-1-yl) piperidine-1-carboxylate and tert-Butyl 4-(5-methyl-4-nitro-pyrazol-1-yl) piperidine-1-carboxylate DMF (9.8 mL) was added to a mixture of 3-methyl-4-nitro-1H-pyrazole (1.00 g, 7.87 mmol), tert-butyl 4-methylsulfonyloxypiperidine-1-carboxylate (2.86 g, 10.2 mmol), and cesium carbonate (3.08 g, 9.44 mmol). The resulting mixture was stirred at 100° C. for 3 hours. The reaction was then allowed to cool to room temperature, diluted with water, and extracted three times with EtOAc. The combined organic layers were washed three times with 5% aqueous LiCl and once with brine, then dried over sodium sulfate, filtered, and concentrated to afford a 2:1 mixture of tert-butyl 4-(3-methyl-4-nitro-pyrazol-1-yl) piperidine-1-carboxylate and tert-butyl 4-(5-methyl-4-nitro-pyrazol-1-yl) piperidine-1-carboxylate (2.79 g, quantitative) as a waxy white solid. 1H NMR (500 MHZ, Chloroform-d): δ 1.32-1.62 (9H, m), 1.79-1.93 (2H, m), 2.09-2.19 (2H, m), 2.48-2.71 (3H, m), 2.76-2.95 (2H, m), 4.10-4.51 (3H, m), 8.04-8.17 (1H, m). m/z: (ES+), [M+H]+=311.1

(b) tert-Butyl 4-(4-amino-3-methyl-pyrazol-1-yl) piperidine-1-carboxylate and tert-Butyl 4-(4-amino-5-methyl-pyrazol-1-yl) piperidine-1-carboxylate Iron powder (2.007 g, 35.93 mmol) was added to a mixture of 2:1 tert-butyl 4-(3-methyl-4-nitro-pyrazol-1-yl) piperidine-1-carboxylate and ter-butyl 4-(5-methyl-4-nitro-pyrazol-1-yl) piperidine-1-carboxylate (2.788 g, 8.98 mmol) and ammonium chloride (1.922 g, 35.93 mmol) in ethanol (22.5 mL) and water (22.5 mL). The resulting mixture was stirred at 60° C. for 1 hour. The reaction was then allowed to cool to room temperature and diluted with DCM (100 mL). The resulting suspension was filtered through Celite and rinsed with DCM and water. The resulting filtrate was transferred to a separatory funnel, and the layers were separated. The aqueous layer was extracted twice with DCM (50 mL), and the combined organic layers were washed with brine, dried over sodium sulfate, filtered, and concentrated to afford a 2:1 mixture of tert-butyl 4-(4-amino-3-methyl-pyrazol-1-yl) piperidine-1-carboxylate and tert-butyl 4-(4-amino-5-methyl-pyrazol-1-yl) piperidine-1-carboxylate (2.55 g, quantitative) as a dark red-brown oil. m/z: (ES+), [M+H]+=281.5

(c) Methyl 3-[[1-(1-tert-butoxycarbonyl-4-piperidyl)-3-methyl-pyrazol-4-yl]amino]-6-chloro-5-cyclopropyl-pyrazine-2-carboxylate and methyl 3-[[1-(1-tert-butoxycarbonyl-4-piperidyl)-5-methyl-pyrazol-4-yl]amino]-6-chloro-5-cyclopropyl-pyrazine-2-carboxylate DIPEA (850 μL, 4.88 mmol) was added to a solution of methyl 6-chloro-5-cyclopropyl-3-fluoro-pyrazine-2-carboxylate (375 mg, 1.63 mmol) and 2:1 tert-butyl 4-(4-amino-3-methyl-pyrazol-1-yl) piperidine-1-carboxylate and tert-butyl 4-(4-amino-5-methyl-pyrazol-1-yl) piperidine-1-carboxylate (912 mg, 3.25 mmol) in DMF (7.3 mL). The resulting mixture was allowed to stir at 100° C. for 2 hours. The reaction was then concentrated. The resulting residue was purified by silica gel chromatography, using 0 to 5% MeOH-DCM as eluent, and 0 to 0.1% methanolic ammonia as modifier, to afford a 55:45 mixture of methyl 3-[[1-(1-tert-butoxycarbonyl-4-piperidyl)-3-methyl-pyrazol-4-yl]amino]-6-chloro-5-cyclopropyl-pyrazine-2-carboxylate and methyl 3-[[1-(1-tert-butoxycarbonyl-4-piperidyl)-5-methyl-pyrazol-4-yl]amino]-6-chloro-5-cyclopropyl-pyrazine-2-carboxylate (0.804 g, quantitative) as brown solid. 1H NMR (500 MHz, Chloroform-d): δ 1.00-1.16 (2H, m), 1.16-1.27 (2H, m), 1.47-1.51 (11H, m), 1.82-1.93 (2H, m), 2.09-2.18 (2H, m), 2.23-2.34 (3H, m), 2.44-2.61 (1H, m), 3.94-4.01 (3H, m), 4.07-4.49 (3H, m), 7.71-7.85 (1H, m), 9.37-9.85 (1H, m). m/z: (ES+), [M+H]+=491.2

(d) Methyl 3-[[1-(1-tert-butoxycarbonyl-4-piperidyl)-3-methyl-pyrazol-4-yl]amino]-5-cyclopropyl-6-(1-methylbenzimidazol-4-yl)pyrazine-2-carboxylate and methyl 3-[[1-(1-tert-butoxycarbonyl-4-piperidyl)-5-methyl-pyrazol-4-yl]amino]-5-cyclopropyl-6-(1-methylbenzimidazol-4-yl)pyrazine-2-carboxylate A mixture of 1-methyl-4-(4,4,5,5-tetramethyl-1,3,2-dioxaborolan-2-yl)benzimidazole (841 mg, 3.26 mmol), 55:45 methyl 3-[[1-(1-tert-butoxycarbonyl-4-piperidyl)-3-methyl-pyrazol-4-yl]amino]-6-chloro-5-cyclopropyl-pyrazine-2-carboxylate and methyl 3-[[1-(1-tert-butoxycarbonyl-4-piperidyl)-5-methyl-pyrazol-4-yl]amino]-6-chloro-5-cyclopropyl-pyrazine-2-carboxylate (800 mg, 1.63 mmol), $Pd(dppf)Cl_2$ dichloromethane adduct (133 mg, 0.160 mmol), and cesium fluoride (743 mg, 4.89 mmol) was evacuated and backfilled three times with nitrogen. 1,4-Dioxane (14.8 mL) and water (1.5 mL) were added. The resulting slurry was evacuated and backfilled three times with nitrogen, then stirred at 80° C. for 21 hours. The reaction was then concentrated. The resulting residue was purified by silica gel chromatography, using 0 to 5% MeOH-DCM as eluent, and 0 to 0.1% methanolic ammonia as modifier, to afford a 60:40 mixture of methyl 3-[[1-(1-tert-butoxycarbonyl-4-piperidyl)-3-methyl-pyrazol-4-yl]amino]-5-cyclopropyl-6-(1-methylbenzimidazol-4-yl)pyrazine-2-carboxylate and methyl 3-[[1-(1-tert-butoxycarbonyl-4-piperidyl)-5-methyl-pyrazol-4-yl]amino]-5-cyclopropyl-6-(1-methylbenzimidazol-4-yl)pyrazine-2-carboxylate (0.655 g, 69% yield) as an orange oil. 1H NMR (500 MHZ, Chloroform-d): 8 0.77-1.00 (2H, m), 1.20-1.40 (2H, m), 1.47 (9H, br d), 1.80-2.04 (3H, m), 2.26-2.37 (3H, m), 2.89 (2H, br d), 3.81-3.89 (3H, m), 3.93 (3H, br dd), 4.06-4.46 (3H, m), 7.36-7.48 (3H, m), 7.87 (1H, br dd), 7.88-8.00 (1H, m), 9.50-9.91 (1H, m). 2 protons were buried under a pinacol impurity peak. m/z: (ES+), [M+H]+=586.6

(e) Methyl 5-cyclopropyl-6-(1-methylbenzimidazol-4-yl)-3-[[3-methyl-1-(4-piperidyl)pyrazol-4-yl]amino]pyrazine-2-carboxylate and methyl 5-cyclopropyl-6-(1-methylbenzimidazol-4-yl)-3-[[5-methyl-1-(4-piperidyl)pyrazol-4-yl]amino]pyrazine-2-carboxylate 4 M HCl in 1,4-dioxane (5.60 mL, 22.3 mmol) was added to a 60:40 mixture of methyl 3-[[1-(1-tert-butoxycarbonyl-4-piperidyl)-3-methyl-pyrazol-4-yl]amino]-5-cyclopropyl-6-(1-methylbenzimidazol-4-yl)pyrazine-2-carboxylate and methyl 3-[[1-(1-tert-butoxycarbonyl-4-piperidyl)-5-methyl-pyrazol-4-yl]amino]-5-cyclopropyl-6-(1-methylbenzimidazol-4-yl)pyrazine-2-carboxylate (655 mg, 1.12 mmol). The resulting mixture was stirred at room temperature for 2 hours. The reaction was then concentrated to afford a 60:40 mixture of methyl 5-cyclopropyl-6-(1-methylbenzimidazol-4-yl)-3-[[3-methyl-1-(4-piperidyl)pyrazol-4-yl]amino]pyrazine-2-carboxylate hydrochloride and methyl 5-cyclopropyl-6-(1-methylbenzimidazol-4-yl)-3-[[5-methyl-1-(4-piperidyl)pyrazol-4-yl]amino]pyrazine-2-carboxylate hydrochloride (0.584 g, quantitative). m/z: (ES+), [M+H]+=486.7

(f) Methyl 5-cyclopropyl-6-(1-methylbenzimidazol-4-yl)-3-[[3-methyl-1-(1-methyl-4-piperidyl)pyrazol-4-yl]amino]pyrazine-2-carboxylate and methyl 5-cyclopropyl-6-(1-methylbenzimidazol-4-yl)-3-[[5-methyl-1-(1-methyl-4-piperidyl)pyrazol-4-yl]amino]pyrazine-2-carboxylate DIPEA (488 μL, 2.79 mmol) was added to a 60:40 mixture of methyl 5-cyclopropyl-6-(1-methylbenzimidazol-4-yl)-3-[[3-methyl-1-(4-piperidyl)pyrazol-4-yl]amino]pyrazine-2-carboxylate hydrochloride and methyl 5-cyclopropyl-6-(1-methylbenzimidazol-4-yl)-3-[[5-methyl-1-(4-piperidyl)pyrazol-4-yl]amino]pyrazine-2-carboxylate hydrochloride (584 mg, 1.12 mmol) in DMF (4.60 mL). The resulting solution stirred at room temperature for 5 minutes. 37% aqueous formaldehyde (500 μL, 6.70 mmol) and a few drops of acetic acid were added sequentially. Sodium triacetoxyborohydride (710 mg, 3.35 mmol) was added portion-wise as a solid. The resulting mixture was allowed to stir at room temperature for 15 min. The reaction was then diluted with water and concentrated. The resulting residue was purified by silica gel chromatography, using 0 to 10% MeOH-DCM as eluent, and 0 to 0.2% methanolic ammonia, to afford a 60:40 mixture of methyl 5-cyclopropyl-6-(1-methylbenzimidazol-4-yl)-3-[[3-methyl-1-(1-methyl-4-piperidyl)pyrazol-4-yl]amino]pyrazine-2-carboxylate and methyl 5-cyclopropyl-6-(1-methylbenzimidazol-4-yl)-3-[[5-methyl-1-(1-methyl-4-piperidyl)pyrazol-4-yl]amino]pyrazine-2-carboxylate (0.448 g, 80% yield) as a yellow solid. 1H NMR (500 MHZ, Chloroform-d). m/z: (ES+), [M+H]+=501.4

(g) 5-Cyclopropyl-6-(1-methylbenzimidazol-4-yl)-3-[[3-methyl-1-(1-methyl-4-piperidyl)pyrazol-4-yl]amino]pyrazine-2-carboxamide and 5-cyclopropyl-6-(1-methylbenzimidazol-4-yl)-3_ [[5-methyl-1-(1-methyl-4-piperidyl)pyrazol-4-yl]amino]pyrazine-2-carboxamide 7 N Methanolic ammonia (6.3 mL, 44 mmol) was added to a 60:40 mixture of methyl 5-cyclopropyl-6-(1-methylbenzimidazol-4-yl)-3-[[3-methyl-1-(1-methyl-4-piperidyl)pyrazol-4-yl]amino]pyrazine-2-carboxylate and methyl 5-cyclopropyl-6-(1-methylbenzimidazol-4-yl)-3-[[5-methyl-1-(1-methyl-4-piperidyl)pyrazol-4-yl]amino]pyrazine-2-carboxylate (440 mg, 0.88 mmol). The resulting mixture was stirred at 100° C. for 1 hour in a Biotage microwave reactor. The reaction was then concentrated. The resulting residue was purified by silica gel chromatography, using 0 to 20% MeOH-DCM as eluent, and 0 to 0.4% methanolic ammonia as modifier, to afford a yellow film. This material was further purified by preparative SFC, using a 5 micron, 21 mm×250 mm ChiralPak IJ column, isocratic 20% MeOH-s$CO_2$ as eluent, and 0.2% ammonium as modifier, to afford 5-cyclopropyl-6-(1-methylbenzimidazol-4-yl)-3-[[3-methyl-1-(1-methyl-4-piperidyl)pyrazol-4-yl]amino]pyrazine-2-carboxamide (115 mg, 27% yield) as a yellow solid and 5-cyclopropyl-6-(1-methylbenzimidazol-4-yl)-3-[[5-methyl-1-(1-methyl-4-piperidyl)pyrazol-4-yl]amino]pyrazine-2-carboxamide (88 mg, 21% yield) as a yellow solid.

5-cyclopropyl-6-(1-methylbenzimidazol-4-yl)-3-[[3-methyl-1-(1-methyl-4-piperidyl)pyrazol-4-yl]amino]pyrazine-2-carboxamide: 1H NMR (500 MHz, DMSO-d6): δ 0.82-0.94 (2H, m), 1.01-1.12 (2H, m), 1.79-1.93 (3H, m), 1.96-2.09 (4H, m), 2.19 (6H, s), 2.83 (2H, br d), 3.87 (3H, s), 3.95-4.06 (1H, m), 7.31-7.44 (2H, m), 7.64 (1H, br d), 7.73 (1H, br s), 7.91 (1H, br s), 7.99 (1H, s), 8.20 (1H, s), 10.74 (1H, s). m/z: (ES+), [M+H]+=486.4

5-cyclopropyl-6-(1-methylbenzimidazol-4-yl)-3-[[5-methyl-1-(1-methyl-4-piperidyl)pyrazol-4-yl]amino]pyrazine-2-carboxamide: 1H NMR (500 MHz, DMSO-d6): δ 0.78-0.88 (2H, m), 0.94-1.04 (2H, m), 1.79 (2H, br s), 1.83-1.91 (1H, m), 1.97-2.10 (4H, m), 2.20 (3H, s), 2.26 (3H, s), 2.86 (2H, br d), 3.87 (3H, s), 4.01-4.14 (1H, m), 7.31-7.43 (2H, m), 7.63 (1H, br d), 7.71 (1H, br s), 7.79 (1H, s), 7.89 (1H, br s), 8.19 (1H, s), 10.58 (1H, s). m/z: (ES+), [M+H]+=486.4

What is claimed is:

1. A compound of Formula (I)

(I)

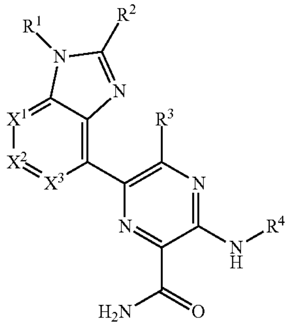

wherein $X^1$, $X^2$ and $X^3$ are independently selected from $CR^5$ or N, with the provisos that when $X^1$ is N, $X^3$ is $CR^5$ and when $X^3$ is N, $X^1$ is $CR^5$, $R^1$ is cyclopropyl or $C_{1-3}$alkyl, wherein said $C_{1-3}$alkyl is substituted by 0, 1, 2 or 3 F;

$R^2$ is H, $NH_2$ or $C_{1-2}$alkyl, wherein said $C_{1-2}$alkyl is substituted by 0, 1, 2 or 3 F;

$R^3$ is selected from H, $R^6$, $OR^6$, $NHR^6$, Cl, CN, CCH, $NH_2$, $SCH_3$, cyclopropyl, cyclobutyl, NH((5- to 6-membered)heteroaryl containing 1 or 2 N), NH($C_{1-2}$alkyl)N($CH_3$)$_2$, oxetan-3-yl, NH-cyclopropyl and O-cyclopropyl;

$R^4$ is selected from aryl or heteroaryl, wherein said aryl or heteroaryl is substituted by 0, 1, 2, 3 or 4 substituents independently selected from F, Cl and $R^6$, and 0, 1 or 2 substituents independently selected from $NH_2$, CN, $OR^6$, $R^7$, $R^8$, $R^9$, $OR^8$, $OCH_2R^8$, C(O)$R^8$, C(O)$CH_3$, C(O)$NHCH_3$, $CH_2C(O)NHCH_3$, $C(CH_3)_2R^8$, $CH(CH_3)R^8$ and $CH_2R^8$;

$R^5$ is independently selected from H, F, Cl and $C_{1-2}$alkyl, wherein said $C_{1-2}$alkyl is substituted by 0, 1, 2 or 3 substituents independently selected from F, CN, $NH_2$ and $OC_{1-2}$alkyl, wherein said $OC_{1-2}$alkyl is substituted by 0, 1, 2 or 3 substituents independently selected from F and Cl;

$R^6$ is $C_{1-4}$alkyl, wherein said $C_{1-4}$alkyl is substituted by 0, 1, 2 or 3 F, O($C_{1-2}$alkyl) and 0 or 1 substituents selected from OH, CN, N($CH_3$)$_2$ and (4- to 5-membered)heterocycloalkyl containing one 0;

$R^7$ is selected from NH-cyclopropyl, [dimethyl(oxo)-$\lambda^6$-sulfanylidene]amino, ($C_{1-4}$alkyl)sulfonimidoyl, $SO_2CH_3$, $OSO_2CH_3$, $C(CH_3)_2SO_2CH_3$, $SO_2NHCH_3$, $SO_2N(CH_3)_2$, morpholine-4-sulfonyl, 4-methylpiperazine-sulfonyl, morpholinyl, $CCCH_3$, cyclopropyl, wherein said cyclopropyl is substituted by 0 or 1 substituents selected from F, CN, OH or $SO_2CH_3$, cyclobutyl, wherein said cyclobutyl is substituted by 0 or 1 OH, and imidazolyl, wherein said imidazolyl is substituted by 0 or 1 $R^{11}$;

$R^8$ is selected from $SO_2CH_3$ or heterocycloalkyl, wherein said heterocycloalkyl is substituted by 0, 1, 2, 3 or 4 substituents independently selected from F, Cl, $R^6$ and $OR^6$, and 0, 1 or 2 substituents independently selected from cyclopropyl, OH, $C(O)CH_2OH$, 4-methylpiperazinyl, C(O)$CH_3$ and C(O)N($CH_3$)$_2$;

$R^9$ is selected from $OR^{10}$ N($R^{10}$)$_2$, $NR^{11}(CH_2)_2N(CH_3)_2$, —($CH_2$)$_2$(5- to 6-membered)heterocycloalkyl, wherein said (5- to 6-membered)heterocycloalkyl is substituted by 0 or 1 substituents selected from $R^{11}$, —O($CH_2$)$_2$(5- to 6-membered)heterocycloalkyl, wherein said (5- to 6-membered)heterocycloalkyl is substituted by 0 or 1 substituents selected from $R^1$ and azetinyl substituted by 0 or 1 substituents selected from N($CH_3$)$_2$ and C(O)$CH_3$;

$R^{10}$ is independently selected from H and $C_{1-2}$alkyl, wherein said $C_{1-2}$alkyl is substituted by 0, 1, 2 or 3 substituents independently selected from F, CN, $NH_2$ and $OC_{1-2}$alkyl, wherein said $C_{1-2}$alkyl is substituted by 0, 1, 2 or 3 substituents independently selected from F and Cl; and $R^{11}$ is $C_{1-3}$alkyl, wherein said $C_{1-3}$alkyl is substituted by 0, 1, 2 or 3 F and 0 or 1 cyclopropyl;

or a pharmaceutically acceptable salt thereof.

2. The compound according to claim 1 wherein $X^1$, $X^2$ and $X^3$ are independently selected from $CR^5$;

or a pharmaceutically acceptable salt thereof.

3. The compound according to claim 1 wherein $X^1$ and $X^3$ are independently selected from $CR^5$;

$X^2$ is N;

or a pharmaceutically acceptable salt thereof.

4. The compound according to claim 1 of Formula (IA), (IA)

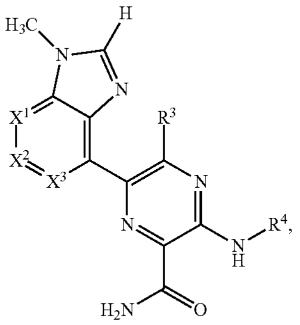

wherein $X^1$, $X^2$ and $X^3$ are independently selected from $CR^5$;

$R^5$ is H;

or a pharmaceutically acceptable salt thereof.

5. The compound according to claim 4 wherein $R^3$ is selected from $R^6$, $NHR^6$ and cyclopropyl;

$R^6$ is $C_{1-4}$alkyl, wherein said $C_{1-4}$alkyl is substituted by 0, 1, 2 or 3 F;

$R^4$ is selected from phenyl, wherein said phenyl is substituted by 0 or 1 substituent selected from F, Cl and $R^6$, and a substituent selected from morpholinyl, wherein said morpholinyl is substituted by 0, 1 or 2 substituents independently selected from F, Cl, $R^6$ and $OR^6$, and 0 or 1 substituent selected from cyclopropyl, C(O)$CH_3$ and C(O)N($CH_3$)$_2$;

or a pharmaceutically acceptable salt thereof.

6. The compound according to claim 4 wherein $R^3$ is selected from $R^6$, $NHR^6$ and cyclopropyl;

$R^6$ is $C_{1-4}$alkyl, wherein said $C_{1-4}$alkyl is substituted by 0, 1, 2 or 3 F;

$R^4$ is selected from (5-membered)heteroaryl, wherein said (5-membered)heteroaryl is substituted by 0, 1 or 2 substituents independently selected from F, Cl and $R^6$, and 0 or 1 substituent selected from $R^7$;

$R^7$ is selected from cyclopropyl, wherein said cyclopropyl is substituted by 0 or 1 substituents selected from F, CN, OH or $SO_2CH_3$;

or a pharmaceutically acceptable salt thereof.

7. The compound according to claim 1 of Formula (IB), (IB)

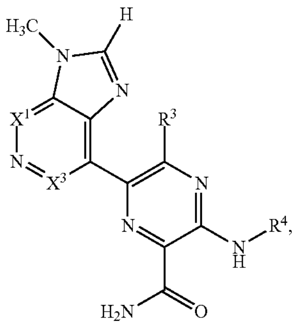

wherein $X^1$ and $X^3$ are independently selected from $CR^5$;

$X^2$ is N;

$R^5$ is H;

or a pharmaceutically acceptable salt thereof.

8. The compound according to claim 7 wherein $R^3$ is selected from $R^6$, $NHR^6$ and cyclopropyl;

$R^6$ is $C_{1-4}$alkyl, wherein said $C_{1-4}$alkyl is substituted by 0, 1, 2 or 3 F;

$R^4$ is selected from phenyl, wherein said phenyl is substituted by 0 or 1 substituent selected from F, Cl and $R^6$, and a substituent selected from morpholinyl, wherein said morpholinyl is substituted by 0, 1 or 2 substituents independently selected from F, Cl, $R^6$ and $OR^6$, and 0 or 1 substituent selected from cyclopropyl, $C(O)CH_3$ and $C(O)N(CH_3)_2$;

or a pharmaceutically acceptable salt thereof.

9. The compound according to claim 7 wherein $R^3$ is selected from $R^6$, $NHR^6$ and cyclopropyl;

$R^6$ is $C_{1-4}$alkyl, wherein said $C_{1-4}$alkyl is substituted by 0, 1, 2 or 3 F;

$R^4$ is selected from (5-membered)heteroaryl, wherein said (5-membered)heteroaryl is substituted by 0, 1 or 2 substituents independently selected from F, Cl and $R^6$, and 0 or 1 substituent selected from $R^7$;

$R^7$ is selected from cyclopropyl, wherein said cyclopropyl is substituted by 0 or 1 substituents selected from F, CN, OH or $SO_2CH_3$;

or a pharmaceutically acceptable salt thereof.

10. The compound according to claim 1 of Formula (IC), (IC)

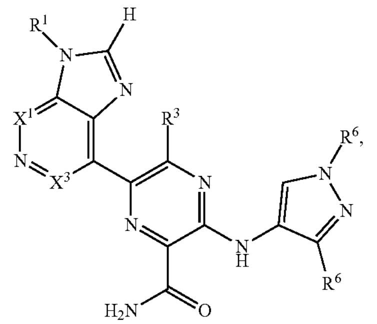

wherein $X^1$ and $X^3$ are independently selected from $CR^5$;

$X^2$ is N;

$R^5$ is H;

$R^1$ is $C_{1-3}$alkyl, wherein said $C_{1-3}$alkyl is substituted by 0, 1, 2 or 3 F;

or a pharmaceutically acceptable salt thereof.

11. The compound according to claim 10 wherein $R^1$ is $C_{1-3}$alkyl, wherein said $C_{1-3}$alkyl is substituted by 0, 1, 2 or 3 F;

$R^3$ is selected from $R^6$, $NHR^6$ and cyclopropyl;

$R^6$ is $C_{1-4}$alkyl, wherein said $C_{1-4}$alkyl is substituted by 0, 1, 2 or 3 F;

or a pharmaceutically acceptable salt thereof.

12. The compound according to claim 10 wherein $R^3$ is cyclopropyl;

$R^6$ is $C_{1-4}$alkyl, wherein said $C_{1-4}$alkyl is substituted by 0, 1, 2 or 3 F;

or a pharmaceutically acceptable salt thereof.

13. The compound according to claim 1 selected from:

6-(1-Methylbenzimidazol-4-yl)-3-(4-morpholinoanilino)pyrazine-2-carboxamide,

5-Methyl-6-(1-methylbenzimidazol-4-yl)-3-(4-morpholinoanilino)pyrazine-2-carboxamide, 5-Methoxy-6-(1-methylbenzimidazol-4-yl)-3-(4-morpholinoanilino)pyrazine-2-carboxamide, 5-[2-(Dimethylamino)ethoxy]-6-(1-methylbenzimidazol-4-yl)-3-(4-morpholinoanilino)pyrazine-2-carboxamide, 5-Cyclopropyl-6-(1-methylbenzimidazol-4-yl)-3-(4-morpholinoanilino)pyrazine-2-carboxamide, 5-Methyl-6-(3-methylimidazo[4,5-c]pyridin-7-yl)-3-(4-morpholinoanilino)pyrazine-2-carboxamide, 5-(Methylamino)-6-(1-methylbenzimidazol-4-yl)-3-(4-morpholinoanilino)pyrazine-2-carboxamide, 5-(Methylamino)-6-(3-methylimidazo[4,5-c]pyridin-7-yl)-3-(4-morpholinoanilino)pyrazine-2-carboxamide, 6-(1-Methylbenzimidazol-4-yl)-5-methylsulfanyl-3-(4-morpholinoanilino)pyrazine-2-carboxamide, 5-(Ethylamino)-6-(1-methylbenzimidazol-4-yl)-3-(4-morpholinoanilino)pyrazine-2-carboxamide, 5-(Cyclopropylamino)-6-(1-methylbenzimidazol-4-yl)-3-(4-morpholinoanilino)pyrazine-2-carboxamide, 5-Amino-6-(1-methylbenzimidazol-4-yl)-3-(4-morpholinoanilino)pyrazine-2-carboxamide, 5-[[(2R)-2-Hydroxypropyl]amino]-6-(1-methylbenzimidazol-4-yl)-3-(4-morpholinoanilino)pyrazine-2-carboxamide, 5-[[(2S)-2-Hydroxypropyl]amino]-6-(1-methylbenzimidazol-4-yl)-3-(4-morpholinoanilino)pyrazine-2-carboxamide, 6-(1-Methylbenzimidazol-4-yl)-3-(4-morpholinoanilino)-5-(2,2,2-trifluoroethylamino)pyrazine-2-carboxamide, 5-(2,2-Difluoroethylamino)-6-(1-methylbenzimidazol-4-yl)-3-(4-morpholinoanilino)pyrazine-2-carboxamide, 5-[2-(Dimethylamino)ethylamino]-6-(1-methylbenzimidazol-4-yl)-3-(4-morpholinoanilino)pyrazine-2-carboxamide, 5-(2-Hydroxyethylamino)-6-(1-methylbenzimidazol-4-yl)-3-(4-morpholinoanilino)pyrazine-2-carboxamide, 6-(1-Methylbenzimidazol-4-yl)-3-(4-morpholinoanilino)-5-(prop-2-ynylamino)pyrazine-2-carboxamide, 6-(1-Methylbenzimidazol-4-yl)-3-(4-morpholinoanilino)-5-[[rel-(1R,2R)-2-methylcyclopropyl]amino]pyrazine-2-carboxamide, 6-(1-methylbenzimidazol-4-yl)-3-(4-morpholinoanilino)-5-[[rel-(1S,2S)-2-methylcyclopropyl]amino]pyrazine-2-carboxamide, 5-(Cyanomethylamino)-6-(1-methylbenzimidazol-4-yl)-3-(4-morpholinoanilino)pyrazine-2-carboxamide, 5-[[(2R)-2-Fluoropropyl]amino]-6-(1-methylbenzimidazol-4-yl)-3-(4-morpholinoanilino)pyrazine-2-carboxamide, 5-[[(2S)-2-Fluoropropyl]amino]-6-(1-methylbenzimidazol-4-yl)-3-(4-morpholinoanilino)pyrazine-2-carboxamide, 6-(1-Methylbenzimidazol-4-yl)-3-(4-morpholinoanilino)-5-(oxetan-3-ylmethylamino)pyrazine-2-carboxamide, 5-Ethynyl-6-(1-methylbenzimidazol-4-yl)-3-(4-morpholinoanilino)pyrazine-2-carboxamide, 5-(Difluoromethyl)-6-(1-methylbenzimidazol-4-yl)-3-(4-morpholinoanilino)pyrazine-2-carboxamide, 5-Chloro-6-(1-methylbenzimidazol-4-yl)-3-(4-morpholinoanilino)pyrazine-2-carboxamide, 6-(1-Methylbenzimidazol-4-yl)-5-[(1-methylpyrazol-4-yl)amino]-3-(4-morpholinoanilino)pyrazine-2-carboxamide,
6-(1-Methylbenzimidazol-4-yl)-3-(4-morpholinoanilino)-5-(2-pyridylamino)pyrazine-2-carboxamide,
6-(3-Methylimidazo[4,5-c]pyridin-7-yl)-3-(4-morpholinoanilino)-5-(oxetan-3-yl)pyrazine-2-carboxamide,
5-Ethoxy-6-(3-methylimidazo[4,5-c]pyridin-7-yl)-3-(4-morpholinoanilino)pyrazine-2-carboxamide,
6-(3-Methylimidazo[4,5-c]pyridin-7-yl)-3-(4-morpholinoanilino)-5-(trifluoromethyl)pyrazine-2-carboxamide,
6-(3-Methylimidazo[4,5-c]pyridin-7-yl)-5-methylsulfanyl-3-(4-morpholinoanilino)pyrazine-2-carboxamide,
5-[(1-Methylcyclopropyl)amino]-6-(3-methylimidazo[4,5-c]pyridin-7-yl)-3-(4-morpholinoanilino)pyrazine-2-carboxamide,
5-Cyano-6-(3-methylimidazo[4,5-c]pyridin-7-yl)-3-(4-morpholinoanilino)pyrazine-2-carboxamide,
5-(Cyclopropylamino)-6-(3-methylimidazo[4,5-c]pyridin-7-yl)-3-(4-morpholinoanilino)pyrazine-2-carboxamide,
5-Amino-6-(3-methylimidazo[4,5-c]pyridin-7-yl)-3-(4-morpholinoanilino)pyrazine-2-carboxamide,
6-(3-Methylimidazo[4,5-c]pyridin-7-yl)-3-(4-morpholinoanilino)pyrazine-2-carboxamide,
5-Methoxy-6-(3-methylimidazo[4,5-c]pyridin-7-yl)-3-(4-morpholinoanilino)pyrazine-2-carboxamide,
5-Cyclopropyl-6-(3-methylimidazo[4,5-c]pyridin-7-yl)-3-(4-morpholinoanilino)pyrazine-2-carboxamide,
5-(Difluoromethyl)-6-(3-methylimidazo[4,5-c]pyridin-7-yl)-3-(4-morpholinoanilino)pyrazine-2-carboxamide,
5-Methyl-6-(1-methylimidazo[4,5-d]pyridazin-4-yl)-3-(4-morpholinoanilino)pyrazine-2-carboxamide,
5-Methyl-6-(7-methylimidazo[4,5-c]pyridazin-4-yl)-3-(4-morpholinoanilino)pyrazine-2-carboxamide,
5-(Methylamino)-6-(7-methylimidazo[4,5-c]pyridazin-4-yl)-3-(4-morpholinoanilino)pyrazine-2-carboxamide,
6-(3-Ethylimidazo[4,5-c]pyridin-7-yl)-5-(methylamino)-3-(4-morpholinoanilino)pyrazine-2-carboxamide,
6-(3-Cyclopropylimidazo[4,5-c]pyridin-7-yl)-5-(methylamino)-3-(4-morpholinoanilino)pyrazine-2-carboxamide,
6-[3-(Difluoromethyl)imidazo[4,5-c]pyridin-7-yl]-5-(methylamino)-3-(4-morpholinoanilino)pyrazine-2-carboxamide,
6-(7-Chloro-1-methyl-benzimidazol-4-yl)-5-(methylamino)-3-(4-morpholinoanilino)pyrazine-2-carboxamide,
6-(7-Cyano-1-methyl-benzimidazol-4-yl)-5-(methylamino)-3-(4-morpholinoanilino)pyrazine-2-carboxamide,
6-(3,4-Dimethylimidazo[4,5-c]pyridin-7-yl)-5-(methylamino)-3-(4-morpholinoanilino)pyrazine-2-carboxamide,
3-(2-Fluoro-4-morpholino-anilino)-5-(methylamino)-6-(3-methylimidazo[4,5-c]pyridin-7-yl)pyrazine-2-carboxamide,
3-(2,3-Difluoro-4-morpholino-anilino)-5-(methylamino)-6-(3-methylimidazo[4,5-c]pyridin-7-yl)pyrazine-2-carboxamide,
3-(2-Fluoro-3-methyl-4-morpholino-anilino)-5-(methylamino)-6-(3-methylimidazo[4,5-c]pyridin-7-yl)pyrazine-2-carboxamide,
3-(3-Chloro-2-fluoro-4-morpholino-anilino)-5-(methylamino)-6-(3-methylimidazo[4,5-c]pyridin-7-yl)pyrazine-2-carboxamide,
5-(Methylamino)-6-(3-methylimidazo[4,5-c]pyridin-7-yl)-3-(2,3,5-trifluoro-4-morpholino-anilino)pyrazine-2-carboxamide,
3-(2-Fluoro-5-methyl-4-morpholino-anilino)-5-(methylamino)-6-(3-methylimidazo[4,5-c]pyridin-7-yl)pyrazine-2-carboxamide,
3-(3,5-Difluoro-4-morpholino-anilino)-5-(methylamino)-6-(3-methylimidazo[4,5-c]pyridin-7-yl)pyrazine-2-carboxamide,
3-(3-Chloro-4-morpholino-anilino)-5-(methylamino)-6-(1-methylbenzimidazol-4-yl)pyrazine-2-carboxamide,
3-(3-Chloro-4-morpholino-anilino)-5-(methylamino)-6-(3-methylimidazo[4,5-c]pyridin-7-yl)pyrazine-2-carboxamide,
5-(Methylamino)-6-(3-methylimidazo[4,5-c]pyridin-7-yl)-3-(3-methyl-4-morpholino-anilino)pyrazine-2-carboxamide,
3-(3,5-Dimethyl-4-morpholino-anilino)-5-(methylamino)-6-(3-methylimidazo[4,5-c]pyridin-7-yl)pyrazine-2-carboxamide,
3-(3-Cyano-4-morpholino-anilino)-5-(methylamino)-6-(3-methylimidazo[4,5-c]pyridin-7-yl)pyrazine-2-carboxamide,
3-(3-Methoxy-4-morpholino-anilino)-5-(methylamino)-6-(3-methylimidazo[4,5-c]pyridin-7-yl)pyrazine-2-carboxamide,
3-[3-(Difluoromethyl)-4-morpholino-anilino]-5-(methylamino)-6-(3-methylimidazo[4,5-c]pyridin-7-yl)pyrazine-2-carboxamide,
5-(Methylamino)-6-(3-methylimidazo[4,5-c]pyridin-7-yl)-3-(2-methyl-4-morpholino-anilino)pyrazine-2-carboxamide,
3-(2-Methoxy-4-morpholino-anilino)-5-(methylamino)-6-(3-methylimidazo[4,5-c]pyridin-7-yl)pyrazine-2-carboxamide,
3-(2-Chloro-4-morpholino-anilino)-5-(methylamino)-6-(3-methylimidazo[4,5-c]pyridin-7-yl)pyrazine-2-carboxamide,
5-(Methylamino)-6-(3-methylimidazo[4,5-c]pyridin-7-yl)-3-[(5-methyl-6-morpholino-3-pyridyl)amino]pyrazine-2-carboxamide,
5-(Methylamino)-6-(3-methylimidazo[4,5-c]pyridin-7-yl)-3-[[5-methyl-6-[(3S)-3-methylmorpholin-4-yl]-3-pyridyl]amino]pyrazine-2-carboxamide,
5-(Methylamino)-6-(3-methylimidazo[4,5-c]pyridin-7-yl)-3-[[5-methyl-6-[(2S)-2-methylmorpholin-4-yl]-3-pyridyl]amino]pyrazine-2-carboxamide,
5-Cyclopropyl-6-(3-methylimidazo[4,5-c]pyridin-7-yl)-3-[[6-[(3R)-3-methylmorpholin-4-yl]-3-pyridyl]amino]pyrazine-2-carboxamide,
3-[(5-Cyano-6-morpholino-3-pyridyl)amino]-5-(methylamino)-6-(3-methylimidazo[4,5-c]pyridin-7-yl)pyrazine-2-carboxamide,
3-((4-(1,4-Oxazepan-4-yl)phenyl)amino)-6-(3-methyl-3H-imidazo[4,5-c]pyridin-7-yl)-5-(methylamino)pyrazine-2-carboxamide,
5-(Methylamino)-6-(3-methylimidazo[4,5-c]pyridin-7-yl)-3-[[5-methyl-6-[(3R)-3-methylmorpholin-4-yl]-3-pyridyl]amino]pyrazine-2-carboxamide,
5-(Methylamino)-6-(3-methylimidazo[4,5-c]pyridin-7-yl)-3-[4-[(1R,4R)-2-oxa-5-azabicyclo[2.2.1]heptan-5-yl]anilino]pyrazine-2-carboxamide, 5-(Methylamino)-6-(3-methylimidazo[4,5-c]pyridin-7-yl)-3-[4-[(1S,4S)-2-oxa-5-azabicyclo[2.2.1]heptan-5-yl]anilino]pyrazine-2-carboxamide, 3-[2-Fluoro-4-[(1S,4S)-2-oxa-5-azabicyclo[2.2.1]heptan-5-yl]anilino]-5-(methylamino)-6-(3-methylimidazo[4,5-c]pyridin-7-yl)pyrazine-2-carboxamide, 3-[2,3-Difluoro-4-[(1S,4S)-2-oxa-5-azabicyclo[2.2.1]heptan-5-yl]anilino]-5-(methylamino)-6-(3-methylimidazo[4,5-c]pyridin-7-yl)pyrazine-2-carboxamide, 5-(Methylamino)-6-(3-methylimidazo[4,5-c]pyridin-7-yl)-3-[2,3,5-trifluoro-4-[(1S,4S)-2-oxa-5-azabicyclo[2.2.1]heptan-5-yl]anilino]pyrazine-2-carboxamide, 5-(Methylamino)-6-(3-methylimidazo[4,5-c]pyridin-7-yl)-3-[4-(6-oxa-3-azabicyclo[3.1.1]heptan-3-yl)anilino]pyrazine-2-carboxamide, 5-(Methylamino)-6-(3-methylimidazo[4,5-c]pyridin-7-yl)-3-[4-(8-oxa-3-azabicyclo[3.2.1]octan-3-yl)anilino]pyrazine-2-carboxamide, 5-(Methylamino)-6-(3-methylimidazo[4,5-c]pyridin-7-yl)-3-[4-(2-oxa-6-azaspiro[3.3]heptan-6-yl)anilino]pyrazine-2-carboxamide, 3-Anilino-5-(methylamino)-6-(3-methylimidazo[4,5-c]pyridin-7-yl)pyrazine-2-carboxamide, 3-[4-(Difluoromethoxy)anilino]-5-(methylamino)-6-(3-methylimidazo[4,5-c]pyridin-7-yl)pyrazine-2-carboxamide, 5-Cyclopropyl-3-[4-(1-hydroxy-1-methyl-ethyl)anilino]-6-(3-methylimidazo[4,5-c]pyridin-7-yl)pyrazine-2-carboxamide, 3-(4-Isopropoxyanilino)-5-(methylamino)-6-(3-methylimidazo[4,5-c]pyridin-7-yl)pyrazine-2-carboxamide,

[4-[[3-Carbamoyl-6-(methylamino)-5-(3-methylimidazo[4,5-c]pyridin-7-yl)pyrazin-2-yl]amino]phenyl]methanesulfonate, 3-[4-(2-Methoxyethoxy)anilino]-5-(methylamino)-6-(3-methylimidazo[4,5-c]pyridin-7-yl)pyrazine-2-carboxamide, 3-[4-[2-(Dimethylamino)ethoxy]anilino]-5-(methylamino)-6-(3-methylimidazo[4,5-c]pyridin-7-yl)pyrazine-2-carboxamide, 3-[4-(2-Hydroxyethoxy)anilino]-5-(methylamino)-6-(3-methylimidazo[4,5-c]pyridin-7-yl)pyrazine-2-carboxamide, 5-(Methylamino)-6-(3-methylimidazo[4,5-c]pyridin-7-yl)-3-[4-(2-morpholinoethoxy)anilino]pyrazine-2-carboxamide, 3-(4-Aminoanilino)-5-(methylamino)-6-(1-methylbenzimidazol-4-yl)pyrazine-2-carboxamide, 3-[4-[2-Methoxyethyl(methyl)amino]anilino]-5-(methylamino)-6-(3-methylimidazo[4,5-c]pyridin-7-yl)pyrazine-2-carboxamide, 3-[4-[Bis(2-methoxyethyl)amino]anilino]-5-(methylamino)-6-(3-methylimidazo[4,5-c]pyridin-7-yl)pyrazine-2-carboxamide, 5-(Methylamino)-6-(3-methylimidazo[4,5-c]pyridin-7-yl)-3-[(2-methyl-4-pyridyl)amino]pyrazine-2-carboxamide formate salt, 3-[(2-Methoxy-4-pyridyl)amino]-5-(methylamino)-6-(3-methylimidazo[4,5-c]pyridin-7-yl)pyrazine-2-carboxamide, 3-[(2-Methoxy-6-methyl-4-pyridyl)amino]-5-(methylamino)-6-(7-methylimidazo[4,5-c]pyridazin-4-yl)pyrazine-2-carboxamide hydrochloride, 3-[(2,6-Dimethyl-4-pyridyl)amino]-5-(methylamino)-6-(3-methylimidazo[4,5-c]pyridin-7-yl)pyrazine-2-carboxamide, 5-Cyclopropyl-3-[(2,6-dimethyl-4-pyridyl)amino]-6-(3-methylimidazo[4,5-c]pyridin-7-yl)pyrazine-2-carboxamide, 3-[(2-Methoxy-6-methyl-4-pyridyl)amino]-5-(methylamino)-6-(3-methylimidazo[4,5-c]pyridin-7-yl)pyrazine-2-carboxamide, 3-[[2-(2-Methoxyethoxy)-6-methyl-4-pyridyl]amino]-5-(methylamino)-6-(3-methylimidazo[4,5-c]pyridin-7-yl)pyrazine-2-carboxamide, 3-[(2-Cyano-6-methyl-4-pyridyl)amino]-5-(methylamino)-6-(3-methylimidazo[4,5-c]pyridin-7-yl)pyrazine-2-carboxamide, 3-[(1,5-Dimethyl-6-oxo-3-pyridyl)amino]-5-(methylamino)-6-(3-methylimidazo[4,5-c]pyridin-7-yl)pyrazine-2-carboxamide, 3-[[1-(Difluoromethyl)-6-oxo-3-pyridyl]amino]-5-(methylamino)-6-(3-methylimidazo[4,5-c]pyridin-7-yl)pyrazine-2-carboxamide, 5-(Methylamino)-3-[4-[(1R,4R)-5-methyl-2,5-diazabicyclo[2.2.1]heptan-2-yl]anilino]-6-(3-methylimidazo[4,5-c]pyridin-7-yl)pyrazine-2-carboxamide bis-formate salt, 5-(Methylamino)-3-[4-(8-methyl-3,8-diazabicyclo[3.2.1]octan-3-yl)anilino]-6-(3-methylimidazo[4,5-c]pyridin-7-yl)pyrazine-2-carboxamide, 3-[4-[(3S,5R)-3,5-Dimethylpiperazin-1-yl]anilino]-6-(3-methylimidazo[4,5-c]pyridin-7-yl)-5-(trifluoromethyl)pyrazine-2-carboxamide, 3-[4-[(3S,5R)-3,5-Dimethylpiperazin-1-yl]-3,5-difluoroanilino]-5-(methylamino)-6-(3-methylimidazo[4,5-c]pyridin-7-yl)pyrazine-2-carboxamide, 5-(Methylamino)-3-[4-(3-methyl-3,8-diazabicyclo[3.2.1]octan-8-yl)anilino]-6-(3-methylimidazo[4,5-c]pyridin-7-yl)pyrazine-2-carboxamide formate salt, 5-(Methylamino)-3-[4-[(1S,4S)-5-methyl-2,5-diazabicyclo[2.2.1]heptan-2-yl]anilino]-6-(3-methylimidazo[4,5-c]pyridin-7-yl)pyrazine-2-carboxamide, 3-[4-[(3S,5R)-3,5-Dimethylpiperazin-1-yl]-3,5-dimethylanilino]-5-(methylamino)-6-(3-methylimidazo[4,5-c]pyridin-7-yl)pyrazine-2-carboxamide, 3-[4-[2-(Dimethylamino)ethyl-methyl-amino]anilino]-5-(methylamino)-6-(3-methylimidazo[4,5-c]pyridin-7-yl)pyrazine-2-carboxamide bis-formate salt, 3-[4-[3-(Dimethylamino)azetidin-1-yl]anilino]-5-(methylamino)-6-(3-methylimidazo[4,5-c]pyridin-7-yl)pyrazine-2-carboxamide bis-formate salt, 3-[3-Cyano-4-[(3S,5R)-3, 5-dimethylpiperazin-1-yl]anilino]-5-(methylamino)-6-(3-methylimidazo[4,5-c]pyridin-7-yl)pyrazine-2-carboxamide, 3-[2,3-Difluoro-4-[4-(4-methylpiperazin-1-yl)-1-piperidyl]anilino]-5-(methylamino)-6-(3-methylimidazo[4,5-c]pyridin-7-yl)pyrazine-2-carboxamide, 3-[[6-(4-Isopropylpiperazin-1-yl)-5-methyl-3-pyridyl]amino]-5-(methylamino)-6-(3-methylimidazo[4,5-c]pyridin-7-yl)pyrazine-2-carboxamide, 3-[[5-Methoxy-6-(4-methylpiperazin-1-yl)-3-pyridyl]amino]-5-(methylamino)-6-(3-methylimidazo[4,5-c]pyridin-7-yl)pyrazine-2-carboxamide, 5-(Methylamino)-6-(3-methylimidazo[4,5-c]pyridin-7-yl)-3-[[5-methyl-6-[(1R,4R)-5-methyl-2,5-diazabicyclo[2.2.1]heptan-2-yl]-3-pyridyl]amino]pyrazine-2-carboxamide, 3-[[5-Chloro-6-[(1R,4R)-5-methyl-2,5-diazabicyclo[2.2.1]heptan-2-yl]-3-pyridyl]amino]-5-(methylamino)-6-(3-methylimidazo[4,5-c]pyridin-7-yl)pyrazine-2-carboxamide, 5-(Methylamino)-3-[(6-methyl-5,7-dihydropyrrolo[3,4-b]pyridin-3-yl)amino]-6-(3-methylimidazo[4,5-c]pyridin-7-yl)pyrazine-2-carboxamide, 3-[(6-Ethyl-5,7-dihydropyrrolo[3,4-b]pyridin-3-yl)amino]-5-(methylamino)-6-(3-methylimidazo[4,5-c]pyridin-7-yl)pyrazine-2-carboxamide, 3-[(6-Isopropyl-5,7-dihydropyrrolo[3,4-b]pyridin-3-yl)amino]-5-(methylamino)-6-(3-methylimidazo[4,5-c]pyridin-7-yl)pyrazine-2-carboxamide formate salt, 3-[4-[(Dimethylamino)methyl]anilino]-5-(methylamino)-6-(3-methylimidazo[4,5-c]pyridin-7-yl)pyrazine-2-carboxamide, 5-(Methylamino)-6-(3-methylimidazo[4,5-c]pyridin-7-yl)-3-[4-(pyrrolidin-1-ylmethyl)anilino]pyrazine-2-carboxamide bis-formate salt, 5-(Methylamino)-6-(3-methylimidazo[4,5-c]pyridin-7-yl)-3-[4-(morpholinomethyl)anilino]pyrazine-2-carboxamide, 5-(Methylamino)-6-(3-methylimidazo[4,5-c]pyridin-7-yl)-3-[4-[(4-methylpiperazin-1-yl)methyl]anilino]pyrazine-2-carboxamide, 5-(Methylamino)-6-(3-methylimidazo[4,5-c]pyridin-7-yl)-3-[4-(2-oxa-6-azaspiro[3.3]heptan-6-ylmethyl)anilino]pyrazine-2-carboxamide, 5-(Methylamino)-6-(3-methylimidazo[4,5-c]pyridin-7-yl)-3-[4-[rel-(1R)-1-(4-methylpiperazin-1-yl)ethyl]anilino]pyrazine-2-carboxamide formate salt, 5-(Methylamino)-6-(3-methylimidazo[4,5-c]pyridin-7-yl)-3-[4-[rel-(1S)-1-(4-methylpiperazin-1-yl)ethyl]anilino]pyrazine-2-carboxamide formate salt, 5-(Methylamino)-6-(3-methylimidazo[4,5-c]pyridin-7-yl)-3-[4-[rel-(1R)-1-morpholinoethyl]anilino]pyrazine-2-carboxamide formate salt, 5-(Methylamino)-6-(3-methylimidazo[4,5-c]pyridin-7-yl)-3-[4-[rel-(1S)-1-morpholinoethyl]anilino]pyrazine-2-carboxamide formate salt, 5-(Methylamino)-6-(3-methylimidazo[4,5-c]pyridin-7-yl)-3-[4-[1-methyl-1-(4-methylpiperazin-1-yl)ethyl]anilino]pyrazine-2-carboxamide, 5-(Methylamino)-6-(3-methylimidazo[4,5-c]pyridin-7-yl)-3-[4-(1-methyl-1-morpholino-ethyl)anilino]pyrazine-2-carboxamide, (R)-3-((4-((3-Fluoropyrrolidin-1-yl)methyl)phenyl)amino)-6-(3-methyl-3H-imidazo[4,5-c]pyridin-7-yl)-5-(methylamino)pyrazine-2-carboxamide formate salt, 3-[4-[[(3S)-3-Fluoropyrrolidin-1-yl]methyl]anilino]-5-(methylamino)-6-(3-methylimidazo[4,5-c]pyridin-7-yl)pyrazine-2-carboxamide formate salt, 3-[4-[(3,3-Difluoropyrrolidin-1-yl)methyl]anilino]-5-(methylamino)-6-(3-methylimidazo[4,5-c]pyridin-7-yl)pyrazine-2-carboxamide formate salt, 3-[4-[[(3S)-3,4-Dimethylpiperazin-1-yl]methyl]anilino]-5-(methylamino)-6-(3-methylimidazo[4,5-c]pyridin-7-yl)pyrazine-2-carboxamide tris-formate salt, 3-[4-[[(3R)-3,4-dimethylpiperazin-1-yl]methyl]anilino]-5-(methylamino)-6-(3-methylimidazo[4,5-c]pyridin-7-yl)pyrazine-2-carboxamide formate salt, 5-(Methylamino)-6-(3-methylimidazo[4,5-c]pyridin-7-yl)-3-[[6-(morpholinomethyl)-3-pyridyl]amino]pyrazine-2-carboxamide formate salt, 3-[2-Fluoro-4-[(4-methylpiperazin-1-yl)methyl]anilino]-5-(methylamino)-6-(3-methylimidazo[4,5-c]pyridin-7-yl)pyrazine-2-carboxamide, 3-[3-Chloro-4-[(4-methylpiperazin-1-yl)methyl]anilino]-5-(methylamino)-6-(3-methylimidazo[4,5-c]pyridin-7-yl)pyrazine-2-carboxamide formate salt, 3-[2-Fluoro-4-(morpholinomethyl)anilino]-5-(methylamino)-6-(3-methylimidazo[4,5-c]pyridin-7-yl)pyrazine-2-carboxamide formate salt, 3-[2,3-Difluoro-4-(morpholinomethyl)anilino]-5-(methylamino)-6-(3-methylimidazo[4,5-c]pyridin-7-yl)pyrazine-2-carboxamide, 3-[2-Fluoro-4-[[(1S,4S)-2-oxa-5-azabicyclo[2.2.1]heptan-5-yl]methyl]anilino]-5-(methylamino)-6-(3-methylimidazo[4,5-c]pyridin-7-yl)pyrazine-2-carboxamide, 3-[2-Fluoro-4-[[(1R,4R)-2-oxa-5-azabicyclo[2.2.1]heptan-5-yl]methyl]anilino]-5-(methylamino)-6-(3-methylimidazo[4,5-c]pyridin-7-yl)pyrazine-2-carboxamide, 3-[2,3-Difluoro-4-[[(1R,4R)-2-oxa-5-azabicyclo[2.2.1]heptan-5-yl]methyl]anilino]-5-(methylamino)-6-(3-methylimidazo[4,5-c]pyridin-7-yl)pyrazine-2-carboxamide, 3-[2-Chloro-4-(2-oxa-6-azaspiro[3.3]heptan-6-ylmethyl)anilino]-5-(methylamino)-6-(3-methylimidazo[4,5-c]pyridin-7-yl)pyrazine-2-carboxamide formate salt, 5-(Methylamino)-6-(3-methylimidazo[4,5-c]pyridin-7-yl)-3-[4-(2-morpholinoethyl)anilino]pyrazine-2-carboxamide, 5-(Methylamino)-6-(3-methylimidazo[4,5-c]pyridin-7-yl)-3-[4-[2-(4-methylpiperazin-1-yl)ethyl]anilino]pyrazine-2-carboxamide, 5-Cyclopropyl-6-(3-methylimidazo[4,5-c]pyridin-7-yl)-3-[4-(pyrrolidin-1-ylmethyl)anilino]pyrazine-2-carboxamide, 5-Cyclopropyl-6-(3-methylimidazo[4,5-c]pyridin-7-yl)-3-[4-[(4-methylpiperazin-1-yl)methyl]anilino]pyrazine-2-carboxamide, 5-Methoxy-6-(3-methylimidazo[4,5-c]pyridin-7-yl)-3-[4-[(4-methylpiperazin-1-yl)methyl]anilino]pyrazine-2-carboxamide, 5-(Difluoromethyl)-6-(3-methylimidazo[4,5-c]pyridin-7-yl)-3-[4-[(4-methylpiperazin-1-yl)methyl]anilino]pyrazine-2-carboxamide, 5-(Difluoromethyl)-6-(3-methylimidazo[4,5-c]pyridin-7-yl)-3-[4-(morpholinomethyl)anilino]pyrazine-2-carboxamide, 3-[2-Fluoro-4-(morpholinomethyl)anilino]-5-methoxy-6-(3-methylimidazo[4,5-c]pyridin-7-yl)pyrazine-2-carboxamide, 3-[2,3-Difluoro-4-(morpholinomethyl)anilino]-5-methoxy-6-(3-methylimidazo[4,5-c]pyridin-7-yl)pyrazine-2-carboxamide, 5-Methyl-6-(1-methylbenzimidazol-4-yl)-3-[4-[rel-(3S)-4-methylmorpholin-3-yl]anilino]pyrazine-2-carboxamide, 5-Methyl-6-(1-methylbenzimidazol-4-yl)-3-[4-[rel-(3R)-4-methylmorpholin-3-yl]anilino]pyrazine-2-carboxamide, 5-Methyl-6-(1-methylbenzimidazol-4-yl)-3-[4-[rel-(2R)-4-methylmorpholin-2-yl]anilino]pyrazine-2-carboxamide, 5-Methyl-6-(1-methylbenzimidazol-4-yl)-3-[4-[rel-(2S)-4-methylmorpholin-2-yl]anilino]pyrazine-2-carboxamide, 5-(Methylamino)-6-(3-methylimidazo[4,5-c]pyridin-7-yl)-3-[4-(4-piperidyloxy)anilino]pyrazine-2-carboxamide, 3-[4-[(1-Acetyl-4-piperidyl)oxy]anilino]-5-(methylamino)-6-(3-methylimidazo[4,5-c]pyridin-7-yl)pyrazine-2-carboxamide, 5-(Methylamino)-6-(3-methylimidazo[4,5-c]pyridin-7-yl)-3-[4-[(1-methyl-4-piperidyl)oxy]anilino]pyrazine-2-carboxamide, 3-[4-[[1-(2-Hydroxyacetyl)-4-piperidyl]oxy]anilino]-5-(methylamino)-6-(3-methylimidazo[4,5-c]pyridin-7-yl)pyrazine-2-carboxamide, 5-Methoxy-6-(3-methylimidazo[4,5-c]pyridin-7-yl)-3-[4-[(1-methyl-4-piperidyl)oxy]anilino]pyrazine-2-carboxamide, 5-Cyclopropyl-6-(3-methylimidazo[4,5-c]pyridin-7-yl)-3-[4-[(1-methyl-4-piperidyl)oxy]anilino]pyrazine-2-carboxamide, 3-[3,5-Difluoro-4-[(1-methyl-4-piperidyl)oxy]anilino]-5-(methylamino)-6-(3-methylimidazo[4,5-c]pyridin-7-yl)pyrazine-2-carboxamide, 3-[4-[(1-Isopropyl-4-piperidyl)oxy]anilino]-5-(methylamino)-6-(3-methylimidazo[4,5-c]pyridin-7-yl)pyrazine-2-carboxamide formate salt, 3-[4-[[(2S,4R)-4-Hydroxy-1-methyl-pyrrolidin-2-yl]methoxy]anilino]-5-methyl-6-(1-methylbenzimidazol-4-yl)pyrazine-2-carboxamide, 3-[4-[[(2R,4S)-4-Hydroxy-1-methyl-pyrrolidin-2-yl]methoxy]anilino]-5-methyl-6-(1-methylbenzimidazol-4-yl)pyrazine-2-carboxamide, 3-[4-[[(2R,4S)-4-Methoxy-1-methyl-pyrrolidin-2-yl]methoxy]anilino]-5-methyl-6-(1-methylbenzimidazol-4-yl)pyrazine-2-carboxamide, 3-[4-[[(2S,4R)-4-Methoxy-1-methyl-pyrrolidin-2-yl]methoxy]anilino]-5-methyl-6-(1-methylbenzimidazol-4-yl)pyrazine-2-carboxamide, 5-(Methylamino)-6-(3-methylimidazo[4,5-c]pyridin-7-yl)-3-[3-(4-methylpiperazin-1-yl)anilino]pyrazine-2-carboxamide, 5-(Methylamino)-6-(3-methylimidazo[4,5-c]pyridin-7-yl)-3-[3-(1-methyl-4-piperidyl)anilino]pyrazine-2-carboxamide formate salt, 5-(Methylamino)-6-(3-methylimidazo[4,5-c]pyridin-7-yl)-3-[4-(4-methylimidazol-1-yl)anilino]pyrazine-2-carboxamide, 5-(Methylamino)-6-(3-methylimidazo[4,5-c]pyridin-7-yl)-3-([1,2,4]triazolo[4,3-a]pyridin-6-ylamino)pyrazine-2-carboxamide, 3-[4-(1-Hydroxy-1-methyl-ethyl)anilino]-5-(methylamino)-6-(3-methylimidazo[4,5-c]pyridin-7-yl)pyrazine-2-carboxamide, 5-Cyclopropyl-3-[[6-(1-hydroxy-1-methyl-ethyl)-3-pyridyl]amino]-6-(3-methylimidazo[4,5-c]pyridin-7-yl)pyrazine-2-carboxamide, 3-[(2-Imino-2-oxo-1,3-dihydro-2-benzothiophen-5-yl)amino]-5-methyl-6-(1-methylbenzimidazol-4-yl)pyrazine-2-carboxamide, rel-(R)-3-[4-(Ethylsulfonimidoyl)-3, 5-dimethyl-anilino]-5-methyl-6-(1-methylbenzimidazol-4-yl)pyrazine-2-carboxamide, rel-(S)-3-[4-(Ethylsulfonimidoyl)-3,5-dimethyl-anilino]-5-methyl-6-(1-methylbenzimidazol-4-yl)pyrazine-2-carboxamide, 3-[(2,2-Dioxo-1,3-dihydro-2-benzothiophen-5-yl)amino]-5-(methylamino)-6-(3-methylimidazo[4,5-c]pyridin-7-yl)pyrazine-2-carboxamide, 5-(Methylamino)-3-[(1-methyl-2,2-dioxo-3H-2,1-benzothiazol-5-yl)amino]-6-(3-methylimidazo[4,5-c]pyridin-7-yl)pyrazine-2-carboxamide, 5-Cyclopropyl-3-[(1-methyl-2,2-dioxo-3H-2,1-benzothiazol-5-yl)amino]-6-(3-methylimidazo[4,5-c]pyridin-7-yl)pyrazine-2-carboxamide, 5-Methoxy-3-[(1-methyl-2,2-dioxo-3H-2,1-benzothiazol-5-yl)amino]-6-(3-methylimidazo[4,5-c]pyridin-7-yl)pyrazine-2-carboxamide, 3-[4-(1,1-Dioxo-1,4-thiazinan-4-yl)anilino]-5-(methylamino)-6-(3-methylimidazo[4,5-c]pyridin-7-yl)pyrazine-2-carboxamide, 3-[4-[[Dimethyl(oxo)-$\lambda^6$-sulfanylidene]amino]anilino]-5-(methylamino)-6-(3-methylimidazo[4,5-c]pyridin-7-yl)pyrazine-2-carboxamide, 3-[4-[[Dimethyl(oxo)-$\lambda^6$-sulfanylidene]amino]-2-fluoro-anilino]-5-(methylamino)-6-(3-methylimidazo[4,5-c]pyridin-7-yl)pyrazine-2-carboxamide, 3-[4-[[Dimethyl(oxo)-$\lambda^6$-sulfanylidene]amino]-2,3-difluoro-anilino]-5-(methylamino)-6-(3-methylimidazo[4,5-c]pyridin-7-yl)pyrazine-2-carboxamide formate salt, 3-[4-(1,1-Dioxo-1,2-thiazolidin-2-yl)anilino]-5-(methylamino)-6-(3-methylimidazo[4,5-c]pyridin-7-yl)pyrazine-2-carboxamide, 3-[4-(1,1-Dioxothiazinan-2-yl)anilino]-5-(methylamino)-6-(3-methylimidazo[4,5-c]pyridin-7-yl)pyrazine-2-carboxamide, 3-(2-Fluoro-4-methylsulfonyl-anilino)-5-(methylamino)-6-(3-methylimidazo[4,5-c]pyridin-7-yl)pyrazine-2-carboxamide, (R)-3-[4-(Ethylsulfonimidoyl)anilino]-5-(methylamino)-6-(3-methylimidazo[4,5-c]pyridin-7-yl)pyrazine-2-carboxamide, (S)-3-[4-(Ethylsulfonimidoyl)anilino]-5-(methylamino)-6-(3-methylimidazo[4,5-c]pyridin-7-yl)pyrazine-2-carboxamide, rel-(R)-3-[4-(Isopropylsulfonimidoyl)anilino]-5-(methylamino)-6-(3-methylimidazo[4,5-c]pyridin-7-yl)pyrazine-2-carboxamide, rel-(S)-3-[4-(Isopropylsulfonimidoyl)anilino]-5-(methylamino)-6-(3-methylimidazo[4,5-c]pyridin-7-yl)pyrazine-2-carboxamide, 3-[4-(tert-Butylsulfonimidoyl)anilino]-5-(methylamino)-6-(3-methylimidazo[4,5-c]pyridin-7-yl)pyrazine-2-carboxamide, 5-(Methylamino)-6-(3-methylimidazo[4,5-c]pyridin-7-yl)-3-[4-(1-methylsulfonylcyclopropyl)anilino]pyrazine-2-carboxamide, 5-Methoxy-6-(3-methylimidazo[4,5-c]pyridin-7-yl)-3-[4-(1-methylsulfonylcyclopropyl)anilino]pyrazine-2-carboxamide, 5-Methoxy-6-(3-methylimidazo[4,5-c]pyridin-7-yl)-3-[(1-methylpyrazol-4-yl)amino]pyrazine-2-carboxamide, 5-(Methylamino)-6-(3-methylimidazo[4,5-c]pyridin-7-yl)-3-[(1-tetrahydropyran-4-ylpyrazol-4-yl)amino]pyrazine-2-carboxamide, 3-[(1-Isopropylpyrazol-4-yl)amino]-5-(methylamino)-6-(3-methylimidazo[4,5-c]pyridin-7-yl)pyrazine-2-carboxamide, 3-[[1-(1,1-Dioxothian-4-yl)pyrazol-4-yl]amino]-5-(methylamino)-6-(3-methylimidazo[4,5-c]pyridin-7-yl)pyrazine-2-carboxamide, 5-(Methylamino)-6-(3-methylimidazo[4,5-c]pyridin-7-yl)-3-[[1-(1-methyl-4-piperidyl)pyrazol-4-yl]amino]pyrazine-2-carboxamide, 5-(Methylamino)-6-(1-methylbenzimidazol-4-yl)-3-[[3-methyl-1-(1-methyl-4-piperidyl)pyrazol-4-yl]amino]pyrazine-2-carboxamide formate salt, 3-[(1,3-Dimethylpyrazol-4-yl)amino]-5-(methylamino)-6-(3-methylimidazo[4,5-c]pyridin-7-yl)pyrazine-2-carboxamide, 5-(Methylamino)-6-(3-methylimidazo[4,5-c]pyridin-7-yl)-3-[[3-methyl-1-(2,2,2-trifluoroethyl)pyrazol-4-yl]amino]pyrazine-2-carboxamide, 3-[[1-(2,2-Difluoroethyl)-3-methyl-pyrazol-4-yl]amino]-5-(methylamino)-6-(3-methylimidazo[4,5-c]pyridin-7-yl)pyrazine-2-carboxamide, 3-[[1-(2,2-Difluoroethyl)-5-methyl-pyrazol-4-yl]amino]-5-(methylamino)-6-(3-methylimidazo[4,5-c]pyridin-7-yl)pyrazine-2-carboxamide, 3-[[1-(1-Cyano-1-methyl-ethyl)-3-methyl-pyrazol-4-yl]amino]-5-(methylamino)-6-(3-methylimidazo[4,5-c]pyridin-7-yl)pyrazine-2-carboxamide, 5-Cyclopropyl-3-[(1,3-dimethylpyrazol-4-yl)amino]-6-(3-methylimidazo[4,5-c]pyridin-7-yl)pyrazine-2-carboxamide, 5-Cyclopropyl-6-(3-methylimidazo[4,5-c]pyridin-7-yl)-3-[[3-methyl-1-(2,2,2-trifluoroethyl)pyrazol-4-yl]amino]pyrazine-2-carboxamide, 5-Cyclopropyl-6-(3-methylimidazo[4,5-c]pyridin-7-yl)-3-[[5-methyl-1-(2,2,2-trifluoroethyl)pyrazol-4-yl]amino]pyrazine-2-carboxamide, 5-Cyclopropyl-3-[[1-(2,2-difluoroethyl)-3-methyl-pyrazol-4-yl]amino]-6-(3-methylimidazo[4,5-c]pyridin-7-yl)pyrazine-2-carboxamide, 3-[[1-(1-Cyano-1-methyl-ethyl)-3-methyl-pyrazol-4-yl]amino]-5-cyclopropyl-6-(3-methylimidazo[4,5-c]pyridin-7-yl)pyrazine-2-carboxamide, 3-[[1-(1-Cyanocyclopropyl)-3-methyl-pyrazol-4-yl]amino]-5-cyclopropyl-6-(3-methylimidazo[4,5-c]pyridin-7-yl)pyrazine-2-carboxamide, 5-Cyclopropyl-3-[(1,5-dimethylpyrazol-4-yl)amino]-6-(3-methylimidazo[4,5-c]pyridin-7-yl)pyrazine-2-carboxamide, 5-Cyclopropyl-6-(3-methylimidazo[4,5-c]pyridin-7-yl)-3-[(3-methyl-1H-pyrazol-4-yl)amino]pyrazine-2-carboxamide, 5-Cyclopropyl-6-(3-methylimidazo[4,5-c]pyridin-7-yl)-3-[[3-methyl-1-[rel-(2R)-2,3-difluoropropyl]pyrazol-4-yl]amino]pyrazine-2-carboxamide, 5-Cyclopropyl-6-(3-methylimidazo[4,5-c]pyridin-7-yl)-3-[[3-methyl-1-[rel-(2S)-2,3-difluoropropyl]pyrazol-4-yl]amino]pyrazine-2-carboxamide, 5-Cyclopropyl-6-(3-methylimidazo[4,5-c]pyridin-7-yl)-3-[[5-methyl-1-[rel-(2R)-2,3-difluoropropyl]pyrazol-4-yl]amino]pyrazine-2-carboxamide, 5-Cyclopropyl-6-(3-methylimidazo[4,5-c]pyridin-7-yl)-3-[[5-methyl-1-[rel-(2S)-2,3-difluoropropyl]pyrazol-4-yl]amino]pyrazine-2-carboxamide, 5-Cyclopropyl-6-(3-methylimidazo[4,5-c]pyridin-7-yl)-3-[[3-methyl-1-(oxetan-3-yl)pyrazol-4-yl]amino]pyrazine-2-carboxamide, 5-Cyclopropyl-6-(3-methylimidazo[4,5-c]pyridin-7-yl)-3-[[5-methyl-1-(oxetan-3-yl)pyrazol-4-yl]amino]pyrazine-2-carboxamide, 5-Cyclopropyl-3-[[1-(2,2-difluoroethyl)-5-methyl-pyrazol-4-yl]amino]-6-(3-methylimidazo[4,5-c]pyridin-7-yl)pyrazine-2-carboxamide, 5-Cyclopropyl-3-[[1-(3,3-difluoropropyl)-3-methyl-pyrazol-4-yl]amino]-6-(3-methylimidazo[4,5-c]pyridin-7-yl)pyrazine-2-carboxamide, 5-Cyclopropyl-3-[[1-(3,3-difluoropropyl)-5-methyl-pyrazol-4-yl]amino]-6-(3-methylimidazo[4,5-c]pyridin-7-yl)pyrazine-2-carboxamide, 5-Cyclopropyl-6-(3-methylimidazo[4,5-c]pyridin-7-yl)-3-[(3-methyl-1-tetrahydropyran-4-yl-pyrazol-4-yl)amino]pyrazine-2-carboxamide, 5-Cyclopropyl-6-(3-methylimidazo[4,5-c]pyridin-7-yl)-3-[(5-methyl-1-tetrahydropyran-4-yl-pyrazol-4-yl)amino]pyrazine-2-carboxamide, 5-Cyclopropyl-6-(1-methylbenzimidazol-4-yl)-3-[[3-methyl-1-(1-methyl-4-piperidyl)pyrazol-4-yl]amino]pyrazine-2-carboxamide, 5-Cyclopropyl-6-(1-methylbenzimidazol-4-yl)-3-[[5-methyl-1-(1-methyl-4-piperidyl)pyrazol-4-yl]amino]pyrazine-2-carboxamide, or a pharmaceutically acceptable salt thereof.

14. A pharmaceutical composition comprising the compound according to claim 1, or a pharmaceutically acceptable salt thereof, optionally in admixture with a pharmaceutically acceptable adjuvant, diluent or carrier.

* * * * *